US011753640B2

(12) United States Patent
Hagedorn et al.

(10) Patent No.: US 11,753,640 B2

(45) Date of Patent: Sep. 12, 2023

(54) OLIGONUCLEOTIDES FOR MODULATING TAU EXPRESSION

(71) Applicant: Hoffmann-La Roche Inc., Little Falls, NJ (US)

(72) Inventors: Peter Hagedorn, Hørsholm (DK); Anja Mølhart Høg, Hillerød (DK); Richard E. Olson, Cambridge, MA (US); Marianne L. Jensen, Køge (DK)

(73) Assignee: Hoffmann-La Roche Inc., Little Falls, NJ (US)

( * ) Notice: Subject to any disclaimer, the term of this patent is extended or adjusted under 35 U.S.C. 154(b) by 46 days.

(21) Appl. No.: 17/139,161

(22) Filed: Dec. 31, 2020

(65) Prior Publication Data

US 2021/0123054 A1 Apr. 29, 2021

Related U.S. Application Data

(63) Continuation of application No. PCT/EP2019/067799, filed on Jul. 3, 2019.

(60) Provisional application No. 62/726,005, filed on Aug. 31, 2018, provisional application No. 62/693,851, filed on Jul. 3, 2018.

(51) Int. Cl.
*C12N 15/113* (2010.01)

(52) U.S. Cl.
CPC .... *C12N 15/113* (2013.01); *C12Y 301/26004* (2013.01); *C12N 2310/11* (2013.01); *C12N 2310/315* (2013.01); *C12N 2310/32* (2013.01); *C12N 2310/321* (2013.01); *C12N 2310/3231* (2013.01); *C12N 2310/341* (2013.01); *C12N 2310/351* (2013.01); *C12N 2330/30* (2013.01)

(58) Field of Classification Search
CPC ... C12N 15/11; C12N 15/113; C12N 2310/11; C12N 2310/321; C12N 2310/315; C12N 2310/341; C12N 2310/346; C12N 2310/3341; C12N 9/22; C12N 2310/3231
See application file for complete search history.

(56) References Cited

U.S. PATENT DOCUMENTS

| | | | |
|---|---|---|---|
| 4,711,955 | A | 12/1987 | Ward et al. |
| 5,525,711 | A | 6/1996 | Hawkins et al. |
| 5,792,608 | A | 8/1998 | Swaminathan et al. |
| 5,885,968 | A | 3/1999 | Biessen et al. |
| 8,090,542 | B2 | 1/2012 | Khvorova et al. |
| 8,349,809 | B2 | 1/2013 | Brown |
| 8,513,207 | B2 | 8/2013 | Brown |
| 9,458,153 | B2 | 10/2016 | Han et al. |
| 9,683,235 | B2 | 6/2017 | Freier |
| 10,093,671 | B2 | 10/2018 | Han et al. |
| 11,279,929 | B2 | 3/2022 | Hagedorn et al. |
| 2005/0026164 | A1 | 2/2005 | Zhou |
| 2005/0272080 | A1 | 12/2005 | Palma et al. |
| 2006/0257851 | A1 | 11/2006 | Bentwich |
| 2010/0173974 | A1 | 7/2010 | Brown |
| 2010/0197762 | A1 | 8/2010 | Swayze |
| 2011/0118337 | A1 | 5/2011 | Chau et al. |
| 2012/0040460 | A1 | 2/2012 | Rigoutsos et al. |
| 2013/0253036 | A1 | 9/2013 | Collard et al. |
| 2015/0191722 | A1 | 7/2015 | Krieg et al. |
| 2015/0275205 | A1 | 10/2015 | Miller et al. |
| 2019/0111073 | A1 | 4/2019 | Kammler et al. |
| 2019/0211339 | A1 | 7/2019 | Agarwal et al. |
| 2020/0010831 | A1 | 1/2020 | Hagedorn et al. |
| 2020/0147123 | A1 | 5/2020 | Kammler et al. |
| 2021/0123054 | A1 | 4/2021 | Hagedorn et al. |
| 2022/0177884 | A1 * | 6/2022 | Hagedorn ............ C12N 15/113 |

FOREIGN PATENT DOCUMENTS

| | | | |
|---|---|---|---|
| EP | 0302175 | A2 | 2/1989 |
| EP | 1013661 | A1 | 6/2000 |
| EP | 1152009 | A1 | 11/2001 |
| EP | 1752536 | A1 | 2/2007 |
| EP | 1013661 | B1 | 1/2012 |
| EP | 2213738 | B1 | 10/2012 |
| EP | 2742136 | A1 | 6/2014 |
| EP | 1152009 | B2 | 9/2017 |
| EP | 2742136 | B1 | 9/2017 |
| JP | 2015-516953 | A | 6/2015 |
| RU | 2645259 | C2 | 2/2018 |

(Continued)

OTHER PUBLICATIONS

Carmona et al., The role of TREM2 in Alzheimer's disease and other neurodegenerative disorders, 2018, Lancet Neurology, 17, 721 (Year: 2018).*
Morley et al., Alzheimer Disease, 2018, Clin. Geriatric Med. 34, 591 (Year: 2018).*
Evers et al., Antisense oligonucleotides in therapy for neurodegenerative disorders, 2015, Advanced Drug Delivery Review, 87,90-103 (Year: 2015).*
Decision on granting a patent for invention for Russian Patent Application No. 2021101957/10, dated Jan. 13, 2022 (16 pages).
Office Action for Iranian Patent Application No. 140050140003000170, dated Dec. 13, 2021 (13 pages).
International Search Report and Written Opinion for International Patent Application No. PCT/EP2019/067799, dated Dec. 20, 2019 (20 pages).

(Continued)

*Primary Examiner* — J. E. Angell
*Assistant Examiner* — Keyur A Vyas
(74) *Attorney, Agent, or Firm* — Clark & Elbing, LLP; Thomas J. Takara

(57) ABSTRACT

The present invention relates to antisense oligonucleotides that are capable of modulating expression of Tau in a target cell. The oligonucleotides hybridize to MAPT mRNA. The present invention further relates to conjugates of the oligonucleotide and pharmaceutical compositions and methods for treatment of Tauopathies, Alzheimzer's disease, fronto-temporal dementia (FTD), FTDP-17, progressive supranuclear palsy (PSP), chronic traumatic encephalopathy (CTE), corticobasal ganglionic degeneration (CBD), epilepsy, Dravet syndrome, depression, seizure disorders and movement disorders.

8 Claims, 6 Drawing Sheets

Specification includes a Sequence Listing.

(56) References Cited

FOREIGN PATENT DOCUMENTS

| | | | |
|---|---|---|---|
| WO | WO-93/07883 | A1 | 4/1993 |
| WO | WO-98/39352 | A1 | 9/1998 |
| WO | WO-99/14226 | A2 | 3/1999 |
| WO | WO-00/47599 | A1 | 8/2000 |
| WO | WO-00/66604 | A2 | 11/2000 |
| WO | WO-00/66604 | A3 | 1/2001 |
| WO | WO-01/23613 | A1 | 4/2001 |
| WO | WO-03/022987 | A2 | 3/2003 |
| WO | WO-2003/022987 | A9 | 3/2003 |
| WO | WO-2004/046160 | A2 | 6/2004 |
| WO | WO-2005/014806 | A2 | 2/2005 |
| WO | WO-2007/031091 | A2 | 3/2007 |
| WO | WO-2007/090071 | A2 | 8/2007 |
| WO | WO-2007/106407 | A2 | 9/2007 |
| WO | WO-2007/134181 | A2 | 11/2007 |
| WO | WO-2007/146511 | A2 | 12/2007 |
| WO | WO-2008/049085 | A1 | 4/2008 |
| WO | WO-2008/113832 | A2 | 9/2008 |
| WO | WO-2008/150729 | A2 | 12/2008 |
| WO | WO-2008/154401 | A2 | 12/2008 |
| WO | WO-2009/006478 | A2 | 1/2009 |
| WO | WO-2009/006478 | A3 | 2/2009 |
| WO | WO-2008/150729 | A3 | 3/2009 |
| WO | WO-2007/146511 | A8 | 4/2009 |
| WO | WO-2009/067647 | A1 | 5/2009 |
| WO | WO-2009/090182 | A1 | 7/2009 |
| WO | WO-2009/124238 | A1 | 10/2009 |
| WO | WO-2010/036698 | A1 | 4/2010 |
| WO | WO-2010/040571 | A2 | 4/2010 |
| WO | WO-2010/040571 | A3 | 4/2010 |
| WO | WO-2010/077578 | A1 | 7/2010 |
| WO | WO-2010/093788 | A2 | 8/2010 |
| WO | WO-2010/093788 | A3 | 8/2010 |
| WO | WO-2010/142423 | A2 | 12/2010 |
| WO | WO-2011/017521 | A2 | 2/2011 |
| WO | WO-2011/017521 | A4 | 2/2011 |
| WO | WO-2011/156202 | A1 | 12/2011 |
| WO | WO-2012/024170 | A2 | 2/2012 |
| WO | WO-2012/024170 | A3 | 2/2012 |
| WO | WO-2012/055362 | A1 | 5/2012 |
| WO | WO-2012/109395 | A1 | 8/2012 |
| WO | WO-2012/143379 | A1 | 10/2012 |
| WO | WO-2012/145697 | A1 | 10/2012 |
| WO | WO-2013/003520 | A1 | 1/2013 |
| WO | WO-2013/022984 | A1 | 2/2013 |
| WO | WO-2013/036868 | A1 | 3/2013 |
| WO | WO-2013/041962 | A1 | 3/2013 |
| WO | WO-2013/148260 | A1 | 10/2013 |
| WO | WO-2013/154798 | A1 | 10/2013 |
| WO | WO-2013/159109 | A1 | 10/2013 |
| WO | WO-2013/166264 | A2 | 11/2013 |
| WO | WO-2013/166264 | A3 | 11/2013 |
| WO | WO-2014/012081 | A2 | 1/2014 |
| WO | WO-2014/036429 | A1 | 3/2014 |
| WO | WO-2014/076195 | A1 | 5/2014 |
| WO | WO-2014/076196 | A1 | 5/2014 |
| WO | WO-2014/153236 | A1 | 9/2014 |
| WO | WO-2014/179620 | A1 | 11/2014 |
| WO | WO-2014/179629 | A2 | 11/2014 |
| WO | WO-2014/207232 | A1 | 12/2014 |
| WO | WO-2015/002971 | A2 | 1/2015 |
| WO | WO-2015/010135 | A2 | 1/2015 |
| WO | WO-2014/207232 | A4 | 3/2015 |
| WO | WO-2015/031694 | A2 | 3/2015 |
| WO | WO-2015/113922 | A1 | 8/2015 |
| WO | WO-2015/113990 | A1 | 8/2015 |
| WO | WO-2015/173164 | A1 | 11/2015 |
| WO | WO-2015/173208 | A2 | 11/2015 |
| WO | WO-2015/173208 | A3 | 11/2015 |
| WO | WO-2016/019063 | A1 | 2/2016 |
| WO | WO-2016/055601 | A1 | 4/2016 |
| WO | WO-2016/079181 | A1 | 5/2016 |
| WO | WO-2016/126995 | A1 | 8/2016 |
| WO | WO-2016/127002 | A1 | 8/2016 |
| WO | WO-2016/151523 | A1 | 9/2016 |
| WO | WO-2016/177655 | A1 | 11/2016 |
| WO | WO-2017/015175 | A1 | 1/2017 |
| WO | WO-2017/027350 | A2 | 2/2017 |
| WO | WO-2017/066712 | A2 | 4/2017 |
| WO | WO-2017/066712 | A9 | 4/2017 |
| WO | WO-2017/106370 | A1 | 6/2017 |
| WO | WO-2017/109679 | A1 | 6/2017 |
| WO | WO-2017/178656 | A1 | 10/2017 |
| WO | WO-2017/216390 | A1 | 12/2017 |
| WO | WO-2017/216391 | A1 | 12/2017 |
| WO | WO-2018/059718 | A1 | 4/2018 |
| WO | WO-2018/064593 | A1 | 4/2018 |
| WO | WO-2019/145543 | A1 | 8/2019 |
| WO | WO-2020/007892 | A1 | 1/2020 |

OTHER PUBLICATIONS

International Preliminary Report on Patentability for International Patent Application No. PCT/EP2019/067799, dated Jan. 5, 2021 (10 pages).

Andorfer et al., "Hyperphosphorylation and aggregation of tau in mice expressing normal human tau isoforms," J Neurochem. 86(3): 582-590 (2003) (9 pages).

Ansel et al., "Pharmaceutical Dosage Forms and Drug Delivery Systems," Williams & Wilkins, 6th Edition, pp. 105-116, 194-200; 1456-1457 (1995) (41 pages).

Bastin et al., "Salt Selection and Optimisation Procedures for Pharmaceutical New Chemical Entities," Organic Process Research & Development. 4:427-435 (2000) (9 pages).

Bergstrom D E, "Unnatural Nucleosides with Unusual Base Pairing Properties," Curr Protoc Nucleic Acid Chem. Chapter 1: Unit 1.4 (2009) (1 page).

Caruthers et al., "Chemical Synthesis of Deoxyoligonucleotides by the Phosphoramidite Method," Methods Enzymol. 154: 287-313 (1987) (27 pages).

Chambers et al., "Highly Efficient Neural Conversion of Human ES and IPS Cells by Dual Inhibition of SMAD Signaling," Nat Biotechnol. 27(3):275-280 (2009) (13 pages).

Collin et al., "Neuronal Uptake of Tau/Ps422 Antibody and Reduced Progression of Tau Pathology in a Mouse Model of Alzheimer's Disease," Brain. 137(Pt 10):2834-2846 (2014) (13 pages).

DeVos et al., "Antisense Reduction of Tau in Adult Mice Protects Against Seizures," J Neuroscience. 33(31):12887-12897 (2013) (11 pages).

Deleavey et al., "Designing Chemically Modified Oligonucleotides for Targeted Gene Silencing," Chem Biol. 19(8):937-954 (2012) (18 pages).

Fluiter et al., "Filling The Gap in LNA Antisense Oligo Gapmers: The Effects of Unlocked Nucleic Acid (UNA) and 4?-C-Hydroxymethyl-DNA Modifications on Rnase H Recruitment and Efficacy of an LNA Gapmer," Mol Biosyst. 5(8):838-843 (2009) (6 pages).

Freier et al., "The Ups and Downs of Nucleic Acid Duplex Stability: Structure-Stability Studies on Chemically-Modified DNA:RNA Duplexes," Nucleic Acid Res. 25(22):4429-4443 (1997) (15 pages).

Greene et al., "Protective Groups in Organic Synthesis," 3rd Ed., Wiley, N.Y. (1999) (6 pages).

Gong et al., "Multifactorial Hypothesis and Multi-targets for Alzheimer's Disease," J Alzheimers Dis. 64(s1); S107-S117 (2018) (11 pages).

DeVos et al., "Tau Reduction Prevents Neuronal Loss and Reverses Pathological Tau Deposition and Seeding in Mice with Tauopathy," Sci Transl Med. 9(374):eaag0481 (2017) (30 pages).

Grueninger et al., "Phosphorylation of Tau at S422 is Enhanced by Abeta in TauPS2APP Triple Transgenic Mice," Neurobiol Dis. 37(2):294-306 (2010) (13 pages).

Hansen et al., "Entropy titration. A Calorimetric Method for the Determination of ΔG° (K), ΔH° and ΔS°$^1$," Chemical Communications. 36-38, (1965) (3 pages).

Hirao et al., "Natural versus Artificial Creation of Base Pairs in DNA: Origin of Nucleobases from the Perspectives of Unnatural Base Pair Studies," Acc Chem Res. 45(12): 2055-2065 (2012) (11 pages).

(56) References Cited

OTHER PUBLICATIONS

Holdgate et al., "Measurements of Binding Thermodynamics in Drug Discovery," Drug Discov Today. 10(22):1543-1550 (2005) (8 pages).
Langer, "New Methods of Drug Delivery," Science. 249(4976):1527-1533 (1990) (7 pages).
Mangos et al., "Efficient RNase H-directed Cleavage of RNA Promoted by Antisense DNA or 2'F-ANA Constructs Containing Acyclic Nucleotide Inserts," J Am Chem Soc. 125(3):654-661 (2003) (8 pages).
Manoharan, "Oligonucleotide Conjugates as Potential Antisense Drugs with Improved Uptake, Biodistribution, Targeted Delivery, and Mechanism of Action," Antisense and Nucleic Acid Drug Dev. 12(2):103-128 (2004) (26 pages).
Mergny et al., "Analysis of Thermal Melting Curves," Oligonucleotides. 13(6):515-537 (2003) (23 pages).
Mitsuoka et al., "A Bridged Nucleic Acid, 2',4'-BNA COC: Synthesis of Fully Modified Oligonucleotides Bearing Thymine, 5-Methylcytosine, Adenine and Guanine 2',4'-BNA COC Monomers and RNA-selective Nucleic-Acid Recognition," Nucleic Acids Res. 37(4):1225-1238 (2009) (14 pages).
Morita et al., "2'-O,4'-C-Ethylene-Bridged Nucleic Acids (ENA): Highly Nuclease-Resistant and Thermodynamically Stable Oligonucleotides for Antisense Drug," Bioorg Med Chem Lett. 12(1): 73-76 (2002) (4 pages).
McTigue et al., "Sequence-Dependent Thermodynamic Parameters for Locked Nucleic Acid (LNA)-DNA Duplex Formation," Biochemistry. 43(18):5388-5405 (2004) (18 pages).
Polydoro et al., "Age-Dependent Impairment of Cognitive and Synaptic Function in the htau Mouse Model of Tau Pathology," J Neurosci. 29(34):10741-10749 (2009) (9 pages).
Gennaro et al., "Remington's Pharmaceutical Sciences," Mack Publishing Company. 17th ed., (1985) (9 pages).
Rukov et al., "Dissecting the Target Specificity of RNase H Recruiting Oligonucleotides Using Massively Parallel Reporter Analysis of Short RNA Motifs," Nucleic Acids Res. 43(17):8476-8487 (2015) (12 pages).
SantaLucia J Jr., "A Unified View of Polymer, Dumbbell, and Oligonucleotide DNA Nearest-neighbor Thermodynamics," Proc Natl Acad Sci U S A. 95(4):1460-1465 (1998) (6 pages).
Schoch et al., "Antisense Oligonucleotides: Translation from Mouse Models to Human Neurodegenerative Diseases," Neuron. 94(6): 1056-1070 (2017) (15 pages).
Seth et al., "Synthesis and Biophysical Evaluation of 2',4'-Constrained 2'O-Methoxyethyl and 2',4'-Constrained 2'O-Ethyl Nucleic Acid Analogues," J Org Chem. 75(5): 1569-1581 (2010) (7 pages).
Sud et al., "Antisense-mediated Exon Skipping Decreases Tau Protein Expression: A Potential Therapy for Tauopathies," Mol Ther Nucleic Acids. 3(7):180 1-11 (2014) (11 pages).
Sugimoto et al., "Thermodynamic Parameters to Predict Stability of RNA/DNA Hybrid Duplexes," Biochemistry. 34(35): 11211-11216 (1995) (6 pages).
Uhlmann, "Recent advances in the medicinal chemistry of antisense olignonucleotides," Curr Opin Drug Discov Devel. 3(2): 203-213 (2000) (11 pages).
Vester et al., "Chemically Modified Oligonucleotides with Efficient RNase H Response," Bioorg Med Chem Lett.18(7): 2296-2300 (2008) (5 pages).
Wan et al., "The Medicinal Chemistry of Therapeutic Oligonucleotides," J Med Chem. 59(21):9645-9667 (2016) (23 pages).
Bergstrom, "Unnatural Nucleosides with Unusual Base Pairing Properties," Curr Protoc Nucleic Acid Chem. Chapter 1(Unit 1.4):1. 4.1-1.4.32 (2009) (32 pages).
Manoharan, "Chapter 16: Oligonucleotide Conjugates in Antisense Technology." *Antisense Drug Technology: Principles, Strategies, and Applications*. Marcel Dekker, Inc., 391-469 (2001) (85 pages).
Invitation to Pay Additional Fees and, Where Applicable, Protest Fee for International Application No. PCT/EP2019/067799, mailed Oct. 25, 2019 (12 pages).

* cited by examiner

CMP ID NO: 9_103

CMP ID NO: 9_104

CMP ID NO: 11_1

CMP ID NO: 49_38

CMP ID NO: 49_189

OLIGONUCLEOTIDES FOR MODULATING TAU EXPRESSION

SEQUENCE LISTING

The instant application contains a Sequence Listing which has been submitted electronically in ASCII format and is hereby incorporated by reference in its entirety. Said ASCII copy, created on Dec. 23, 2020 is named 51551-004003_Sequence_Listing_12.23.20_ST25 and is 359,691 bytes in size.

FIELD OF INVENTION

The present invention relates to oligonucleotides (oligomers) that are complementary to microtubule-associated protein Tau (MAPT) transcript, leading to reduction of the expression of Tau. Reduction of MAPT transcripts and/or Tau protein expression is beneficial for a range of medical disorders, such as such as Tauopathies, Alzheimzer's disease, fronto-temporal dementia (FTD), FTDP-17, progressive supranuclear palsy (PSP), chronic traumatic encephalopathy (CTE), corticobasal ganglionic degeneration (CBD), epilepsy, Dravet syndrome, depression, seizure disorders and movement disorders.

BACKGROUND

Tau is a microtubule-associated protein (MAP) that interacts with tubulin and is involved in microtubule assembly and stabilization. Microtubules are critical structural components of the cellular cytoskeleton and are involved in various cellular processes, including mitosis, cytokinesis, and vesicular transport. Tau protein is present in multiple cell and tissue types, but is particularly abundant in neurons where it plays a critical role in regulating axonal transport and function.

Alterations in Tau expression levels and/or function contribute to the pathophysiology of various neurodegenerative disorders. For example, aggregates of misfolded and hyper-phosphorylated Tau are found in the neurofibrillary inclusions associated with Alzheimer's disease (AD) and related Tauopathies such as progressive supranuclear palsy (PSP), corticobasal ganglionic degeneration (CBD), chronic traumatic encephalopathy (CTE), fronto-temporal dementia FTD) and FTD with parkinsonism linked to chromosome 17 (FTDP-17), Pick's disease (PiD), argyrophilic grain disease (AGD), tangle-predominant senile dementia (TPSD), primary age-related Tauopathy (PART), Down syndrome and lytico-bodig disease. Upregulation of pathological Tau is associated with infantile Tauopathies including hemimegalencephaly (HME), tuberous sclerosis complex; focal cortical dysplasia type 2b; and ganglioglioma. In addition, abnormal Tau expression and/or function may also be associated with other diseases such as Hallervorden-Spatz syndrome, also known as neurodegeneration with brain iron accumulation type 1 (NBIA1), gangliocytomas, and subacute sclerosing panencephalitis. Tau may also play a role in seizure disorders (e.g., epilepsy), network dysfunction (e.g., depression), and movement disorders (e.g., Parkinson's disease).

Antisense molecules as well as siRNA molecules can reduce Tau protein levels by targeting MAPT pre-mRNA or mRNA transcripts have been described, see for example De Vos et al 2013 Journal of Neuroscience Vol 33 pp 12887, WO2013/148260, WO2014/153236, WO2015/010135, WO2016/126995, WO2016/151523, WO2017/09679 and WO2018/064593. Antisense oligonucleotides than can induce splice modulation of the MAPT transcript have also been described in Sud et al 2014 Mol Ther Nucl Acid 3 e180 and WO2016/019063.

Tau-associated disorders such as AD are the most common cause of dementia in the elderly, and robust and effective agents for the treatment of AD and related neurodegenerative diseases, including Tauopathies, seizure disorders, and movement disorders, are greatly needed.

OBJECTIVE OF THE INVENTION

The present invention provides antisense oligonucleotides which reduce Tau both in vivo and in vitro. The invention identified three specific target regions in the MAPT pre-mRNA located in intron 1 or 2 of the human MAPT pre-mRNA which may be targeted by antisense oligonucleotides to give effective Tau inhibition. In particular targeting position 12051 to 12111, 39562 to 39593 and or 72837 to 72940 of SEQ ID NO: 1 is advantageous in terms of reducing Tau. The invention also provides effective antisense oligonucleotide sequences and compounds which are capable of reducing Tau, and their use in treatment of diseases or disorders such as neurodegenerative diseases including Tauopathies, Alzheimer's disease, FTDP-17, seizure disorders and movement disorders.

SUMMARY OF INVENTION

The present invention relates to oligonucleotides targeting a Tau encoding nucleic acid which is capable of modulating the expression of Tau and the use of the oligonucleotide to treat or prevent diseases related to the functioning of the Tau.

Accordingly, in a first aspect the invention provides oligonucleotides 10 to 30 nucleotides in length which comprise a contiguous nucleotide sequence of at least 10 nucleotides in length with at least 90% complementarity to specific regions of MAPT represented by SEQ ID NO: 3, 4 and 5.

The oligonucleotide can be an antisense oligonucleotide, preferably with a gapmer design. Preferably, the oligonucleotide is capable of inhibiting the expression of Tau by cleavage of a target nucleic acid. The cleavage is preferably achieved via nuclease recruitment.

In a further aspect, the invention provides pharmaceutical compositions comprising the oligonucleotides of the invention and pharmaceutically acceptable diluents, carriers, salts and/or adjuvants.

In a further aspect, the invention provides methods for in vivo or in vitro method for modulation of Tau expression in a target cell which is expressing Tau, by administering an oligonucleotide or composition of the invention in an effective amount to said cell.

In a further aspect the invention provides methods for treating or preventing a disease, disorder or dysfunction associated with in vivo activity of Tau comprising administering a therapeutically or prophylactically effective amount of the oligonucleotide of the invention to a subject suffering from or susceptible to the disease, disorder or dysfunction.

In a further aspect the oligonucleotide or composition of the invention is used for the treatment or prevention of Alzheimer's disease (AD), progressive supranuclear palsy (PSP), fronto-temporal dementia (FTD) or FTDP-17.

Figure 1:
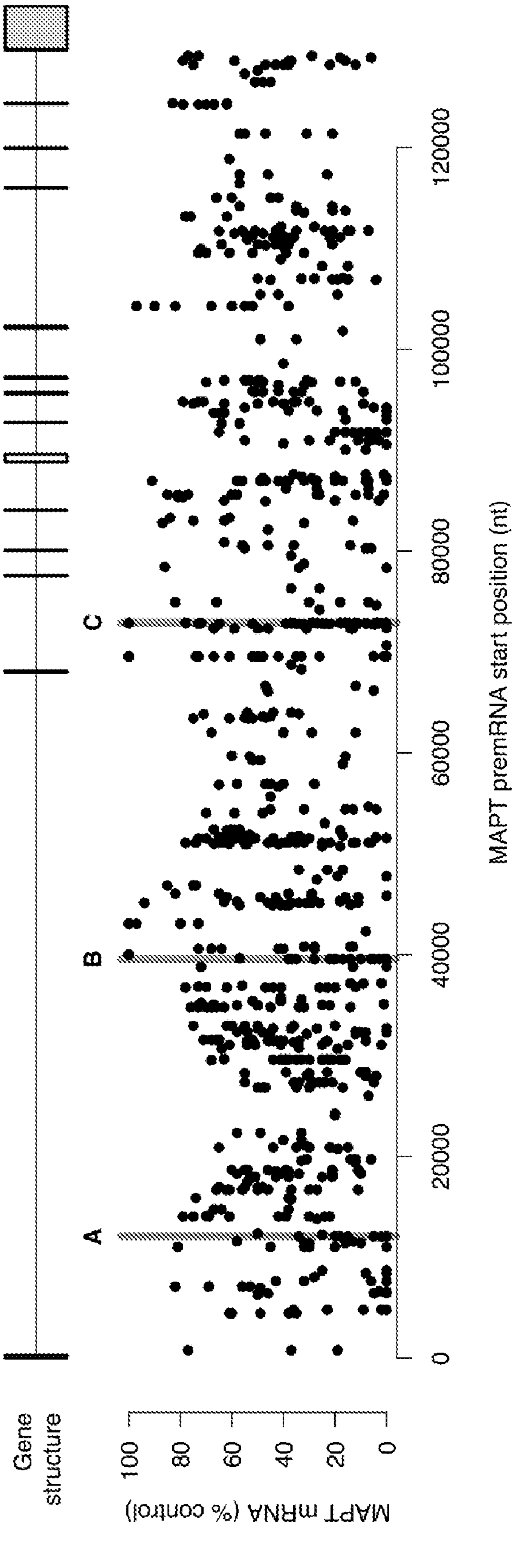
FIG. 1: Screening result from oligonucleotide library (example 1) covering all intron regions on MAPT. Each dot represents an oligonucleotide compound, the x-axis illustrates its position on the MAPT transcript and the y-axis shows the amount of MAPT mRNA remaining when compared to control (low number correspond to large reduction of MAPT). A, B and C indicate three regions on the MAPT transcript selected as target regions for further oligonucleotide compounds.

The compounds illustrated in FIGS. 2, 3, 4, 5 and 6 are shown in the protonated form—the S atom on the phosphorothioate linkage is protonated—it will be understood that the presence of the proton will depend on the acidity of the environment of the molecule, and the presence of an alternative cation (e.g. when the oligonucleotide is in salt form). Protonated phosphorothioates exist in tautomeric forms.

DEFINITIONS

Oligonucleotide

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification and isolation. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides, such as 2' sugar modified nucleosides.

Antisense Oligonucleotides

The term "Antisense oligonucleotide" as used herein is defined as oligonucleotides capable of modulating expression of a target gene by hybridizing to a target nucleic acid, in particular to a contiguous sequence on a target nucleic acid. The antisense oligonucleotides are not essentially double stranded and are therefore not siRNAs or shRNAs. Preferably, the antisense oligonucleotides of the present invention are single stranded. It is understood that single stranded oligonucleotides of the present invention can form hairpins or intermolecular duplex structures (duplex between two molecules of the same oligonucleotide), as long as the degree of intra or inter self-complementarity is less than 50% across of the full length of the oligonucleotide.

Advantageously, the single stranded antisense oligonucleotide of the invention does not contain RNA nucleosides, since this will decrease nuclease resistance.

Advantageously, the antisense oligonucleotide of the invention comprises one or more modified nucleosides or nucleotides, such as 2' sugar modified nucleosides. Furthermore, it is advantageous that the nucleosides which are not modified are DNA nucleosides.

Contiguous Nucleotide Sequence

The term "contiguous nucleotide sequence" refers to the region of the oligonucleotide which is complementary to the target nucleic acid or target sequence. The term is used interchangeably herein with the term "contiguous nucleobase sequence" and the term "oligonucleotide motif sequence". In some embodiments all the nucleotides of the oligonucleotide constitute the contiguous nucleotide sequence. In some embodiments the oligonucleotide comprises the contiguous nucleotide sequence, such as a F-G-F' gapmer region, and may optionally comprise further nucleotide(s), for example a nucleotide linker region which may be used to attach a functional group to the contiguous nucleotide sequence. The nucleotide linker region may or may not be complementary to the target nucleic acid. It is understood that the contiguous nucleotide sequence of the oligonucleotide cannot be longer than the oligonucleotide as such and that the oligonucleotide cannot be shorter than the contiguous nucleotide sequence.

Nucleotides

Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

Modified Nucleoside

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. In a preferred embodiment the modified nucleoside comprises a modified sugar moiety. The term modified nucleoside may also be used herein interchangeably with the term "nucleoside analogue" or modified "units" or modified "monomers". Nucleosides with an unmodified DNA or RNA sugar moiety are termed DNA or RNA nucleosides herein. Nucleosides with modifications in the base region of the DNA or RNA nucleoside are still generally termed DNA or RNA if they allow Watson Crick base pairing.

Modified Internucleoside Linkage

The term "modified internucleoside linkage" is defined as generally understood by the skilled person as linkages other than phosphodiester (PO) linkages, that covalently couples two nucleosides together. The oligonucleotides of the invention may therefore comprise modified internucleoside linkages. In some embodiments, the modified internucleoside linkage increases the nuclease resistance of the oligonucleotide compared to a phosphodiester linkage. For naturally occurring oligonucleotides, the internucleoside linkage includes phosphate groups creating a phosphodiester bond between adjacent nucleosides. Modified internucleoside linkages are particularly useful in stabilizing oligonucleotides for in vivo use, and may serve to protect against nuclease cleavage at regions of DNA or RNA nucleosides in the oligonucleotide of the invention, for example within the gap region G of a gapmer oligonucleotide, as well as in regions of modified nucleosides, such as region F and F'.

In an embodiment, the oligonucleotide comprises one or more internucleoside linkages modified from the natural phosphodiester, such as one or more modified internucleoside linkages that is for example more resistant to nuclease attack. Nuclease resistance may be determined by incubating the oligonucleotide in blood serum or by using a nuclease resistance assay (e.g. snake venom phosphodiesterase (SVPD)), both are well known in the art. Internucleoside linkages which are capable of enhancing the nuclease resistance of an oligonucleotide are referred to as nuclease resistant internucleoside linkages. In some embodiments at least 50% of the internucleoside linkages in the oligonucleotide, or contiguous nucleotide sequence thereof, are modified, such as at least 60%, such as at least 70%, such as at least 75%, such as at least 80% or such as at least 90% of the internucleoside linkages in the oligonucleotide, or contiguous nucleotide sequence thereof, are modified. In some embodiments all of the internucleoside linkages of the oligonucleotide, or contiguous nucleotide sequence thereof, are modified. It will be recognized that, in some embodiments the nucleosides which link the oligonucleotide of the invention to a non-nucleotide functional group, such as a conjugate, may be phosphodiester. In some embodiments all of the internucleoside linkages of the oligonucleotide, or contiguous nucleotide sequence thereof, are nuclease resistant internucleoside linkages.

Modified internucleoside linkages may be selected from the group comprising phosphorothioate, diphosphorothioate and boranophosphate. In some embodiments, the modified internucleoside linkages are compatible with the RNaseH recruitment of the oligonucleotide of the invention, for example phosphorothioate, diphosphorothioate or boranophosphate.

In some embodiments the internucleoside linkage comprises sulphur (S), such as a phosphorothioate internucleoside linkage.

With the oligonucleotides of the invention it is advantageous to use phosphorothioate internucleoside linkages.

Phosphorothioate internucleoside linkages are particularly useful due to nuclease resistance, beneficial pharmacokinetics and ease of manufacture. In some embodiments at least 50% of the internucleoside linkages in the oligonucleotide, or contiguous nucleotide sequence thereof, are phosphorothioate, such as at least 60%, such as at least 70%, such as at least 75%, such as at least 80% or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate.

In some embodiments, the oligonucleotide of the invention comprises both phosphorothioate internucleoside linkages and at least one phosphodiester linkage, such as 2, 3 or 4 phosphodiester linkages, in addition to the phosphorodithioate linkage(s). In a gapmer oligonucleotide, phosphodiester linkages, when present, are suitably not located between contiguous DNA nucleosides in the gap region G.

In some embodiments, the oligonucleotide comprises one or more neutral internucleoside linkage, particularly a internucleoside linkage selected from phosphotriester, methylphosphonate, MMI, amide-3, formacetal or thioformacetal.

Further internucleoside linkages are disclosed in WO2009/124238 (incorporated herein by reference). In an embodiment the internucleoside linkage is selected from linkers disclosed in WO2007/031091 (incorporated herein by reference). Particularly, the internucleoside linkage may be selected from —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR"—CO—O—, —NR$^H$—CO—NR$^H$—, and/or the internucleoside linker may be selected form the group consisting of: —O—CO—O—, —O—CO—NR"—, —NR$^H$—CO—CH$_2$—, —O—CH$_2$—CO—NR$^H$—, —O—CH$_2$—CH$_2$—NR$^H$—, —CO—NR$^H$—CH$_2$—, —CH$_2$—NR$^H$CO—, —O—CH$_2$—CH$_2$—S—, —S—CH$_2$—CH$_2$—O—, —S—CH$_2$—CH$_2$—S—, —CH$_2$—SO$_2$—CH$_2$—, —CH$_2$—CO—NR$^H$—, —O—CH$_2$—CH$_2$—NR$^H$—CO—, —CH$_2$—NCH$_3$—O—CH$_2$—, where R$^H$ is selected from hydrogen and C1-4-alkyl.

Nuclease resistant linkages, such as phosphorthioate linkages, are particularly useful in oligonucleotide regions capable of recruiting nuclease when forming a duplex with the target nucleic acid, such as region G for gapmers. Phosphorothioate linkages may, however, also be useful in non-nuclease recruiting regions and/or affinity enhancing regions such as regions F and F' for gapmers. Gapmer oligonucleotides may, in some embodiments comprise one or more phosphodiester linkages in region F or F', or both region F and F', where all the internucleoside linkages in region G may be phosphorothioate.

Advantageously, all the internucleoside linkages of the contiguous nucleotide sequence of the oligonucleotide are phosphorothioate, or all the internucleoside linkages of the oligonucleotide are phosphorothioate linkages.

Nucleobase

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

In some embodiments the nucleobase moiety is modified by changing the purine or pyrimidine into a modified purine or pyrimidine, such as substituted purine or substituted pyrimidine, such as a nucleobase selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

Modified Oligonucleotide

The term modified oligonucleotide describes an oligonucleotide comprising one or more sugar-modified nucleosides and/or modified internucleoside linkages. The term chimeric" oligonucleotide is a term that has been used in the literature to describe oligonucleotides with modified nucleosides.

Complementarity

The term "complementarity" describes the capacity for Watson-Crick base-pairing of nucleosides/nucleotides. Watson-Crick base pairs are guanine (G)-cytosine (C) and adenine (A)-thymine (T)/uracil (U). It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol 45 page 2055 and Bergstrom (2009) Current Protocols in Nucleic Acid Chemistry Suppl. 37 1.4.1).

The term "% complementary" as used herein, refers to the proportion of nucleotides (in percent) of a contiguous nucleotide sequence in a nucleic acid molecule (e.g. oligonucleotide) which across the contiguous nucleotide sequence, are complementary to a reference sequence (e.g. a target sequence or sequence motif). The percentage of complementarity is thus calculated by counting the number of aligned nucleobases that are complementary (from Watson Crick base pair) between the two sequences (when aligned with the target sequence 5'-3' and the oligonucleotide sequence from 3'-5'), dividing that number by the total number of nucleotides in the oligonucleotide and multiplying by 100. In such a comparison a nucleobase/nucleotide which does not align (form a base pair) is termed a mismatch. Insertions and deletions are not allowed in the calculation of % complementarity of a contiguous nucleotide sequence. It will be understood that in determining complementarity, chemical modifications of the nucleobases are disregarded as long as the functional capacity of the nucleobase to form Watson Crick base pairing is retained (e.g. 5'-methyl cytosine is considered identical to a cytosine for the purpose of calculating % identity).

The term "fully complementary", refers to 100% complementarity.

The following is an example of an oligonucleotide that is fully complementary to the target nucleic acid.

The following is an example of an oligonucleotide (SEQ ID NO: 49) that is fully complementary to the target nucleic acid (SEQ ID NO: 4).

```
                                   (SEQ ID NO: 4)
5' gaaggttgaaatgagaattgatttgagttaaa 3'

                                  (SEQ ID NO: 49)
3' actcttaactaaactcaatt 5'
```

Identity

The term "Identity" as used herein, refers to the proportion of nucleotides (expressed in percent) of a contiguous nucleotide sequence in a nucleic acid molecule (e.g. oligonucleotide) which across the contiguous nucleotide sequence, are identical to a reference sequence (e.g. a sequence motif). The percentage of identity is thus calculated by counting the number of aligned nucleobases that are identical (a Match) between two sequences (in the contiguous nucleotide sequence of the compound of the invention and in the reference sequence), dividing that number by the total number of nucleotides in the oligonucleotide and multiplying by 100. Therefore, Percentage of Identity=(Matches×100)/Length of aligned region (e.g. the contiguous nucleotide sequence). Insertions and deletions are not allowed in the calculation the percentage of identity of a contiguous nucleotide sequence. It will be understood that in determining identity, chemical modifications of the nucleobases are disregarded as long as the functional capacity of the nucleobase to form Watson Crick base pairing is retained (e.g. 5-methyl cytosine is considered identical to a cytosine for the purpose of calculating % identity).

Hybridization

The term "hybridizing" or "hybridizes" as used herein is to be understood as two nucleic acid strands (e.g. an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, *Oligonucleotides* 13:515-537). The standard state Gibbs free energy ΔG° is a more accurate representation of binding affinity and is related to the dissociation constant ($K_d$) of the reaction by $\Delta G° = -RT \ln(K_d)$, where R is the gas constant and T is the absolute temperature. Therefore, a very low ΔG° of the reaction between an oligonucleotide and the target nucleic acid reflects a strong hybridization between the oligonucleotide and target nucleic acid. ΔG° is the energy associated with a reaction where aqueous concentrations are 1 M, the pH is 7, and the temperature is 37° C. The hybridization of oligonucleotides to a target nucleic acid is a spontaneous reaction and for spontaneous reactions ΔG° is less than zero. ΔG° can be measured experimentally, for example, by use of the isothermal titration calorimetry (ITC) method as described in Hansen et al., 1965, *Chem. Comm.* 36-38 and Hoidgate et al., 2005, *Drug Discov Today*. The skilled person will know that commercial equipment is available for ΔG° measurements. ΔG° can also be estimated numerically by using the nearest neighbor model as described by SantaLucia, 1998, *Proc Natl Acad Sci USA*. 95: 1460-1465 using appropriately derived thermodynamic parameters described by Sugimoto et al., 1995, *Biochemistry* 34:11211-11216 and McTigue et al., 2004, *Biochemistry* 43:5388-5405. In order to have the possibility of modulating its intended nucleic acid target by hybridization, oligonucleotides of the present invention hybridize to a target nucleic acid with estimated ΔG° values below −10 kcal for oligonucleotides that are 10-30 nucleotides in length. In some embodiments the degree or strength of hybridization is measured by the standard state Gibbs free energy ΔG°. The oligonucleotides may hybridize to a target nucleic acid with estimated ΔG° values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated ΔG° value of −10 to −60 kcal, such as −12 to −40, such as from −15 to −30 kcal or −16 to −27 kcal such as −18 to −25 kcal.

Target Nucleic Acid

According to the present invention, the target nucleic acid is a nucleic acid which encodes mammalian Tau and may for example be a gene, a RNA, a mRNA, and pre-mRNA, a mature mRNA or a cDNA sequence. The target may therefore be referred to as a Tau target nucleic acid or MAPT target nucleic acid, these terms can be used interchangeably. The oligonucleotide of the invention may for example target exon regions of a mammalian MAPT, or may for example target intron region in the MAPT pre-mRNA (see Table 1).

TABLE 1

| human MAPT Exons and Introns | | | | | |
|---|---|---|---|---|---|
| Exonic regions in the human Tau premRNA (SEQ ID NO 2) | | | Intronic regions in the human Tau premRNA (SEQ ID NO 2) | | |
| ID | start | end | ID | start | end |
| e1 | 1 | 303 | i1 | 304 | 67979 |
| e2 | 67980 | 68129 | i2 | 68130 | 77517 |
| e3 | 77518 | 77604 | i3 | 77605 | 80043 |
| e4 | 80044 | 80130 | i4 | 80131 | 84033 |
| e5 | 84034 | 84099 | i5 | 84100 | 88837 |
| e6 | 88838 | 89590 | i6 | 89591 | 92699 |
| e7 | 92700 | 92755 | i7 | 92756 | 95537 |
| e8 | 95538 | 95735 | i8 | 95736 | 97119 |
| e9 | 97120 | 97246 | i8 | 97247 | 102058 |
| e10 | 102059 | 102324 | i9 | 102325 | 115969 |
| e11 | 115970 | 116062 | i10 | 116063 | 119902 |
| e12 | 119903 | 119984 | i11 | 119985 | 124287 |
| e13 | 124288 | 124400 | i12 | 124401 | 129623 |
| e14 | 129624 | 134004 | | | |

Suitably, the target nucleic acid encodes a Tau protein, in particular mammalian Tau, such as human Tau (See for example tables 2 and 3) which provides pre-mRNA sequences for human, and monkey Tau).

In some embodiments, the target nucleic acid is selected from the group consisting of SEQ ID NO: 1 and 2 or naturally occurring variants thereof (e.g. sequences encoding a mammalian Tau protein. If employing the oligonucleotide of the invention in research or diagnostics the target nucleic acid may be a cDNA or a synthetic nucleic acid derived from DNA or RNA.

For in vivo or in vitro application, the oligonucleotide of the invention is typically capable of inhibiting the expression of the Tau protein in a cell which is expressing the MAPT target nucleic acid. The contiguous sequence of nucleobases of the oligonucleotide of the invention is typically complementary to the MAPT target nucleic acid, as measured across the length of the oligonucleotide, optionally with the exception of one or two mismatches, and optionally excluding nucleotide based linker regions which may link the oligonucleotide to an optional functional group such as a conjugate, or other non-complementary terminal nucleotides (e.g. region D' or D"). The target nucleic acid may, in some embodiments, be a RNA or DNA, such as a messenger RNA, such as a mature mRNA or a pre-mRNA.

In some embodiments the target nucleic acid is a RNA or DNA which encodes mammalian Tau protein, such as human Tau, e.g. the human MAPTpre-mRNA sequence, such as that disclosed as SEQ ID NO 1. Further information on exemplary target nucleic acids is provided in tables 2 and 3.

TABLE 2

| Genome and assembly information for Tau across species. | | | | | | |
|---|---|---|---|---|---|---|
| | | | Genomic coordinates | | | NCBI reference sequence* accession |
| Species | Chr. | Strand | Start | End | Assembly | number for mRNA |
| Human | 17 | fwd | 45894382 | 46028334 | GRCh38.p12 | NG_007398.1 |
| Cynomolgus monkey | 16 | fwd | 58257786 | 58390183 | Macaca_ fascicularis _ 5.0 | From 58257786 to 58390183 in NC_022287.1 |

Fwd = forward strand.

The genome coordinates provide the pre-mRNA sequence (genomic sequence).

The NCBI reference provides the mRNA sequence (cDNA sequence).

*The National Center for Biotechnology Information reference sequence database is a comprehensive, integrated, non-redundant, well-annotated set of reference sequences including genomic, transcript, and protein. It is hosted at www.ncbi.nlm.nih.gov/refseq.

TABLE 3

| Sequence details for Tau/MAPT across species. | | | |
|---|---|---|---|
| Species | RNA type | Length (nt) | SEQ ID NO |
| Human | prem RNA | 134004 | 1 |
| Monkey | prem RNA | 132218 | 2 |

Target Sequence

The term "target sequence" as used herein refers to a sequence of nucleotides present in the target nucleic acid which comprises the nucleobase sequence which is complementary to the oligonucleotide of the invention. In some embodiments, the target sequence consists of a region on the target nucleic acid with a nucleobase sequence that is complementary to the contiguous nucleotide sequence of the oligonucleotide of the invention. This region of the target nucleic acid may interchangeably be referred to as the target nucleotide sequence, target sequence or target region. In some embodiments the target sequence is longer than the complementary sequence of a single oligonucleotide, and may, for example represent a preferred region of the target nucleic acid which may be targeted by several oligonucleotides of the invention.

In some embodiments the target sequence is a sequence selected from any region in table 4 (R_1-R_2254). In particular, the target sequence may be selected from one of the region within the group of regions consisting of R_223, R_738 or R_1298.

TABLE 4

Regions (reg.) on SEQ ID NO: 1 which may be targeted using an oligonucleotide of the invention

| Reg. | length (nt) | Position on SEQ ID NO: 1 start | Position on SEQ ID NO: 1 end | Reg. | length (nt) | Position on SEQ ID NO: 1 start | Position on SEQ ID NO: 1 end | Reg. | length (nt) | Position on SEQ ID NO: 1 start | Position on SEQ ID NO: 1 end |
|---|---|---|---|---|---|---|---|---|---|---|---|
| R_1 | 32 | 4 | 35 | R_752 | 23 | 40118 | 40140 | R_1503 | 88 | 85545 | 85632 |
| R_2 | 32 | 37 | 68 | R_753 | 40 | 40209 | 40248 | R_1504 | 20 | 85662 | 85681 |
| R_3 | 32 | 70 | 101 | R_754 | 24 | 40273 | 40296 | R_1505 | 75 | 85710 | 85784 |
| R_4 | 25 | 103 | 127 | R_755 | 63 | 40301 | 40363 | R_1506 | 35 | 85786 | 85820 |
| R_5 | 187 | 156 | 342 | R_756 | 35 | 40461 | 40495 | R_1507 | 24 | 85822 | 85845 |
| R_6 | 33 | 344 | 376 | R_757 | 27 | 40497 | 40523 | R_1508 | 24 | 85864 | 85887 |
| R_7 | 37 | 385 | 421 | R_758 | 33 | 40547 | 40579 | R_1509 | 20 | 85879 | 85898 |
| R_8 | 47 | 440 | 486 | R_759 | 42 | 40587 | 40628 | R_1510 | 41 | 85889 | 85929 |
| R_9 | 22 | 488 | 509 | R_760 | 41 | 40630 | 40670 | R_1511 | 25 | 85964 | 85988 |
| R_10 | 38 | 511 | 548 | R_761 | 34 | 40697 | 40730 | R_1512 | 23 | 85994 | 86016 |
| R_11 | 63 | 580 | 642 | R_762 | 57 | 40772 | 40828 | R_1513 | 56 | 86064 | 86119 |
| R_12 | 20 | 649 | 668 | R_763 | 36 | 40831 | 40866 | R_1514 | 71 | 86189 | 86259 |
| R_13 | 32 | 710 | 741 | R_764 | 60 | 40868 | 40927 | R_1515 | 32 | 86266 | 86297 |
| R_14 | 37 | 743 | 779 | R_765 | 28 | 40941 | 40968 | R_1516 | 54 | 86319 | 86372 |
| R_15 | 27 | 792 | 818 | R_766 | 29 | 40971 | 40999 | R_1517 | 38 | 86383 | 86420 |
| R_16 | 23 | 814 | 836 | R_767 | 96 | 41031 | 41126 | R_1518 | 31 | 86427 | 86457 |
| R_17 | 115 | 839 | 953 | R_768 | 43 | 41128 | 41170 | R_1519 | 33 | 86478 | 86510 |
| R_18 | 25 | 955 | 979 | R_769 | 22 | 41218 | 41239 | R_1520 | 36 | 86676 | 86711 |
| R_19 | 80 | 981 | 1060 | R_770 | 28 | 41266 | 41293 | R_1521 | 20 | 86715 | 86734 |
| R_20 | 23 | 1071 | 1093 | R_771 | 25 | 41311 | 41335 | R_1522 | 20 | 86742 | 86761 |
| R_21 | 26 | 1095 | 1120 | R_772 | 50 | 41356 | 41405 | R_1523 | 29 | 86809 | 86837 |
| R_22 | 32 | 1177 | 1208 | R_773 | 55 | 41425 | 41479 | R_1524 | 51 | 86873 | 86923 |
| R_23 | 78 | 1239 | 1316 | R_774 | 23 | 41483 | 41505 | R_1525 | 48 | 86939 | 86986 |
| R_24 | 34 | 1334 | 1367 | R_775 | 47 | 41518 | 41564 | R_1526 | 21 | 86989 | 87009 |
| R_25 | 68 | 1401 | 1468 | R_776 | 36 | 41586 | 41621 | R_1527 | 46 | 87080 | 87125 |
| R_26 | 82 | 1470 | 1551 | R_777 | 77 | 41641 | 41717 | R_1528 | 23 | 87140 | 87162 |
| R_27 | 95 | 1566 | 1660 | R_778 | 48 | 41762 | 41809 | R_1529 | 24 | 87164 | 87187 |
| R_28 | 43 | 1708 | 1750 | R_779 | 42 | 41830 | 41871 | R_1530 | 45 | 87209 | 87253 |
| R_29 | 71 | 1762 | 1832 | R_780 | 57 | 41888 | 41944 | R_1531 | 21 | 87261 | 87281 |
| R_30 | 37 | 1841 | 1877 | R_781 | 25 | 41964 | 41988 | R_1532 | 37 | 87297 | 87333 |
| R_31 | 26 | 1878 | 1903 | R_782 | 30 | 42005 | 42034 | R_1533 | 61 | 87367 | 87427 |
| R_32 | 21 | 1960 | 1980 | R_783 | 31 | 42096 | 42126 | R_1534 | 69 | 87595 | 87663 |
| R_33 | 20 | 1982 | 2001 | R_784 | 30 | 42141 | 42170 | R_1535 | 29 | 87665 | 87693 |
| R_34 | 27 | 2018 | 2044 | R_785 | 32 | 42172 | 42203 | R_1536 | 20 | 87679 | 87698 |
| R_35 | 22 | 2061 | 2082 | R_786 | 56 | 42279 | 42334 | R_1537 | 20 | 87760 | 87779 |
| R_36 | 24 | 2196 | 2219 | R_787 | 63 | 42336 | 42398 | R_1538 | 21 | 87915 | 87935 |
| R_37 | 30 | 2237 | 2266 | R_788 | 44 | 42439 | 42482 | R_1539 | 21 | 87952 | 87972 |
| R_38 | 27 | 2334 | 2360 | R_789 | 29 | 42486 | 42514 | R_1540 | 20 | 87962 | 87981 |
| R_39 | 22 | 2362 | 2383 | R_790 | 30 | 42518 | 42547 | R_1541 | 47 | 88017 | 88063 |
| R_40 | 22 | 2419 | 2440 | R_791 | 24 | 42581 | 42604 | R_1542 | 32 | 88099 | 88130 |
| R_41 | 31 | 2472 | 2502 | R_792 | 32 | 42631 | 42662 | R_1543 | 33 | 88133 | 88165 |
| R_42 | 21 | 2506 | 2526 | R_793 | 24 | 42681 | 42704 | R_1544 | 22 | 88176 | 88197 |
| R_43 | 21 | 2541 | 2561 | R_794 | 21 | 42712 | 42732 | R_1545 | 36 | 88216 | 88251 |
| R_44 | 31 | 2565 | 2595 | R_795 | 49 | 42745 | 42793 | R_1546 | 35 | 88279 | 88313 |
| R_45 | 21 | 2598 | 2618 | R_796 | 35 | 42841 | 42875 | R_1547 | 30 | 88353 | 88382 |
| R_46 | 28 | 2725 | 2752 | R_797 | 45 | 42877 | 42921 | R_1548 | 38 | 88384 | 88421 |
| R_47 | 38 | 2769 | 2806 | R_798 | 22 | 42937 | 42958 | R_1549 | 37 | 88439 | 88475 |
| R_48 | 59 | 2915 | 2973 | R_799 | 20 | 42969 | 42988 | R_1550 | 54 | 88493 | 88546 |
| R_49 | 50 | 2978 | 3027 | R_800 | 45 | 42976 | 43020 | R_1551 | 29 | 88561 | 88589 |
| R_50 | 21 | 3035 | 3055 | R_801 | 20 | 43035 | 43054 | R_1552 | 21 | 88594 | 88614 |
| R_51 | 24 | 3072 | 3095 | R_802 | 72 | 43047 | 43118 | R_1553 | 23 | 88617 | 88639 |
| R_52 | 22 | 3171 | 3192 | R_803 | 23 | 43136 | 43158 | R_1554 | 24 | 88648 | 88671 |
| R_53 | 28 | 3207 | 3234 | R_804 | 56 | 43188 | 43243 | R_1555 | 30 | 88678 | 88707 |
| R_54 | 25 | 3236 | 3260 | R_805 | 20 | 43239 | 43258 | R_1556 | 27 | 88715 | 88741 |
| R_55 | 33 | 3262 | 3294 | R_806 | 20 | 43279 | 43298 | R_1557 | 24 | 88774 | 88797 |
| R_56 | 58 | 3302 | 3359 | R_807 | 27 | 43304 | 43330 | R_1558 | 48 | 88820 | 88867 |
| R_57 | 21 | 3364 | 3384 | R_808 | 30 | 43346 | 43375 | R_1559 | 35 | 88877 | 88911 |
| R_58 | 36 | 3417 | 3452 | R_809 | 64 | 43408 | 43471 | R_1560 | 52 | 88919 | 88970 |
| R_59 | 56 | 3476 | 3531 | R_810 | 52 | 43481 | 43532 | R_1561 | 26 | 88978 | 89003 |
| R_60 | 20 | 3533 | 3552 | R_811 | 22 | 43538 | 43559 | R_1562 | 32 | 89011 | 89042 |
| R_61 | 20 | 3554 | 3573 | R_812 | 29 | 43561 | 43589 | R_1563 | 26 | 89044 | 89069 |
| R_62 | 22 | 3648 | 3669 | R_813 | 37 | 43593 | 43629 | R_1564 | 51 | 89100 | 89150 |
| R_63 | 21 | 3681 | 3701 | R_814 | 24 | 43637 | 43660 | R_1565 | 34 | 89196 | 89229 |
| R_64 | 20 | 3756 | 3775 | R_815 | 21 | 43697 | 43717 | R_1566 | 28 | 89231 | 89258 |
| R_65 | 24 | 3808 | 3831 | R_816 | 21 | 43719 | 43739 | R_1567 | 24 | 89261 | 89284 |
| R_66 | 35 | 3833 | 3867 | R_817 | 34 | 43772 | 43805 | R_1568 | 24 | 89286 | 89309 |
| R_67 | 46 | 3869 | 3914 | R_818 | 21 | 43818 | 43838 | R_1569 | 42 | 89374 | 89415 |
| R_68 | 27 | 3916 | 3942 | R_819 | 72 | 43916 | 43987 | R_1570 | 24 | 89430 | 89453 |
| R_69 | 21 | 3956 | 3976 | R_820 | 23 | 44002 | 44024 | R_1571 | 48 | 89466 | 89513 |
| R_70 | 41 | 4009 | 4049 | R_821 | 26 | 44041 | 44066 | R_1572 | 31 | 89528 | 89558 |
| R_71 | 29 | 4069 | 4097 | R_822 | 43 | 44103 | 44145 | R_1573 | 46 | 89563 | 89608 |
| R_72 | 37 | 4117 | 4153 | R_823 | 44 | 44167 | 44210 | R_1574 | 24 | 89610 | 89633 |

TABLE 4-continued

Regions (reg.) on SEQ ID NO: 1 which may be targeted using an oligonucleotide of the invention

| Reg. | length (nt) | Position on SEQ ID NO: 1 start | end | Reg. | length (nt) | Position on SEQ ID NO: 1 start | end | Reg. | length (nt) | Position on SEQ ID NO: 1 start | end |
|---|---|---|---|---|---|---|---|---|---|---|---|
| R_73 | 23 | 4160 | 4182 | R_824 | 73 | 44216 | 44288 | R_1575 | 28 | 89725 | 89752 |
| R_74 | 38 | 4191 | 4228 | R_825 | 23 | 44284 | 44306 | R_1576 | 25 | 89754 | 89778 |
| R_75 | 24 | 4263 | 4286 | R_826 | 38 | 44298 | 44335 | R_1577 | 21 | 89780 | 89800 |
| R_76 | 75 | 4288 | 4362 | R_827 | 56 | 44380 | 44435 | R_1578 | 27 | 89802 | 89828 |
| R_77 | 40 | 4388 | 4427 | R_828 | 20 | 44449 | 44468 | R_1579 | 38 | 89833 | 89870 |
| R_78 | 46 | 4429 | 4474 | R_829 | 50 | 44463 | 44512 | R_1580 | 23 | 89882 | 89904 |
| R_79 | 44 | 4525 | 4568 | R_830 | 21 | 44530 | 44550 | R_1581 | 20 | 89961 | 89980 |
| R_80 | 28 | 4600 | 4627 | R_831 | 25 | 44543 | 44567 | R_1582 | 35 | 89982 | 90016 |
| R_81 | 38 | 4646 | 4683 | R_832 | 38 | 44552 | 44589 | R_1583 | 44 | 90049 | 90092 |
| R_82 | 26 | 4696 | 4721 | R_833 | 28 | 44610 | 44637 | R_1584 | 27 | 90129 | 90155 |
| R_83 | 32 | 4732 | 4763 | R_834 | 25 | 44629 | 44653 | R_1585 | 21 | 90264 | 90284 |
| R_84 | 35 | 4787 | 4821 | R_835 | 45 | 44651 | 44695 | R_1586 | 35 | 90287 | 90321 |
| R_85 | 20 | 4837 | 4856 | R_836 | 28 | 44763 | 44790 | R_1587 | 40 | 90444 | 90483 |
| R_86 | 36 | 4900 | 4935 | R_837 | 21 | 44820 | 44840 | R_1588 | 73 | 90558 | 90630 |
| R_87 | 27 | 5033 | 5059 | R_838 | 32 | 44857 | 44888 | R_1589 | 20 | 90632 | 90651 |
| R_88 | 28 | 5066 | 5093 | R_839 | 47 | 44888 | 44934 | R_1590 | 28 | 90702 | 90729 |
| R_89 | 46 | 5098 | 5143 | R_840 | 20 | 44994 | 45013 | R_1591 | 35 | 90771 | 90805 |
| R_90 | 24 | 5145 | 5168 | R_841 | 21 | 45032 | 45052 | R_1592 | 27 | 90794 | 90820 |
| R_91 | 20 | 5184 | 5203 | R_842 | 23 | 45054 | 45076 | R_1593 | 24 | 90814 | 90837 |
| R_92 | 40 | 5205 | 5244 | R_843 | 22 | 45078 | 45099 | R_1594 | 30 | 90827 | 90856 |
| R_93 | 28 | 5246 | 5273 | R_844 | 38 | 45129 | 45166 | R_1595 | 21 | 90839 | 90859 |
| R_94 | 20 | 5329 | 5348 | R_845 | 21 | 45203 | 45223 | R_1596 | 21 | 90876 | 90896 |
| R_95 | 58 | 5366 | 5423 | R_846 | 66 | 45238 | 45303 | R_1597 | 26 | 90901 | 90926 |
| R_96 | 41 | 5425 | 5465 | R_847 | 33 | 45304 | 45336 | R_1598 | 29 | 90972 | 91000 |
| R_97 | 58 | 5524 | 5581 | R_848 | 37 | 45338 | 45374 | R_1599 | 24 | 91032 | 91055 |
| R_98 | 20 | 5583 | 5602 | R_849 | 35 | 45391 | 45425 | R_1600 | 42 | 91057 | 91098 |
| R_99 | 30 | 5635 | 5664 | R_850 | 24 | 45526 | 45549 | R_1601 | 30 | 91135 | 91164 |
| R_100 | 51 | 5694 | 5744 | R_851 | 25 | 45551 | 45575 | R_1602 | 25 | 91189 | 91213 |
| R_101 | 42 | 5775 | 5816 | R_852 | 27 | 45673 | 45699 | R_1603 | 26 | 91247 | 91272 |
| R_102 | 53 | 5838 | 5890 | R_853 | 69 | 45708 | 45776 | R_1604 | 21 | 91274 | 91294 |
| R_103 | 32 | 5892 | 5923 | R_854 | 48 | 45821 | 45868 | R_1605 | 29 | 91296 | 91324 |
| R_104 | 53 | 5925 | 5977 | R_855 | 37 | 45907 | 45943 | R_1606 | 20 | 91396 | 91415 |
| R_105 | 28 | 6001 | 6028 | R_856 | 42 | 45987 | 46028 | R_1607 | 31 | 91471 | 91501 |
| R_106 | 21 | 6039 | 6059 | R_857 | 37 | 46043 | 46079 | R_1608 | 71 | 91521 | 91591 |
| R_107 | 64 | 6106 | 6169 | R_858 | 36 | 46104 | 46139 | R_1609 | 48 | 91667 | 91714 |
| R_108 | 65 | 6176 | 6240 | R_859 | 30 | 46146 | 46175 | R_1610 | 23 | 91755 | 91777 |
| R_109 | 35 | 6242 | 6276 | R_860 | 25 | 46178 | 46202 | R_1611 | 29 | 91788 | 91816 |
| R_110 | 29 | 6276 | 6304 | R_861 | 21 | 46261 | 46281 | R_1612 | 32 | 91858 | 91889 |
| R_111 | 38 | 6306 | 6343 | R_862 | 50 | 46304 | 46353 | R_1613 | 28 | 91915 | 91942 |
| R_112 | 22 | 6374 | 6395 | R_863 | 40 | 46373 | 46412 | R_1614 | 35 | 91965 | 91999 |
| R_113 | 22 | 6422 | 6443 | R_864 | 29 | 46435 | 46463 | R_1615 | 29 | 92052 | 92080 |
| R_114 | 28 | 6464 | 6491 | R_865 | 27 | 46465 | 46491 | R_1616 | 20 | 92131 | 92150 |
| R_115 | 23 | 6524 | 6546 | R_866 | 36 | 46522 | 46557 | R_1617 | 20 | 92152 | 92171 |
| R_116 | 23 | 6574 | 6596 | R_867 | 37 | 46590 | 46626 | R_1618 | 32 | 92181 | 92212 |
| R_117 | 54 | 6615 | 6668 | R_868 | 22 | 46663 | 46684 | R_1619 | 43 | 92227 | 92269 |
| R_118 | 28 | 6725 | 6752 | R_869 | 60 | 46686 | 46745 | R_1620 | 29 | 92271 | 92299 |
| R_119 | 49 | 6738 | 6786 | R_870 | 34 | 46811 | 46844 | R_1621 | 98 | 92306 | 92403 |
| R_120 | 25 | 6788 | 6812 | R_871 | 28 | 46845 | 46872 | R_1622 | 22 | 92420 | 92441 |
| R_121 | 59 | 6819 | 6877 | R_872 | 85 | 46896 | 46980 | R_1623 | 31 | 92463 | 92493 |
| R_122 | 22 | 6908 | 6929 | R_873 | 23 | 47027 | 47049 | R_1624 | 23 | 92495 | 92517 |
| R_123 | 26 | 6931 | 6956 | R_874 | 69 | 47051 | 47119 | R_1625 | 27 | 92574 | 92600 |
| R_124 | 24 | 6958 | 6981 | R_875 | 62 | 47178 | 47239 | R_1626 | 134 | 92643 | 92776 |
| R_125 | 35 | 6984 | 7018 | R_876 | 42 | 47430 | 47471 | R_1627 | 57 | 92793 | 92849 |
| R_126 | 32 | 7020 | 7051 | R_877 | 20 | 47473 | 47492 | R_1628 | 43 | 92866 | 92908 |
| R_127 | 23 | 7097 | 7119 | R_878 | 38 | 47519 | 47556 | R_1629 | 45 | 92910 | 92954 |
| R_128 | 83 | 7121 | 7203 | R_879 | 33 | 47605 | 47637 | R_1630 | 26 | 92956 | 92981 |
| R_129 | 21 | 7205 | 7225 | R_880 | 34 | 47652 | 47685 | R_1631 | 23 | 92983 | 93005 |
| R_130 | 32 | 7242 | 7273 | R_881 | 33 | 47699 | 47731 | R_1632 | 46 | 93007 | 93052 |
| R_131 | 20 | 7289 | 7308 | R_882 | 29 | 47733 | 47761 | R_1633 | 30 | 93022 | 93051 |
| R_132 | 21 | 7376 | 7396 | R_883 | 36 | 47769 | 47804 | R_1634 | 22 | 93094 | 93115 |
| R_133 | 20 | 7397 | 7416 | R_884 | 22 | 47806 | 47827 | R_1635 | 21 | 93117 | 93137 |
| R_134 | 23 | 7439 | 7461 | R_885 | 28 | 47848 | 47875 | R_1636 | 39 | 93139 | 93177 |
| R_135 | 23 | 7463 | 7485 | R_886 | 31 | 47999 | 48029 | R_1637 | 117 | 93214 | 93330 |
| R_136 | 28 | 7492 | 7519 | R_887 | 36 | 48043 | 48078 | R_1638 | 37 | 93359 | 93395 |
| R_137 | 26 | 7569 | 7594 | R_888 | 37 | 48080 | 48116 | R_1639 | 46 | 93409 | 93454 |
| R_138 | 38 | 7622 | 7659 | R_889 | 42 | 48118 | 48159 | R_1640 | 32 | 93508 | 93539 |
| R_139 | 25 | 7705 | 7729 | R_890 | 78 | 48195 | 48272 | R_1641 | 28 | 93541 | 93568 |
| R_140 | 20 | 7705 | 7724 | R_891 | 70 | 48294 | 48363 | R_1642 | 33 | 93570 | 93602 |
| R_141 | 28 | 7774 | 7801 | R_892 | 28 | 48377 | 48404 | R_1643 | 22 | 93647 | 93668 |
| R_142 | 20 | 7855 | 7874 | R_893 | 20 | 48406 | 48425 | R_1644 | 26 | 93674 | 93699 |
| R_143 | 23 | 7885 | 7907 | R_894 | 22 | 48438 | 48459 | R_1645 | 28 | 93716 | 93743 |
| R_144 | 35 | 7933 | 7967 | R_895 | 20 | 48485 | 48504 | R_1646 | 72 | 93770 | 93841 |

TABLE 4-continued

Regions (reg.) on SEQ ID NO: 1 which may be targeted using an oligonucleotide of the invention

| Reg. | length (nt) | Position on SEQ ID NO: 1 start | end | Reg. | length (nt) | Position on SEQ ID NO: 1 start | end | Reg. | length (nt) | Position on SEQ ID NO: 1 start | end |
|---|---|---|---|---|---|---|---|---|---|---|---|
| R_145 | 21 | 7937 | 7957 | R_896 | 23 | 48532 | 48554 | R_1647 | 36 | 93897 | 93932 |
| R_146 | 20 | 7937 | 7956 | R_897 | 32 | 48564 | 48595 | R_1648 | 25 | 94007 | 94031 |
| R_147 | 23 | 7948 | 7970 | R_898 | 43 | 48627 | 48669 | R_1649 | 25 | 94121 | 94145 |
| R_148 | 26 | 7952 | 7977 | R_899 | 32 | 48671 | 48702 | R_1650 | 20 | 94227 | 94246 |
| R_149 | 25 | 7953 | 7977 | R_900 | 30 | 48744 | 48773 | R_1651 | 69 | 94295 | 94363 |
| R_150 | 30 | 8009 | 8038 | R_901 | 24 | 48782 | 48805 | R_1652 | 49 | 94371 | 94419 |
| R_151 | 31 | 8043 | 8073 | R_902 | 21 | 48797 | 48817 | R_1653 | 40 | 94426 | 94465 |
| R_152 | 20 | 8125 | 8144 | R_903 | 22 | 48802 | 48823 | R_1654 | 73 | 94478 | 94550 |
| R_153 | 21 | 8146 | 8166 | R_904 | 54 | 48808 | 48861 | R_1655 | 35 | 94571 | 94605 |
| R_154 | 36 | 8168 | 8203 | R_905 | 38 | 48924 | 48961 | R_1656 | 63 | 94607 | 94669 |
| R_155 | 44 | 8245 | 8288 | R_906 | 20 | 48966 | 48985 | R_1657 | 41 | 94788 | 94828 |
| R_156 | 29 | 8324 | 8352 | R_907 | 25 | 49010 | 49034 | R_1658 | 73 | 94844 | 94916 |
| R_157 | 43 | 8355 | 8397 | R_908 | 21 | 49067 | 49087 | R_1659 | 21 | 94929 | 94949 |
| R_158 | 23 | 8399 | 8421 | R_909 | 61 | 49145 | 49205 | R_1660 | 21 | 94979 | 94999 |
| R_159 | 26 | 8457 | 8482 | R_910 | 81 | 49207 | 49287 | R_1661 | 31 | 95087 | 95117 |
| R_160 | 54 | 8486 | 8539 | R_911 | 35 | 49289 | 49323 | R_1662 | 25 | 95173 | 95197 |
| R_161 | 43 | 8541 | 8583 | R_912 | 41 | 49325 | 49365 | R_1663 | 23 | 95244 | 95266 |
| R_162 | 26 | 8585 | 8610 | R_913 | 99 | 49400 | 49498 | R_1664 | 38 | 95278 | 95315 |
| R_163 | 26 | 8637 | 8662 | R_914 | 30 | 49507 | 49536 | R_1665 | 28 | 95355 | 95382 |
| R_164 | 37 | 8678 | 8714 | R_915 | 24 | 49538 | 49561 | R_1666 | 95 | 95390 | 95484 |
| R_165 | 24 | 8742 | 8765 | R_916 | 23 | 49563 | 49585 | R_1667 | 159 | 95486 | 95644 |
| R_166 | 37 | 8812 | 8848 | R_917 | 27 | 49612 | 49638 | R_1668 | 30 | 95646 | 95675 |
| R_167 | 37 | 8868 | 8904 | R_918 | 33 | 49654 | 49686 | R_1669 | 101 | 95695 | 95795 |
| R_168 | 21 | 9015 | 9035 | R_919 | 37 | 49697 | 49733 | R_1670 | 33 | 95807 | 95839 |
| R_169 | 28 | 9065 | 9092 | R_920 | 28 | 49751 | 49778 | R_1671 | 24 | 95863 | 95886 |
| R_170 | 20 | 9180 | 9199 | R_921 | 20 | 49870 | 49889 | R_1672 | 22 | 95888 | 95909 |
| R_171 | 23 | 9191 | 9213 | R_922 | 42 | 49890 | 49931 | R_1673 | 31 | 95915 | 95945 |
| R_172 | 24 | 9203 | 9226 | R_923 | 38 | 49964 | 50001 | R_1674 | 30 | 95951 | 95980 |
| R_173 | 28 | 9215 | 9242 | R_924 | 106 | 50003 | 50108 | R_1675 | 28 | 96033 | 96060 |
| R_174 | 21 | 9244 | 9264 | R_925 | 29 | 50110 | 50138 | R_1676 | 37 | 96057 | 96093 |
| R_175 | 23 | 9260 | 9282 | R_926 | 24 | 50394 | 50417 | R_1677 | 28 | 96159 | 96186 |
| R_176 | 25 | 9266 | 9290 | R_927 | 42 | 50473 | 50514 | R_1678 | 40 | 96287 | 96326 |
| R_177 | 23 | 9266 | 9288 | R_928 | 27 | 50578 | 50604 | R_1679 | 43 | 96331 | 96373 |
| R_178 | 24 | 9267 | 9290 | R_929 | 42 | 50606 | 50647 | R_1680 | 39 | 96450 | 96488 |
| R_179 | 21 | 9267 | 9287 | R_930 | 42 | 50692 | 50733 | R_1681 | 30 | 96492 | 96521 |
| R_180 | 22 | 9267 | 9288 | R_931 | 20 | 50763 | 50782 | R_1682 | 44 | 96523 | 96566 |
| R_181 | 23 | 9268 | 9290 | R_932 | 34 | 50808 | 50841 | R_1683 | 22 | 96589 | 96610 |
| R_182 | 21 | 9270 | 9290 | R_933 | 48 | 50847 | 50894 | R_1684 | 22 | 96655 | 96676 |
| R_183 | 23 | 9289 | 9311 | R_934 | 55 | 50955 | 51009 | R_1685 | 52 | 96714 | 96765 |
| R_184 | 20 | 9292 | 9311 | R_935 | 21 | 51011 | 51031 | R_1686 | 23 | 96776 | 96798 |
| R_185 | 22 | 9330 | 9351 | R_936 | 58 | 51071 | 51128 | R_1687 | 25 | 96798 | 96822 |
| R_186 | 20 | 9334 | 9353 | R_937 | 85 | 51138 | 51222 | R_1688 | 36 | 96838 | 96873 |
| R_187 | 22 | 10083 | 10104 | R_938 | 22 | 51273 | 51294 | R_1689 | 44 | 96895 | 96938 |
| R_188 | 23 | 10092 | 10114 | R_939 | 40 | 51330 | 51369 | R_1690 | 21 | 96940 | 96960 |
| R_189 | 38 | 10119 | 10156 | R_940 | 20 | 51343 | 51362 | R_1691 | 24 | 96993 | 97016 |
| R_190 | 20 | 10255 | 10274 | R_941 | 71 | 51498 | 51568 | R_1692 | 24 | 97038 | 97061 |
| R_191 | 21 | 10257 | 10277 | R_942 | 35 | 51570 | 51604 | R_1693 | 22 | 97073 | 97094 |
| R_192 | 28 | 10305 | 10332 | R_943 | 20 | 51639 | 51658 | R_1694 | 25 | 97106 | 97130 |
| R_193 | 63 | 10358 | 10420 | R_944 | 31 | 51680 | 51710 | R_1695 | 20 | 97132 | 97151 |
| R_194 | 28 | 10498 | 10525 | R_945 | 75 | 51712 | 51786 | R_1696 | 23 | 97162 | 97184 |
| R_195 | 27 | 10597 | 10623 | R_946 | 57 | 51788 | 51844 | R_1697 | 38 | 97186 | 97223 |
| R_196 | 24 | 10625 | 10648 | R_947 | 57 | 51846 | 51902 | R_1698 | 32 | 97225 | 97256 |
| R_197 | 56 | 10666 | 10721 | R_948 | 33 | 51928 | 51960 | R_1699 | 41 | 97258 | 97298 |
| R_198 | 27 | 10741 | 10767 | R_949 | 33 | 51962 | 51994 | R_1700 | 34 | 97300 | 97333 |
| R_199 | 21 | 10777 | 10797 | R_950 | 20 | 52012 | 52031 | R_1701 | 20 | 97342 | 97361 |
| R_200 | 38 | 10799 | 10836 | R_951 | 52 | 52024 | 52075 | R_1702 | 21 | 97486 | 97506 |
| R_201 | 30 | 10840 | 10869 | R_952 | 20 | 52183 | 52202 | R_1703 | 24 | 97532 | 97555 |
| R_202 | 24 | 10871 | 10894 | R_953 | 31 | 52316 | 52346 | R_1704 | 20 | 97592 | 97611 |
| R_203 | 30 | 10911 | 10940 | R_954 | 54 | 52348 | 52401 | R_1705 | 21 | 97606 | 97626 |
| R_204 | 49 | 10942 | 10990 | R_955 | 24 | 52408 | 52431 | R_1706 | 20 | 97690 | 97709 |
| R_205 | 21 | 10992 | 11012 | R_956 | 25 | 52433 | 52457 | R_1707 | 43 | 97694 | 97736 |
| R_206 | 69 | 11018 | 11086 | R_957 | 68 | 52452 | 52519 | R_1708 | 26 | 97740 | 97765 |
| R_207 | 30 | 11089 | 11118 | R_958 | 42 | 52521 | 52562 | R_1709 | 28 | 97767 | 97794 |
| R_208 | 42 | 11127 | 11168 | R_959 | 41 | 52569 | 52609 | R_1710 | 64 | 97820 | 97883 |
| R_209 | 25 | 11193 | 11217 | R_960 | 21 | 52626 | 52646 | R_1711 | 32 | 97928 | 97959 |
| R_210 | 68 | 11279 | 11346 | R_961 | 21 | 52676 | 52696 | R_1712 | 40 | 98008 | 98047 |
| R_211 | 42 | 11367 | 11408 | R_962 | 71 | 52704 | 52774 | R_1713 | 49 | 98103 | 98151 |
| R_212 | 43 | 11410 | 11452 | R_963 | 31 | 52784 | 52814 | R_1714 | 33 | 98166 | 98198 |
| R_213 | 54 | 11458 | 11511 | R_964 | 22 | 52826 | 52847 | R_1715 | 26 | 98200 | 98225 |
| R_214 | 79 | 11556 | 11634 | R_965 | 25 | 52874 | 52898 | R_1716 | 32 | 98324 | 98355 |
| R_215 | 37 | 11648 | 11684 | R_966 | 80 | 52915 | 52994 | R_1717 | 21 | 98333 | 98353 |
| R_216 | 31 | 11691 | 11721 | R_967 | 21 | 53027 | 53047 | R_1718 | 21 | 98467 | 98487 |

TABLE 4-continued

Regions (reg.) on SEQ ID NO: 1 which may be targeted using an oligonucleotide of the invention

| Reg. | length (nt) | Position on SEQ ID NO: 1 start | end | Reg. | length (nt) | Position on SEQ ID NO: 1 start | end | Reg. | length (nt) | Position on SEQ ID NO: 1 start | end |
|---|---|---|---|---|---|---|---|---|---|---|---|
| R_217 | 28 | 11724 | 11751 | R_968 | 44 | 53130 | 53173 | R_1719 | 22 | 98506 | 98527 |
| R_218 | 81 | 11800 | 11880 | R_969 | 21 | 53175 | 53195 | R_1720 | 31 | 98577 | 98607 |
| R_219 | 20 | 11905 | 11924 | R_970 | 24 | 53181 | 53204 | R_1721 | 32 | 98681 | 98712 |
| R_220 | 21 | 11928 | 11948 | R_971 | 22 | 53233 | 53254 | R_1722 | 23 | 98751 | 98773 |
| R_221 | 50 | 11950 | 11999 | R_972 | 20 | 53262 | 53281 | R_1723 | 37 | 98789 | 98825 |
| R_222 | 20 | 12030 | 12049 | R_973 | 22 | 53315 | 53336 | R_1724 | 37 | 98930 | 98966 |
| R_223 | 61 | 12051 | 12111 | R_974 | 20 | 53352 | 53371 | R_1725 | 40 | 98969 | 99008 |
| R_224 | 23 | 12147 | 12169 | R_975 | 72 | 53390 | 53461 | R_1726 | 21 | 99015 | 99035 |
| R_225 | 25 | 12171 | 12195 | R_976 | 42 | 53473 | 53514 | R_1727 | 45 | 99231 | 99275 |
| R_226 | 23 | 12197 | 12219 | R_977 | 25 | 53534 | 53558 | R_1728 | 38 | 99345 | 99382 |
| R_227 | 45 | 12221 | 12265 | R_978 | 30 | 53560 | 53589 | R_1729 | 46 | 99387 | 99432 |
| R_228 | 43 | 12304 | 12346 | R_979 | 23 | 53600 | 53622 | R_1730 | 25 | 99434 | 99458 |
| R_229 | 51 | 12353 | 12403 | R_980 | 28 | 53637 | 53664 | R_1731 | 21 | 99515 | 99535 |
| R_230 | 23 | 12405 | 12427 | R_981 | 24 | 53696 | 53719 | R_1732 | 23 | 99565 | 99587 |
| R_231 | 62 | 12475 | 12536 | R_982 | 21 | 53738 | 53758 | R_1733 | 21 | 99658 | 99678 |
| R_232 | 28 | 12538 | 12565 | R_983 | 22 | 53753 | 53774 | R_1734 | 43 | 99718 | 99760 |
| R_233 | 28 | 12587 | 12614 | R_984 | 23 | 53759 | 53781 | R_1735 | 30 | 99762 | 99791 |
| R_234 | 21 | 12615 | 12635 | R_985 | 30 | 53793 | 53822 | R_1736 | 62 | 99820 | 99881 |
| R_235 | 29 | 12637 | 12665 | R_986 | 23 | 53895 | 53917 | R_1737 | 21 | 99933 | 99953 |
| R_236 | 38 | 12684 | 12721 | R_987 | 25 | 53910 | 53934 | R_1738 | 26 | 99986 | 100011 |
| R_237 | 34 | 12746 | 12779 | R_988 | 21 | 53979 | 53999 | R_1739 | 29 | 100013 | 100041 |
| R_238 | 20 | 12799 | 12818 | R_989 | 20 | 53996 | 54015 | R_1740 | 71 | 100063 | 100133 |
| R_239 | 33 | 12822 | 12854 | R_990 | 21 | 54027 | 54047 | R_1741 | 32 | 100169 | 100200 |
| R_240 | 37 | 12856 | 12892 | R_991 | 28 | 54049 | 54076 | R_1742 | 21 | 100248 | 100268 |
| R_241 | 20 | 12894 | 12913 | R_992 | 40 | 54162 | 54201 | R_1743 | 30 | 100263 | 100292 |
| R_242 | 23 | 12933 | 12955 | R_993 | 20 | 54218 | 54237 | R_1744 | 38 | 100296 | 100333 |
| R_243 | 50 | 13057 | 13106 | R_994 | 77 | 54239 | 54315 | R_1745 | 22 | 100359 | 100380 |
| R_244 | 37 | 13133 | 13169 | R_995 | 50 | 54317 | 54366 | R_1746 | 23 | 100375 | 100397 |
| R_245 | 51 | 13227 | 13277 | R_996 | 21 | 54368 | 54388 | R_1747 | 23 | 100384 | 100406 |
| R_246 | 22 | 13348 | 13369 | R_997 | 32 | 54406 | 54437 | R_1748 | 24 | 100639 | 100662 |
| R_247 | 29 | 13380 | 13408 | R_998 | 33 | 54439 | 54471 | R_1749 | 24 | 100645 | 100668 |
| R_248 | 41 | 13410 | 13450 | R_999 | 20 | 54507 | 54526 | R_1750 | 20 | 100666 | 100685 |
| R_249 | 32 | 13452 | 13483 | R_1000 | 55 | 54528 | 54582 | R_1751 | 23 | 100695 | 100717 |
| R_250 | 45 | 13483 | 13527 | R_1001 | 21 | 54584 | 54604 | R_1752 | 20 | 100746 | 100765 |
| R_251 | 32 | 13529 | 13560 | R_1002 | 42 | 54606 | 54647 | R_1753 | 34 | 100771 | 100804 |
| R_252 | 21 | 13569 | 13589 | R_1003 | 118 | 54651 | 54768 | R_1754 | 21 | 100801 | 100821 |
| R_253 | 50 | 13591 | 13640 | R_1004 | 23 | 54833 | 54855 | R_1755 | 26 | 100823 | 100848 |
| R_254 | 88 | 13770 | 13857 | R_1005 | 28 | 54857 | 54884 | R_1756 | 20 | 100857 | 100876 |
| R_255 | 20 | 13861 | 13880 | R_1006 | 57 | 54887 | 54943 | R_1757 | 34 | 100899 | 100932 |
| R_256 | 32 | 13882 | 13913 | R_1007 | 29 | 54973 | 55001 | R_1758 | 21 | 100965 | 100985 |
| R_257 | 55 | 13936 | 13990 | R_1008 | 21 | 55014 | 55034 | R_1759 | 32 | 101017 | 101048 |
| R_258 | 39 | 13992 | 14030 | R_1009 | 28 | 55074 | 55101 | R_1760 | 21 | 101085 | 101105 |
| R_259 | 34 | 14033 | 14066 | R_1010 | 21 | 55134 | 55154 | R_1761 | 26 | 101195 | 101220 |
| R_260 | 35 | 14068 | 14102 | R_1011 | 38 | 55171 | 55208 | R_1762 | 23 | 101227 | 101249 |
| R_261 | 27 | 14104 | 14130 | R_1012 | 31 | 55210 | 55240 | R_1763 | 30 | 101324 | 101353 |
| R_262 | 20 | 14140 | 14159 | R_1013 | 80 | 55248 | 55327 | R_1764 | 20 | 101357 | 101376 |
| R_263 | 51 | 14180 | 14230 | R_1014 | 25 | 55329 | 55353 | R_1765 | 21 | 101415 | 101435 |
| R_264 | 20 | 14232 | 14251 | R_1015 | 23 | 55365 | 55387 | R_1766 | 20 | 101444 | 101463 |
| R_265 | 107 | 14253 | 14359 | R_1016 | 43 | 55424 | 55466 | R_1767 | 37 | 101465 | 101501 |
| R_266 | 72 | 14367 | 14438 | R_1017 | 51 | 55539 | 55589 | R_1768 | 25 | 101497 | 101521 |
| R_267 | 69 | 14503 | 14571 | R_1018 | 27 | 55591 | 55617 | R_1769 | 42 | 101523 | 101564 |
| R_268 | 27 | 14595 | 14621 | R_1019 | 29 | 55619 | 55647 | R_1770 | 26 | 101576 | 101601 |
| R_269 | 35 | 14629 | 14663 | R_1020 | 30 | 55653 | 55682 | R_1771 | 34 | 101620 | 101653 |
| R_270 | 58 | 14732 | 14789 | R_1021 | 29 | 55724 | 55752 | R_1772 | 36 | 101679 | 101714 |
| R_271 | 25 | 14805 | 14829 | R_1022 | 33 | 55778 | 55810 | R_1773 | 39 | 101734 | 101772 |
| R_272 | 56 | 14851 | 14906 | R_1023 | 76 | 55848 | 55923 | R_1774 | 24 | 101779 | 101802 |
| R_273 | 53 | 14954 | 15006 | R_1024 | 33 | 55992 | 56024 | R_1775 | 71 | 101817 | 101887 |
| R_274 | 39 | 15026 | 15064 | R_1025 | 29 | 56026 | 56054 | R_1776 | 67 | 101913 | 101979 |
| R_275 | 21 | 15066 | 15086 | R_1026 | 59 | 56080 | 56138 | R_1777 | 28 | 101989 | 102016 |
| R_276 | 22 | 15138 | 15159 | R_1027 | 26 | 56155 | 56180 | R_1778 | 28 | 102025 | 102052 |
| R_277 | 107 | 15157 | 15263 | R_1028 | 22 | 56196 | 56217 | R_1779 | 33 | 102054 | 102086 |
| R_278 | 24 | 15249 | 15272 | R_1029 | 21 | 56225 | 56245 | R_1780 | 23 | 102088 | 102110 |
| R_279 | 22 | 15277 | 15298 | R_1030 | 31 | 56274 | 56304 | R_1781 | 44 | 102112 | 102155 |
| R_280 | 38 | 15300 | 15337 | R_1031 | 24 | 56338 | 56361 | R_1782 | 22 | 102161 | 102182 |
| R_281 | 24 | 15414 | 15437 | R_1032 | 22 | 56410 | 56431 | R_1783 | 65 | 102202 | 102266 |
| R_282 | 21 | 15476 | 15496 | R_1033 | 36 | 56433 | 56468 | R_1784 | 23 | 102268 | 102290 |
| R_283 | 23 | 15617 | 15639 | R_1034 | 22 | 56521 | 56542 | R_1785 | 35 | 102292 | 102326 |
| R_284 | 58 | 15671 | 15728 | R_1035 | 30 | 56567 | 56596 | R_1786 | 32 | 102352 | 102383 |
| R_285 | 36 | 15730 | 15765 | R_1036 | 55 | 56641 | 56695 | R_1787 | 29 | 102385 | 102413 |
| R_286 | 29 | 15840 | 15868 | R_1037 | 44 | 56697 | 56740 | R_1788 | 29 | 102526 | 102554 |
| R_287 | 27 | 15870 | 15896 | R_1038 | 43 | 56761 | 56803 | R_1789 | 77 | 102579 | 102655 |
| R_288 | 50 | 15926 | 15975 | R_1039 | 72 | 56805 | 56876 | R_1790 | 39 | 102744 | 102782 |

TABLE 4-continued

Regions (reg.) on SEQ ID NO: 1 which may be targeted using an oligonucleotide of the invention

| Reg. | length (nt) | Position on SEQ ID NO: 1 start | Position on SEQ ID NO: 1 end | Reg. | length (nt) | Position on SEQ ID NO: 1 start | Position on SEQ ID NO: 1 end | Reg. | length (nt) | Position on SEQ ID NO: 1 start | Position on SEQ ID NO: 1 end |
|---|---|---|---|---|---|---|---|---|---|---|---|
| R_289 | 27 | 16008 | 16034 | R_1040 | 30 | 56885 | 56914 | R_1791 | 32 | 102841 | 102872 |
| R_290 | 46 | 16109 | 16154 | R_1041 | 44 | 56916 | 56959 | R_1792 | 22 | 103017 | 103038 |
| R_291 | 27 | 16159 | 16185 | R_1042 | 67 | 56961 | 57027 | R_1793 | 20 | 103118 | 103137 |
| R_292 | 30 | 16245 | 16274 | R_1043 | 30 | 57033 | 57062 | R_1794 | 20 | 103196 | 103215 |
| R_293 | 44 | 16296 | 16339 | R_1044 | 20 | 57167 | 57186 | R_1795 | 23 | 103346 | 103368 |
| R_294 | 20 | 16316 | 16335 | R_1045 | 49 | 57211 | 57259 | R_1796 | 24 | 103400 | 103423 |
| R_295 | 48 | 16371 | 16418 | R_1046 | 24 | 57348 | 57371 | R_1797 | 27 | 103456 | 103482 |
| R_296 | 36 | 16447 | 16482 | R_1047 | 43 | 57434 | 57476 | R_1798 | 54 | 103494 | 103547 |
| R_297 | 36 | 16485 | 16520 | R_1048 | 73 | 57536 | 57608 | R_1799 | 21 | 103557 | 103577 |
| R_298 | 26 | 16532 | 16557 | R_1049 | 86 | 57641 | 57726 | R_1800 | 34 | 103637 | 103670 |
| R_299 | 21 | 16582 | 16602 | R_1050 | 27 | 57754 | 57780 | R_1801 | 58 | 103683 | 103740 |
| R_300 | 83 | 16604 | 16686 | R_1051 | 20 | 57786 | 57805 | R_1802 | 25 | 103782 | 103806 |
| R_301 | 63 | 16688 | 16750 | R_1052 | 21 | 57807 | 57827 | R_1803 | 20 | 103851 | 103870 |
| R_302 | 75 | 16766 | 16840 | R_1053 | 27 | 57829 | 57855 | R_1804 | 26 | 103876 | 103901 |
| R_303 | 24 | 16918 | 16941 | R_1054 | 41 | 57857 | 57897 | R_1805 | 21 | 103997 | 104017 |
| R_304 | 32 | 16947 | 16978 | R_1055 | 51 | 57899 | 57949 | R_1806 | 49 | 104093 | 104141 |
| R_305 | 31 | 17007 | 17037 | R_1056 | 26 | 57981 | 58006 | R_1807 | 61 | 104143 | 104203 |
| R_306 | 45 | 17039 | 17083 | R_1057 | 48 | 58008 | 58055 | R_1808 | 28 | 104263 | 104290 |
| R_307 | 25 | 17085 | 17109 | R_1058 | 26 | 58057 | 58082 | R_1809 | 22 | 104331 | 104352 |
| R_308 | 30 | 17111 | 17140 | R_1059 | 32 | 58097 | 58128 | R_1810 | 24 | 104354 | 104377 |
| R_309 | 29 | 17179 | 17207 | R_1060 | 40 | 58138 | 58177 | R_1811 | 36 | 104379 | 104414 |
| R_310 | 34 | 17292 | 17325 | R_1061 | 38 | 58192 | 58229 | R_1812 | 72 | 104416 | 104487 |
| R_311 | 28 | 17292 | 17319 | R_1062 | 26 | 58235 | 58260 | R_1813 | 23 | 104504 | 104526 |
| R_312 | 28 | 17309 | 17336 | R_1063 | 57 | 58375 | 58431 | R_1814 | 54 | 104544 | 104597 |
| R_313 | 21 | 17316 | 17336 | R_1064 | 25 | 58444 | 58468 | R_1815 | 20 | 104599 | 104618 |
| R_314 | 21 | 17319 | 17339 | R_1065 | 55 | 58484 | 58538 | R_1816 | 22 | 104632 | 104653 |
| R_315 | 22 | 17326 | 17347 | R_1066 | 26 | 58555 | 58580 | R_1817 | 25 | 104710 | 104734 |
| R_316 | 52 | 17349 | 17400 | R_1067 | 20 | 58582 | 58601 | R_1818 | 22 | 104738 | 104759 |
| R_317 | 20 | 17416 | 17435 | R_1068 | 23 | 58604 | 58626 | R_1819 | 40 | 104783 | 104822 |
| R_318 | 39 | 17445 | 17483 | R_1069 | 32 | 58650 | 58681 | R_1820 | 42 | 104824 | 104865 |
| R_319 | 43 | 17485 | 17527 | R_1070 | 70 | 58740 | 58809 | R_1821 | 21 | 104919 | 104939 |
| R_320 | 74 | 17587 | 17660 | R_1071 | 32 | 58889 | 58920 | R_1822 | 23 | 105014 | 105036 |
| R_321 | 38 | 17667 | 17704 | R_1072 | 25 | 58927 | 58951 | R_1823 | 58 | 105040 | 105097 |
| R_322 | 25 | 17706 | 17730 | R_1073 | 22 | 58953 | 58974 | R_1824 | 25 | 105111 | 105135 |
| R_323 | 45 | 17796 | 17840 | R_1074 | 35 | 58993 | 59027 | R_1825 | 50 | 105137 | 105186 |
| R_324 | 53 | 17855 | 17907 | R_1075 | 48 | 59029 | 59076 | R_1826 | 22 | 105188 | 105209 |
| R_325 | 44 | 17909 | 17952 | R_1076 | 45 | 59079 | 59123 | R_1827 | 40 | 105283 | 105322 |
| R_326 | 20 | 17954 | 17973 | R_1077 | 31 | 59125 | 59155 | R_1828 | 31 | 105393 | 105423 |
| R_327 | 34 | 17975 | 18008 | R_1078 | 31 | 59183 | 59213 | R_1829 | 29 | 105427 | 105455 |
| R_328 | 20 | 18010 | 18029 | R_1079 | 20 | 59243 | 59262 | R_1830 | 72 | 105457 | 105528 |
| R_329 | 46 | 18031 | 18076 | R_1080 | 35 | 59264 | 59298 | R_1831 | 30 | 105544 | 105573 |
| R_330 | 26 | 18078 | 18103 | R_1081 | 24 | 59303 | 59326 | R_1832 | 39 | 105683 | 105721 |
| R_331 | 29 | 18136 | 18164 | R_1082 | 39 | 59328 | 59366 | R_1833 | 36 | 105732 | 105767 |
| R_332 | 33 | 18208 | 18240 | R_1083 | 31 | 59380 | 59410 | R_1834 | 23 | 106011 | 106033 |
| R_333 | 54 | 18261 | 18314 | R_1084 | 20 | 59490 | 59509 | R_1835 | 45 | 106334 | 106378 |
| R_334 | 22 | 18333 | 18354 | R_1085 | 39 | 59551 | 59589 | R_1836 | 21 | 106380 | 106400 |
| R_335 | 34 | 18410 | 18443 | R_1086 | 76 | 59591 | 59666 | R_1837 | 23 | 106407 | 106429 |
| R_336 | 27 | 18446 | 18472 | R_1087 | 46 | 59713 | 59758 | R_1838 | 23 | 106475 | 106497 |
| R_337 | 86 | 18474 | 18559 | R_1088 | 26 | 59837 | 59862 | R_1839 | 47 | 106562 | 106608 |
| R_338 | 25 | 18590 | 18614 | R_1089 | 40 | 59878 | 59917 | R_1840 | 42 | 106645 | 106686 |
| R_339 | 21 | 18627 | 18647 | R_1090 | 23 | 59957 | 59979 | R_1841 | 44 | 106677 | 106720 |
| R_340 | 37 | 18650 | 18686 | R_1091 | 37 | 59998 | 60034 | R_1842 | 29 | 106677 | 106705 |
| R_341 | 33 | 18688 | 18720 | R_1092 | 63 | 60133 | 60195 | R_1843 | 22 | 106728 | 106749 |
| R_342 | 30 | 18742 | 18771 | R_1093 | 22 | 60201 | 60222 | R_1844 | 40 | 106783 | 106822 |
| R_343 | 20 | 18773 | 18792 | R_1094 | 23 | 60281 | 60303 | R_1845 | 22 | 106824 | 106845 |
| R_344 | 32 | 18782 | 18813 | R_1095 | 37 | 60291 | 60327 | R_1846 | 31 | 106847 | 106877 |
| R_345 | 20 | 18843 | 18862 | R_1096 | 27 | 60360 | 60386 | R_1847 | 31 | 106879 | 106909 |
| R_346 | 24 | 18864 | 18887 | R_1097 | 23 | 60429 | 60451 | R_1848 | 64 | 106923 | 106986 |
| R_347 | 24 | 18900 | 18923 | R_1098 | 52 | 60536 | 60587 | R_1849 | 35 | 106988 | 107022 |
| R_348 | 35 | 18935 | 18969 | R_1099 | 24 | 60605 | 60628 | R_1850 | 35 | 107046 | 107080 |
| R_349 | 38 | 18971 | 19008 | R_1100 | 28 | 60656 | 60683 | R_1851 | 26 | 107085 | 107110 |
| R_350 | 23 | 19080 | 19102 | R_1101 | 90 | 60703 | 60792 | R_1852 | 25 | 107122 | 107146 |
| R_351 | 51 | 19106 | 19156 | R_1102 | 48 | 60794 | 60841 | R_1853 | 40 | 107239 | 107278 |
| R_352 | 21 | 19158 | 19178 | R_1103 | 49 | 60841 | 60889 | R_1854 | 57 | 107338 | 107394 |
| R_353 | 25 | 19262 | 19286 | R_1104 | 31 | 60921 | 60951 | R_1855 | 36 | 107405 | 107440 |
| R_354 | 22 | 19310 | 19331 | R_1105 | 21 | 60953 | 60973 | R_1856 | 22 | 107442 | 107463 |
| R_355 | 28 | 19333 | 19360 | R_1106 | 30 | 60979 | 61008 | R_1857 | 22 | 107465 | 107486 |
| R_356 | 24 | 19362 | 19385 | R_1107 | 23 | 61040 | 61062 | R_1858 | 22 | 107506 | 107527 |
| R_357 | 44 | 19394 | 19437 | R_1108 | 20 | 61117 | 61136 | R_1859 | 28 | 107553 | 107580 |
| R_358 | 47 | 19493 | 19539 | R_1109 | 22 | 61148 | 61169 | R_1860 | 53 | 107582 | 107634 |
| R_359 | 26 | 19569 | 19594 | R_1110 | 106 | 61165 | 61270 | R_1861 | 37 | 107639 | 107675 |
| R_360 | 34 | 19624 | 19657 | R_1111 | 21 | 61274 | 61294 | R_1862 | 34 | 107679 | 107712 |

TABLE 4-continued

Regions (reg.) on SEQ ID NO: 1 which may be targeted using an oligonucleotide of the invention

| Reg. | length (nt) | Position on SEQ ID NO: 1 start | end | Reg. | length (nt) | Position on SEQ ID NO: 1 start | end | Reg. | length (nt) | Position on SEQ ID NO: 1 start | end |
|---|---|---|---|---|---|---|---|---|---|---|---|
| R_361 | 38 | 19659 | 19696 | R_1112 | 25 | 61392 | 61416 | R_1863 | 36 | 107775 | 107810 |
| R_362 | 32 | 19713 | 19744 | R_1113 | 22 | 61447 | 61468 | R_1864 | 25 | 107868 | 107892 |
| R_363 | 56 | 19746 | 19801 | R_1114 | 25 | 61486 | 61510 | R_1865 | 24 | 107893 | 107916 |
| R_364 | 43 | 19839 | 19881 | R_1115 | 23 | 61495 | 61517 | R_1866 | 24 | 108016 | 108039 |
| R_365 | 24 | 19894 | 19917 | R_1116 | 27 | 61518 | 61544 | R_1867 | 42 | 108071 | 108112 |
| R_366 | 24 | 19960 | 19983 | R_1117 | 23 | 61586 | 61608 | R_1868 | 21 | 108176 | 108196 |
| R_367 | 21 | 19985 | 20005 | R_1118 | 32 | 61646 | 61677 | R_1869 | 30 | 108213 | 108242 |
| R_368 | 30 | 20006 | 20035 | R_1119 | 34 | 61784 | 61817 | R_1870 | 72 | 108263 | 108334 |
| R_369 | 21 | 20037 | 20057 | R_1120 | 23 | 61870 | 61892 | R_1871 | 32 | 108390 | 108421 |
| R_370 | 20 | 20069 | 20088 | R_1121 | 43 | 61904 | 61946 | R_1872 | 27 | 108441 | 108467 |
| R_371 | 20 | 20151 | 20170 | R_1122 | 22 | 61948 | 61969 | R_1873 | 31 | 108479 | 108509 |
| R_372 | 25 | 20182 | 20206 | R_1123 | 33 | 61997 | 62029 | R_1874 | 21 | 108524 | 108544 |
| R_373 | 22 | 20237 | 20258 | R_1124 | 21 | 62076 | 62096 | R_1875 | 58 | 108546 | 108603 |
| R_374 | 22 | 20267 | 20288 | R_1125 | 22 | 62103 | 62124 | R_1876 | 33 | 108669 | 108701 |
| R_375 | 27 | 20363 | 20389 | R_1126 | 20 | 62133 | 62152 | R_1877 | 26 | 108721 | 108746 |
| R_376 | 25 | 20375 | 20399 | R_1127 | 26 | 62162 | 62187 | R_1878 | 30 | 108822 | 108851 |
| R_377 | 21 | 20482 | 20502 | R_1128 | 20 | 62239 | 62258 | R_1879 | 32 | 108859 | 108890 |
| R_378 | 27 | 20485 | 20511 | R_1129 | 24 | 62243 | 62266 | R_1880 | 30 | 108909 | 108938 |
| R_379 | 22 | 20497 | 20518 | R_1130 | 20 | 62266 | 62285 | R_1881 | 41 | 108996 | 109036 |
| R_380 | 24 | 20566 | 20589 | R_1131 | 24 | 62307 | 62330 | R_1882 | 43 | 109038 | 109080 |
| R_381 | 22 | 20591 | 20612 | R_1132 | 27 | 62332 | 62358 | R_1883 | 22 | 109104 | 109125 |
| R_382 | 20 | 20610 | 20629 | R_1133 | 22 | 62433 | 62454 | R_1884 | 41 | 109145 | 109185 |
| R_383 | 22 | 20679 | 20700 | R_1134 | 22 | 62561 | 62582 | R_1885 | 25 | 109237 | 109261 |
| R_384 | 28 | 20702 | 20729 | R_1135 | 50 | 62600 | 62649 | R_1886 | 41 | 109263 | 109303 |
| R_385 | 35 | 20741 | 20775 | R_1136 | 29 | 62678 | 62706 | R_1887 | 34 | 109306 | 109339 |
| R_386 | 43 | 20790 | 20832 | R_1137 | 32 | 62708 | 62739 | R_1888 | 48 | 109355 | 109402 |
| R_387 | 35 | 20880 | 20914 | R_1138 | 20 | 62846 | 62865 | R_1889 | 20 | 109404 | 109423 |
| R_388 | 22 | 20892 | 20913 | R_1139 | 46 | 62871 | 62916 | R_1890 | 28 | 109425 | 109452 |
| R_389 | 21 | 21011 | 21031 | R_1140 | 23 | 62945 | 62967 | R_1891 | 31 | 109454 | 109484 |
| R_390 | 26 | 21138 | 21163 | R_1141 | 52 | 62978 | 63029 | R_1892 | 20 | 109494 | 109513 |
| R_391 | 20 | 21158 | 21177 | R_1142 | 43 | 63043 | 63085 | R_1893 | 25 | 109519 | 109543 |
| R_392 | 24 | 21248 | 21271 | R_1143 | 31 | 63087 | 63117 | R_1894 | 60 | 109554 | 109613 |
| R_393 | 26 | 21324 | 21349 | R_1144 | 35 | 63119 | 63153 | R_1895 | 34 | 109631 | 109664 |
| R_394 | 35 | 21351 | 21385 | R_1145 | 31 | 63155 | 63185 | R_1896 | 26 | 109666 | 109691 |
| R_395 | 29 | 21441 | 21469 | R_1146 | 54 | 63193 | 63246 | R_1897 | 22 | 109693 | 109714 |
| R_396 | 53 | 21557 | 21609 | R_1147 | 23 | 63249 | 63271 | R_1898 | 23 | 109757 | 109779 |
| R_397 | 31 | 21611 | 21641 | R_1148 | 29 | 63362 | 63390 | R_1899 | 34 | 109822 | 109855 |
| R_398 | 38 | 21645 | 21682 | R_1149 | 33 | 63404 | 63436 | R_1900 | 23 | 109866 | 109888 |
| R_399 | 40 | 21743 | 21782 | R_1150 | 33 | 63462 | 63494 | R_1901 | 140 | 109935 | 110074 |
| R_400 | 59 | 21819 | 21877 | R_1151 | 27 | 63501 | 63527 | R_1902 | 20 | 110077 | 110096 |
| R_401 | 20 | 21949 | 21968 | R_1152 | 29 | 63569 | 63597 | R_1903 | 29 | 110137 | 110165 |
| R_402 | 27 | 22001 | 22027 | R_1153 | 36 | 63599 | 63634 | R_1904 | 29 | 110216 | 110244 |
| R_403 | 63 | 22041 | 22103 | R_1154 | 20 | 63634 | 63653 | R_1905 | 32 | 110254 | 110285 |
| R_404 | 53 | 22125 | 22177 | R_1155 | 46 | 63769 | 63814 | R_1906 | 33 | 110294 | 110326 |
| R_405 | 48 | 22179 | 22226 | R_1156 | 20 | 63826 | 63845 | R_1907 | 31 | 110328 | 110358 |
| R_406 | 20 | 22247 | 22266 | R_1157 | 24 | 63848 | 63871 | R_1908 | 44 | 110383 | 110426 |
| R_407 | 48 | 22277 | 22324 | R_1158 | 54 | 63873 | 63926 | R_1909 | 24 | 110421 | 110444 |
| R_408 | 31 | 22334 | 22364 | R_1159 | 48 | 63941 | 63988 | R_1910 | 20 | 110563 | 110582 |
| R_409 | 105 | 22370 | 22474 | R_1160 | 45 | 63990 | 64034 | R_1911 | 32 | 110584 | 110615 |
| R_410 | 37 | 22475 | 22511 | R_1161 | 20 | 64059 | 64078 | R_1912 | 28 | 110598 | 110625 |
| R_411 | 32 | 22644 | 22675 | R_1162 | 20 | 64322 | 64341 | R_1913 | 54 | 110612 | 110665 |
| R_412 | 34 | 22686 | 22719 | R_1163 | 20 | 64382 | 64401 | R_1914 | 29 | 110781 | 110809 |
| R_413 | 28 | 22763 | 22790 | R_1164 | 24 | 64487 | 64510 | R_1915 | 51 | 110823 | 110873 |
| R_414 | 34 | 22792 | 22825 | R_1165 | 34 | 64532 | 64565 | R_1916 | 22 | 110875 | 110896 |
| R_415 | 22 | 22844 | 22865 | R_1166 | 27 | 64550 | 64576 | R_1917 | 27 | 110899 | 110925 |
| R_416 | 23 | 22875 | 22897 | R_1167 | 24 | 65195 | 65218 | R_1918 | 25 | 110992 | 111016 |
| R_417 | 27 | 22959 | 22985 | R_1168 | 20 | 65195 | 65214 | R_1919 | 38 | 111036 | 111073 |
| R_418 | 22 | 22990 | 23011 | R_1169 | 28 | 65736 | 65763 | R_1920 | 26 | 111108 | 111133 |
| R_419 | 23 | 23019 | 23041 | R_1170 | 30 | 65810 | 65839 | R_1921 | 20 | 111141 | 111160 |
| R_420 | 49 | 23066 | 23114 | R_1171 | 26 | 65850 | 65875 | R_1922 | 21 | 111162 | 111182 |
| R_421 | 35 | 23131 | 23165 | R_1172 | 32 | 65877 | 65908 | R_1923 | 35 | 111184 | 111218 |
| R_422 | 22 | 23168 | 23189 | R_1173 | 29 | 65917 | 65945 | R_1924 | 22 | 111234 | 111255 |
| R_423 | 46 | 23191 | 23236 | R_1174 | 55 | 66048 | 66102 | R_1925 | 20 | 111298 | 111317 |
| R_424 | 45 | 23238 | 23282 | R_1175 | 41 | 66123 | 66163 | R_1926 | 26 | 111319 | 111344 |
| R_425 | 23 | 23318 | 23340 | R_1176 | 37 | 66165 | 66201 | R_1927 | 61 | 111403 | 111463 |
| R_426 | 21 | 23497 | 23517 | R_1177 | 66 | 66203 | 66268 | R_1928 | 57 | 111467 | 111523 |
| R_427 | 24 | 23518 | 23541 | R_1178 | 49 | 66291 | 66339 | R_1929 | 23 | 111525 | 111547 |
| R_428 | 22 | 23562 | 23583 | R_1179 | 34 | 66392 | 66425 | R_1930 | 24 | 111567 | 111590 |
| R_429 | 26 | 23585 | 23610 | R_1180 | 45 | 66469 | 66513 | R_1931 | 26 | 111592 | 111617 |
| R_430 | 46 | 23626 | 23671 | R_1181 | 23 | 66545 | 66567 | R_1932 | 24 | 111631 | 111654 |
| R_431 | 34 | 23637 | 23670 | R_1182 | 27 | 66591 | 66617 | R_1933 | 22 | 111666 | 111687 |
| R_432 | 21 | 23650 | 23670 | R_1183 | 24 | 66635 | 66658 | R_1934 | 21 | 111692 | 111712 |

TABLE 4-continued

Regions (reg.) on SEQ ID NO: 1 which may be targeted using an oligonucleotide of the invention

| Reg. | length (nt) | Position on SEQ ID NO: 1 start | end | Reg. | length (nt) | Position on SEQ ID NO: 1 start | end | Reg. | length (nt) | Position on SEQ ID NO: 1 start | end |
|---|---|---|---|---|---|---|---|---|---|---|---|
| R_433 | 28 | 23718 | 23745 | R_1184 | 22 | 66660 | 66681 | R_1935 | 49 | 111732 | 111780 |
| R_434 | 87 | 23748 | 23834 | R_1185 | 49 | 66690 | 66738 | R_1936 | 31 | 111815 | 111845 |
| R_435 | 41 | 23836 | 23876 | R_1186 | 29 | 66755 | 66783 | R_1937 | 21 | 111908 | 111928 |
| R_436 | 30 | 23889 | 23918 | R_1187 | 36 | 66789 | 66824 | R_1938 | 39 | 111934 | 111972 |
| R_437 | 83 | 23975 | 24057 | R_1188 | 23 | 66792 | 66814 | R_1939 | 26 | 111974 | 111999 |
| R_438 | 99 | 24059 | 24157 | R_1189 | 23 | 66865 | 66887 | R_1940 | 58 | 112001 | 112058 |
| R_439 | 37 | 24219 | 24255 | R_1190 | 27 | 66889 | 66915 | R_1941 | 28 | 112064 | 112091 |
| R_440 | 33 | 24319 | 24351 | R_1191 | 48 | 66991 | 67038 | R_1942 | 24 | 112066 | 112089 |
| R_441 | 20 | 24342 | 24361 | R_1192 | 24 | 67116 | 67139 | R_1943 | 21 | 112122 | 112142 |
| R_442 | 71 | 24354 | 24424 | R_1193 | 24 | 67155 | 67178 | R_1944 | 24 | 112157 | 112180 |
| R_443 | 28 | 24447 | 24474 | R_1194 | 27 | 67185 | 67211 | R_1945 | 21 | 112221 | 112241 |
| R_444 | 21 | 24515 | 24535 | R_1195 | 35 | 67231 | 67265 | R_1946 | 26 | 112253 | 112278 |
| R_445 | 31 | 24536 | 24566 | R_1196 | 20 | 67316 | 67335 | R_1947 | 23 | 112428 | 112450 |
| R_446 | 20 | 24552 | 24571 | R_1197 | 23 | 67337 | 67359 | R_1948 | 26 | 112444 | 112469 |
| R_447 | 26 | 24592 | 24617 | R_1198 | 31 | 67361 | 67391 | R_1949 | 30 | 112501 | 112530 |
| R_448 | 26 | 24656 | 24681 | R_1199 | 37 | 67467 | 67503 | R_1950 | 20 | 112511 | 112530 |
| R_449 | 25 | 24716 | 24740 | R_1200 | 27 | 67498 | 67524 | R_1951 | 69 | 112757 | 112825 |
| R_450 | 20 | 24721 | 24740 | R_1201 | 23 | 67499 | 67521 | R_1952 | 20 | 112884 | 112903 |
| R_451 | 57 | 24817 | 24873 | R_1202 | 37 | 67517 | 67553 | R_1953 | 44 | 112905 | 112948 |
| R_452 | 41 | 24903 | 24943 | R_1203 | 26 | 67604 | 67629 | R_1954 | 28 | 112979 | 113006 |
| R_453 | 26 | 24958 | 24983 | R_1204 | 25 | 67624 | 67648 | R_1955 | 62 | 113062 | 113123 |
| R_454 | 20 | 24985 | 25004 | R_1205 | 26 | 67708 | 67733 | R_1956 | 36 | 113141 | 113176 |
| R_455 | 48 | 25014 | 25061 | R_1206 | 21 | 67806 | 67826 | R_1957 | 23 | 113172 | 113194 |
| R_456 | 55 | 25122 | 25176 | R_1207 | 27 | 67877 | 67903 | R_1958 | 26 | 113203 | 113228 |
| R_457 | 29 | 25178 | 25206 | R_1208 | 43 | 67905 | 67947 | R_1959 | 37 | 113277 | 113313 |
| R_458 | 25 | 25249 | 25273 | R_1209 | 36 | 67987 | 68022 | R_1960 | 32 | 113364 | 113395 |
| R_459 | 30 | 25279 | 25308 | R_1210 | 50 | 68024 | 68073 | R_1961 | 43 | 113397 | 113439 |
| R_460 | 40 | 25310 | 25349 | R_1211 | 92 | 68092 | 68183 | R_1962 | 118 | 113452 | 113569 |
| R_461 | 53 | 25369 | 25421 | R_1212 | 24 | 68216 | 68239 | R_1963 | 46 | 113572 | 113617 |
| R_462 | 52 | 25427 | 25478 | R_1213 | 52 | 68257 | 68308 | R_1964 | 21 | 113628 | 113648 |
| R_463 | 66 | 25514 | 25579 | R_1214 | 32 | 68390 | 68421 | R_1965 | 21 | 113662 | 113682 |
| R_464 | 21 | 25618 | 25638 | R_1215 | 48 | 68442 | 68489 | R_1966 | 36 | 113690 | 113725 |
| R_465 | 51 | 25679 | 25729 | R_1216 | 20 | 68486 | 68505 | R_1967 | 32 | 113729 | 113760 |
| R_466 | 39 | 25731 | 25769 | R_1217 | 21 | 68546 | 68566 | R_1968 | 28 | 113782 | 113809 |
| R_467 | 28 | 25825 | 25852 | R_1218 | 25 | 68556 | 68580 | R_1969 | 21 | 113997 | 114017 |
| R_468 | 72 | 25881 | 25952 | R_1219 | 20 | 68561 | 68580 | R_1970 | 22 | 114007 | 114028 |
| R_469 | 23 | 25964 | 25986 | R_1220 | 23 | 68610 | 68632 | R_1971 | 57 | 114039 | 114095 |
| R_470 | 59 | 25988 | 26046 | R_1221 | 25 | 68679 | 68703 | R_1972 | 32 | 114174 | 114205 |
| R_471 | 25 | 26061 | 26085 | R_1222 | 35 | 68736 | 68770 | R_1973 | 28 | 114235 | 114262 |
| R_472 | 34 | 26088 | 26121 | R_1223 | 62 | 68806 | 68867 | R_1974 | 21 | 114349 | 114369 |
| R_473 | 24 | 26162 | 26185 | R_1224 | 22 | 68885 | 68906 | R_1975 | 38 | 114395 | 114432 |
| R_474 | 30 | 26194 | 26223 | R_1225 | 22 | 68908 | 68929 | R_1976 | 31 | 114434 | 114464 |
| R_475 | 28 | 26233 | 26260 | R_1226 | 20 | 68931 | 68950 | R_1977 | 20 | 114529 | 114548 |
| R_476 | 38 | 26335 | 26372 | R_1227 | 29 | 68950 | 68978 | R_1978 | 34 | 114624 | 114657 |
| R_477 | 24 | 26395 | 26418 | R_1228 | 34 | 69017 | 69050 | R_1979 | 65 | 114711 | 114775 |
| R_478 | 24 | 26455 | 26478 | R_1229 | 25 | 69053 | 69077 | R_1980 | 22 | 114904 | 114925 |
| R_479 | 27 | 26480 | 26506 | R_1230 | 20 | 69083 | 69102 | R_1981 | 42 | 114930 | 114971 |
| R_480 | 42 | 26521 | 26562 | R_1231 | 27 | 69123 | 69149 | R_1982 | 22 | 114982 | 115003 |
| R_481 | 67 | 26684 | 26750 | R_1232 | 30 | 69160 | 69189 | R_1983 | 20 | 115005 | 115024 |
| R_482 | 24 | 26752 | 26775 | R_1233 | 35 | 69210 | 69244 | R_1984 | 42 | 115026 | 115067 |
| R_483 | 35 | 26822 | 26856 | R_1234 | 53 | 69248 | 69300 | R_1985 | 28 | 115092 | 115119 |
| R_484 | 22 | 26937 | 26958 | R_1235 | 23 | 69304 | 69326 | R_1986 | 57 | 115121 | 115177 |
| R_485 | 38 | 26984 | 27021 | R_1236 | 34 | 69393 | 69426 | R_1987 | 28 | 115179 | 115206 |
| R_486 | 24 | 27022 | 27045 | R_1237 | 29 | 69428 | 69456 | R_1988 | 31 | 115228 | 115258 |
| R_487 | 54 | 27053 | 27106 | R_1238 | 45 | 69458 | 69502 | R_1989 | 24 | 115263 | 115286 |
| R_488 | 91 | 27154 | 27244 | R_1239 | 43 | 69547 | 69589 | R_1990 | 37 | 115306 | 115342 |
| R_489 | 35 | 27283 | 27317 | R_1240 | 20 | 69601 | 69620 | R_1991 | 44 | 115361 | 115404 |
| R_490 | 25 | 27339 | 27363 | R_1241 | 20 | 69633 | 69652 | R_1992 | 20 | 115467 | 115486 |
| R_491 | 75 | 27386 | 27460 | R_1242 | 29 | 69656 | 69684 | R_1993 | 30 | 115628 | 115657 |
| R_492 | 41 | 27493 | 27533 | R_1243 | 39 | 69705 | 69743 | R_1994 | 26 | 115665 | 115690 |
| R_493 | 22 | 27602 | 27623 | R_1244 | 42 | 69769 | 69810 | R_1995 | 34 | 115687 | 115720 |
| R_494 | 33 | 27631 | 27663 | R_1245 | 22 | 69829 | 69850 | R_1996 | 28 | 115804 | 115831 |
| R_495 | 23 | 27691 | 27713 | R_1246 | 28 | 69912 | 69939 | R_1997 | 26 | 115833 | 115858 |
| R_496 | 33 | 27736 | 27768 | R_1247 | 32 | 69941 | 69972 | R_1998 | 27 | 115937 | 115963 |
| R_497 | 24 | 27752 | 27775 | R_1248 | 31 | 70029 | 70059 | R_1999 | 119 | 115965 | 116083 |
| R_498 | 26 | 27777 | 27802 | R_1249 | 41 | 70065 | 70105 | R_2000 | 23 | 116085 | 116107 |
| R_499 | 20 | 27777 | 27796 | R_1250 | 27 | 70162 | 70188 | R_2001 | 42 | 116121 | 116162 |
| R_500 | 23 | 27778 | 27800 | R_1251 | 43 | 70200 | 70242 | R_2002 | 33 | 116193 | 116225 |
| R_501 | 30 | 27859 | 27888 | R_1252 | 20 | 70217 | 70236 | R_2003 | 24 | 116276 | 116299 |
| R_502 | 38 | 27909 | 27946 | R_1253 | 20 | 70345 | 70364 | R_2004 | 26 | 116356 | 116381 |
| R_503 | 49 | 27956 | 28004 | R_1254 | 35 | 70366 | 70400 | R_2005 | 29 | 116405 | 116433 |
| R_504 | 45 | 28071 | 28115 | R_1255 | 57 | 70433 | 70489 | R_2006 | 46 | 116441 | 116486 |

TABLE 4-continued

Regions (reg.) on SEQ ID NO: 1 which may be targeted using an oligonucleotide of the invention

| Reg. | length (nt) | Position on SEQ ID NO: 1 start | end | Reg. | length (nt) | Position on SEQ ID NO: 1 start | end | Reg. | length (nt) | Position on SEQ ID NO: 1 start | end |
|---|---|---|---|---|---|---|---|---|---|---|---|
| R_505 | 33 | 28124 | 28156 | R_1256 | 21 | 70515 | 70535 | R_2007 | 29 | 116488 | 116516 |
| R_506 | 20 | 28152 | 28171 | R_1257 | 26 | 70537 | 70562 | R_2008 | 40 | 116518 | 116557 |
| R_507 | 24 | 28181 | 28204 | R_1258 | 40 | 70583 | 70622 | R_2009 | 46 | 116653 | 116698 |
| R_508 | 25 | 28251 | 28275 | R_1259 | 20 | 70657 | 70676 | R_2010 | 28 | 116700 | 116727 |
| R_509 | 33 | 28295 | 28327 | R_1260 | 22 | 70688 | 70709 | R_2011 | 46 | 116729 | 116774 |
| R_510 | 28 | 28345 | 28372 | R_1261 | 34 | 70723 | 70756 | R_2012 | 43 | 116927 | 116969 |
| R_511 | 51 | 28383 | 28433 | R_1262 | 23 | 70758 | 70780 | R_2013 | 32 | 116997 | 117028 |
| R_512 | 38 | 28441 | 28478 | R_1263 | 21 | 70782 | 70802 | R_2014 | 23 | 117043 | 117065 |
| R_513 | 24 | 28553 | 28576 | R_1264 | 21 | 70808 | 70828 | R_2015 | 35 | 117068 | 117102 |
| R_514 | 37 | 28598 | 28634 | R_1265 | 26 | 70818 | 70843 | R_2016 | 28 | 117148 | 117175 |
| R_515 | 35 | 28669 | 28703 | R_1266 | 31 | 70912 | 70942 | R_2017 | 36 | 117195 | 117230 |
| R_516 | 23 | 28733 | 28755 | R_1267 | 22 | 71039 | 71060 | R_2018 | 20 | 117243 | 117262 |
| R_517 | 31 | 28758 | 28788 | R_1268 | 25 | 71104 | 71128 | R_2019 | 37 | 117273 | 117309 |
| R_518 | 21 | 28857 | 28877 | R_1269 | 24 | 71195 | 71218 | R_2020 | 32 | 117329 | 117360 |
| R_519 | 38 | 28922 | 28959 | R_1270 | 43 | 71467 | 71509 | R_2021 | 59 | 117432 | 117490 |
| R_520 | 58 | 29019 | 29076 | R_1271 | 36 | 71519 | 71554 | R_2022 | 21 | 117509 | 117529 |
| R_521 | 22 | 29115 | 29136 | R_1272 | 24 | 71560 | 71583 | R_2023 | 23 | 117557 | 117579 |
| R_522 | 66 | 29198 | 29263 | R_1273 | 30 | 71606 | 71635 | R_2024 | 65 | 117580 | 117644 |
| R_523 | 24 | 29297 | 29320 | R_1274 | 21 | 71637 | 71657 | R_2025 | 27 | 117646 | 117672 |
| R_524 | 41 | 29335 | 29375 | R_1275 | 22 | 71672 | 71693 | R_2026 | 22 | 117708 | 117729 |
| R_525 | 21 | 29386 | 29406 | R_1276 | 56 | 71744 | 71799 | R_2027 | 47 | 117730 | 117776 |
| R_526 | 22 | 29433 | 29454 | R_1277 | 35 | 71827 | 71861 | R_2028 | 37 | 117778 | 117814 |
| R_527 | 40 | 29473 | 29512 | R_1278 | 21 | 71863 | 71883 | R_2029 | 24 | 117881 | 117904 |
| R_528 | 29 | 29531 | 29559 | R_1279 | 32 | 71913 | 71944 | R_2030 | 40 | 117904 | 117943 |
| R_529 | 41 | 29586 | 29626 | R_1280 | 25 | 71946 | 71970 | R_2031 | 30 | 117945 | 117974 |
| R_530 | 29 | 29635 | 29663 | R_1281 | 23 | 72022 | 72044 | R_2032 | 28 | 117993 | 118020 |
| R_531 | 36 | 29665 | 29700 | R_1282 | 28 | 72092 | 72119 | R_2033 | 48 | 118064 | 118111 |
| R_532 | 93 | 29750 | 29842 | R_1283 | 22 | 72095 | 72116 | R_2034 | 27 | 118113 | 118139 |
| R_533 | 35 | 29853 | 29887 | R_1284 | 21 | 72121 | 72141 | R_2035 | 27 | 118141 | 118167 |
| R_534 | 22 | 29907 | 29928 | R_1285 | 50 | 72147 | 72196 | R_2036 | 29 | 118169 | 118197 |
| R_535 | 77 | 29964 | 30040 | R_1286 | 31 | 72204 | 72234 | R_2037 | 33 | 118210 | 118242 |
| R_536 | 38 | 30093 | 30130 | R_1287 | 23 | 72230 | 72252 | R_2038 | 45 | 118386 | 118430 |
| R_537 | 30 | 30169 | 30198 | R_1288 | 36 | 72236 | 72271 | R_2039 | 48 | 118446 | 118493 |
| R_538 | 32 | 30210 | 30241 | R_1289 | 31 | 72285 | 72315 | R_2040 | 24 | 118532 | 118555 |
| R_539 | 20 | 30243 | 30262 | R_1290 | 85 | 72314 | 72398 | R_2041 | 46 | 118634 | 118679 |
| R_540 | 20 | 30303 | 30322 | R_1291 | 52 | 72400 | 72451 | R_2042 | 44 | 118774 | 118817 |
| R_541 | 23 | 30324 | 30346 | R_1292 | 37 | 72443 | 72479 | R_2043 | 54 | 118841 | 118894 |
| R_542 | 27 | 30362 | 30388 | R_1293 | 31 | 72482 | 72512 | R_2044 | 20 | 118912 | 118931 |
| R_543 | 30 | 30390 | 30419 | R_1294 | 40 | 72566 | 72605 | R_2045 | 21 | 118999 | 119019 |
| R_544 | 31 | 30462 | 30492 | R_1295 | 49 | 72607 | 72655 | R_2046 | 44 | 119283 | 119326 |
| R_545 | 22 | 30534 | 30555 | R_1296 | 86 | 72657 | 72742 | R_2047 | 33 | 119353 | 119385 |
| R_546 | 28 | 30557 | 30584 | R_1297 | 63 | 72752 | 72814 | R_2048 | 39 | 119392 | 119430 |
| R_547 | 24 | 30596 | 30619 | R_1298 | 125 | 72816 | 72940 | R_2049 | 65 | 119441 | 119505 |
| R_548 | 30 | 30626 | 30655 | R_1299 | 31 | 72955 | 72985 | R_2050 | 21 | 119566 | 119586 |
| R_549 | 41 | 30675 | 30715 | R_1300 | 20 | 72987 | 73006 | R_2051 | 55 | 119604 | 119658 |
| R_550 | 33 | 30726 | 30758 | R_1301 | 40 | 73008 | 73047 | R_2052 | 24 | 119660 | 119683 |
| R_551 | 29 | 30787 | 30815 | R_1302 | 24 | 73049 | 73072 | R_2053 | 42 | 119685 | 119726 |
| R_552 | 62 | 30819 | 30880 | R_1303 | 37 | 73118 | 73154 | R_2054 | 33 | 119736 | 119768 |
| R_553 | 79 | 30972 | 31050 | R_1304 | 26 | 73163 | 73188 | R_2055 | 32 | 119770 | 119801 |
| R_554 | 67 | 31053 | 31119 | R_1305 | 29 | 73212 | 73240 | R_2056 | 34 | 119804 | 119837 |
| R_555 | 56 | 31121 | 31176 | R_1306 | 22 | 73279 | 73300 | R_2057 | 116 | 119885 | 120000 |
| R_556 | 22 | 31178 | 31199 | R_1307 | 22 | 73315 | 73336 | R_2058 | 59 | 120128 | 120186 |
| R_557 | 22 | 31207 | 31228 | R_1308 | 30 | 73338 | 73367 | R_2059 | 34 | 120317 | 120350 |
| R_558 | 27 | 31227 | 31253 | R_1309 | 23 | 73387 | 73409 | R_2060 | 24 | 120530 | 120553 |
| R_559 | 27 | 31255 | 31281 | R_1310 | 52 | 73411 | 73462 | R_2061 | 22 | 120571 | 120592 |
| R_560 | 58 | 31310 | 31367 | R_1311 | 26 | 73498 | 73523 | R_2062 | 35 | 120611 | 120645 |
| R_561 | 26 | 31383 | 31408 | R_1312 | 24 | 73525 | 73548 | R_2063 | 98 | 120663 | 120760 |
| R_562 | 20 | 31419 | 31438 | R_1313 | 83 | 73562 | 73644 | R_2064 | 20 | 120924 | 120943 |
| R_563 | 36 | 31440 | 31475 | R_1314 | 36 | 73646 | 73681 | R_2065 | 22 | 121093 | 121114 |
| R_564 | 26 | 31503 | 31528 | R_1315 | 20 | 73703 | 73722 | R_2066 | 29 | 121117 | 121145 |
| R_565 | 34 | 31530 | 31563 | R_1316 | 27 | 73725 | 73751 | R_2067 | 39 | 121244 | 121282 |
| R_566 | 23 | 31585 | 31607 | R_1317 | 62 | 73776 | 73837 | R_2068 | 48 | 121365 | 121412 |
| R_567 | 21 | 31611 | 31631 | R_1318 | 20 | 73845 | 73864 | R_2069 | 37 | 121414 | 121450 |
| R_568 | 21 | 31614 | 31634 | R_1319 | 61 | 73894 | 73954 | R_2070 | 25 | 121649 | 121673 |
| R_569 | 32 | 31675 | 31706 | R_1320 | 91 | 73955 | 74045 | R_2071 | 40 | 121687 | 121726 |
| R_570 | 23 | 31708 | 31730 | R_1321 | 32 | 74079 | 74110 | R_2072 | 45 | 121728 | 121772 |
| R_571 | 39 | 31737 | 31775 | R_1322 | 28 | 74115 | 74142 | R_2073 | 22 | 121795 | 121816 |
| R_572 | 68 | 31763 | 31830 | R_1323 | 62 | 74144 | 74205 | R_2074 | 24 | 121939 | 121962 |
| R_573 | 27 | 31763 | 31789 | R_1324 | 27 | 74214 | 74240 | R_2075 | 28 | 122038 | 122065 |
| R_574 | 20 | 31803 | 31822 | R_1325 | 62 | 74244 | 74305 | R_2076 | 30 | 122218 | 122247 |
| R_575 | 23 | 31832 | 31854 | R_1326 | 28 | 74320 | 74347 | R_2077 | 27 | 122273 | 122299 |
| R_576 | 50 | 31952 | 32001 | R_1327 | 24 | 74350 | 74373 | R_2078 | 21 | 122301 | 122321 |

TABLE 4-continued

Regions (reg.) on SEQ ID NO: 1 which may be targeted using an oligonucleotide of the invention

| Reg. | length (nt) | Position on SEQ ID NO: 1 start | end | Reg. | length (nt) | Position on SEQ ID NO: 1 start | end | Reg. | length (nt) | Position on SEQ ID NO: 1 start | end |
|---|---|---|---|---|---|---|---|---|---|---|---|
| R_577 | 22 | 32110 | 32131 | R_1328 | 46 | 74386 | 74431 | R_2079 | 30 | 122318 | 122347 |
| R_578 | 20 | 32114 | 32133 | R_1329 | 23 | 74433 | 74455 | R_2080 | 32 | 122356 | 122387 |
| R_579 | 35 | 32143 | 32177 | R_1330 | 31 | 74463 | 74493 | R_2081 | 21 | 122428 | 122448 |
| R_580 | 45 | 32179 | 32223 | R_1331 | 48 | 74497 | 74544 | R_2082 | 21 | 122432 | 122452 |
| R_581 | 26 | 32208 | 32233 | R_1332 | 40 | 74546 | 74585 | R_2083 | 24 | 123020 | 123043 |
| R_582 | 49 | 32225 | 32273 | R_1333 | 20 | 74604 | 74623 | R_2084 | 30 | 123038 | 123067 |
| R_583 | 27 | 32289 | 32315 | R_1334 | 65 | 74648 | 74712 | R_2085 | 26 | 123052 | 123077 |
| R_584 | 34 | 32317 | 32350 | R_1335 | 29 | 74725 | 74753 | R_2086 | 22 | 123258 | 123279 |
| R_585 | 32 | 32352 | 32383 | R_1336 | 35 | 74764 | 74798 | R_2087 | 28 | 123291 | 123318 |
| R_586 | 25 | 32390 | 32414 | R_1337 | 57 | 74805 | 74861 | R_2088 | 22 | 123402 | 123423 |
| R_587 | 46 | 32416 | 32461 | R_1338 | 56 | 74863 | 74918 | R_2089 | 27 | 123644 | 123670 |
| R_588 | 37 | 32497 | 32533 | R_1339 | 37 | 74936 | 74972 | R_2090 | 20 | 123819 | 123838 |
| R_589 | 37 | 32691 | 32727 | R_1340 | 28 | 74974 | 75001 | R_2091 | 26 | 123841 | 123866 |
| R_590 | 23 | 32753 | 32775 | R_1341 | 53 | 75003 | 75055 | R_2092 | 25 | 123965 | 123989 |
| R_591 | 38 | 32794 | 32831 | R_1342 | 22 | 75019 | 75040 | R_2093 | 24 | 123997 | 124020 |
| R_592 | 24 | 32835 | 32858 | R_1343 | 30 | 75097 | 75126 | R_2094 | 35 | 124034 | 124068 |
| R_593 | 55 | 32890 | 32944 | R_1344 | 51 | 75126 | 75176 | R_2095 | 44 | 124075 | 124118 |
| R_594 | 52 | 32959 | 33010 | R_1345 | 28 | 75362 | 75389 | R_2096 | 50 | 124156 | 124205 |
| R_595 | 37 | 33025 | 33061 | R_1346 | 29 | 75417 | 75445 | R_2097 | 75 | 124247 | 124321 |
| R_596 | 23 | 33063 | 33085 | R_1347 | 54 | 75482 | 75535 | R_2098 | 23 | 124353 | 124375 |
| R_597 | 62 | 33087 | 33148 | R_1348 | 27 | 75552 | 75578 | R_2099 | 34 | 124377 | 124410 |
| R_598 | 23 | 33160 | 33182 | R_1349 | 27 | 75580 | 75606 | R_2100 | 84 | 124472 | 124555 |
| R_599 | 21 | 33190 | 33210 | R_1350 | 26 | 75593 | 75618 | R_2101 | 20 | 124557 | 124576 |
| R_600 | 24 | 33222 | 33245 | R_1351 | 41 | 75815 | 75855 | R_2102 | 32 | 124648 | 124679 |
| R_601 | 56 | 33258 | 33313 | R_1352 | 30 | 75919 | 75948 | R_2103 | 22 | 124688 | 124709 |
| R_602 | 26 | 33317 | 33342 | R_1353 | 20 | 75944 | 75963 | R_2104 | 20 | 124700 | 124719 |
| R_603 | 25 | 33344 | 33368 | R_1354 | 37 | 75964 | 76000 | R_2105 | 35 | 124712 | 124746 |
| R_604 | 20 | 33379 | 33398 | R_1355 | 20 | 76123 | 76142 | R_2106 | 70 | 124748 | 124817 |
| R_605 | 22 | 33395 | 33416 | R_1356 | 30 | 76156 | 76185 | R_2107 | 21 | 124824 | 124844 |
| R_606 | 20 | 33395 | 33414 | R_1357 | 80 | 76199 | 76278 | R_2108 | 23 | 124859 | 124881 |
| R_607 | 22 | 33400 | 33421 | R_1358 | 23 | 76296 | 76318 | R_2109 | 35 | 124883 | 124917 |
| R_608 | 22 | 33457 | 33478 | R_1359 | 21 | 76327 | 76347 | R_2110 | 20 | 124919 | 124938 |
| R_609 | 22 | 33512 | 33533 | R_1360 | 24 | 76341 | 76364 | R_2111 | 57 | 124940 | 124996 |
| R_610 | 23 | 33532 | 33554 | R_1361 | 61 | 76366 | 76426 | R_2112 | 38 | 125015 | 125052 |
| R_611 | 24 | 33532 | 33555 | R_1362 | 26 | 76467 | 76492 | R_2113 | 21 | 125032 | 125052 |
| R_612 | 28 | 33535 | 33562 | R_1363 | 35 | 76520 | 76554 | R_2114 | 29 | 125064 | 125092 |
| R_613 | 21 | 33547 | 33567 | R_1364 | 58 | 76571 | 76628 | R_2115 | 37 | 125107 | 125143 |
| R_614 | 20 | 33548 | 33567 | R_1365 | 57 | 76697 | 76753 | R_2116 | 42 | 125198 | 125239 |
| R_615 | 23 | 33582 | 33604 | R_1366 | 22 | 76755 | 76776 | R_2117 | 50 | 125241 | 125290 |
| R_616 | 20 | 33588 | 33607 | R_1367 | 23 | 76822 | 76844 | R_2118 | 42 | 125292 | 125333 |
| R_617 | 24 | 33618 | 33641 | R_1368 | 42 | 76863 | 76904 | R_2119 | 31 | 125346 | 125376 |
| R_618 | 26 | 33675 | 33700 | R_1369 | 26 | 76906 | 76931 | R_2120 | 22 | 125378 | 125399 |
| R_619 | 29 | 33726 | 33754 | R_1370 | 51 | 76944 | 76994 | R_2121 | 46 | 125401 | 125446 |
| R_620 | 47 | 33775 | 33821 | R_1371 | 69 | 77037 | 77105 | R_2122 | 33 | 125700 | 125732 |
| R_621 | 20 | 33835 | 33854 | R_1372 | 26 | 77153 | 77178 | R_2123 | 32 | 125734 | 125765 |
| R_622 | 49 | 33856 | 33904 | R_1373 | 85 | 77180 | 77264 | R_2124 | 48 | 125803 | 125850 |
| R_623 | 64 | 33948 | 34011 | R_1374 | 35 | 77271 | 77305 | R_2125 | 35 | 125912 | 125946 |
| R_624 | 20 | 34025 | 34044 | R_1375 | 41 | 77307 | 77347 | R_2126 | 45 | 125948 | 125992 |
| R_625 | 20 | 34072 | 34091 | R_1376 | 27 | 77433 | 77459 | R_2127 | 73 | 126012 | 126084 |
| R_626 | 31 | 34139 | 34169 | R_1377 | 24 | 77462 | 77485 | R_2128 | 60 | 126087 | 126146 |
| R_627 | 78 | 34179 | 34256 | R_1378 | 30 | 77508 | 77537 | R_2129 | 32 | 126341 | 126372 |
| R_628 | 49 | 34258 | 34306 | R_1379 | 36 | 77561 | 77596 | R_2130 | 22 | 126374 | 126395 |
| R_629 | 29 | 34379 | 34407 | R_1380 | 39 | 77615 | 77653 | R_2131 | 25 | 126388 | 126412 |
| R_630 | 21 | 34417 | 34437 | R_1381 | 50 | 77655 | 77704 | R_2132 | 20 | 126473 | 126492 |
| R_631 | 27 | 34449 | 34475 | R_1382 | 20 | 77719 | 77738 | R_2133 | 22 | 126484 | 126505 |
| R_632 | 24 | 34495 | 34518 | R_1383 | 26 | 77762 | 77787 | R_2134 | 24 | 126660 | 126683 |
| R_633 | 21 | 34516 | 34536 | R_1384 | 29 | 77807 | 77835 | R_2135 | 23 | 126691 | 126713 |
| R_634 | 21 | 34562 | 34582 | R_1385 | 23 | 77837 | 77859 | R_2136 | 34 | 126715 | 126748 |
| R_635 | 21 | 34572 | 34592 | R_1386 | 26 | 77861 | 77886 | R_2137 | 22 | 126822 | 126843 |
| R_636 | 22 | 34576 | 34597 | R_1387 | 22 | 77910 | 77931 | R_2138 | 20 | 126885 | 126904 |
| R_637 | 32 | 34612 | 34643 | R_1388 | 45 | 77933 | 77977 | R_2139 | 38 | 127054 | 127091 |
| R_638 | 24 | 34646 | 34669 | R_1389 | 36 | 78017 | 78052 | R_2140 | 40 | 127111 | 127150 |
| R_639 | 65 | 34681 | 34745 | R_1390 | 24 | 78074 | 78097 | R_2141 | 30 | 127201 | 127230 |
| R_640 | 139 | 34765 | 34903 | R_1391 | 47 | 78136 | 78182 | R_2142 | 21 | 127232 | 127252 |
| R_641 | 60 | 34943 | 35002 | R_1392 | 93 | 78184 | 78276 | R_2143 | 76 | 127258 | 127333 |
| R_642 | 52 | 35012 | 35063 | R_1393 | 24 | 78282 | 78305 | R_2144 | 59 | 127359 | 127417 |
| R_643 | 83 | 35065 | 35147 | R_1394 | 99 | 78319 | 78417 | R_2145 | 33 | 127419 | 127451 |
| R_644 | 21 | 35160 | 35180 | R_1395 | 42 | 78420 | 78461 | R_2146 | 52 | 127567 | 127618 |
| R_645 | 29 | 35188 | 35216 | R_1396 | 23 | 78478 | 78500 | R_2147 | 38 | 127620 | 127657 |
| R_646 | 21 | 35218 | 35238 | R_1397 | 21 | 78647 | 78667 | R_2148 | 49 | 127656 | 127704 |
| R_647 | 59 | 35269 | 35327 | R_1398 | 34 | 78736 | 78769 | R_2149 | 37 | 127706 | 127742 |
| R_648 | 26 | 35330 | 35355 | R_1399 | 20 | 78891 | 78910 | R_2150 | 60 | 127761 | 127820 |

TABLE 4-continued

Regions (reg.) on SEQ ID NO: 1 which may be targeted using an oligonucleotide of the invention

| Reg. | length (nt) | Position on SEQ ID NO: 1 start | end | Reg. | length (nt) | Position on SEQ ID NO: 1 start | end | Reg. | length (nt) | Position on SEQ ID NO: 1 start | end |
|---|---|---|---|---|---|---|---|---|---|---|---|
| R_649 | 44 | 35372 | 35415 | R_1400 | 26 | 78926 | 78951 | R_2151 | 25 | 127953 | 127977 |
| R_650 | 20 | 35417 | 35436 | R_1401 | 21 | 78953 | 78973 | R_2152 | 30 | 128097 | 128126 |
| R_651 | 43 | 35442 | 35484 | R_1402 | 69 | 78997 | 79065 | R_2153 | 40 | 128187 | 128226 |
| R_652 | 22 | 35482 | 35503 | R_1403 | 21 | 79067 | 79087 | R_2154 | 58 | 128237 | 128294 |
| R_653 | 74 | 35505 | 35578 | R_1404 | 25 | 79091 | 79115 | R_2155 | 20 | 128323 | 128342 |
| R_654 | 20 | 35599 | 35618 | R_1405 | 21 | 79122 | 79142 | R_2156 | 32 | 128408 | 128439 |
| R_655 | 25 | 35620 | 35644 | R_1406 | 24 | 79160 | 79183 | R_2157 | 37 | 128425 | 128461 |
| R_656 | 39 | 35654 | 35692 | R_1407 | 31 | 79187 | 79217 | R_2158 | 22 | 128463 | 128484 |
| R_657 | 26 | 35697 | 35722 | R_1408 | 75 | 79219 | 79293 | R_2159 | 56 | 128500 | 128555 |
| R_658 | 30 | 35724 | 35753 | R_1409 | 27 | 79308 | 79334 | R_2160 | 21 | 128565 | 128585 |
| R_659 | 23 | 35756 | 35778 | R_1410 | 71 | 79366 | 79436 | R_2161 | 29 | 128586 | 128614 |
| R_660 | 22 | 35777 | 35798 | R_1411 | 34 | 79469 | 79502 | R_2162 | 53 | 128631 | 128683 |
| R_661 | 40 | 35838 | 35877 | R_1412 | 41 | 79534 | 79574 | R_2163 | 59 | 128685 | 128743 |
| R_662 | 24 | 35879 | 35902 | R_1413 | 28 | 79576 | 79603 | R_2164 | 99 | 128738 | 128836 |
| R_663 | 20 | 35887 | 35906 | R_1414 | 23 | 79605 | 79627 | R_2165 | 23 | 128850 | 128872 |
| R_664 | 21 | 35894 | 35914 | R_1415 | 24 | 79712 | 79735 | R_2166 | 20 | 128896 | 128915 |
| R_665 | 62 | 35928 | 35989 | R_1416 | 35 | 79738 | 79772 | R_2167 | 63 | 128922 | 128984 |
| R_666 | 27 | 36002 | 36028 | R_1417 | 37 | 79793 | 79829 | R_2168 | 25 | 129031 | 129055 |
| R_667 | 20 | 36025 | 36044 | R_1418 | 38 | 79847 | 79884 | R_2169 | 28 | 129071 | 129098 |
| R_668 | 21 | 36030 | 36050 | R_1419 | 48 | 79924 | 79971 | R_2170 | 69 | 129104 | 129172 |
| R_669 | 64 | 36099 | 36162 | R_1420 | 31 | 80108 | 80138 | R_2171 | 27 | 129196 | 129222 |
| R_670 | 30 | 36171 | 36200 | R_1421 | 34 | 80140 | 80173 | R_2172 | 38 | 129235 | 129272 |
| R_671 | 39 | 36202 | 36240 | R_1422 | 77 | 80211 | 80287 | R_2173 | 30 | 129330 | 129359 |
| R_672 | 56 | 36242 | 36297 | R_1423 | 55 | 80307 | 80361 | R_2174 | 33 | 129345 | 129377 |
| R_673 | 47 | 36307 | 36353 | R_1424 | 26 | 80366 | 80391 | R_2175 | 40 | 129401 | 129440 |
| R_674 | 34 | 36404 | 36437 | R_1425 | 38 | 80419 | 80456 | R_2176 | 24 | 129427 | 129450 |
| R_675 | 22 | 36439 | 36460 | R_1426 | 20 | 80472 | 80491 | R_2177 | 22 | 129443 | 129464 |
| R_676 | 20 | 36493 | 36512 | R_1427 | 21 | 80505 | 80525 | R_2178 | 34 | 129488 | 129521 |
| R_677 | 24 | 36514 | 36537 | R_1428 | 40 | 80527 | 80566 | R_2179 | 79 | 129540 | 129618 |
| R_678 | 20 | 36568 | 36587 | R_1429 | 37 | 80571 | 80607 | R_2180 | 69 | 129617 | 129685 |
| R_679 | 32 | 36589 | 36620 | R_1430 | 40 | 80618 | 80657 | R_2181 | 29 | 129705 | 129733 |
| R_680 | 25 | 36622 | 36646 | R_1431 | 29 | 80671 | 80699 | R_2182 | 65 | 129735 | 129799 |
| R_681 | 22 | 36654 | 36675 | R_1432 | 36 | 80732 | 80767 | R_2183 | 48 | 129801 | 129848 |
| R_682 | 26 | 36678 | 36703 | R_1433 | 39 | 80791 | 80829 | R_2184 | 37 | 129884 | 129920 |
| R_683 | 28 | 36728 | 36755 | R_1434 | 37 | 80830 | 80866 | R_2185 | 42 | 129918 | 129959 |
| R_684 | 41 | 36790 | 36830 | R_1435 | 53 | 80868 | 80920 | R_2186 | 38 | 129988 | 130025 |
| R_685 | 60 | 36862 | 36921 | R_1436 | 30 | 80996 | 81025 | R_2187 | 26 | 130084 | 130109 |
| R_686 | 37 | 36940 | 36976 | R_1437 | 25 | 81027 | 81051 | R_2188 | 24 | 130125 | 130148 |
| R_687 | 55 | 37002 | 37056 | R_1438 | 55 | 81053 | 81107 | R_2189 | 36 | 130150 | 130185 |
| R_688 | 44 | 37124 | 37167 | R_1439 | 68 | 81109 | 81176 | R_2190 | 21 | 130247 | 130267 |
| R_689 | 29 | 37169 | 37197 | R_1440 | 24 | 81225 | 81248 | R_2191 | 80 | 130269 | 130348 |
| R_690 | 25 | 37232 | 37256 | R_1441 | 68 | 81264 | 81331 | R_2192 | 30 | 130384 | 130413 |
| R_691 | 21 | 37258 | 37278 | R_1442 | 23 | 81344 | 81366 | R_2193 | 21 | 130424 | 130444 |
| R_692 | 75 | 37280 | 37354 | R_1443 | 64 | 81377 | 81440 | R_2194 | 37 | 130564 | 130600 |
| R_693 | 93 | 37399 | 37491 | R_1444 | 26 | 81481 | 81506 | R_2195 | 21 | 130663 | 130683 |
| R_694 | 22 | 37465 | 37486 | R_1445 | 31 | 81571 | 81601 | R_2196 | 43 | 130690 | 130732 |
| R_695 | 21 | 37491 | 37511 | R_1446 | 44 | 81608 | 81651 | R_2197 | 61 | 130735 | 130795 |
| R_696 | 20 | 37543 | 37562 | R_1447 | 47 | 81694 | 81740 | R_2198 | 109 | 130797 | 130905 |
| R_697 | 23 | 37582 | 37604 | R_1448 | 27 | 81757 | 81783 | R_2199 | 51 | 130941 | 130991 |
| R_698 | 31 | 37608 | 37638 | R_1449 | 36 | 81780 | 81815 | R_2200 | 23 | 131025 | 131047 |
| R_699 | 21 | 37660 | 37680 | R_1450 | 25 | 81817 | 81841 | R_2201 | 21 | 131064 | 131084 |
| R_700 | 21 | 37720 | 37740 | R_1451 | 46 | 81866 | 81911 | R_2202 | 35 | 131119 | 131153 |
| R_701 | 35 | 37778 | 37812 | R_1452 | 23 | 81916 | 81938 | R_2203 | 62 | 131155 | 131216 |
| R_702 | 72 | 37825 | 37896 | R_1453 | 27 | 81946 | 81972 | R_2204 | 39 | 131269 | 131307 |
| R_703 | 35 | 37926 | 37960 | R_1454 | 20 | 82028 | 82047 | R_2205 | 22 | 131309 | 131330 |
| R_704 | 42 | 37962 | 38003 | R_1455 | 55 | 82049 | 82103 | R_2206 | 32 | 131350 | 131381 |
| R_705 | 20 | 38119 | 38138 | R_1456 | 71 | 82122 | 82192 | R_2207 | 52 | 131432 | 131483 |
| R_706 | 28 | 38162 | 38189 | R_1457 | 32 | 82216 | 82247 | R_2208 | 43 | 131501 | 131543 |
| R_707 | 23 | 38215 | 38237 | R_1458 | 47 | 82278 | 82324 | R_2209 | 20 | 131565 | 131584 |
| R_708 | 22 | 38249 | 38270 | R_1459 | 25 | 82498 | 82522 | R_2210 | 90 | 131606 | 131695 |
| R_709 | 79 | 38284 | 38362 | R_1460 | 27 | 82549 | 82575 | R_2211 | 79 | 131697 | 131775 |
| R_710 | 30 | 38419 | 38448 | R_1461 | 48 | 82606 | 82653 | R_2212 | 69 | 131758 | 131826 |
| R_711 | 25 | 38476 | 38500 | R_1462 | 26 | 82655 | 82680 | R_2213 | 20 | 131877 | 131896 |
| R_712 | 21 | 38486 | 38506 | R_1463 | 27 | 82699 | 82725 | R_2214 | 21 | 131898 | 131918 |
| R_713 | 22 | 38520 | 38541 | R_1464 | 67 | 82735 | 82801 | R_2215 | 23 | 131951 | 131973 |
| R_714 | 47 | 38548 | 38594 | R_1465 | 56 | 82833 | 82888 | R_2216 | 37 | 131975 | 132011 |
| R_715 | 22 | 38603 | 38624 | R_1466 | 29 | 82898 | 82926 | R_2217 | 25 | 132017 | 132041 |
| R_716 | 27 | 38623 | 38649 | R_1467 | 26 | 82928 | 82953 | R_2218 | 29 | 132061 | 132089 |
| R_717 | 22 | 38709 | 38730 | R_1468 | 45 | 82990 | 83034 | R_2219 | 22 | 132091 | 132112 |
| R_718 | 21 | 38734 | 38754 | R_1469 | 73 | 83083 | 83155 | R_2220 | 32 | 132138 | 132169 |
| R_719 | 46 | 38777 | 38822 | R_1470 | 39 | 83180 | 83218 | R_2221 | 36 | 132182 | 132217 |
| R_720 | 33 | 38853 | 38885 | R_1471 | 70 | 83255 | 83324 | R_2222 | 26 | 132253 | 132278 |

TABLE 4-continued

Regions (reg.) on SEQ ID NO: 1 which may be targeted using an oligonucleotide of the invention

| Reg. | length (nt) | Position on SEQ ID NO: 1 start | end | Reg. | length (nt) | Position on SEQ ID NO: 1 start | end | Reg. | length (nt) | Position on SEQ ID NO: 1 start | end |
|---|---|---|---|---|---|---|---|---|---|---|---|
| R_721 | 27 | 38897 | 38923 | R_1472 | 35 | 83346 | 83380 | R_2223 | 48 | 132280 | 132327 |
| R_722 | 23 | 38982 | 39004 | R_1473 | 23 | 83409 | 83431 | R_2224 | 33 | 132403 | 132435 |
| R_723 | 26 | 39007 | 39032 | R_1474 | 111 | 83433 | 83543 | R_2225 | 58 | 132437 | 132494 |
| R_724 | 23 | 39007 | 39029 | R_1475 | 39 | 83553 | 83591 | R_2226 | 33 | 132496 | 132528 |
| R_725 | 20 | 39016 | 39035 | R_1476 | 54 | 83628 | 83681 | R_2227 | 60 | 132541 | 132600 |
| R_726 | 21 | 39026 | 39046 | R_1477 | 36 | 83710 | 83745 | R_2228 | 22 | 132619 | 132640 |
| R_727 | 30 | 39048 | 39077 | R_1478 | 32 | 83776 | 83807 | R_2229 | 23 | 132656 | 132678 |
| R_728 | 31 | 39140 | 39170 | R_1479 | 23 | 83809 | 83831 | R_2230 | 21 | 132758 | 132778 |
| R_729 | 24 | 39161 | 39184 | R_1480 | 53 | 83854 | 83906 | R_2231 | 39 | 132780 | 132818 |
| R_730 | 36 | 39188 | 39223 | R_1481 | 20 | 83960 | 83979 | R_2232 | 47 | 132827 | 132873 |
| R_731 | 28 | 39235 | 39262 | R_1482 | 43 | 83995 | 84037 | R_2233 | 27 | 132893 | 132919 |
| R_732 | 39 | 39264 | 39302 | R_1483 | 73 | 84051 | 84123 | R_2234 | 65 | 132917 | 132981 |
| R_733 | 52 | 39328 | 39379 | R_1484 | 40 | 84142 | 84181 | R_2235 | 20 | 132983 | 133002 |
| R_734 | 59 | 39391 | 39449 | R_1485 | 52 | 84217 | 84268 | R_2236 | 67 | 133014 | 133080 |
| R_735 | 30 | 39463 | 39492 | R_1486 | 28 | 84270 | 84297 | R_2237 | 46 | 133082 | 133127 |
| R_736 | 20 | 39492 | 39511 | R_1487 | 20 | 84354 | 84373 | R_2238 | 39 | 133129 | 133167 |
| R_737 | 20 | 39519 | 39538 | R_1488 | 21 | 84440 | 84460 | R_2239 | 31 | 133169 | 133199 |
| R_738 | 37 | 39557 | 39593 | R_1489 | 31 | 84488 | 84518 | R_2240 | 34 | 133201 | 133234 |
| R_739 | 34 | 39595 | 39628 | R_1490 | 22 | 84653 | 84674 | R_2241 | 27 | 133251 | 133277 |
| R_740 | 34 | 39639 | 39672 | R_1491 | 29 | 84727 | 84755 | R_2242 | 20 | 133282 | 133301 |
| R_741 | 26 | 39682 | 39707 | R_1492 | 38 | 84851 | 84888 | R_2243 | 37 | 133343 | 133379 |
| R_742 | 20 | 39709 | 39728 | R_1493 | 21 | 84887 | 84907 | R_2244 | 30 | 133404 | 133433 |
| R_743 | 23 | 39746 | 39768 | R_1494 | 58 | 84932 | 84989 | R_2245 | 77 | 133435 | 133511 |
| R_744 | 23 | 39753 | 39775 | R_1495 | 35 | 84991 | 85025 | R_2246 | 48 | 133528 | 133575 |
| R_745 | 20 | 39777 | 39796 | R_1496 | 24 | 85109 | 85132 | R_2247 | 22 | 133676 | 133697 |
| R_746 | 20 | 39798 | 39817 | R_1497 | 60 | 85135 | 85194 | R_2248 | 54 | 133710 | 133763 |
| R_747 | 41 | 39833 | 39873 | R_1498 | 27 | 85206 | 85232 | R_2249 | 20 | 133765 | 133784 |
| R_748 | 20 | 39876 | 39895 | R_1499 | 26 | 85239 | 85264 | R_2250 | 29 | 133786 | 133814 |
| R_749 | 36 | 39907 | 39942 | R_1500 | 32 | 85327 | 85358 | R_2251 | 40 | 133816 | 133855 |
| R_750 | 47 | 39990 | 40036 | R_1501 | 24 | 85390 | 85413 | R_2252 | 42 | 133857 | 133898 |
| R_751 | 36 | 40074 | 40109 | R_1502 | 24 | 85520 | 85543 | R_2253 | 63 | 133900 | 133962 |
| | | | | | | | | R_2254 | 40 | 133964 | 134003 |

In some embodiments the target sequence is a sequence selected from a human MAPT mRNA intron, such as a Tau human mRNA intron 1 or 2 (see table 1 above).

The oligonucleotide of the invention comprises a contiguous nucleotide sequence which is complementary to or hybridizes to the target nucleic acid, such as a target sequence described herein.

The target sequence to which the oligonucleotide is complementary or hybridizes to generally comprises a contiguous nucleobases sequence of at least 10 nucleotides. The contiguous nucleotide sequence is between 10 to 100 nucleotides, such as 12 to 60, such as 13 to 50, such as 14 to 30, such as 15 to 25, such as 16 to 20 contiguous nucleotides.

In one embodiment of the invention the target sequence is SEQ ID NO: 3, corresponding to region A. In certain embodiments the target sequence is selected from position 12051-12111 of SEQ ID NO: 1 such as positon 12051-12079, position 12085-12111 or position 12060-12078 of SEQ ID NO: 1.

In another embodiment of the invention the target sequence is SEQ ID NO: 4, corresponding to region B. In certain embodiments the target sequence is selected from position 39562-39593 of SEQ ID NO: 1 such as positon 39573-39592 of SEQ ID NO: 1.

In another embodiment of the invention the target sequence is SEQ ID NO: 5, corresponding to region C. In certain embodiments the target sequence is selected from position 72837-72940 of SEQ ID NO: 1 such as positon 72861-72891 or position 72862-72890 of SEQ ID NO: 1.

Target Cell

The term a "target cell" as used herein refers to a cell which is expressing the target nucleic acid. In some embodiments the target cell may be in vivo or in vitro. In some embodiments the target cell is a mammalian cell such as a rodent cell, such as a mouse cell or a rat cell, or a primate cell such as a monkey cell or a human cell.

In preferred embodiments the target cell expresses Tau mRNA, such as the Tau pre-mRNA or Tau mature mRNA. The poly A tail of Tau mRNA is typically disregarded for antisense oligonucleotide targeting.

Naturally Occurring Variant

The term "naturally occurring variant" refers to variants of MAPT gene or transcripts which originate from the same genetic loci as the target nucleic acid, but may differ for example, by virtue of degeneracy of the genetic code causing a multiplicity of codons encoding the same amino acid, or due to alternative splicing of pre-mRNA, or the presence of polymorphisms, such as single nucleotide polymorphisms (SNPs), and allelic variants. Based on the presence of the sufficient complementary sequence to the oligonucleotide, the oligonucleotide of the invention may therefore target the target nucleic acid and naturally occurring variants thereof.

In some embodiments, the naturally occurring variants have at least 95% such as at least 98% or at least 99% homology to a mammalian MAPT target nucleic acid, such as a target nucleic acid selected form the group consisting of SEQ ID NO 1 and 2. In some embodiments the naturally occurring variants have at least 99% homology to the human MAPT target nucleic acid of SEQ ID NO: 1.

Modulation of Expression

The term "modulation of expression" as used herein is to be understood as an overall term for an oligonucleotide's ability to alter the amount of Tau when compared to the amount of Tau before administration of the oligonucleotide. Alternatively, modulation of expression may be determined by reference to a control experiment. It is generally understood that the control is an individual or target cell treated with a saline composition or an individual or target cell treated with a non-targeting oligonucleotide (mock).

One type of modulation is the ability of an oligonucleotide to inhibit, down-regulate, reduce, suppress, remove, stop, block, prevent, lessen, lower, avoid or terminate expression of Tau, e.g. by degradation of mRNA or blockage of transcription. Another type of modulation is an oligonucleotide's ability to restore, increase or enhance expression of Tau, e.g. by repair of splice sites or prevention of splicing or removal or blockage of inhibitory mechanisms such as microRNA repression.

High Affinity Modified Nucleosides

A high affinity modified nucleoside is a modified nucleotide which, when incorporated into the oligonucleotide enhances the affinity of the oligonucleotide for its complementary target, for example as measured by the melting temperature ($T^m$). A high affinity modified nucleoside of the present invention preferably result in an increase in melting temperature between +0.5 to +12° C., more preferably between +1.5 to +10° C. and most preferably between +3 to +8° C. per modified nucleoside. Numerous high affinity modified nucleosides are known in the art and include for example, many 2' substituted nucleosides as well as locked nucleic acids (LNA) (see e.g. Freier & Altmann; Nucl. Acid Res., 1997, 25, 4429-4443 and Uhlmann; Curr. Opinion in Drug Development, 2000, 3(2), 293-213).

Sugar Modifications

The oligomer of the invention may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of oligonucleotides, such as affinity and/or nuclease resistance.

Such modifications include those where the ribose ring structure is modified, e.g. by replacement with a hexose ring (HNA), or a bicyclic ring, which typically have a biradicle bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'—OH group naturally found in DNA and RNA nucleosides. Substituents may, for example be introduced at the 2', 3', 4' or 5' positions.

2' Sugar Modified Nucleosides

A 2' sugar modified nucleoside is a nucleoside which has a substituent other than H or —OH at the 2' position (2' substituted nucleoside) or comprises a 2' linked biradicle capable of forming a bridge between the 2' carbon and a second carbon in the ribose ring, such as LNA (2'-4' biradicle bridged) nucleosides.

Indeed, much focus has been spent on developing 2' sugar substituted nucleosides, and numerous 2' substituted nucleosides have been found to have beneficial properties when incorporated into oligonucleotides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl. Acid Res., 1997, 25, 4429-4443 and Uhlmann; Curr. Opinion in Drug Development, 2000, 3(2), 293-213, and Deleavey and Damha, Chemistry and Biology 2012, 19, 937. Below are illustrations of some 2' substituted modified nucleosides.

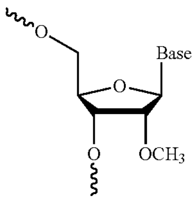

2'-O-Me

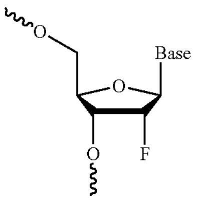

2'F-RNA

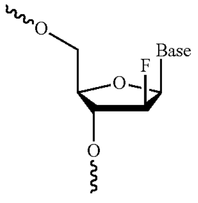

2'F-ANA

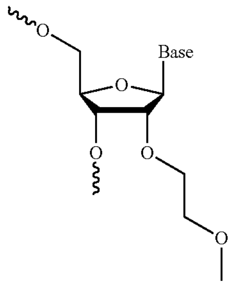

2'-O-MOE

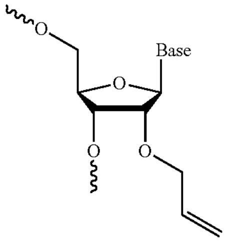

2'-O-Alyl

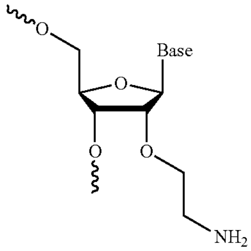

2'-O-Ethylamine

In relation to the present invention 2' substituted sugar modified nucleosides does not include 2' bridged nucleosides like LNA.

Locked Nucleic Acid Nucleosides (LNA Nucleoside)

A "LNA nucleoside" is a 2'-sugar modified nucleoside which comprises a biradical linking the C2' and C4' of the ribose sugar ring of said nucleoside (also referred to as a "2'-4' bridge"), which restricts or locks the conformation of the ribose ring. These nucleosides are also termed bridged nucleic acid or bicyclic nucleic acid (BNA) in the literature. The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex.

Non limiting, exemplary LNA nucleosides are disclosed in WO 99/014226, WO 00/66604, WO 98/039352, WO 2004/046160, WO 00/047599, WO 2007/134181, WO 2010/077578, WO 2010/036698, WO 2007/090071, WO 2009/006478, WO 2011/156202, WO 2008/154401, WO 2009/067647, WO 2008/150729, Morita et al., Bioorganic & Med. Chem. Lett. 12, 73-76, Seth et al. J. Org. Chem. 2010, Vol 75(5) pp. 1569-81, Mitsuoka et al., Nucleic Acids Research 2009, 37(4), 1225-1238, and Wan and Seth, J. Medical Chemistry 2016, 59, 9645-9667.

The 2'-4' bridge comprises 2 to 4 bridging atoms and is in particular of formula —X—Y— wherein X is oxygen, sulfur, —$CR^aR^b$—, —$C(R^a)$=$C(R^b)$—, —C(=$CR^aR^b$)—, —$C(R^a)$=N—, —$Si(R^a)_2$—, —$SO_2$—, —$NR^a$—; —O—$NR^a$—, —$NR^a$—O—, —C(=J)-, Se, —O—$NR^a$—, —$NR^a$—$CR^aR^b$—, —$N(R^a)$—O— or —O—$CR^aR^b$—;

Y is oxygen, sulfur, —$(CR^aR^b)_n$—, —$CR^aR^b$—O—$CR^aR^b$—, —$C(R^a)$=$C(R^b)$—, —$C(R^a)$=N—, —$Si(R^a)_2$—, —$SO_2$—, —$NR^a$—, —C(=J)-, Se, —O—$NR^a$—, —$NR^a$—$CR^aR^b$—, —$N(R^a)$—O— or —O—$CR^aR^b$—;

with the proviso that —X—Y— is not —O—O—, $Si(R^a)_2$—$Si(R^a)_2$—, —$SO_2$—$SO_2$—, —$C(R^a)$=$C(R^b)$—$C(R^a)$=$C(R^b)$, —$C(R^a)$=N—$C(R^a)$=N—, —$C(R^a)$=N—$C(R^a)$=$C(R^b)$, —$C(R^a)$=$C(R^b)$—$C(R^a)$=N— or —Se—Se—;

J is oxygen, sulfur, =$CH_2$ or =$N(R^a)$;

$R^a$ and $R^b$ are independently selected from hydrogen, halogen, hydroxyl, cyano, thiohydroxyl, alkyl, substituted alkyl, alkenyl, substituted alkenyl, alkynyl, substituted alkynyl, alkoxy, substituted alkoxy, alkoxyalkyl, alkenyloxy, carboxyl, alkoxycarbonyl, alkylcarbonyl, formyl, aryl, heterocyclyl, amino, alkylamino, carbamoyl, alkylaminocarbonyl, aminoalkylaminocarbonyl, alkylaminoalkylaminocarbonyl, alkylcarbonylamino, carbamido, alkanoyloxy, sulfonyl, alkylsulfonyloxy, nitro, azido, thiohydroxylsulfidealkylsulfanyl, aryloxycarbonyl, aryloxy, arylcarbonyl, heteroaryl, heteroaryloxycarbonyl, heteroaryloxy, heteroarylcarbonyl, —OC(=$X^a$)$R^c$, —OC(=$X^a$)$NR^cR^d$ and —$NR^e$C(=$X^a$)$NR^cR^d$;

or two geminal $R^a$ and $R^b$ together form optionally substituted methylene;

or two geminal $R^a$ and $R^b$, together with the carbon atom to which they are attached, form cycloalkyl or halocycloalkyl, with only one carbon atom of —X—Y—;

wherein substituted alkyl, substituted alkenyl, substituted alkynyl, substituted alkoxy and substituted methylene are alkyl, alkenyl, alkynyl and methylene substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl, formyl, heterocylyl, aryl and heteroaryl;

$X^a$ is oxygen, sulfur or —$NR^c$;

$R^c$, $R^d$ and $R^e$ are independently selected from hydrogen and alkyl; and n is 1, 2 or 3.

In a further particular embodiment of the invention, X is oxygen, sulfur, —$NR^a$—, —$CR^aR^b$— or —C(=$CR^aR^b$)—, particularly oxygen, sulfur, —NH—, —$CH_2$— or —C(=$CH_2$)—, more particularly oxygen.

In another particular embodiment of the invention, Y is —$CR^aR^b$—, —$CR^aR^b$—$CR^aR^b$— or —$CR^aR^b$—$CR^aR^b$—$CR^aR^b$—, particularly —$CH_2$—$CHCH_3$—, —$CHCH_3$—$CH_2$—, —$CH_2$—$CH_2$— or —$CH_2$—$CH_2$—$CH_2$—.

In a particular embodiment of the invention, —X—Y— is —O—($CR^aR^b$)—, —S—$CR^aR^b$—, —$N(R^a)CR^aR^b$—, —$CR^aR^b$—$CR^aR^b$—, —O—$CR^aR^b$—O—$CR^aR^b$—, —$CR^aR^b$—O—$CR^aR^b$—, —C(=$CR^aR^b$)—$CR^aR^b$—, —$N(R^a)CR^aR^b$—, —O—$N(R^a)$—$CR^aR^b$— or —$N(R^a)$—O—$CR^aR^b$—.

In a particular embodiment of the invention, $R^a$ and $R^b$ are independently selected from the group consisting of hydrogen, halogen, hydroxyl, alkyl and alkoxyalkyl, in particular hydrogen, halogen, alkyl and alkoxyalkyl.

In another embodiment of the invention, $R^a$ and $R^b$ are independently selected from the group consisting of hydrogen, fluoro, hydroxyl, methyl and —$CH_2$—O—$CH_3$, in particular hydrogen, fluoro, methyl and —$CH_2$—O—$CH_3$.

Advantageously, one of $R^a$ and $R^b$ of —X—Y— is as defined above and the other ones are all hydrogen at the same time.

In a further particular embodiment of the invention, $R^a$ is hydrogen or alkyl, in particular hydrogen or methyl.

In another particular embodiment of the invention, $R^b$ is hydrogen or or alkyl, in particular hydrogen or methyl.

In a particular embodiment of the invention, one or both of $R^a$ and $R^b$ are hydrogen.

In a particular embodiment of the invention, only one of $R^a$ and $R^b$ is hydrogen.

In one particular embodiment of the invention, one of $R^a$ and $R^b$ is methyl and the other one is hydrogen.

In a particular embodiment of the invention, $R^a$ and $R^b$ are both methyl at the same time.

In a particular embodiment of the invention, —X—Y— is —O—$CH_2$—, —S—$CH_2$—, —S—$CH(CH_3)$—, —NH—$CH_2$—, —O—$CH_2CH_2$—, —O—$CH(CH_2$—O—$CH_3)$—, —O—$CH(CH_2CH_3)$—, —O—$CH(CH_3)$—, —O—$CH_2$—O—$CH_2$—, —O—$CH_2$—O—$CH_2$—, —$CH_2$—O—$CH_2$—, —C(=$CH_2$)$CH_2$—, —C(=$CH_2$)$CH(CH_3)$—, —$N(OCH_3)CH_2$— or —$N(CH_3)CH_2$—;

In a particular embodiment of the invention, —X—Y— is —O—$CR^aR^b$— wherein $R^a$ and $R^b$ are independently selected from the group consisting of hydrogen, alkyl and alkoxyalkyl, in particular hydrogen, methyl and —$CH_2$—O—$CH_3$.

In a particular embodiment, —X—Y— is —O—$CH_2$— or —O—$CH(CH_3)$—, particularly —O—$CH_2$—.

The 2'-4' bridge may be positioned either below the plane of the ribose ring (beta-D-configuration), or above the plane of the ring (alpha-L-configuration), as illustrated in formula (A) and formula (B) respectively.

The LNA nucleoside according to the invention is in particular of formula (A) or (B)

(A)

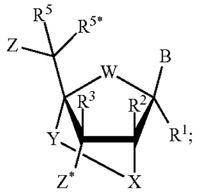

(B)

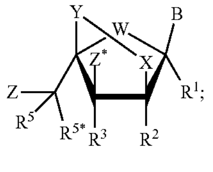

wherein

W is oxygen, sulfur, —N($R^a$)— or —$CR^aR^b$—, in particular oxygen;

B is a nucleobase or a modified nucleobase;

Z is an internucleoside linkage to an adjacent nucleoside or a 5'-terminal group;

Z* is an internucleoside linkage to an adjacent nucleoside or a 3'-terminal group;

$R^1$, $R^2$, $R^3$, $R^5$ and $R^{5*}$ are independently selected from hydrogen, halogen, alkyl, haloalkyl, alkenyl, alkynyl, hydroxy, alkoxy, alkoxyalkyl, azido, alkenyloxy, carboxyl, alkoxycarbonyl, alkylcarbonyl, formyl and aryl; and X, Y, $R^a$ and $R^b$ are as defined above.

In a particular embodiment, in the definition of —X—Y—, $R^a$ is hydrogen or alkyl, in particular hydrogen or methyl. In another particular embodiment, in the definition of —X—Y—, $R^b$ is hydrogen or alkyl, in particular hydrogen or methyl. In a further particular embodiment, in the definition of —X—Y—, one or both of $R^a$ and $R^b$ are hydrogen. In a particular embodiment, in the definition of —X—Y—, only one of $R^a$ and $R^b$ is hydrogen. In one particular embodiment, in the definition of —X—Y—, one of $R^a$ and $R^b$ is methyl and the other one is hydrogen. In a particular embodiment, in the definition of —X—Y—, $R^a$ and $R^b$ are both methyl at the same time.

In a further particular embodiment, in the definition of X, $R^a$ is hydrogen or alkyl, in particular hydrogen or methyl. In another particular embodiment, in the definition of X, $R^b$ is hydrogen or alkyl, in particular hydrogen or methyl. In a particular embodiment, in the definition of X, one or both of $R^a$ and $R^b$ are hydrogen. In a particular embodiment, in the definition of X, only one of $R^a$ and $R^b$ is hydrogen. In one particular embodiment, in the definition of X, one of $R^a$ and $R^b$ is methyl and the other one is hydrogen. In a particular embodiment, in the definition of X, $R^a$ and $R^b$ are both methyl at the same time.

In a further particular embodiment, in the definition of Y, $R^a$ is hydrogen or alkyl, in particular hydrogen or methyl. In another particular embodiment, in the definition of Y, $R^b$ is hydrogen or alkyl, in particular hydrogen or methyl. In a particular embodiment, in the definition of Y, one or both of $R^a$ and $R^b$ are hydrogen. In a particular embodiment, in the definition of Y, only one of $R^a$ and $R^b$ is hydrogen. In one particular embodiment, in the definition of Y, one of $R^a$ and $R^b$ is methyl and the other one is hydrogen. In a particular embodiment, in the definition of Y, $R^a$ and $R^b$ are both methyl at the same time.

In a particular embodiment of the invention $R^1$, $R^2$, $R^3$, $R^5$ and $R^{5*}$ are independently selected from hydrogen and alkyl, in particular hydrogen and methyl.

In a further particular advantageous embodiment of the invention, $R^1$, $R^2$, $R^3$, $R^5$ and $R^{5*}$ are all hydrogen at the same time.

In another particular embodiment of the invention, $R^1$, $R^2$, $R^3$, are all hydrogen at the same time, one of $R^5$ and $R^{5*}$ is hydrogen and the other one is as defined above, in particular alkyl, more particularly methyl.

In a particular embodiment of the invention, $R^5$ and $R^{5*}$ are independently selected from hydrogen, halogen, alkyl, alkoxyalkyl and azido, in particular from hydrogen, fluoro, methyl, methoxyethyl and azido. In particular advantageous embodiments of the invention, one of $R^5$ and $R^{5*}$ is hydrogen and the other one is alkyl, in particular methyl, halogen, in particular fluoro, alkoxyalkyl, in particular methoxyethyl or azido; or $R^5$ and $R^{5*}$ are both hydrogen or halogen at the same time, in particular both hydrogen of fluoro at the same time. In such particular embodiments, W can advantageously be oxygen, and —X—Y— advantageously —O—$CH_2$—.

In a particular embodiment of the invention, —X—Y— is —O—$CH_2$—, W is oxygen and $R^1$, $R^2$, $R^3$, $R^5$ and $R^{5*}$ are all hydrogen at the same time. Such LNA nucleosides are disclosed in WO 99/014226, WO 00/66604, WO 98/039352 and WO 2004/046160 which are all hereby incorporated by reference, and include what are commonly known in the art as beta-D-oxy LNA and alpha-L-oxy LNA nucleosides.

In another particular embodiment of the invention, —X—Y— is —S—$CH_2$—, W is oxygen and $R^1$, $R^2$, $R^3$, $R^5$ and $R^{5*}$ are all hydrogen at the same time. Such thio LNA nucleosides are disclosed in WO 99/014226 and WO 2004/046160 which are hereby incorporated by reference.

In another particular embodiment of the invention, —X—Y— is —NH—$CH_2$—, W is oxygen and $R^1$, $R^2$, $R^3$, $R^5$ and $R^{5*}$ are all hydrogen at the same time. Such amino LNA nucleosides are disclosed in WO 99/014226 and WO 2004/046160 which are hereby incorporated by reference.

In another particular embodiment of the invention, —X—Y— is —O—$CH_2CH_2$— or —$OCH_2CH_2CH_2$—, W is oxygen, and $R^1$, $R^2$, $R^3$, $R^5$ and $R^{5*}$ are all hydrogen at the same time. Such LNA nucleosides are disclosed in WO 00/047599 and Morita et al., Bioorganic & Med. Chem. Lett. 12, 73-76, which are hereby incorporated by reference, and include what are commonly known in the art as 2'-O-4'C-ethylene bridged nucleic acids (ENA).

In another particular embodiment of the invention, —X—Y— is —O—$CH_2$—, W is oxygen, $R^1$, $R^2$, Ware all hydrogen at the same time, one of $R^5$ and $R^{5*}$ is hydrogen and the other one is not hydrogen, such as alkyl, for example methyl. Such 5' substituted LNA nucleosides are disclosed in WO 2007/134181 which is hereby incorporated by reference.

In another particular embodiment of the invention, —X—Y— is —O—$CR^aR^b$—, wherein one or both of $R^a$ and $R^b$ are not hydrogen, in particular alkyl such as methyl, W is oxygen, $R^1$, $R^2$, $R^3$ are all hydrogen at the same time, one of $R^5$ and $R^{5*}$ is hydrogen and the other one is not hydrogen, in particular alkyl, for example methyl. Such bis modified LNA nucleosides are disclosed in WO 2010/077578 which is hereby incorporated by reference.

In another particular embodiment of the invention, —X—Y— is —O—$CHR^a$—, W is oxygen and $R^1$, $R^2$, $R^3$, $R^5$ and $R^{5*}$ are all hydrogen at the same time. Such 6'-substituted LNA nucleosides are disclosed in WO 2010/036698 and WO 2007/090071 which are both hereby incorporated by reference. In such 6'-substituted LNA nucleosides, $R^a$ is in particular C1-C6 alkyl, such as methyl.

In another particular embodiment of the invention, —X—Y— is —O—CH($CH_2$—O—$CH_3$)— ("2' O-methoxyethyl bicyclic nucleic acid", Seth et al. J. Org. Chem. 2010, Vol 75(5) pp. 1569-81).

In another particular embodiment of the invention, —X—Y— is —O—CH($CH_2CH_3$)— ("2'O-ethyl bicyclic nucleic acid", Seth at al., J. Org. Chem. 2010, Vol 75(5) pp. 1569-81).

In another particular embodiment of the invention, —X—Y— is —O—CH($CH_2$—O—$CH_3$)—, W is oxygen and FC, $R^2$, $R^3$, $R^5$ and $R^{5*}$ are all hydrogen at the same time. Such LNA nucleosides are also known in the art as cyclic MOEs (cMOE) and are disclosed in WO 2007/090071.

In another particular embodiment of the invention, —X—Y— is —O—CH($CH_3$)—.

In another particular embodiment of the invention, —X—Y— is —O—$CH_2$—O—$CH_2$— (Seth et al., J. Org. Chem 2010 op. cit.)

In another particular embodiment of the invention, —X—Y— is —O—CH($CH_3$)—, W is oxygen and $R^1$, $R^2$, $R^3$, $R^5$ and $R^{5*}$ are all hydrogen at the same time. Such 6'-methyl LNA nucleosides are also known in the art as cET nucleosides, and may be either (S)-cET or (R)-cET diastereoisomers, as disclosed in WO 2007/090071 (beta-D) and WO 2010/036698 (alpha-L) which are both hereby incorporated by reference.

In another particular embodiment of the invention, —X—Y— is —O—$CR^aR^b$—, wherein neither $R^a$ nor $R^b$ is hydrogen, W is oxygen and $R^1$, $R^2$, $R^3$, $R^5$ and $R^{5*}$ are all hydrogen at the same time. In a particular embodiment, $R^a$ and $R^b$ are both alkyl at the same time, in particular both methyl at the same time. Such 6'-di-substituted LNA nucleosides are disclosed in WO 2009/006478 which is hereby incorporated by reference.

In another particular embodiment of the invention, —X—Y— is —S—$CHR^a$—, W is oxygen and $R^1$, $R^2$, $R^3$, $R^5$ and $R^{5*}$ are all hydrogen at the same time. Such 6'-substituted thio LNA nucleosides are disclosed in WO 2011/156202 which is hereby incorporated by reference. In a particular embodiment of such 6'-substituted thio LNA, $R^a$ is alkyl, in particular methyl.

In a particular embodiment of the invention, —X—Y— is —C(=$CH_2$)C($R^aR^b$)—, —C(=CHF)C($R^aR^b$)— or —C(=$CF_2$)C($R^aR^b$)—, W is oxygen and $R^1$, $R^2$, $R^3$, $R^5$ and $R^{5*}$ are all hydrogen at the same time. $R^a$ and $R^b$ are advantagesously independently selected from hydrogen, halogen, alkyl and alkoxyalkyl, in particular hydrogen, methyl, fluoro and methoxymethyl. $R^a$ and $R^b$ are in particular both hydrogen or methyl at the same time or one of $R^a$ and $R^b$ is hydrogen and the other one is methyl. Such vinyl carbo LNA nucleosides are disclosed in WO 2008/154401 and WO 2009/067647 which are both hereby incorporated by reference.

In a particular embodiment of the invention, —X—Y— is —N($OR^a$)—$CH_2$—, W is oxygen and $R^1$, $R^2$, $R^3$, $R^5$ and $R^{5*}$ are all hydrogen at the same time. In a particular embodiment, $R^a$ is alkyl such as methyl. Such LNA nucleosides are also known as N substituted LNAs and are disclosed in WO 2008/150729 which is hereby incorporated by reference.

In a particular embodiment of the invention, —X—Y— is —O—N($R^a$)—, —N($R^a$)—O—, —$NR^a$—$CR^aR^b$—$CR^aR^b$— or —$NR^a$—$CR^aR^b$—, W is oxygen and $R^1$, $R^2$, $R^3$, $R^5$ and $R^{5*}$ are all hydrogen at the same time. $R^a$ and $R^b$ are advantagesously independently selected from hydrogen, halogen, alkyl and alkoxyalkyl, in particular hydrogen, methyl, fluoro and methoxymethyl. In a particular embodiment, $R^a$ is alkyl, such as methyl, $R^b$ is hydrogen or methyl, in particular hydrogen. (Seth et al., J. Org. Chem 2010 op. cit.).

In a particular embodiment of the invention, —X—Y— is —O—N($CH_3$)— (Seth et al., J. Org. Chem 2010 op. cit.).

In a particular embodiment of the invention, $R^5$ and $R^{5*}$ are both hydrogen at the same time. In another particular embodiment of the invention, one of $R^5$ and $R^{5*}$ is hydrogen and the other one is alkyl, such as methyl. In such embodiments, $R^1$, $R^2$ and $R^3$ can be in particular hydrogen and —X—Y— can be in particular —O—$CH_2$— or —O—CHC$(R^a)_3$—, such as —O—CH($CH_3$)—.

In a particular embodiment of the invention, —X—Y— is —$CR^aR^b$—O—$CR^aR^b$—, such as —$CH_2$—O—$CH_2$—, W is oxygen and $R^1$, $R^2$, $R^3$, $R^5$ and $R^{5*}$ are all hydrogen at the same time. In such particular embodiments, $R^a$ can be in particular alkyl such as methyl, $R^b$ hydrogen or methyl, in particular hydrogen. Such LNA nucleosides are also known as conformationally restricted nucleotides (CRNs) and are disclosed in WO 2013/036868 which is hereby incorporated by reference.

In a particular embodiment of the invention, —X—Y— is —O—$CR^aR^b$—O—$CR^aR^b$—, such as —O—$CH_2$—O—$CH_2$—, W is oxygen and $R^1$, $R^2$, $R^3$, $R^5$ and $R^{5*}$ are all hydrogen at the same time. $R^a$ and $R^b$ are advantageously independently selected from hydrogen, halogen, alkyl and alkoxyalkyl, in particular hydrogen, methyl, fluoro and methoxymethyl. In such a particular embodiment, $R^a$ can be in particular alkyl such as methyl, $R^b$ hydrogen or methyl, in particular hydrogen. Such LNA nucleosides are also known as COC nucleotides and are disclosed in Mitsuoka et al., Nucleic Acids Research 2009, 37(4), 1225-1238, which is hereby incorporated by reference.

It will be recognized than, unless specified, the LNA nucleosides may be in the beta-D or alpha-L stereoisoform.

Particular examples of LNA nucleosides of the invention are presented in Scheme 1 (wherein B is as defined above).

Scheme 1

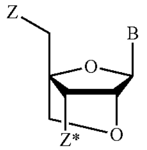
β-D-oxy LNA

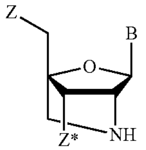
β-D-amino LNA

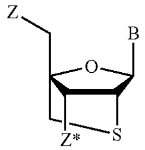
β-D-thio LNA

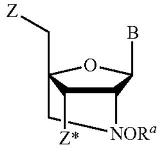
β-D-amino substituted LNA

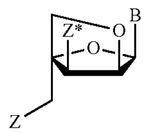
α-L-oxy LNA

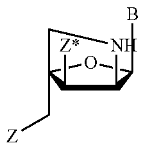
α-L-amino LNA

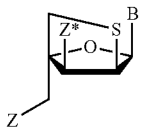
α-L-thio LNA

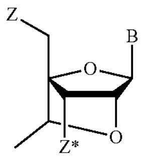
6'-methyl-β-D-oxy LNA

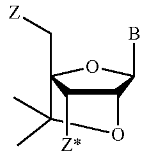
6'-dimethyl-β-D-oxy LNA

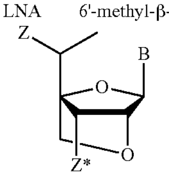
5'-methyl-β-D-oxy LNA

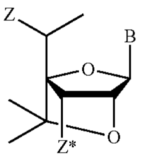
5'-methyl-6'-dimethyl-β-D-oxy LNA

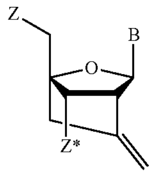
carbocyclic(vinyl)-β-D-oxy LNA

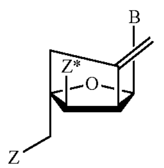
carbocyclic(vinyl)-α-L-oxy LNA

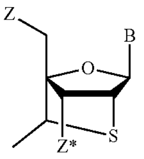
6'-methyl-β-D-thio LNA

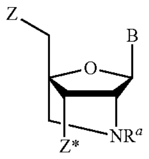
β-D-amino substituted LNA

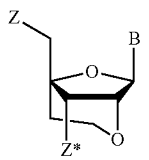
ENA

-continued

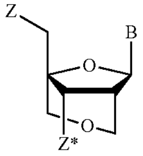

COC

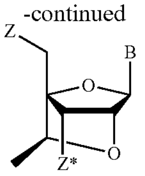

(S)-cET

Particular LNA nucleosides are beta-D-oxy-LNA, 6'-methyl-beta-D-oxy LNA such as (S)-6'-methyl-beta-D-oxy-LNA (ScET) and ENA.

If one of the starting materials or compounds of the invention contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3rd Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethylsilylethyl carbamate (Teoc), carbobenzyloxy (Cbz) and p-methoxybenzyloxycarbonyl (Moz).

The compounds described herein can contain several asymmetric centers and can be present in the form of optically pure enantiomers, mixtures of enantiomers such as, for example, racemates, mixtures of diastereoisomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

Chemical Group Definitions

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain $C_1$-$C_8$ alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. Particular examples of alkyl are methyl, ethyl and propyl.

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl, cyclohexyl, cycloheptyl and cyclooctyl, more particularly cyclopropyl and cyclobutyl. A particular example of "cycloalkyl" is cyclopropyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec.butoxy and tert.butoxy. Particular "alkoxy" are methoxy and ethoxy. Methoxyethoxy is a particular example of "alkoxyalkoxy".

The term "oxy", alone or in combination, signifies the —O— group.

The term "alkenyl", alone or in combination, signifies a straight-chain or branched hydrocarbon residue comprising an olefinic bond and up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl.

The term "alkynyl", alone or in combination, signifies a straight-chain or branched hydrocarbon residue comprising a triple bond and up to 8, preferably up to 6, particularly preferred up to 4 carbon atoms.

The terms "halogen" or "halo", alone or in combination, signifies fluorine, chlorine, bromine or iodine and particularly fluorine, chlorine or bromine, more particularly fluorine. The term "halo", in combination with another group, denotes the substitution of said group with at least one halogen, particularly substituted with one to five halogens, particularly one to four halogens, i.e. one, two, three or four halogens.

The term "haloalkyl", alone or in combination, denotes an alkyl group substituted with at least one halogen, particularly substituted with one to five halogens, particularly one to three halogens. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl or trifluoromethyl. Fluoromethyl, difluoromethyl and trifluoromethyl are particular "haloalkyl".

The term "halocycloalkyl", alone or in combination, denotes a cycloalkyl group as defined above substituted with at least one halogen, particularly substituted with one to five halogens, particularly one to three halogens. Particular example of "halocycloalkyl" are halocyclopropyl, in particular fluorocyclopropyl, difluorocyclopropyl and trifluorocyclopropyl.

The terms "hydroxyl" and "hydroxy", alone or in combination, signify the —OH group.

The terms "thiohydroxyl" and "thiohydroxy", alone or in combination, signify the —SH group.

The term "carbonyl", alone or in combination, signifies the —C(O)— group.

The term "carboxy" or "carboxyl", alone or in combination, signifies the —COOH group.

The term "amino", alone or in combination, signifies the primary amino group (—$NH_2$), the secondary amino group (—NH—), or the tertiary amino group (—N—).

The term "alkylamino", alone or in combination, signifies an amino group as defined above substituted with one or two alkyl groups as defined above.

The term "sulfonyl", alone or in combination, means the —$SO_2$ group.

The term "sulfinyl", alone or in combination, signifies the —SO— group.

The term "sulfanyl", alone or in combination, signifies the —S— group.

The term "cyano", alone or in combination, signifies the —CN group.

The term "azido", alone or in combination, signifies the —$N_3$ group.

The term "nitro", alone or in combination, signifies the $NO_2$ group.

The term "formyl", alone or in combination, signifies the —C(O)H group.

The term "carbamoyl", alone or in combination, signifies the —C(O)$NH_2$ group.

The term "cabamido", alone or in combination, signifies the —NH—C(O)—$NH_2$ group.

The term "aryl", alone or in combination, denotes a monovalent aromatic carbocyclic mono- or bicyclic ring system comprising 6 to 10 carbon ring atoms, optionally substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl and formyl. Examples of aryl include phenyl and naphthyl, in particular phenyl.

The term "heteroaryl", alone or in combination, denotes a monovalent aromatic heterocyclic mono- or bicyclic ring system of 5 to 12 ring atoms, comprising 1, 2, 3 or 4 heteroatoms selected from N, O and S, the remaining ring atoms being carbon, optionally substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl and formyl. Examples of heteroaryl include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, quinoxalinyl, carbazolyl or acridinyl.

The term "heterocyclyl", alone or in combination, signifies a monovalent saturated or partly unsaturated mono- or bicyclic ring system of 4 to 12, in particular 4 to 9 ring atoms, comprising 1, 2, 3 or 4 ring heteroatoms selected from N, O and S, the remaining ring atoms being carbon, optionally substituted with 1 to 3 substituents independently selected from halogen, hydroxyl, alkyl, alkenyl, alkynyl, alkoxy, alkoxyalkyl, alkenyloxy, carboxyl, alkoxycarbonyl, alkylcarbonyl and formyl. Examples for monocyclic saturated heterocyclyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl or dihydropyranyl.

Pharmaceutically Acceptable Salts

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

Protecting Group

The term "protecting group", alone or in combination, signifies a group which selectively blocks a reactive site in a multifunctional compound such that a chemical reaction can be carried out selectively at another unprotected reactive site. Protecting groups can be removed. Exemplary protecting groups are amino-protecting groups, carboxy-protecting groups or hydroxy-protecting groups.

Nuclease Mediated Degradation

Nuclease mediated degradation refers to an oligonucleotide capable of mediating degradation of a complementary nucleotide sequence when forming a duplex with such a sequence.

In some embodiments, the oligonucleotide may function via nuclease mediated degradation of the target nucleic acid, where the oligonucleotides of the invention are capable of recruiting a nuclease, particularly and endonuclease, preferably endoribonuclease (RNase), such as RNase H. Examples of oligonucleotide designs which operate via nuclease mediated mechanisms are oligonucleotides which typically comprise a region of at least 5 or 6 consecutive DNA nucleosides and are flanked on one side or both sides by affinity enhancing nucleosides, for example gapmers, headmers and tailmers.

RNase H Activity and Recruitment

The RNase H activity of an antisense oligonucleotide refers to its ability to recruit RNase H when in a duplex with a complementary RNA molecule. WO01/23613 provides in vitro methods for determining RNaseH activity, which may be used to determine the ability to recruit RNaseH. Typically an oligonucleotide is deemed capable of recruiting RNase H if it, when provided with a complementary target nucleic acid sequence, has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers with phosphorothioate linkages between all monomers in the oligonucleotide, and using the methodology provided by Example 91-95 of WO01/23613 (hereby incorporated by reference). For use in determining RHase H activity, recombinant human RNase H1 is available from Lubio Science GmbH, Lucerne, Switzerland.

Gapmer

The antisense oligonucleotide of the invention, or contiguous nucleotide sequence thereof, may be a gapmer, also termed gapmer oligonucleotide or gapmer designs. The antisense gapmers are commonly used to inhibit a target nucleic acid via RNase H mediated degradation. A gapmer oligonucleotide comprises at least three distinct structural regions a 5'-flank, a gap and a 3'-flank, F-G-F' in the '5→3' orientation. The "gap" region (G) comprises a stretch of contiguous DNA nucleotides which enable the oligonucleotide to recruit RNase H. The gap region is flanked by a 5' flanking region (F) comprising one or more sugar modified nucleosides, advantageously high affinity sugar modified nucleosides, and by a 3' flanking region (F') comprising one or more sugar modified nucleosides, advantageously high affinity sugar modified nucleosides. The one or more sugar modified nucleosides in region F and F' enhance the affinity of the oligonucleotide for the target nucleic acid (i.e. are affinity enhancing sugar modified nucleosides). In some embodiments, the one or more sugar modified nucleosides in region F and F' are 2' sugar modified nucleosides, such as high affinity 2' sugar modifications, such as independently selected from LNA and 2'-MOE.

In a gapmer design, the 5' and 3' most nucleosides of the gap region are DNA nucleosides, and are positioned adjacent to a sugar modified nucleoside of the 5' (F) or 3' (F') region respectively. The flanks may further be defined by having at least one sugar modified nucleoside at the end most distant from the gap region, i.e. at the 5' end of the 5' flank and at the 3' end of the 3' flank.

Regions F-G-F' form a contiguous nucleotide sequence. Antisense oligonucleotides of the invention, or the contiguous nucleotide sequence thereof, may comprise a gapmer region of formula F-G-F'.

The overall length of the gapmer design F-G-F' may be, for example 12 to 32 nucleosides, such as 13 to 24, such as 14 to 22 nucleosides, Such as from 14 to 17, such as 16 to 18 nucleosides, such as 16 to 20 nucleotides.

By way of example, the gapmer oligonucleotide of the present invention can be represented by the following formulae:

$F_{1-8}$-$G_{6-16}$-$F'_{2-8}$, such as $F_{2-8}$-$G_{6-14}$-$F'_{2-8}$, such as $F_{3-8}$-$G_{6-14}$-$F_{2-8}$ with the proviso that the overall length of the gapmer regions F-G-F' is at least 10, such as at least 12, such as at least 14 nucleotides in length.

In an aspect of the invention the antisense oligonucleotide or contiguous nucleotide sequence thereof consists of or comprises a gapmer of formula 5'-F-G-F'-3', where region F and F' independently comprise or consist of 1-8 nucleosides, of which 2-4 are 2' sugar modified and defines the 5' and 3' end of the F and F' region, and G is a region between 6 and 16 nucleosides which are capable of recruiting RNaseH.

Regions F, G and F' are further defined below and can be incorporated into the F-G-F' formula.

Gapmer—Region G

Region G (gap region) of the gapmer is a region of nucleosides which enables the oligonucleotide to recruit RNaseH, such as human RNase H1, typically DNA nucleosides. RNaseH is a cellular enzyme which recognizes the duplex between DNA and RNA, and enzymatically cleaves the RNA molecule. Suitably gapmers may have a gap region (G) of at least 5 or 6 contiguous DNA nucleosides, such as 5-16 contiguous DNA nucleosides, such as 6-15 contiguous DNA nucleosides, such as 7-14 contiguous DNA nucleosides, such as 8-12 contiguous DNA nucleotides, such as 8-12 contiguous DNA nucleotides in length. The gap region G may, in some embodiments consist of 6, 7, 8, 9, 10, 11, 12, 13, 14, 15 or 16 contiguous DNA nucleosides. Cytosine (C) DNA in the gap region may in some instances be methylated, such residues are either annotated as 5'-methyl-cytosine ($^{me}$C or with an e instead of a c). Methylation of cytosine DNA in the gap is advantageous if cg dinucleotides are present in the gap to reduce potential toxicity, the modification does not have significant impact on efficacy of the oligonucleotides. 5' substituted DNA nucleosides, such as 5' methyl DNA nucleoside have been reported for use in DNA gap regions (EP 2 742 136).

In some embodiments the gap region G may consist of 6, 7, 8, 9, 10, 11, 12, 13, 14, 15 or 16 contiguous phosphorothioate linked DNA nucleosides. In some embodiments, all internucleoside linkages in the gap are phosphorothioate linkages.

Whilst traditional gapmers have a DNA gap region, there are numerous examples of modified nucleosides which allow for RNaseH recruitment when they are used within the gap region. Modified nucleosides which have been reported as being capable of recruiting RNaseH when included within a gap region include, for example, alpha-L-LNA, C4' alkylated DNA (as described in PCT/EP2009/050349 and Vester et al., Bioorg. Med. Chem. Lett. 18 (2008) 2296-2300, both incorporated herein by reference), arabinose derived nucleosides like ANA and 2'F-ANA (Mangos et al. 2003 J. AM. CHEM. SOC. 125, 654-661), UNA (unlocked nucleic acid) (as described in Fluiter et al., Mol. Biosyst., 2009, 10, 1039 incorporated herein by reference). UNA is unlocked nucleic acid, typically where the bond between C2 and C3 of the ribose has been removed, forming an unlocked “sugar” residue. The modified nucleosides used in such gapmers may be nucleosides which adopt a 2' endo (DNA like) structure when introduced into the gap region, i.e. modifications which allow for RNaseH recruitment). In some embodiments the DNA Gap region (G) described herein may optionally contain 1 to 3 sugar modified nucleosides which adopt a 2' endo (DNA like) structure when introduced into the gap region.

Region G—“Gap-Breaker”

Alternatively, there are numerous reports of the insertion of a modified nucleoside which confers a 3' endo conformation into the gap region of gapmers, whilst retaining some RNaseH activity. Such gapmers with a gap region comprising one or more 3'endo modified nucleosides are referred to as “gap-breaker” or “gap-disrupted” gapmers, see for example WO2013/022984. Gap-breaker oligonucleotides retain sufficient region of DNA nucleosides within the gap region to allow for RNaseH recruitment. The ability of gapbreaker oligonucleotide design to recruit RNaseH is typically sequence or even compound specific—see Rukov et al. 2015 Nucl. Acids Res. Vol. 43 pp. 8476-8487, which discloses “gapbreaker” oligonucleotides which recruit RNaseH which in some instances provide a more specific cleavage of the target RNA. Modified nucleosides used within the gap region of gap-breaker oligonucleotides may for example be modified nucleosides which confer a 3'endo confirmation, such 2'-O-methyl (OMe) or 2'-O-MOE (MOE) nucleosides, or beta-D LNA nucleosides (the bridge between C2' and C4' of the ribose sugar ring of a nucleoside is in the beta conformation), such as beta-D-oxy LNA or ScET nucleosides.

As with gapmers containing region G described above, the gap region of gap-breaker or gap-disrupted gapmers, have a DNA nucleosides at the 5' end of the gap (adjacent to the 3' nucleoside of region F), and a DNA nucleoside at the 3' end of the gap (adjacent to the 5' nucleoside of region F'). Gapmers which comprise a disrupted gap typically retain a region of at least 3 or 4 contiguous DNA nucleosides at either the 5' end or 3' end of the gap region.

Exemplary designs for gap-breaker oligonucleotides include $F_{1-8}$-[$D_{3-4}$-$E_1$-$D_{3-4}$]-$F'_{1-8}$ $F_{1-8}$-[$D_{1-4}$-$E_1$-$D_{3-4}$]-$F'_{1-8}$ $F_{1-8}$-[$D_{3-4}$-$E_1$-$D_{1-4}$]-$F'_{1-8}$ wherein region G is within the brackets [$D_n$-$E_r$-$D_m$], D is a contiguous sequence of DNA nucleosides, E is a modified nucleoside (the gap-breaker or gap-disrupting nucleoside), and F and F' are the flanking regions as defined herein, and with the proviso that the overall length of the gapmer regions F-G-F' is at least 12, such as at least 14 nucleotides in length.

In some embodiments, region G of a gap disrupted gapmer comprises at least 6 DNA nucleosides, such as 6, 7, 8, 9, 10, 11, 12, 13, 14, 15 or 16 DNA nucleosides. As described above, the DNA nucleosides may be contiguous or may optionally be interspersed with one or more modified nucleosides, with the proviso that the gap region G is capable of mediating RNaseH recruitment.

Gapmer—Flanking Regions, F and F'

Region F is positioned immediately adjacent to the 5' DNA nucleoside of region G. The 3' most nucleoside of region F is a sugar modified nucleoside, such as a high affinity sugar modified nucleoside, for example a 2' substituted nucleoside, such as a MOE nucleoside, or an LNA nucleoside.

Region F' is positioned immediately adjacent to the 3' DNA nucleoside of region G. The 5' most nucleoside of region F' is a sugar modified nucleoside, such as a high affinity sugar modified nucleoside, for example a 2' substituted nucleoside, such as a MOE nucleoside, or an LNA nucleoside.

Region F is 1-8 contiguous nucleotides in length, such as 2-6, such as 3-4 contiguous nucleotides in length. Advantageously the 5' most nucleoside of region F is a sugar modified nucleoside. In some embodiments the two 5' most nucleoside of region F are sugar modified nucleoside. In some embodiments the 5' most nucleoside of region F is an LNA nucleoside. In some embodiments the two 5' most nucleoside of region F are LNA nucleosides. In some embodiments the two 5' most nucleoside of region F are 2' substituted nucleoside nucleosides, such as two 3' MOE nucleosides. In some embodiments the 5' most nucleoside of region F is a 2' substituted nucleoside, such as a MOE nucleoside.

Region F' is 2-8 contiguous nucleotides in length, such as 3-6, such as 4-5 contiguous nucleotides in length. Advantageously, embodiments the 3' most nucleoside of region F' is a sugar modified nucleoside. In some embodiments the two 3' most nucleoside of region F' are sugar modified nucleoside. In some embodiments the two 3' most nucleoside of region F' are LNA nucleosides. In some embodiments the 3' most nucleoside of region F' is an LNA nucleoside. In some embodiments the two 3' most nucleoside of region F' are 2' substituted nucleoside nucleosides, such as two 3' MOE nucleosides. In some embodiments the 3' most nucleoside of region F' is a 2' substituted nucleoside, such as a MOE nucleoside.

It should be noted that when the length of region F or F' is one, it is advantageously an LNA nucleoside.

In some embodiments, region F and F' independently consists of or comprises a contiguous sequence of sugar modified nucleosides. In some embodiments, the sugar modified nucleosides of region F may be independently selected from 2'-O-alkyl-RNA units, 2'-O-methyl-RNA, 2'-amino-DNA units, 2'-fluoro-DNA units, 2'-alkoxy-RNA, MOE units, LNA units, arabino nucleic acid (ANA) units and 2'-fluoro-ANA units.

In some embodiments, region F and F' independently comprises both LNA and a 2' substituted modified nucleosides (mixed wing design).

In some embodiments, region F and F' consists of only one type of sugar modified nucleosides, such as only MOE or only beta-D-oxy LNA or only ScET. Such designs are also termed uniform flanks or uniform gapmer design.

In some embodiments, all the nucleosides of region F or F', or F and F' are LNA nucleosides, such as independently selected from beta-D-oxy LNA, ENA or ScET nucleosides. In some embodiments region F consists of 1-5, such as 2-4, such as 3-4 such as 1, 2, 3, 4 or 5 contiguous LNA nucleosides. In some embodiments, all the nucleosides of region F and F' are beta-D-oxy LNA nucleosides.

In some embodiments, all the nucleosides of region F or F', or F and F' are 2' substituted nucleosides, such as OMe or MOE nucleosides. In some embodiments region F consists of 1, 2, 3, 4, 5, 6, 7, or 8 contiguous OMe or MOE nucleosides. In some embodiments only one of the flanking regions can consist of 2' substituted nucleosides, such as OMe or MOE nucleosides. In some embodiments it is the 5' (F) flanking region that consists 2' substituted nucleosides, such as OMe or MOE nucleosides whereas the 3' (F') flanking region comprises at least one LNA nucleoside, such as beta-D-oxy LNA nucleosides or cET nucleosides. In some embodiments it is the 3' (F') flanking region that consists 2' substituted nucleosides, such as OMe or MOE nucleosides whereas the 5' (F) flanking region comprises at least one LNA nucleoside, such as beta-D-oxy LNA nucleosides or cET nucleosides.

In some embodiments, all the modified nucleosides of region F and F' are LNA nucleosides, such as independently selected from beta-D-oxy LNA, ENA or ScET nucleosides, wherein region F or F', or F and F' may optionally comprise DNA nucleosides (an alternating flank, see definition of these for more details). In some embodiments, all the modified nucleosides of region F and F' are beta-D-oxy LNA nucleosides, wherein region F or F', or F and F' may optionally comprise DNA nucleosides (an alternating flank, see definition of these for more details).

In some embodiments the 5' most and the 3' most nucleosides of region F and F' are LNA nucleosides, such as beta-D-oxy LNA nucleosides or ScET nucleosides.

In some embodiments, the internucleoside linkage between region F and region G is a phosphorothioate internucleoside linkage. In some embodiments, the internucleoside linkage between region F' and region G is a phosphorothioate internucleoside linkage. In some embodiments, the internucleoside linkages between the nucleosides of region F or F', F and F' are phosphorothioate internucleoside linkages.

LNA Gapmer

An LNA gapmer is a gapmer wherein either one or both of region F and F' comprises or consists of LNA nucleosides. A beta-D-oxy gapmer is a gapmer wherein either one or both of region F and F' comprises or consists of beta-D-oxy LNA nucleosides.

In some embodiments the LNA gapmer is of formula: $[LNA]_{1-5}$-[region G]-$[LNA]_{1-5}$, wherein region G is as defined in the Gapmer region G definition.

In one embodiment the LNA gapmer is of the formula $[LNA]_4$-$[\text{region G}]_{10-12}$-$[LNA]_4$ MOE Gapmers A MOE gapmers is a gapmer wherein regions F and F' consist of MOE nucleosides. In some embodiments the MOE gapmer is of design $[MOE]_{1-8}$-$[\text{Region G}]_{5-16}$-$[MOE]_{1-8}$, such as $[MOE]_{2-7}$-$[\text{Region G}]_{6-14}$-$[MOE]_{2-7}$, such as $[MOE]_{3-6}$-$[\text{Region G}]_{8-12}$-$[MOE]_{3-6}$, wherein region G is as defined in the Gapmer definition. MOE gapmers with a 5-10-5 design (MOE-DNA-MOE) have been widely used in the art.

Mixed Wing Gapmer

A mixed wing gapmer is an LNA gapmer wherein one or both of region F and F' comprise a 2' substituted nucleoside, such as a 2' substituted nucleoside independently selected from the group consisting of 2'-O-alkyl-RNA units, 2'-O-methyl-RNA, 2'-amino-DNA units, 2'-fluoro-DNA units, 2'-alkoxy-RNA, MOE units, arabino nucleic acid (ANA) units and 2'-fluoro-ANA units, such as MOE nucleosides. In some embodiments wherein at least one of region F and F', or both region F and F' comprise at least one LNA nucleoside, the remaining nucleosides of region F and F' are independently selected from the group consisting of MOE and LNA. In some embodiments wherein at least one of region F and F', or both region F and F' comprise at least two LNA nucleosides, the remaining nucleosides of region F and F' are independently selected from the group consisting of MOE and LNA. In some mixed wing embodiments, one or both of region F and F' may further comprise one or more DNA nucleosides.

Mixed wing gapmer designs are disclosed in WO2008/049085 and WO2012/109395, both of which are hereby incorporated by reference.

Alternating Flank Gapmers

Flanking regions may comprise both LNA and DNA nucleoside and are referred to as “alternating flanks” as they comprise an alternating motif of LNA-DNA-LNA nucleosides. Gapmers comprising such alternating flanks are referred to as “alternating flank gapmers”. “Alternative flank gapmers” are LNA gapmer oligonucleotides where at least one of the flanks (F or F') comprises DNA in addition to the LNA nucleoside(s). In some embodiments at least one of region F or F', or both region F and F', comprise both LNA nucleosides and DNA nucleosides. In such embodiments, the flanking region F or F', or both F and F' comprise at least three nucleosides, wherein the 5' and 3' most nucleosides of the F and/or F' region are LNA nucleosides.

Alternating flank LNA gapmers are disclosed in WO2016/127002.

An alternating flank region may comprise up to 3 contiguous DNA nucleosides, such as 1 to 2 or 1 or 2 or 3 contiguous DNA nucleosides.

The alternating flak can be annotated as a series of integers, representing a number of LNA nucleosides (L) followed by a number of DNA nucleosides (D), for example $[L]_{1-3}$-$[D]_{1-4}$-$[L]_{1-3}$ $[L]_{1-2}$-$[D]_{1-2}$-$[L]_{1-2}$-$[D]_{1-2}$-$[L]_{1-2}$ In oligonucleotide designs these will often be represented as numbers such that 2-2-1 represents 5' $[L]_2$-$[D]_2$-[L] 3', and 1-1-1-1-1 represents 5' [L]-[D]-[L]-[D]-[L] 3'. The length of the flank (region F and F') in oligonucleotides with alternating flanks may independently be 3 to 10 nucleosides, such as 4 to 8, such as 5 to 6 nucleosides, such as 4, 5, 6 or 7 modified nucleosides. In some embodiments only one of the flanks in the gapmer oligonucleotide is alternating while the other is constituted of LNA nucleotides. It may be advantageous to have at least two LNA nucleosides at the 3' end of the 3' flank (F'), to confer additional exonuclease resistance. In one embodiment the flanks in the alternating flank gapmer have an overall length from 5- to 8 nucleosides of which 3 to 5 are LNA nucleosides. Some examples of oligonucleotides with alternating flanks are:

$[L]_{1-5}$-$[D]_{1-4}$-$[L]_{1-3}$-$[G]_{5-16}$-$[L]_{2-6}$ $[L]_{1-2}$-$[D]_{2-3}$-$[L]_{3-4}$-$[G]_{5-7}$-$[L]_{1-2}$-$[D]_{2-3}$-$[L]_{2-3}$ $[L]_{1-2}$-$[D]_{1-2}$-$[L]_{1-2}$-$[D]_{1-2}$-$[L]_{1-2}$-$[G]_{5-16}$-$[L]_{1-2}$-$[D]_{1-3}$-$[L]_{2-4}$ $[L]_{1-5}$-$[G]_{5-16}$-[L]-[D]-[L]-[D]-$[L]_2$ $[L]_4$-$[G]_{6-10}$-[L]-$[D]_3$-$[L]_2$ with the proviso that the overall length of the gapmer is at least 12, such as at least 14 nucleotides in length.

Region D' or D" in an Oligonucleotide

The oligonucleotide of the invention may in some embodiments comprise or consist of the contiguous nucleotide sequence of the oligonucleotide which is complementary to the target nucleic acid, such as the gapmer F-G-F', and further 5' and/or 3' nucleosides. The further 5' and/or 3' nucleosides may or may not be fully complementary to the target nucleic acid. Such further 5' and/or 3' nucleosides may be referred to as region D' and D" herein.

The addition of region D' or D" may be used for the purpose of joining the contiguous nucleotide sequence, such as the gapmer, to a conjugate moiety or another functional group. When used for joining the contiguous nucleotide sequence with a conjugate moiety is can serve as a biocleavable linker. Alternatively, it may be used to provide exonucleoase protection or for ease of synthesis or manufacture.

Region D' and D" can be attached to the 5' end of region F or the 3' end of region F', respectively to generate designs of the following formulas D'-F-G-F', F-G-F'-D" or D'-F-G-F'-D". In this instance the F-G-F' is the gapmer portion of the oligonucleotide and region D' or D" constitute a separate part of the oligonucleotide.

Region D' or D" may independently comprise or consist of 1, 2, 3, 4 or 5 additional nucleotides, which may be complementary or non-complementary to the target nucleic acid. The nucleotide adjacent to the F or F' region is not a sugar-modified nucleotide, such as a DNA or RNA or base modified versions of these. The D' or D' region may serve as a nuclease susceptible biocleavable linker (see definition of linkers). In some embodiments the additional 5' and/or 3' end nucleotides are linked with phosphodiester linkages, and are DNA or RNA. Nucleotide based biocleavable linkers suitable for use as region D' or D" are disclosed in WO2014/076195, which include by way of example a phosphodiester linked DNA dinucleotide. The use of biocleavable linkers in poly-oligonucleotide constructs is disclosed in WO2015/113922, where they are used to link multiple antisense constructs (e.g. gapmer regions) within a single oligonucleotide.

In one embodiment the oligonucleotide of the invention comprises a region D' and/or D" in addition to the contiguous nucleotide sequence which constitutes the gapmer.

In some embodiments, the oligonucleotide of the present invention can be represented by the following formulae:

F-G-F'; in particular $F_{2-8}$-$G_{6-16}$-$F_{2-8}$

D'-F-G-F', in particular $D'_{2-3}$-$F_{1-8}$-$G_{6-16}$-$F'_{2-8}$

F-G-F'-D", in particular $F_{2-8}$-$G_{6-16}$-$F'_{2-8}$-$D''_{1-3}$

D'-F-G-F'-D", in particular $D'_{1-3}$-$F_{2-8}$-$G_{6-16}$-$F'_{2-8}$-$D''_{1-3}$ In some embodiments the internucleoside linkage positioned between region D' and region F is a phosphodiester linkage. In some embodiments the internucleoside linkage positioned between region F' and region D" is a phosphodiester linkage.

Conjugate

The term conjugate as used herein refers to an oligonucleotide which is covalently linked to a non-nucleotide moiety (conjugate moiety or region C or third region).

Conjugation of the oligonucleotide of the invention to one or more non-nucleotide moieties may improve the pharmacology of the oligonucleotide, e.g. by affecting the activity, cellular distribution, cellular uptake or stability of the oligonucleotide. In some embodiments the conjugate moiety modify or enhance the pharmacokinetic properties of the oligonucleotide by improving cellular distribution, bioavailability, metabolism, excretion, permeability, and/or cellular uptake of the oligonucleotide. In particular, the conjugate may target the oligonucleotide to a specific organ, tissue or cell type and thereby enhance the effectiveness of the oligonucleotide in that organ, tissue or cell type. At the same time the conjugate may serve to reduce activity of the oligonucleotide in non-target cell types, tissues or organs, e.g. off target activity or activity in non-target cell types, tissues or organs.

Oligonucleotide conjugates and their synthesis has also been reported in comprehensive reviews by Manoharan in Antisense Drug Technology, Principles, Strategies, and Applications, S. T. Crooke, ed., Ch. 16, Marcel Dekker, Inc., 2001 and Manoharan, Antisense and Nucleic Acid Drug Development, 2002, 12, 103, each of which is incorporated herein by reference in its entirety.

In an embodiment, the non-nucleotide moiety (conjugate moiety) is selected from the group consisting of carbohydrates (e.g. GalNAc), cell surface receptor ligands, drug substances, hormones, lipophilic substances, polymers, proteins, peptides, toxins (e.g. bacterial toxins), vitamins, viral proteins (e.g. capsids) or combinations thereof.

In some embodiments, the conjugate is an antibody or an antibody fragment which has a specific affinity for a transferrin receptor, for example as disclosed in WO 2012/143379 herby incorporated by reference. In some embodiments the non-nucleotide moiety is an antibody or antibody fragment, such as an antibody or antibody fragment that facilitates delivery across the blood-brain-barrier, in particular an antibody or antibody fragment targeting the transferrin receptor.

Linkers

A linkage or linker is a connection between two atoms that links one chemical group or segment of interest to another chemical group or segment of interest via one or more covalent bonds. Conjugate moieties can be attached to the oligonucleotide directly or through a linking moiety (e.g. linker or tether). Linkers serve to covalently connect a third region, e.g. a conjugate moiety (Region C), to a first region, e.g. an oligonucleotide or contiguous nucleotide sequence complementary to the target nucleic acid (region A).

In some embodiments of the invention the conjugate or oligonucleotide conjugate of the invention may optionally, comprise a linker region (second region or region B and/or region Y) which is positioned between the oligonucleotide or contiguous nucleotide sequence complementary to the target nucleic acid (region A or first region) and the conjugate moiety (region C or third region).

Region B refers to biocleavable linkers comprising or consisting of a physiologically labile bond that is cleavable under conditions normally encountered or analogous to those encountered within a mammalian body. Conditions under which physiologically labile linkers undergo chemical transformation (e.g., cleavage) include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic enzymes or hydrolytic enzymes or nucleases. In one embodiment the biocleavable linker is susceptible to S1 nuclease cleavage. In a preferred embodiment the nuclease susceptible linker comprises between 1 and 10 nucleosides, such as 1, 2, 3, 4, 5, 6, 7, 8, 9 or 10 nucleosides, more preferably between 2 and 6 nucleosides and most preferably between 2 and 4 linked nucleosides comprising at least two consecutive phosphodiester linkages, such as at least 3 or 4 or 5 consecutive phosphodiester linkages. Preferably the nucleosides are DNA or RNA. Phosphodiester containing biocleavable linkers are described in more detail in WO 2014/076195 (hereby incorporated by reference).

Region Y refers to linkers that are not necessarily biocleavable but primarily serve to covalently connect a conjugate moiety (region C or third region), to an oligonucleotide (region A or first region). The region Y linkers may comprise a chain structure or an oligomer of repeating units such as ethylene glycol, amino acid units or amino alkyl groups The oligonucleotide conjugates of the present invention can be constructed of the following regional elements A-C, A-B—C, A-B—Y—C, A-Y—B—C or A-Y—C. In some embodiments the linker (region Y) is an amino alkyl, such as a C2-C36 amino alkyl group, including, for example C6 to C12 amino alkyl groups. In a preferred embodiment the linker (region Y) is a C6 amino alkyl group.

Treatment

The term 'treatment' as used herein refers to both treatment of an existing disease (e.g. a disease or disorder as herein referred to), or prevention of a disease, i.e. prophylaxis. It will therefore be recognized that treatment as referred to herein may, in some embodiments, be prophylactic.

In some embodiments treatment is performed on a patient who has been diagnosed with a neurological disorder, such as a neurological disorder selected from the group consisting of neurodegenerative diseases including Tauopathies, Alzheimer's disease (AD), progressive supranuclear palsy (PSP), corticobasal ganglionic degeneration (CBD), chronic traumatic encephalopathy (CTE), fronto-temporal dementia FTD) and FTD with parkinsonism linked to chromosome 17 (FTDP-17), Pick's disease (PiD), argyrophilic grain disease (AGD), tangle-predominant senile dementia (TPSD), primary age-related Tauopathy (PART), Down syndrome and lytico-bodig disease. Upregulation of pathological Tau is associated with infantile Tauopathies including hemimegalencephaly (HME), tuberous sclerosis complex; focal cortical dysplasia type 2b; and ganglioglioma. In addition, abnormal Tau expression and/or function may also be associated with other diseases such as Hallervorden-Spatz syndrome, also known as neurodegeneration with brain iron accumulation type 1 (NBIA1), gangliocytomas, and subacute sclerosing panencephalitis. Tau may also play a role in seizure disorders (e.g., epilepsy), network dysfunction (e.g., depression), and movement disorders (e.g., Parkinson's disease).

DETAILED DESCRIPTION OF THE INVENTION

The Oligonucleotides of the Invention

The invention relates to oligonucleotides capable of modulating expression of Tau, such as inhibiting (down-regulating) Tau. The modulation is achieved by hybridizing to a target nucleic acid encoding Tau. The target nucleic acid may be a mammalian MAPT mRNA sequence, such as a sequence selected from the group consisting of SEQ ID NO: 1 and 2.

The oligonucleotide of the invention is an antisense oligonucleotide which targets MAPT resulting in reduced Tau expression.

In some embodiments the antisense oligonucleotide of the invention is capable of modulating the expression of the target by inhibiting or down-regulating it. Preferably, such modulation produces an inhibition of expression of at least 20% compared to the normal expression level of the target, more preferably at least 30%, at least 40%, at least 50%, at least 60%, at least 70%, at least 80%, or at least 90% inhibition compared to the normal expression level of the target. In some embodiments oligonucleotides of the invention may be capable of inhibiting expression levels of Tau mRNA by at least 60% or 70% in vitro following application of 5 μM oligonucleotide to primary neuronal cells. In some embodiments compounds of the invention may be capable of inhibiting expression levels of Tau protein by at least 50% in vitro following application of 0.5 μM oligonucleotide to primary neuronal cells. Suitably, the examples provide assays which may be used to measure Tau RNA or protein inhibition (e.g. example 1 and 3). The target modulation is triggered by the hybridization between a contiguous nucleotide sequence of the oligonucleotide and the target nucleic acid. In some embodiments the oligonucleotide of the invention comprises mismatches between the oligonucleotide and the target nucleic acid. Despite mismatches hybridization to the target nucleic acid may still be sufficient to show a desired modulation of Tau expression. Reduced binding affinity resulting from mismatches may advantageously be compensated by increased number of nucleotides in the oligonucleotide and/or an increased number of modified nucleosides capable of increasing the binding affinity to the target, such as 2' sugar modified nucleosides, including LNA, present within the oligonucleotide sequence.

An aspect of the present invention relates to an antisense oligonucleotide which comprises a contiguous nucleotide sequence of at least 10 nucleotides in length with at least 90% complementarity to SEQ ID NO: 3, 4 or 5.

In some embodiments, the oligonucleotide comprises a contiguous sequence of 10 to 30 nucleotides in length, which is at least 90% complementary, such as at least 91%, such as at least 92%, such as at least 93%, such as at least 94%, such as at least 95%, such as at least 96%, such as at least 97%, such as at least 98%, or 100% complementary with a region of the target nucleic acid or a target sequence.

It is advantageous if the oligonucleotide of the invention, or contiguous nucleotide sequence thereof is fully complementary (100% complementary) to a region of the target nucleic acid, or in some embodiments may comprise one or two mismatches between the oligonucleotide and the target nucleic acid.

In some embodiments the oligonucleotide comprises a contiguous nucleotide sequence of 10 to 30 nucleotides in length with at least 90% complementary, such as fully (or 100%) complementary, to contiguous nucleotides within position 12051 to 12111, 39562 to 39593 or 72837 to 72940 of SEQ ID NO: 1.

In some embodiments the oligonucleotide sequence is 100% complementary to a corresponding target nucleic acid region present in SEQ ID NO: 1 and SEQ ID NO: 2.

It is advantageous if the antisense oligonucleotide is complementary to a target sequence selected from one of the regions listed in table 4. In some embodiments the contiguous nucleotide sequence of the antisense oligonucleotide is at least 90% complementary to, such as fully complementary to a target sequence selected R1-R2254 (table 4) In some embodiments the oligonucleotide sequence is 100% complementary to R_223, R_738 or R_1298 (see table 4).

In some embodiment the oligonucleotide or contiguous nucleotide sequence is 90% complementary, such as fully complementary, to a region of the target nucleic acid, wherein the target nucleic acid region is selected from the group consisting of position 12051-12111 of SEQ ID NO: 1 such as positon 12051-12079, position 12085-12111 or position 12060-12078 of SEQ ID NO: 1.

In another embodiment the oligonucleotide or contiguous nucleotide sequence is 90% complementary, such as fully complementary, to a region of the target nucleic acid, wherein the target nucleic acid region is selected from the group consisting of position 39562-39593 of SEQ ID NO: 1 such as positon 39573-39592 of SEQ ID NO: 1.

In another embodiment of the oligonucleotide or contiguous nucleotide sequence is 90% complementary, such as fully complementary, to a region of the target nucleic acid, wherein the target nucleic acid region is selected from the group consisting of position 72837-72940 of SEQ ID NO: 1 such as positon 72861-72891 or position 72862-72890 of SEQ ID NO: 1.

In some embodiments the oligonucleotide comprises a contiguous nucleotide sequence of 16 to 22 nucleotides, such as 16 to 20 nucleotides, in length with 100% complementary, to contiguous nucleotides within position 12060 to 12078 or 39573 to 39592 or 72862-72890 of SEQ ID NO: 1.

In some embodiments, the oligonucleotide of the invention comprises or consists of 10 to 35 nucleotides in length, such as from 10 to 30, such as 11 to 25, such as from 12 to 22, such as from 14 to 20 or 14 to 18 contiguous nucleotides in length. In one embodiment, the oligonucleotide comprises or consists of 16 to 22 nucleotides in length. In a preferred embodiment, the oligonucleotide comprises or consists of 16 to 20 nucleotides in length.

In some embodiments, the oligonucleotide or contiguous nucleotide sequence thereof comprises or consists of 22 or less nucleotides, such as 20 or less nucleotides, such as 16, 17, 18, 19 or 20 nucleotides. It is to be understood that any range given herein includes the range endpoints. Accordingly, if an oligonucleotide is said to include from 10 to 30 nucleotides, both 10 and 30 nucleotides are included.

In some embodiments, the contiguous nucleotide sequence comprises or consists of 10, 11, 12, 13, 14, 15, 16, 17, 18, 19, 20, 21, 22, 23, 24, 25, 26, 27, 28, 29 or 30 contiguous nucleotides in length. In a preferred embodiment, the oligonucleotide comprises or consists of 16, 17, 18, 19 or 20 nucleotides in length.

In some embodiments, the oligonucleotide or contiguous nucleotide sequence comprises or consists of a sequence selected from the group consisting of sequences listed in table 5 (Materials and Method section).

In some embodiments, the antisense oligonucleotide or contiguous nucleotide sequence comprises or consists of 10 to 30 nucleotides in length with at least 90% identity, preferably 100% identity, to a sequence selected from the group consisting of SEQ ID NO: 6 to 65 (see motif sequences listed in table 5).

In some embodiments, the antisense oligonucleotide or contiguous nucleotide sequence comprises or consists of 10 to 30 nucleotides in length with at least 90% identity, preferably 100% identity, to a sequence selected from the group consisting of SEQ ID NO: 9, 11, 49, 53, 56 and 62 (see motif sequences listed in table 5).

In some embodiments, the antisense oligonucleotide or contiguous nucleotide sequence comprises or consists of 10 to 30 nucleotides in length with at least 90% identity, preferably 100% identity, to a sequence selected from the group consisting of SEQ ID NO: 6 to 37 (see motif sequences listed in table 5).

In some embodiments, the antisense oligonucleotide or contiguous nucleotide sequence comprises or consists of 10 to 30 nucleotides in length with at least 90% identity, preferably 100% identity, to a sequence of SEQ ID NO: 9 or 11 (see motif sequences listed in table 5).

In some embodiments, the antisense oligonucleotide or contiguous nucleotide sequence comprises or consists of 10 to 30 nucleotides in length with at least 90% identity, preferably 100% identity, to a sequence selected from the group consisting of SEQ ID NO: 38 to 51 (see motif sequences listed in table 5).

In some embodiments, the antisense oligonucleotide or contiguous nucleotide sequence comprises or consists of 10 to 30 nucleotides in length with at least 90% identity, preferably 100% identity, to a sequence of SEQ ID NO: 49 or 51 (see motif sequences listed in table 5).

In some embodiments, the antisense oligonucleotide or contiguous nucleotide sequence comprises or consists of 10 to 30 nucleotides in length with at least 90% identity, preferably 100% identity, to a sequence selected from the group consisting of SEQ ID NO: 52 to 65 (see motif sequences listed in table 5).

In some embodiments, the antisense oligonucleotide or contiguous nucleotide sequence comprises or consists of 10 to 30 nucleotides in length with at least 90% identity, preferably 100% identity, to a sequence of SEQ ID NO: 56 or 62 (see motif sequences listed in table 5).

It is understood that the contiguous nucleobase sequences (motif sequence) can be modified to for example increase nuclease resistance and/or binding affinity to the target nucleic acid.

The pattern in which the modified nucleosides (such as high affinity modified nucleosides) are incorporated into the oligonucleotide sequence is generally termed oligonucleotide design.

The oligonucleotides of the invention are designed with modified nucleosides and DNA nucleosides. Advantageously, high affinity modified nucleosides are used.

In an embodiment, the oligonucleotide comprises at least 1 modified nucleoside, such as at least 2, at least 3, at least 4, at least 5, at least 6, at least 7, at least 8, at least 9, at least 10, at least 11, at least 12, at least 13, at least 14, at least 15 or at least 16 modified nucleosides. In an embodiment the oligonucleotide comprises from 1 to 10 modified nucleosides, such as from 2 to 9 modified nucleosides, such as from 3 to 8 modified nucleosides, such as from 4 to 7 modified nucleosides, such as 6 or 7 modified nucleosides. Suitable modifications are described in the "Definitions" section under "modified nucleoside", "high affinity modified nucleosides", "sugar modifications", "2' sugar modifications" and Locked nucleic acids (LNA)".

In an embodiment, the oligonucleotide comprises one or more sugar modified nucleosides, such as 2' sugar modified nucleosides. Preferably the oligonucleotide of the invention comprises one or more 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides. It is advantageous if one or more of the modified nucleoside(s) is a locked nucleic acid (LNA).

In a further embodiment the oligonucleotide comprises at least one modified internucleoside linkage. Suitable internucleoside modifications are described in the "Definitions" section under "Modified internucleoside linkage". It is advantageous if at least 75%, such as 80%, such as all, the internucleoside linkages within the contiguous nucleotide sequence are phosphorothioate or boranophosphate internucleoside linkages. In some embodiments all the internucleotide linkages in the contiguous sequence of the oligonucleotide are phosphorothioate linkages.

In some embodiments, the oligonucleotide of the invention comprises at least one LNA nucleoside, such as 1, 2, 3, 4, 5, 6, 7, or 8 LNA nucleosides, such as from 2 to 6 LNA nucleosides, such as from 3 to 7 LNA nucleosides, 4 to 8 LNA nucleosides or 3, 4, 5, 6, 7 or 8 LNA nucleosides. In some embodiments, at least 75% of the modified nucleosides in the oligonucleotide are LNA nucleosides, such as 80%, such as 85%, such as 90% of the modified nucleosides are LNA nucleosides, in particular beta-D-oxy LNA or ScET. In a still further embodiment all the modified nucleosides in the oligonucleotide are LNA nucleosides. In a further embodiment, the oligonucleotide may comprise both beta-D-oxy-LNA, and one or more of the following LNA nucleosides: thio-LNA, amino-LNA, oxy-LNA, ScET and/or ENA in either the beta-D or alpha-L configurations or combinations thereof. In a further embodiment, all LNA cytosine units are 5-methyl-cytosine. It is advantageous for the nuclease stability of the oligonucleotide or contiguous nucleotide sequence to have at least 1 LNA nucleoside at the 5' end and at least 2 LNA nucleosides at the 3' end of the nucleotide sequence.

In an embodiment of the invention the oligonucleotide of the invention is capable of recruiting RNase H.

In the current invention an advantageous structural design is a gapmer design as described in the "Definitions" section under for example "Gapmer", "LNA Gapmer", "MOE gapmer" and "Mixed Wing Gapmer" "Alternating Flank Gapmer". The gapmer design includes gapmers with uniform flanks, mixed wing flanks, alternating flanks, and gapbreaker designs. In the present invention it is advantageous if the oligonucleotide of the invention is a gapmer with an F-G-F' design, particular gapmer of formula 5'-F-G-F'-3', where region F and F' independently comprise 1-8 nucleosides, of which 2-5 are 2' sugar modified and defines the 5' and 3' end of the F and F' region, and G is a region between 6 and 16 nucleosides which are capable of recruiting RNaseH, such as a region comprising 6-16 DNA nucleosides.

In some embodiments the gapmer is an LNA gapmer.

In some embodiments of the invention the LNA gapmer is selected from the following uniform flank designs 4-10-4, 3-11-4, 4-11-4, 4-12-4 or 4-14-2.

In some embodiments of the invention the LNA gapmer is selected from the following alternating flanks designs 3-1-3-10-2, 1-3-4-6-1-3-2, 1-2-1-2-2-8-4, or 3-3-1-8-2-1-2.

Table 5 (Materials and Method section) lists preferred designs of each motif sequence.

In all instances the F-G-F' design may further include region D' and/or D" as described in the "Definitions" section under "Region D' or D" in an oligonucleotide". In some embodiments the oligonucleotide of the invention has 1, 2 or 3 phosphodiester linked nucleoside units, such as DNA units, at the 5' or 3' end of the gapmer region.

For some embodiments of the invention, the oligonucleotide is selected from the group of oligonucleotide compounds with CMP-ID-NO: 6_1; 7_1; 8_1; 9_1; 9_2; 9_3; 9_4; 9_5; 9_6; 9_7; 9_8; 9_9; 9_10; 9_11; 9_12; 9_13; 9_14; 9_15; 9_16; 9_17; 9_18; 9_19; 9_20; 9_21; 9_22;

9_23; 9_24; 9_25; 9_26; 9_27; 9_28; 9_29; 9_30; 9_31; 9_32; 9_33; 9_34; 9_35; 9_36; 9_37; 9_38; 9_39; 9_40; 9_41; 9_42; 9_43; 9_44; 9_45; 9_46; 9_47; 9_48; 9_49; 9_50; 9_51; 9_52; 9_53; 9_54; 9_55; 9_56; 9_57; 9_58; 9_59; 9_60; 9_61; 9_62; 9_63; 9_64; 9_65; 9_66; 9_67; 9_68; 9_69; 9_70; 9_71; 9_72; 9_73; 9_74; 9_75; 9_76; 9_77; 9_78; 9_79; 9_80; 9_81; 9_82; 9_83; 9_84; 9_85; 9_86; 9_87; 9_88; 9_89; 9_90; 9_91; 9_92; 9_93; 9_94; 9_95; 9_96; 9_97; 9_98; 9_99; 9_100; 9_101; 9_102; 9_103; 9_104; 9_105; 9_106; 10_1; 10_2; 10_3; 10_4; 10_5; 10_6; 10_7; 10_8; 10_9; 10_10; 10_11; 10_12; 10_13; 10_14; 10_15; 10_16; 10_17; 10_18; 10_19; 10_20; 10_21; 10_22; 10_23; 10_24; 10_25; 10_26; 10_27; 10_28; 10_29; 10_30; 10_31; 10_32; 10_33; 10_34; 10_35; 10_36; 10_37; 10_38; 10_39; 10_40; 10_41; 10_42; 10_43; 10_44; 10_45; 10_46; 10_47; 10_48; 10_49; 10_50; 10_51; 10_52; 10_53; 10_54; 10_55; 10_56; 10_57; 10_58; 10_59; 10_60; 10_61; 10_62; 10_63; 10_64; 10_65; 10_66; 10_67; 10_68; 10_69; 10_70; 10_71; 10_72; 10_73; 10_74; 10_75; 10_76; 10_77; 10_78; 10_79; 10_80; 10_81; 10_82; 10_83; 10_84; 10_85; 10_86; 10_87; 10_88; 10_89; 11_1; 12_1; 13_1; 14_1; 15_1; 16_1; 17_1; 18_1; 19_1; 20_1; 21_1; 22_1; 23_1; 24_1; 24_2; 24_3; 24_4; 24_5; 24_6; 24_7; 24_8; 24_9; 24_10; 24_11; 24_12; 24_13; 24_14; 24_15; 24_16; 24_17; 24_18; 24_19; 24_20; 24_21; 24_22; 24_23; 24_24; 24_25; 24_26; 24_27; 24_28; 24_29; 24_30; 24_31; 24_32; 24_33; 24_34; 24_35; 24_36; 24_37; 24_38; 24_39; 24_40; 24_41; 24_42; 24_43; 24_44; 24_45; 24_46; 24_47; 24_48; 24_49; 24_50; 24_51; 24_52; 24_53; 24_54; 24_55; 24_56; 24_57; 24_58; 24_59; 24_60; 24_61; 24_62; 25_1; 25_2; 25_3; 25_4; 25_5; 25_6; 25_7; 25_8; 25_9; 25_10; 25_11; 25_12; 25_13; 25_14; 25_15; 25_16; 25_17; 25_18; 25_19; 25_20; 25_21; 25_22; 25_23; 25_24; 25_25; 25_26; 25_27; 25_28; 25_29; 25_30; 25_31; 25_32; 25_33; 25_34; 25_35; 25_36; 25_37; 25_38; 25_39; 25_40; 25_41; 25_42; 25_43; 26_1; 26_2; 26_3; 26_4; 26_5; 26_6; 26_7; 26_8; 26_9; 26_10; 26_11; 26_12; 26_13; 26_14; 26_15; 26_16; 26_17; 26_18; 26_19; 26_20; 26_21; 26_22; 26_23; 26_24; 26_25; 26_26; 26_27; 26_28; 26_29; 26_30; 26_31; 27_1; 28_1; 28_2; 28_3; 28_4; 28_5; 28_6; 28_7; 28_8; 28_9; 28_10; 28_11; 28_12; 28_13; 28_14; 28_15; 28_16; 28_17; 28_18; 28_19; 28_20; 28_21; 28_22; 28_23; 28_24; 28_25; 28_26; 28_27; 28_28; 28_29; 28_30; 28_31; 28_32; 28_33; 29_1; 29_2; 29_3; 29_4; 29_5; 29_6; 29_7; 29_8; 29_9; 29_10; 29_11; 29_12; 29_13; 29_14; 30_1; 30_2; 30_3; 30_4; 30_5; 30_6; 30_7; 30_8; 30_9; 30_10; 30_11; 30_12; 30_13; 30_14; 30_15; 30_16; 30_17; 30_18; 30_19; 30_20; 30_21; 30_22; 30_23; 30_24; 30_25; 31_1; 31_2; 31_3; 32_1; 32_2; 32_3; 32_4; 32_5; 32_6; 32_7; 32_8; 32_9; 32_10; 32_11; 32_12; 32_13; 32_14; 32_15; 32_16; 32_17; 32_18; 32_19; 32_20; 32_21; 32_22; 32_23; 32_24; 32_25; 32_26; 32_27; 32_28; 32_29; 32_30; 32_31; 32_32; 32_33; 32_34; 32_35; 32_36; 32_37; 32_38; 32_39; 32_40; 32_41; 32_42; 32_43; 32_44; 32_45; 32_46; 32_47; 32_48; 32_49; 32_50; 32_51; 33_1; 33_2; 33_3; 33_4; 33_5; 33_6; 33_7; 33_8; 33_9; 33_10; 33_11; 33_12; 33_13; 33_14; 33_15; 33_16; 33_17; 33_18; 33_19; 33_20; 33_21; 33_22; 33_23; 33_24; 33_25; 33_26; 33_27; 33_28; 33_29; 33_30; 33_31; 33_32; 33_33; 34_1; 35_1; 35_2; 35_3; 36_1; 37_1; 38_1; 39_1; 40_1; 41_1; 42_1; 43_1; 44_1; 45_1; 46_1; 47_1; 48_1; 49_1; 49_2; 49_3; 49_4; 49_5; 49_6; 49_7; 49_8; 49_9; 49_10; 49_11; 49_12; 49_13; 49_14; 49_15; 49_16; 49_17; 49_18; 49_19; 49_20; 49_21; 49_22; 49_23; 49_24; 49_25; 49_26; 49_27; 49_28; 49_29; 49_30; 49_31; 49_32; 49_33; 49_34; 49_35; 49_36; 49_37; 49_38; 49_39; 49_40; 49_41; 49_42; 49_43; 49_44; 49_45; 49_46; 49_47; 49_48; 49_49; 49_50; 49_51; 49_52; 49_53; 49_54; 49_55; 49_56; 49_57; 49_58; 49_59; 49_60; 49_61; 49_62; 49_63; 49_64; 49_65; 49_66; 49_67; 49_68; 49_69; 49_70; 49_71; 49_72; 49_73; 49_74; 49_75; 49_76; 49_77; 49_78; 49_79; 49_80; 49_81; 49_82; 49_83; 49_84; 49_85; 49_86; 49_87; 49_88; 49_89; 49_90; 49_91; 49_92; 49_93; 49_94; 49_95; 49_96; 49_97; 49_98; 49_99; 49_100; 49_101; 49_102; 49_103; 49_104; 49_105; 49_106; 49_107; 49_108; 49_109; 49_110; 49_111; 49_112; 49_113; 49_114; 49_115; 49_116; 49_117; 49_118; 49_1_19; 49_120; 49_121; 49_122; 49_123; 49_124; 49_125; 49_126; 49_127; 49_128; 49_129; 49_130; 49_131; 49_132; 49_133; 49_134; 49_135; 49_136; 49_137; 49_138; 49_139; 49_140; 49_141; 49_142; 49_143; 49_144; 49_145; 49_146; 49_147; 49_148; 49_149; 49_150; 49_151; 49_152; 49_153; 49_154; 49_155; 49_156; 49_157; 49_158; 49_159; 49_160; 49_161; 49_162; 49_163; 49_164; 49_165; 49_166; 49_167; 49_168; 49_169; 49_170; 49_171; 49_172; 49_173; 49_174; 49_175; 49_176; 49_177; 49_178; 49_179; 49_180; 49_181; 49_182; 49_183; 49_184; 49_185; 49_186; 49_187; 49_188; 49_189; 49_190; 49_191; 49_192; 50_1; 51_1; 52_1; 53_1; 54_1; 55_1; 56_1; 57_1; 58_1; 59_1; 60_1; 61_1; 62_1; 63_1; 64_1 and 65_1.

For certain embodiments of the invention, the oligonucleotide is selected from the group of oligonucleotide compounds with CMP-ID-NO: 9_102; 9_103; 9_104; 11_1; 49_38; 49_51; 49_179; 49_189; 53_1; 56_1 and 62_1.

For certain embodiments of the invention, the oligonucleotide is selected from the group of oligonucleotide compounds with CMP-ID-NO: 9_102; 9_103; 9_104 and 11_1.

For certain embodiments of the invention, the oligonucleotide is selected from the group of oligonucleotide compounds with CMP-ID-NO: 49_38; 49_51; 49_179 and 49_189.

For certain embodiments of the invention, the oligonucleotide is selected from the group of oligonucleotide compounds with CMP-ID-NO: 53_1; 56_1 and 62_1.

A particular advantageous antisense oligonucleotide in the context of the invention is an oligonucleotide compound selected from the group consisting of

```
                                        SEQ ID NO: 9
CTTtAATttaatcactcAT; CMP ID NO: 9_102

                                        SEQ ID NO: 9
CTTTaatttaatcacTCAT; CMP ID NO: 9_103

                                        SEQ ID NO: 9
CTTTaatttaatcaCtCAT; CMP ID NO: 9_104

                                       SEQ ID NO: 11
CTTTaatttaatcaCTCA; CMP ID NO: 11_1

                                       SEQ ID NO: 49
TtaaCTCAaatcaaTtctCA; CMP ID NO: 49_38

                                       SEQ ID NO: 49
TtaActCAaatcaattCTCA; CMP ID NO: 49_51

                                       SEQ ID NO: 49
TTAactCaaatcaatTCtCA; CMP ID NO: 49_179

                                       SEQ ID NO: 49
TTAActcaaatcaattCTCA; CMP ID NO: 49_189

                                       SEQ ID NO: 53
CAACaccttttaattcATTA; CMP ID NO: 53_1
```

-continued

SEQ ID NO: 56
CTCAtcaacaccttttaaTT; CMP ID NO: 56_1

SEQ ID NO: 62
TTAactcatcaacaCCTT; CMP ID NO: 62_1 wherein capital letters are beta-D-oxy LNA nucleosides, lowercase letters are DNA nucleosides, all LNA C are 5-methyl cytosine, all internucleoside linkages are phosphorothioate internucleoside linkages.

Figure 2:
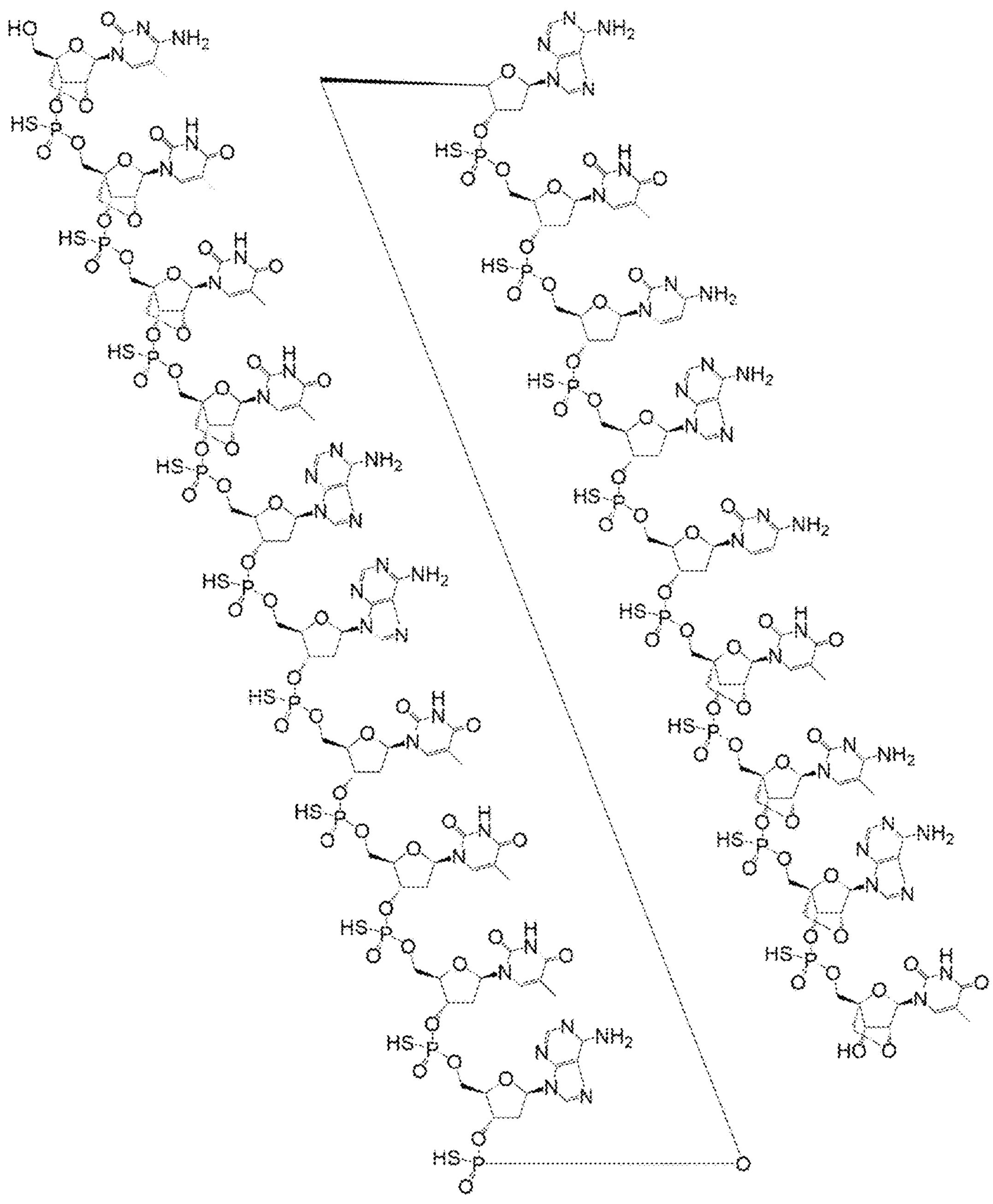
FIG. 2: Compound 9_103 (sequence of nucleobases is shown in SEQ ID NO 9)

In one embodiment the antisense oligonucleotide is CMP ID NO: 9_103 as shown in FIG. 2.

Figure 3:
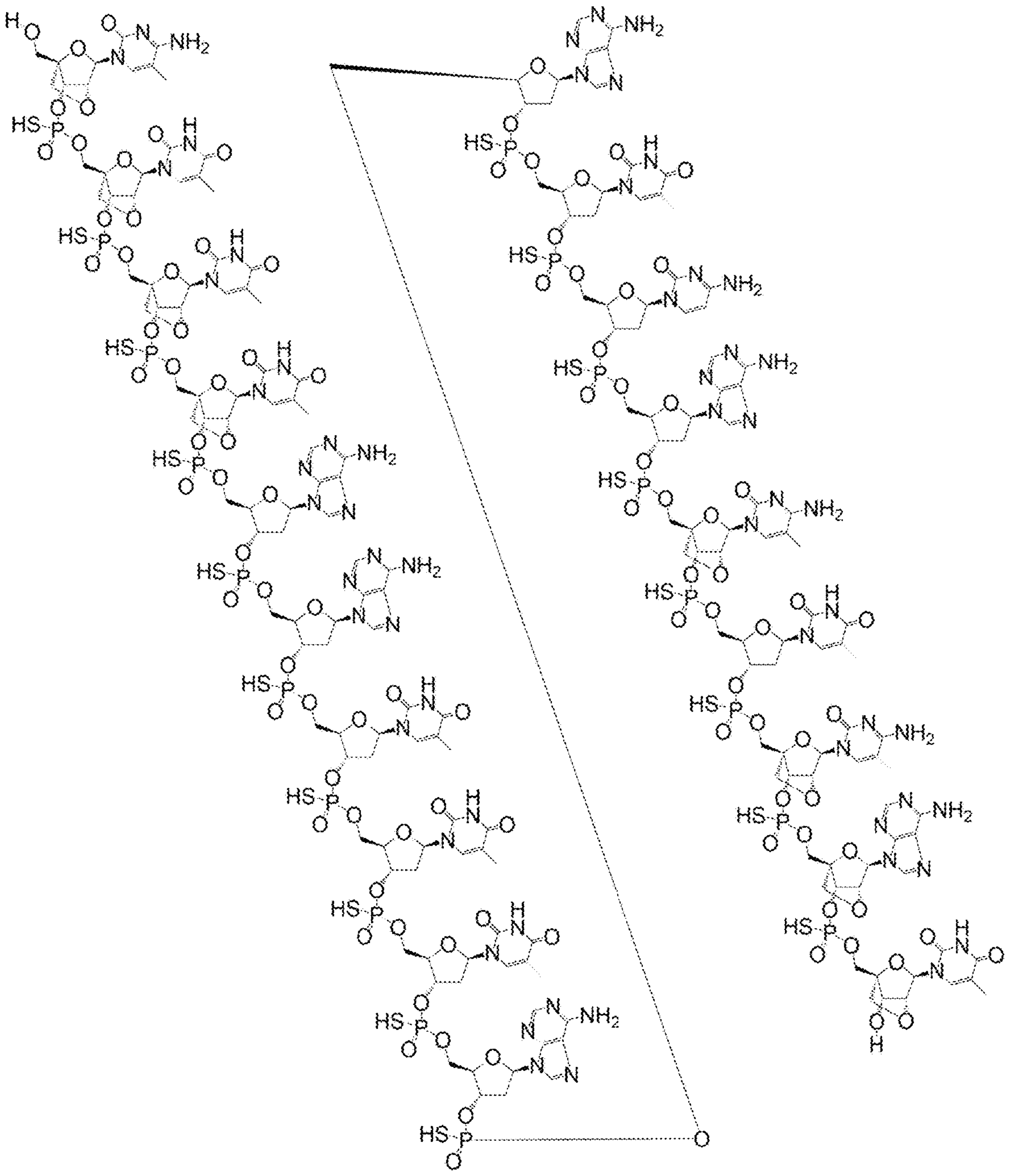
FIG. 3: Compound 9_104 (sequence of nucleobases is shown in SEQ ID NO 9)

In one embodiment the antisense oligonucleotide is CMP ID NO: 9_104 as shown in FIG. 3.

Figure 4:
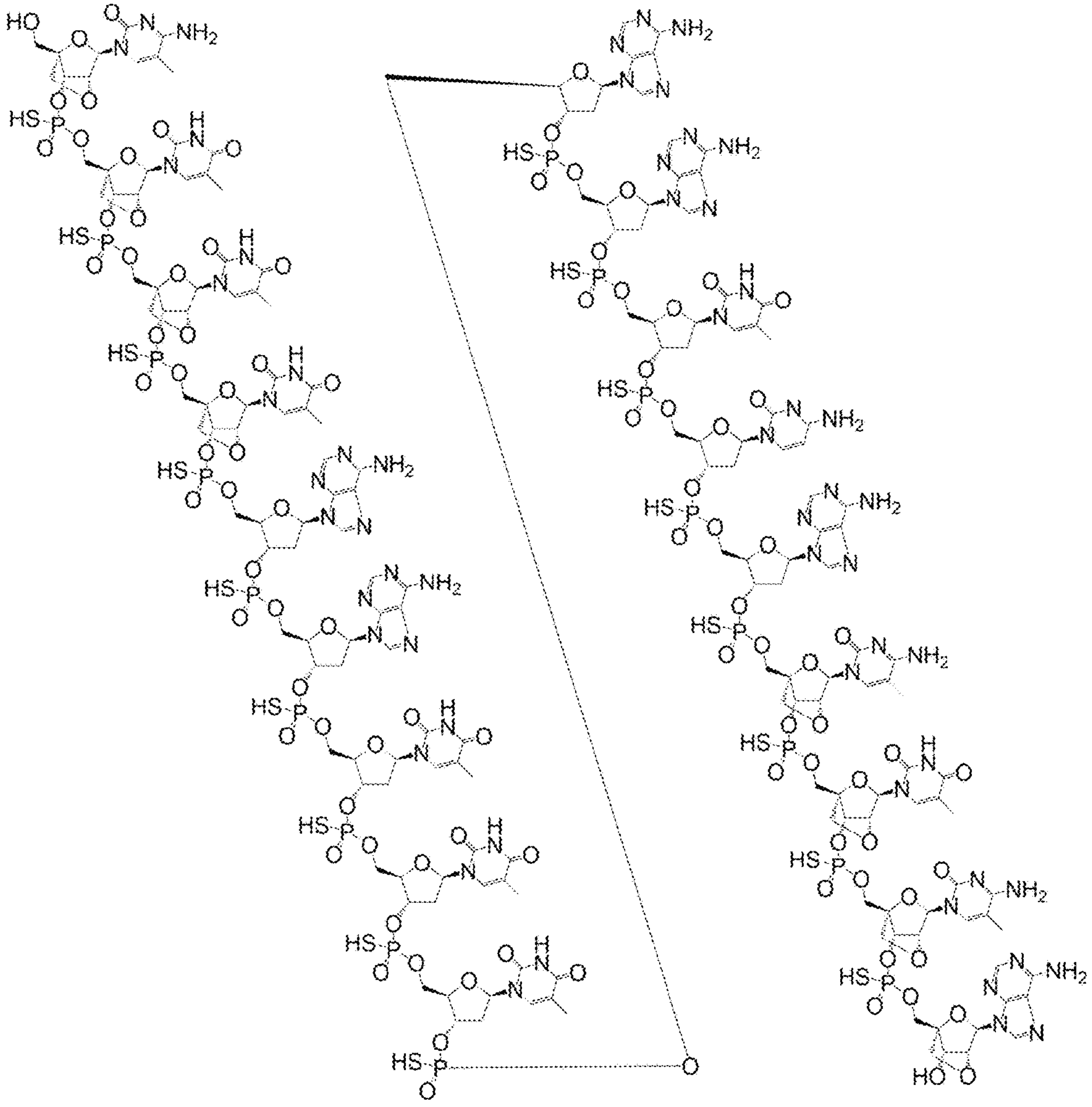
FIG. 4: Compound 11_1 (sequence of nucleobases is shown in SEQ ID NO 11)

In one embodiment the antisense oligonucleotide is CMP ID NO: 11_1 as shown in FIG. 4.

Figure 5:
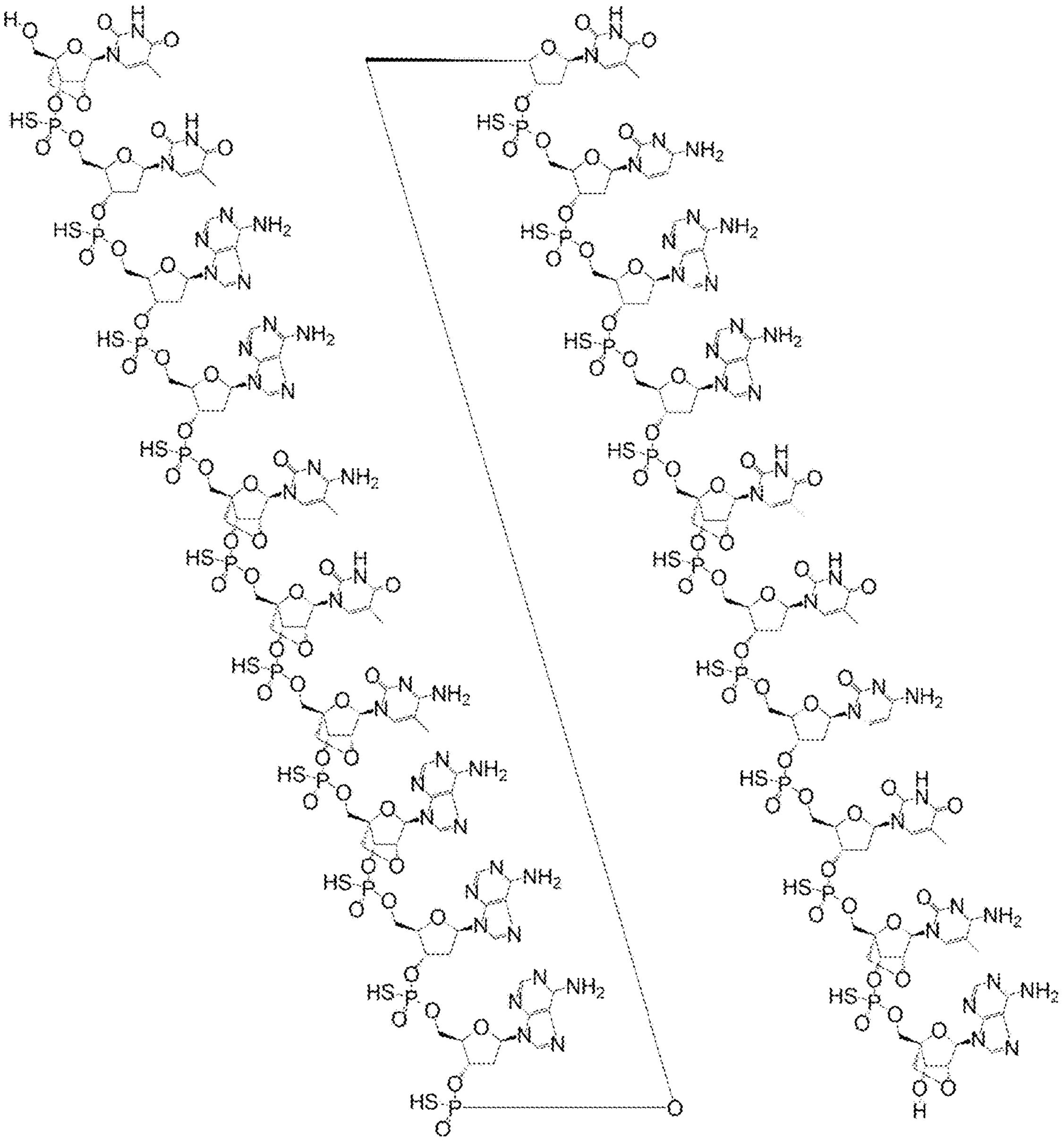
FIG. 5: Compound 49_38 (sequence of nucleobases is shown in SEQ ID NO 49)

In one embodiment the antisense oligonucleotide is CMP ID NO: 49_38 as shown in FIG. 5.

Figure 6:
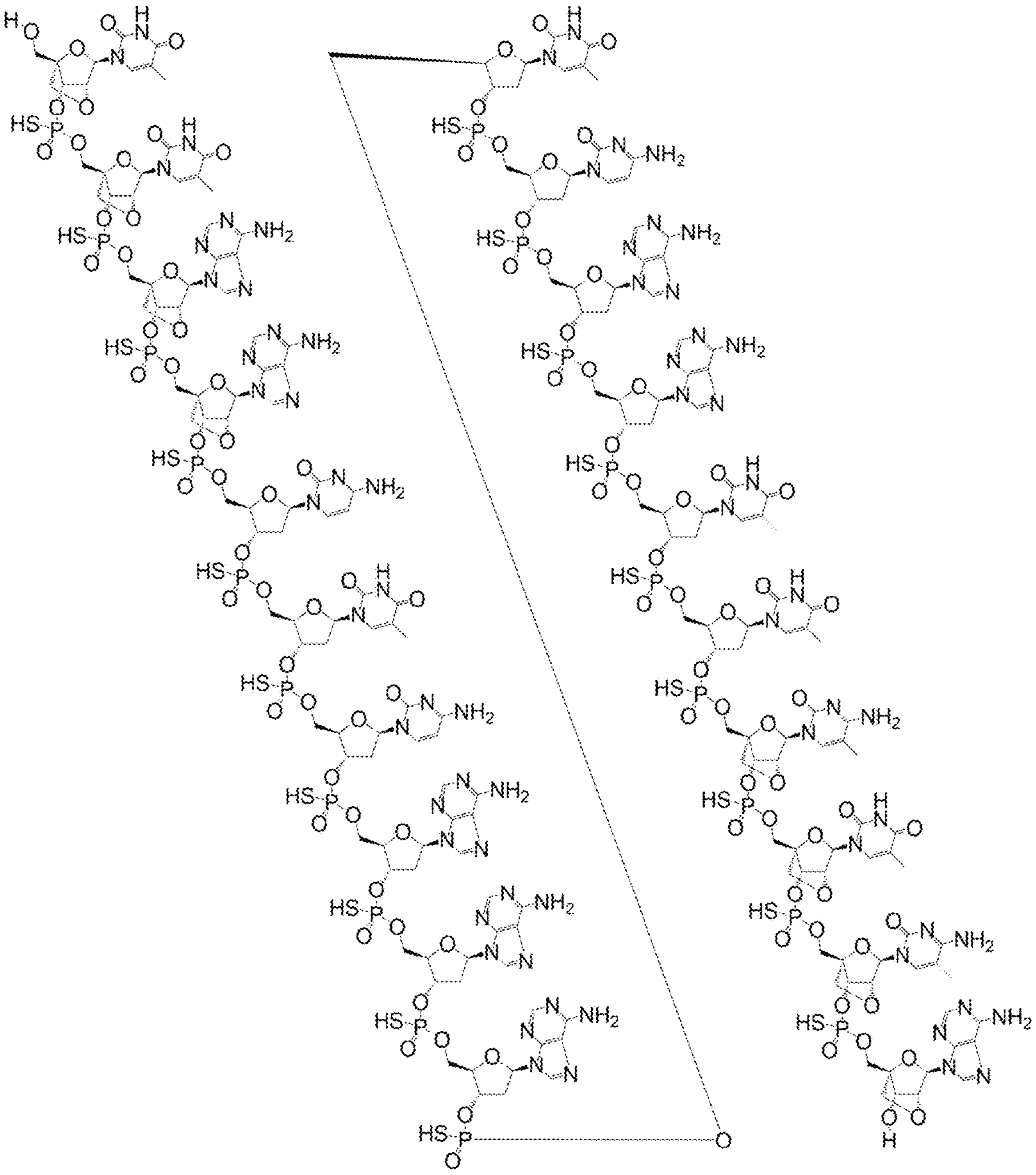
FIG. 6: Compound 49_189 (sequence of nucleobases is shown in SEQ ID NO 49)

In one embodiment the antisense oligonucleotide is CMP ID NO: 49_189 as shown in FIG. 6.

Method of Manufacture

In a further aspect, the invention provides methods for manufacturing the oligonucleotides of the invention comprising reacting nucleotide units and thereby forming covalently linked contiguous nucleotide units comprised in the oligonucleotide. Preferably, the method uses phophoramidite chemistry (see for example Caruthers et al, 1987, Methods in Enzymology vol. 154, pages 287-313). In a further embodiment the method further comprises reacting the contiguous nucleotide sequence with a conjugating moiety (ligand) to covalently attach the conjugate moiety to the oligonucleotide. In a further aspect a method is provided for manufacturing the composition of the invention, comprising mixing the oligonucleotide or conjugated oligonucleotide of the invention with a pharmaceutically acceptable diluent, solvent, carrier, salt and/or adjuvant.

Pharmaceutical Salt

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin, Organic Process Research & Development 2000, 4, 427-435 or in Ansel, In: Pharmaceutical Dosage Forms and Drug Delivery Systems, 6th ed. (1995), pp. 196 and 1456-1457. For example, the pharmaceutically acceptable salt of the compounds provided herein may be a sodium salt.

In a further aspect the invention provides a pharmaceutically acceptable salt of the antisense oligonucleotide or a conjugate thereof. In a preferred embodiment, the pharmaceutically acceptable salt is a sodium or a potassium salt.

Pharmaceutical Composition

In a further aspect, the invention provides pharmaceutical compositions comprising any of the aforementioned oligonucleotides and/or oligonucleotide conjugates or salts thereof and a pharmaceutically acceptable diluent, carrier, salt and/or adjuvant. A pharmaceutically acceptable diluent includes phosphate-buffered saline (PBS) and pharmaceutically acceptable salts include, but are not limited to, sodium and potassium salts. In some embodiments the pharmaceutically acceptable diluent is sterile phosphate buffered saline. In some embodiments the oligonucleotide is used in the pharmaceutically acceptable diluent at a concentration of 50-300 μM solution.

Suitable formulations for use in the present invention are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990). WO 2007/031091 provides further suitable and preferred examples of pharmaceutically acceptable diluents, carriers and adjuvants (hereby incorporated by reference). Suitable dosages, formulations, administration routes, compositions, dosage forms, combinations with other therapeutic agents, pro-drug formulations are also provided in WO2007/031091.

Oligonucleotides or oligonucleotide conjugates of the invention may be mixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

In some embodiments, the oligonucleotide or oligonucleotide conjugate of the invention is a prodrug. In particular, with respect to oligonucleotide conjugates the conjugate moiety is cleaved off the oligonucleotide once the prodrug is delivered to the site of action, e.g. the target cell.

Applications

The oligonucleotides of the invention may be utilized as research reagents for, for example, diagnostics, therapeutics and prophylaxis.

In research, such oligonucleotides may be used to specifically modulate the synthesis of Tau protein in cells (e.g. in vitro cell cultures) and experimental animals thereby facilitating functional analysis of the target or an appraisal of its usefulness as a target for therapeutic intervention. Typically, the target modulation is achieved by degrading or inhibiting the mRNA producing the protein, thereby prevent protein formation or by degrading or inhibiting a modulator of the gene or mRNA producing the protein.

If employing the oligonucleotide of the invention in research or diagnostics the target nucleic acid may be a cDNA or a synthetic nucleic acid derived from DNA or RNA.

The present invention provides an in vivo or in vitro method for modulating Tau expression in a target cell which is expressing Tau, said method comprising administering an oligonucleotide of the invention in an effective amount to said cell.

In some embodiments, the target cell, is a mammalian cell in particular a human cell. The target cell may be an in vitro cell culture or an in vivo cell forming part of a tissue in a mammal. In preferred embodiments the target cell is present in the brain or central nervous system. In particular cells in the brain stem, cerebellum, cerebal cortex, frontal cortex, medulla/pons and midbrain and spinal cord are relevant target regions. For the treatment of progressive supranuclear palsy (PSP) target reduction in the brain regions medulla/pons and midbrain are advantageous. For the treatment of Alzheimer target reduction in the brain regions cerebal cortex, medulla/pons and midbrain are advantageous. In particular, in neurons, nerves cells, axons and basal ganglia are relevant cell types.

In diagnostics the oligonucleotides may be used to detect and quantitate MAPT expression in cell and tissues by northern blotting, in-situ hybridisation or similar techniques.

For therapeutics, the oligonucleotides may be administered to an animal or a human, suspected of having a disease or disorder, which can be treated by modulating the expression of Tau.

The invention provides methods for treating or preventing a disease, comprising administering a therapeutically or prophylactically effective amount of an oligonucleotide, an oligonucleotide conjugate or a pharmaceutical composition of the invention to a subject suffering from or susceptible to the disease.

The invention also relates to an oligonucleotide, a composition or a conjugate as defined herein for use as a medicament.

The oligonucleotide, oligonucleotide conjugate or a pharmaceutical composition according to the invention is typically administered in an effective amount.

The invention also provides for the use of the oligonucleotide or oligonucleotide conjugate of the invention as described for the manufacture of a medicament for the treatment of a disorder as referred to herein, or for a method of the treatment of as a disorder as referred to herein.

The disease or disorder, as referred to herein, is associated with expression of Tau. In some embodiments disease or disorder may be associated with a mutation in the Tau gene or a gene whose protein product is associated with or interacts with Tau. Therefore, in some embodiments, the target nucleic acid is a mutated form of the Tau sequence and in other embodiments, the target nucleic acid is a regulator of the Tau sequence.

The methods of the invention are preferably employed for treatment or prophylaxis against diseases caused by abnormal levels and/or activity of Tau.

The invention further relates to use of an oligonucleotide, oligonucleotide conjugate or a pharmaceutical composition as defined herein for the manufacture of a medicament for the treatment of abnormal levels and/or activity of Tau.

In one embodiment, the invention relates to oligonucleotides, oligonucleotide conjugates or pharmaceutical compositions for use in the treatment of diseases or disorders selected from wherein the disease is selected from Tauopathies, Alzheimer's disease (AD), progressive supranuclear palsy (PSP), corticobasal ganglionic degeneration (CBD), chronic traumatic encephalopathy (CTE), fronto-temporal dementia (FTD), FTDP-17, Pick's disease (PiD), argyrophilic grain disease (AGD), tangle-predominant senile dementia (TPSD), primary age-related Tauopathy (PART), Down syndrome, lytico-bodig disease, infantile Tauopathies including hem imegalencephaly (HME), tuberous sclerosis complex, focal cortical dysplasia type 2b, ganglioglioma, Hallervorden-Spatz syndrome, neurodegeneration with brain iron accumulation type 1 (NBIA1), gangliocytomas, subacute sclerosing panencephalitis, seizure disorders (e.g., epilepsy), network dysfunction (e.g., depression) and movement disorders (e.g., Parkinson's disease).

In certain embodiments the disease is selected from Alzheimer's disease (AD), progressive supranuclear palsy (PSP), fronto-temporal dementia (FTD) or FTDP-17.

Administration

The oligonucleotides or pharmaceutical compositions of the present invention may be administered via parenteral (such as, intravenous, subcutaneous, intra-muscular, intracerebral, intracerebroventricular intraocular, or intrathecal administration).

In some embodiments, the administration is via intrathecal administration.

Advantageously, e.g. for treatment of neurological disorders, the oligonucleotide or pharmaceutical compositions of the present invention are administered intrathecally or intracranially, e.g. via intracerebral or intraventricular administration.

The invention also provides for the use of the oligonucleotide or conjugate thereof, such as pharmaceutical salts or compositions of the invention, for the manufacture of a medicament wherein the medicament is in a dosage form for subcutaneous administration.

The invention also provides for the use of the oligonucleotide of the invention, or conjugate thereof, such as pharmaceutical salts or compositions of the invention, for the manufacture of a medicament wherein the medicament is in a dosage form for intrathecal administration.

The invention also provides for the use of the oligonucleotide or oligonucleotide conjugate of the invention as described for the manufacture of a medicament wherein the medicament is in a dosage form for intrathecal administration.

Combination Therapies

In some embodiments the oligonucleotide, oligonucleotide conjugate or pharmaceutical composition of the invention is for use in a combination treatment with another therapeutic agent. The therapeutic agent can for example be the standard of care for the diseases or disorders described above.

EMBODIMENTS

The following embodiments of the present invention may be used in combination with any other embodiments described herein.

1. An antisense oligonucleotide of 10 to 50 nucleotides in length, which comprises a contiguous nucleotide sequence of at least 10 nucleotides in length, such as 10-30 nucleotides in length, with at least 90% complementarity, such as 100% complementarity, to any target sequence in table 4 (R_1-R_2254).
2. The oligonucleotide of embodiment 1, wherein the target sequence is selected from one of the target regions R_223, R_738 or R_1298, corresponds to SEQ ID NO: 3, 4 or 5, respectively.

3. The oligonucleotide of embodiment 1 or 2, wherein the contiguous nucleotide sequence is 100% complementary to contiguous nucleotides within position 12051 to 12111, 39562 to 39593 or 72837 to 72940 of SEQ ID NO: 1.
4. The oligonucleotide of embodiment 1 to 3, wherein the contiguous nucleotide sequence is at last 16 nucleotides and 100% complementary, to contiguous nucleotides within position 12060 to 12078, position 39573 to 39592 or position 72862-72890 of SEQ ID NO: 1.
5. The oligonucleotide of embodiment 1 to 4, wherein the oligonucleotide comprises a sequence selected from the group consisting of SEQ ID NO: 6-65.
6. The oligonucleotide of embodiment 1 to 5, wherein the oligonucleotide comprises a sequence of SEQ ID NO: 9 or 11.
7. The oligonucleotide of embodiment 1 to 5, wherein the oligonucleotide comprises a sequence of SEQ ID NO: 49.
8. The oligonucleotide of embodiment 1 to 5, wherein the oligonucleotide comprises a sequence selected from the group consisting of SEQ ID NO: 53, 56 and 62.
9. The oligonucleotide of embodiment 1, 2 or 5 or 6, wherein the contiguous nucleotide sequence has zero to three mismatches compared to the target sequence it is complementary to.
10. The oligonucleotide of embodiment 9, wherein the contiguous nucleotide sequence has one mismatch compared to the target sequence.
11. The oligonucleotide of embodiment 9, wherein the contiguous nucleotide sequence has two mismatches compared to the target sequence.
12. The oligonucleotide of embodiment 9, wherein the contiguous nucleotide sequence is fully complementary to the target sequence.
13. The oligonucleotide of embodiment 1 to 12, wherein the oligonucleotide is capable of modulating expression of Tau.
14. The oligonucleotide of embodiment 13, wherein the oligonucleotide is capable of reducing expression of Tau.
15. The oligonucleotide of embodiment 1 to 14, wherein the oligonucleotide is capable of hybridizing to the target sequence with a $\Delta G°$ below $-10$ kcal.
16. The oligonucleotide of embodiment 1 to 15, wherein the target sequence is located in RNA.
17. The oligonucleotide of embodiment 16, wherein the RNA is mRNA.
18. The oligonucleotide of embodiment 17, wherein the mRNA is pre-mRNA.
19. The oligonucleotide of embodiment 1-18, wherein the contiguous nucleotide sequence comprises or consists of at least 14 contiguous nucleotides, particularly 15, 16, 17, 18, 19, 20, 21, or 22 contiguous nucleotides.
20. The oligonucleotide of embodiment 1-18, wherein the contiguous nucleotide sequence comprises or consists of from 16 to 22 nucleotides.
21. The oligonucleotide of embodiment 20, wherein the contiguous nucleotide sequence comprises or consists of from 18 to 20 nucleotides.
22. The oligonucleotide of embodiment 1-21, wherein the oligonucleotide comprises or consists of 14 to 30 nucleotides in length.
23. The oligonucleotide of embodiment 22, wherein the oligonucleotide comprises or consists of 16 to 24 nucleotides in length.
24. The oligonucleotide of embodiment 22 or 24, wherein the oligonucleotide comprises or consists of 18 to 20 nucleotides in length.
25. The oligonucleotide of embodiment 1-24, wherein the oligonucleotide or contiguous nucleotide sequence is single stranded.
26. The oligonucleotide of embodiment 1-25, wherein the oligonucleotide is not siRNA nor self-complementary.
27. The oligonucleotide of embodiment 1-26, comprising one or more modified nucleosides.
28. The oligonucleotide of embodiment 27, wherein the one or more modified nucleoside is a high-affinity modified nucleosides.
29. The oligonucleotide of embodiment 27 or 28, wherein the one or more modified nucleoside is a 2' sugar modified nucleoside.
30. The oligonucleotide of embodiment 29, wherein the one or more 2' sugar modified nucleoside is independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, 2'-fluoro-ANA and LNA nucleosides.
31. The oligonucleotide of embodiment 29 or 30, wherein the one or more 2' sugar modified nucleoside is a LNA nucleoside.
32. The antisense oligonucleotide of embodiment 31, wherein the LNA nucleoside is selected from oxy-LNA, amino-LNA, thio-LNA, cET, and ENA.
33. The antisense oligonucleotide of embodiment 31 or 32, wherein the modified LNA nucleoside is oxy-LNA with the following 2'-4' bridge —O—$CH_2$—.
34. The antisense oligonucleotide of embodiment 33, wherein the oxy-LNA is beta-D-oxy-LNA.
35. The antisense oligonucleotide of embodiment 31 or 32, wherein the modified LNA nucleoside is cET with the following 2'-4' bridge —O—$CH(CH_3)$—.
36. The antisense oligonucleotide of embodiment 35, wherein the cET is (S)cET, i.e. 6'(S) methyl-beta-D-oxy-LNA.
37. The antisense oligonucleotide of embodiment 31 or 32, wherein the LNA is ENA, with the following 2'-4' bridge —O—$CH_2$—$CH_2$—.
38. The oligonucleotide of embodiment 29 or 30, wherein the one or more 2' sugar modified nucleoside is a MOE nucleoside
39. The oligonucleotide of any one of embodiments 1-38, wherein the oligonucleotide comprises at least one modified internucleoside linkage.
40. The oligonucleotide of embodiment 39, wherein the modified internucleoside linkage is nuclease resistant.
41. The oligonucleotide of embodiment 39 or 40, wherein at least 50% of the internucleoside linkages within the contiguous nucleotide sequence are phosphorothioate internucleoside linkages or boranophosphate internucleoside linkages.
42. The oligonucleotide of embodiment 39 or 41, wherein 80% the internucleoside linkages within the contiguous nucleotide sequence are phosphorothioate internucleoside linkages.
43. The oligonucleotide of embodiment 39 to 42, wherein all the internucleoside linkages within the contiguous nucleotide sequence are phosphorothioate internucleoside linkages.
44. The oligonucleotide of embodiment 1-43, wherein the oligonucleotide is capable of recruiting RNase H.

45. The oligonucleotide of embodiment 44, wherein the oligonucleotide or the contiguous nucleotide sequence is a gapmer.
46. The oligonucleotide of embodiment 45, wherein the gapmer has the formula 5'-F-G-F'-3', where the F and F' wing regions independently comprise or consist of 1-8 nucleosides, of which 2-5 are 2' sugar modified nucleosides in accordance with embodiment 32 to 38 and G is a region between 6 and 16 nucleosides which are capable of recruiting RNaseH.
47. The antisense oligonucleotide of embodiment 46, wherein each wing region (F and F') is characterized by having at least one 2' sugar modified nucleoside at the 5' terminal and the 3' terminal of the wing and the G region has at least one DNA nucleoside adjacent to the wing regions (e.g. 5' and 3' terminal of the G region).
48. The oligonucleotide of embodiment 46 or 47, wherein all the 2' sugar modified nucleosides in region F and F' are identical LNA nucleosides.
49. The oligonucleotide of embodiment 48, wherein all the LNA nucleosides are oxy-LNA nucleosides.
50. The oligonucleotide of embodiment 46 or 47, wherein all the 2' sugar modified nucleosides in region F and F' are identical MOE nucleosides.
51. The oligonucleotide of embodiment 46-50, wherein
 a. the F region is between 3 and 8 nucleotides in length and consists of 3-5 identical LNA nucleosides and 0-4 DNA nucleosides; and
 b. the F' region is between 2 and 6 nucleotides in length and consists of 2-4 identical LNA nucleosides and 0-2 DNA nucleosides; and
 c. region G is between 6 and 14 DNA nucleotides.
52. The oligonucleotide of embodiment 46 or 47, wherein at least one of region F or F' further comprises at least one 2' substituted modified nucleoside independently selected from the group consisting of 2'-O-alkyl-RNA, 2'-O-methyl-RNA, 2'-alkoxy-RNA, 2'-O-methoxyethyl-RNA, 2'-amino-DNA and 2'-fluoro-DNA.
53. The oligonucleotide of embodiment 46 to 50 or 52, wherein the RNaseH recruiting nucleosides in region G are independently selected from DNA, alpha-L-LNA, C4' alkylated DNA, ANA and 2'F-ANA and UNA.
54. The oligonucleotide of embodiment 53, wherein the nucleosides in region G is DNA and/or alpha-L-LNA nucleosides.
55. The oligonucleotide of embodiment 53 or 54, wherein region G consists of at least 75% DNA nucleosides.
56. The oligonucleotide of embodiment 53 to 55, wherein all the nucleotides in the G region are DNA.
57. The oligonucleotide of embodiment 1-56, wherein the oligonucleotide is selected from CMP ID NO: 9_102; 9_103; 9_104; 11_1; 49_38; 49_51; 49_179; 49_189; 53_1; 56_1 and 62_1.
58. The oligonucleotide of embodiment 57, wherein the oligonucleotide is a compound selected from the group consisting of

```
                                    SEQ ID NO: 9
CTTtAATttaatcactcAT; CMP ID NO: 9_102

                                    SEQ ID NO: 9
CTTTaatttaatcacTCAT; CMP ID NO: 9_103

                                    SEQ ID NO: 9
CTTTaatttaatcaCtCAT; CMP ID NO: 9_104
```

-continued

```
                                    SEQ ID NO: 11
CTTTaatttaatcaCTCA; CMP ID NO: 11_1

                                    SEQ ID NO: 49
TtaaCTCAaatcaaTtctCA; CMP ID NO: 49_38

                                    SEQ ID NO: 49
TtaActCAaatcaattCTCA; CMP ID NO: 49_51

                                    SEQ ID NO: 49
TTAactCaaatcaatTCtCA; CMP ID NO: 49_179

                                    SEQ ID NO: 49
TTAActcaaatcaattCTCA; CMP ID NO: 49_189

                                    SEQ ID NO: 53
CAACacctttaattcATTA; CMP ID NO: 53_1

                                    SEQ ID NO: 56
CTCAtcaacaccttttaaTT; CMP ID NO: 56_1

                                    SEQ ID NO: 62
TTAactcatcaacaCCTT; CMP ID NO: 62_1
```

wherein capital letters are beta-D-oxy LNA nucleosides, lowercase letters are DNA nucleosides, all LNA C are 5-methyl cytosine, all internucleoside linkages are phosphorothioate internucleoside linkages.
59. The antisense oligonucleotide according to any one of embodiments 1-58, wherein the antisense oligonucleotide is CMP ID NO: 9_103 as shown in FIG. 2.
60. The antisense oligonucleotide according to any one of embodiments 1-58, wherein the antisense oligonucleotide is CMP ID NO: 9_104 as shown in FIG. 3.
61. The antisense oligonucleotide according to any one of embodiments 1-58, wherein the antisense oligonucleotide is CMP ID NO: 11_1 as shown in FIG. 4.
62. The antisense oligonucleotide according to any one of embodiments 1-58, wherein the antisense oligonucleotide is CMP ID NO: 49_38 as shown in FIG. 5.
63. The antisense oligonucleotide according to any one of embodiments 1-58, wherein the antisense oligonucleotide is CMP ID NO: 49_189 as shown in FIG. 6.
64. A conjugate comprising the oligonucleotide according to any one of claims 1-58, and at least one conjugate moiety covalently attached to said oligonucleotide.
65. The oligonucleotide conjugate of embodiment 59, wherein the conjugate moiety is selected from carbohydrates, cell surface receptor ligands, drug substances, hormones, lipophilic substances, polymers, proteins, peptides, toxins, vitamins, viral proteins or combinations thereof.
66. The oligonucleotide conjugate of embodiment 59 or 65, wherein the conjugate facilitates delivery across the blood brain barrier.
67. The oligonucleotide conjugate of embodiment 66, wherein the conjugate is an antibody or antibody fragment targeting the transferrin receptor.
68. The oligonucleotide conjugate of embodiment 59-67, comprising a linker which is positioned between the oligonucleotide and the conjugate moiety.
69. The oligonucleotide conjugate of embodiment 68, wherein the linker is a physiologically labile linker.
70. A pharmaceutical composition comprising the oligonucleotide of embodiment 1-58 or a conjugate of embodiment 59-69 and a pharmaceutically acceptable diluent, carrier, salt and/or adjuvant.
71. A method for manufacturing the oligonucleotide of embodiment 1-58, comprising reacting nucleotide units thereby forming covalently linked contiguous nucleotide units comprised in the oligonucleotide.

72. The method of embodiment 71, further comprising reacting the contiguous nucleotide sequence with a non-nucleotide conjugation moiety.
73. A method for manufacturing the composition of embodiment 70, comprising mixing the oligonucleotide with a pharmaceutically acceptable diluent, carrier, salt and/or adjuvant.
74. An in vivo or in vitro method for modulating Tau expression in a target cell which is expressing Tau, said method comprising administering an oligonucleotide of embodiment 1-57 or a conjugate of embodiment 59-69 or the pharmaceutical composition of embodiment 70 in an effective amount to said cell.
75. A method for treating or preventing a disease comprising administering a therapeutically or prophylactically effective amount of an oligonucleotide of embodiment 1-58 or a conjugate of embodiment 59-69 or the pharmaceutical composition of embodiment 70 to a subject suffering from or susceptible to the disease.
76. The oligonucleotide of embodiment 1-57 or a conjugate of embodiment 59-69 or the pharmaceutical composition of embodiment 70, for use as a medicament for treatment or prevention of a disease in a subject.
77. Use of the oligonucleotide of oligonucleotide of embodiment 1-58 or a conjugate of embodiment 59-69 for the preparation of a medicament for treatment or prevention of a disease in a subject.
78. The method, the oligonucleotide or the use of embodiments 75-77, wherein the disease is associated with in vivo activity of Tau.
79. The method, the oligonucleotide or the use of embodiments 75-78, wherein the disease is associated with overexpression of Tau and/or abnormal levels of Tau.
80. The method, the oligonucleotide or the use of embodiments 79, wherein the Tau is reduced by at least 30%, or at least or at least 40%, or at least 50%, or at least 60%, or at least 70%, or at least 80%, or at least 90%, or at least 95% compared to the expression without the oligonucleotide of embodiment 1-58 or a conjugate of embodiment 59-69 or the pharmaceutical composition of embodiment 70.
81. The method, the oligonucleotide or the use of embodiments 75-79, wherein the disease is selected from Tauopathies, Alzheimer's disease (AD), progressive supranuclear palsy (PSP), corticobasal ganglionic degeneration (CBD), chronic traumatic encephalopathy (CTE), fronto-temporal dementia (FTD), FTDP-17, Pick's disease (PiD), argyrophilic grain disease (AGD), tangle-predominant senile dementia (TPSD), primary age-related Tauopathy (PART), Down syndrome, lytico-bodig disease, infantile Tauopathies including hemimegalencephaly (HME), tuberous sclerosis complex, focal cortical dysplasia type 2b, ganglioglioma, Hallervorden-Spatz syndrome, neurodegeneration with brain iron accumulation type 1 (NBIA1), gangliocytomas, subacute sclerosing panencephalitis, seizure disorders (e.g., epilepsy), network dysfunction (e.g., depression) and movement disorders (e.g., Parkinson's disease).
82. The method, the oligonucleotide or the use of embodiments 75-79 wherein the disease is selected from Alzheimer's disease (AD), progressive supranuclear palsy (PSP), fronto-temporal dementia (FTD) or FTDP-17.
83. The method, the oligonucleotide or the use of embodiments 75-82, wherein the subject is a mammal.
84. The method, the oligonucleotide or the use of embodiment 83, wherein the mammal is human.

EXAMPLES

Materials and Methods

Oligonucleotide Motif Sequences and Oligonucleotide Compounds

| SEQ ID NO | motif sequence | Design | Oligonucleotide Compound | CMP ID NO | Start on SEQ ID NO: 1 | Region |
|---|---|---|---|---|---|---|
| 6 | tcactcatgccttaatc | 4-11-2 | TCACtcatgccttaaTC | 6_1 | 12051 | A |
| 7 | taatcactcatgcctta | 4-9-4 | TAATcactcatgcCTTA | 7_1 | 12054 | A |
| 8 | taatcactcatgcctt | 4-8-4 | TAATcactcatgCCTT | 8_1 | 12055 | A |
| 9 | ctttaatttaatcactcat | 1-10-1-2-1-1-3 | CtttaatttaaTcaCtCAT | 9_1 | 12060 | A |
| 9 | ctttaatttaatcactcat | 1-10-1-1-2-1-3 | CtttaatttaaTcACtCAT | 9_2 | 12060 | A |
| 9 | ctttaatttaatcactcat | 1-10-2-3-3 | CtttaatttaaTCactCAT | 9_3 | 12060 | A |
| 9 | ctttaatttaatcactcat | 1-10-2-2-4 | CtttaatttaaTCacTCAT | 9_4 | 12060 | A |
| 9 | ctttaatttaatcactcat | 1-10-2-1-1-2-2 | CtttaatttaaTCaCtcAT | 9_5 | 12060 | A |
| 9 | ctttaatttaatcactcat | 1-10-2-1-1-1-3 | CtttaatttaaTCaCtCAT | 9_6 | 12060 | A |
| 9 | ctttaatttaatcactcat | 1-10-3-3-2 | CtttaatttaaTCActcAT | 9_7 | 12060 | A |
| 9 | ctttaatttaatcactcat | 1-10-3-2-3 | CtttaatttaaTCActCAT | 9_8 | 12060 | A |
| 9 | ctttaatttaatcactcat | 1-10-3-1-4 | CtttaatttaaTCAcTCAT | 9_9 | 12060 | A |
| 9 | ctttaatttaatcactcat | 1-10-4-2-2 | CtttaatttaaTCACtcAT | 9_10 | 12060 | A |
| 9 | ctttaatttaatcactcat | 1-5-1-8-4 | CtttaaTttaatcacTCAT | 9_11 | 12060 | A |
| 9 | ctttaatttaatcactcat | 1-5-1-7-1-1-3 | CtttaaTttaatcaCtCAT | 9_12 | 12060 | A |

-continued

| SEQ ID NO | motif sequence | Design | Oligonucleotide Compound | CMP ID NO | Start on SEQ ID NO: 1 | Region |
|---|---|---|---|---|---|---|
| 9 | ctttaatttaatcactcat | 1-5-1-6-1-2-3 | CtttaaTttaatcActCAT | 9_13 | 12060 | A |
| 9 | ctttaatttaatcactcat | 1-5-1-6-1-1-4 | CtttaaTttaatcAcTCAT | 9_14 | 12060 | A |
| 9 | ctttaatttaatcactcat | 1-5-1-6-2-1-3 | CtttaaTttaatcACtCAT | 9_15 | 12060 | A |
| 9 | ctttaatttaatcactcat | 1-4-1-9-4 | CtttaAtttaatcacTCAT | 9_16 | 12060 | A |
| 9 | ctttaatttaatcactcat | 1-4-2-8-4 | CtttaATttaatcacTCAT | 9_17 | 12060 | A |
| 9 | ctttaatttaatcactcat | 1-3-1-10-4 | CtttAatttaatcacTCAT | 9_18 | 12060 | A |
| 9 | ctttaatttaatcactcat | 1-3-1-9-1-1-3 | CtttAatttaatcaCtCAT | 9_19 | 12060 | A |
| 9 | ctttaatttaatcactcat | 1-3-1-1-1-8-4 | CtttAaTttaatcacTCAT | 9_20 | 12060 | A |
| 9 | ctttaatttaatcactcat | 1-3-2-9-4 | CtttAAtttaatcacTCAT | 9_21 | 12060 | A |
| 9 | ctttaatttaatcactcat | 1-3-3-8-4 | CtttAATttaatcacTCAT | 9_22 | 12060 | A |
| 9 | ctttaatttaatcactcat | 1-2-1-11-4 | CttTaatttaatcacTCAT | 9_23 | 12060 | A |
| 9 | ctttaatttaatcactcat | 1-2-1-10-1-1-3 | CttTaatttaatcaCtCAT | 9_24 | 12060 | A |
| 9 | ctttaatttaatcactcat | 1-2-1-2-1-8-4 | CttTaaTttaatcacTCAT | 9_25 | 12060 | A |
| 9 | ctttaatttaatcactcat | 1-2-1-1-1-9-4 | CttTaAtttaatcacTCAT | 9_26 | 12060 | A |
| 9 | ctttaatttaatcactcat | 1-2-1-1-2-8-4 | CttTaATttaatcacTCAT | 9_27 | 12060 | A |
| 9 | ctttaatttaatcactcat | 1-2-2-11-3 | CttTAatttaatcactCAT | 9_28 | 12060 | A |
| 9 | ctttaatttaatcactcat | 1-2-2-10-4 | CttTAatttaatcacTCAT | 9_29 | 12060 | A |
| 9 | ctttaatttaatcactcat | 1-2-2-9-1-2-2 | CttTAatttaatcaCtcAT | 9_30 | 12060 | A |
| 9 | ctttaatttaatcactcat | 1-2-2-9-1-1-3 | CttTAatttaatcaCtCAT | 9_31 | 12060 | A |
| 9 | ctttaatttaatcactcat | 1-2-2-1-1-8-4 | CttTAaTttaatcacTCAT | 9_32 | 12060 | A |
| 9 | ctttaatttaatcactcat | 1-2-3-9-4 | CttTAAtttaatcacTCAT | 9_33 | 12060 | A |
| 9 | ctttaatttaatcactcat | 1-2-4-10-2 | CttTAATttaatcactcAT | 9_34 | 12060 | A |
| 9 | ctttaatttaatcactcat | 1-2-4-8-4 | CttTAATttaatcacTCAT | 9_35 | 12060 | A |
| 9 | ctttaatttaatcactcat | 1-1-1-3-1-8-4 | CtTtaaTttaatcacTCAT | 9_36 | 12060 | A |
| 9 | ctttaatttaatcactcat | 1-1-1-2-1-9-4 | CtTtaAtttaatcacTCAT | 9_37 | 12060 | A |
| 9 | ctttaatttaatcactcat | 1-1-1-2-2-8-4 | CtTtaATttaatcacTCAT | 9_38 | 12060 | A |
| 9 | ctttaatttaatcactcat | 1-1-1-1-1-10-4 | CtTtAatttaatcacTCAT | 9_39 | 12060 | A |
| 9 | ctttaatttaatcactcat | 1-1-1-1-1-9-1-1-3 | CtTtAatttaatcaCtCAT | 9_40 | 12060 | A |
| 9 | ctttaatttaatcactcat | 1-1-1-1-1-1-1-8-4 | CtTtAaTttaatcacTCAT | 9_41 | 12060 | A |
| 9 | ctttaatttaatcactcat | 1-1-1-1-2-9-4 | CtTtAAtttaatcacTCAT | 9_42 | 12060 | A |
| 9 | ctttaatttaatcactcat | 1-1-1-1-3-8-4 | CtTtAATttaatcacTCAT | 9_43 | 12060 | A |
| 9 | ctttaatttaatcactcat | 1-1-2-11-4 | CtTTaatttaatcacTCAT | 9_44 | 12060 | A |
| 9 | ctttaatttaatcactcat | 1-1-2-10-1-2-2 | CtTTaatttaatcaCtcAT | 9_45 | 12060 | A |
| 9 | ctttaatttaatcactcat | 1-1-2-10-1-1-3 | CtTTaatttaatcaCtCAT | 9_46 | 12060 | A |
| 9 | ctttaatttaatcactcat | 1-1-2-2-1-8-4 | CtTTaaTttaatcacTCAT | 9_47 | 12060 | A |
| 9 | ctttaatttaatcactcat | 1-1-2-1-1-9-4 | CtTTaAtttaatcacTCAT | 9_48 | 12060 | A |
| 9 | ctttaatttaatcactcat | 1-1-2-1-2-10-2 | CtTTaATttaatcactcAT | 9_49 | 12060 | A |

-continued

| SEQ ID NO | motif sequence | Design | Oligonucleotide Compound | CMP ID NO | Start on SEQ ID NO: 1 | Region |
|---|---|---|---|---|---|---|
| 9 | ctttaatttaatcactcat | 1-1-2-1-2-8-4 | CtTTaATttaatcacTCAT | 9_50 | 12060 | A |
| 9 | ctttaatttaatcactcat | 1-1-3-11-3 | CtTTAatttaatcactCAT | 9_51 | 12060 | A |
| 9 | ctttaatttaatcactcat | 1-1-3-10-4 | CtTTAatttaatcacTCAT | 9_52 | 12060 | A |
| 9 | ctttaatttaatcactcat | 1-1-3-9-1-2-2 | CtTTAatttaatcaCtcAT | 9_53 | 12060 | A |
| 9 | ctttaatttaatcactcat | 1-1-3-9-1-1-3 | CtTTAatttaatcaCtCAT | 9_54 | 12060 | A |
| 9 | ctttaatttaatcactcat | 1-1-3-1-1-10-2 | CtTTAaTttaatcactcAT | 9_55 | 12060 | A |
| 9 | ctttaatttaatcactcat | 1-1-3-1-1-8-4 | CtTTAaTttaatcacTCAT | 9_56 | 12060 | A |
| 9 | ctttaatttaatcactcat | 1-1-4-11-2 | CtTTAAtttaatcactcAT | 9_57 | 12060 | A |
| 9 | ctttaatttaatcactcat | 1-1-4-9-4 | CtTTAAtttaatcacTCAT | 9_58 | 12060 | A |
| 9 | ctttaatttaatcactcat | 2-11-1-2-3 | CTttaatttaatcActCAT | 9_59 | 12060 | A |
| 9 | ctttaatttaatcactcat | 2-11-1-1-4 | CTttaatttaatcAcTCAT | 9_60 | 12060 | A |
| 9 | ctttaatttaatcactcat | 2-11-2-1-3 | CTttaatttaatcACtCAT | 9_61 | 12060 | A |
| 9 | ctttaatttaatcactcat | 2-9-2-4-2 | CTttaatttaaTCactcAT | 9_62 | 12060 | A |
| 9 | ctttaatttaatcactcat | 2-9-2-3-3 | CTttaatttaaTCactCAT | 9_63 | 12060 | A |
| 9 | ctttaatttaatcactcat | 2-9-2-2-4 | CTttaatttaaTCacTCAT | 9_64 | 12060 | A |
| 9 | ctttaatttaatcactcat | 2-9-2-1-1-2-2 | CTttaatttaaTCaCtcAT | 9_65 | 12060 | A |
| 9 | ctttaatttaatcactcat | 2-9-2-1-1-1-3 | CTttaatttaaTCaCtCAT | 9_66 | 12060 | A |
| 9 | ctttaatttaatcactcat | 2-9-3-3-2 | CTttaatttaaTCActcAT | 9_67 | 12060 | A |
| 9 | ctttaatttaatcactcat | 2-9-3-2-3 | CTttaatttaaTCActCAT | 9_68 | 12060 | A |
| 9 | ctttaatttaatcactcat | 2-9-4-2-2 | CTttaatttaaTCACtcAT | 9_69 | 12060 | A |
| 9 | ctttaatttaatcactcat | 2-4-1-9-3 | CTttaaTttaatcactCAT | 9_70 | 12060 | A |
| 9 | ctttaatttaatcactcat | 2-4-1-8-4 | CTttaaTttaatcacTCAT | 9_71 | 12060 | A |
| 9 | ctttaatttaatcactcat | 2-4-1-7-1-2-2 | CTttaaTttaatcaCtcAT | 9_72 | 12060 | A |
| 9 | ctttaatttaatcactcat | 2-4-1-7-1-1-3 | CTttaaTttaatcaCtCAT | 9_73 | 12060 | A |
| 9 | ctttaatttaatcactcat | 2-4-1-6-1-2-3 | CTttaaTttaatcActCAT | 9_74 | 12060 | A |
| 9 | ctttaatttaatcactcat | 2-4-1-6-1-1-4 | CTttaaTttaatcAcTCAT | 9_75 | 12060 | A |
| 9 | ctttaatttaatcactcat | 2-4-1-6-2-2-2 | CTttaaTttaatcACtcAT | 9_76 | 12060 | A |
| 9 | ctttaatttaatcactcat | 2-4-1-6-2-1-3 | CTttaaTttaatcACtCAT | 9_77 | 12060 | A |
| 9 | ctttaatttaatcactcat | 2-2-1-11-3 | CTttAatttaatcactCAT | 9_78 | 12060 | A |
| 9 | ctttaatttaatcactcat | 2-2-1-10-4 | CTttAatttaatcacTCAT | 9_79 | 12060 | A |
| 9 | ctttaatttaatcactcat | 2-2-1-9-1-1-3 | CTttAatttaatcaCtCAT | 9_80 | 12060 | A |
| 9 | ctttaatttaatcactcat | 2-2-1-1-1-8-4 | CTttAaTttaatcacTCAT | 9_81 | 12060 | A |
| 9 | ctttaatttaatcactcat | 2-2-2-9-4 | CTttAAtttaatcacTCAT | 9_82 | 12060 | A |
| 9 | ctttaatttaatcactcat | 2-2-3-8-4 | CTttAATttaatcacTCAT | 9_83 | 12060 | A |
| 9 | ctttaatttaatcactcat | 2-1-1-10-1-2-2 | CTtTaatttaatcaCtcAT | 9_84 | 12060 | A |
| 9 | ctttaatttaatcactcat | 2-1-1-10-1-1-3 | CTtTaatttaatcaCtCAT | 9_85 | 12060 | A |
| 9 | ctttaatttaatcactcat | 2-1-1-1-1-9-4 | CTtTaAtttaatcacTCAT | 9_86 | 12060 | A |
| 9 | ctttaatttaatcactcat | 2-1-1-1-2-10-2 | CTtTaATttaatcactcAT | 9_87 | 12060 | A |

-continued

| SEQ ID NO | motif sequence | Design | Oligonucleotide Compound | CMP ID NO | Start on SEQ ID NO: 1 | Region |
|---|---|---|---|---|---|---|
| 9 | ctttaatttaatcactcat | 2-1-2-1 1-3 | CTtTAatttaatcactCAT | 9_88 | 12060 | A |
| 9 | ctttaatttaatcactcat | 2-1-2-10-4 | CTtTAatttaatcacTCAT | 9_89 | 12060 | A |
| 9 | ctttaatttaatcactcat | 2-1-2-9-1-2-2 | CTtTAatttaatcaCtcAT | 9_90 | 12060 | A |
| 9 | ctttaatttaatcactcat | 2-1-2-9-1-1-3 | CTtTAatttaatcaCtCAT | 9_91 | 12060 | A |
| 9 | ctttaatttaatcactcat | 2-1-2-1-1-10-2 | CTtTAaTttaatcactcAT | 9_92 | 12060 | A |
| 9 | ctttaatttaatcactcat | 2-1-3-1 1-2 | CTtTAAtttaatcactcAT | 9_93 | 12060 | A |
| 9 | ctttaatttaatcactcat | 2-1-3-9-4 | CTtTAAtttaatcacTCAT | 9_94 | 12060 | A |
| 9 | ctttaatttaatcactcat | 2-1-4-10-2 | CTtTAATttaatcactcAT | 9_95 | 12060 | A |
| 9 | ctttaatttaatcactcat | 3-2-2-10-2 | CTTtaATttaatcactcAT | 9_96 | 12060 | A |
| 9 | ctttaatttaatcactcat | 3-1-1-11-3 | CTTtAatttaatcactCAT | 9_97 | 12060 | A |
| 9 | ctttaatttaatcactcat | 3-1-1-10-4 | CTTtAatttaatcacTCAT | 9_98 | 12060 | A |
| 9 | ctttaatttaatcactcat | 3-1-1-9-1-2-2 | CTTtAatttaatcaCtcAT | 9_99 | 12060 | A |
| 9 | ctttaatttaatcactcat | 3-1-1-9-1-1-3 | CTTtAatttaatcaCtCAT | 9_100 | 12060 | A |
| 9 | ctttaatttaatcactcat | 3-1-2-9-4 | CTTtAAtttaatcacTCAT | 9_101 | 12060 | A |
| 9 | ctttaatttaatcactcat | 3-1-3-10-2 | CTTtAATttaatcactcAT | 9_102 | 12060 | A |
| 9 | ctttaatttaatcactcat | 4-11-4 | CTTTaatttaatcacTCAT | 9_103 | 12060 | A |
| 9 | ctttaatttaatcactcat | 4-10-1-1-3 | CTTTaatttaatcaCtCAT | 9_104 | 12060 | A |
| 9 | ctttaatttaatcactcat | 4-2-1-10-2 | CTTTaaTttaatcactcAT | 9_105 | 12060 | A |
| 9 | ctttaatttaatcactcat | 4-1-1-9-4 | CTTTaAtttaatcacTCAT | 9_106 | 12060 | A |
| 10 | gctttaatttaatcactcat | 1-11-1-2-1-1-3 | GctttaatttaaTcaCtCAT | 10_1 | 12060 | A |
| 10 | gctttaatttaatcactcat | 1-11-2-4-2 | GctttaatttaaTCactcAT | 10_2 | 12060 | A |
| 10 | gctttaatttaatcactcat | 1-11-2-3-3 | GctttaatttaaTCactCAT | 10_3 | 12060 | A |
| 10 | gctttaatttaatcactcat | 1-11-2-2-4 | GctttaatttaaTCacTCAT | 10_4 | 12060 | A |
| 10 | gctttaatttaatcactcat | 1-11-2-1-1-2-2 | GctttaatttaaTCaCtcAT | 10_5 | 12060 | A |
| 10 | gctttaatttaatcactcat | 1-11-2-1-1-1-3 | GctttaatttaaTCaCtCAT | 10_6 | 12060 | A |
| 10 | gctttaatttaatcactcat | 1-11-3-3-2 | GctttaatttaaTCActcAT | 10_7 | 12060 | A |
| 10 | gctttaatttaatcactcat | 1-11-4-2-2 | GctttaatttaaTCACtcAT | 10_8 | 12060 | A |
| 10 | gctttaatttaatcactcat | 1-6-1-9-3 | GctttaaTttaatcactCAT | 10_9 | 12060 | A |
| 10 | gctttaatttaatcactcat | 1-6-1-8-4 | GctttaaTttaatcacTCAT | 10_10 | 12060 | A |
| 10 | gctttaatttaatcactcat | 1-6-1-7-1-2-2 | GctttaaTttaatcaCtcAT | 10_11 | 12060 | A |
| 10 | gctttaatttaatcactcat | 1-6-1-7-1-1-3 | GctttaaTttaatcaCtCAT | 10_12 | 12060 | A |
| 10 | gctttaatttaatcactcat | 1-6-1-4-1-2-1-1-3 | GctttaaTttaaTcaCtCAT | 10_13 | 12060 | A |
| 10 | gctttaatttaatcactcat | 1-6-1-4-2-3-3 | GctttaaTttaaTCactCAT | 10_14 | 12060 | A |
| 10 | gctttaatttaatcactcat | 1-6-1-4-2-1-1-2-2 | GctttaaTttaaTCaCtcAT | 10_15 | 12060 | A |
| 10 | gctttaatttaatcactcat | 1-6-1-4-3-3-2 | GctttaaTttaaTCActcAT | 10_16 | 12060 | A |
| 10 | gctttaatttaatcactcat | 1-5-1-9-4 | GctttaAtttaatcacTCAT | 10_17 | 12060 | A |
| 10 | gctttaatttaatcactcat | 1-4-1-10-4 | GctttAatttaatcacTCAT | 10_18 | 12060 | A |

-continued

| SEQ ID NO | motif sequence | Design | Oligonucleotide Compound | CMP ID NO | Start on SEQ ID NO: 1 | Region |
|---|---|---|---|---|---|---|
| 10 | gctttaatttaatcactcat | 1-4-1-9-1-1-3 | GctttAatttaatcaCtCAT | 10_19 | 12060 | A |
| 10 | gctttaatttaatcactcat | 1-4-1-1-1-8-4 | GctttAaTttaatcacTCAT | 10_20 | 12060 | A |
| 10 | gctttaatttaatcactcat | 1-4-2-9-4 | GctttAAtttaatcacTCAT | 10_21 | 12060 | A |
| 10 | gctttaatttaatcactcat | 1-4-3-8-4 | GctttAATttaatcacTCAT | 10_22 | 12060 | A |
| 10 | gctttaatttaatcactcat | 1-3-1-11-4 | GcttTaatttaatcacTCAT | 10_23 | 12060 | A |
| 10 | gctttaatttaatcactcat | 1-3-1-10-1-2-2 | GcttTaatttaatcaCtcAT | 10_24 | 12060 | A |
| 10 | gctttaatttaatcactcat | 1-3-1-10-1-1-3 | GcttTaatttaatcaCtCAT | 10_25 | 12060 | A |
| 10 | gctttaatttaatcactcat | 1-3-1-2-1-8-4 | GcttTaaTttaatcacTCAT | 10_26 | 12060 | A |
| 10 | gctttaatttaatcactcat | 1-3-1-1-1-9-4 | GcttTaAtttaatcacTCAT | 10_27 | 12060 | A |
| 10 | gctttaatttaatcactcat | 1-3-2-10-4 | GcttTAatttaatcacTCAT | 10_28 | 12060 | A |
| 10 | gctttaatttaatcactcat | 1-3-2-9-1-2-2 | GcttTAatttaatcaCtcAT | 10_29 | 12060 | A |
| 10 | gctttaatttaatcactcat | 1-3-2-9-1-1-3 | GcttTAatttaatcaCtCAT | 10_30 | 12060 | A |
| 10 | gctttaatttaatcactcat | 1-2-1-3-1-8-4 | GctTtaaTttaatcacTCAT | 10_31 | 12060 | A |
| 10 | gctttaatttaatcactcat | 1-2-1-2-1-9-4 | GctTtaAtttaatcacTCAT | 10_32 | 12060 | A |
| 10 | gctttaatttaatcactcat | 1-2-1-1-1-10-4 | GctTtAatttaatcacTCAT | 10_33 | 12060 | A |
| 10 | gctttaatttaatcactcat | 1-2-1-1-1-9-1-2-2 | GctTtAatttaatcaCtcAT | 10_34 | 12060 | A |
| 10 | gctttaatttaatcactcat | 1-2-1-1-1-9-1-1-3 | GctTtAatttaatcaCtCAT | 10_35 | 12060 | A |
| 10 | gctttaatttaatcactcat | 1-2-1-1-1-1-1-8-4 | GctTtAaTttaatcacTCAT | 10_36 | 12060 | A |
| 10 | gctttaatttaatcactcat | 1-2-1-1-2-9-4 | GctTtAAtttaatcacTCAT | 10_37 | 12060 | A |
| 10 | gctttaatttaatcactcat | 1-2-2-11-4 | GctTTaatttaatcacTCAT | 10_38 | 12060 | A |
| 10 | gctttaatttaatcactcat | 1-2-2-10-1-2-2 | GctTTaatttaatcaCtcAT | 10_39 | 12060 | A |
| 10 | gctttaatttaatcactcat | 1-2-2-10-1-1-3 | GctTTaatttaatcaCtCAT | 10_40 | 12060 | A |
| 10 | gctttaatttaatcactcat | 1-2-2-1-1-9-4 | GctTTaAtttaatcacTCAT | 10_41 | 12060 | A |
| 10 | gctttaatttaatcactcat | 1-2-3-9-1-2-2 | GctTTAatttaatcaCtcAT | 10_42 | 12060 | A |
| 10 | gctttaatttaatcactcat | 1-1-1-9-2-4-2 | GcTttaatttaaTCactcAT | 10_43 | 12060 | A |
| 10 | gctttaatttaatcactcat | 1-1-1-9-2-3-3 | GcTttaatttaaTCactCAT | 10_44 | 12060 | A |
| 10 | gctttaatttaatcactcat | 1-1-1-9-2-1-1-2-2 | GcTttaatttaaTCaCtcAT | 10_45 | 12060 | A |
| 10 | gctttaatttaatcactcat | 1-1-1-9-3-3-2 | GcTttaatttaaTCActcAT | 10_46 | 12060 | A |
| 10 | gctttaatttaatcactcat | 1-1-1-4-1-9-3 | GcTttaaTttaatcactCAT | 10_47 | 12060 | A |
| 10 | gctttaatttaatcactcat | 1-1-1-4-1-8-4 | GcTttaaTttaatcacTCAT | 10_48 | 12060 | A |
| 10 | gctttaatttaatcactcat | 1-1-1-4-1-7-1-2-2 | GcTttaaTttaatcaCtcAT | 10_49 | 12060 | A |
| 10 | gctttaatttaatcactcat | 1-1-1-4-1-7-1-1-3 | GcTttaaTttaatcaCtCAT | 10_50 | 12060 | A |
| 10 | gctttaatttaatcactcat | 1-1-1-3-1-9-4 | GcTttaAtttaatcacTCAT | 10_51 | 12060 | A |
| 10 | gctttaatttaatcactcat | 1-1-1-2-1-10-4 | GcTttAatttaatcacTCAT | 10_52 | 12060 | A |
| 10 | gctttaatttaatcactcat | 1-1-1-2-1-9-1-2-2 | GcTttAatttaatcaCtcAT | 10_53 | 12060 | A |
| 10 | gctttaatttaatcactcat | 1-1-1-2-1-9-1-1-3 | GcTttAatttaatcaCtCAT | 10_54 | 12060 | A |
| 10 | gctttaatttaatcactcat | 1-1-1-2-1-1-1-8-4 | GcTttAaTttaatcacTCAT | 10_55 | 12060 | A |
| 10 | gctttaatttaatcactcat | 1-1-1-2-2-9-4 | GcTttAAtttaatcacTCAT | 10_56 | 12060 | A |

-continued

| SEQ ID NO | motif sequence | Design | Oligonucleotide Compound | CMP ID NO | Start on SEQ ID NO: 1 | Region |
|---|---|---|---|---|---|---|
| 10 | gctttaatttaatcactcat | 1-1-1-1-1-11-4 | GcTtTaatttaatcacTCAT | 10_57 | 12060 | A |
| 10 | gctttaatttaatcactcat | 1-1-1-1-1-10-1-1-3 | GcTtTaatttaatcaCtCAT | 10_58 | 12060 | A |
| 10 | gctttaatttaatcactcat | 1-1-1-1-1-2-1-8-4 | GcTtTaaTttaatcacTCAT | 10_59 | 12060 | A |
| 10 | gctttaatttaatcactcat | 1-1-1-1-1-1-1-9-4 | GcTtTaAtttaatcacTCAT | 10_60 | 12060 | A |
| 10 | gctttaatttaatcactcat | 1-1-1-1-2-9-1-2-2 | GcTtTAatttaatcaCtcAT | 10_61 | 12060 | A |
| 10 | gctttaatttaatcactcat | 1-1-1-1-3-11-2 | GcTtTAAtttaatcactcAT | 10_62 | 12060 | A |
| 10 | gctttaatttaatcactcat | 1-1-2-3-1-8-4 | GcTTtaaTttaatcacTCAT | 10_63 | 12060 | A |
| 10 | gctttaatttaatcactcat | 1-1-2-2-1-11-2 | GcTTtaAtttaatcactcAT | 10_64 | 12060 | A |
| 10 | gctttaatttaatcactcat | 1-1-2-2-1-9-4 | GcTTtaAtttaatcacTCAT | 10_65 | 12060 | A |
| 10 | gctttaatttaatcactcat | 1-1-2-1-1-10-4 | GcTTtAatttaatcacTCAT | 10_66 | 12060 | A |
| 10 | gctttaatttaatcactcat | 1-1-2-1-1-9-1-1-3 | GcTTtAatttaatcaCtCAT | 10_67 | 12060 | A |
| 10 | gctttaatttaatcactcat | 1-1-2-1-2-11-2 | GcTTtAAtttaatcactcAT | 10_68 | 12060 | A |
| 10 | gctttaatttaatcactcat | 1-1-3-10-2-1-2 | GcTTTaatttaatcaCTcAT | 10_69 | 12060 | A |
| 10 | gctttaatttaatcactcat | 1-1-4-9-1-2-2 | GcTTTAatttaatcaCtcAT | 10_70 | 12060 | A |
| 10 | gctttaatttaatcactcat | 2-11-1-4-2 | GCtttaatttaatCactcAT | 10_71 | 12060 | A |
| 10 | gctttaatttaatcactcat | 2-10-2-4-2 | GCtttaatttaaTCactcAT | 10_72 | 12060 | A |
| 10 | gctttaatttaatcactcat | 2-5-1-10-2 | GCtttaaTttaatcactcAT | 10_73 | 12060 | A |
| 10 | gctttaatttaatcactcat | 2-5-1-9-3 | GCtttaaTttaatcactCAT | 10_74 | 12060 | A |
| 10 | gctttaatttaatcactcat | 2-5-1-7-1-2-2 | GCtttaaTttaatcaCtcAT | 10_75 | 12060 | A |
| 10 | gctttaatttaatcactcat | 2-4-2-10-2 | GCtttaATttaatcactcAT | 10_76 | 12060 | A |
| 10 | gctttaatttaatcactcat | 2-3-1-9-1-2-2 | GCtttAatttaatcaCtcAT | 10_77 | 12060 | A |
| 10 | gctttaatttaatcactcat | 2-3-2-11-2 | GCtttAAtttaatcactcAT | 10_78 | 12060 | A |
| 10 | gctttaatttaatcactcat | 2-2-1-10-1-2-2 | GCttTaatttaatcaCtcAT | 10_79 | 12060 | A |
| 10 | gctttaatttaatcactcat | 2-2-1-1-1-11-2 | GCttTaAtttaatcactcAT | 10_80 | 12060 | A |
| 10 | gctttaatttaatcactcat | 2-2-3-11-2 | GCttTAAtttaatcactcAT | 10_81 | 12060 | A |
| 10 | gctttaatttaatcactcat | 2-1-1-2-1-11-2 | GCtTtaAtttaatcactcAT | 10_82 | 12060 | A |
| 10 | gctttaatttaatcactcat | 2-1-1-1-1-9-1-2-2 | GCtTtAatttaatcaCtcAT | 10_83 | 12060 | A |
| 10 | gctttaatttaatcactcat | 2-1-1-1-2-11-2 | GCtTtAAtttaatcactcAT | 10_84 | 12060 | A |
| 10 | gctttaatttaatcactcat | 3-10-1-4-2 | GCTttaatttaatCactcAT | 10_85 | 12060 | A |
| 10 | gctttaatttaatcactcat | 3-4-1-10-2 | GCTttaaTttaatcactcAT | 10_86 | 12060 | A |
| 10 | gctttaatttaatcactcat | 3-3-1-11-2 | GCTttaAtttaatcactcAT | 10_87 | 12060 | A |
| 10 | gctttaatttaatcactcat | 3-2-2-11-2 | GCTttAAtttaatcactcAT | 10_88 | 12060 | A |
| 10 | gctttaatttaatcactcat | 3-1-1-9-1-1-1-1-2 | GCTtTaatttaatcAcTcAT | 10_89 | 12060 | A |
| 11 | ctttaatttaatcactca | 4-10-4 | CTTTaatttaatcaCTCA | 11_1 | 12061 | A |
| 12 | ctttaatttaatcactc | 4-9-4 | CTTTaatttaatcACTC | 12_1 | 12062 | A |
| 13 | tccaagtcaatgcctggctt | 3-14-3 | TCCaagtcaatgcctggCTT | 13_1 | 12076 | A |
| 14 | atccaagtcaatgcctggct | 3-14-3 | ATCcaagtcaatgcctgGCT | 14_1 | 12077 | A |

-continued

| SEQ ID NO | motif sequence | Design | Oligonucleotide Compound | CMP ID NO | Start on SEQ ID NO: 1 | Region |
|---|---|---|---|---|---|---|
| 15 | accatccaagtcaatgcctg | 3-14-3 | ACCatccaagtcaatgcCTG | 15_1 | 12080 | A |
| 16 | caccatccaagtcaatgcct | 3-14-3 | CACcatccaagtcaatgCCT | 16_1 | 12081 | A |
| 17 | tacaccatccaagtcaatgc | 3-14-3 | TACaccatccaagtcaaTGC | 17_1 | 12083 | A |
| 18 | ttacaccatccaagtcaatg | 3-14-3 | TTAcaccatccaagtcaATG | 18_1 | 12084 | A |
| 19 | acaccatccaagtcaat | 3-10-4 | ACAccatccaagtCAAT | 19_1 | 12085 | A |
| 20 | tacaccatccaagtcaa | 3-10-4 | TACaccatccaagTCAA | 20_1 | 12086 | A |
| 21 | ttacaccatccaagtca | 4-11-2 | TTACaccatccaagtCA | 21_1 | 12087 | A |
| 22 | ttacaccatccaagtc | 4-9-3 | TTACaccatccaaGTC | 22_1 | 12088 | A |
| 23 | aatattacaccatccaa | 4-9-4 | AATAttacaccatCCAA | 23_1 | 12091 | A |
| 24 | agaatattacaccatccaa | 1-3-1-10-4 | AgaaTattacaccatCCAA | 24_1 | 12091 | A |
| 24 | agaatattacaccatccaa | 1-3-1-9-1-1-3 | AgaaTattacaccaTcCAA | 24_2 | 12091 | A |
| 24 | agaatattacaccatccaa | 1-3-1-9-2-1-2 | AgaaTattacaccaTCcAA | 24_3 | 12091 | A |
| 24 | agaatattacaccatccaa | 1-3-1-8-1-2-3 | AgaaTattacaccAtcCAA | 24_4 | 12091 | A |
| 24 | agaatattacaccatccaa | 1-3-1-8-1-1-4 | AgaaTattacaccAtCCAA | 24_5 | 12091 | A |
| 24 | agaatattacaccatccaa | 1-3-1-8-2-1-3 | AgaaTattacaccATcCAA | 24_6 | 12091 | A |
| 24 | agaatattacaccatccaa | 1-3-1-8-3-1-2 | AgaaTattacaccATCcAA | 24_7 | 12091 | A |
| 24 | agaatattacaccatccaa | 1-3-1-7-1-1-2-1-2 | AgaaTattacacCaTCcAA | 24_8 | 12091 | A |
| 24 | agaatattacaccatccaa | 1-3-1-6-1-1-1-1-1-2 | AgaaTattacaCcAtCcAA | 24_9 | 12091 | A |
| 24 | agaatattacaccatccaa | 1-3-1-6-1-1-2-1-3 | AgaaTattacaCcATcCAA | 24_10 | 12091 | A |
| 24 | agaatattacaccatccaa | 1-2-1-11-4 | AgaAtattacaccatCCAA | 24_11 | 12091 | A |
| 24 | agaatattacaccatccaa | 1-2-1-10-1-1-3 | AgaAtattacaccaTcCAA | 24_12 | 12091 | A |
| 24 | agaatattacaccatccaa | 1-2-2-11-3 | AgaATattacaccatcCAA | 24_13 | 12091 | A |
| 24 | agaatattacaccatccaa | 1-2-2-9-2-1-2 | AgaATattacaccaTCcAA | 24_14 | 12091 | A |
| 24 | agaatattacaccatccaa | 1-2-2-8-1-2-3 | AgaATattacaccAtcCAA | 24_15 | 12091 | A |
| 24 | agaatattacaccatccaa | 1-2-2-8-1-1-1-2 | AgaATattacaccAtCCAA | 24_16 | 12091 | A |
| 24 | agaatattacaccatccaa | 1-2-2-8-3-1-2 | AgaATattacaccATCcAA | 24_17 | 12091 | A |
| 24 | agaatattacaccatccaa | 1-2-2-7-2-1-1-1-2 | AgaATattacacCAtCcAA | 24_18 | 12091 | A |
| 24 | agaatattacaccatccaa | 1-1-1-10-1-1-4 | AgAatattacaccAtCCAA | 24_19 | 12091 | A |
| 24 | agaatattacaccatccaa | 1-1-1-10-3-1-2 | AgAatattacaccATCcAA | 24_20 | 12091 | A |
| 24 | agaatattacaccatccaa | 1-1-1-1-1-11-3 | AgAaTattacaccatcCAA | 24_21 | 12091 | A |
| 24 | agaatattacaccatccaa | 1-1-1-1-1-9-2-1-2 | AgAaTattacaccaTCcAA | 24_22 | 12091 | A |
| 24 | agaatattacaccatccaa | 1-1-1-1-1-8-1-2-3 | AgAaTattacaccAtcCAA | 24_23 | 12091 | A |
| 24 | agaatattacaccatccaa | 1-1-1-1-1-8-1-1-1-2 | AgAaTattacaccAtCcAA | 24_24 | 12091 | A |
| 24 | agaatattacaccatccaa | 1-1-1-1-1-8-3-1-2 | AgAaTattacaccATCcAA | 24_25 | 12091 | A |
| 24 | agaatattacaccatccaa | 1-1-1-1-1-7-1-3-3 | AgAaTattacacCatcCAA | 24_26 | 12091 | A |
| 24 | agaatattacaccatccaa | 1-1-1-1-1-6-1-4-3 | AgAaTattacaCcatcCAA | 24_27 | 12091 | A |
| 24 | agaatattacaccatccaa | 1-1-1-1-2-6-2-3-2 | AgAaTAttacacCAtccAA | 24_28 | 12091 | A |
| 24 | agaatattacaccatccaa | 1-1-2-10-2-1-2 | AgAAtattacaccaTCcAA | 24_29 | 12091 | A |

-continued

| SEQ ID NO | motif sequence | Design | Oligonucleotide Compound | CMP ID NO | Start on SEQ ID NO: 1 | Region |
|---|---|---|---|---|---|---|
| 24 | agaatattacaccatccaa | 1-1-3-11-3 | AgAATattacaccatcCAA | 24_30 | 12091 | A |
| 24 | agaatattacaccatccaa | 1-1-3-10-1-1-2 | AgAATattacaccatCcAA | 24_31 | 12091 | A |
| 24 | agaatattacaccatccaa | 1-1-3-9-2-1-2 | AgAATattacaccaTCcAA | 24_32 | 12091 | A |
| 24 | agaatattacaccatccaa | 1-1-3-8-1-2-3 | AgAATattacaccAtcCAA | 24_33 | 12091 | A |
| 24 | agaatattacaccatccaa | 1-1-3-8-1-1-1-1-2 | AgAATattacaccAtCcAA | 24_34 | 12091 | A |
| 24 | agaatattacaccatccaa | 1-1-3-7-1-1-2-1-2 | AgAATattacacCaTCcAA | 24_35 | 12091 | A |
| 24 | agaatattacaccatccaa | 2-3-1-8-2-1-2 | AGaatAttacaccaTCcAA | 24_36 | 12091 | A |
| 24 | agaatattacaccatccaa | 2-3-1-6-1-3-3 | AGaatAttacacCatcCAA | 24_37 | 12091 | A |
| 24 | agaatattacaccatccaa | 2-2-1-11-3 | AGaaTattacaccatcCAA | 24_38 | 12091 | A |
| 24 | agaatattacaccatccaa | 2-2-1-10-1-1-2 | AGaaTattacaccatCcAA | 24_39 | 12091 | A |
| 24 | agaatattacaccatccaa | 2-2-1-9-2-1-2 | AGaaTattacaccaTCcAA | 24_40 | 12091 | A |
| 24 | agaatattacaccatccaa | 2-2-1-8-1-2-3 | AGaaTattacaccAtcCAA | 24_41 | 12091 | A |
| 24 | agaatattacaccatccaa | 2-2-1-8-1-1-1-1-2 | AGaaTattacaccAtCcAA | 24_42 | 12091 | A |
| 24 | agaatattacaccatccaa | 2-2-1-8-3-1-2 | AGaaTattacaccATCcAA | 24_43 | 12091 | A |
| 24 | agaatattacaccatccaa | 2-2-1-6-1-1-1-1-1-1-2 | AGaaTattacaCcAtCcAA | 24_44 | 12091 | A |
| 24 | agaatattacaccatccaa | 2-2-2-6-1-2-1-1-2 | AGaaTAttacacCatCcAA | 24_45 | 12091 | A |
| 24 | agaatattacaccatccaa | 2-1-1-10-2-1-2 | AGaAtattacaccaTCcAA | 24_46 | 12091 | A |
| 24 | agaatattacaccatccaa | 2-1-1-1-1-6-1-1-2-1-2 | AGaAtAttacacCaTCcAA | 24_47 | 12091 | A |
| 24 | agaatattacaccatccaa | 2-1-2-11-3 | AGaATattacaccatcCAA | 24_48 | 12091 | A |
| 24 | agaatattacaccatccaa | 2-1-2-10-1-1-2 | AGaATattacaccatCcAA | 24_49 | 12091 | A |
| 24 | agaatattacaccatccaa | 2-1-2-9-2-1-2 | AGaATattacaccaTCcAA | 24_50 | 12091 | A |
| 24 | agaatattacaccatccaa | 2-1-2-8-1-2-3 | AGaATattacaccAtcCAA | 24_51 | 12091 | A |
| 24 | agaatattacaccatccaa | 2-1-2-8-1-1-1-1-2 | AGaATattacaccAtCcAA | 24_52 | 12091 | A |
| 24 | agaatattacaccatccaa | 2-1-3-9-1-1-2 | AGaATAttacaccatCcAA | 24_53 | 12091 | A |
| 24 | agaatattacaccatccaa | 3-11-2-1-2 | AGAatattacaccaTCcAA | 24_54 | 12091 | A |
| 24 | agaatattacaccatccaa | 3-10-1-2-3 | AGAatattacaccAtcCAA | 24_55 | 12091 | A |
| 24 | agaatattacaccatccaa | 3-10-1-1-1-1-2 | AGAatattacaccAtCcAA | 24_56 | 12091 | A |
| 24 | agaatattacaccatccaa | 3-1-1-10-1-1-2 | AGAaTattacaccatCcAA | 24_57 | 12091 | A |
| 24 | agaatattacaccatccaa | 3-1-1-8-1-3-2 | AGAaTattacaccAtccAA | 24_58 | 12091 | A |
| 24 | agaatattacaccatccaa | 3-1-1-8-1-1-1-1-2 | AGAaTattacaccAtCcAA | 24_59 | 12091 | A |
| 24 | agaatattacaccatccaa | 4-11-1-1-2 | AGAAtattacaccatCcAA | 24_60 | 12091 | A |
| 24 | agaatattacaccatccaa | 4-8-1-4-2 | AGAAtattacacCatccAA | 24_61 | 12091 | A |
| 24 | agaatattacaccatccaa | 4-1-1-9-1-1-2 | AGAAtAttacaccatCcAA | 24_62 | 12091 | A |
| 25 | cagaatattacaccatccaa | 1-4-1-9-1-1-3 | CagaaTattacaccaTcCAA | 25_1 | 12091 | A |
| 25 | cagaatattacaccatccaa | 1-4-1-9-2-1-2 | CagaaTattacaccaTCcAA | 25_2 | 12091 | A |
| 25 | cagaatattacaccatccaa | 1-4-1-7-1-2-1-1-2 | CagaaTattacacCatCcAA | 25_3 | 12091 | A |
| 25 | cagaatattacaccatccaa | 1-4-1-6-1-1-1-1-1-1-2 | CagaaTattacaCcAtCcAA | 25_4 | 12091 | A |

-continued

| SEQ ID NO | motif sequence | Design | Oligonucleotide Compound | CMP ID NO | Start on SEQ ID NO: 1 | Region |
|---|---|---|---|---|---|---|
| 25 | cagaatattacaccatccaa | 1-3-1-10-2-1-2 | CagaAtattacaccaTCcAA | 25_5 | 12091 | A |
| 25 | cagaatattacaccatccaa | 1-3-1-7-2-4-2 | CagaAtattacaCCatccAA | 25_6 | 12091 | A |
| 25 | cagaatattacaccatccaa | 1-3-1-1-1-6-2-3-2 | CagaAtAttacacCAtccAA | 25_7 | 12091 | A |
| 25 | cagaatattacaccatccaa | 1-3-2-11-3 | CagaATattacaccatcCAA | 25_8 | 12091 | A |
| 25 | cagaatattacaccatccaa | 1-3-2-10-1-1-2 | CagaATattacaccatCcAA | 25_9 | 12091 | A |
| 25 | cagaatattacaccatccaa | 1-3-2-9-2-1-2 | CagaATattacaccaTCcAA | 25_10 | 12091 | A |
| 25 | cagaatattacaccatccaa | 1-3-2-8-1-1-1-1-2 | CagaATattacaccAtCcAA | 25_11 | 12091 | A |
| 25 | cagaatattacaccatccaa | 1-2-1-11-2-1-2 | CagAatattacaccaTCcAA | 25_12 | 12091 | A |
| 25 | cagaatattacaccatccaa | 1-2-1-10-1-2-3 | CagAatattacaccAtcCAA | 25_13 | 12091 | A |
| 25 | cagaatattacaccatccaa | 1-2-1-2-1-6-1-1-2-1-2 | CagAatAttacacCaTCcAA | 25_14 | 12091 | A |
| 25 | cagaatattacaccatccaa | 1-2-1-1-1-11-3 | CagAaTattacaccatcCAA | 25_15 | 12091 | A |
| 25 | cagaatattacaccatccaa | 1-2-1-1-1-9-2-1-2 | CagAaTattacaccaTCcAA | 25_16 | 12091 | A |
| 25 | cagaatattacaccatccaa | 1-2-1-1-1-8-1-2-3 | CagAaTattacaccAtcCAA | 25_17 | 12091 | A |
| 25 | cagaatattacaccatccaa | 1-2-1-1-1-8-1-1-1-1-2 | CagAaTattacaccAtCcAA | 25_18 | 12091 | A |
| 25 | cagaatattacaccatccaa | 1-2-1-1-1-7-1-1-2-1-2 | CagAaTattacacCaTCcAA | 25_19 | 12091 | A |
| 25 | cagaatattacaccatccaa | 1-2-1-1-2-6-1-2-1-1-2 | CagAaTAttacacCatCcAA | 25_20 | 12091 | A |
| 25 | cagaatattacaccatccaa | 1-2-2-8-2-3-2 | CagAAtattacacCAtccAA | 25_21 | 12091 | A |
| 25 | cagaatattacaccatccaa | 1-2-2-8-2-1-1-1-2 | CagAAtattacacCAtCcAA | 25_22 | 12091 | A |
| 25 | cagaatattacaccatccaa | 1-1-1-2-1-11-3 | CaGaaTattacaccatcCAA | 25_23 | 12091 | A |
| 25 | cagaatattacaccatccaa | 1-1-1-2-1-10-1-1-2 | CaGaaTattacaccatCcAA | 25_24 | 12091 | A |
| 25 | cagaatattacaccatccaa | 1-1-1-2-1-9-2-1-2 | CaGaaTattacaccaTCcAA | 25_25 | 12091 | A |
| 25 | cagaatattacaccatccaa | 1-1-1-2-1-8-1-2-3 | CaGaaTattacaccAtcCAA | 25_26 | 12091 | A |
| 25 | cagaatattacaccatccaa | 1-1-1-2-1-8-1-1-1-1-2 | CaGaaTattacaccAtCcAA | 25_27 | 12091 | A |
| 25 | cagaatattacaccatccaa | 1-1-1-2-1-6-1-5-2 | CaGaaTattacaCcatccAA | 25_28 | 12091 | A |
| 25 | cagaatattacaccatccaa | 1-1-1-1-1-11-1-1-2 | CaGaAtattacaccatCcAA | 25_29 | 12091 | A |
| 25 | cagaatattacaccatccaa | 1-1-1-1-1-10-2-1-2 | CaGaAtattacaccaTCcAA | 25_30 | 12091 | A |
| 25 | cagaatattacaccatccaa | 1-1-1-1-1-1-1-9-1-1-2 | CaGaAtAttacaccatCcAA | 25_31 | 12091 | A |
| 25 | cagaatattacaccatccaa | 1-1-1-1-1-1-1-6-2-3-2 | CaGaAtAttacacCAtccAA | 25_32 | 12091 | A |
| 25 | cagaatattacaccatccaa | 1-1-2-10-1-1-1-1-2 | CaGAatattacaccAtCcAA | 25_33 | 12091 | A |
| 25 | cagaatattacaccatccaa | 1-1-2-8-1-1-1-3-2 | CaGAatattacaCcAtccAA | 25_34 | 12091 | A |
| 25 | cagaatattacaccatccaa | 2-3-1-10-1-1-2 | CAgaaTattacaccatCcAA | 25_35 | 12091 | A |
| 25 | cagaatattacaccatccaa | 2-3-1-8-1-3-2 | CAgaaTattacaccAtccAA | 25_36 | 12091 | A |
| 25 | cagaatattacaccatccaa | 2-3-1-8-1-1-1-1-2 | CAgaaTattacaccAtCcAA | 25_37 | 12091 | A |
| 25 | cagaatattacaccatccaa | 2-2-1-11-1-1-2 | CAgaAtattacaccatCcAA | 25_38 | 12091 | A |
| 25 | cagaatattacaccatccaa | 2-1-1-10-1-3-2 | CAgAatattacaccAtccAA | 25_39 | 12091 | A |
| 25 | cagaatattacaccatccaa | 2-1-1-10-1-1-1-1-2 | CAgAatattacaccAtCcAA | 25_40 | 12091 | A |
| 25 | cagaatattacaccatccaa | 2-1-1-1-1-8-1-3-2 | CAgAaTattacaccAtccAA | 25_41 | 12091 | A |
| 25 | cagaatattacaccatccaa | 2-1-1-1-1-7-1-4-2 | CAgAaTattacacCatccAA | 25_42 | 12091 | A |

-continued

| SEQ ID NO | motif sequence | Design | Oligonucleotide Compound | CMP ID NO | Start on SEQ ID NO: 1 | Region |
|---|---|---|---|---|---|---|
| 25 | cagaatattacaccatccaa | 2-1-2-11-1-1-2 | CAgAAtattacaccatCcAA | 25_43 | 12091 | A |
| 26 | gaatattacaccatccaa | 1-10-2-1-4 | GaatattacacCAtCCAA | 26_1 | 12091 | A |
| 26 | gaatattacaccatccaa | 1-10-3-1-3 | GaatattacacCATcCAA | 26_2 | 12091 | A |
| 26 | gaatattacaccatccaa | 1-10-4-1-2 | GaatattacacCATCcAA | 26_3 | 12091 | A |
| 26 | gaatattacaccatccaa | 1-3-1-9-4 | GaatAttacaccatCCAA | 26_4 | 12091 | A |
| 26 | gaatattacaccatccaa | 1-2-1-10-4 | GaaTattacaccatCCAA | 26_5 | 12091 | A |
| 26 | gaatattacaccatccaa | 1-2-1-8-1-1-4 | GaaTattacaccAtCCAA | 26_6 | 12091 | A |
| 26 | gaatattacaccatccaa | 1-2-2-6-2-1-1-1-2 | GaaTAttacacCAtCcAA | 26_7 | 12091 | A |
| 26 | gaatattacaccatccaa | 1-1-1-11-4 | GaAtattacaccatCCAA | 26_8 | 12091 | A |
| 26 | gaatattacaccatccaa | 1-1-1-1-1-9-4 | GaAtAttacaccatCCAA | 26_9 | 12091 | A |
| 26 | gaatattacaccatccaa | 1-1-1-1-1-6-4-1-2 | GaAtAttacacCATCcAA | 26_10 | 12091 | A |
| 26 | gaatattacaccatccaa | 1-1-2-10-4 | GaATtattacaccatCCAA | 26_11 | 12091 | A |
| 26 | gaatattacaccatccaa | 1-1-2-9-2-1-2 | GaATattacaccaTCcAA | 26_12 | 12091 | A |
| 26 | gaatattacaccatccaa | 1-1-2-8-1-1-4 | GaATattacaccAtCCAA | 26_13 | 12091 | A |
| 26 | gaatattacaccatccaa | 1-1-2-8-3-1-2 | GaATattacaccATCcAA | 26_14 | 12091 | A |
| 26 | gaatattacaccatccaa | 1-1-2-7-2-2-3 | GaATattacacCAtcCAA | 26_15 | 12091 | A |
| 26 | gaatattacaccatccaa | 2-10-1-1-4 | GAatattacaccAtCCAA | 26_16 | 12091 | A |
| 26 | gaatattacaccatccaa | 2-10-3-1-2 | GAatattacaccATCcAA | 26_17 | 12091 | A |
| 26 | gaatattacaccatccaa | 2-9-4-1-2 | GAatattacacCATCcAA | 26_18 | 12091 | A |
| 26 | gaatattacaccatccaa | 2-2-1-6-4-1-2 | GAatAttacacCATCcAA | 26_19 | 12091 | A |
| 26 | gaatattacaccatccaa | 2-1-1-11-3 | GAaTattacaccatcCAA | 26_20 | 12091 | A |
| 26 | gaatattacaccatccaa | 2-1-1-9-2-1-2 | GAaTattacaccaTCcAA | 26_21 | 12091 | A |
| 26 | gaatattacaccatccaa | 2-1-1-8-1-2-3 | GAaTattacaccAtcCAA | 26_22 | 12091 | A |
| 26 | gaatattacaccatccaa | 2-1-1-8-3-1-2 | GAaTattacaccATCcAA | 26_23 | 12091 | A |
| 26 | gaatattacaccatccaa | 2-1-1-7-1-3-3 | GAaTattacacCatcCAA | 26_24 | 12091 | A |
| 26 | gaatattacaccatccaa | 2-1-1-7-2-3-2 | GAaTattacacCAtccAA | 26_25 | 12091 | A |
| 26 | gaatattacaccatccaa | 3-11-4 | GAAtattacaccatCCAA | 26_26 | 12091 | A |
| 26 | gaatattacaccatccaa | 3-10-2-1-2 | GAAtattacaccaTCcAA | 26_27 | 12091 | A |
| 26 | gaatattacaccatccaa | 3-8-2-1-1-1-2 | GAAtattacacCAtCcAA | 26_28 | 12091 | A |
| 26 | gaatattacaccatccaa | 4-11-3 | GAATattacaccatcCAA | 26_29 | 12091 | A |
| 26 | gaatattacaccatccaa | 4-8-1-2-3 | GAATattacaccAtcCAA | 26_30 | 12091 | A |
| 26 | gaatattacaccatccaa | 4-7-1-1-2-1-2 | GAATattacacCaTCcAA | 26_31 | 12091 | A |
| 27 | aatattacaccatcca | 4-8-4 | AATAttacaccaTCCA | 27_1 | 12092 | A |
| 28 | agaatattacaccatcca | 1-3-1-10-3 | AgaaTattacaccatCCA | 28_1 | 12092 | A |
| 28 | agaatattacaccatcca | 1-3-1-9-1-1-2 | AgaaTattacaccaTcCA | 28_2 | 12092 | A |
| 28 | agaatattacaccatcca | 1-3-1-8-1-1-3 | AgaaTattacaccAtCCA | 28_3 | 12092 | A |
| 28 | agaatattacaccatcca | 1-3-1-8-2-1-2 | AgaaTattacaccATcCA | 28_4 | 12092 | A |

-continued

| SEQ ID NO | motif sequence | Design | Oligonucleotide Compound | CMP ID NO | Start on SEQ ID NO: 1 | Region |
|---|---|---|---|---|---|---|
| 28 | agaatattacaccatcca | 1-2-1-11-3 | AgaAtattacaccatCCA | 28_5 | 12092 | A |
| 28 | agaatattacaccatcca | 1-2-1-10-4 | AgaAtattacaccaTCCA | 28_6 | 12092 | A |
| 28 | agaatattacaccatcca | 1-2-1-1-1-8-1-1-2 | AgaAtAttacaccaTcCA | 28_7 | 12092 | A |
| 28 | agaatattacaccatcca | 1-2-1-1-1-6-1-3-2 | AgaAtAttacacCatcCA | 28_8 | 12092 | A |
| 28 | agaatattacaccatcca | 1-2-2-11-2 | AgaATattacaccatcCA | 28_9 | 12092 | A |
| 28 | agaatattacaccatcca | 1-2-2-8-1-2-2 | AgaATattacaccAtcCA | 28_10 | 12092 | A |
| 28 | agaatattacaccatcca | 1-1-1-11-4 | AgAatattacaccaTCCA | 28_11 | 12092 | A |
| 28 | agaatattacaccatcca | 1-1-1-10-1-1-3 | AgAatattacaccAtCCA | 28_12 | 12092 | A |
| 28 | agaatattacaccatcca | 1-1-1-9-2-2-2 | AgAatattacacCAtcCA | 28_13 | 12092 | A |
| 28 | agaatattacaccatcca | 1-1-1-2-1-6-1-3-2 | AgAatAttacacCatcCA | 28_14 | 12092 | A |
| 28 | agaatattacaccatcca | 1-1-1-2-1-6-1-2-3 | AgAatAttacacCatCCA | 28_15 | 12092 | A |
| 28 | agaatattacaccatcca | 1-1-1-1-1-11-2 | AgAaTattacaccatcCA | 28_16 | 12092 | A |
| 28 | agaatattacaccatcca | 1-1-1-1-1-10-3 | AgAaTattacaccatCCA | 28_17 | 12092 | A |
| 28 | agaatattacaccatcca | 1-1-1-1-1-8-1-2-2 | AgAaTattacaccAtcCA | 28_18 | 12092 | A |
| 28 | agaatattacaccatcca | 1-1-1-1-1-8-1-1-3 | AgAaTattacaccAtCCA | 28_19 | 12092 | A |
| 28 | agaatattacaccatcca | 1-1-1-1-1-7-1-3-2 | AgAaTattacacCatcCA | 28_20 | 12092 | A |
| 28 | agaatattacaccatcca | 1-1-1-1-1-6-1-4-2 | AgAaTattacaCcatcCA | 28_21 | 12092 | A |
| 28 | agaatattacaccatcca | 1-1-1-1-2-6-1-3-2 | AgAaTAttacacCatcCA | 28_22 | 12092 | A |
| 28 | agaatattacaccatcca | 1-1-2-11-3 | AgAAtattacaccatCCA | 28_23 | 12092 | A |
| 28 | agaatattacaccatcca | 1-1-3-11-2 | AgAATattacaccatcCA | 28_24 | 12092 | A |
| 28 | agaatattacaccatcca | 1-1-3-8-1-2-2 | AgAATattacaccAtcCA | 28_25 | 12092 | A |
| 28 | agaatattacaccatcca | 2-2-1-11-2 | AGaaTattacaccatcCA | 28_26 | 12092 | A |
| 28 | agaatattacaccatcca | 2-2-1-8-1-2-2 | AGaaTattacaccAtcCA | 28_27 | 12092 | A |
| 28 | agaatattacaccatcca | 2-1-1-11-3 | AGaAtattacaccatCCA | 28_28 | 12092 | A |
| 28 | agaatattacaccatcca | 2-1-2-11-2 | AGaATattacaccatcCA | 28_29 | 12092 | A |
| 28 | agaatattacaccatcca | 2-1-2-8-1-2-2 | AGaATattacaccAtcCA | 28_30 | 12092 | A |
| 28 | agaatattacaccatcca | 3-10-1-2-2 | AGAatattacaccAtcCA | 28_31 | 12092 | A |
| 28 | agaatattacaccatcca | 3-1-1-11-2 | AGAaTattacaccatcCA | 28_32 | 12092 | A |
| 28 | agaatattacaccatcca | 3-1-1-8-1-2-2 | AGAaTattacaccAtcCA | 28_33 | 12092 | A |
| 29 | cagaatattacaccatcca | 1-4-1-9-1-1-2 | CagaaTattacaccaTcCA | 29_1 | 12092 | A |
| 29 | cagaatattacaccatcca | 1-3-1-11-3 | CagaAtattacaccatCCA | 29_2 | 12092 | A |
| 29 | cagaatattacaccatcca | 1-3-1-7-1-4-2 | CagaAtattacaCcatcCA | 29_3 | 12092 | A |
| 29 | cagaatattacaccatcca | 1-3-2-11-2 | CagaATattacaccatcCA | 29_4 | 12092 | A |
| 29 | cagaatattacaccatcca | 1-3-2-8-1-2-2 | CagaATattacaccAtcCA | 29_5 | 12092 | A |
| 29 | cagaatattacaccatcca | 1-3-2-7-1-3-2 | CagaATattacacCatcCA | 29_6 | 12092 | A |
| 29 | cagaatattacaccatcca | 1-2-1-1-1-11-2 | CagAaTattacaccatcCA | 29_7 | 12092 | A |
| 29 | cagaatattacaccatcca | 1-2-1-1-1-8-1-2-2 | CagAaTattacaccAtcCA | 29_8 | 12092 | A |
| 29 | cagaatattacaccatcca | 1-2-3-11-2 | CagAATattacaccatcCA | 29_9 | 12092 | A |

-continued

| SEQ ID NO | motif sequence | Design | Oligonucleotide Compound | CMP ID NO | Start on SEQ ID NO: 1 | Region |
|---|---|---|---|---|---|---|
| 29 | cagaatattacaccatcca | 1-1-1-2-1-11-2 | CaGaaTattacaccatcCA | 29_10 | 12092 | A |
| 29 | cagaatattacaccatcca | 1-1-1-2-1-8-1-2-2 | CaGaaTattacaccAtcCA | 29_11 | 12092 | A |
| 29 | cagaatattacaccatcca | 1-1-2-10-1-2-2 | CaGAatattacaccAtcCA | 29_12 | 12092 | A |
| 29 | cagaatattacaccatcca | 2-1-1-10-1-2-2 | CAgAatattacaccAtcCA | 29_13 | 12092 | A |
| 29 | cagaatattacaccatcca | 2-1-1-7-1-2-1-2-2 | CAgAatattacAccAtcCA | 29_14 | 12092 | A |
| 30 | gaatattacaccatcca | 1-10-2-1-3 | GaatattacacCAtCCA | 30_1 | 12092 | A |
| 30 | gaatattacaccatcca | 1-3-1-8-4 | GaatAttacaccaTCCA | 30_2 | 12092 | A |
| 30 | gaatattacaccatcca | 1-2-1-10-3 | GaaTattacaccatCCA | 30_3 | 12092 | A |
| 30 | gaatattacaccatcca | 1-2-1-8-1-1-3 | GaaTattacaccAtCCA | 30_4 | 12092 | A |
| 30 | gaatattacaccatcca | 1-1-1-11-3 | GaAtattacaccatCCA | 30_5 | 12092 | A |
| 30 | gaatattacaccatcca | 1-1-1-10-4 | GaAtattacaccaTCCA | 30_6 | 12092 | A |
| 30 | gaatattacaccatcca | 1-1-1-8-2-1-3 | GaAtattacacCAtCCA | 30_7 | 12092 | A |
| 30 | gaatattacaccatcca | 1-1-1-7-2-3-2 | GaAtattacaCCatcCA | 30_8 | 12092 | A |
| 30 | gaatattacaccatcca | 1-1-1-1-1-6-3-1-2 | GaAtAttacacCATcCA | 30_9 | 12092 | A |
| 30 | gaatattacaccatcca | 1-1-2-10-3 | GaATattacaccatCCA | 30_10 | 12092 | A |
| 30 | gaatattacaccatcca | 1-1-2-8-1-1-3 | GaATattacaccAtCCA | 30_11 | 12092 | A |
| 30 | gaatattacaccatcca | 2-11-4 | GAatattacaccaTCCA | 30_12 | 12092 | A |
| 30 | gaatattacaccatcca | 2-10-1-1-3 | GAatattacaccAtCCA | 30_13 | 12092 | A |
| 30 | gaatattacaccatcca | 2-2-1-9-3 | GAatAttacaccatCCA | 30_14 | 12092 | A |
| 30 | gaatattacaccatcca | 2-2-1-6-1-3-2 | GAatAttacacCatcCA | 30_15 | 12092 | A |
| 30 | gaatattacaccatcca | 2-1-1-11-2 | GAaTattacaccatcCA | 30_16 | 12092 | A |
| 30 | gaatattacaccatcca | 2-1-1-10-3 | GAaTattacaccatCCA | 30_17 | 12092 | A |
| 30 | gaatattacaccatcca | 2-1-1-8-1-2-2 | GAaTattacaccAtcCA | 30_18 | 12092 | A |
| 30 | gaatattacaccatcca | 2-1-1-8-1-1-3 | GAaTattacaccAtCCA | 30_19 | 12092 | A |
| 30 | gaatattacaccatcca | 2-1-1-7-2-2-2 | GAaTattacacCAtcCA | 30_20 | 12092 | A |
| 30 | gaatattacaccatcca | 2-1-1-6-1-4-2 | GAaTattacaCcatcCA | 30_21 | 12092 | A |
| 30 | gaatattacaccatcca | 3-11-3 | GAAtattacaccatCCA | 30_22 | 12092 | A |
| 30 | gaatattacaccatcca | 3-8-1-3-2 | GAAtattacacCatcCA | 30_23 | 12092 | A |
| 30 | gaatattacaccatcca | 4-11-2 | GAATattacaccatcCA | 30_24 | 12092 | A |
| 30 | gaatattacaccatcca | 4-8-1-2-2 | GAATattacaccAtcCA | 30_25 | 12092 | A |
| 31 | tcagaatattacaccatcca | 1-1-1-3-1-11-2 | TcAgaaTattacaccatcCA | 31_1 | 12092 | A |
| 31 | tcagaatattacaccatcca | 1-1-1-3-1-8-1-2-2 | TcAgaaTattacaccAtcCA | 31_2 | 12092 | A |
| 31 | tcagaatattacaccatcca | 1-1-1-2-1-10-1-1-2 | TcAgaAtattacaccaTcCA | 31_3 | 12092 | A |
| 32 | agaatattacaccatcc | 1-3-1-9-3 | AgaaTattacaccaTCC | 32_1 | 12093 | A |
| 32 | agaatattacaccatcc | 1-3-1-8-4 | AgaaTattacaccATCC | 32_2 | 12093 | A |
| 32 | agaatattacaccatcc | 1-3-2-6-1-2-2 | AgaaTAttacacCatCC | 32_3 | 12093 | A |
| 32 | agaatattacaccatcc | 1-2-1-10-3 | AgaAtattacaccaTCC | 32_4 | 12093 | A |

-continued

| SEQ ID NO | motif sequence | Design | Oligonucleotide Compound | CMP ID NO | Start on SEQ ID NO: 1 | Region |
|---|---|---|---|---|---|---|
| 32 | agaatattacaccatcc | 1-2-1-6-2-1-1-1-2 | AgaAtattacACcAtCC | 32_5 | 12093 | A |
| 32 | agaatattacaccatcc | 1-2-1-1-1-6-1-2-2 | AgaAtAttacacCatCC | 32_6 | 12093 | A |
| 32 | agaatattacaccatcc | 1-2-2-9-3 | AgaATattacaccaTCC | 32_7 | 12093 | A |
| 32 | agaatattacaccatcc | 1-2-2-8-1-1-2 | AgaATattacaccAtCC | 32_8 | 12093 | A |
| 32 | agaatattacaccatcc | 1-2-2-8-4 | AgaATattacaccATCC | 32_9 | 12093 | A |
| 32 | agaatattacaccatcc | 1-1-1-11-3 | AgAatattacaccaTCC | 32_10 | 12093 | A |
| 32 | agaatattacaccatcc | 1-1-1-10-4 | AgAatattacaccATCC | 32_11 | 12093 | A |
| 32 | agaatattacaccatcc | 1-1-1-8-1-1-1-1-2 | AgAatattacaCcAtCC | 32_12 | 12093 | A |
| 32 | agaatattacaccatcc | 1-1-1-8-1-1-4 | AgAatattacaCcATCC | 32_13 | 12093 | A |
| 32 | agaatattacaccatcc | 1-1-1-7-1-3-3 | AgAatattacAccaTCC | 32_14 | 12093 | A |
| 32 | agaatattacaccatcc | 1-1-1-7-2-3-2 | AgAatattacACcatCC | 32_15 | 12093 | A |
| 32 | agaatattacaccatcc | 1-1-1-7-3-2-2 | AgAatattacACCatCC | 32_16 | 12093 | A |
| 32 | agaatattacaccatcc | 1-1-1-1-1-9-3 | AgAaTattacaccaTCC | 32_17 | 12093 | A |
| 32 | agaatattacaccatcc | 1-1-1-1-1-8-1-1-2 | AgAaTattacaccAtCC | 32_18 | 12093 | A |
| 32 | agaatattacaccatcc | 1-1-1-1-1-8-4 | AgAaTattacaccATCC | 32_19 | 12093 | A |
| 32 | agaatattacaccatcc | 1-1-1-1-1-7-1-2-2 | AgAaTattacacCatCC | 32_20 | 12093 | A |
| 32 | agaatattacaccatcc | 1-1-1-1-1-6-1-1-1-2 | AgAaTattacaCcAtCC | 32_21 | 12093 | A |
| 32 | agaatattacaccatcc | 1-1-2-10-3 | AgAAtattacaccaTCC | 32_22 | 12093 | A |
| 32 | agaatattacaccatcc | 1-1-2-7-2-2-2 | AgAAtattacaCCatCC | 32_23 | 12093 | A |
| 32 | agaatattacaccatcc | 1-1-2-6-1-1-2-1-2 | AgAAtattacAcCAtCC | 32_24 | 12093 | A |
| 32 | agaatattacaccatcc | 1-1-3-10-2 | AgAATattacaccatCC | 32_25 | 12093 | A |
| 32 | agaatattacaccatcc | 1-1-3-9-3 | AgAATattacaccaTCC | 32_26 | 12093 | A |
| 32 | agaatattacaccatcc | 1-1-3-8-1-1-2 | AgAATattacaccAtCC | 32_27 | 12093 | A |
| 32 | agaatattacaccatcc | 1-1-3-8-4 | AgAATattacaccATCC | 32_28 | 12093 | A |
| 32 | agaatattacaccatcc | 1-1-3-6-1-1-1-2 | AgAATattacaCcAtCC | 32_29 | 12093 | A |
| 32 | agaatattacaccatcc | 2-2-1-10-2 | AGaaTattacaccatCC | 32_30 | 12093 | A |
| 32 | agaatattacaccatcc | 2-2-1-9-3 | AGaaTattacaccaTCC | 32_31 | 12093 | A |
| 32 | agaatattacaccatcc | 2-2-1-8-1-1-2 | AGaaTattacaccAtCC | 32_32 | 12093 | A |
| 32 | agaatattacaccatcc | 2-2-1-8-4 | AGaaTattacaccATCC | 32_33 | 12093 | A |
| 32 | agaatattacaccatcc | 2-1-1-11-2 | AGaAtattacaccatCC | 32_34 | 12093 | A |
| 32 | agaatattacaccatcc | 2-1-1-10-3 | AGaAtattacaccaTCC | 32_35 | 12093 | A |
| 32 | agaatattacaccatcc | 2-1-1-8-1-1-3 | AGaAtattacacCaTCC | 32_36 | 12093 | A |
| 32 | agaatattacaccatcc | 2-1-1-6-1-2-4 | AGaAtattacAccATCC | 32_37 | 12093 | A |
| 32 | agaatattacaccatcc | 2-1-2-10-2 | AGaATattacaccatCC | 32_38 | 12093 | A |
| 32 | agaatattacaccatcc | 2-1-2-8-1-1-2 | AGaATattacaccAtCC | 32_39 | 12093 | A |
| 32 | agaatattacaccatcc | 3-11-3 | AGAatattacaccaTCC | 32_40 | 12093 | A |
| 32 | agaatattacaccatcc | 3-10-1-1-2 | AGAatattacaccAtCC | 32_41 | 12093 | A |
| 32 | agaatattacaccatcc | 3-7-1-3-3 | AGAatattacAccaTCC | 32_42 | 12093 | A |

-continued

| SEQ ID NO | motif sequence | Design | Oligonucleotide Compound | CMP ID NO | Start on SEQ ID NO: 1 | Region |
|---|---|---|---|---|---|---|
| 32 | agaatattacaccatcc | 3-7-1-2-1-1-2 | AGAatattacAccAtCC | 32_43 | 12093 | A |
| 32 | agaatattacaccatcc | 3-7-1-1-1-2-2 | AGAatattacAcCatCC | 32_44 | 12093 | A |
| 32 | agaatattacaccatcc | 3-2-1-9-2 | AGAatAttacaccatCC | 32_45 | 12093 | A |
| 32 | agaatattacaccatcc | 3-1-1-10-2 | AGAaTattacaccatCC | 32_46 | 12093 | A |
| 32 | agaatattacaccatcc | 3-1-1-8-1-1-2 | AGAaTattacaccAtCC | 32_47 | 12093 | A |
| 32 | agaatattacaccatcc | 4-11-2 | AGAAtattacaccatCC | 32_48 | 12093 | A |
| 32 | agaatattacaccatcc | 4-10-3 | AGAAtattacaccaTCC | 32_49 | 12093 | A |
| 32 | agaatattacaccatcc | 4-8-1-2-2 | AGAAtattacacCatCC | 32_50 | 12093 | A |
| 32 | agaatattacaccatcc | 4-6-1-1-1-2-2 | AGAAtattacAcCatCC | 32_51 | 12093 | A |
| 33 | cagaatattacaccatcc | 1-4-1-9-3 | CagaaTattacaccaTCC | 33_1 | 12093 | A |
| 33 | cagaatattacaccatcc | 1-3-1-10-3 | CagaAtattacaccaTCC | 33_2 | 12093 | A |
| 33 | cagaatattacaccatcc | 1-3-1-7-1-2-3 | CagaAtattacaCcaTCC | 33_3 | 12093 | A |
| 33 | cagaatattacaccatcc | 1-3-1-6-1-3-3 | CagaAtattacAccaTCC | 33_4 | 12093 | A |
| 33 | cagaatattacaccatcc | 1-3-1-6-2-3-2 | CagaAtattacACcatCC | 33_5 | 12093 | A |
| 33 | cagaatattacaccatcc | 1-3-2-10-2 | CagaATattacaccatCC | 33_6 | 12093 | A |
| 33 | cagaatattacaccatcc | 1-3-2-9-3 | CagaATattacaccaTCC | 33_7 | 12093 | A |
| 33 | cagaatattacaccatcc | 1-3-2-8-1-1-2 | CagaATattacaccAtCC | 33_8 | 12093 | A |
| 33 | cagaatattacaccatcc | 1-2-1-11-3 | CagAatattacaccaTCC | 33_9 | 12093 | A |
| 33 | cagaatattacaccatcc | 1-2-1-2-1-8-3 | CagAatAttacaccaTCC | 33_10 | 12093 | A |
| 33 | cagaatattacaccatcc | 1-2-1-1-1-9-3 | CagAaTattacaccaTCC | 33_11 | 12093 | A |
| 33 | cagaatattacaccatcc | 1-2-2-10-3 | CagAAtattacaccaTCC | 33_12 | 12093 | A |
| 33 | cagaatattacaccatcc | 1-2-2-8-1-1-3 | CagAAtattacacCaTCC | 33_13 | 12093 | A |
| 33 | cagaatattacaccatcc | 1-2-3-6-1-3-2 | CagAATattacaCcatCC | 33_14 | 12093 | A |
| 33 | cagaatattacaccatcc | 1-1-1-3-1-6-2-1-2 | CaGaatAttacacCAtCC | 33_15 | 12093 | A |
| 33 | cagaatattacaccatcc | 1-1-1-2-1-8-1-1-2 | CaGaaTattacaccAtCC | 33_16 | 12093 | A |
| 33 | cagaatattacaccatcc | 1-1-1-1-1-11-2 | CaGaAtattacaccatCC | 33_17 | 12093 | A |
| 33 | cagaatattacaccatcc | 1-1-1-1-1-10-3 | CaGaAtattacaccaTCC | 33_18 | 12093 | A |
| 33 | cagaatattacaccatcc | 1-1-1-1-1-7-1-3-2 | CaGaAtattacaCcatCC | 33_19 | 12093 | A |
| 33 | cagaatattacaccatcc | 1-1-1-1-1-6-2-1-1-1-2 | CaGaAtattacACcAtCC | 33_20 | 12093 | A |
| 33 | cagaatattacaccatcc | 1-1-2-10-1-1-2 | CaGAatattacaccAtCC | 33_21 | 12093 | A |
| 33 | cagaatattacaccatcc | 2-3-1-10-2 | CAgaaTattacaccatCC | 33_22 | 12093 | A |
| 33 | cagaatattacaccatcc | 2-3-1-8-1-1-2 | CAgaaTattacaccAtCC | 33_23 | 12093 | A |
| 33 | cagaatattacaccatcc | 2-2-1-11-2 | CAgaAtattacaccatCC | 33_24 | 12093 | A |
| 33 | cagaatattacaccatcc | 2-2-1-10-3 | CAgaAtattacaccaTCC | 33_25 | 12093 | A |
| 33 | cagaatattacaccatcc | 2-2-1-1-1-6-1-2-2 | CAgaAtAttacacCatCC | 33_26 | 12093 | A |
| 33 | cagaatattacaccatcc | 2-1-1-11-3 | CAgAatattacaccaTCC | 33_27 | 12093 | A |
| 33 | cagaatattacaccatcc | 2-1-1-10-1-1-2 | CAgAatattacaccAtCC | 33_28 | 12093 | A |

-continued

| SEQ ID NO | motif sequence | Design | Oligonucleotide Compound | CMP ID NO | Start on SEQ ID NO: 1 | Region |
|---|---|---|---|---|---|---|
| 33 | cagaatattacaccatcc | 2-1-1-1-1-10-2 | CAgAaTattacaccatCC | 33_29 | 12093 | A |
| 33 | cagaatattacaccatcc | 2-1-1-1-1-8-1-1-2 | CAgAaTattacaccAtCC | 33_30 | 12093 | A |
| 33 | cagaatattacaccatcc | 2-1-2-11-2 | CAgAAtattacaccatCC | 33_31 | 12093 | A |
| 33 | cagaatattacaccatcc | 2-1-2-6-1-4-2 | CAgAAtattacAccatCC | 33_32 | 12093 | A |
| 33 | cagaatattacaccatcc | 3-1-1-11-2 | CAGaAtattacaccatCC | 33_33 | 12093 | A |
| 34 | gaatattacaccatcc | 4-8-4 | GAATattacaccATCC | 34_1 | 12093 | A |
| 35 | tcagaatattacaccatcc | 2-4-1-10-2 | TCagaaTattacaccatCC | 35_1 | 12093 | A |
| 35 | tcagaatattacaccatcc | 2-3-1-11-2 | TCagaAtattacaccatCC | 35_2 | 12093 | A |
| 35 | tcagaatattacaccatcc | 2-3-1-6-1-4-2 | TCagaAtattacAccatCC | 35_3 | 12093 | A |
| 36 | agaatattacaccatc | 4-8-4 | AGAAtattacacCATC | 36_1 | 12094 | A |
| 37 | cagaatattacaccat | 4-8-4 | CAGAatattacaCCAT | 37_1 | 12095 | A |
| 38 | caattctcatttcaaccttc | 2-14-4 | CAattctcatttcaacCTTC | 38_1 | 39562 | B |
| 39 | tcaattctcatttcaacctt | 2-15-3 | TCaattctcatttcaacCTT | 39_1 | 39563 | B |
| 40 | atcaattctcatttcaacct | 3-15-2 | ATCaattctcatttcaacCT | 40_1 | 39564 | B |
| 41 | aatcaattctcatttcaacc | 4-13-3 | AATCaattctcatttcaACC | 41_1 | 39565 | B |
| 42 | aaatcaattctcatttcaac | 4-12-4 | AAATcaattctcatttCAAC | 42_1 | 39566 | B |
| 43 | caaatcaattctcatttcaa | 4-12-4 | CAAAtcaattctcattTCAA | 43_1 | 39567 | B |
| 44 | tcaaatcaattctcatttca | 3-13-4 | TCAaatcaattctcatTTCA | 44_1 | 39568 | B |
| 45 | ctcaaatcaattctcatttc | 4-13-3 | CTCAaatcaattctcatTTC | 45_1 | 39569 | B |
| 46 | actcaaatcaattctcattt | 4-12-4 | ACTCaaatcaattctcATTT | 46_1 | 39570 | B |
| 47 | aactcaaatcaattctcatt | 4-12-4 | AACTcaaatcaattctCATT | 47_1 | 39571 | B |
| 48 | taactcaaatcaattctcat | 4-12-4 | TAACtcaaatcaattcTCAT | 48_1 | 39572 | B |
| 49 | ttaactcaaatcaattctca | 1-5-1-10-3 | TtaactCaaatcaattcTCA | 49_1 | 39573 | B |
| 49 | ttaactcaaatcaattctca | 1-5-2-10-2 | TtaactCAaatcaattctCA | 49_2 | 39573 | B |
| 49 | ttaactcaaatcaattctca | 1-5-2-9-3 | TtaactCAaatcaattcTCA | 49_3 | 39573 | B |
| 49 | ttaactcaaatcaattctca | 1-4-2-11-2 | TtaacTCaaatcaattctCA | 49_4 | 39573 | B |
| 49 | ttaactcaaatcaattctca | 1-4-3-10-2 | TtaacTCAaatcaattctCA | 49_5 | 39573 | B |
| 49 | ttaactcaaatcaattctca | 1-3-1-11-1-1-2 | TtaaCtcaaatcaattCtCA | 49_6 | 39573 | B |
| 49 | ttaactcaaatcaattctca | 1-3-1-11-4 | TtaaCtcaaatcaattCTCA | 49_7 | 39573 | B |
| 49 | ttaactcaaatcaattctca | 1-3-1-10-2-1-2 | TtaaCtcaaatcaatTCtCA | 49_8 | 39573 | B |
| 49 | ttaactcaaatcaattctca | 1-3-1-9-1-3-2 | TtaaCtcaaatcaaTtctCA | 49_9 | 39573 | B |
| 49 | ttaactcaaatcaattctca | 1-3-1-9-1-2-3 | TtaaCtcaaatcaaTtcTCA | 49_10 | 39573 | B |
| 49 | ttaactcaaatcaattctca | 1-3-1-9-1-1-1-2 | TtaaCtcaaatcaaTtCtCA | 49_11 | 39573 | B |
| 49 | ttaactcaaatcaattctca | 1-3-1-9-1-4 | TtaaCtcaaatcaaTtCTCA | 49_12 | 39573 | B |
| 49 | ttaactcaaatcaattctca | 1-3-1-9-3-2 | TtaaCtcaaatcaaTTCtCA | 49_13 | 39573 | B |
| 49 | ttaactcaaatcaattctca | 1-3-1-7-1-4-3 | TtaaCtcaaatcAattcTCA | 49_14 | 39573 | B |
| 49 | ttaactcaaatcaattctca | 1-3-1-2-1-9-3 | TtaaCtcAaatcaattcTCA | 49_15 | 39573 | B |
| 49 | ttaactcaaatcaattctca | 1-3-1-2-1-8-1-1-2 | TtaaCtcAaatcaattCtCA | 49_16 | 39573 | B |

-continued

| SEQ ID NO | motif sequence | Design | Oligonucleotide Compound | CMP ID NO | Start on SEQ ID NO: 1 | Region |
|---|---|---|---|---|---|---|
| 49 | ttaactcaaatcaattctca | 1-3-1-2-1-8-4 | TtaaCtcAaatcaattCTCA | 49_17 | 39573 | B |
| 49 | ttaactcaaatcaattctca | 1-3-1-2-1-7-1-2-2 | TtaaCtcAaatcaatTctCA | 49_18 | 39573 | B |
| 49 | ttaactcaaatcaattctca | 1-3-1-2-1-7-2-1-2 | TtaaCtcAaatcaatTCtCA | 49_19 | 39573 | B |
| 49 | ttaactcaaatcaattctca | 1-3-1-2-1-6-1-3-2 | TtaaCtcAaatcaaTtctCA | 49_20 | 39573 | B |
| 49 | ttaactcaaatcaattctca | 1-3-1-2-1-6-1-2-3 | TtaaCtcAaatcaaTtcTCA | 49_21 | 39573 | B |
| 49 | ttaactcaaatcaattctca | 1-3-1-2-1-6-1-1-1-1-2 | TtaaCtcAaatcaaTtCtCA | 49_22 | 39573 | B |
| 49 | ttaactcaaatcaattctca | 1-3-1-2-1-6-1-1-4 | TtaaCtcAaatcaaTtCTCA | 49_23 | 39573 | B |
| 49 | ttaactcaaatcaattctca | 1-3-1-2-1-6-3-1-2 | TtaaCtcAaatcaaTTCtCA | 49_24 | 39573 | B |
| 49 | ttaactcaaatcaattctca | 1-3-1-1-1-11-2 | TtaaCtCaaatcaattctCA | 49_25 | 39573 | B |
| 49 | ttaactcaaatcaattctca | 1-3-1-1-1-10-3 | TtaaCtCaaatcaattcTCA | 49_26 | 39573 | B |
| 49 | ttaactcaaatcaattctca | 1-3-1-1-1-9-1-1-2 | TtaaCtCaaatcaattCtCA | 49_27 | 39573 | B |
| 49 | ttaactcaaatcaattctca | 1-3-1-1-1-9-4 | TtaaCtCaaatcaattCTCA | 49_28 | 39573 | B |
| 49 | ttaactcaaatcaattctca | 1-3-1-1-1-8-2-1-2 | TtaaCtCaaatcaatTCtCA | 49_29 | 39573 | B |
| 49 | ttaactcaaatcaattctca | 1-3-1-1-2-10-2 | TtaaCtCAaatcaattctCA | 49_30 | 39573 | B |
| 49 | ttaactcaaatcaattctca | 1-3-1-1-2-9-3 | TtaaCtCAaatcaattcTCA | 49_31 | 39573 | B |
| 49 | ttaactcaaatcaattctca | 1-3-1-1-2-8-1-1-2 | TtaaCtCAaatcaattCtCA | 49_32 | 39573 | B |
| 49 | ttaactcaaatcaattctca | 1-3-1-1-2-6-1-3-2 | TtaaCtCAaatcaaTtctCA | 49_33 | 39573 | B |
| 49 | ttaactcaaatcaattctca | 1-3-1-1-2-6-1-1-1-1-2 | TtaaCtCAaatcaaTtCtCA | 49_34 | 39573 | B |
| 49 | ttaactcaaatcaattctca | 1-3-3-11-2 | TtaaCTCaaatcaattctCA | 49_35 | 39573 | B |
| 49 | ttaactcaaatcaattctca | 1-3-3-9-1-1-2 | TtaaCTCaaatcaattCtCA | 49_36 | 39573 | B |
| 49 | ttaactcaaatcaattctca | 1-3-4-10-2 | TtaaCTCAaatcaattctCA | 49_37 | 39573 | B |
| 49 | ttaactcaaatcaattctca | 1-3-4-6-1-3-2 | TtaaCTCAaatcaaTtctCA | 49_38 | 39573 | B |
| 49 | ttaactcaaatcaattctca | 1-2-1-11-2-1-2 | TtaActcaaatcaatTCtCA | 49_39 | 39573 | B |
| 49 | ttaactcaaatcaattctca | 1-2-1-10-1-1-1-1-2 | TtaActcaaatcaaTtCtCA | 49_40 | 39573 | B |
| 49 | ttaactcaaatcaattctca | 1-2-1-10-1-1-4 | TtaActcaaatcaaTtCTCA | 49_41 | 39573 | B |
| 49 | ttaactcaaatcaattctca | 1-2-1-3-1-8-1-1-2 | TtaActcAaatcaattCtCA | 49_42 | 39573 | B |
| 49 | ttaactcaaatcaattctca | 1-2-1-3-1-7-2-1-2 | TtaActcAaatcaatTCtCA | 49_43 | 39573 | B |
| 49 | ttaactcaaatcaattctca | 1-2-1-3-1-6-1-2-3 | TtaActcAaatcaaTtcTCA | 49_44 | 39573 | B |
| 49 | ttaactcaaatcaattctca | 1-2-1-3-1-6-1-1-1-1-2 | TtaActcAaatcaaTtCtCA | 49_45 | 39573 | B |
| 49 | ttaactcaaatcaattctca | 1-2-1-2-1-9-1-1-2 | TtaActCaaatcaattCtCA | 49_46 | 39573 | B |
| 49 | ttaactcaaatcaattctca | 1-2-1-2-1-9-4 | TtaActCaaatcaattCTCA | 49_47 | 39573 | B |
| 49 | ttaactcaaatcaattctca | 1-2-1-2-1-8-2-1-2 | TtaActCaaatcaatTCtCA | 49_48 | 39573 | B |
| 49 | ttaactcaaatcaattctca | 1-2-1-2-2-10-2 | TtaActCAaatcaattctCA | 49_49 | 39573 | B |
| 49 | ttaactcaaatcaattctca | 1-2-1-2-2-8-1-1-2 | TtaActCAaatcaattCtCA | 49_50 | 39573 | B |
| 49 | ttaactcaaatcaattctca | 1-2-1-2-2-8-4 | TtaActCAaatcaattCTCA | 49_51 | 39573 | B |
| 49 | ttaactcaaatcaattctca | 1-2-1-2-2-7-2-1-2 | TtaActCAaatcaatTCtCA | 49_52 | 39573 | B |
| 49 | ttaactcaaatcaattctca | 1-2-1-2-2-6-1-3-2 | TtaActCAaatcaaTtctCA | 49_53 | 39573 | B |

-continued

| SEQ ID NO | motif sequence | Design | Oligonucleotide Compound | CMP ID NO | Start on SEQ ID NO: 1 | Region |
|---|---|---|---|---|---|---|
| 49 | ttaactcaaatcaattctca | 1-2-1-2-2-6-1-1-1-1-2 | TtaActCAaatcaaTtCtCA | 49_54 | 39573 | B |
| 49 | ttaactcaaatcaattctca | 1-2-1-1-2-9-1-1-2 | TtaAcTCaaatcaattCtCA | 49_55 | 39573 | B |
| 49 | ttaactcaaatcaattctca | 1-2-2-11-1-1-2 | TtaACtcaaatcaattCtCA | 49_56 | 39573 | B |
| 49 | ttaactcaaatcaattctca | 1-2-2-11-4 | TtaACtcaaatcaattCTCA | 49_57 | 39573 | B |
| 49 | ttaactcaaatcaattctca | 1-2-2-10-2-1-2 | TtaACtcaaatcaatTCtCA | 49_58 | 39573 | B |
| 49 | ttaactcaaatcaattctca | 1-2-2-9-1-3-2 | TtaACtcaaatcaaTtctCA | 49_59 | 39573 | B |
| 49 | ttaactcaaatcaattctca | 1-2-2-9-1-1-1-1-2 | TtaACtcaaatcaaTtCtCA | 49_60 | 39573 | B |
| 49 | ttaactcaaatcaattctca | 1-2-2-9-1-1-4 | TtaACtcaaatcaaTtCTCA | 49_61 | 39573 | B |
| 49 | ttaactcaaatcaattctca | 1-2-2-9-3-1-2 | TtaACtcaaatcaaTTCtCA | 49_62 | 39573 | B |
| 49 | ttaactcaaatcaattctca | 1-2-2-7-1-5-2 | TtaACtcaaatcAattctCA | 49_63 | 39573 | B |
| 49 | ttaactcaaatcaattctca | 1-2-2-2-1-10-2 | TtaACtcAaatcaattctCA | 49_64 | 39573 | B |
| 49 | ttaactcaaatcaattctca | 1-2-2-2-1-8-1-1-2 | TtaACtcAaatcaattCtCA | 49_65 | 39573 | B |
| 49 | ttaactcaaatcaattctca | 1-2-2-2-1-8-4 | TtaACtcAaatcaattCTCA | 49_66 | 39573 | B |
| 49 | ttaactcaaatcaattctca | 1-2-2-2-1-7-2-1-2 | TtaACtcAaatcaatTCtCA | 49_67 | 39573 | B |
| 49 | ttaactcaaatcaattctca | 1-2-2-2-1-6-1-3-2 | TtaACtcAaatcaaTtctCA | 49_68 | 39573 | B |
| 49 | ttaactcaaatcaattctca | 1-2-2-2-1-6-1-1-1-1-2 | TtaACtcAaatcaaTtCtCA | 49_69 | 39573 | B |
| 49 | ttaactcaaatcaattctca | 1-2-2-2-1-6-1-1-4 | TtaACtcAaatcaaTtCTCA | 49_70 | 39573 | B |
| 49 | ttaactcaaatcaattctca | 1-2-2-2-1-6-3-1-2 | TtaACtcAaatcaaTTCtCA | 49_71 | 39573 | B |
| 49 | ttaactcaaatcaattctca | 1-2-2-1-1-11-2 | TtaACtCaaatcaattctCA | 49_72 | 39573 | B |
| 49 | ttaactcaaatcaattctca | 1-2-2-1-1-9-1-1-2 | TtaACtCaaatcaattCtCA | 49_73 | 39573 | B |
| 49 | ttaactcaaatcaattctca | 1-2-2-1-1-9-4 | TtaACtCaaatcaattCTCA | 49_74 | 39573 | B |
| 49 | ttaactcaaatcaattctca | 1-2-2-1-1-8-2-1-2 | TtaACtCaaatcaatTCtCA | 49_75 | 39573 | B |
| 49 | ttaactcaaatcaattctca | 1-2-2-1-2-10-2 | TtaACtCAaatcaattctCA | 49_76 | 39573 | B |
| 49 | ttaactcaaatcaattctca | 1-2-2-1-2-8-1-1-2 | TtaACtCAaatcaattCtCA | 49_77 | 39573 | B |
| 49 | ttaactcaaatcaattctca | 1-2-2-1-2-6-1-3-2 | TtaACtCAaatcaaTtctCA | 49_78 | 39573 | B |
| 49 | ttaactcaaatcaattctca | 1-2-4-9-1-1-2 | TtaACTCaaatcaattCtCA | 49_79 | 39573 | B |
| 49 | ttaactcaaatcaattctca | 1-1-1-11-1-1-1-1-2 | TtAactcaaatcaaTtCtCA | 49_80 | 39573 | B |
| 49 | ttaactcaaatcaattctca | 1-1-1-10-1-2-1-1-2 | TtAactcaaatcaAttCtCA | 49_81 | 39573 | B |
| 49 | ttaactcaaatcaattctca | 1-1-1-10-1-1-2-1-2 | TtAactcaaatcaAtTCtCA | 49_82 | 39573 | B |
| 49 | ttaactcaaatcaattctca | 1-1-1-10-2-1-1-1-2 | TtAactcaaatcaATtCtCA | 49_83 | 39573 | B |
| 49 | ttaactcaaatcaattctca | 1-1-1-10-4-1-2 | TtAactcaaatcaATTCtCA | 49_84 | 39573 | B |
| 49 | ttaactcaaatcaattctca | 1-1-1-4-1-7-2-1-2 | TtAactcAaatcaatTCtCA | 49_85 | 39573 | B |
| 49 | ttaactcaaatcaattctca | 1-1-1-4-1-6-1-1-1-1-2 | TtAactcAaatcaaTtCtCA | 49_86 | 39573 | B |
| 49 | ttaactcaaatcaattctca | 1-1-1-3-1-9-1-1-2 | TtAactCaaatcaattCtCA | 49_87 | 39573 | B |
| 49 | ttaactcaaatcaattctca | 1-1-1-3-1-9-4 | TtAactCaaatcaattCTCA | 49_88 | 39573 | B |
| 49 | ttaactcaaatcaattctca | 1-1-1-3-1-8-2-1-2 | TtAactCaaatcaatTCtCA | 49_89 | 39573 | B |
| 49 | ttaactcaaatcaattctca | 1-1-1-3-2-8-1-1-2 | TtAactCAaatcaattCtCA | 49_90 | 39573 | B |
| 49 | ttaactcaaatcaattctca | 1-1-1-3-2-7-2-1-2 | TtAactCAaatcaatTCtCA | 49_91 | 39573 | B |

-continued

| SEQ ID NO | motif sequence | Design | Oligonucleotide Compound | CMP ID NO | Start on SEQ ID NO: 1 | Region |
|---|---|---|---|---|---|---|
| 49 | ttaactcaaatcaattctca | 1-1-1-3-2-6-1-1-1-1-2 | TtAactCAaatcaaTtCtCA | 49_92 | 39573 | B |
| 49 | ttaactcaaatcaattctca | 1-1-1-3-2-6-3-1-2 | TtAactCAaatcaaTTCtCA | 49_93 | 39573 | B |
| 49 | ttaactcaaatcaattctca | 1-1-1-1-1-11-1-1-2 | TtAaCtcaaatcaattCtCA | 49_94 | 39573 | B |
| 49 | ttaactcaaatcaattctca | 1-1-1-1-1-10-2-1-2 | TtAaCtcaaatcaatTCtCA | 49_95 | 39573 | B |
| 49 | ttaactcaaatcaattctca | 1-1-1-1-1-9-1-3-2 | TtAaCtcaaatcaaTtctCA | 49_96 | 39573 | B |
| 49 | ttaactcaaatcaattctca | 1-1-1-1-1-9-1-1-1-1-2 | TtAaCtcaaatcaaTtCtCA | 49_97 | 39573 | B |
| 49 | ttaactcaaatcaattctca | 1-1-1-1-1-9-1-1-4 | TtAaCtcaaatcaaTtCTCA | 49_98 | 39573 | B |
| 49 | ttaactcaaatcaattctca | 1-1-1-1-1-9-3-1-2 | TtAaCtcaaatcaaTTCtCA | 49_99 | 39573 | B |
| 49 | ttaactcaaatcaattctca | 1-1-1-1-1-7-1-5-2 | TtAaCtcaaatcAattctCA | 49_100 | 39573 | B |
| 49 | ttaactcaaatcaattctca | 1-1-1-1-1-2-1-10-2 | TtAaCtcAaatcaattctCA | 49_101 | 39573 | B |
| 49 | ttaactcaaatcaattctca | 1-1-1-1-1-2-1-8-1-1-2 | TtAaCtcAaatcaattCtCA | 49_102 | 39573 | B |
| 49 | ttaactcaaatcaattctca | 1-1-1-1-1-2-1-8-4 | TtAaCtcAaatcaattCTCA | 49_103 | 39573 | B |
| 49 | ttaactcaaatcaattctca | 1-1-1-1-1-2-1-7-2-1-2 | TtAaCtcAaatcaatTCtCA | 49_104 | 39573 | B |
| 49 | ttaactcaaatcaattctca | 1-1-1-1-1-2-1-6-1-3-2 | TtAaCtcAaatcaaTtctCA | 49_105 | 39573 | B |
| 49 | ttaactcaaatcaattctca | 1-1-1-1-1-2-1-6-1-1-1-1-2 | TtAaCtcAaatcaaTtCtCA | 49_106 | 39573 | B |
| 49 | ttaactcaaatcaattctca | 1-1-1-1-1-2-1-6-1-1-4 | TtAaCtcAaatcaaTtCTCA | 49_107 | 39573 | B |
| 49 | ttaactcaaatcaattctca | 1-1-1-1-1-2-1-6-3-1-2 | TtAaCtcAaatcaaTTCtCA | 49_108 | 39573 | B |
| 49 | ttaactcaaatcaattctca | 1-1-1-1-1-1-1-11-2 | TtAaCtCaaatcaattctCA | 49_109 | 39573 | B |
| 49 | ttaactcaaatcaattctca | 1-1-1-1-1-1-1-9-1-1-2 | TtAaCtCaaatcaattCtCA | 49_110 | 39573 | B |
| 49 | ttaactcaaatcaattctca | 1-1-1-1-1-1-1-8-2-1-2 | TtAaCtCaaatcaatTCtCA | 49_111 | 39573 | B |
| 49 | ttaactcaaatcaattctca | 1-1-1-1-1-1-2-10-2 | TtAaCtCAaatcaattctCA | 49_112 | 39573 | B |
| 49 | ttaactcaaatcaattctca | 1-1-1-1-1-1-2-8-1-1-2 | TtAaCtCAaatcaattCtCA | 49_113 | 39573 | B |
| 49 | ttaactcaaatcaattctca | 1-1-1-1-1-1-2-6-1-3-2 | TtAaCtCAaatcaaTtctCA | 49_114 | 39573 | B |
| 49 | ttaactcaaatcaattctca | 1-1-2-11-2-1-2 | TtAActcaaatcaatTCtCA | 49_115 | 39573 | B |
| 49 | ttaactcaaatcaattctca | 1-1-2-10-1-1-1-1-2 | TtAActcaaatcaaTtCtCA | 49_116 | 39573 | B |
| 49 | ttaactcaaatcaattctca | 1-1-2-3-1-8-1-1-2 | TtAActcAaatcaattCtCA | 49_117 | 39573 | B |
| 49 | ttaactcaaatcaattctca | 1-1-2-3-1-7-2-1-2 | TtAActcAaatcaatTCtCA | 49_118 | 39573 | B |
| 49 | ttaactcaaatcaattctca | 1-1-2-3-1-6-1-1-1-1-2 | TtAActcAaatcaaTtCtCA | 49_119 | 39573 | B |
| 49 | ttaactcaaatcaattctca | 1-1-2-2-1-9-1-1-2 | TtAActCaaatcaattCtCA | 49_120 | 39573 | B |
| 49 | ttaactcaaatcaattctca | 1-1-2-2-1-8-2-1-2 | TtAActCaaatcaatTCtCA | 49_121 | 39573 | B |
| 49 | ttaactcaaatcaattctca | 1-1-2-2-2-8-1-1-2 | TtAActCAaatcaattCtCA | 49_122 | 39573 | B |
| 49 | ttaactcaaatcaattctca | 1-1-2-2-2-7-2-1-2 | TtAActCAaatcaatTCtCA | 49_123 | 39573 | B |
| 49 | ttaactcaaatcaattctca | 1-1-2-2-2-6-1-1-1-1-2 | TtAActCAaatcaaTtCtCA | 49_124 | 39573 | B |
| 49 | ttaactcaaatcaattctca | 1-1-3-11-1-1-2 | TtAACtcaaatcaattCtCA | 49_125 | 39573 | B |
| 49 | ttaactcaaatcaattctca | 1-1-3-11-4 | TtAACtcaaatcaattCTCA | 49_126 | 39573 | B |
| 49 | ttaactcaaatcaattctca | 1-1-3-10-2-1-2 | TtAACtcaaatcaatTCtCA | 49_127 | 39573 | B |
| 49 | ttaactcaaatcaattctca | 1-1-3-9-1-3-2 | TtAACtcaaatcaaTtctCA | 49_128 | 39573 | B |

-continued

| SEQ ID NO | motif sequence | Design | Oligonucleotide Compound | CMP ID NO | Start on SEQ ID NO: 1 | Region |
|---|---|---|---|---|---|---|
| 49 | ttaactcaaatcaattctca | 1-1-3-9-1-1-1-1-2 | TtAACtcaaatcaaTtCtCA | 49_129 | 39573 | B |
| 49 | ttaactcaaatcaattctca | 1-1-3-9-3-1-2 | TtAACtcaaatcaaTTCtCA | 49_130 | 39573 | B |
| 49 | ttaactcaaatcaattctca | 1-1-3-7-1-5-2 | TtAACtcaaatcAattctCA | 49_131 | 39573 | B |
| 49 | ttaactcaaatcaattctca | 1-1-3-2-1-10-2 | TtAACtcAaatcaattctCA | 49_132 | 39573 | B |
| 49 | ttaactcaaatcaattctca | 1-1-3-2-1-8-1-1-2 | TtAACtcAaatcaattCtCA | 49_133 | 39573 | B |
| 49 | ttaactcaaatcaattctca | 1-1-3-2-1-7-2-1-2 | TtAACtcAaatcaatTCtCA | 49_134 | 39573 | B |
| 49 | ttaactcaaatcaattctca | 1-1-3-2-1-6-1-3-2 | TtAACtcAaatcaaTtctCA | 49_135 | 39573 | B |
| 49 | ttaactcaaatcaattctca | 1-1-3-2-1-6-1-1-1-1-2 | TtAACtcAaatcaaTtCtCA | 49_136 | 39573 | B |
| 49 | ttaactcaaatcaattctca | 1-1-3-2-1-6-3-1-2 | TtAACtcAaatcaaTTCtCA | 49_137 | 39573 | B |
| 49 | ttaactcaaatcaattctca | 1-1-3-1-1-11-2 | TtAACtCaaatcaattctCA | 49_138 | 39573 | B |
| 49 | ttaactcaaatcaattctca | 1-1-3-1-1-9-1-1-2 | TtAACtCaaatcaattCtCA | 49_139 | 39573 | B |
| 49 | ttaactcaaatcaattctca | 1-1-3-1-1-9-4 | TtAACtCaaatcaattCTCA | 49_140 | 39573 | B |
| 49 | ttaactcaaatcaattctca | 1-1-3-1-1-8-2-1-2 | TtAACtCaaatcaatTCtCA | 49_141 | 39573 | B |
| 49 | ttaactcaaatcaattctca | 1-1-3-1-2-8-1-1-2 | TtAACtCAaatcaattCtCA | 49_142 | 39573 | B |
| 49 | ttaactcaaatcaattctca | 1-1-3-1-2-6-1-3-2 | TtAACtCAaatcaaTtctCA | 49_143 | 39573 | B |
| 49 | ttaactcaaatcaattctca | 2-5-1-8-1-1-2 | TTaactcAaatcaattCtCA | 49_144 | 39573 | B |
| 49 | ttaactcaaatcaattctca | 2-5-1-7-2-1-2 | TTaactcAaatcaatTCtCA | 49_145 | 39573 | B |
| 49 | ttaactcaaatcaattctca | 2-5-1-6-1-1-1-2 | TTaactcAaatcaaTtCtCA | 49_146 | 39573 | B |
| 49 | ttaactcaaatcaattctca | 2-5-1-6-3-1-2 | TTaactcAaatcaaTTCtCA | 49_147 | 39573 | B |
| 49 | ttaactcaaatcaattctca | 2-4-2-8-1-1-2 | TTaactCAaatcaattCtCA | 49_148 | 39573 | B |
| 49 | ttaactcaaatcaattctca | 2-4-2-7-2-1-2 | TTaactCAaatcaatTCtCA | 49_149 | 39573 | B |
| 49 | ttaactcaaatcaattctca | 2-2-1-11-1-1-2 | TTaaCtcaaatcaattCtCA | 49_150 | 39573 | B |
| 49 | ttaactcaaatcaattctca | 2-2-1-11-4 | TTaaCtcaaatcaattCTCA | 49_151 | 39573 | B |
| 49 | ttaactcaaatcaattctca | 2-2-1-10-2-1-2 | TTaaCtcaaatcaatTCtCA | 49_152 | 39573 | B |
| 49 | ttaactcaaatcaattctca | 2-2-1-9-1-3-2 | TTaaCtcaaatcaaTtctCA | 49_153 | 39573 | B |
| 49 | ttaactcaaatcaattctca | 2-2-1-9-1-1-1-1-2 | TTaaCtcaaatcaaTtCtCA | 49_154 | 39573 | B |
| 49 | ttaactcaaatcaattctca | 2-2-1-7-1-5-2 | TTaaCtcaaatcAattctCA | 49_155 | 39573 | B |
| 49 | ttaactcaaatcaattctca | 2-2-1-2-1-10-2 | TTaaCtcAaatcaattctCA | 49_156 | 39573 | B |
| 49 | ttaactcaaatcaattctca | 2-2-1-2-1-8-1-1-2 | TTaaCtcAaatcaattCtCA | 49_157 | 39573 | B |
| 49 | ttaactcaaatcaattctca | 2-2-1-2-1-8-4 | TTaaCtcAaatcaattCTCA | 49_158 | 39573 | B |
| 49 | ttaactcaaatcaattctca | 2-2-1-2-1-7-2-1-2 | TTaaCtcAaatcaatTCtCA | 49_159 | 39573 | B |
| 49 | ttaactcaaatcaattctca | 2-2-1-2-1-6-1-3-2 | TTaaCtcAaatcaaTtctCA | 49_160 | 39573 | B |
| 49 | ttaactcaaatcaattctca | 2-2-1-2-1-6-1-1-1-1-2 | TTaaCtcAaatcaaTtCtCA | 49_161 | 39573 | B |
| 49 | ttaactcaaatcaattctca | 2-2-1-1-1-11-2 | TTaaCtCaaatcaattctCA | 49_162 | 39573 | B |
| 49 | ttaactcaaatcaattctca | 2-2-1-1-1-9-1-1-2 | TTaaCtCaaatcaattCtCA | 49_163 | 39573 | B |
| 49 | ttaactcaaatcaattctca | 2-2-1-1-2-10-2 | TTaaCtCAaatcaattctCA | 49_164 | 39573 | B |
| 49 | ttaactcaaatcaattctca | 2-2-1-1-2-6-1-3-2 | TTaaCtCAaatcaaTtctCA | 49_165 | 39573 | B |
| 49 | ttaactcaaatcaattctca | 2-1-1-10-1-1-1-1-2 | TTaActcaaatcaaTtCtCA | 49_166 | 39573 | B |

-continued

| SEQ ID NO | motif sequence | Design | Oligonucleotide Compound | CMP ID NO | Start on SEQ ID NO: 1 | Region |
|---|---|---|---|---|---|---|
| 49 | ttaactcaaatcaattctca | 2-1-1-2-1-9-1-1-2 | TTaActCaaatcaattCtCA | 49_167 | 39573 | B |
| 49 | ttaactcaaatcaattctca | 2-1-1-2-2-8-1-1-2 | TTaActCAaatcaattCtCA | 49_168 | 39573 | B |
| 49 | ttaactcaaatcaattctca | 2-1-2-9-1-1-1-1-2 | TTaACtcaaatcaaTtCtCA | 49_169 | 39573 | B |
| 49 | ttaactcaaatcaattctca | 2-1-2-2-1-7-2-1-2 | TTaACtcAaatcaatTCtCA | 49_170 | 39573 | B |
| 49 | ttaactcaaatcaattctca | 2-1-2-2-1-6-1-1-1-1-2 | TTaACtcAaatcaaTtCtCA | 49_171 | 39573 | B |
| 49 | ttaactcaaatcaattctca | 3-11-1-1-1-1-2 | TTAactcaaatcaaTtCtCA | 49_172 | 39573 | B |
| 49 | ttaactcaaatcaattctca | 3-10-1-2-1-1-2 | TTAactcaaatcaAttCtCA | 49_173 | 39573 | B |
| 49 | ttaactcaaatcaattctca | 3-10-1-1-2-1-2 | TTAactcaaatcaAtTCtCA | 49_174 | 39573 | B |
| 49 | ttaactcaaatcaattctca | 3-4-1-7-2-1-2 | TTAactcAaatcaatTCtCA | 49_175 | 39573 | B |
| 49 | ttaactcaaatcaattctca | 3-4-1-6-1-1-1-1-2 | TTAactcAaatcaaTtCtCA | 49_176 | 39573 | B |
| 49 | ttaactcaaatcaattctca | 3-3-1-9-1-1-2 | TTAactCaaatcaattCtCA | 49_177 | 39573 | B |
| 49 | ttaactcaaatcaattctca | 3-3-1-9-4 | TTAactCaaatcaattCTCA | 49_178 | 39573 | B |
| 49 | ttaactcaaatcaattctca | 3-3-1-8-2-1-2 | TTAactCaaatcaatTCtCA | 49_179 | 39573 | B |
| 49 | ttaactcaaatcaattctca | 3-3-2-8-1-1-2 | TTAactCAaatcaattCtCA | 49_180 | 39573 | B |
| 49 | ttaactcaaatcaattctca | 3-1-1-11-1-1-2 | TTAaCtcaaatcaattCtCA | 49_181 | 39573 | B |
| 49 | ttaactcaaatcaattctca | 3-1-1-9-1-3-2 | TTAaCtcaaatcaaTtctCA | 49_182 | 39573 | B |
| 49 | ttaactcaaatcaattctca | 3-1-1-9-1-1-1-1-2 | TTAaCtcaaatcaaTtCtCA | 49_183 | 39573 | B |
| 49 | ttaactcaaatcaattctca | 3-1-1-7-1-5-2 | TTAaCtcaaatcAattctCA | 49_184 | 39573 | B |
| 49 | ttaactcaaatcaattctca | 3-1-1-2-1-10-2 | TTAaCtcAaatcaattctCA | 49_185 | 39573 | B |
| 49 | ttaactcaaatcaattctca | 3-1-1-2-1-8-1-1-2 | TTAaCtcAaatcaattCtCA | 49_186 | 39573 | B |
| 49 | ttaactcaaatcaattctca | 3-1-1-2-1-6-1-3-2 | TTAaCtcAaatcaaTtctCA | 49_187 | 39573 | B |
| 49 | ttaactcaaatcaattctca | 3-1-1-1-1-11-2 | TTAaCtCaaatcaattctCA | 49_188 | 39573 | B |
| 49 | ttaactcaaatcaattctca | 4-12-4 | TTAActcaaatcaattCTCA | 49_189 | 39573 | B |
| 49 | ttaactcaaatcaattctca | 4-11-2-1-2 | TTAActcaaatcaatTCtCA | 49_190 | 39573 | B |
| 49 | ttaactcaaatcaattctca | 4-3-1-7-2-1-2 | TTAActcAaatcaatTCtCA | 49_191 | 39573 | B |
| 49 | ttaactcaaatcaattctca | 4-2-1-9-1-1-2 | TTAActCaaatcaattCtCA | 49_192 | 39573 | B |
| 50 | tttaactcaaatcaattctc | 4-12-4 | TTTAactcaaatcaatTCTC | 50_1 | 39574 | B |
| 51 | tttaactcaaatcaattct | 4-11-4 | TTTAactcaaatcaaTTCT | 51_1 | 39575 | B |
| 52 | ccttttaattcattag | 4-8-4 | CCTTttaattcaTTAG | 52_1 | 72861 | C |
| 53 | caacaccttttaattcatta | 4-12-4 | CAACaccttttaattcATTA | 53_1 | 72862 | C |
| 54 | aacaccttttaattcatt | 4-10-4 | AACAccttttaattCATT | 54_1 | 72863 | C |
| 55 | catcaacaccttttaattca | 2-14-4 | CAtcaacaccttttaaTTCA | 55_1 | 72865 | C |
| 56 | ctcatcaacaccttttaatt | 4-14-2 | CTCAtcaacaccttttaaTT | 56_1 | 72867 | C |
| 57 | actcatcaacaccttttaat | 2-14-4 | ACtcatcaacaccttTTAAT | 57_1 | 72868 | C |
| 58 | aactcatcaacaccttttaa | 3-13-4 | AACtcatcaacaccttTTAA | 58_1 | 72869 | C |
| 59 | taactcatcaacacctttta | 4-14-2 | TAACtcatcaacaccttttTA | 59_1 | 72870 | C |
| 60 | ttaactcatcaacacctttt | 4-13-3 | TTAActcatcaacacctTTT | 60_1 | 72871 | C |

-continued

| SEQ ID NO | motif sequence | Design | Oligonucleotide Compound | CMP ID NO | Start on SEQ ID NO: 1 | Region |
|---|---|---|---|---|---|---|
| 61 | ttaactcatcaacaccttt | 3-12-4 | TTAactcatcaacacCTTT | 61_1 | 72872 | C |
| 62 | ttaactcatcaacacctt | 3-11-4 | TTAactcatcaacaCCTT | 62_1 | 72873 | C |
| 63 | ttaactcatcaacacct | 4-9-4 | TTAActcatcaacACCT | 63_1 | 72874 | C |
| 64 | gttaactcatcaacacc | 4-10-3 | GTTAactcatcaacACC | 64_1 | 72875 | C |
| 65 | gttaactcatcaacac | 4-9-3 | GTTAactcatcaaCAC | 65_1 | 72876 | C |
| 66 | atttccaaattcacttttac | 1-1-3-10-2-1-2 | AtTTCcaaattcactTTtAC | 66_1 | 133964 | — |
| 67 | ccgttttcttaccaccct | 5-10-5 | CC$_o$GTTttettaeeAC$_o$CCT | 67_1 | 114184 | — |

Motif sequences represent the contiguous sequence of nucleobases present in the oligonucleotide.

Designs refer to the gapmer design, F-G-F'. In classic gapmer design e.g. 3-10-3 all the nucleotides in the flanks (F and F') are constituted of the same 2'-sugar modified nucleoside, e.g. LNA, cET, or MOE, and a stretch of DNA in the middle forming the gap (G). In gapmers with alternating flank designs the flanks of oligonucleotide is annotated as a series of integers, representing a number of 2' sugar modified nucleosides (M) followed by a number of DNA nucleosides (D). For example a flank with a 2-2-1 motif represents 5' $[M]_2$-$[D]_2$-[M] 3' and a 1-1-1-1-1 motif represents 5' [M]-[D]-[M]-[D]-[M] 3'. Both flanks have a 2' sugar modified nucleoside at the 5' and 3' terminal. The gap region (G), which is constituted of a number of DNA nucleosides (typically between 6 and 16), is located between the flanks.

The heading "Oligonucleotide compound" in the table represents a specific design of the motif sequence. Capital letters represent beta-D-oxy LNA nucleosides, Underlined capital letter represent MOE nucleosides, lowercase letters represent DNA nucleosides, all LNA C are 5-methyl cytosine, e represents a 5-methyl cytosine DNA, all internucleoside linkages are phosphorothioate internucleoside linkages unless marked by a subscript letter between the nucleotides, subscript o represents a phosphodiester linkage.

Oligonucleotide Synthesis

Oligonucleotide synthesis is generally known in the art. Below is a protocol which may be applied. The oligonucleotides of the present invention may have been produced by slightly varying methods in terms of apparatus, support and concentrations used.

Oligonucleotides are synthesized on uridine universal supports using the phosphoramidite approach on an Oligomaker 48 at 1 μmol scale. At the end of the synthesis, the oligonucleotides are cleaved from the solid support using aqueous ammonia for 5-16 hours at 60*C. The oligonucleotides are purified by reverse phase HPLC (RP-HPLC) or by solid phase extractions and characterized by UPLC, and the molecular mass is further confirmed by ESI-MS.

Elongation of the Oligonucleotide:

The coupling of β-cyanoethyl-phosphoramidites (DNA-A(Bz), DNA-G(ibu), DNA-C(Bz), DNA-T, LNA-5-methyl-C(Bz), LNA-A(Bz), LNA-G(dmf), or LNA-T) is performed by using a solution of 0.1 M of the 5'-O-DMT-protected amidite in acetonitrile and DCI (4,5-dicyanoimidazole) in acetonitrile (0.25 M) as activator. For the final cycle a phosphoramidite with desired modifications can be used, e.g. a C6 linker for attaching a conjugate group or a conjugate group as such. Thiolation for introduction of phosphorthioate linkages is carried out by using xanthane hydride (0.01 M in acetonitrile/pyridine 9:1). Phosphodiester linkages can be introduced using 0.02 M iodine in THF/Pyridine/water 7:2:1. The rest of the reagents are the ones typically used for oligonucleotide synthesis.

For post solid phase synthesis conjugation a commercially available C6 amino linker phorphoramidite can be used in the last cycle of the solid phase synthesis and after deprotection and cleavage from the solid support the aminolinked deprotected oligonucleotide is isolated. The conjugates are introduced via activation of the functional group using standard synthesis methods.

Purification by RP-HPLC:

The crude compounds are purified by preparative RP-HPLC on a Phenomenex Jupiter C18 10μ 150×10 mm column. 0.1 M ammonium acetate pH 8 and acetonitrile is used as buffers at a flow rate of 5 mL/min. The collected fractions are lyophilized to give the purified compound typically as a white solid.

Abbreviations:

DCI: 4,5-Dicyanoimidazole

DCM: Dichloromethane

DMF: Dimethylformamide

DMT: 4,4'-Dimethoxytrityl

THF: Tetrahydrofurane

Bz: Benzoyl

Ibu: Isobutyryl

RP-HPLC: Reverse phase high performance liquid chromatography $T_m$ Assay:

Oligonucleotide and RNA target (phosphate linked, PO) duplexes are diluted to 3 mM in 500 ml RNase-free water and mixed with 500 ml 2×$T_m$-buffer (200 mM NaCl, 0.2 mM EDTA, 20 mM Naphosphate, pH 7.0). The solution is heated to 95° C. for 3 min and then allowed to anneal in room temperature for 30 min. The duplex melting temperatures ($T_m$) is measured on a Lambda 40 UV/VIS Spectrophotometer equipped with a Peltier temperature programmer PTP6 using PE Templab software (Perkin Elmer). The temperature is ramped up from 20° C. to 95° C. and then down to 25° C., recording absorption at 260 nm. First derivative and the local maximums of both the melting and annealing are used to assess the duplex $T_m$.

Primary Neuronal Cell Cultures

Primary neuronal cultures were established from the forebrain of E18 transgenic mice expressing the human tau transgene on a mouse tau knockout background. (Andorfer et al. J Neurochem 86:582-590 (2003)). Primary neurons were generated by papain digestion according to manufacturer's protocol (Worthington Biochemical Corporation, LK0031050). Briefly, forebrains were dissected from hTau mouse E18 BAC-Tg embryos expressing the entire human microtubule-associated protein Tau (MAPT) gene on a murine MAPT-null background and were incubated at 37° C. for 30-45 minutes in papain/DNase/Earle's balanced salt solution (EBSS) solution. After trituration and centrifugation of cell pellet, the reaction was stopped by incubation with EBSS containing protease inhibitors, bovine serum albumin (BSA) and DNase. The cells were triturated and washed with Neurobasal (NB, Invitrogen) supplemented with 2% B-27, 100 μg/ml penicillin, 85 μg/ml streptomycin, and 0.5 mM glutamine.

Transgenic Tau Mouse (hTau Mouse)

Male and female transgenic mice (30-40 g) expressing a tau transgene derived from a human PAC, H1 haplotype driven by the tau promoter (Polydoro et. al., *J. Neurosci.* (2009) 29(34): 10741-9), and in which the native mouse Tau gene was deleted, were used to assess tolerability, pharmacodynamic endpoints and tissue drug concentrations.

Animals were held in colony rooms maintained at constant temperature (21±2° C.) and humidity (50±10%) and illuminated for 12 hours per day (lights on at 0600 hours). All animals had ad libitum access to food and water throughout the studies. Behavioral studies were conducted between 0700 and 1500 hours.

Intracerebroventricular (ICV) injections were performed using a Hamilton micro syringe fitted with a 27 or 30-gauge needle, according to the method of Haley and McCormick. The needle was equipped with a polyethylene guard at 2.5 mm from the tip in order to limit its penetration into the brain. Mice were anesthetized using isoflurane anesthetic (1.5-4%). The mouse to be injected was held by the loose skin at the back of the neck with the thumb and first fingers of one hand. Applying gentle but firm pressure, the head of the animal was then immobilized by pressing against a firm flat level surface. The needle tip was then inserted through the scalp and the skull, about 1 mm lateral and 1 mm caudal to bregma. Once the needle was positioned, ASO was given in a volume of 5 microliters in saline vehicle and injected into the right (or left) lateral ventricle over 20-30 seconds. The needle was left in place for 10 seconds before removal. This procedure requires no surgery or incision. Animals were warmed on heating pads until they recovered from the procedure.

3 days and/or 4 weeks post administration mice were sacrificed with isoflurane overdose followed by rapid decapitation and brain tissue (right, frontal cortical region) was collected on dry ice for later Tau qPCR.

Media Used for Cell Culturing and Differentiation of Human Stem Cell Derived Neurons N2B27+SFA Media=N2B27+S,F,A Cytokines

| Cytokines used | Ref | Provider | Stock | Final use in N2B27 (dilution) |
|---|---|---|---|---|
| SHH (sonic hedgehog) | 100-45 | Peprotech | 100 ug/ml in PBS + 0.1% BSA | 1:500 (200 ng/ml) |
| FGF8 | 100-25 | Peprotech | 100 ug/ml in | 1:1000 (100 ng/ml) |
| AA (Aa2-P) | A8960 | Sigma | PBS + 0.1% BSA 100 mM in DMEM:F12 | 1:1000 |

N2B27+BGAA Media=N2B27+B,G,Aa,cA Cytokines+P/S+Laminin

| Cytokines used | Ref | Provider | Stock | Final use in N2B27 (dilution) |
|---|---|---|---|---|
| BDNF | 450-02 | Peprotech | 20 ug/ml in PBS + 0.1% BSA | 1:1000 |
| GDNF | 450-10 | Peprotech | 10 ug/ml in PBS + 0.1% BSA | 1:1000 |
| AA (Aa2-P) | A8960 | Sigma | 100 mM in DMEM:F12 | 1:1000 |
| cAMP | D 009 | BIOLOG Life Science | 200 mM in water | 1:400 |
| PenStrep | 15140-122 | Gibco | | 1% |
| Laminin | 11243217001 | Roche | 1 mg/ml | 1:500 |

Example 1: In Vitro Screening of ASO's Targeting MAPT Introns

An antisense oligonucleotide (ASO) screening was performed in primary neuronal cells from humanized Tau mice with 807 ASO's targeting the MAPT introns.

The ability of ASOs to reduce MAPT mRNA in vitro was measured by QUANTIGENE® analysis. Each tau mRNA reduction was standardized by subtracting an assay background signal and normalizing each well via the housekeeping gene tubulin mRNA signal.

Primary neuronal cell cultures were prepared as described in the "Materials and Method" section and plated on poly-D-lysine coated 384 well plates at 10,000 cells per well and maintained in Neurobasal media containing B27, glutamax and Penicillin-Streptomycin. ASO's were diluted in water and added to cells at DIV01 to a final concentration of 0.5 μM. Following ASO addition, neurons were incubated at 37° C. and 5% $CO_2$ for 5 days to achieve steady state reduction of mRNA. Media was removed and cells were washed 1× in DPBS. Measurement of lysate messenger RNA was performed using the QUANTIGENE® 2.0 Reagent System (AFFYMETRIX®), which quantitates RNA using a branched DNA-signal amplification method reliant on the specifically designed RNA capture probe set. The cells were lysed using working cell lysis buffer solution made by adding 50 μl proteinase K to 5 ml of pre-warmed Lysis mix and diluted to 1:4 final dilution with $dH_2O$. The working lysis buffer was added to the plate (45 μl/well), triturated to mix, sealed and incubated for 30 min at 55° C. Following lysis the wells were stored at −80° C. or assayed immediately.

Lysates were diluted in lysis mix dependent on the specific capture probe used (tau or tubulin). 27 μl/well total was then added to the capture plate (384 well polystyrene plate coated with capture probes). Working probe sets reagents were generated by combining 2.2 ml of nuclease-free water, 1.2 ml of lysis mixture, 184 μl blocking reagent, and 66.8 μl of specific 2.0 probe set human MAPT catalogue #15486 and mouse beta 3 tubulin, catalogue #SB-17245, per manufacturer instructions (QUANTIGENE® 2.0 AFFYMETRIX®). Then 7 μl working probe set reagents were added to 27 μl lysate dilution (or 27 μl lysis mix for background samples) on the capture plate. Plates were centrifuged and then incubated for 16-20 hours at 55° C. to hybridize (target RNA capture). Signal amplification and detection of target RNA began by washing plates with buffer 3 times to remove unbound material. 2.0 Pre-Amplifier hybridization reagent (30 μl/well) was added, incubated at 55° C. for 1 hour then aspirated and wash buffer was added and aspirated 3 times. The 2.0 Amplifier hybridization reagent was then added as described (30 μl/well), incubated for 1 hour at 55° C. and the wash was repeated as described previously. The 2.0 Label Probe hybridization reagent was added next (30 μl/well), incubated for 1 hour at 50° C. and the wash was repeated as described previously. Lastly, the plates were centrifuged to remove any excess wash buffer and 2.0 Substrate was added (30 μl/well). Plates were incubated for 5 minutes at room temperature and plates were imaged on a PerkinElmer Envision multilabel reader in luminometer mode within 15 minutes.

For the gene of interest, the average assay background signal was subtracted from the average signal of each technical replicate. The background-subtracted, average signals for the gene of interest are divided by the background-subtracted average signal for the housekeeping tubulin RNA. The percent inhibition for the treated sample was calculated relative to untreated sample (i.e. the lower the value the larger the inhibition). Variability in background of untreated samples may result in percent inhibition of a treated sample that are equal to or higher than background, and in these cases, percent inhibition is expressed as 100% inhibition of control (i.e. no inhibition).

FIG. 1 shows the MAPT mRNA reduction achieved by all 807 ASO's. In the figure three regions A, B and C on the MAPT target nucleic acid are indicated. These regions have a high prevalence of ASO's that reduce the target to 40% or less compared to control (100%).

Example 2: In Vitro Screening of ASO's Targeting Selected Regions on MAPT

Based on the screening in Example 1, a new library of ASO's were designed to target region A, B and C as illustrated in FIG. 1. The motif sequences and the oligonucleotide compounds are shown in table 5 above.

The screening was conducted as described in Example 1. The results are shown in table 6.

TABLE 6 in vitro screening of anti-MAPT compounds

| CMP ID NO | Compound | % MAPT mRNA of control |
|---|---|---|
| 6_1 | TCACtcatgccttaaTC | 2 |
| 7_1 | TAATcactcatgcCTTA | 15 |
| 8_1 | TAATcactcatgCCTT | 34 |
| 9_1 | CtttaatttaaTcaCtCAT | 41 |
| 9_2 | CtttaatttaaTcACtCAT | 36 |
| 9_3 | CtttaatttaaTCactCAT | 28 |
| 9_4 | CtttaatttaaTCacTCAT | 31 |
| 9_5 | CtttaatttaaTCaCtcAT | 28 |
| 9_6 | CtttaatttaaTCaCtCAT | 55 |
| 9_7 | CtttaatttaaTCActcAT | 30 |
| 9_8 | CtttaatttaaTCActCAT | 21 |
| 9_9 | CtttaatttaaTCAcTCAT | 61 |
| 9_10 | CtttaatttaaTCACtcAT | 24 |
| 9_11 | CtttaaTttaatcacTCAT | 14 |
| 9_12 | CtttaaTttaatcaCtCAT | 22 |
| 9_13 | CtttaaTttaatcActCAT | 33 |
| 9_14 | CtttaaTttaatcAcTCAT | 9 |
| 9_15 | CtttaaTttaatcACtCAT | 20 |
| 9_16 | CtttaAtttaatcacTCAT | 17 |
| 9_18 | CtttAatttaatcacTCAT | 10 |
| 9_19 | CtttAatttaatcaCtCAT | 17 |
| 9_20 | CtttAaTttaatcacTCAT | 0 |
| 9_21 | CtttAAtttaatcacTCAT | 3 |
| 9_22 | CtttAATttaatcacTCAT | 1 |
| 9_23 | CttTaatttaatcacTCAT | 13 |
| 9_24 | CttTaatttaatcaCtCAT | 13 |
| 9_25 | CttTaaTttaatcacTCAT | 4 |
| 9_26 | CttTaAtttaatcacTCAT | 4 |
| 9_27 | CttTaATttaatcacTCAT | 1 |
| 9_28 | CttTAatttaatcactCAT | 12 |
| 9_29 | CttTAatttaatcacTCAT | 1 |
| 9_30 | CttTAatttaatcaCtcAT | 15 |
| 9_31 | CttTAatttaatcaCtCAT | 4 |
| 9_32 | CttTAaTttaatcacTCAT | 1 |
| 9_33 | CttTAAtttaatcacTCAT | 1 |
| 9_34 | CttTAATttaatcactcAT | 4 |
| 9_35 | CttTAATttaatcacTCAT | 1 |
| 9_36 | CtTtaaTttaatcacTCAT | 5 |
| 9_37 | CtTtaAtttaatcacTCAT | 7 |
| 9_38 | CtTtaATttaatcacTCAT | 2 |
| 9_39 | CtTtAatttaatcacTCAT | 3 |
| 9_40 | CtTtAatttaatcaCtCAT | 9 |
| 9_41 | CtTtAaTttaatcacTCAT | 4 |
| 9_42 | CtTtAAtttaatcacTCAT | 1 |
| 9_43 | CtTtAATttaatcacTCAT | 1 |
| 9_44 | CtTTaatttaatcacTCAT | 2 |
| 9_45 | CtTTaatttaatcaCtcAT | 15 |
| 9_46 | CtTTaatttaatcaCtCAT | 3 |
| 9_47 | CtTTaaTttaatcacTCAT | 2 |

TABLE 6-continued in vitro screening of anti-MAPT compounds

| CMP ID NO | Compound | % MAPT mRNA of control |
|---|---|---|
| 9_48 | CtTTaAtttaatcacTCAT | 1 |
| 9_49 | CtTTaATttaatcactcAT | 1 |
| 9_50 | CtTTaATttaatcacTCAT | 1 |
| 9_51 | CtTTAatttaatcactCAT | 1 |
| 9_52 | CtTTAatttaatcacTCAT | 1 |
| 9_53 | CtTTAatttaatcaCtcAT | 6 |
| 9_54 | CtTTAatttaatcaCtCAT | 2 |
| 9_56 | CtTTAaTttaatcacTCAT | 1 |
| 9_57 | CtTTAAtttaatcactcAT | 1 |
| 9_58 | CtTTAAtttaatcacTCAT | 1 |
| 9_59 | CTttaatttaatcActCAT | 39 |
| 9_60 | CTttaatttaatcAcTCAT | 10 |
| 9_61 | CTttaatttaatcACtCAT | 20 |
| 9_62 | CTttaatttaaTCactcAT | 26 |
| 9_63 | CTttaatttaaTCactCAT | 14 |
| 9_64 | CTttaatttaaTCacTCAT | 14 |
| 9_65 | CTttaatttaaTCaCtcAT | 15 |
| 9_66 | CTttaatttaaTCaCtCAT | 38 |
| 9_67 | CTttaatttaaTCActcAT | 9 |
| 9_68 | CTttaatttaaTCActCAT | 12 |
| 9_69 | CTttaatttaaTCACtcAT | 9 |
| 9_70 | CTttaaTttaatcactCAT | 42 |
| 9_71 | CTttaaTttaatcacTCAT | 6 |
| 9_72 | CTttaaTttaatcaCtcAT | 49 |
| 9_73 | CTttaaTttaatcaCtCAT | 15 |
| 9_74 | CTttaaTttaatcActCAT | 16 |
| 9_75 | CTttaaTttaatcAcTCAT | 12 |
| 9_76 | CTttaaTttaatcACtcAT | 32 |
| 9_77 | CTttaaTttaatcACtCAT | 15 |
| 9_78 | CTttAatttaatcactCAT | 21 |
| 9_79 | CTttAatttaatcacTCAT | 3 |
| 9_80 | CTttAatttaatcaCtCAT | 10 |
| 9_81 | CTttAaTttaatcacTCAT | 2 |
| 9_82 | CTttAAtttaatcacTCAT | 1 |
| 9_84 | CTtTaatttaatcaCtcAT | 22 |
| 9_85 | CTtTaatttaatcaCtCAT | 8 |
| 9_86 | CTtTaAtttaatcacTCAT | 2 |
| 9_89 | CTtTAatttaatcacTCAT | 1 |
| 9_90 | CTtTAatttaatcaCtcAT | 5 |
| 9_92 | CTtTAaTttaatcactcAT | 1 |
| 9_94 | CTtTAAtttaatcacTCAT | 1 |
| 9_97 | CTTtAatttaatcactCAT | 0 |
| 9_98 | CTTtAatttaatcacTCAT | 1 |
| 9_99 | CTTtAatttaatcaCtcAT | 7 |
| 9_100 | CTTtAatttaatcaCtCAT | 3 |
| 9_101 | CTTtAAtttaatcacTCAT | 1 |
| 9_103 | CTTTaatttaatcacTCAT | 0 |
| 9_105 | CTTTaaTttaatcactcAT | 0 |
| 9_106 | CTTTaAtttaatcacTCAT | 1 |
| 10_1 | GctttaatttaaTcaCtCAT | 35 |
| 10_2 | GctttaatttaaTCactcAT | 56 |
| 10_3 | GctttaatttaaTCactCAT | 18 |
| 10_4 | GctttaatttaaTCacTCAT | 21 |
| 10_5 | GctttaatttaaTCaCtcAT | 16 |
| 10_6 | GctttaatttaaTCaCtCAT | 35 |
| 10_7 | GctttaatttaaTCActcAT | 22 |
| 10_8 | GctttaatttaaTCACtcAT | 12 |
| 10_9 | GctttaaTttaatcactCAT | 61 |
| 10_10 | GctttaaTttaatcacTCAT | 19 |
| 10_11 | GctttaaTttaatcaCtcAT | 76 |
| 10_12 | GctttaaTttaatcaCtCAT | 12 |
| 10_13 | GctttaaTttaaTcaCtCAT | 15 |
| 10_14 | GctttaaTttaaTCactCAT | 7 |
| 10_15 | GctttaaTttaaTCaCtcAT | 14 |
| 10_16 | GctttaaTttaaTCActcAT | 10 |
| 10_17 | GctttaAtttaatcacTCAT | 28 |
| 10_18 | GctttAatttaatcacTCAT | 16 |
| 10_19 | GctttAatttaatcaCtCAT | 13 |
| 10_20 | GctttAaTttaatcacTCAT | 2 |
| 10_21 | GctttAAtttaatcacTCAT | 3 |
| 10_22 | GctttAATttaatcacTCAT | 1 |
| 10_23 | GcttTaatttaatcacTCAT | 18 |
| 10_24 | GcttTaatttaatcaCtcAT | 51 |
| 10_25 | GcttTaatttaatcaCtCAT | 8 |
| 10_26 | GcttTaaTttaatcacTCAT | 4 |

TABLE 6-continued in vitro screening of anti-MAPT compounds

| CMP ID NO | Compound | % MAPT mRNA of control |
|---|---|---|
| 10_27 | GcttTaAtttaatcacTCAT | 3 |
| 10_28 | GcttTAatttaatcacTCAT | 2 |
| 10_29 | GcttTAatttaatcaCtcAT | 13 |
| 10_30 | GcttTAatttaatcaCtCAT | 3 |
| 10_31 | GctTtaaTttaatcacTCAT | 4 |
| 10_32 | GctTtaAtttaatcacTCAT | 6 |
| 10_33 | GctTtAatttaatcacTCAT | 3 |
| 10_34 | GctTtAatttaatcaCtcAT | 18 |
| 10_35 | GctTtAatttaatcaCtCAT | 6 |
| 10_36 | GctTtAaTttaatcacTCAT | 2 |
| 10_37 | GctTtAAtttaatcacTCAT | 1 |
| 10_38 | GctTTaatttaatcacTCAT | 1 |
| 10_39 | GctTTaatttaatcaCtcAT | 12 |
| 10_40 | GctTTaatttaatcaCtCAT | 3 |
| 10_41 | GctTTaAtttaatcacTCAT | 1 |
| 10_42 | GctTTAatttaatcaCtcAT | 5 |
| 10_43 | GcTttaatttaaTCactcAT | 15 |
| 10_44 | GcTttaatttaaTCactCAT | 11 |
| 10_45 | GcTttaatttaaTCaCtcAT | 15 |
| 10_46 | GcTttaatttaaTCActcAT | 7 |
| 10_47 | GcTttaaTttaatcactCAT | 23 |
| 10_48 | GcTttaaTttaatcacTCAT | 6 |
| 10_49 | GcTttaaTttaatcaCtcAT | 34 |
| 10_50 | GcTttaaTttaatcaCtCAT | 12 |
| 10_51 | GcTttaAtttaatcacTCAT | 10 |
| 10_52 | GcTttAatttaatcacTCAT | 5 |
| 10_53 | GcTttAatttaatcaCtcAT | 26 |
| 10_54 | GcTttAatttaatcaCtCAT | 10 |
| 10_55 | GcTttAaTttaatcacTCAT | 3 |
| 10_56 | GcTttAAtttaatcacTCAT | 2 |
| 10_57 | GcTtTaatttaatcacTCAT | 5 |
| 10_58 | GcTtTaatttaatcaCtCAT | 9 |
| 10_59 | GcTtTaaTttaatcacTCAT | 5 |
| 10_60 | GcTtTaAtttaatcacTCAT | 4 |
| 10_61 | GcTtTAatttaatcaCtcAT | 10 |
| 10_62 | GcTtTAAtttaatcactcAT | 4 |
| 10_63 | GcTTtaaTttaatcacTCAT | 2 |

TABLE 6-continued in vitro screening of anti-MAPT compounds

| CMP ID NO | Compound | % MAPT mRNA of control |
|---|---|---|
| 10_64 | GcTTtaAtttaatcactcAT | 21 |
| 10_65 | GcTTtaAtttaatcacTCAT | 2 |
| 10_66 | GcTTtAatttaatcacTCAT | 2 |
| 10_67 | GcTTtAatttaatcaCtCAT | 1 |
| 10_68 | GcTTtAAtttaatcactcAT | 4 |
| 10_69 | GcTTTaatttaatcaCTcAT | 1 |
| 10_70 | GcTTTAatttaatcaCtcAT | 5 |
| 10_71 | GCtttaatttaatCactcAT | 71 |
| 10_72 | GCtttaatttaaTCactcAT | 22 |
| 10_73 | GCtttaaTttaatcactcAT | 76 |
| 10_74 | GCtttaaTttaatcactCAT | 25 |
| 10_75 | GCtttaaTttaatcaCtcAT | 43 |
| 10_76 | GCtttaATttaatcactcAT | 25 |
| 10_77 | GCtttAatttaatcaCtcAT | 13 |
| 10_78 | GCtttAAtttaatcactcAT | 22 |
| 10_79 | GCttTaatttaatcaCtcAT | 16 |
| 10_80 | GCttTaAtttaatcactcAT | 8 |
| 10_81 | GCttTAAtttaatcactcAT | 3 |
| 10_82 | GCtTtaAtttaatcactcAT | 21 |
| 10_83 | GCtTtAatttaatcaCtcAT | 7 |
| 10_84 | GCtTtAAtttaatcactcAT | 3 |
| 10_85 | GCTttaatttaatCactcAT | 29 |
| 10_86 | GCTttaaTttaatcactcAT | 32 |
| 10_87 | GCTttaAtttaatcactcAT | 38 |
| 10_88 | GCTttAAtttaatcactcAT | 6 |
| 10_89 | GCTtTaatttaatcAcTcAT | 9 |
| 11_1 | CTTTaatttaatcaCTCA | 0 |
| 12_1 | CTTTaatttaatcACTC | 0 |
| 19_1 | ACAccatccaagtCAAT | 20 |
| 20_1 | TACaccatccaagTCAA | 18 |
| 21_1 | TTACaccatccaagtCA | 0 |
| 22_1 | TTACaccatccaaGTC | 5 |
| 23_1 | AATAttacaccatCCAA | 0 |
| 24_1 | AgaaTattacaccatCCAA | 11 |
| 24_2 | AgaaTattacaccaTcCAA | 8 |
| 24_3 | AgaaTattacaccaTCcAA | 6 |
| 24_4 | AgaaTattacaccAtcCAA | 11 |
| 24_5 | AgaaTattacaccAtCCAA | 14 |

TABLE 6-continued in vitro screening of anti-MAPT compounds

| CMP ID NO | Compound | % MAPT mRNA of control |
|---|---|---|
| 24_6 | AgaaTattacaccATcCAA | 6 |
| 24_7 | AgaaTattacaccATCcAA | 2 |
| 24_8 | AgaaTattacacCaTCcAA | 12 |
| 24_9 | AgaaTattacaCcAtCcAA | 11 |
| 24_10 | AgaaTattacaCcATcCAA | 18 |
| 24_11 | AgaAtattacaccatCCAA | 10 |
| 24_12 | AgaAtattacaccaTcCAA | 12 |
| 24_13 | AgaATattacaccatcCAA | 1 |
| 24_14 | AgaATattacaccaTCcAA | 1 |
| 24_15 | AgaATattacaccAtcCAA | 9 |
| 24_16 | AgaATattacaccAtCcAA | 0 |
| 24_17 | AgaATattacaccATCcAA | 10 |
| 24_18 | AgaATattacacCAtCcAA | 3 |
| 24_19 | AgAatattacaccAtCCAA | 10 |
| 24_20 | AgAatattacaccATCcAA | 13 |
| 24_21 | AgAaTattacaccatcCAA | 0 |
| 24_22 | AgAaTattacaccaTCcAA | 3 |
| 24_23 | AgAaTattacaccAtcCAA | 13 |
| 24_24 | AgAaTattacaccAtCcAA | 1 |
| 24_25 | AgAaTattacaccATCcAA | 8 |
| 24_26 | AgAaTattacacCatcCAA | 3 |
| 24_27 | AgAaTattacaCcatcCAA | 1 |
| 24_28 | AgAaTAttacacCAtccAA | 5 |
| 24_29 | AgAAtattacaccaTCcAA | 13 |
| 24_30 | AgAATattacaccatcCAA | 10 |
| 24_31 | AgAATattacaccatCcAA | 4 |
| 24_32 | AgAATattacaccaTCcAA | 12 |
| 24_33 | AgAATattacaccAtcCAA | 13 |
| 24_34 | AgAATattacaccAtCcAA | 5 |
| 24_35 | AgAATattacacCaTCcAA | 4 |
| 24_36 | AGaatAttacaccaTCcAA | 5 |
| 24_37 | AGaatAttacacCatcCAA | 2 |
| 24_38 | AGaaTattacaccatcCAA | 11 |
| 24_39 | AGaaTattacaccatCcAA | 3 |
| 24_40 | AGaaTattacaccaTCcAA | 17 |
| 24_41 | AGaaTattacaccAtcCAA | 9 |
| 24_42 | AGaaTattacaccAtCcAA | 2 |
| 24_43 | AGaaTattacaccATCcAA | 5 |
| 24_44 | AGaaTattacaCcAtCcAA | 9 |
| 24_45 | AGaaTAttacacCatCcAA | 3 |
| 24_46 | AGaAtattacaccaTCcAA | 9 |
| 24_47 | AGaAtAttacacCaTCcAA | 26 |
| 24_48 | AGaATattacaccatcCAA | 8 |
| 24_49 | AGaATattacaccatCcAA | 0 |
| 24_50 | AGaATattacaccaTCcAA | 2 |
| 24_51 | AGaATattacaccAtcCAA | 4 |
| 24_52 | AGaATattacaccAtCcAA | 0 |
| 24_53 | AGaATAttacaccatCcAA | 1 |
| 24_54 | AGAatattacaccaTCcAA | 5 |
| 24_55 | AGAatattacaccAtcCAA | 1 |
| 24_56 | AGAatattacaccAtCcAA | 0 |
| 24_57 | AGAaTattacaccatCcAA | 0 |
| 24_58 | AGAaTattacaccAtccAA | 13 |
| 24_59 | AGAaTattacaccAtCcAA | 11 |
| 24_60 | AGAAtattacaccatCcAA | 11 |
| 24_61 | AGAAtattacacCatccAA | 56 |
| 24_62 | AGAAtAttacaccatCcAA | 4 |
| 25_1 | CagaaTattacaccaTcCAA | 8 |
| 25_2 | CagaaTattacaccaTCcAA | 11 |
| 25_3 | CagaaTattacacCatCcAA | 9 |
| 25_4 | CagaaTattacaCcAtCcAA | 12 |
| 25_5 | CagaAtattacaccaTCcAA | 20 |
| 25_6 | CagaAtattacaCCatccAA | 10 |
| 25_7 | CagaAtAttacacCAtccAA | 6 |
| 25_8 | CagaATattacaccatcCAA | 5 |
| 25_9 | CagaATattacaccatCcAA | 6 |
| 25_10 | CagaATattacaccaTCcAA | 9 |
| 25_11 | CagaATattacaccAtCcAA | 12 |
| 25_12 | CagAatattacaccaTCcAA | 11 |
| 25_13 | CagAatattacaccAtcCAA | 2 |
| 25_14 | CagAatAttacacCaTCcAA | 19 |
| 25_15 | CagAaTattacaccatcCAA | 13 |
| 25_16 | CagAaTattacaccaTCcAA | 7 |
| 25_17 | CagAaTattacaccAtcCAA | 0 |
| 25_18 | CagAaTattacaccAtCcAA | 13 |

TABLE 6-continued in vitro screening of anti-MAPT compounds

| CMP ID NO | Compound | % MAPT mRNA of control |
|---|---|---|
| 25_19 | CagAaTattacacCaTCcAA | 6 |
| 25_20 | CagAaTAttacacCatCcAA | 12 |
| 25_21 | CagAAtattacacCAtccAA | 2 |
| 25_22 | CagAAtattacacCAtCcAA | 25 |
| 25_23 | CaGaaTattacaccatcCAA | 2 |
| 25_24 | CaGaaTattacaccatCcAA | 3 |
| 25_25 | CaGaaTattacaccaTCcAA | 5 |
| 25_26 | CaGaaTattacaccAtcCAA | 0 |
| 25_27 | CaGaaTattacaccAtCcAA | 10 |
| 25_28 | CaGaaTattacaCcatccAA | 4 |
| 25_29 | CaGaAtattacaccatCcAA | 6 |
| 25_30 | CaGaAtattacaccaTCcAA | 3 |
| 25_31 | CaGaAtAttacaccatCcAA | 6 |
| 25_32 | CaGaAtAttacacCAtccAA | 2 |
| 25_33 | CaGAatattacaccAtCcAA | 5 |
| 25_34 | CaGAatattacaCcAtccAA | 10 |
| 25_35 | CAgaaTattacaccatCcAA | 5 |
| 25_36 | CAgaaTattacaccAtccAA | 5 |
| 25_37 | CAgaaTattacaccAtCcAA | 3 |
| 25_38 | CAgaAtattacaccatCcAA | 26 |
| 25_39 | CAgAatattacaccAtccAA | 1 |
| 25_40 | CAgAatattacaccAtCcAA | 11 |
| 25_41 | CAgAaTattacaccAtccAA | 6 |
| 25_42 | CAgAaTattacacCatccAA | 73 |
| 25_43 | CAgAAtattacaccatCcAA | 1 |
| 26_1 | GaatattacacCAtCCAA | 11 |
| 26_2 | GaatattacacCATcCAA | 13 |
| 26_3 | GaatattacacCATCcAA | 10 |
| 26_4 | GaatAttacaccatCCAA | 0 |
| 26_5 | GaaTattacaccatCCAA | 2 |
| 26_6 | GaaTattacaccAtCCAA | 0 |
| 26_7 | GaaTAttacacCAtCcAA | 8 |
| 26_8 | GaAtattacaccatCCAA | 1 |
| 26_9 | GaAtAttacaccatCCAA | 1 |
| 26_10 | GaAtAttacacCATCcAA | 22 |
| 26_11 | GaATattacaccatCCAA | 1 |
| 26_12 | GaATattacaccaTCcAA | 2 |

TABLE 6-continued in vitro screening of anti-MAPT compounds

| CMP ID NO | Compound | % MAPT mRNA of control |
|---|---|---|
| 26_13 | GaATattacaccAtCCAA | 3 |
| 26_14 | GaATattacaccATCcAA | 3 |
| 26_15 | GaATattacacCAtcCAA | 1 |
| 26_16 | GAatattacaccAtCCAA | 0 |
| 26_17 | GAatattacaccATCcAA | 1 |
| 26_18 | GAatattacacCATCcAA | 8 |
| 26_19 | GAatAttacacCATCcAA | 22 |
| 26_20 | GAaTattacaccatcCAA | 1 |
| 26_21 | GAaTattacaccaTCcAA | 1 |
| 26_22 | GAaTattacaccAtcCAA | 4 |
| 26_23 | GAaTattacaccATCcAA | 5 |
| 26_24 | GAaTattacacCatcCAA | 9 |
| 26_25 | GAaTattacacCAtccAA | 2 |
| 26_26 | GAAtattacaccatCCAA | 3 |
| 26_27 | GAAtattacaccaTCcAA | 3 |
| 26_28 | GAAtattacacCAtCcAA | 5 |
| 26_29 | GAATattacaccatcCAA | 0 |
| 26_30 | GAATattacaccAtcCAA | 0 |
| 26_31 | GAATattacacCaTCcAA | 24 |
| 27_1 | AATAttacaccaTCCA | 0 |
| 28_1 | AgaaTattacaccatCCA | 1 |
| 28_2 | AgaaTattacaccaTcCA | 6 |
| 28_3 | AgaaTattacaccAtCCA | 1 |
| 28_4 | AgaaTattacaccATcCA | 5 |
| 28_5 | AgaAtattacaccatCCA | 5 |
| 28_6 | AgaAtattacaccaTCCA | 6 |
| 28_7 | AgaAtAttacaccaTcCA | 3 |
| 28_8 | AgaAtAttacacCatcCA | 4 |
| 28_9 | AgaATattacaccatcCA | 2 |
| 28_10 | AgaATattacaccAtcCA | 0 |
| 28_11 | AgAatattacaccaTCCA | 8 |
| 28_12 | AgAatattacaccAtCCA | 1 |
| 28_13 | AgAatattacacCAtcCA | 1 |
| 28_14 | AgAatAttacacCatcCA | 3 |
| 28_15 | AgAatAttacacCatCCA | 6 |
| 28_16 | AgAaTattacaccatcCA | 3 |
| 28_17 | AgAaTattacaccatCCA | 1 |
| 28_18 | AgAaTattacaccAtcCA | 3 |

TABLE 6-continued in vitro screening of anti-MAPT compounds

| CMP ID NO | Compound | % MAPT mRNA of control |
|---|---|---|
| 28_19 | AgAaTattacaccAtCCA | 0 |
| 28_20 | AgAaTattacacCatcCA | 6 |
| 28_21 | AgAaTattacaCcatcCA | 3 |
| 28_22 | AgAaTAttacacCatcCA | 5 |
| 28_23 | AgAAtattacaccatCCA | 0 |
| 28_24 | AgAATattacaccatcCA | 2 |
| 28_25 | AgAATattacaccAtcCA | 3 |
| 28_26 | AGaaTattacaccatcCA | 2 |
| 28_27 | AGaaTattacaccAtcCA | 1 |
| 28_28 | AGaAtattacaccatCCA | 1 |
| 28_29 | AGaATattacaccatcCA | 0 |
| 28_30 | AGaATattacaccAtcCA | 1 |
| 28_31 | AGAatattacaccAtcCA | 1 |
| 28_32 | AGAaTattacaccatcCA | 1 |
| 28_33 | AGAaTattacaccAtcCA | 5 |
| 29_1 | CagaaTattacaccaTcCA | 1 |
| 29_2 | CagaAtattacaccatCCA | 4 |
| 29_3 | CagaAtattacaCcatcCA | 15 |
| 29_4 | CagaATattacaccatcCA | 6 |
| 29_5 | CagaATattacaccAtcCA | 12 |
| 29_6 | CagaATattacacCatcCA | 3 |
| 29_7 | CagAaTattacaccatcCA | 2 |
| 29_8 | CagAaTattacaccAtcCA | 9 |
| 29_9 | CagAATattacaccatcCA | 0 |
| 29_10 | CaGaaTattacaccatcCA | 0 |
| 29_11 | CaGaaTattacaccAtcCA | 7 |
| 29_12 | CaGAatattacaccAtcCA | 4 |
| 29_13 | CAgAatattacaccAtcCA | 0 |
| 29_14 | CAgAatattacAccAtcCA | 2 |
| 30_1 | GaatattacacCAtCCA | 20 |
| 30_2 | GaatAttacaccaTCCA | 2 |
| 30_3 | GaaTattacaccatCCA | 1 |
| 30_4 | GaaTattacaccAtCCA | 1 |
| 30_5 | GaAtattacaccatCCA | 0 |
| 30_6 | GaAtattacaccaTCCA | 1 |
| 30_7 | GaAtattacacCAtCCA | 4 |
| 30_8 | GaAtattacaCCatcCA | 2 |
| 30_9 | GaAtAttacacCATcCA | 20 |
| 30_10 | GaATattacaccatCCA | 1 |
| 30_11 | GaATattacaccAtCCA | 4 |
| 30_12 | GAatattacaccaTCCA | 1 |
| 30_13 | GAatattacaccAtCCA | 1 |
| 30_14 | GAatAttacaccatCCA | 2 |
| 30_15 | GAatAttacacCatcCA | 3 |
| 30_16 | GAaTattacaccatcCA | 5 |
| 30_17 | GAaTattacaccatCCA | 0 |
| 30_18 | GAaTattacaccAtcCA | 5 |
| 30_19 | GAaTattacaccAtCCA | 3 |
| 30_20 | GAaTattacacCAtcCA | 2 |
| 30_21 | GAaTattacaCcatcCA | 2 |
| 30_22 | GAAtattacaccatCCA | 4 |
| 30_23 | GAAtattacacCatcCA | 2 |
| 30_24 | GAATattacaccatcCA | 1 |
| 30_25 | GAATattacaccAtcCA | 3 |
| 31_1 | TcAgaaTattacaccatcCA | 10 |
| 31_2 | TcAgaaTattacaccAtcCA | 3 |
| 31_3 | TcAgaAtattacaccaTcCA | 7 |
| 32_1 | AgaaTattacaccaTCC | 1 |
| 32_2 | AgaaTattacaccATCC | 1 |
| 32_3 | AgaaTAttacacCatCC | 0 |
| 32_4 | AgaAtattacaccaTCC | 5 |
| 32_5 | AgaAtattacACcAtCC | 39 |
| 32_6 | AgaAtAttacacCatCC | 7 |
| 32_7 | AgaATattacaccaTCC | 1 |
| 32_8 | AgaATattacaccAtCC | 0 |
| 32_9 | AgaATattacaccATCC | 1 |
| 32_10 | AgAatattacaccaTCC | 1 |
| 32_11 | AgAatattacaccATCC | 5 |
| 32_12 | AgAatattacaCcAtCC | 5 |
| 32_13 | AgAatattacaCcATCC | 15 |
| 32_14 | AgAatattacAccaTCC | 3 |
| 32_15 | AgAatattacACcatCC | 0 |
| 32_16 | AgAatattacACCatCC | 18 |
| 32_17 | AgAaTattacaccaTCC | 4 |
| 32_18 | AgAaTattacaccAtCC | 3 |

TABLE 6-continued in vitro screening of anti-MAPT compounds

| CMP ID NO | Compound | % MAPT mRNA of control |
|---|---|---|
| 32_19 | AgAaTattacaccATCC | 3 |
| 32_20 | AgAaTattacacCatCC | 10 |
| 32_21 | AgAaTattacaCcAtCC | 18 |
| 32_22 | AgAAtattacaccaTCC | 5 |
| 32_23 | AgAAtattacaCCatCC | 6 |
| 32_24 | AgAAtattacAcCAtCC | 34 |
| 32_25 | AgAATattacaccatCC | 1 |
| 32_26 | AgAATattacaccaTCC | 1 |
| 32_27 | AgAATattacaccAtCC | 2 |
| 32_28 | AgAATattacaccATCC | 2 |
| 32_29 | AgAATattacaCcAtCC | 13 |
| 32_30 | AGaaTattacaccatCC | 5 |
| 32_31 | AGaaTattacaccaTCC | 0 |
| 32_32 | AGaaTattacaccAtCC | 4 |
| 32_33 | AGaaTattacaccATCC | 1 |
| 32_34 | AGaAtattacaccatCC | 2 |
| 32_35 | AGaAtattacaccaTCC | 1 |
| 32_36 | AGaAtattacacCaTCC | 4 |
| 32_37 | AGaAtattacAccATCC | 11 |
| 32_38 | AGaATattacaccatCC | 0 |
| 32_39 | AGaATattacaccAtCC | 0 |
| 32_40 | AGAatattacaccaTCC | 4 |
| 32_41 | AGAatattacaccAtCC | 0 |
| 32_42 | AGAatattacAccaTCC | 2 |
| 32_43 | AGAatattacAccAtCC | 10 |
| 32_44 | AGAatattacAcCatCC | 12 |
| 32_45 | AGAatAttacaccatCC | 3 |
| 32_46 | AGAaTattacaccatCC | 1 |
| 32_47 | AGAaTattacaccAtCC | 1 |
| 32_48 | AGAAtattacaccatCC | 0 |
| 32_49 | AGAAtattacaccaTCC | 0 |
| 32_50 | AGAAtattacacCatCC | 0 |
| 32_51 | AGAAtattacAcCatCC | 5 |
| 33_1 | CagaaTattacaccaTCC | 7 |
| 33_2 | CagaAtattacaccaTCC | 55 |
| 33_3 | CagaAtattacaCcaTCC | 19 |
| 33_4 | CagaAtattacAccaTCC | 8 |

TABLE 6-continued in vitro screening of anti-MAPT compounds

| CMP ID NO | Compound | % MAPT mRNA of control |
|---|---|---|
| 33_5 | CagaAtattacACcatCC | 20 |
| 33_6 | CagaATattacaccatCC | 1 |
| 33_7 | CagaATattacaccaTCC | 2 |
| 33_8 | CagaATattacaccAtCC | 3 |
| 33_9 | CagAatattacaccaTCC | 1 |
| 33_10 | CagAatAttacaccaTCC | 10 |
| 33_11 | CagAaTattacaccaTCC | 0 |
| 33_12 | CagAAtattacaccaTCC | 11 |
| 33_13 | CagAAtattacacCaTCC | 4 |
| 33_14 | CagAATattacaCcatCC | 3 |
| 33_15 | CaGaatAttacacCAtCC | 5 |
| 33_16 | CaGaaTattacaccAtCC | 1 |
| 33_17 | CaGaAtattacaccatCC | 1 |
| 33_18 | CaGaAtattacaccaTCC | 14 |
| 33_19 | CaGaAtattacaCcatCC | 6 |
| 33_20 | CaGaAtattacACcAtCC | 53 |
| 33_21 | CaGAatattacaccAtCC | 0 |
| 33_22 | CAgaaTattacaccatCC | 0 |
| 33_23 | CAgaaTattacaccAtCC | 1 |
| 33_24 | CAgaAtattacaccatCC | 3 |
| 33_25 | CAgaAtattacaccaTCC | 61 |
| 33_26 | CAgaAtAttacacCatCC | 5 |
| 33_27 | CAgAatattacaccaTCC | 8 |
| 33_28 | CAgAatattacaccAtCC | 0 |
| 33_29 | CAgAaTattacaccatCC | 0 |
| 33_30 | CAgAaTattacaccAtCC | 1 |
| 33_31 | CAgAAtattacaccatCC | 13 |
| 33_32 | CAgAAtattacAccatCC | 1 |
| 33_33 | CAGaAtattacaccatCC | 10 |
| 34_1 | GAATattacaccATCC | 0 |
| 35_1 | TCagaaTattacaccatCC | 10 |
| 35_2 | TCagaAtattacaccatCC | 11 |
| 35_3 | TCagaAtattacAccatCC | 9 |
| 36_1 | AGAAtattacacCATC | 0 |
| 37_1 | CAGAatattacaCCAT | 0 |
| 38_1 | CAattctcatttcaacCTTC | 14 |
| 39_1 | TCaattctcatttcaacCTT | 35 |
| 40_1 | ATCaattctcatttcaacCT | 17 |

TABLE 6-continued in vitro screening of anti-MAPT compounds

| CMP ID NO | Compound | % MAPT mRNA of control |
|---|---|---|
| 41_1 | AATCaattctcatttcaACC | 28 |
| 42_1 | AAATcaattctcatttCAAC | 38 |
| 43_1 | CAAAtcaattctcattTCAA | 22 |
| 44_1 | TCAaatcaattctcatTTCA | 0 |
| 45_1 | CTCAaatcaattctcatTTC | 6 |
| 46_1 | ACTCaaatcaattctcATTT | 5 |
| 47_1 | AACTcaaatcaattctCATT | 37 |
| 48_1 | TAACtcaaatcaattcTCAT | 20 |
| 49_1 | TtaactCaaatcaattcTCA | 46 |
| 49_2 | TtaactCAaatcaattctCA | 35 |
| 49_3 | TtaactCAaatcaattcTCA | 9 |
| 49_4 | TtaacTCaaatcaattctCA | 33 |
| 49_5 | TtaacTCAaatcaattctCA | 6 |
| 49_6 | TtaaCtcaaatcaattCtCA | 63 |
| 49_7 | TtaaCtcaaatcaattCTCA | 18 |
| 49_8 | TtaaCtcaaatcaatTCtCA | 19 |
| 49_9 | TtaaCtcaaatcaaTtctCA | 80 |
| 49_10 | TtaaCtcaaatcaaTtcTCA | 26 |
| 49_11 | TtaaCtcaaatcaaTtCtCA | 30 |
| 49_12 | TtaaCtcaaatcaaTtCTCA | 18 |
| 49_13 | TtaaCtcaaatcaaTTCtCA | 32 |
| 49_14 | TtaaCtcaaatcAattcTCA | 22 |
| 49_15 | TtaaCtcAaatcaattcTCA | 20 |
| 49_16 | TtaaCtcAaatcaattCtCA | 28 |
| 49_17 | TtaaCtcAaatcaattCTCA | 7 |
| 49_18 | TtaaCtcAaatcaatTctCA | 19 |
| 49_19 | TtaaCtcAaatcaatTCtCA | 9 |
| 49_20 | TtaaCtcAaatcaaTtctCA | 33 |
| 49_21 | TtaaCtcAaatcaaTtcTCA | 13 |
| 49_22 | TtaaCtcAaatcaaTtCtCA | 16 |
| 49_23 | TtaaCtcAaatcaaTtCTCA | 12 |
| 49_24 | TtaaCtcAaatcaaTTCtCA | 19 |
| 49_25 | TtaaCtCaaatcaattctCA | 33 |
| 49_26 | TtaaCtCaaatcaattcTCA | 14 |
| 49_27 | TtaaCtCaaatcaattCtCA | 17 |
| 49_28 | TtaaCtCaaatcaattCTCA | 7 |
| 49_29 | TtaaCtCaaatcaatTCtCA | 7 |

TABLE 6-continued in vitro screening of anti-MAPT compounds

| CMP ID NO | Compound | % MAPT mRNA of control |
|---|---|---|
| 49_30 | TtaaCtCAaatcaattctCA | 7 |
| 49_32 | TtaaCtCAaatcaattCtCA | 10 |
| 49_33 | TtaaCtCAaatcaaTtctCA | 10 |
| 49_34 | TtaaCtCAaatcaaTtCtCA | 6 |
| 49_35 | TtaaCTCaaatcaattctCA | 10 |
| 49_36 | TtaaCTCaaatcaattCtCA | 7 |
| 49_37 | TtaaCTCAaatcaattctCA | 4 |
| 49_39 | TtaActcaaatcaatTCtCA | 24 |
| 49_40 | TtaActcaaatcaaTtCtCA | 26 |
| 49_41 | TtaActcaaatcaaTtCTCA | 17 |
| 49_42 | TtaActcAaatcaattCtCA | 33 |
| 49_43 | TtaActcAaatcaatTCtCA | 11 |
| 49_44 | TtaActcAaatcaaTtcTCA | 15 |
| 49_45 | TtaActcAaatcaaTtCtCA | 24 |
| 49_46 | TtaActCaaatcaattCtCA | 20 |
| 49_47 | TtaActCaaatcaattCTCA | 6 |
| 49_48 | TtaActCaaatcaatTCtCA | 6 |
| 49_49 | TtaActCAaatcaattctCA | 18 |
| 49_50 | TtaActCAaatcaattCtCA | 9 |
| 49_53 | TtaActCAaatcaaTtctCA | 12 |
| 49_54 | TtaActCAaatcaaTtCtCA | 6 |
| 49_55 | TtaAcTCaaatcaattCtCA | 7 |
| 49_56 | TtaACtcaaatcaattCtCA | 30 |
| 49_57 | TtaACtcaaatcaattCTCA | 7 |
| 49_58 | TtaACtcaaatcaatTCtCA | 11 |
| 49_59 | TtaACtcaaatcaaTtctCA | 47 |
| 49_60 | TtaACtcaaatcaaTtCtCA | 18 |
| 49_61 | TtaACtcaaatcaaTtCTCA | 9 |
| 49_62 | TtaACtcaaatcaaTTCtCA | 17 |
| 49_63 | TtaACtcaaatcAattctCA | 40 |
| 49_64 | TtaACtcAaatcaattctCA | 23 |
| 49_65 | TtaACtcAaatcaattCtCA | 13 |
| 49_67 | TtaACtcAaatcaatTCtCA | 4 |
| 49_68 | TtaACtcAaatcaaTtctCA | 19 |
| 49_69 | TtaACtcAaatcaaTtCtCA | 12 |
| 49_70 | TtaACtcAaatcaaTtCTCA | 9 |
| 49_71 | TtaACtcAaatcaaTTCtCA | 16 |
| 49_72 | TtaACtCaaatcaattctCA | 12 |

TABLE 6-continued in vitro screening of anti-MAPT compounds

| CMP ID NO | Compound | % MAPT mRNA of control |
|---|---|---|
| 49_73 | TtaACtCaaatcaattCtCA | 9 |
| 49_74 | TtaACtCaaatcaattCTCA | 4 |
| 49_75 | TtaACtCaaatcaatTCtCA | 4 |
| 49_76 | TtaACtCAaatcaattctCA | 3 |
| 49_78 | TtaACtCAaatcaaTtctCA | 3 |
| 49_79 | TtaACTCaaatcaattCtCA | 6 |
| 49_80 | TtAactcaaatcaaTtCtCA | 11 |
| 49_81 | TtAactcaaatcaAttCtCA | 35 |
| 49_82 | TtAactcaaatcaAtTCtCA | 18 |
| 49_83 | TtAactcaaatcaATtCtCA | 21 |
| 49_84 | TtAactcaaatcaATTCtCA | 36 |
| 49_85 | TtAactcAaatcaatTCtCA | 7 |
| 49_86 | TtAactcAaatcaaTtCtCA | 6 |
| 49_87 | TtAactCaaatcaattCtCA | 19 |
| 49_88 | TtAactCaaatcaattCTCA | 7 |
| 49_89 | TtAactCaaatcaatTCtCA | 6 |
| 49_90 | TtAactCAaatcaattCtCA | 9 |
| 49_92 | TtAactCAaatcaaTtCtCA | 3 |
| 49_93 | TtAactCAaatcaaTTCtCA | 11 |
| 49_94 | TtAaCtcaaatcaattCtCA | 34 |
| 49_95 | TtAaCtcaaatcaatTCtCA | 11 |
| 49_96 | TtAaCtcaaatcaaTtctCA | 56 |
| 49_97 | TtAaCtcaaatcaaTtCtCA | 15 |
| 49_98 | TtAaCtcaaatcaaTtCTCA | 14 |
| 49_99 | TtAaCtcaaatcaaTTCtCA | 30 |
| 49_100 | TtAaCtcaaatcAattctCA | 46 |
| 49_101 | TtAaCtcAaatcaattctCA | 24 |
| 49_102 | TtAaCtcAaatcaattCtCA | 22 |
| 49_103 | TtAaCtcAaatcaattCTCA | 8 |
| 49_104 | TtAaCtcAaatcaatTCtCA | 6 |
| 49_105 | TtAaCtcAaatcaaTtctCA | 28 |
| 49_106 | TtAaCtcAaatcaaTtCtCA | 31 |
| 49_107 | TtAaCtcAaatcaaTtCTCA | 29 |
| 49_108 | TtAaCtcAaatcaaTTCtCA | 38 |
| 49_109 | TtAaCtCaaatcaattctCA | 21 |
| 49_110 | TtAaCtCaaatcaattCtCA | 19 |
| 49_111 | TtAaCtCaaatcaatTCtCA | 9 |
| 49_112 | TtAaCtCAaatcaattctCA | 10 |
| 49_113 | TtAaCtCAaatcaattCtCA | 10 |
| 49_114 | TtAaCtCAaatcaaTtctCA | 6 |
| 49_115 | TtAActcaaatcaatTCtCA | 6 |
| 49_116 | TtAActcaaatcaaTtCtCA | 9 |
| 49_117 | TtAActcAaatcaattCtCA | 11 |
| 49_118 | TtAActcAaatcaatTCtCA | 3 |
| 49_119 | TtAActcAaatcaaTtCtCA | 11 |
| 49_120 | TtAActCaaatcaattCtCA | 33 |
| 49_121 | TtAActCaaatcaatTCtCA | 2 |
| 49_123 | TtAActCAaatcaatTCtCA | 1 |
| 49_125 | TtAACtcaaatcaattCtCA | 6 |
| 49_126 | TtAACtcaaatcaattCTCA | 5 |
| 49_127 | TtAACtcaaatcaatTCtCA | 9 |
| 49_128 | TtAACtcaaatcaaTtctCA | 33 |
| 49_129 | TtAACtcaaatcaaTtCtCA | 12 |
| 49_130 | TtAACtcaaatcaaTTCtCA | 19 |
| 49_131 | TtAACtcaaatcAattctCA | 25 |
| 49_132 | TtAACtcAaatcaattctCA | 15 |
| 49_133 | TtAACtcAaatcaattCtCA | 6 |
| 49_134 | TtAACtcAaatcaatTCtCA | 10 |
| 49_135 | TtAACtcAaatcaaTtctCA | 15 |
| 49_136 | TtAACtcAaatcaaTtCtCA | 22 |
| 49_137 | TtAACtcAaatcaaTTCtCA | 33 |
| 49_138 | TtAACtCaaatcaattctCA | 8 |
| 49_139 | TtAACtCaaatcaattCtCA | 6 |
| 49_141 | TtAACtCaaatcaatTCtCA | 11 |
| 49_143 | TtAACtCAaatcaaTtctCA | 3 |
| 49_144 | TTaactcAaatcaattCtCA | 14 |
| 49_145 | TTaactcAaatcaatTCtCA | 6 |
| 49_146 | TTaactcAaatcaaTtCtCA | 6 |
| 49_147 | TTaactcAaatcaaTTCtCA | 9 |
| 49_148 | TTaactCAaatcaattCtCA | 6 |
| 49_149 | TTaactCAaatcaatTCtCA | 2 |
| 49_150 | TTaaCtcaaatcaattCtCA | 26 |
| 49_151 | TTaaCtcaaatcaattCTCA | 8 |
| 49_152 | TTaaCtcaaatcaatTCtCA | 11 |
| 49_153 | TTaaCtcaaatcaaTtctCA | 41 |

TABLE 6-continued in vitro screening of anti-MAPT compounds

| CMP ID NO | Compound | % MAPT mRNA of control |
|---|---|---|
| 49_154 | TTaaCtcaaatcaaTtCtCA | 14 |
| 49_155 | TTaaCtcaaatcAattctCA | 38 |
| 49_156 | TTaaCtcAaatcaattctCA | 23 |
| 49_157 | TTaaCtcAaatcaattCtCA | 13 |
| 49_158 | TTaaCtcAaatcaattCTCA | 4 |
| 49_159 | TTaaCtcAaatcaatTCtCA | 6 |
| 49_160 | TTaaCtcAaatcaaTtctCA | 20 |
| 49_161 | TTaaCtcAaatcaaTtCtCA | 12 |
| 49_162 | TTaaCtCaaatcaattctCA | 18 |
| 49_163 | TTaaCtCaaatcaattCtCA | 10 |
| 49_164 | TTaaCtCAaatcaattctCA | 7 |
| 49_166 | TTaActcaaatcaaTtCtCA | 17 |
| 49_167 | TTaActCaaatcaattCtCA | 7 |
| 49_168 | TTaActCAaatcaattCtCA | 3 |
| 49_169 | TTaACtcaaatcaaTtCtCA | 12 |
| 49_170 | TTaACtcAaatcaatTCtCA | 9 |
| 49_171 | TTaACtcAaatcaaTtCtCA | 25 |
| 49_172 | TTAactcaaatcaaTtCtCA | 16 |
| 49_173 | TTAactcaaatcaAttCtCA | 27 |
| 49_174 | TTAactcaaatcaAtTCtCA | 14 |
| 49_175 | TTAactcAaatcaatTCtCA | 5 |
| 49_176 | TTAactcAaatcaaTtCtCA | 6 |
| 49_177 | TTAactCaaatcaattCtCA | 15 |
| 49_178 | TTAactCaaatcaattCTCA | 4 |
| 49_180 | TTAactCAaatcaattCtCA | 6 |
| 49_181 | TTAaCtcaaatcaattCtCA | 23 |
| 49_182 | TTAaCtcaaatcaaTtctCA | 38 |
| 49_183 | TTAaCtcaaatcaaTtCtCA | 17 |
| 49_184 | TTAaCtcaaatcAattctCA | 40 |
| 49_185 | TTAaCtcAaatcaattctCA | 19 |
| 49_186 | TTAaCtcAaatcaattCtCA | 13 |
| 49_187 | TTAaCtcAaatcaaTtctCA | 13 |
| 49_188 | TTAaCtCaaatcaattctCA | 18 |
| 49_189 | TTAActcaaatcaattCTCA | 3 |
| 49_190 | TTAActcaaatcaatTCtCA | 9 |
| 49_191 | TTAActcAaatcaatTCtCA | 3 |
| 49_192 | TTAActCaaatcaattCtCA | 6 |

TABLE 6-continued in vitro screening of anti-MAPT compounds

| CMP ID NO | Compound | % MAPT mRNA of control |
|---|---|---|
| 50_1 | TTTAactcaaatcaatTCTC | 1 |
| 51_1 | TTTAactcaaatcaaTTCT | 10 |
| 52_1 | CCTTttaattcaTTAG | 72 |
| 53_1 | CAACacctttttaattcATTA | 0 |
| 54_1 | AACAcctttttaattCATT | 27 |
| 55_1 | CAtcaacacctttttaaTTCA | 100 |
| 56_1 | CTCAtcaacacctttttaaTT | 15 |
| 57_1 | ACtcatcaacacctttTAAT | 37 |
| 58_1 | AACtcatcaacaccttTTAA | 16 |
| 59_1 | TAACtcatcaacacctttTA | 18 |
| 60_1 | TTAActcatcaacacctTTT | 12 |
| 61_1 | TTAactcatcaacacCTTT | 4 |
| 62_1 | TTAactcatcaacaCCTT | 3 |
| 63_1 | TTAActcatcaacACCT | 0 |
| 64_1 | GTTAactcatcaacACC | 29 |
| 65_1 | GTTAactcatcaaCAC | 78 |

Example 3: IC50 Values of Selected Oligonucleotides

The IC50 of some of the best performing oligonucleotides from Example 2 was determined in vitro in primary neuronal cells using a 96 well assay.

Primary neuronal cell cultures were prepared as described in the "Materials and Method" section and plated on poly-D-lysine coated 96 well plates at 50,000 cells per well and maintained in Neurobasal media containing B27, glutamax and Penicillin-Streptomycin. ASOs were diluted in water (for IC50 determinations) and added to cells at 1 day post plating (DIV01). For IC50 determinations, neurons were treated with a top concentration of 0.5 to 5 μM and a concentration response dilution of about 1:4 was used to define the IC50. CMP ID NO: 66_1, corresponding to ASO-001933 in WO2016/126995, was included as a positive control. Following ASO treatment, neurons were incubated at 37° C. for 5 days to achieve steady state reduction of mRNA. Media was removed and cells lysed as follows. Measurement of lysate messenger RNA was performed using the QUANTIGENE® 2.0 Reagent System (AFFYMETRIX®), which quantitated RNA using a branched DNA-signal amplification method reliant on the specifically designed RNA capture probe set. The working cell lysis buffer solution was made by adding 50 μl proteinase K to 5 ml of pre-warmed Lysis mix and diluted to 1:4 final dilution with $dH_2O$. The working lysis buffer was added to the plate (150 μl/well), triturated to mix, sealed and incubated for 30 min at 55° C. Following lysis the wells were stored at −80° C. or assayed immediately.

Lysates were diluted in lysis mix dependent on the specific capture probe used (tau or tubulin). 80 μl/well total were then added to the capture plate (96 well polystyrene plate coated with capture probes). Working probe sets reagents were generated by combining nuclease-free water 12.1 μl, lysis mixture 6.6 μl, blocking reagent 1 μl, specific 2.0 probe set 0.3 μl human MAPT catalogue #15486 and either mouse beta 3 tubulin, catalogue #SB-17245, per manufacturer instructions (QUANTIGENE® 2.0 AFFYMETRIX®). Then 20 μl working probe set reagents were added to 80 μl lysate dilution (or 80 μl lysis mix for background samples) on the capture plate. Plates were centrifuged and then incubated for 16-20 hours at 55° C. to hybridize (target RNA capture). Signal amplification and detection of target RNA was begun by washing plates with buffer 3 times to remove unbound material. 2.0 Pre-Amplifier hybridization reagent (100 μl/well) was added, incubated at 55° C. for 1 hour then aspirated and wash buffer was added and aspirated 3 times. The 2.0 Amplifier hybridization reagent was then added as described (100 μl/well), incubated for 1 hour at 55° C. and the wash was repeated as described previously. The 2.0 Label Probe hybridization reagent was added next (100 μl/well), incubated for 1 hour at 50° C. and the wash was repeated as described previously. Lastly, the plates were centrifuged to remove any excess wash buffer and 2.0 Substrate was added (100 μl/well). Plates were incubated for 5 minutes at room temperature and plates were imaged on a PerkinElmer Envision multilabel reader in luminometer mode within 15 minutes.

Data determination: For the gene of interest, the average assay background signal was subtracted from the average signal of each technical replicate. The background-subtracted, average signals for the gene of interest are divided by the background-subtracted average signal for the housekeeping tubulin RNA. The percent inhibition for the treated sample was calculated relative to untreated sample (i.e. the lower the value the larger the inhibition). Variability in background of untreated samples may result in percent inhibition of a treated sample that are equal to or higher than background, and in these cases, percent inhibition is expressed as 100% inhibition of control (i.e. no inhibition). The results are shown in table 7.

TABLE 7

IC50 of anti-MAPT compounds

| CMP ID NO | Compound | Region | IC50 (nM) |
|---|---|---|---|
| 9_103 | CTTTaatttaatcacTCAT | A | 12.2 |
| 11_1 | CTTTaatttaatcaCTCA | A | 9.4 |
| 34_1 | GAATattacaccATCC | A | 32.0 |
| 37_1 | CAGAatattacaCCAT | A | 15.6 |
| 49_189 | TTAActcaaatcaattCTCA | B | 11.8 |
| 56_1 | CTCAtcaacaccttttaaTT | C | 44.0 |
| 62_1 | TTAactcatcaacaCCTT | C | 40.5 |
| 63_1 | TTAActcatcaacACCT | C | 37.1 |
| 66_1 | AtTTCcaaattcactTTtAC | — | 44.3 |

Example 4: In Vivo Tolerability and In Vivo Tau mRNA Reduction

Some of the best performing oligonucleotides from Example 2 were tested in vivo in a humanized Tau mouse to assess acute tolerability in CNS as well as MAPT mRNA reduction 3 days or 28 days after a single injection.

Transgenic Tau mice were administered with 100 μg ASO by intracerebroventricular (ICV) injection (see Materials and Method section, Transgenic Tau mouse). CMP ID NO: 66_1, corresponding to ASO-001933 in WO2016/126995, was included as a positive control. Animals were observed for behavioral side effects for one hour following the single injection of ASO ICV. The acute tolerability for the severity of side effects was scored on a scale of zero (no side effects) to 20 (convulsions resulting in euthanasia). The tolerability scale was divided into 5 neurobehavioral categories: 1) hyperactivity 2) decreased activity and arousal 3) motor dysfunction/ataxia 4) abnormal posture and breathing and 5) tremor/convulsions. Each category was scored on a scale of 0-4, with the worst possible total score of 20. Animals were observed for changes in behavior in the home cage, and then they were removed from the home cage for more detailed observations which included measurement of grip strength and righting reflex. Data from acute tolerability of ASO of the invention are presented in table 8.

The MAPT mRNA reduction in right, frontal cortical region was analyzed by qPCR as follows. Collected mouse brain tissue (see Materials and Methods section, Transgenic Tau mouse) was homogenized in a 10×volume of a high salt/sucrose buffer (10 mM Tris-HCl, pH 7.4, 800 mM NaCl, 10% sucrose (w/v), 1 mM EGTA) supplemented with phosphatase inhibitor cocktail sets 2 and 3, 1 mM PMSF (Sigma, Saint Louis, Mo.), and complete protease inhibitor cocktail EDTA-free (Roche, Indianapolis, Ind.) using a Quiagen TissueLyzer II. The homogenate was centrifuged at 20,000×g for 20 minutes at 4° C. The supernatant was centrifuged at 100,000×g for 1 hour at 4° C.

For cDNA synthesis and subsequent PCR, 300 ng of RNA from brain tissue supernatants was added to 1 well of a 96 well plate (Axygen, PCR-96-C-S). To each well 7.5 μl of master mix (5 μL of 2.5 mM NTP mix and 2.5 μL random primers per reaction) was added and the plate was centrifuged at 1000 rpm and placed in thermocycler for 3 min at 70° C. Plates were immediately cooled on ice and 4 μl of reaction master mix was added. Prior to PCR, plates were briefly centrifuged to collect sample in bottom of well. cDNA synthesis was carried out at 42° C. for 60 min, 95° C. for 10 min followed by a hold at 4° C. cDNA Samples were diluted 1:3 with molecular biology grade water and stored at −20° C. until further use.

For PCR, each sample was run in triplicate with two probe sets (MAPT: Taqman Expression assays Hs00902193_m1; GAPDH Taqman Expression assays Hs01922876_u1). To each reaction 4 μl of previously diluted cDNA and 6 μL of master mix was added and plates were centrifuged. Samples were incubated at 95° C. for 20 sec follow by 40 cycles at 95° C. for 1 sec and 60° C. for 20 sec.

Data were analyzed using the delta delta Ct method where each sample was first normalized to GAPDH and then expressed as percent of untreated control (percent inhibition). If the percent inhibition was equal to or higher than in control cells, percent inhibition was expressed as zero inhibition.

TABLE 8

Acute tolerability in hTau mice and MAPT mRNA reduction 3 days and 4 weeks post treatment in vivo

| CMP ID NO | Compound | Region | Acute tolerability | % MAPT mRNA of saline Day 3 | % MAPT mRNA of saline 4 weeks |
|---|---|---|---|---|---|
| 9_103 | CTTTaatttaatcacTCAT | A | 0.5 | 16 | 16 |
| 11_1 | CTTTaatttaatcaCTCA | A | 0.0 | 16 | 18 |
| 9_104 | CTTTaatttaatcaCtCAT | A | 0.25 | NA | 28 |
| 9_102 | CTTtAATttaatcactcAT | A | 1.75 | NA | 20 |
| 34_1 | GAATattacaccATCC | A | 0.0 | 36 | 20 |
| 9_91 | CTtTAatttaatcaCtCAT | A | 0.50 | NA | 84 |
| 9_83 | CTttAATttaatcacTCAT | A | 0.75 | NA | 31 |
| 9_17 | CtttaATttaatcacTCAT | A | 0.50 | NA | 65 |
| 9_88 | CTtTAatttaatcactCAT | A | 0.50 | NA | 43 |
| 9_96 | CTTtaATttaatcactcAT | A | 2.50 | NA | 54 |
| 9_95 | CTtTAATttaatcactcAT | A | 4.13 | NA | 34 |
| 9_93 | CTtTAAtttaatcactcAT | A | 1.88 | NA | 52 |
| 9_87 | CTtTaATttaatcactcAT | A | 1.63 | NA | 46 |
| 9_55 | CtTTAaTttaatcactcAT | A | 2.50 | NA | 54 |
| 37_1 | CAGAatattacaCCAT | A | 0.0 | 27 | NA |
| 49_189 | TTAActcaaatcaattCTCA | B | 0.0 | 29 | 29 |
| 49_38 | TtaaCTCAaatcaaTtctCA | B | 1.50 | NA | 18 |
| 49_179 | TTAactCaaatcaatTCtCA | B | 1.0 | NA | 32 |
| 49_51 | TtaActCAaatcaattCTCA | B | 1.25 | NA | 31 |
| 49_124 | TtAActCAaatcaaTtCtCA | B | 1.50 | NA | 48 |
| 49_165 | TTaaCtCAaatcaaTtctCA | B | 0.88 | NA | 44 |
| 49_91 | TtAactCAaatcaatTCtCA | B | 0.63 | NA | 60 |
| 49_52 | TtaActCAaatcaatTCtCA | B | 2.88 | NA | 56 |
| 49_140 | TtAACtCaaatcaattCTCA | B | 0.25 | NA | 43 |
| 49_66 | TtaACtcAaatcaattCTCA | B | 0.0 | NA | 36 |
| 49_142 | TtAACtCAaatcaattCtCA | B | 0.5 | NA | 36 |
| 49_122 | TtAActCAaatcaattCtCA | B | 0.75 | NA | 56 |
| 49_77 | TtaACtCAaatcaattCtCA | B | 1.13 | NA | 55 |
| 50_1 | TTTAactcaaatcaatTCTC | B | NA | 26 | NA |
| 53_1 | CAACaccttttaattcATTA | C | NA | 21 | NA |
| 56_1 | CTCAtcaacaccttttaaTT | C | 0.2 | 25 | NA |
| 62_1 | TTAactcatcaacaCCIT | C | 0.0 | 39 | 28 |
| 63_1 | TTAActcatcaacACCT | C | 0.5 | 13 | NA |
| 66_1 | AtTTCcaaattcactTTtAC | — | 0.83 | 37 | 44 |

NA = not assessed

Example 5: In Vitro Efficacy in Human Embryonic Stem Cell (hESC) Derived Neurons Selected ASO's from example 2 were tested at three different concentrations (200 nM, 8 nM and 0.32 nM) in an alternative in vitro assay using human embryonic stem cell (hESC) derived neurons. For comparative purposes two prior art oligonucleotides targeting MAPT were included, namely CMP ID NO: 66_1 corresponding to ASO-001933 in WO2016/126995 and CPM ID NO: 67:1 corresponding to compound No 814907 in WO2018/064593.

Culturing and ASO Treatment of Human Embryonic Stem Cells (ESCs):

Neural stem cells (NSCs) were derived from human ESCs according to published procedures (Chambers et al. 2009 Nat. Biotech. 7, 275-280). The neural stem cells (NSCs) were proliferated into ventralized progenitors during 1 week in SFA medium, and was then differentiated into neurons in BGAA medium during 6 weeks, for media content, please see the Materials and methods section.

Cells were seeded at a density of 10,000 cells/$cm^2$ in N2B27+SFA medium in a flask coated with poly-ornithine and laminin. Media was changed at day 4. After 7 days in N2B27+SFA medium cells were trypsinized, and seeded as ventralized progenitors in N2B27+BGAA media at a density of 50,000 cell/well in 96 well plates.

Media was changed twice a week and treatment with ASO was started at the first media change and continued for 6 weeks. Then cells were harvested as described below.

gPCR Analysis:

Treated neurons were harvested as follows: removal of media followed by addition of 125 μL PURELINK®Pro 96 Lysis buffer and 125 μl . . . 70% ethanol. RNA was purified according to the manufacture's instruction and eluted in a final volume of 50 μL water, resulting in an RNA concentration of 10-20 ng/μL. Next, RNA was diluted 10 fold in water prior to the one-step qPCR reaction.

For the one-step qPCR reaction, qPCR-mix (qScriptTMXLE 1-step RT-qPCR TOUGHMIX®Low ROX from QauntaBio) was mixed with two Taqman probes at a ratio 10:1:1 (qPCR mix: probe1:probe2) to generate the mastermix. The qPCR was performed as technical replicates and Taqman probes were acquired from LifeTechnologies: MAPT_Hs00902193_m1; GAPDH 4325792 (house keeping gene used for normalization).

The mastermix (6 μL) and RNA (4 μL, 1-2 ng/μL) were then mixed in a qPCR plate (MICROAMP®optical 384 well, catalog no. 4309849). After sealing the plate, the plate was given a quick spin, 1000 g for 1 minute at RT, and transferred to a Viia™ 7 system (Applied Biosystems, Thermo). The following PCR conditions were used: 50° C. for 15 minutes; 95° C. for 3 minutes; 40 cycles of: 95° C. for 5 sec, followed by a temperature decrease of 1.6° C./sec, followed by 60° C. for 45 sec. The data was analyzed using the QuantStudio™ Real_time PCR Software. The percent inhibition for the ASO treated samples was calculated relative to the control treated samples (low values indicate high reduction of MAPT). The results are shown in table 9 as the average of the two technical repeats.

Tau Protein and pTau Protein Measurement in hESC Neurons:

PBS-washed cells were extracted into a buffer containing Cytobuster protein extraction reagent (Merck-Millipore #71009), 1% Phosphatase Inhibitor Cocktail 3 (Sigma #P0044), 1% Proteases Inhibitor Set III (Calbiochem #539134), 1% DNAse-I (Roche #4536282001) and 10 mM $MgCl_2$. The cell extract was lysed by pipetting up and down and then stored at −20° C. until use.

Total Tau levels in the cell extracts were measured by AlphaLISA using an in house assay format comprising the Tau-specific antibodies 5A6 (DSHB Antibody Registry ID: AB_528487) and Roche in house Tau monoclonal antibody Tau 4/2. The latter antibody was generated by immunizing mice with human full-length Tau i.e. longest human brain isoform, 441 amino acids. Tau 4/2 binds to an C-terminal epitope in Tau located between amino acids 369 and 441. Briefly, cell extracts were diluted into AlphaLISA Hi Block assay buffer (PerkinElmer AL004C) and mixed with biotinylated 5A6 and Tau 4/2-coated AlphaLISa acceptor beads. After incubation for 1 hr at room temperature, streptavidin-coated donor beads are added to the mixture. After incubation for 30 min, the samples were measured in an Envision plate reader (ex 680 nm, em 615 nm). A standard curve was constructed using recombinant human Tau (Merck-Millipore #AG960).

PhosphoTau (Tau-pS422) levels in the cell extracts were measured by AlphaLISA using the Roche in house assay format comprising Tau-specific antibody 5A6 (DSHB Antibody Registry ID: AB_528487) and Tau-pS422-specific antibody 5.6.11 (described in WO2010/142423 and Collin et al 2014 Brain vol 137 P 2834-2846). Cell extracts are diluted into assay buffer B before assay. Buffer B comprises 25 mM HEPES pH7.4, 0.5% Triton X-100, 0.1% Top Block (LuBio Science), 1 mg/ml Dextran500, 10% ELISA Blocking Reagent (Roche). A standard curve was prepared using ERK-phosphorylated Tau prepared as follows: recombinant human Tau was produced as described in Grueninger et al (Neurobiology of Disease 37 [2010] pp 294-306). Recombinant His-tagged ERK2 (produced in house) was activated by incubation with activated MEKK1 (produced in house). Activated ERK2 was then incubated with Tau at a molar ratio of 1:50 in buffer containing 2 mM ATP. ERk2 was subsequently removed by passage over Ni-NTA agarose (Qiagen). The extent of phosphorylation at S422 was subsequently determined by mass spectroscopy.

The results are shown in table 9.

TABLE 9

MAPT reduction and Tau protein reduction in hESC derived neurons following treatment at three different concentrations.

| CMP ID NO ASO conc | MAPT as % of control | | | Total Tau protein % of control | | | PhosphoTau protein % of control | | |
|---|---|---|---|---|---|---|---|---|---|
| (nM) | 200 | 8 | 0.32 | 200 | 8 | 0.32 | 200 | 8 | 0.32 |
| 9_104 | 5.4 | 36.6 | 100.9 | 7.0 | 40.3 | 88.3 | 0.6 | 12.0 | 54.0 |
| 9_103 | 1.2 | 15.6 | 71.8 | 1.8 | 23.2 | 66.2 | 0.1 | 19.8 | 92.9 |
| 11_1 | 1.0 | 12.5 | 72.3 | 1.5 | 25.9 | 65.1 | 0.1 | 17.5 | 70.4 |
| 49_38 | 5.7 | 36.3 | 83.5 | 6.8 | 45.5 | 79.6 | 1.3 | 51.6 | 116.6 |
| 49_189 | 7.0 | 36.5 | 90.2 | 10.4 | 48.1 | 102.9 | 5.0 | 59.6 | 137.3 |
| 53_1 | 4.8 | 32.9 | 79.4 | 8.8 | 45.7 | 79.0 | 3.1 | 48.6 | 127.6 |
| 66_1 | 11.0 | 40.2 | 81.9 | 10.9 | 48.4 | 69.9 | 3.6 | 57.9 | 94.2 |
| 9_102 | 2.0 | 34.9 | 99.0 | 3.0 | 44.3 | 87.4 | 0.3 | 37.7 | 113.8 |
| 49_179 | 10.5 | 53.6 | 96.4 | 12.4 | 70.7 | 91.7 | 3.5 | 76.0 | 112.0 |
| 49_51 | 6.7 | 39.8 | 76.1 | 5.9 | 60.2 | 92.2 | 1.3 | 68.2 | 161.6 |
| 56_1 | 2.8 | 36.8 | 93.2 | 3.6 | 49.3 | 96.6 | 0.3 | 37.9 | 111.9 |
| 62_1 | 4.5 | 38.6 | 86.2 | 5.8 | 48.4 | 88.1 | 1.5 | 47.8 | 119.0 |
| 67_1 | 31.1 | 57.0 | 86.0 | 35.9 | 58.4 | 79.2 | 26.2 | 65.8 | 115.5 |

Example 6: IC50 of Selected Compounds from Example 5

A selection of the efficacious ASO's from example 5 were tested in the same hESC derived neuron assay together with the two prior art controls (CMP ID 66_1 and CMP ID 67_1) to determine IC50 of the target mRNA reduction as well as the Tau protein reduction.

The experiment was conducted as described in example 5 using the following oligonucleotide concentrations: 1000, 200, 40, 8, 1.6, 0.32, 0.064, 0.0128, 0.00256 nM.

The IC50 values were fitted using the GraphPad PRISM software. The results are shown in table 10.

TABLE 10

IC50 and max efficacy (as % of control) with respect to MAPT and TAU protein

| CMP ID NO | Compound | IC50 MAPT (nM) | Max efficacy MAPT | IC50 TAU (nM) | Max efficacy MAPT |
|---|---|---|---|---|---|
| 9_103 | CTTTaatttaatcacTCAT | 2.0 | 0.6 | 1.4 | 1.1 |
| 49_38 | TtaaCTCAaatcaaTtctCA | 8.2 | 2.6 | 6.1 | 1.6 |
| 53_1 | CAACaccttttaattcATTA | 7.6 | 1.7 | 15.0 | 1.9 |
| 66_1 | AtTTCcaaattcactTTtAC | 9.7 | 8.1 | 11.8 | 4.9 |
| 67_1 | $\underline{CC_{O}GTTttcettacceeAC_{O}CCT}$ | 17.7 | 22.6 | 43.3 | 23.4 |

From these data it can be seen that CMP ID NO 9_103 and 49_38 of the invention are more efficacious and have a better IC50 than the prior art compounds on all parameter, whereas CMP ID NO 53_1 seems to have a better maximal knock-down than the prior art compounds and a similar IC50 as CMP ID NO: 66_1.

Example 7: In Vivo Activity in Specific Brain Regions of hTau Mouse

A selection of the ASO's from example 5 were tested for their ability to reduce the target in vivo in specific brain regions of a humanized Tau mouse (hTau mouse) four weeks after a single low dose ICV administration.

The humanized Tau mouse used in this example is an in house Roche hTau P301S transgenic mouse line which overexpresses human Tau (longest human brain isoform) with the point mutation P301S on a mouse Tau background.

Humanized Tau mice were administered with 25 μg ASO by intracerebroventricular (ICV) injection as described below. CMP ID NO: 66_1, corresponding to ASO-001933 in WO2016/126995, was included for comparative purposes.

In Vivo ICV Mouse Evaluation:

Animal Care:

Animals of mixed sex with a weight of 16-23-grams were held in colony rooms maintained at constant temperature (22±2° C.) and humidity (55±10%) and illuminated for 12 hours per day (lights on at 0600 hours). All animals had ad libitum access to food and water throughout the studies. All mouse protocols were approved by the Danish National Committee for Ethics in Animal Experiments.

Intra-Cerebroventricular Injections:

The compounds were administered to mice by intracerebroventricular (ICV) injections. 6-8 mice of mixed sexes were included in each treatment group. Prior to the ICV dosing, the mice were weighed and anaesthetized with isofluran or Propofol (30 mg/kg). Intracerebroventricular injections were performed using a Hamilton micro syringe with a FEP catheter fitted with a 23 gauge needle fixed in a stand adjusted to penetrate the correct distance (3.9 mm) through the skin and skull and into the right lateral ventricle. The mouse to be injected was held at the scruff of the neck with the thumb and first fingers of one hand. Applying gentle but firm pressure, the head was pressed upwards so that the needle pierced the skull 1-2 mm right of the midline (medio lateral) and 1-2 mm behind the eye. The 5 μl bolus of test compound or vehicle was injected over 30 seconds with a previously determined infusion rate. To avoid reflux the mouse was held in this position for another 5 seconds before carefully being pulled downwards, away from the needle. This procedure required no surgery or incision. Animals were placed under a heating lamp until they recovered from the procedure.

At study termination (4 weeks), brain tissue (cortex, medulla/pons and midbrain) was collected on dry ice for analysis of tau mRNA and protein.

Tissue Homogenization:

Mouse brain tissue samples were homogenized in the MagNA Pure LC RNA Isolation Tissue Lysis Buffer (Roche, Indianapolis, Ind.) using a Qiagen TissueLyzer II. The homogenates were incubated for 30 minutes at room temperature for complete lysis. After lysis the homogenates were centrifuged for 3 minutes at 13000 rpm and the supernatant used for analysis.

RNA Purification from Tissue:

RNA was purified from 350 μL of supernatant using the MagNA Pure 96 instrument using the kit Cellular RNA Large Volume Kit (Roche, Indianapolis, Ind.). RNA samples were normalized to 2 ng/μL in RNase-Free water and stored at −20° C. until further use. MAPT mRNA levels were quantified as described in example 5.

Tau Protein Measurement from Mouse Brain Tissue:

Pre-weighed frozen tissue was extracted with 10 volumes (wt/vol) of extraction buffer comprising 10 mM TrisCl pH 7.4, 800 mM NaCl, 1 mM EGTA, 10% sucrose, 1% Phosphatase Inhibitor Cocktail 3 (Sigma #P0044), 1% Proteases Inhibitor Set III (Calbiochem #539134). A homogenate was prepared using the PreCellys tissue disruptor (20 sec, 6500 rpm). The homogenate was then centrifuged at 10'000×g for 20 min at 4° C. and the supernatant retained for analysis.

Tau levels in the extracts were measured by AlphaLISA using the total Tau AlphaLISA kit supplied by Perkin Elmer (Cat. Nr. AL271C). The antibodies used in this assay were BT2 and Tau-12 provided with the kit, both of which bind to the central region of tau. Extracts were diluted into HiBlock assay buffer and 5 μl of each sample was then used in assay. The assay was otherwise performed as described by the supplier Results from mRNA and protein quantification are shown in table 11.

TABLE 11 in vivo efficacy in selected brain regions 4 weeks after a single ICV dose of 25 µg ASO. MAPT mRNA as % control are shown for four brain regions and Tau protein as % of control is shown for one brain region

| CMP ID | mRNA % ctrl | | | | | | | | Protein % ctrl | |
|---|---|---|---|---|---|---|---|---|---|---|
| | Cortex A1 | | Cortex A2 | | Medulla-Pons | | Midbrain | | Cortex B2 | |
| NO | Avg | Std | Avg | Std | Avg | Std | Avf | Std | Avg | Std |
| 9_104 | 74 | 12 | 77 | 14 | 68 | 19 | 65 | 18 | 73 | 18 |
| 9_103 | 80 | 13 | 80 | 10 | 66 | 17 | 64 | 12 | 69 | 16 |
| 11_1 | 58 | 12 | 62 | 15 | 54 | 16 | 48 | 19 | 63 | 11 |
| 49_38 | 63 | 12 | 67 | 9 | 55 | 18 | 49 | 16 | 76 | 15 |
| 49_189 | 75 | 5 | 70 | 10 | 54 | 4 | 55 | 6 | 84 | 13 |
| 53_1 | 80 | 10 | 93 | 7 | 81 | 12 | 81 | 16 | 101 | 11 |
| 66_1 | 94 | 20 | 98 | 6 | 101 | 4 | 99 | 11 | 112 | 8 |

From these data it can be observed that even at the fairly low concentration of 25 µg, reduction of more than 20% is seen in most brain regions for the compounds of the invention, where as the control compound show vertually no reduction of the target at this concentration.

Example 8: In Vivo Dose Response and Time Course in the hTau Mouse

The dose response of two ASO's (CMP ID NO: 9_103 and 49_189) was evaluated using three different doses (25, 50 and 100 µg) and target reduction was measure in specific brain regions 1 week and 4 weeks after administration. For comparative purposes two prior art compounds (CMP ID NO: 66_1_103 and 67_1) were included at some of the doses in the one-week study.

The experiment was essentially conducted as described in example 7. Tau protein was however not measured in the dose response study which was run for 1 week since the Tau protein has a half life beyond one week. The results are shown in Tables 12 and 13.

TABLE 12 in vivo efficacy in selected brain regions 1 week after a single ICV dose at 25 µg, 50 µg or 100 µg ASO or 4 weeks after a single ICV dose at 100 µg ASO. MAPT mRNA as % control are shown for four brain regions.

| Brain region | ASO conc µg | CMP ID NO Time | 9_103 | 49_38 | 66_1 | 67_1 | 9_103 | 49_38 |
|---|---|---|---|---|---|---|---|---|
| | | | 1 week | | | | 4 weeks | |
| Cortex A1 | 25 | Avg | 51 | 69 | NA | NA | NA | NA |
| | | Std | 13 | 8 | NA | NA | NA | NA |
| | 50 | Avg | 52 | 52 | 68 | NA | NA | NA |
| | | Std | 12 | 14 | 14 | NA | NA | NA |
| | 100 | Avg | 33 | 39 | 60 | 71 | 36 | 37 |
| | | Std | 10 | 24 | 12 | 25 | 17 | 26 |
| Cortex A2 | 25 | Avg | 73 | 59 | NA | NA | NA | NA |
| | | Std | 12 | 12 | NA | NA | NA | NA |
| | 50 | Avg | 68 | 39 | 73 | NA | NA | NA |
| | | Std | 15 | 7 | 8 | NA | NA | NA |
| | 100 | Avg | 42 | 43 | 77 | 63 | 51 | 46 |
| | | Std | 21 | 30 | 12 | 20 | 13 | 30 |
| Midbrain | 25 | Avg | 79 | 43 | NA | NA | NA | NA |
| | | Std | 20 | 4 | NA | NA | NA | NA |
| | 50 | Avg | 50 | 26 | 68 | NA | NA | NA |
| | | Std | 14 | 6 | 11 | NA | NA | NA |
| | 100 | Avg | 51 | 38 | 78 | 76 | 60 | 38 |
| | | Std | 29 | 31 | 21 | 27 | 28 | 35 |
| Medulla-Pons | 25 | Avg | 81 | 41 | | NA | NA | NA |
| | | Std | 21 | 6 | | NA | NA | NA |
| | 50 | Avg | 57 | 26 | 70 | NA | NA | NA |
| | | Std | 18 | 5 | 10 | NA | NA | NA |
| | 100 | Avg | 58 | 37 | 80 | 82 | 61 | 40 |
| | | Std | 34 | 31 | 23 | 28 | 29 | 33 |

NA = not assessed

TABLE 13 in vivo reduction of Tau protein as % of control 4 weeks after a single ICV dose at 100 μg ASO.

| Brain region | Cortex B1 | |
|---|---|---|
| CMP ID NO | Avg | Std |
| 9_103 | 56 | 18 |
| 49_38 | 43 | 35 |

From the data in table 12 and 13 it can be seen that the compounds of the invention perform significantly better than the prior art compounds, in particular when dosed at 100 μg. It can also be observed that the MAPT reduction is maintained over the 4 weeks. Furthermore, the compounds of the invention show a significant reduction of Tau protein after 4 weeks treatment with a single dose of 100 μg compound.

The invention claimed is:

1. An antisense oligonucleotide of formula CAACaccttt-taattcATTA (CMP ID NO: 53_1; SEQ ID NO: 53) or a pharmaceutically acceptable salt thereof, wherein capital letters are beta-D-oxy LNA nucleosides, lowercase letters are DNA nucleosides, all LNA C nucleobases are 5-methyl cytosine, and all internucleoside linkages are phosphorothioate internucleoside linkages.

2. The antisense oligonucleotide of claim 1, wherein the oligonucleotide is capable of reducing expression of Tau in a target cell and wherein the oligonucleotide is capable of recruiting RNase H.

3. A conjugate comprising the antisense oligonucleotide of claim 1 and at least one conjugate moiety covalently attached to the oligonucleotide.

4. A pharmaceutical composition comprising the antisense oligonucleotide of claim 1, and a pharmaceutically acceptable diluent, solvent, carrier, salt, and/or adjuvant.

5. An in vivo or in vitro method for modulating Tau expression in a target cell expressing Tau, the method comprising administering the antisense oligonucleotide of claim 1 in an effective amount to the target cell.

6. A method for treating a disease comprising administering a therapeutically effective amount of the antisense oligonucleotide of claim 1 to a subject suffering from or susceptible to the disease, wherein the disease is Alzheimer's disease (AD), progressive supranuclear palsy (PSP), frontotemporal dementia (FTD), or FTD with parkinsonism linked to chromosome 17 (FTDP-17).

7. The method of claim 6, wherein the disease is progressive supranuclear palsy (PSP).

8. The method of claim 6, wherein the disease is Alzheimer's disease (AD).

* * * * *

UNITED STATES PATENT AND TRADEMARK OFFICE

CERTIFICATE OF CORRECTION

PATENT NO. : 11,753,640 B2
APPLICATION NO. : 17/139161
DATED : September 12, 2023
INVENTOR(S) : Hagedorn et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 133 days.

Signed and Sealed this
First Day of July, 2025

Coke Morgan Stewart
*Acting Director of the United States Patent and Trademark Office*

SEQUENCE LISTING

```
<160> NUMBER OF SEQ ID NOS: 67

<210> SEQ ID NO 1
<211> LENGTH: 134004
<212> TYPE: DNA
<213> ORGANISM: Homo sapiens

<400> SEQUENCE: 1

acggccgagc ggcagggcgc tcgcgcgcgc ccactagtgg ccggaggaga aggctcccgc     60

ggaggccgcg ctgcccgccc cctcccctgg ggaggctcgc gttcccgctg ctcgcgcctg    120

cgccgcccgc cggcctcagg aacgcgccct cttcgccggc gcgcgccctc gcagtcaccg    180

ccacccacca gctccggcac caacagcagc gccgctgcca ccgcccacct tctgccgccg    240

ccaccacagc caccttctcc tcctccgctg tcctctcccg tcctcgcctc tgtcgactat    300

caggtaagcg ccgcggctcc gaaatctgcc tcgccgtccg cctctgtgca cccctgcgcc    360

gccgcccctc gccctccctc tccgcagact ggggcttcgt gcgccgggca tcggtcgggg    420

ccaccgcagg gcccctccct gcctcccctg ctcgggggct ggggccaggg cggcctggaa    480

agggacctga gcaagggatg cacgcacgcg tgagtgcgcg cgtgtgtgtg tgctggaggg    540

tcttcaccac cagattcgcg cagaccccag gtggaggctg tgccggcagg gtggggcgcg    600

gcggcggtga cttgggggag gggctgccc ttcactctcg actgcagcct tttgccgcaa    660

tgggcgtgtg tgtgtgtgtg tgtgtgtgtg tgtgtgtgtg tgtgtgtgtg gaggggtccg    720

ataacgaccc ccgaaaccga atctgaaatc cgctgtccct gccgctgttc gccatcagct    780

ctaagaaaga cgtggatcgg gttctagaaa agatgactcc ctgcacgccc ctccctgcac    840

ctcccgagca gtgattccga cagggccttc actgcccctg attttaggcg ggggccggcc    900

ccctcccctt ttcctccttc agaaacccgt aggggacatt tgggggctgg gagaaatcga    960

ggagatgggg aggggtccac gcgctgtcac tttagttgcc cttccccctg cgcacgcctg   1020

gcacagagac gcgagcagcg ccgtgcctga gaacagtgcg cggatcccac tgtgcacgct   1080

cgcaaaggca gggttcacct ggcctggcga tgtggacgga ctcggcggcc gctggtcccc   1140

gttcgcgggc acgcacagcc gcagccacgc acggatgggc gcggggctgc aggtgcatct   1200

cggggcggat ttctttctca gcgctcggag cgcagggcgc ccggcgtgtg cgctccctgc   1260

cggaggcgcg gggctggcgc gcagggctcg cccctcactg cggcagtggg tgtggaccct   1320

ggtgggcgag gaagggggag gataggctgt gcctcctccc actcccgccc ccagcccccc   1380
```

-continued

```
ttttttttccc cctcggaacg cgaggtgcca tcttttttcg gcgtgtcacg tctttacggt 1440
gccatgccaa accgggtggc cgggcttcat aggacagggc ggggcctggc attaaaggga 1500
gggggacaat cagcgctgaa atcttggcgt tttgctgctg cgggcgtgag cactgggggc 1560
gttcgcccag caccttcttc gggggctctt tgctttgtct gtagaggtta cgtgatctgc 1620
gctcccagcc ctggtttctg gcttttattc tgagggtgtt cagtcaacct ccccccctacg 1680
cccatgcgcc tctctttcct ttttcgctcc tcatttccga gcccattgtt ggatctcgag 1740
gcttgctggg ttcgatgaac tcgagtcaac cccccgaccc ccggcacgca tggaacgggc 1800
gtgaccgcgc gcagcctcgt ctcggagtct gccggcgccg ggaagcttct gaagggatgg 1860
gattcgagtc tccgtgcgcg ctgcgggcgg cggcagaggg atctcgcccc tccctacacc 1920
ccaagtgtcc tgagggccac gccacaccag gttgcccagc gagggacgct ggctacccat 1980
ccggggatgg gtggggagcc ctggcggggc ctctccggct ttacgccctg ttgcttcgcc 2040
tggccggaga atgtgaggaa ggggcataag gttactggtg cttcggccac acccatcttt 2100
ctgagcccac tggactgggc gcagaggggg gattgccatg gaaaccacag gtgtccggag 2160
aggggatctt ggggctggcc tcacccccttc cctgcggaga ttggggaccc tggggtaggg 2220
ggagccgcgc ccagtcggcc tcctggagga cacgggagga agccccgaac ccccgcgcct 2280
gaggctgttt ctgattggcc cctggaggcc gcagacacgc agataggcgg ccctgggtgt 2340
atttttatta atattatgtc cgtactgatt aatattattt atcttaaata aatttcaccc 2400
gtgtccaagt tcaccgcgcc cccaaaaccg agtctggggc ggcaggggga actcctggcc 2460
aacgaatcca tgcctcgccc tcctgtgatg aacctggtac gcacggtttt ctggttaatt 2520
ctatcgctga aaactggtgc ggggggcgca cttctgagac ggaagagcat ctaggagctg 2580
aatcctccac gcgggtcgcc caggttgatc tgaatttctg gggaatggct tggctgcccg 2640
cccgggacca ggccgaccct ccttgacggt ggcgtagagg gctggagcct gggtactgcg 2700
aggctcctcg catggctggg cccgccgcga ggggttgcag agcggctcag ggatcgattc 2760
aagcatcgtc tctcctccct cgcccccaga cagagctggg cgcggggttc cccttccaga 2820
tggagcgagg gtctcggggt ggccccggaa aaggggagcc cgcggccacg gctacgtatt 2880
gccatctcgc gagcagagat gtcacctcct gcctttggag gaaagggagc ccggtgggga 2940
tgagcgcatt tagcccaatg ctgggaacaa agcgcactcc gcgcttctgc gatttcgctc 3000
cattttgaaa tgtgttggcg ctttggtggg gccgctgcgg tgggcaaggc cgggggcgct 3060
gttaatggag gaacctcagg gggacggtcc ttcgtaggaa actctatcct ggctctgcgc 3120
gcgctttaag gaaatggctt ccctccagga cctcgaggga tgcagctttt gcgcggatga 3180
cggtggggtg ctgaaccagc cggtgcgcct ctggaaatgt ctgggcacgg atcctggggc 3240
catcgacgac tcctccccat tcccagcagg cgggagctct tacattccga gcgagtgacc 3300
cctctcaccc tctggcgctc acacacctgt aactccaaac ctccgtctca gaatggtcca 3360
ggctggaagg gatgatgggg gctccgacag cgactgccta gctcacccct ctgcgtgctc 3420
aggctccagg ctcagcagga ccaatttgag ttctatctga tccccctcgg cccttaact 3480
gacccatcct acaggagaca gggaaatgtc tttcctaccg cggttgattc tggggtgtca 3540
ttttgtgttt tgtgatggct gcttatattt actgtataag cattgtattt actgtataag 3600
cattgtatta taattactgt ataagctgct tatatttact gtataagcat ctccaaatcc 3660
tccctctacg taaacaaatt aatggataaa cagataagtg tatcccctgc ccccacccct 3720
gctacgcagg tccggagtga ctcttgaagc tcatacattc cttggccaag tttgcttctc 3780
```

-continued

```
taacagatgt ttatatagca ataacctggc ttggctcttg ggttcacctt tggacgattt   3840
ggggaagggg cttgttggct ttgctgggtt ttggatgagt gacagtccat gactgttcct   3900
gctggaaggg cgtgactttt aagtggtttc taatatcagg cattgctcct ccgacaggaa   3960
caaaagaaat ggatactgcc cataaattgt tagaaaactt agaatcgctt tgattgagga   4020
aaggttagat ttattccggt tggaaaaagt ggcctttcta ttaaacgtgc cctttgaccc   4080
tcatgccctt ggaggtcggt gccagcctgg agatgggata agattgtggt tttccttctg   4140
ccttttttaac atctgttgtt acagtccatt tgttgaaaat ttaaagaaac tgttttattc   4200
cactttccct cagcatttat gtgtgtggtt tcagtagctc tgtggctata tgtacgaaca   4260
cgtgttattt ttccaattgg acatgtgata attttccaac tggaccttgc cttctattga   4320
tgtatttatt tagcatcttc cttactccct ccttgaaaaa gaatcactca aaaacaaata   4380
aaaacagccg taggggccta atacagtgct agacatacaa gaggtattcg gtccatacca   4440
aatggatttt atccatgaag gataaatggg gaaatacagt gggaagcagg tgggaaactg   4500
cgtttgactc tgctctttcc tccaccacca ctttcctcat caccgtgttc agagaccccc   4560
aaagcccccct cacactccca gaaacacccc cctggccact cctaacttgc catgcccagg   4620
agttaggtgc ttccactagt gacatggagc tggcgtttgg ggggcacctc agcaggtgac   4680
gggaagagaa gaccccagcc tcaccagctg ggctgcagca gggagaggag tcctcatgtt   4740
ccagcaggga ctctcagctg ttttcctgta aaaccatggt tctcaactgg gggccactga   4800
gatgtctaga gagatgtttt tgttttcaca actcggggag ggtgctactg acatcttgtg   4860
ggtagaggcc aggaatgctg ttaaacatcc tacaaggaag gcacaggaca gtctcctaca   4920
tcaaaatatg acccagtccc aatgtcacca ctgctggggt tgacactggc actgctatct   4980
taattacatt cattgagtgt cttttaggag gccctattct aagtgcttgc taagattatc   5040
tcatttaatc ctcacaacac ttccgctatg tagcaggtgc tgttattatc tccgtgatgg   5100
ggaaactgaa gcacagagag ggttagtaac ttgctaaagg tcacagagcc agtgggtggt   5160
ggagctggtt gcctgacact agttccctcc cctctcagcc acatgtgggt ttacttggcc   5220
attgtggact agtctgggaa cccagatatg atctataaca ttgacccagt agaatattga   5280
ttccaaaacc actgtctcac aaatgaattt ttacaagagt ctgtaatcgg agcatgaccc   5340
agaataaggt tagggagatg tggagttaaa gctctcaatt tcttatctgg ccccgacaca   5400
gagagcaagg catttcactc tacattggtg ctctgtttat aaaacaaaga gcaaatatct   5460
cttcctaagg tccttaaacc tcttccccca atccagggtt tctggactgc tctgccatat   5520
gacggggcag ctggtttgat tgacccaggg aaggctggaa atcaagactg ggggatcaag   5580
acgtagattc agtgtggcca aggtcaagtc tctgaggttt agggacatca gatccccagc   5640
ttaggttctg tacctcggca aggtgaaagc gttggcgccc actgatgagg cctgctctga   5700
gattgtgggt gtgggttgag ttgggtgggc ataggcaagt cctcttgtaa gaatcttttg   5760
gcaaagatgg gcctgggagg cttttctcac ttcctggggc ccaggctttg caataagtat   5820
tccattatac tgtggtacct tggggctacc tgagaatcct ctgtctcgcc cctgttgcct   5880
tgccaaagag tttgctgtcc aagaattcct ttcctgtctc caggtgccat gctcctgcca   5940
cctctgccag gttccctgcc tgcccagatg gctcccaact gagtgtgagg aggaatttga   6000
gacaggtttt gagctttctg ggttctccag ttaggaaact ttctgtaagc atgcagatag   6060
aatgggcttc agcaaaatac aaactcgaac aacttccatg tatagtccct taattttctt   6120
```

-continued

```
tgcttttttc atatttcatc aggctccatg ctgagcccaa tcagggaccc gatagaaatc   6180
caaacaccat gtcagcgagt ccccaagaaa tgcattttgt gccaaggcta ttcaaggaag   6240
gtttgggagc agctcaaggg cagacactgt taccctcccc caggtcccca gtgcagggca   6300
gtgttctgca tgtggaggca gtttggccta atggttaagg aggtaggctc tgatcgggcc   6360
tcctgggcac aaatcccagc tccctgctca ctgtgagacc taagccatat tgtttagctg   6420
cttggagagt tttttgtcat ccacaacttg gagtatgatg gtacctgtct cacgggttgc   6480
catggggttc acacaagcta acccggtact cactagggcc aagcacatag taactgctca   6540
gtaaatggca tcatcggcgg tgtcctgtgg atgagtgctt gtgattggct gaatgaccag   6600
aggggtctaa agatcctggt gatggaatca gttgtacaga taaattgtta cactgagtag   6660
ggatcaagat aggaaaagtc ggcaactacc cagctcccct gcaccaaact gggcagaagt   6720
ggatcctctg aaaattgcac acacccatgt ttaaatgtac acacagaact cttgccacag   6780
gcaagcggag atttgtcatc tgctgtccct gcctcatctt cttcctgaaa tccactccat   6840
gccaggaata aactgcatgc tctccaccag cccaaactga cctgccttcc cgccagccat   6900
cccgggcagg gtgacctggc ttagtacatc gggttcagag atctttccag tttactcgtt   6960
gaataaaaag tgagggctga tcgagaaagt aatggcagtc agggaaggcg aaggaggtaa   7020
agaagagatt ttacaaatga agtaattcaa cagagtgctg acattggtaa actggcaaac   7080
agatttcagg gtggttggtt gagagtagag tagaaaagga ttaaataaag caaacttgtg   7140
gtgtactgaa tcttaggaat tccatgtatc caataagtat agtcatttat gaattaataa   7200
attcggccta agaagccttc ttatcgctta aatcaagact aagtaacaat atatcagttt   7260
taaaaagtca ttatatcaga aaatcattta aatgatacac atagatttcc aagattttac   7320
tttaaccgaa actatataaa tgtgaatttg ttcacccatc ttttgacaca gggctcaggt   7380
cttctcttgg tgtctggatc agccagttga aatttcttgt ctgttttgcc tatgccacat   7440
taataatgca ctgtctgggt cctccgattt cagtttggat tttgggttta cattgtggag   7500
tcatctgaat gcagaatcct tcagggattt tacttttttt tttttttttc atggtcttta   7560
ccatcccatt tgatagtaaa tattactcac ctttatgaag tctttccaaa acattcaact   7620
aaattttctt aaaatcattg aatgatttga agagcttatt cctcagcact tttactccat   7680
cagcttgcac cttatttttt aatctttttt tgagacggag tctcgctcta tcgcccaggc   7740
ttaagtgcaa tggcgcgatc ttggctcact gcgacctcca cctcctgggt tcaagcaatt   7800
ccgcctcagc ctccgccgta gccgggacta caggtacaca ccataatgct cggctgattt   7860
ttgtattttt gtagggatgg ggtatcgcca tgttggccag gctggtcccg aacttctgac   7920
ccaagtgatc cacccacctc ggcctcccaa agtgctggga ttacaggtgt gagccaccgc   7980
gcccggccag cttgcacctt atttaggata tgtgattatt atagcaagtc tggtgtacat   8040
acaagatttt gaatgggcac agatgacctt tagtaagtgc ttggctgtga taagaggcag   8100
tcctgactgc agatcaggct gtgtggaccc cagccttgca tgtttacaga ccttcatgtc   8160
ttattcttac agggtatcag aagaacacct actggggaaa cttataaatt agtaaaaggt   8220
gggcattctc cccgcccatc ttctgtctgt ctgccaggac tagcacagca ctttgaagtc   8280
attcacatag aatcccaact taagagggta aaatcctcct caacagactg aaaataagtt   8340
taaattccct ttgctatatt aactcccctg aggaaagagt cttagatcaa tgtccaacac   8400
taaaaacagt tttaaatcag caagtgagaa ttaaatctga agcaattgat aataatgttt   8460
cattcattcc tctcctttgg ccccgtccac cctactgcta aatccaggca tcaaagagaa   8520
```

```
gagggacata attatctcta gtcccagctg ctggttttcc ttccagccta tggcccagtt   8580
ttctgtttta ctgagaaggc tggtgatgtt atcttgggat ctaagtctgc agtttcacca   8640
caaaaagtcc agggatgcac tttcatgctt gtgtcctcct ccctgggata gcaaggatat   8700
tagaagaccc ctggctctgt aattgcttgt catgtgctct acagacgcca cagaatgcca   8760
agaacgaagt gctgggaagg acaaattcat ggaaccgtgg gacggtgctc ctcccccagc   8820
gtaaaggaca gctcctcctc ctgaattgga gccagcgttc taaatcatgt gtcaacagag   8880
ttgtcctgga tcggatccag ttctgccatt gatttgcagg tcatttcagt ggtacctgtt   8940
tccagttgtt cttaattgaa cagtggcacc aaactattgt cttgcctcat ccccctccca   9000
tggcctgtcc cccaaaaaga gacttcttgg gtaattaatc agggcaacat caggcagtct   9060
gggcgcggtg gctcacgcct gtaatcccag cactttggga ggccgaggcg ggcagatcat   9120
gaggttagga gattgagacc atcctggctt tgtgaaaccc cgtctctact aaaaatacaa   9180
aaaattagcc gggcgtggtg gcgggcgcct gtagtcccag ctactcgaga ggctgaggca   9240
ggggaatggc gtgaacccgg gaggtggagg ttgcagtgag ccgagatcgc accactgcac   9300
tctagcctgg gcgacagagc tagacttctt ctcaaaaaaa aaaaaaaaaa ggaatctctt   9360
tggttttata tatttttttt tatatatata atatatatta aaatataata tatatattta   9420
tataatataa tatataaata tattatatat tatatatttt tatatattat atattatata   9480
tattatatat tatatattta tatatttata tattatatat atttatatat tatatattta   9540
tatatattat atatttatat ataatatata ttatatatta tatattatat attatatatt   9600
atatatttat atatattata tattatatat attatatatt atatatttat atattatata   9660
tttatatata ttatatatta tatattatat atttatatat tatatattta tatattatat   9720
atatttatat atattatata ttatatatta tatatgtata tattatatat gttatatatt   9780
atatatattt atatatataa tatattgtat atattatata tctaatatat tatatatatt   9840
atatatatta tatattataa tatatattat atattatata tatttttata tatataatat   9900
gtataatata taatatatat aaaaacatat ataatatata ttatatatta tatatatatt   9960
atatatatta tatatattaa atatatttta tatatattat atatattata tatattaaat  10020
atattttata tatattatat atatatacac atatatatat ataaatgagg ccaggctcgg  10080
tggctcacac ttgtaatccc agcactgtgg gaggatcact tgaagccagg agtctgagac  10140
tagcctgggc aacaaaacaa gatcctgtct ctacaaaagg aaactgtaaa aattagctgg  10200
gcatgatggc atgtgtctgt agccctagct acttgggagg ccgaagcagg aggatcgctt  10260
gagcccagga gttcaaggct acagtgagct atgattgtcc catagcactc cagcctgggt  10320
aacacagcaa ggccctgtct ctaaactttt tttttttaat tctatttata tttacatgta  10380
tttaaatgtg aatattcact acctatttgt tgcatgcctg cattttttat actgggcttg  10440
ccaaaaaccc gaacagcttt ctactttgac aatgtatcag aatttaaatc agcaatatgt  10500
taataagcca agcaaaggtt atatatgcaa ataaaactgt tgtctataac ctcctgttac  10560
actggggcac agcaaaagtc atggtgtagt cgcatgtgaa cctgtccctt tcatagctgc  10620
tcattgccag gaaacatcag gaatagccat ttggaagagt catcagccct cccaccatcc  10680
gttttctgtc ttgtcttttc cctatgagca ggggaaattc cacgctggcc ccaatcccca  10740
gtgcagcggc tcagcctctg cctctgctgc tggtccccat gaggccagct tagaaacgga  10800
ggattttgca gaacatccct aaatccgctt gaataatgaa gtgatcattc ataaactcac  10860
```

```
ctgaacctta ttaaaaccta tttaatattt ttcctggata atcctatagg gataacttgc  10920
ctcctgggct tctctccacc gggttcagtt cttcctttag tggtgaagtt cctcccttct  10980
tagcatctca actgtgcctg agaaaaggcc agtggcggct gcactctgtt ccctgtggag  11040
tgttaataaa gactgaataa attgaaataa atccctttca atgtcattaa gtgctataaa  11100
taatcatgaa ccaatgttcg atggctgatg agaaatgcaa gaaaaaattt ttaatcagta  11160
ggattcataa gttgacaatc tggccaagt taaaaaaaat aaaaataaaa agacttttaa  11220
aaagatctta tcgtttgtta ccagtaagac tgaattccag aagcaagcta ctccctcatt  11280
tgtgggcccc tgttatcact ggctgcttag ggttgccaag ccctgaattc atttgtcaac  11340
taagagattt ttggccaaga ttaagatttc ccatgcctcc atatttccat ctgagaaatg  11400
gagattatac tgtcttcccc ctcagaatgg atgataatgt ggtctctctt ctgttcgcat  11460
agtcatagaa ctgaaataaa acaacttaag agaattcctt tgagcttctc agaagtgctg  11520
cagggctggg ggatgcctcc caggagccgc agtcaggtgc tgatctgaag tctttggtgg  11580
gctgacttta gcctgacctg aaatagtata gctgctgcca cctggctccc ttagcgtcag  11640
tcagacggtg cagctggttc ctaggggtga gggctgagcc agcagggtcc gtgcccagga  11700
gggatgcatg ggtggccaca gcccagcctg cactgatctt gtctgtcccc ttctttggaa  11760
ggaaggagcc ccaaaccagg gtgcaagaca gtgggtgggg gtgccttgag catgacctca  11820
agtgatttcc agcccctgcc agtgctgact tctctgggga agggctggga cttccttctg  11880
ggctcaagtc acgacccttg gatggaattt cctgggagct tttctgtttt ttctggagtt  11940
ttcagttttt tcctaaccag acagggactt ggtacagaat ctcatattct aattatgcct  12000
aggagcagcc tctccccacc actcacagtg tttagcatgt gacaggaatc gattaaggca  12060
tgagtgatta aattaaagcc aggcattgac ttggatggtg taatattctg acatctgttt  12120
ggtgtcaaag gcacggggca ggcgcgttaa ttgaactgct tgcacctggc atttgaattg  12180
agccagagcg gggctaaagt cagtttgcct tcaccctgta aatggagggt ttctccggag  12240
cgtggatggt gggaggtatt tcagggtgta tgcataaccc ccaccctgac aatggcccat  12300
ctcttctcca gcgtggccag gtttgagtgc cagtcctggg tgtccagtgg ccccatagcc  12360
ttgcgtttta gtaaaatgct gcccccatta ccacctggtc tgtgcacttc ggtcactgga  12420
atttgccatc ttccagtccc gaatgtggca agccatggag ccttaagctc ttctccctcc  12480
acatcctgga acagacccgc cagtttcttc caggcattgc ctcagtttgc ccctctgttt  12540
ccagtcacac tctcaccagc gataaaatga ttttagacct tatcatctca ccctcggatc  12600
cttatggaaa caataatgag ttgttccctg tttcaattcc aaaattcata tccaatccgt  12660
tttgcatgcc attgccaaat tcctcccaga gcaaccccgt cacctgccct ggccctctcc  12720
aagtgtggtc ctgccatggg catcgcctgc taagccaagc tggcctcgag ctgcctgccc  12780
gggtccccac accttggctc acctccctgc ccagtcccgc ctcctgccag cctgccctgt  12840
ggctccttca tagatgccgt gctctttctg ccccttgctc acccatggca gccttgcccc  12900
tctctccctg ccccaccccc tatttaaatt gacctgacct tcctcagtgt ccatcttccc  12960
cgaagctttc cccagccttg gcactcaagg tccagaggct acgcgtttcc tctcacctgt  13020
ggcagcgccg tgctccccag tgcctcacag tttccttctt gccccccgctt cctgtgtagg  13080
actcatctgc ccacaggttg cacgtcctgt gagggcaagg actgtgtctt atgtgacttt  13140
ccttctccag tcacagagct gggcacatag atagctcaaa accctcttta ttaacacagt  13200
tggatgttga gaaatcaaac aggccaatgt caaatgagct ctccttattt aaatcaagtc  13260
```

-continued

```
agttctccac ctcctagcac tcagttccag tactctatat acatggaaat aataaaaaac 13320
acatttcctt tgaaacattc tataatcgtt cctttgccct acttcagacc aacttaacgc 13380
actccccatt ggtccaaatg agttttgcta tacgaagatg ctgataataa tagcagcagt 13440
ggattattct gctaaaacca ttgcctcgtt aatcctcagt cccgaggtgg ggattattat 13500
cctcattttg cagagaagca aactgagact cagagatttc acagctgggg agggagccag 13560
ctcatccctc tgtccaggcc caagctctct cccgcttgcc ttcctgcctc tgcaacctca 13620
gagcatcccc catctggttc tactgcctgt gctagtcgtg caggagccaa aagacacgtc 13680
tttagtgcta aggactggag aagccatgcc ctccagcctc tgtgaatggg tcatatgtaa 13740
catgagcctg gagaaattat ttgaaaccaa aggcaagcct ctaaaccagg ctgctgcttc 13800
atggcgccgg tgacggcaga accaaattta gtgctgtggg caggtccaca cttatcaaat 13860
agagaagctc atttttcttc cggctcacat caagcatgaa aaatgttcac acataccccc 13920
cacacacaca tgctttccgg aggggtccat gtggctagag gctggaagat gtggatgaga 13980
ggagcctggc aggtaagccc agggaagatg acattcagct tcccagacag catctacagg 14040
gagaaattta attaaaagtg gggcggtttc cctgagcaag gcagacaaag tcagccctct 14100
actgttaaga aaaagggtca cagtgagagg ggaggtgagg agactgagtc tgtattttct 14160
agtctgttgg gctacactac ctgatccccc ttcctcaaaa atccacttta ctttccccat 14220
gtctacacca atgtggttca cactctggga ccaggaaaag ggggagtgat ggggaacaga 14280
gaagggagga gctcacacag ctgaggctgg ggttatgcat atcgaattac ttagaatttg 14340
caacctcaca gggtactttc atggcgttga aatacacttc ccacagccac cctccctcta 14400
actaaaagca agagtcattt ctcagttctg gtcttgcctc ccacgttctc ctccacattt 14460
aagaaaatcc accagctaca aagtgaagat accatatgtg atatcccacc ctagtttctg 14520
ttttatcagg gtttggagca ggtggagcag gcagagggat catttcagcc tataaattgt 14580
attaagggtg agtactgagt cattcttcaa gaaaagtttt agaagcatcc aaaactgaag 14640
ggtggagcca cctggagaca gtatcatcag tcctggcccc gagcatggcc tgcataggcc 14700
cccatggatc ccagcgggag ctgcagagtg cgggcacctt ggcacacagc cctgagtgca 14760
aaattaggag ctgggcagag ggcatctctc tgtcgccatt gggcagccca gggcacactg 14820
gtcatagcct tagaccacga acaccctgtg cccgggggac agatgcaacc agtgtgccct 14880
gggctgccca atggcaacag agagatcgac acctggaccc catgtcacgg ggactccact 14940
actaaggctc ctaagactgc caccttccag tgggataagc cctgcctcct actgggccca 15000
caatgtgcag agaacacttg ggactacctg gctttctgga tacacaaata ttgatccaat 15060
ctggactaat tagaaggtca gtcccaataa caaatcgaag tcagctgggc gtgatggctc 15120
actcctataa tcccagcact ttgggaggct gaggtgggca gatcatttga agccagaagt 15180
tcaagaccag cctgggcaac atagcaaaac cctgtctcta ctaaaaatac aaataattag 15240
gctgggtgtg gtggctcatg cctgtaatcc caacagtttg ggaggctgag gcaggtggtc 15300
acctgaggtc aggagtttga gaccagcctg gccaacaggg tgaaaccccg tgtctactaa 15360
aaacataaaa attagccaag catgatggca tgtgcctata atcctggcta ctagggaggc 15420
tgagacagga gagaatcgct tgaatccagg aggtggttgc agtgagctga gatggtgcca 15480
ctgcactcca gcctggttga cagagcaaga ctctgtctca aaaaaaaaaa aaaaaaaaaa 15540
aaaagccatg cctggtggag cactacgtgt aatctcagct atttgggagg ctgaggcacg 15600
```

agaatcactt gaacctggga ggcagtggtt gcagtgagct gagatcgcgc cactgcactc 15660
cagcctgggc gacagagtga gtgagactcc atttcaaaaa aataataaat ctgagtcact 15720
ttaatattgt tatttggatg tcaacctcta ggtgtttgag acaggagagt gatatggggg 15780
cactggaaac acacaggcac ggggtgtcct cacacttggg tagcccacac gatgtgattt 15840
cagggtgctg ggaggtcccc ccactcccca aattactaac aagtggatag tactttacag 15900
tttatatgat ctcatttgat tcttaacatg agcctgtgag tgaaaaattc cttcccctct 15960
tctacagatt aggacgttga gattcaggga ggttcagagg gattcaggga agtcaagtgg 16020
cacctggagt cccgtggcta atttgaggcc ggtaggggat tcgaacccag gatttgtgct 16080
tcttatgcct gggcttctgc tccctggggc atggtcttcc ccctagcttt cccattcact 16140
gctttagcct aggggtccta ccctttatta aactgccagt gcctcactgc ttttctcccc 16200
caaagacaaa aaaaaagtgt ttttgctttt gttttgtttt tcatgggcag agacctggaa 16260
tttcagcttg agaatttgtg ccatatgata aataaatcaa cagatggctt tttccttaaa 16320
aaaaaaaaaa aaaaaaacta agatgtattt gcagtgaggc ataatttgta ccaaaaagtg 16380
ctcaccacac tgtagtcatg ggggcaggag gcagccgcgg gtgaagggag aaatcttgga 16440
gtccaggcag ccccccttctg ggctgaactg gggagctggg ggtgctgcca gccctgccag 16500
gttctcctag gaggcggcag ctcatatggc tgtgggagga ggcagaggga gcctcatatg 16560
cacccacatt tccagggatc tagaagacag aaggaggaaa accaccatca tgttaaagca 16620
gacagttagg taacacatcc tgtaatacaa gttatttttt ccacatctaa aggctaaaaa 16680
tagttgttag aatttaaaga taattggtaa atgagtttct atccttctag tttcacatca 16740
aatggaatca tgctgccttc acatcactag tgcccgttat ttgtgtttaa tttccacaat 16800
gttgtctaat tccactcttt gggcttcccc agggatccag cctccctcac tcgcccatcg 16860
cagggagatg ctttattcat ctttgtgtct tctgtgccgg gcatagcgca tggcacagaa 16920
taagcactca gtaattgatt cacgagtgaa taaatggatg agtgggtgag ttcaatattg 16980
actacaaaaa ccctaaggcc acactggtga gtggctgcgc ctgtagtccc agctgctggg 17040
gaatctgagg caggaggatc tcttgagccc aggagtttga aactagcctg ggcgatatag 17100
cgagaacctg tctcaaatga caaaaacagg gccaggtgca gtggctcacg cctggaatcc 17160
cagcacttta ggaggccaag atgggaggat cacttgaggc caggagtccg agaccagcct 17220
gggcaacata gggagaccct gtctctacaa aaaatttttt aaaaattagc tgggcatggc 17280
ggtgtgcgct tgtagtccca gctactcagg aggctgaggc aggaggatca cttgagccca 17340
ggaaattgag gctgcagcga gccatgatgg caccactgca ctgcagcctg ggcgtcagaa 17400
cgagacctgc tctcaaaaaa acaaacaaac aacaaaaaaa aaggctttct taaagagact 17460
tgagaacaga aaggggaaca gatacataac ttatatattt atttgttcat ctttccacct 17520
tcctggaggg tggaggggaa caggtctgta tttggagttt tgaatgctaa aagtgggaat 17580
acatgtactg tttgccatga tctgttcaaa agttaagcca aatgccttag attctcctga 17640
aaactggaat gccactgtaa actataagcc ccacttcaaa gataaaagat cttgatgaac 17700
agggctgggt ctgtggactg ggcctctccc caccacacaa ggaagggtgg tgccagttga 17760
aggaaaatca cttaaatcct tgctgtctcc taataaggtg tggtcccagg tagggctgtc 17820
agaattagca aattaaaaca cagggcatct gtgaaaatta gaatttcaga taacaacaaa 17880
taattggcat aggctgcata atgtccctca aagatatcag gtcctaatct ccagaacctg 17940
taaatgtgat cttatttgga aaaggggtct ttgtagatgt ggttaaatta aggattttga 18000
gatgggggga ttatcctgta ttatctaggt aggtcctaaa tgcagtcaca ctcatccttg 18060
taagaggaag gaagagagag atggaaaaca cagaagagaa gacaatgtgg tgatggaggc 18120
agagattgga gtgaggtggc cacaagccaa ggactgctgg cagctaccag cagccagaaa 18180
agtccaggaa ccaattctct cttggagctc cagagggagt gtggccctgc tgacacctta 18240
gcttcaacct agtgatcctg attttggact ttggccttca gaagtgtgag ggaatgaata 18300
tctgttgttt taagccacca agtttatggt catttcctac agcagccaca ggaatcaaaa 18360
acagtaagta tgtcccatgc aatgtttgtg acacacacca aaaatattac ttgttgttca 18420
cctgaaattc aaatttaact gggtctcctg tattttattt ggccaaccta gttcccaggc 18480
ccaaagaaag aggcttttga aatttgcaag aaagctggtt ggagctgtca gaaagtggac 18540
tttgtaaaca cagtaccacc gaaccaattt gaactgtact acctctagac aaaagagagg 18600
gcagtcagac agttgttcgt gatttcttct ttcaacagtc atttgagcac ttactacaaa 18660
acagaagcta tgtgtaaggg tggaggcgtt agctgttaat caggacctcc aggctaagtt 18720
tctgtattag tccgttttca cgctgctgat aaagacatac ccgagactgg ggaatttaca 18780
aaagaaagag gtttaattgg acttacagtt ccaagtggct ggggaagcct cacaatcatg 18840
gcagaaggca aggaggagca agccacatct tacatggatg gcagcagaca gacagggaga 18900
gagagcttgt gcaggggaac tcctcttttt aaaaccatca gatctcgtta gacttattca 18960
ctatcaagag aacagcacag aaaagacctg cccccatgat tcagttactt cccaccagat 19020
ccctcccaca acatgtggga attcaagatg agatttgtta ccatatcagt taccaaccct 19080
tccagataaa tcacgtgaaa tatcgccatt aacagagtga gctcaggtgg ttcttcagtg 19140
catttctgat acctgaacct tccctgggaa tttcacagac catcaggctc tccacccttt 19200
gatagcagga tagcagggcc caggttctgc aggaggagat gttaccacag gcctgaaagg 19260
gagggagggg cagatgctac aggaagatgc tggctctgga ttcgctggag gagctttcaa 19320
gggaagtaga tacacactgt ctccatcatt tcatgtccat cacactctaa aatgctttgg 19380
acaagaagca aatgttaaag acaaatgtgg cccattttcc tgtacaaaga gggctgctcc 19440
catgccaggc tattggcact ggtgggcatg aggcttctct gctgccctgg ccggggggtt 19500
ctctcactca ccattggctc tctgacacct ggagagacca ccacccttgg gctttcatga 19560
tgctcacaga atccacactg ttggagcttt aaggagcctg gatcaactgg aacaggcagg 19620
gagtactagg acagcccagc attgccccaa aatatccagg cctgataaaa gagaaaaaca 19680
ggtagctcac aggaaaagga taaaaaaagg aggagggatt taacatgaaa aggtgcttga 19740
tctccctcat aataaaaaga ctgctgattc catccaggca agtgacagaa aaaaaaaatt 19800
taatttaaaa agactgctga taaaaccaca gcgagacact gctgctcagg gatctgaggg 19860
tgtgggcagc caggctgcca cgcatcatgg gtcggagagg aagaccacac ccctggagca 19920
gagggcggct gatctgtcag atgccctttg acagcacctc agcttccaag aattaaccct 19980
ttctatgtga gcagaggcat ccatgggggg acacactggt gaatcatctg ttatgtagaa 20040
gtctggaaaa catcaggatg gaactggtga aataagtgtg gcctctgacg gaatggagcg 20100
gtccgtctgc actgctgcgg gtgcccctca gatcctgtgg gtcagtgaga aaagcagtga 20160
ggaacaaggc aggtactgtg tactgtcctc tgcgtgcaag gaaggccagc gcatgcaaca 20220
gagtccacac agacatagcc taactctgga aggaagaatg agaatgcagt ttcagtggtg 20280
gcctctggtg gggagaaact gggtgaaggg agatgtcatt tccatttctc tactattaat 20340

```
tttgtattac catgcttaaa tgttactttt tacctttttt tttttttttg agacagggtc  20400
tctctctgtt gcccaggcag gagtgcagtg gtacaatcat ggttcactgc agcctgaacc  20460
tcccaggctc aagcaatcct cccacctcag cctcctgagt agctgggact ataggcacgc  20520
ataccaccgt gcccagctat tttttttaat caagatggag tttttctatg ttgcccaggc  20580
tggtctcaag ctcctggact caagcaatcc tcctgcctca gcctcccaaa gggctgagat  20640
taaaacgtga gtcaccctgc ccagccaatt gctttttaaa aaagattaaa tgcatgtata  20700
cgctcaggca tcagcacact tggaaaggat gaaaatatcc ggaagaaggg ttcttttaaa  20760
aggctcctca agtgatgctg gcaggcatga cgaatgtccc tggtcacaaa agctctgatc  20820
tggcctaacc ctgtcatgtt agagactgga gtgcgtgtgt gtgcgcgcaa agtgtggggg  20880
gatgggggtg agtgtgtgtg gtgtgtaagc atgagtgtgt atgtgtgtgg tgtgggggtg  20940
tgtgctgtgt gagcgtgtgt gagtctgtgt gtgtagtgtg tgtgtgaagt atgtggtgtg  21000
tatgtgtgac gtgaggtgtg tgtggtgtgt gagttgtgta tggtgtgtgc atgagcatgt  21060
gtgtgggcat gtgatgtgtg tgtggtgtgt aagcatgtgt gagtgtgtat gtttgagcat  21120
gtgtggtgtg ttgtgatatg tgtgtggtgt gtgagcatgt gtgtgtgatg tgtctgtgtg  21180
tggtgtgtgt gagcatgtgt gttgtgtgtg tggtgcatgt gtgtggcgtg tgagcgtgtg  21240
tgtgcattgt gtctgtgagc atgtgtgagt gtgtgtgtgt tcagcatata taaggcatgt  21300
aactgaacac agcactttag agggctctcc tggagtcaga gggggtgggt aggaggagaa  21360
gggaggtggg ctagtgtgct gaagtatcta ctccttgtca tagtctgtga caacccagac  21420
tagcccatga gccaccctgt tccctgcatt tccaatgaga cctcggtgga catgttccct  21480
gaggtgaggc tgactgatgt catttgacga tcttgatgcc aaatcctttt atatcaaaaa  21540
caaccagaac actctctttt ctcttagtgc tttcacccag atgaccacat ttcatcctcc  21600
cagccactct gggccaggtg gcactgctgg tttgaaaggg aggtctcccc tggagtaact  21660
tccgtgggcg gattcacacc ctgcccacag tcctgtccca gtcagcccac catggtggtc  21720
tccggttcct ccagaattcc cgcttttcag ctcatcccca cattcccgga gggactgaga  21780
gcgcagcccc agggccctgc tctttggggg ccgtctctac acccagagaa gcagcaaggc  21840
attcctaggt ttctctttca gatgcagaac ttcagtgttc agagatgttc ccactggtcc  21900
tgagagggct cagttcagct ttaatgactg cgctgttgcg tgtgctctgc agagggcggg  21960
tggcccagcg tggctgactg cagttttcct gacgtggagc ccgagcctgc cccgctgttt  22020
attaattaag gatcactctg cttgcagaac cctgaactcc ccagaactgt gaggtgggag  22080
aaccccgaga ggccacctgg ccccacttcc cacctgctgc ccaaaccccc tctctgcctt  22140
cctgacagtc accccaactc ccagtgatcc ccatcaacca tctgacaagg ggactgagag  22200
ggaagagaaa ggaggggccc aaagaggaag gtaaaactgt cgggaacagc cccccaaatgt  22260
gtgacagcct tcagtggagt tgcccacttt cccttttctc ctccctgcag gacctccctt  22320
ctccccagtc ctccccaact tctgaggtta cattgagaaa agtctgcaga gaggtgccag  22380
catcacaagg tgttaaggac cacgagtttg gcattttaac agatgccaga gccacttgag  22440
aaatgtggta actaagccca gagaggtaca gttaacctcc ccagagtcac acagcaggtt  22500
catggcaaag ctggactagc acaggtgtcc ttcccctgca gatccccttc tgtgccccac  22560
atcacctccc tccagtgtct gggccacctg gagatgggcc ctcagactca cccggccaga  22620
ggtgccatct catgggagag gtctggccag gaagcatcga tatttgagat cccaagaaat  22680
gaagacttgg cctgtcagat gacagacttc ggtcatggga acacgtgatc tgttttacac  22740
```

atgcgtcccc tcagcagcag ctttccagaa cattcccact ttcttctgta gtgagaagaa 22800
ctctttccct gcagcctcct gcccaactcc tccttcagtg tctttgcttc agtgtctttg 22860
ataaaccatt ctgctttgca gagtgcgagc tctgccttgc agggttcgca tctgcctgtg 22920
ctgagtaacc aacgctaagg tcgagtggtc ggtcacctct cataagagct agggttgtct 22980
catgctgatg actaggactt gccctcaagg agaaaaataa atcaaaacaa aagcaaaaac 23040
agcaaacatg catctcttaa agaaggctct gagtccaggt aaatttcctt ccactgaagc 23100
agccaggctg aattcgaatt atctttgccc ctgcttaaaa actaatgcaa attttcctag 23160
agaatatcca ctaattcctg gagggggcat gggcattcct gatgcccatg agaggaccat 23220
ttgctcttcc ctcagtatgc taaataacag aagcgacatt tgttgctgga aagtatcagt 23280
gaagttaata aggtttttct tgcccagggt gagggaacag ttcccaatga caaatgctgt 23340
atgggaaggg gctgtagaac tgccagcccc tttggtccat ccgtaaagtg aactctgtgg 23400
atcctggagg attccagcgt cttttttttt ttttcttttt ttttaagaca gagccttgct 23460
gtcacccagg ctggagtgca gtggcacgat ctcagttcac tgcaacctcc gcctcccggg 23520
ttcaagcgat tctcatgtct cggcctcccg agcagcaaga ctacaggtgc gcaccaccat 23580
gcccgactaa tttttgtatt attagtagag acgggggttt cactctgttg gccaggctgg 23640
tctcaaactc ctgacctcag gtgatccacc cgcctcagcc tcccaaagtg ctgggattac 23700
aggcatgagc caccatgccc agccagcatc tttcattttt ctgtctgctt tggccctttc 23760
ctctctcact gtcttccttt tccatttcca aagtcagtcc atctcactat tagcacaaaa 23820
actgctagag cgcttgtcat tggtcatctc tccctgcacc tggctggtct gttcttggcc 23880
actgaagcgt ttcccccagc tgttgcttta atcattttat tgttattatg ccttacttaa 23940
gaaatggata tgagatgcat ttacctgtct cttcctgcca ctctgcagag ccagtaagat 24000
gtggtggaaa gggcccaggc tttggaggag ggctggctgg ggttggatct tggctgcccc 24060
ctactagctg tgtgaccttg ggtaagtagc tggacctctc tgagcctggt tcggaatcat 24120
agcacctctc tttcagggct gctgtaagga atagcagtgg tgtgtataaa gcagagcgca 24180
cagccagcaa ctggccccta gccacactgc tgagcaccta ctgtgataag ctgccattgt 24240
ggtgtgtgaa gcaaagggga aacatgcctg ctgtagtgag cttcctgtag ggcaggttgt 24300
agaaccagag gtgggttcca aggttacaaa gggactctta gtgtattagt ctgttctcac 24360
attactataa agacctacct gagactggat catttataaa gaaaagaggt ttaattggct 24420
cacattggct gggtgcggtg gctcacgcct gtaatcccag cattttggga ggccaaggcc 24480
ggcggatcac ttgaggtcag gaatttgaga ccagcctggc caacatggtg aaaccctgtc 24540
tcttctaaaa taaaatacaa aaattagctg gccatggtgg tgtgcgcctg gaatcccagc 24600
tactcaggag gctgaggtgg aagaattgct tgagcccggg aggtggaggt tgcagtgagc 24660
caagatcgcc ccactgcact ctagcctggg cagcagactg agactctgtc tcaataaaaa 24720
aaaaaaaaaa gaaaagaaaa agaattgcaa gaaataaatt attgtttatg agctatatgg 24780
tctgtggtac cttgttgtgg gactgggagt cttggcgtct ccctgaccct gcctgttgct 24840
gcagcaccgc tcagccctgc ctgctcccta cctgcctccc ctcggcctct cctgcctcca 24900
ccgggcccct ggtgcctcct ctagagacag tcctcctggg accgattgtg ttctcactta 24960
cacgaggcat ccaggactac agataaccag aggaaggggc gcccccccg cctgccctcc 25020
tccctggcat cctcacgctg cagaggtcag agcctcatcc cagcccctta cctgccccta 25080
ctctgtggag aaccgtggtc agttcgccag gccggatcca cgaacggcct tgtggaagat 25140
ggtgagctca cacccagagc tggctccgat gaccctgtct cctttacatg tttctacctt 25200
cccctcccta ccttccccca ctgctgggcg cagagtggag gcagatgagg tttaaagctc 25260
agaagggctt aaacgggttg gggcgcagtg gctcatgcct gtaatcccgg cactttggga 25320
ggccaaggca gaggatcact tgagcccagg agttcgagac caacctgagc aacatagtga 25380
gaccgcgtct ctacaaaaaa taaaataaat aaaattagct ttgcagggtg gcatgcacct 25440
gcagtccctg ctactcagaa ggctgaggtg ggaggatcgc ttgtgcccag gagtttgagg 25500
ctgcagtgag ctatgctggc accacagcac tccagcctga gtaacagaat gagatcctgt 25560
ctcaaaacaa acaaacaaac aaacaaaaga aggcttaaag ggggctccag gtgggcttgg 25620
cagcacaaag ctatgaagtt ctatcttaga cacaagttct gttactgggc ctttgcaggc 25680
tggcctgggt acctggctgc catagacagg gaaccttcca gatgagctgc aggcgtggag 25740
cacaggagcc agggtgctct tcctgggctc tgtccacagg cagaacgtac acagtctttg 25800
tacacgtccg gcggctctgg tgcctatttt tgtttgtgtt tttcttttgt ttggggggat 25860
ggatttggtt tcccccgagc cctctgtcct cctgtcacct ggctggtgct cggcaatgtt 25920
gaccagctgc ctggctggag ttggcagtgg ctaaggctgt gacagctaac atgttcctga 25980
gtcctctcat ttcttcacca taatgccctg ttgagtttgc agatactgtc tctgttttta 26040
tctcccgggg aaactgaggc tcagagtggc taggccacct tcccatggtc cctcagctca 26100
tgagggccac acagggcatt gcggtggcct tctcctcagc cttgaccctc cggccccagc 26160
attgctgcct caaggggtct cctctgctga gccgtgcacc ttctgcctgg cagctccaac 26220
tctgtggctg tgttcagtgg ctcagcactg ccccttgacc ctccctggcc ttctgcggat 26280
gccagactgg agcactctga caaggtctgg ggtggttgta tgggtcctgt gacctctata 26340
cacctcccag tgcctgggaa tcctgcagat acaccctcct tagccgtccc taaccataga 26400
ggacatttct gaggtccccg agagagtggg gcacccctgc aggatccaac tgctgggccc 26460
aggaaggata gcagcagcat gaggggttcc attagccaca aactcacggc atggaacctt 26520
cacccacctc gcccctcatc tgctgtttag cacctggcac gccgtgtata cttactgatt 26580
attacatttt aatggcaaat tatagtggca aacgtatgca tctttgcaca attgttgtac 26640
agcatgatga acaagtcatt aatagtaaag aataaatgtg aaagtgagaa aaatctgact 26700
gccaaagttt ttactccttc cttccctccc cagactttta aatgaaagtt tagggataat 26760
cccttagttg tcctgctagt aggacttgca attaaaagaa ttgggccaag aacacttcta 26820
cgcttctcct tttaggtttg ggtgtaaatt cggggtattt ctcactgatg aaagcctggt 26880
gcagggcaga ccgtgggaag ctttcatttc cggaatggac catcaacatc ccttggagaa 26940
gaattctctt ctccagaccc agacctggtg tcctggcacc cattgggcaa gtgggtccta 27000
gaagacaaac ctggtcagag cctggaggct gcttagcatt ccccacgcac attagcagct 27060
cggagagctc aggaagccgc agcccctcct tgcctcacca gcctggatca ggacagcatc 27120
ccctggaaga cacacagggc ctggcctctg attacccagc ctggagggaa agctcaatcg 27180
agcatcatgt cacccggtgc ccccatgcag ggtggcactg gtgagacccc caagccaatg 27240
ataccacctc acaggagtgc aggcccattg tggccagatc atcttgactt ttcaagataa 27300
atcagaaatc gtatttccat gagatatccc tatttgcaag tgatggtgac taaattagaa 27360
gtttttgaat attgtaacat gttcgtaggc tgtttgtctg gtttaaactc tatctggagg 27420
aattcaagct agacttcagg aataacttct tgaggcaagg attttgagac cttagggaaa 27480
gaaggacgtc ttgggggtat tctgactgtt gtcctcctgg aagggaagaa cagagaacta 27540
gaagactgcc cttagcgaag ttcaaagcac ctaagcccgg gaccctcagc aagtgttctt 27600
gagtcacaga ttctccctga ggcgcctctt tctggctcca tagaatggct gattctgtaa 27660
ctcggtgagt ttgctttttt tttttcctcc atcacccagg ctggagtgca gtgaagctgg 27720
agtgccgtgg agcgatcact gcaacctctg tctcccaggt tcaagcaatt ctccttcctc 27780
agcctcccaa gtagctggga ttacaagcat gcagcaccac acctggctaa tttttgtgtt 27840
tttaatagag acggcccgaa gtgctaggat tacaggcatg agccaccgcg gccagccata 27900
actctgtgac tcttgttaca aaggccttat attttgctct ttgagggtgg ttttggtttg 27960
atgcctgttg gttgccatct tttaactagg gatgttttat caaaatgccc agccaaagtg 28020
tccaaacaaa ttataccttta aagtttgaaa atgtctggca cttctaattc aatgcctgtt 28080
gtgccaggca ctgggctgct gaggaactga gtcccgtccc tgcaggctag ctagagaaca 28140
cacacacaca cacacacaca cacacacaca gagtggtctt acaagtcagt tttatattct 28200
acctatatgc aataaaggta ttattatgtt gaggtgcctt gatataaaaa tttttcttaa 28260
aggagaggat gcctaaaaca ggcattacct gaaacctcct ctctccagca ttggttgtct 28320
tctgtcatga ctcagggttt tcactgagaa tgggatggaa atgtggtcta aagatagggc 28380
caatgttggg actggatccc ctctgggaag tcagaccagg ctagggcagg tccttgaagc 28440
catcaggaaa agcctctgga gccagaaaca aaacaaaaaa aaaatggtgt taactaaact 28500
cagtctcaaa tcctgaatag gactcaagtc aagcaaaata attaaaggag ttagcaaagg 28560
gcaagtcaga gagaccgagc aacaccaatg tcttccggga gccctgtggc gagtgacaga 28620
gcctggactc tggagtagaa ctcatcttgt gtcttcttct gccactcgtt agctgggtga 28680
ccttgagcca agccccttaa cctcttggac cctatgttct tatctctaag taggggctgg 28740
taatatcttc ccctttgagg aatgccctct aaggggtgtt gtgaagattc ggtaaggtgg 28800
caggggtagg actcctggcc agaaacaggc acataataaa tgctaagtct ctccttctct 28860
ccacctgctg gatgctgtag atactaagga tttcgatgtg aatgagacaa aacccctgcc 28920
ttccaggagc ctttgagaat cagagaacta gacccatttc cagaacaagg ggatgcaggg 28980
tctggataaa gttttgggga tcaatagagc agagggctcc cagaggatcc catagggttg 29040
actcctaact caagggcatg agacaacccc caggaagggc accctggaag gggtccggct 29100
gtccctgatt tacttgtggg cactggggga atgcccggag ccatccagcc ctcagggctc 29160
tgtgtgattc tgggttcctc ccataaaaga taatcagatt ctttcacgtt aatgtctttc 29220
tccacctcat tgcacatcat gcagctattc attgactcag caagtatcag ctttgcatgc 29280
gaccttggcc tacccacttt agcttttagt aatagctccc ttcttgaata atacaaccag 29340
tggggaaaca gaacctaact cttacctctg ggaggcttat ttgctttgag aacatatgtc 29400
ctgcagtttt gttcatatgg cagtgaagtt tcgtgcacac actctagagc caggcagcct 29460
gggttcaaag cgcagctctg ccaggtccta actgcatgaa tttgggcaag tcgctcaacc 29520
tctccatgcc tgagtttcct catctgtaag attggagcaa tggtaatacc tgctttttag 29580
ggttgagaag agaattaaat gaattaagat gggtaaagtg cttagagtgg agctttgcaa 29640
gtagtaagtg ctatgtaagt gttcgattta aaatgaaaga cccttaaata cattctttgt 29700
tcatttcaca agcccttcat ttcacaacct tacatttcac aaccaagctc tgtctcccct 29760
ggaatccagc cataactctg ctcacaagtg tgagacaggc cccagcagag ctgcacgaag 29820
aggagagaag gcagcccccc agactcccaa ccccctgtcc aagatggcaa aaccagaaca 29880
cagcctctgt accaccccag caggtattca gaatctgcaa tctccaaagc ccacttcaat 29940
tgtaaatgta gagccacgtg cgctttaagt cacctgtcac tctggaggct cttttgctca 30000
gttcctcacc attagcaggg atgacaggga gtgcaggagt gcggtcgact cccagatatt 30060
ggagagcgct gggctagctg cccattctcc cggcctccac tcctctttgc tgtccagcca 30120
tcacttgctc tttgaaggca aacaaaacag aaaacagtgc caaaagtatg ggaagaaagc 30180
cagcttctcc cctggggtgc ctgtgatgcc atgcccaccc tccctgacca cgcagcccct 30240
gtggaccctc agggccccaa gcccccattt ccatcacatg cgtacaccca tgtgtgtcca 30300
tagccgccca tctcagtcaa taaggctgct cctgcccact tggaatagtg gtgacaacca 30360
ggagtggctt atgggaacta tcccaatggc ctgacagcat gtccgctgca aaccgctgag 30420
gtaggacact gccctcatgt ctagctgatc agcaagaggc gcagttgctt tcttaggtaa 30480
cattgctgct gtgtcctggc cattgctggg gggtggcact taatctacac cagatttttc 30540
cctcctgtat cttccaagct gcttggatct tggtgctgaa ttaggttgga ctttgtcttg 30600
tggggaaggg aggactatag accctcaacg taagcaatgg tcagactatt ctaagaaaac 30660
tcgccgaatt aaagcatgag gtaaatttag ttctgacttc tgtccacccc actgccactg 30720
tcccctttta tcccatgatc ccttgctttt cttttcctcc tctctcccta tctcttgtgt 30780
ttgacgcatg ataggaattc agaaatatat gtttgtggat ttgtttattc acgtagcaaa 30840
ccatttcttg agtgcctacc atgggccagg tagaatgggc ggccccgggc tgcagtggtt 30900
tcttcagccc ctctccaggg tttacactgt gcaagacggt ttgtgatggg tcctcccatc 30960
gaggaccaca ctcttctttc tctgtgcccc ttggtcctca gtctctgacc ccacttcaaa 31020
ggcagcattc actcagggaa gctcccatac aatgctagtc agagtaaaag tttggacaaa 31080
ttgccaggaa gcagcttgtc agtatgcata aacagccttt aaaatattac tactctttga 31140
cccagaattt cacttctagg aatctgtcct aaggaagtag tcacatgcaa aagatttatg 31200
taccaagatg ttcatcaaag tgttgtttta taacaggaag tctcagaagc tggataaata 31260
tccaacctct ggaaatggtt agatagaata gtatgtagcc attagaaaat tatgtctatg 31320
gggtttaaaa tgtcatggga aaacacttct gacataaaag agcatgagaa ctgtatattt 31380
agcataatct taactatgtt ttagaatgca caggaaaaaa atgtacaaac atattcatag 31440
tgatgtctct ggtggtagga ttatgatcag taagtacttc tgtctcttca tattttcctg 31500
tatttgataa tacatgcata tgttgttttt aaaataagaa aaattttaag tttaaaattg 31560
gagctgaaaa gtgtttttag gtcaggcgag gtggctcaca cctgtaatag caccactttg 31620
ggaggctgag gcagtcagat cacttgagcc caggagttcg agaccagcct ggccaacatg 31680
gtgaaacccc atctctacta aaaataaaaa aattagccat gtgtggtggc acacatctgt 31740
aatcccagct acttgggagg ctgaggcatg agaattgctt gaacccagga ggtggaggtt 31800
gcagtgagcc aagatcgtgc cactgcactc tagtctgggc aacagagtaa gactctatgt 31860
caaagaaaaa aaaaaaagaa aagccttttt aaacagtagc agacataact atataatcct 31920
tactaagctg tcggtcaaat ttttatttat atatttattt tattcattta ttatttttag 31980
acagggtctc actctgttgc ccaggctgga gtacagtggc gtgatcatgg ctctcttcaa 32040
acttgacctc ccgggctcaa gtgatcctcc catcttagcc tcccaagtag atgggaccac 32100
aggtgcatac caccacacct ggctaatttt ttttattttt tatttttaga gatggtgttt 32160
actatgttgc ccaggctagt ctcaaactcc tgggctcaag ctatcctccc acctcggcct 32220

```
cccgaagtgc tggggttacc agcatgagcc actgtaccca gccctcaaat ttttaaaaat  32280
ctataagaga cattattgga caattagaga aattcacata tggacttata atagtatcag  32340
agtgtgtggt gtgatggttc tggagggaat ggactttttc tttggagaca ggcttttcta  32400
tgcccaccct tttatcttgc taacttatca tcatccaggt tccagcagaa acattacttc  32460
ccccaggaaa tttcttaagg gtgcagtatc atgatgtctg cagcaaattc tcaaatagct  32520
caggaaaaaa gtacgtgtgt ggtatgagtg tgtgtatgta tgtgtgtata tatatacaca  32580
tatatacaca tatatataca tatatgtgta tatatataca tatatgtgta tatatataca  32640
cacacataca catatatata cacacacaca tacatacatg tatttttata taattatata  32700
tgcagagagt gcaaatgttg ccaagttaaa gattggtgag tctaggtgaa gggaatatgg  32760
tatttattgt attatttgtg caacttttct taagtttgaa aattttcaaa acaaaaaatt  32820
ggaggaagaa ggcatgccag tctaccccaa gccctccatt ggaatgctga aaatctaaac  32880
aatgtgattt ggcaatttca tttcttttct gttgtgggcc agtagtcctt agatgttggg  32940
gaagggggta gtcgctgagg tgtggttgac ttaggatgga agaagcagaa gtcaagactc  33000
ccagggtcaa agtggtttgc tctgctgacc caagtgtggg aggcccagag tcagcgtttc  33060
aggtgtgcta attcagcatg gttctattca cggccaaagt ccaccctggg cacctctctg  33120
gcagcaatct tgggtgactc tactaaggcc aggcctccat gaccctatgt ctggatccca  33180
tatctccacc tctcccactg tctcaggaac ggtgcttagc tttttctttt ccctctcctg  33240
tcttctttgc cagcatgtag aaagtttaaa taattcccct ctttacaaca aaacaaaaca  33300
taccccccttc agtcaaccac cctagctctc ttctcctttt cccagccaga ttttttttaaa  33360
agcatcctag gccaggcgcg gtgactcacg cctgtaattc cagcactttg ggaggccaag  33420
gtgggtggat cacaaggtca ggagatcgag accatcctgg ctaacatggt gaaaccccat  33480
ctctactaaa aatacaaaaa agtagccggg agtggtggca ggtgcctgta gtcccagcta  33540
ctcgggaggc tgaggcagga gaatggcgtg aacctggtag gcggaggttg cagtgagccg  33600
agatggcgcc actgcactcc agcctgggtg acagagtgag actccgtctc aggaaaaaaa  33660
aaaaaaaaaa aaaaaaaagc atcctcagca ctttggcaac tccatctcct cccaacatgt  33720
ccctgttact ggaatccagc caggactcag ccccgatctt tctactctaa ccagttgtct  33780
cagttaacaa ggacaggttt atgctgcagt gacaaacaag atcccaaatt cttgtggctt  33840
cacacatctg gcaccacctc atcttccagc cttaggagtc atcttttagt tccttgaaaa  33900
ctctttacag ttttctgttg gggccttgtc atatactatt cccctggaat gttctttcct  33960
atcccctccc tttcaccttg ctaacttgtg cccatccttc aggtctcagc agaaacatca  34020
cttccttggg gaagttttct ccaacaccca cactacacag gtgtcccatc tacactccta  34080
tgactttgtg gtacttgtct cacttcattt tccactgcct tccccacaag gcacctgcac  34140
aagggcaagg accgtaccac tgtacctatg tcactcattg ctgtggtcac ctgcactctg  34200
gctgcctacc ttaactacac attagaatca cctgaggagc ttttaaagcc acaatgcaag  34260
actccaccct aggccaattg gatccaaatc cctggggtag ggccagacat cagtggagtt  34320
atatatacat atatatattt tgtttgtttg tttgtttgtt ttttgagaca gagttttgct  34380
ctgtcaccca ggctggagtg cagtggcgcg atcttggctc actgcaagct ccgcctctcg  34440
ggttcacacc attctcctgc ctcagcctcc tgagtggctg gaactacaag tgctcgccac  34500
cacgcccagc taattttttt gtgtttttag tagagatggg gtttcaccgt gttagccagg  34560
```

-continued atggtctcga tctcctgacc tcatgatctg cctgcctcat cagcctccca gagtgctggg 34620
attacaggca tgagccactg cacccggcca tcagtggata tatttttaaa gcactgcaga 34680
gaattctgtt gcatcagctt gagaaccact gatctgcctt gtgcttcaca tttaaaactt 34740
ttttttaatg aataaataaa ccccaaaaaa ttaatctccc taagcctccc tagaagatag 34800
gatggtaagg atattttcct aggtaaaaat atgttaattt catatttcat gaaatttcat 34860
gtttcatttc aatcaagctc tgtcatacac cttacatggg gcaagcccag tgcctgggca 34920
gggtgtaatt atactcatta cacaggcaag gaaaagtcac attaggtgat ggagcacaaa 34980
taggcagtta atggtttcag ggctagttag gatatgtttg tctttcaatt gcaagtaata 35040
gaagcccaaa gaaattggtt atttatataa tataattgat tggttcccaa atttgaaaaa 35100
ttcaggaata gacccagctt aggtacagct ggatccagtc actcaaacaa tgtcacaaag 35160
aaccctttga caggaatgta tcctgtgttg actctacttt gctctgagta gtctttcccc 35220
aggtgatgat aaaaatggtc atcatcgcca ggcttgtgtc ctgtttagta ggaatataca 35280
agaagagctc agtaaatgct ggccccacca ctaagcaaaa acaaaacttt tgttgttgtt 35340
attgttgttt taaataacag cttagacctt tcttctttcc ttgttattct ctttcatctg 35400
taatccagtt ttctacttct gaagtataga atgttctgat gatttattct tcattaccca 35460
caacttgcac atgtttattt aaaaatgcca ggattgcctg gccgttgtgt gctgttaacc 35520
tttgtttgct gttagtggat ccctgaagtt caggctccca ggggagcaga taatgggtat 35580
ccagttcctg caatatccac cctctggcaa gccaagttcc ttcctgggta aggttttgcc 35640
tacctgcatt cctagggaag tttctgggcc tgaccaccaa gccagctctg agaaggggtg 35700
cataagcccc accatgcttt ggctctgtcc ctatagaata ttttatgttg ttactgaaaa 35760
ctaaaggaag atgggtgcgg tggctcatgc ctgtaatccc agcactttgg gaggccaaga 35820
cagattgatc actcgatgcc aggagttcaa gaccagcctg gccaacatgg tgaaaccttg 35880
tctctacaaa aacaaaacaa aacaaaaatt agccgggtat ggtggcatgc acctgtggta 35940
ccagctactc aagaggctga ggcacaagaa tctcttgaac ctgggaggta gaggttgcag 36000
tgagccgaga tcgcactact gcattccagc ctgggtgaca gagcaagatt ctgtctccaa 36060
aaaaaaaaaa aaaaagaaaa ggaaagctaa aggagagaga ctaaaatgat atcaggttcc 36120
tggagaacaa acagacatga ttttgcttca tggcaggaca gccggaagaa gtgggattat 36180
atcctcacat tacaaataag aaaactgaga ctcagaatgg ttaagtcact tgtcccaggc 36240
cacacagcca gtaaattaca gaaacagaat ttgaacccaa atcttccagc tccaaagctt 36300
gtgttctttt cactacctcc tgcttaattt tttaatttct aagattagac ccttcatcta 36360
tccatgacac ctgcctgtca tcccctgaaa aaaggtgaac gccgttcaga aatttttcta 36420
gcctgagctc actcccagtt cacttatttt tgctttgtca tggctgccca gtccccactt 36480
gtagaccagg aataggtcat ggctgcgggg actacacgct gtcgctgctg caagggccgg 36540
cctctgtttc cggggctgag tgggggccag acctgccagg agcaccatct tctgtgggtc 36600
ctgcctggat gtcacatccc ggccccaaga agtcactgca aaccttcgta ttattgagct 36660
tcacatccta gaatttgctg tcactgtggc tgctgcatga agttgtcctg agagaaacgg 36720
gcattgtcat taacagggaa attgatggtc tgggggaaaa gtcatcctca ttctcttgca 36780
gatctatggg tgattgagac tggctgatgt tgaaggggtt tctcagccat cgtgtgccat 36840
gttatggaac agtggtgtag ccagccattt gacacccagc gctgaccttt gtttaacaac 36900
ctcacctata tatgacaaaa tgattgtcag aaataatcgt gtaatgaaat gactgtaata 36960
atggccagaa aagaaacgca gatagtaaaa tgtttctctt gttgaactct gtacatataa 37020
ttgcaccagg atttttttca aataaaaagt aaatattata ctacaaaaaa gggaaaaagc 37080
acaagcattt attaaatagc tttctatatc tttctgagtt ttgatccttt gattgcagac 37140
tgatgtaata ttttatgtaa atcattgctt ggttactaag tgaactttaa gaaaagtgag 37200
acgtctgcag aagttgccca taatttagca gctactgtat tgtaccattg atgtacggct 37260
ttattttctt gattaattat ttaaacaata taattcacaa ttttaaaata ataaatttcc 37320
acttaaaatg gtatttaaac tcagcaaaat atatcatcta tgagtaaaat ttgtatttac 37380
caagcaaaaa tattacagtt tgtggttcac atgctgtctc actgttttaa attttaaata 37440
caaaaactcc aagtaggctg ggtgtggtgg ctcacacctg taatcccagt actttgggag 37500
gctgaggcag gcatatcgct tgagttcagg agttcaagat ttgcctgggc aacatagtga 37560
gatcctgtct ctactgaaaa caattagctg ggtgtggtgg cacatgcctg cggtcccagc 37620
tactcaggag gctgagatag gaggatcact tgaaccctgg gggacagagg ttgcagtgag 37680
gcaagattgc accactgcac tccagcctgg gtgacagatt gagaccctgt ctcaaaaaaa 37740
gaaaaaaaaa aaagaaacac aaaaactcca ggtggtcgca cagaatgaca ggactgaagt 37800
aacttagctc caatttctgt cttcataatc actgtcctac cattgtctgt gcttagaatc 37860
tacttgctta atgcaggaac atgtgttctc acagagatgg aaaatgcaaa tggcgccaga 37920
agcaagctgg aaattctgaa ccattaagaa tttactctct gccaggcacg gtggctcacg 37980
cctgtaatcc caggactttg ggaggctgag gcaggcagat catctgaggt caggagttca 38040
agaccagcct ggccaacatg gtgaaacttc atctctacaa aaatacaaaa attagccagg 38100
catgatggtg ggtgcctgta atcccagcta ctcgggaggc tgaggcagga gaatcgcttg 38160
cacctgagag gtggaggttg cagtgagccg agatctatct gcaccattgc acttcagcct 38220
gggagacaga gtaagactcc atctcaaaaa aaaaaaaaaa aaaaaagaac ttactctcaa 38280
aataaatacg tgtggctgac tccacatatg gtagggccaa ctgtataact agaagttctc 38340
caaataactt ctgtggagaa aaaaaagttt attaaaggtt aactttttta aagtgctaac 38400
tagaacctta ctaacactga gatcgcacca attgtttata acttagacag ggccgggtgc 38460
agtggctcat gcctataatc ccaacacttt gggaggccga ggcaggtgga tcacttgatg 38520
tcaggagttc gagaccagcc taaccaacat gatgaaaccc catctctact aaaaatacaa 38580
aaattagcca ggcacggtgg tacacgcctg taatcccagc tactggggag ggtgaggcag 38640
gagaatctct tgaacccagg aggcggagat tgcagtgggc caagatcgca ccattgcact 38700
ctagccccag caacaagagt gaaactctgt ttcaaacaaa caaacaaaaa aaaaaacctc 38760
ttggaccagg aaaatatttt ttaagggagg agtattttat cactggcatt gtttaggatt 38820
gcaggcacat gatgctaatg aaaagcagac taactattag ttggttttat tactgttttt 38880
gaactctctc tctccctttt tttttttttt gagacagagt ctctctctct gtcacccagg 38940
ctggaatgca gtgactgcag tctcagctca ctacatcctc tgcctcctca gttcaagtga 39000
ttctcgtgcc tcagcctccc gagtagctgg gattacaggg caccacacca ggctaagttt 39060
ttgtattttt agtagaggca gggtttcacc atgttgccca ggctggtctc aaactcctgg 39120
cctcaagcga tctgcccatc ttgacctccc aaagtgttgg gattacaggc gtgagccacc 39180
gtgcctagcc ctgtttttga actctctaga gacagtccag cccccttatta cttgtcctga 39240
ggcagctgct cccttcacct ggcccccgc attgtgttcc ggacccttgt cctggtggtg 39300
ctaaagaata tctctgtcga tcctttgggg actggggaaa ctgaggccca gtgccacgcg 39360
atgccatttg ttcagggaag attaggtcat ctgctaggtc cccagtcact tgaccttctt 39420
cccagacagg aagaagctgc tctgggtctc tcagtgctcc acgtgtcttt gcacattgaa 39480
atgttttctg attttttttt ttttttttt gctgttacat ttacttttaa aaaataacaa 39540
gcaataaaat gttacatttg agaaggttga aatgagaatt gatttgagtt aaattctagc 39600
agatttttct tagaagaatg atatcatcat ctccagctac ctgcaattga tctactctga 39660
attaagaaag agacttccat ttgttgttta tattttgcac tcttgatgtg tttctttaaa 39720
ttatggtcat gggccaggtg taggagctca cacctgtaat cccagcacct tgggactctg 39780
aggagggagg atcactggag gccaggagtt caagacctcg tctgtacagt aaattttaaa 39840
aattagccag gcatggtagc attcacctgt agtcttagct acttgggagg ctgagatggg 39900
aggattgctt gagccagaac tttgaggcta cagtgagtta ttttcacgcc actgccctct 39960
agcctggctg acagagcaag acctgcctca aaaaaataag taaaaaataa attaaatttc 40020
aatcattagc agtcattagg atatttaaat acagtatgtt gaatcaaagt tacgcatgtg 40080
tgtatttttt tttccagaga gttgtttatc atgtgggttt taatttaact ttaaaaaaat 40140
gttggctgga cagttgccca aatggtatca tcagccattt ggttgagaac gtatgtcctg 40200
cgggctcctc tgtcactgga gttttgctag ctgacagcca ctggctagtt agagactgca 40260
gtcagcacag atgcaggcgt ggacttgcgc acgtaaccat gtcaatgcaa agccatcact 40320
tcttaaaaat tctgaaccct gctgtctgag atggtggtgc agcggataga actctgctct 40380
aagaggcagt agctaattcc atgtcttctt tgcccttgac tagctgagtg actttgcaca 40440
tggggcttgc ctctctgttg ccttgtctgc aaagtggaat catcttttcc ttgctagaca 40500
gaaggtggac cctggaccta tggccttttt gagtttcccc cccgcttctt agaaggacct 40560
ctgatcctac tgagtttaat acccacgggt taataattgg gaaaagcaaa ggaagcgctt 40620
ctgtttaggt aattatatgc atgtttttgt ctttttctgg ctggaaagat atccaagcca 40680
ctgggaaggt ccgtggctac ccagggtagc cctctctggg gagggctgct atatccaaga 40740
gcccctcatg agaatttgaa aatcgaccat ggtagggcct gctgactttt gacagctaat 40800
ggtgtgctga gaattgtccc tccaaagatg cctttccatt ccctcgggag agtctgggca 40860
gcccctactg gggctggga tgctggctct tccctcagcc tccaccccaa ctgctctctt 40920
ccctcctccc ctccccagcc ccctaatttc tctcacaagg ctttgttctg cagcaacctt 40980
tcctaatgca gtcctggcct cttcgcagct tcattacata accttccgtg gactcctggt 41040
ccaaggatca ccccagaaag ccagtcagag gtaggcacgc agctggggtc catttactta 41100
ccttccccac cccctcggaa ctcagaggtg gtgcaggaat ttggactcca agaattaaca 41160
gctccaccac catcaccaga gccaaaactc aggatgcatg tgcttcatct gctgcttatt 41220
tccagctgag agccagtggt gccatggttc cttagggagc cggtcccctg atgccggctc 41280
ctggccccaa atctctctga tccgggctct tccagaatgt cttgtctcca ccatcgcctt 41340
tgaccaatgg tgtccctttg cctggtaatg tccccttgc ctgatgatgg ccctgtcact 41400
cctctcttta gcacagagga ggctgtttca tcccttcaag cctgccctcc cttcaagtct 41460
tagctcaagt tcaccttctc cgcagagcct tctccaatct tcttgactac gtctcctctc 41520
agctccagca acctctgtct ctggcactga ttccttactt agctaagaga atcacagaca 41580
cttggggctc aggacaatct gctttctctc ttcttaccca tggccttgga ctgtgtgtac 41640
ctctttgtct ccactcccaa acccaacccc cagagggcag agagcatgtt gtctgtccct 41700
ttgctcagca tgaagccatg cgtgtggtag atcggcagag ttccataact tgtgttgacc 41760
gaggggtcac tttgctctga aattacccct gtgtccttca gtatttgcac agatagcttc 41820
ctggccagac cgaatatatc caagggcatg gcccacctct gctcctgttt ccaggtccct 41880
ggtgggggtt agttcatgcc ttcctcataa tctgcccact ggcctggtcc tcaaggtctt 41940
cccaactgct cagccagagt tgagaaaatg ggtcgctcca tcctgtttgt gtcgttctct 42000
ccttcctggc ccactctcct gcccacaggt atccaggggc tgcctgtagc attagaggac 42060
atacatgcac atgcgtgggc atgggacact cacgtagcct ccaagcacag catcaataat 42120
gcattctgtg ctttatagca tggaaagctg ctctaaactt tattacacag tggacatgtc 42180
tgaagcagct cccaaatcca cccctgagtg tgttggaatt ggcaagccta tcacttggga 42240
gtctagtttt tttgttcgtt aataatagat gcttcctgtg gccccagctt ggcaattttg 42300
atttaaagtg atcttaactg aagagactaa tggacgggtc tgaatttgtg ccttttaagc 42360
acaaagtatt gctcttaatt aactggattc tatcctttga gcaggcagag gccttccccc 42420
aagggcgtca ttaacgatcc acatctggac atcttccaaa gccttcttct gtttcaggcc 42480
aaccgcaggt gtgttcctga acacccagga ggctatgaga gccacatatg cctcccaaat 42540
acacacagtg tgcatgccca gggacataga gcagtgtgca aagtcccatt ccatctctct 42600
ccacctggga gaggatggct cttctgtctg attcatggct caaagtggta aaggagctcc 42660
ccactccccg tcccacgcct actcagagtc tgcaaatatg tatgcgatat gagagctcgt 42720
cagttagctg tcttcagtgt ggcgcacatt tgaggagtct gactcccctc cagcacaggc 42780
caatgtgcac tgctctccta tctttgtacc cccactgttg cactgtgcag aggttggagc 42840
catagaagta ccagagctgt gaaaggagag gccccctctc acctctgccc tggtctccat 42900
ccccactttc tctaggaagc tagtaggtgc tgacagggga gagaagggag gggaggggtc 42960
cagaaacagt ggctcatgcc tgcaatccta gcactttggg aggctgaggc aggaggatca 43020
tttgaggtca ggagtttgag accagcctgg gcaatgtagc aagaccctat ctctacaaaa 43080
agaaaaaatg taattagctg ggtgtggtgg tgggcacctg tagtcctagc tacttgggag 43140
gatgaggtgg gaggattgct tgagcccaag agtttgaggt tacagtaagc tgtgattgca 43200
ccactgcact ccagcctggg caacagagct gagaccctat ctcaaaaaaa gaaaaaaaaa 43260
aagaaaggag agagagagaa agaaaagaaa agaaaaaaaa aaaagaaggg aagggaaagc 43320
ccagaagagt gtggggagag gaggcggccg tcattctggg gccctcagtg tgcacaacca 43380
gataacacat gctctgtggg cttttgtacc attttgcttg agcataaaga aaggaaggct 43440
gcccctaaat agaaagcact ctggaggcaa acaaatctga ctccaatcct ggccctgcca 43500
ctttcccagc tgaggactta gacaagcacc ctagcctctt ggacattctc agagccatct 43560
gctgcaagtg ggtgctgcca tacccacctt actgggcagg cttgggggac caagggtggt 43620
aaatggctca gtctttcatg atgcggccac acagcaggtg cgccatccag gtccatttct 43680
ttccttcctt tcccccaaat caagttgtca ttaaagtact agtccacatt aatgaaatca 43740
actgtattaa ttttctattt gctgctataa taaatcatca gaaatttagt ggcttaaacc 43800
aacacaaatg tattacctta cagttctgga ggccagaagc cctccatagg tgtcactggg 43860
ctgaaatcaa ggttttggca aggttgcggt cctttctgga gggtccaggg gagaatccat 43920
tttcttcctt tttccagctt ctaaaggttt catgcattcc ttggctcatg atcttctata 43980
gctatagtca gaaaaatttt ccatcaatca tcttcaaagc cagcaatggc aggatgagtc 44040
ctcacatcac cttgctctga caccagttct ctgcctccct cttccacatg tcaggaccct 44100
catgattact ttgggctcac tctgataatc tgggatgatc tctctatttt agagtcagct 44160
gactgggaac cttaattcca tctacaaccc caattcctct ttgccatgta cagtgacata 44220
ttcacaggtt ctggggatta ggacgagcct gtctctgaaa ggctacttta catgaaaatt 44280
catttttta attaagattt tttttcctc ttgagacaag gtctcactct atggttcagg 44340
ctggagtgca gtggtatgat cacagctcac tgcagcctcg acgtctctgg gctcaggtga 44400
tcctcccacc tcagcttccc tagtagctgg aactacaggg gtgagccccc atgcccagct 44460
aatttttttt tttttttttt tttgagacag agtctcactc agtcacccag gctggtgtgc 44520
agtggtgcaa tctcagctca cagcaacctc cgcctcctgg gttcaagtga ttcttgtgcc 44580
tcagcctccc aaggagctgg gactacaggt gtgcaccacc acgcccgact aatttttgta 44640
tttttagtaa agatggggtt tcaccatgtt ggccaggctg gtctcaaact cctgatctca 44700
agtgatccac caacctcagc ctctcaaagt gctgggatta caggtgtaag ccaacatgcc 44760
cggccccagc taatttttaa atattttttt tgtagagatg gggttttacc attttgtcta 44820
ggctggtctt gaactcctgg gctcaagcaa acctcccacc ttggtctccc aaagtgctgg 44880
gattacagca tgagccactg cactcggcct taagagaaga tttaataatt aatactttac 44940
aacaagatct ggaagaggtg ggatgagtaa ctaaatgagg atacaagtaa cccgggtcat 45000
atttgctaat acccttggtc acattgaact tgatatctta tcagattttc ctaatcagct 45060
cctttagcag cagtgttgca gcatcttatc tcattttgtt ttttgttttt ttgcctagca 45120
catgcctgta aatcactgga ttgaggtgtt tagatgtttg ttgtcctttg gatgcttctt 45180
ataaatccat atttcatggc tccctggaaa gtgctatgca aatgataagc tgcaaggatg 45240
gaaaggaaat tgcagtgctc ctgaattgta aatgggcttt tacgaggagg tttctaatta 45300
ctcgctcttt ctcttgaact gaggagttga agtgtaggtg gcagatccat aacagataat 45360
catgtgtgtg atgtgacttc agcctgagcg tcgaggacca agtcacagag caggaacagc 45420
cactctccag tgtccttggg gctacgtctg aggagaacct gggatttcat atatgacctg 45480
cactggctgg ggggctctct tgacgtaacg tgttccctct gagcatgtta cagattctga 45540
cattcttatg ttccttctgt ggagagacat gtacttagtg acctaactca ctttagcata 45600
tttttgctca tcgtttgtgt agcttaaagg aatcagataa ttaccccctc cccactactt 45660
tcggaagcac aaatgcaatg ccctagaatt gtactgggga ctcaaaaaga aaagagagta 45720
gtaaaatcta ttaaagggga caaagacagc ctatatacta caagctttct atttttatgg 45780
cagagaatgc cattttctaa gtaaacagag aactgcattt gacctgcaat atcaaatgca 45840
tggatttgat gctttggaaa gcaactgttt tctgcgttaa tctgggtgtc ttccgtgaaa 45900
tgtcctcctg cctttggctt aaacactagc tttgtctaca gccattccat cctgaacctg 45960
cccaatcttg tctgaatcct ggtttcacca ctgacaagct gtgtgtcctt gggcaagtta 46020
cttcacctgt ctgtgcttca gagtcctcat ctgtgagttg gggaatctgg acagaatcta 46080
ccccataggg cgtagtgagg atgtgttgaa ttatcccaag tggctacaca gagtaagcac 46140
tcaaatgatg tcatcgttgt catgattgct gttaccagag cctagagttc attctgatac 46200
tcgagtctgt ggcccatcca gcccaggtaa ggaatagttg gaggagttgg gcatgttcag 46260
cttgaagagg agacgacagg ggatatggga tagttgaatc tgtgaagggc cccctgggat 46320
gaagaactgg catgttctgt gtggctccag ggcactgagc aggacccatt tgccaaagtc 46380
tcagggacac agtttctagc tatagacaga aaaattttct gtcactcaga ggatgaaaat 46440
agaatgagcc cccttaagag gtaatgagct ccctgtcatt ggaaggattc cagaagagct 46500
aggtaaccac tttaggtgct atcaaggggc ttttttcttt aaagtccttt ccaaaagctt 46560
ctgagattgc ataaacaata ggaagccatc ttggtgcttt aacacaaact ctccccagtg 46620
atgagggttg agccaaagcc agattggcaa gcagagagga gacttgtgta caaggagttc 46680
ctcgagtcaa ttgctttttc cttgttctag ccagccagag ggctcctgtt ggaaaacagg 46740
agaccggaga ggctgaggcc tgaccaaacc agcttctgca ggccagctgg gaggccacaa 46800
ctcctaccta cgggaaaact gaagggcatc tctattttta gattagcaaa agaaaataaa 46860
tttaagtttg agtctccttt gcaactttta aaagacatct ttattgagat gatcattcac 46920
attctataaa attcccccac tttgagttac aattcagtgg ttttagtctt ccttgatgat 46980
tttgatggtc ttttcttaag gctcttggaa gacccagaag cctctcagac acaggtgggt 47040
gtggagggcg tagcacagag gcagacttct catttcctgg gtctcccctt taatgactct 47100
cagagacccc tccttccccc tgcccctggc ttctacccca ggggtgtaga gttttgccat 47160
tttccaagca gaacttcatt tcctcttctg tgtctacact ctttgtgctt ctttcttgcc 47220
agctttttct cctttgcccg cccttccttc cttccttccc tccctccctc cttccctcct 47280
tccctctttc cctccttccc cccttccacc cttcccccct tccccccttc cctccttcct 47340
tccttccctc cttccttcct tccttcctgc cttccttcct tcctgccttc cttccttcct 47400
gccttccttc cttccttcct tccttccttc cttccttcct ggtatgtgac taatttctgt 47460
ttcaggacat aaatgttgtc caggctgttc tttggtcttt ctgttggata atggacattt 47520
ggcattgaga gaggctgctt tttctgaaat catgttcttg gggcccagaa cctaggtgtg 47580
tgcttctgac tttgttttct tcctgatcca aattctgata tgtccattta aattgatcta 47640
gacccacagg gcactgtggg acagatcctc agtggaacat gactctgtaa cgagagcatt 47700
ttgttttgtc aaaatgagaa catattattg cctttcatct gattgtaaac ataatacatg 47760
tttataaaac agtataatga gacaaaaatg tagacactaa taagggaaaa tctccctaat 47820
tgtatttctc ttcacagaga aagcccctgt tgggcatata tactctagtt tgtttatttg 47880
tttgactaca catatatgta ttcttttctt atgtataaaa attctgaaca tgcacatttc 47940
tgcaactact gttttcactt gatgatgcat ggacctctct agagtgtacg tttcttcttc 48000
cttacaaagc agttggcttc gcccagggta caccaggaca cggttttggc tctgtcccca 48060
gggtgtcacg ggaccagggg atgatctcac agggtctgcc atctgccctg cctggccgga 48120
ggctgcatcg agagggccaa ggggcaccac gtgtcgtggg tactgtcaaa caagagcctt 48180
cagagccttc cacagtcttt cttttgcttc ccagcattgc ttccccgctg gtggactctg 48240
aatctagaac tagctccagg cgcctctcca aattcagacg ggagctgggg cactattata 48300
atgcaaatct aggcaaagcc ctcccaatac caggatccag aatggggtgg ggccctttgc 48360
cctgaaaagc tgtttagttt gaaaatacaa acaggagaca gaaaagtttg gctaaattaa 48420
tggataaagt tttaacgatg gtaaccatag tagggttcat cgacagccag cgatggttct 48480
gaacacttga catgtattaa ctcacctaat ccccacattt tacagacaat gcaaaggagg 48540
ctctgggagg ttgagtgact tgccccaaag tcgcacagct cctaagtgaa ggattcggag 48600
tggactccag gcagcctggt ctgactccct gcactgcgct gtgcttatct ctggccccaa 48660
tgccgccatg cagaagtgtc tgggggcact ttgtctctgt cagacagaat tcggagatgt 48720
gtatgcttgc cctggtatgg cacttctctt tttttgagac agaatctcac tctgtcaccc 48780
tggctggagt gcagtggcat gatctcagct cactgcaacc tccgcctccc aggttcaagc 48840
aattcttgtg cctcagcctc ccaagtagct gggattatag atgtgcacca tcgtgcctag 48900
ctaaattttt gtacttttag taaagatgtt gttttgctgt gttggccaag ctgatctcga 48960
acttttggcc tcaagtgatc tgcctacctc agcctcccaa agtgctggga ttacaggcat 49020
gagccaccat gcctggcagt gtggcacttc ttacgtgtgt tcagcggaca ctgtttatct 49080
tctgtccctc caagacggtg ctgagctcag gtcgttcatt actggcagac aactgctgat 49140
ttccaacaga attgccatcc tcttctcccc tgcgactttc agagtgtgac ctcagactca 49200
aaaattagaa gtgaaaacat cttaaaaact atcacctttt cttcctaatc ctcctctccc 49260
ctccctgtct tccttgttgt ccccatctaa tgaactatca tggcaaaaag agcccatttc 49320
tggtcatttt ctgtggcctt tcaaactccc acctacccca ctgctcctgg gtgcattacc 49380
cgaaagctga gacttcagtg cagaaagtgc caggccctct gtccccccag atcgccttcc 49440
ttgtcttccc tgtgcttgcc tgtcacattg tgtgggttcc agcgctggaa ggaatgagga 49500
acagattctc tggttctcct tttgaagttt accttcgctc caccacttct gagaccttcc 49560
cggaagttgc cccttgtttc tctcctctcc agggctgccc cagagctgcc tctcacctct 49620
tcctgctgtc accccaccac catcagggca gaagttggga caaagcctct cctactggct 49680
cctgcttttc tcccttaggt ccagcctcct cttctccatc ttcaggagtc tccttctcca 49740
ctcacacgtc atgacttcag cacctcgcat cagtccagaa tatgactgct tgttcaagtg 49800
ccacctttct catgcatttt tttctagtga caatcacagc caccctgtgg ggcaggagtg 49860
tcatcatccc catgtttcaa atgaagaatt gcagttcaga gagggcaagt gactggccca 49920
gcctcaacag ctagccagtg gaccccacca gggcttctga ctccagtccg ggttcccttt 49980
ccacccaaat ccatggaggg agctgagccg agaacaggtg tccttcagga agacgtgaag 50040
ccaaagcctc cacctccaaa ctcaggggcc cagggagtcc aggcacccat ccactcacaa 50100
ggctggatat ggtgcattcc aggagagggg ttgggggcga gtggcctctc tgtgtacccg 50160
tggggataga tgcgcaagtg gcatcgccac atcgtgagtc ctggcttcat gggtgagctc 50220
caggtccaac gagaagccaa gcagggggcc cttcaagctc agctttgggc ccgggtcggg 50280
gtacagggta gagcgggcct ccccagcccc tgccatgagg ccaaggcagt gcatcgttcg 50340
cagcgtacat tcagaaacca aagcctagga gctggttatc attccggttt acagctgatg 50400
gaagagcagg tgcttccgag aacccacagt gctctttggc cagtgaccca agggtgcctc 50460
tgagaggcct cgcagcaccc ggaggtgctg ctgaggcaac gccctgactg taagaaggac 50520
cattcatcct cagagagtgg ccgtgatgct gctgcgacag tcccaccatc cctcccgact 50580
ctcactccca acagacttcc cactgtaaag ctgaactctc cagcaaatca cctctcgcca 50640
gactctctcc tcactctctc tgggtccact agaggttcct cagcctctct ttgccttggt 50700
tttcccagct gtaaaatgga gcaaagaggg cctatgtacc cacaaaggtg tggttggagc 50760
gactcctcct acattagggc ctcgagtggg gcttcatgat tggttggtgg aggtctccaa 50820
acccacccag tgccaccgaa ggctgagact gcagatgcaa tgccacaggt gtccttcctc 50880
agcctgggca gctgaacatc atgtgtaaaa cggggataat aagataataa cagccccttg 50940
cacctatgtg gctgtgagga ttaaacaaga taaatgtgta acagtgcctg gctatagaaa 51000
tatttactct tgttattaag ggaagaatat gtgtggctaa aaagggatcg aagatgtaaa 51060
agccaatccc tccccctcta gcatatttaa gggtaatgtt gagttggttt gtggaccatt 51120
tgctgcctgt tagagctgga aggtagggac cccctctcaa cagcgatgct acaaattata 51180
cccattggag gtcaaccaaa agacaaagct tattggctgg acatggtggc tcacacctgt 51240
aatcctagca ctttgggagg ccaaggcagg cggatcactt gagatcagga gttcgagacc 51300
agcctggcca acatggtgaa accccatccc tactaaaaat acaaaaatta gctgggcgtg 51360
gtggtgcaca cctgtaatcc cagctactca ggaggctgag gcaggagaat cactagaacc 51420
caggaggtga aggttgcagt gagccgagat cgcaccactg tactcaaacc gaggcaacag 51480
agggagacgc aatctcaaaa aaaagaaaaa aagacaaagc ttgttaatac cagcatattg 51540
ttaagggaat aaagtaggct gcagaacaac tggtgtaata tggtgccatg tagggaaaat 51600
tacatgtgtg cataggagag gggtctgcaa ggttgtgccc taagatgtta gagtggttcc 51660
tttgcttttc tcttttataa ttttgtattt gacttttaaa taaggaccat aaatcacttt 51720
tataaaatac attctctcca gcccctacta ctcctttaaa gaataagagt ggtttgccca 51780
agaaagacag tttttttgc tctggttttc ttgattctga catcagagga aactccttct 51840
catccacttg gggctctggg ttcaggggat tcatttcagg cagattaaag tggtgaccag 51900
gggcattcgt ggacacaggg agggacagga gcaccatcag tttgtctcac acaaccactg 51960
tcatcctcac tgaaggctgt tgcctgatca aaaacagtat tgggccaggc acggtggctc 52020
acacctgtaa taccaccact ttgggaggct gaggtgagtg gatcacttga ggtcaggagt 52080
tcgagatcaa cctggccaac atggtgaaac cttgtctcta ctaaaagttc aaaaattagc 52140
caggcgtggt gggtgcctgt agtcccagct acttgggagg ctgaggcagg agaattgctt 52200
gaacccgaga ggtagaggtt gcagtgagcc gagatggcac caccacactc cagcctgggc 52260
gaccgagggg gactctgtct taaaaaaaaa aaaaaaaaaa aaaaatatat atatatatat 52320
atgtcaaaaa tggggtagtt tttagatcta tagtagttct aaaaacaaag gccatccaag 52380
catgacagat ttacaagcac tattggctat tccagtagtt acaatggagg agagaagctt 52440
ttagttaaaa caaacaaaca acacaacaaa cccagaaacc ttaggtcaaa accaaaattg 52500
tcctctcaga cacaatctgg gaattttctc atgacagtgg gcattagcca actgacatca 52560
gcagcaacca tccgtgtgca cacagtggca ccacctcctc ccaaaaagca gccttcatct 52620
atgccctcat acaatcgttg attattctct ttggattgag gcccggaatt atttaagttt 52680
cttcttgcca gcatgagtct ttcctttctg tatgctcctt atcttctctc tttaatttgg 52740
cagttctgct tgaaatctgg gtctttcatt agtagtagtt caatttggtt ccagaacatt 52800
ctgtggtgtg atgcaatgtg accagagctc acacttcaga gctcttcaag ggccagtctt 52860
actgagcacc tcccagtggc tgcctgtgtg ctgggcgcca cttgtggtgg gcaggagaga 52920
ggaggggaca caaaaggaga cacagctcct tcttagaagc tcaaagttgg ggaccagctg 52980
ccacagaaga gtatgtttag catctgagac accaagatcc agcgtcacaa gggtgtttat 53040
taagcctcct catctctttc tttttctttt ttttttttt tttcctcagg cagtcttact 53100
ctgtcaccca ggctggagtg cagtggcatg atctcggctc actgcatgca accaccacct 53160
cccgggttta agcaattctc ctgcctcagc ctccccagta gctgggatta caggtgccca 53220
ccaccacacc cagctaattt ttgtgttttt agtagagaca gggtttcacc atgttggtca 53280
ggctggtctc gaactcctga cctcagatga ttcacccacc tcggcctccc agtgtgctgg 53340
gattacaggt gtgagccacc gcgcctggcc ttgctgttga ttcatctata gtatgtttga 53400
cttgatgacc tccagttacc ttagacagag gttctcatct aagctccaac tttccatttc 53460
ctttgtcctc gtctttcccc ttaacccctc cacatttctc tcaaaatcac cccacttcta 53520
aaaaatactg tttatttttc ttttaaattt caaattatct atactcattg aaataaatca 53580
aaatagcatg gaataagcga aaaaaatgga tcccaccctt ccccactccc attccctagg 53640
gctaaccata gttaaccatt taatgactag gtttttttgt tgttgttatt ttttatttat 53700
ttattttgag acagagtctt actctgtcac ccaggctgga gtgcagtggt gtgatctcgg 53760
ctcactgcaa cctctgcctc ccaggttcaa gcattctcct gcctctgcct cctgagtagc 53820
tgggattaca ggtgcctgcc accacacctg gctaattttt gtacttttgg tagagacagg 53880
gtttctcaat gttagccagg ctggtctcga actcctggcc tcaagtgatc tgcccacctt 53940
ggccttccaa aatactggga ttaaggtatg agccaccgca cccagccctc ctgggctctt 54000
ttcctttagt tgcactcgct ccccgctcct ggagtagagg gatttccgag agactgtggg 54060
ctccagcctt cacctaggcc caggactagg atgcctgccc taacatttat ctttatacct 54120
taaagcaaaa cagctggacc ataagcattc aagaacaaac tgtgaataag gagaaagttc 54180
tcccaggaaa caagagcttt agttatgttg ggccagccct tatattcctt agctgttacc 54240
agtcactgct tgatttaatc tcggctatca cttggcctga caggtctgct gctggtgcca 54300
ggatgtctgg gttttgaagc ctggctccat tacatacttc ctgtgtgacc ttgggcaact 54360
tactcaacct gtctgttcct cagtttcccc agctgtatta tgtcagcata atagtttgtt 54420
gtgtgaatta aatgaggtaa taactggaaa tgcttcaaac atggttccta tcatgagaaa 54480
tcctgctttc cgcctaaatg tgctggaaaa ttcctggtgg tgcagaacag gagaccagag 54540
caaaggaaag acagggtgca gaagccaaaa attaccttgg agaacaaagc gcatgttaag 54600
gttatttttg gattctaggt ttatctctgc ttggtcttca gttacctaca agagatccat 54660
ttaggggatt tttgtttgtt tttaacgata gctttattga gatataattc atatgccata 54720
aaagtcactc ttttaaaatg tttccggtat attcacaagg ctgtgcagcc ttccctgtcc 54780
ttgattccag tctgagtttt taactgaagg gataaggagg accacgcttt ccccagacca 54840
gaaccgcggg ccagggggcg attccgctga gtcaccgcgg gcgcctggtg cgcggcggcg 54900
gagcccggga ccttccttgg ctgcccccta gcgagggccg cagcgcagcc tgagacaccc 54960
gccggggccg ctccacggcc gtcggattta gactggaagc tcggtccagg tccccagctt 55020
gatgcgcccg cggtgtagga gaccagcccg actcgagctt cccctgagcc cctggactct 55080
tgactccagc agggcctggg taatgaacgt cagctcccct ttcccaaagg ggttgctctg 55140
ttgggaaggc acccgtttga tacagtagca tagagatggg ttttagcatc aaaatatcag 55200
aattcaagcc ttgctctctg cttactagct gtgtgaccct aaaaaggttt ctgaacgtct 55260
ctgagcttca gtttcctcat cattccttct cacggggtgg ttgtgagcat tacagagatc 55320
ctctctgtga agcccctgtg agtggctcat cctgagggct gaaataaaca tgttattaat 55380
aatccaaaac tggcaaggga tgttgactgg tccccctccc ttgcccaagg agctttctag 55440
aacctgagtt atcattacca aactgtactg ccttgagtaa gaaagttaga aggaatggga 55500
aggatggtgg caggtggagg aaggcggatt ggtcatcacc tccttgcagc aagaaacagc 55560
cccagatcgt gggaaaccta cagacctgct agacagacta ggagcaaaag ctggggcttt 55620
aagaatcccc agggaggttc tcctgagaga gtagccagtt ggattttgta agcagagatt 55680
tgtttgggga ggaggtgaca acgtagggag cagaggggca aagctgtcgg gaatcctgcc 55740
ttgagggcag ggatgtgtgt tggggggagt tgggtcactg gggctcggtg gccttgggca 55800
agtttctacc tctcaggtcc tttacccacc tagggtcgcc atcctgccca cctcacaggt 55860
tacagtgagc ctggatgcac tgtcatgggc aggtgcccag gaaaatggca gacatgttcc 55920
aaacagcacg cagcattccc cagtgatgcc cagggtcacc ttggaggtgg gcgagatgcc 55980
tggggtttct cgtccacccc acaacacctc aggggacagc caaagctgtc ccttcaggta 56040
agctgcacag aagatgtgaa ctctgctgca aagactctat tctttgggag caaaagggac 56100
ccagggtctc acctgcacat ccctgtccct gagggcctag gggttcttgg aggccccagc 56160
cttggcaaaa tgaggaagaa ggtgaaggtt gtctgggccc ctgccaggct ccttcctcgg 56220
ccacgcactc cccttcctgc acacacaccc ttctccctcc accccatctc cattgttgtc 56280
agaaaagtca caataaaaag gtccatattg tctagttccc atacttttaa tttttaaaat 56340
tttatttatt tatttattta tgtatttttt gagacagagt cttaacccag gctggagttc 56400
agtggcatga tctaggctca ctgcaacctc tccctcctgg gttcaagtga ttctcatgcc 56460
tcagcctccc gagtagctga gattacagat atgtgccact atgcccagct aatttttgta 56520
tttttagtag agacggggtt tcaccatgtt ggccaggctg gtctcgaact cctggcctca 56580
agtgatctgc ctgcctgagc ctccggaagt gctgggattt caggtgtgag ccaccgcact 56640
cggctccaca cttttcactt attaaaagac tgtggtgtcc atcaatggat gaatgaataa 56700
accaatgtgg actatccctc ccattaccca aggaatgaag cacggagccg tgccaagatc 56760
tggattcaca gtgaaagaag ccagtcacca aaagccacgt gctgtgtgac ttcccttata 56820
cgaaatatcc agaagagata catccatggt gacagaaagt agatgagcag ctggggactg 56880
gcgaagggga gaagggggag cagctgtcta tgaggtccag cctttcttct gggtttggtg 56940
agaatgtttt ggaactagat agaggtgata gttgtacaac attgtgaatg tactaaatgc 57000
cactgaatca ttcattttaa atcgttcttt acgttgcatg aattttaagt caatcaaaaa 57060
cagttgtttg aaaagagaaa agcctatggg tagcggcagc agtgattgga tttatgattc 57120
gattccatgg ctcatccctc ccctgcctca ccccctcgcc ctccgacgtc ttcttctttt 57180
actctgaact gttatctttg ttctcatctc tctctctctc tctcaaccct gcagacactt 57240
ttccctttct ttgtctgccc ccaccctcca gatttccgtg tctccagtgt ctccctacga 57300
ggcatgaatt gagactggga gggtgtgatt ctgaagaagg caccaacagt gactcagcta 57360
gccccttccc ccaccccgcc ccccgggcct caatttagct aaaaaaccac agggacggac 57420
tcaggaggca ataccctttcc aagggtccct aaaaaatgtc ccattttagt gtccaggttt 57480
cactcaactt tagtgcctcc cctaaaatgt gttccttacc tcccacccca ctgcatctaa 57540
gtcactgcct gagaaaacag gattgaggaa aggagaaagg aagagagaga gagaggagga 57600
gagagagaga gagggaggaa ggctgatgga tttagaaaag aagaaaacaa gtggtctgag 57660
gaaaacagcc ttggtgtgtt tattttcctg tctgtgtatc gcttctcggc cttttggcta 57720
agatcaagtg tattttcctg tctgtgtgtc tcgcttagat tacagggatc tgtgggtgat 57780
gacacgtctg gtccaggctg cgtagtcacc tcaagggcat gcttattgat gtgtttttca 57840
attcactatc tttgcatggg agtcccaggc caagaggcac agctgcgcca tttgtctgtt 57900
ggtttagata tcctttatcc agttcttcca gagaaatcat cctgcccttc tggaggaggt 57960
gggcagcagg ggtcagagat gggagggaaa ggaaggagcc aggtccttgg ctaggatgcc 58020
agggtcccct gcctctcacc tggcctgggc tggaggcctc ctgctgtcct gtcactgatc 58080
actaccccgc cccagcctcc tgagttagaa gacacaggct aaagtagagt atttcttcat 58140
tgaaaaaccc atacaaaata aaggttcata aaaaataaaa atttagactg ggtgctgtgg 58200
ctcacacctg tgatcccagc actttgggag gccaaggcag gtggatcgct tgagccctgg 58260

```
ggttcatgac cagcctgggc aacatagtga aaccccatct ctacaaaaaa tacaaaaaat  58320
tagccaggca tggtggtgca tacctgtggt cccagcttct cagcctatgg acccacatag  58380
aatacaatgt cagcataaga agggagccct ggggtcacca aatggtttgg gcggcaaaga  58440
acctgaaggt tgagagaagt ggcttggtta cccagctgtt ggatgtgaga cctggccact  58500
gcttcttcca taccctagac ctgcaccctg acatctcaag taaaaagttg ggggatgttt  58560
tatggtccag gatgaaggaa gggcagtgag gggcagcgga gcatcacttt gcatttctgt  58620
ctgcctctta ctggctgtgt gacctggggc aggtaacttc ccagactcct gggaatcata  58680
acacctatga tgatgatgat gatgatgatg atgatgatga tgacacctac ctcaaggatt  58740
gccctgaagg gtcacagaga tgcctgcaag gcacctgcat ggagcaagcg ccccttctct  58800
ggcaggtgct gggtgagcac tacctgctgc caggccctgg ggctatggca ctgcgtgacc  58860
ctgcaagtcc tacctggcga agctgtcgtt cttgtgctca gtcagtgttg gttgtaagac  58920
tgagaagagt cacttcattt tgctctccag ggacatcttt ctgggtccta ttttctgcct  58980
atgtcaagta gcgcctcaag gatgctcctg aaaatgggct tgtctttctt aacatggcag  59040
gtaggtccca aagcattagc atggggcagc tgacctagcc cagccaatgc agtgcagtga  59100
ctcttgcaac cgagtctaat cagaaggtcc atgaacctac gagcatttcc tgtcccagga  59160
tcagggtgga ggctgagcct ccctgcttag agattcttcc catgcattcc actttttttcc  59220
ccaaaagaaa atattgaccc ttgagaggca cacagtttat ttattttgca tagtaaatag  59280
tagcctgtat tttaaggatg agttgatttc tgcatcagcc cctgtaggtc atcagccttc  59340
tattggtgca tctgactctc tctagccctg cagggatggt ggaggggggag gggaaggagg  59400
gatctttatt ggaaaccagg acagtgagac tcattgccct gtcatctgct ctgtggtgct  59460
gaatgaggca gcccaacaga gaaataccct gagcgagcat ccccagcctc caaaacagtg  59520
gcgcattgcc ctgagtcctg ggaatgacct ttgattctcc tgctcctgac ttggaaccca  59580
tggaaacctc tagaagcagc tgaggaaaac ccaacatgaa aagcagaact ccacactgag  59640
aatataggag gtgatcggaa catacaatga ttcttgctaa gaccgattca cagtttttct  59700
ttttttcga tcgaagaaat actggagaag cctaaagaag gagtctaaaa actctggcac  59760
gtgggccaaa actgtccttg agctaagaat gattttcaca tttttaagtg gttgaaaaat  59820
gaaataaaat aagatgatgt tttgtgacac atgaaagcta tgggaaattc aaattctaat  59880
atctataaat agtgttttat cagaacacag tcatgctcat ttatttatgc tcgatggctg  59940
ctttcccgct acaattacgt tgagcagtta caacagagac cacgtggccc acaaagcctt  60000
acaatattta ctatctggcc ctttccagaa aaaaatgtgc cgactcttga ccttaacctc  60060
agcaatttgg gaggccgagg caggcggatc gcttgagctc tggagttcat gaccagcctg  60120
ggcaacatag taagactcca tctctacaaa aaatacaaaa cattagccag gcatggtggt  60180
gcacacctgt ggtcctagcc actcgggaga ctgaggtggg aggatcgcct gagcccagga  60240
agtcgaggct gcagtgagct gtgatggcac cactgcacct cagcctgggc gacagagcaa  60300
gaccttgtct ccaaataaat aaataatgca aagtaaaata aataaaacca tataaaaagg  60360
aatcaattta aaattataat gaaagctggc cgggcatggt ggctcacgcc tgtaatccca  60420
gcactttggg aggctgaggt gggtggatca cgaggccagg agatcgagac catcttggct  60480
aacacggtga aaccccgtct ctactaaaaa tacaaaaaaa aaattagccg ggcacagtgg  60540
cgggcgcctg tagtcccagc tactcgggag gctgaggcag gagaatgtct tgaacccggg  60600
aggtggagct tgcagtgagc cgagatcgtg ccacttgcag tccagcctgg gcgaaagagc  60660
```

gagactccgt ctcaaaaaca aaaacaaaaa caaaaacaaa aaaaaattat aatgaaagcc 60720
aaggggcata gtagaacaaa ttttctagag ctcattaagt caaatgagtc accagttagt 60780
aaaacgcagt cacggggaag agagggcagg attctttgaa gcagcggctc tcctaaaaac 60840
aacccaccct tgtccagctg ccttccctcc tgagggtgtt ccctttgact gtgtgacccc 60900
catcccctat ttcccaaccg tccaagccca cctctagcat aatacgagct tttaatccct 60960
ctccctgacc ccaacccgat tttgaagccc agtctagtat tttctcaaat acacttcttg 61020
gctccattcc ttcctttcca tcacctctgc cttttcactg catgcttgga ccactgcagt 61080
cagctcccta tgaacagttg ctctctaccc atccaatcgg ccccgcctgc tgctgccaaa 61140
ttcaccgagg gcacctctgt ggtgctgcct gtggacaaag tccaagccag ccacctcacc 61200
cacctacagg tgagtgggga gcagccagcg tgtccagtgg tttaccccat cgccacagac 61260
ttggtgatgt gtcgatgtgc agagaagggg tgttggcagc cacaacacaa gcaaccccgc 61320
cccatgtgag atctaagatg ggcgtgctgg gagccacctc tgagaatcca acagaaggca 61380
gaggggagaa cggctcacac ggcacaaaca ctccttcctt tttttttttt ctttttcctt 61440
tttgaaagga gtctcactct attgcccagg caggagtgca gtggtgcaat ctcagctcac 61500
tgcaacctcc gcctcctagg ttcaagcgat tctccagcct cagcttccca agtagctggg 61560
attacaggta cactccacca tgcccggcta atttttgtgt ttttagtaga gacggggttt 61620
ccctatgttg gccaggctgg tcttgagctc ctgacctcag gtgatctgcc tgccttggcc 61680
tcccaaagtg ctgggattac aggtgtgagc catggggcct agcctccttc catttaaatg 61740
tatgcctaat ttgcccattg agaacggctg agacgcattt taagtggcca gggtctactt 61800
agagttagtg ctcatgacca ggcccaggtc aagcctggct ggccagatgg tgcctttgac 61860
ctgctctgtc tctgtgcaaa ggaatgagct gaaggatggg ggtgcagtgt gtgggcagtg 61920
ggctggggct ggcaggactc agtgactaag ggaagagaac tttcctcact accagcctgt 61980
cttttcaggg caccgcgggg ggctttggga cttggtgatg aacacagcac agagagctgt 62040
ccagcatgcg ggtccctggc ttctcacact tcccaggctc cttcagaggc tctctccaaa 62100
gggagctgct ctctctagaa cccatgaatt tggaatatag gcaaccactg cattggggac 62160
cactgacctc aaacatagag accagagcaa atggggctca tcacgtgaaa ctcatctgga 62220
actctagcag gttcttttat atatatatat atatatatat attttttatt attatacttt 62280
aagttctagg gtacatgtgc acaacatgca ggtttgttac atatgtatac atgtgccatg 62340
ttggtgtgct gcacccatta attcatcatt tacattaggt atatctccta atgctatccc 62400
tccccactcc ccccacccca caacaggccc cagtgtgtga tgttcccctt cctgtgtcca 62460
agtgttctca ttgttcaatt cccacctacg agtgagaaca tgctgtgttt ggttttttttg 62520
tccttgcgat agtttgctga gaatgatggt ttccagcttc atccatgtcc ctacaaagga 62580
catgaactca tcatttttta tggctgcata gtattccatg gtgtatatgt gccacatttt 62640
cttaatccag tctatcattg ttggacattt gggttggttc caagtctttg ctattgtgaa 62700
tagtgccgca ataaacatac gtgtgcatgt gtctttataa cagcatgatt tatattcctt 62760
tggttatata cccagtaatg agatggctgg gtcaaatggt atttctagtt ctagatccct 62820
gaggaatcgc cacactgtct tccacaatgg ttgaactagt ttacagtcct accaacagtg 62880
taaaagtgtt cctatttctc cacatcctct ccagcagctg ttgtttcctg actttttaat 62940
gatcgccatt ctaactggtg tgagatgtta tctcatggtg gttttgattt gcatttctct 63000
gatggccagt gatgatgagc attttttcac atgtctgttg gcgaactcta gcagcttctt 63060
ttcacaagtt catggagaga ggtttcccac tgagggaatc acatctgtct gatcaaaaga 63120
ggcttgggaa atggctctcc tgttcattcc ctgaaaacct ctgatggaac cactgccact 63180
gtggcagccc cagcactggc accccagcca tgattggtgc cccagccaca tctctgctgt 63240
gagccccaga gccctggtta attaatcatc cacgtgttga tggggagagg cccattcaca 63300
aaagcgacat aaagcccagg gagacgtggc cgtggcaaga agggtgtggg actacattcc 63360
gcccccaact gagagattca gaaaccagaa aaaaatggaa aaacatactg tgctcttggg 63420
tgggaaaact aaatatcatg aagggagcaa tttttatagt tttggcctat aatacaattc 63480
cagccgaaat cccagtggaa ctttgagaat ttgcaggaaa aaaaaaaatg tctaaagtac 63540
atctggaaga caaacttaca agaaggtcaa ataattttga aaaagaaaat gatatctaag 63600
cccacctaga gaataagact tgagatccaa agctaaatca ggaggctcta gcaaaattga 63660
cagataagca ggacagagtg catggtgcat tcacctgggg aagagggcag attggtctac 63720
aaataggcct gggtccactg actttagctg ttatatttgg ggagaaactt ttcaacctca 63780
ctccatctta aacctaaaaa tattccagat gaattaataa atataaaaaa ttagaccact 63840
aaaaatgtag aagaaaatgg atgatctttc tataccatag agcaatggaa taaatcacaa 63900
aggaaaacag atttgactat ataaaactta aaccctgccc atcaaaaacc atcagaaacc 63960
aaaataaaag gcaaccaact ggagaagata gttgccacaa atatgatcaa gggttaatgt 64020
tattcataaa ttaagagccc acacaagtca ttagaataag cactgagacc tgaacagaca 64080
agcaaaaaga atgagagtgg gtcggcgcgg cggctcatgc ctgtaatccc agcactttgg 64140
aaggctgaag caggcggatc acttgatccc aggagttcca acaccagcct gagcaacatg 64200
gtgaaaccct gcctctacaa aagtcataaa tattagccgg gtgtgatggc acacgcctgt 64260
agtcccagct actcaggagg ctgaggtggg tggatcactt gagcccggga ggtagagtct 64320
gcagtgagcc aagatcacac cgctgcactc cagctggagc aacagagtga gaccctgact 64380
taaaagaaaa aaaaaaaaaa agaggagaaa aatgctgatc tcactagtaa ttaaaacatc 64440
aggccaggcg cagtggctca cacctttaat cccagcactc tgggaggctg aggcaggcag 64500
atcacttgag atcaggagtt ctagaccagc ttggccaaca tggtgaaatc ccgtctctac 64560
aaaaaataca aaaattcgcc aagcgtggtg gcacatgcct gtgatcccag ctactcggga 64620
ggctgagaca ggagaattgc ttgaacacgg gaggcagagg ttgcagtaag ctgagatcgt 64680
accattccag tccagcctgg gctacagagc gagactctgt cccagaaaaa attaaaacat 64740
cacatattta aacaactcta ggatatcatt taaaaaaaca ttaatagact gttttttaga 64800
gcacttttag gttcacagtg aaactgagtg gaaggtacag agacttcccg tatgttccct 64860
gccctccacg tacagcctcc cccactgcca acgtcctgca ccagagtggt acacttgtta 64920
caaccaatga atcctcatta acatatcatt atcacccaag ttcatagttt acattagtaa 64980
aacatcatct ttcatctata agcacaaaaa tttttggca tttatttagg tgtatgatta 65040
actcagtgtt gacaagactc acacttcata cccacttgca ctgcatctga gaagcaattg 65100
gtgtctacag ccgctacacc ctcaacaagc ccgatcttgt ttgaaaagca attggtgatg 65160
cttctcaaaa ttctatggac aaagtcagcc gggcatggtg gctcatgcct gtaatcccta 65220
aactttggga ggccgaggca ggcagatcac ctgaggtctg gtgaaaccct gtctctacta 65280
aaaatgcaaa aattacccag gcatggtggc tggggcctgt aatcccagct actcgggagg 65340
ctgaggcagg agaatcgctt gaagcaagga ggcggaggtt tcagtgagcc aagattgcac 65400
cactgcactc cagcctgggt gacaagagtg aaactccatc taaaaaaaaa aaattatgga 65460
caaagttttt caaaaagata tttaatgcaa ctttatttgt aatattggaa catctgaggc 65520
catttcagtg ctaactatta ggggatggtt aggaaaatat ggtacatatg tggaaaggaa 65580
catttggtag ttagtgcccc tgatgtttac aaaggctttt agtgaccaac aaatgctcat 65640
gctataatct tatgtgaaaa aagcaagtag cataattgca actatatttt taatgcatag 65700
aataaaaggc tagaaggaaa tatcacagat ccttgacata cattcccaaa cctttgtaaa 65760
tccgcggatt catgaaaaca gacacatttg cacaagtgcc tgatcttttc tgttatacat 65820
tcattagaag tcaagccctg gtgccacaaa gtatctgcct tttcaaatgt gatcagaatg 65880
ttctcttttg cttcaaggcc atttttcacg aagcagtggc atttttgcct cttcatcaga 65940
gtcaccgtgt gccctggagg actgagaaca gcagagccgt tttaggatgg gacagggcag 66000
ccaggaggat tgggctcact ccctactgag tgcctcactc ccgtacagcc cccatagagg 66060
aagaggggtt caaatttatt cctcagccag atggcatgtg ccgcctgtcc tggaatttca 66120
catcacttat gatggaccaa aattccaaaa gctgaatcca tgattgtcaa agtctggtat 66180
ggcaggatgt caacagtaat cgtttctggg cagagggatg attttctctt cccatcttgc 66240
tttgtataaa tacattttct ataataaggt tgtattactt ttctcatcaa gaaatagcaa 66300
agtactgttt tactcaaaat atgaatagag ccaggcatgg tggcagctta tgcctgtaat 66360
cccaacactt tgagaggcgg atatgggagg atcactttag cccaggagtt tgagaccagc 66420
ctgggcaaca tagtgagacc cccgtcccca ctcccccaaa gaaaacccac aaagcattta 66480
tcctggatta ttcacagggg ccaaaaaaaa aaaaaaattc aggcctccta tagccatgag 66540
ctacgaatat gaaaatatgc aaatgtgtaa gaaaagccag cacatccgat ttttactttt 66600
actttcacac ctctgtccac catgttccaa gagaagaaac ttggtcattg aaaggaatag 66660
atcaaatcca aagaacaaaa ccactgtgct cattaaactt cttagtgttc acaaagcttt 66720
agctgcaggt tgaatggggc aacccgaatt ggctggctca cctgggctgc agggagcaga 66780
gatcgcgaca ctgcactcca gcctgggcaa caaagcgaga ctctatctca aaaaaaaaaa 66840
agttcataaa ttcaaagtta tgaattattt ttaaaataat aataatttac aataaagatg 66900
aggacaaagt gtgagtaaat ggtggtttct atccagctct gttgagctga agtggcatct 66960
ccctgctggg gcttttgggg aagaagggtg tgtgttgctc ttcagatccc aagcctcatg 67020
cccctactgg gccctgtggg gtgcttctca gcccaccagg agagccaccg ttggaacaca 67080
cacgtggggg acctggtggg tgccggtgtg gtgaatgggg gccacagcct gactccagga 67140
agccagcaaa ctcggagctg gaggagtcag gacacccccg atgagtcaag agttggtttt 67200
gctgccagtt gacatctgat tgaaccatct cttcacttct ccgtgcctca ctttccttac 67260
cagacaggct ctgctgatgc tgtccctctc ctgttcagtc gtgccctcac cgttaaagag 67320
aaagagcaaa ctgctgggca gcagcattga ttttttaat gaagtggaaa gagagctggg 67380
aataacaagt cgggcccacc tcacctgcct cacctggtgg gtttatttgt tttgtttttt 67440
ttttttgtt ttgagacaga gtttcaccct gtcacccagg ctggagtgca gtggtgtaat 67500
ctcagctcac tgcaacctcc acctgccagg ttcaattgat tctcctgcct cagcctcccc 67560
agtagctggg attacaggca cctgccacat gcctggctaa ttattgtatt tttagtagag 67620
atggggtttt accatgttgg ccaggctggt ctcgatctcc tgacctcagg tgatccaccc 67680
acctcggcct cccaaagtgc tgagatcaca ggcgtgagcc accatgcctg gccgtcacct 67740
ggtggtgttg aatatgaact gctgcggtgt tggtaaatta agcaagcaga tagatgtaaa 67800
taacgcttgg gcaggaatat ggagcacggg atgaggatgg gcggccaact gttagagagg 67860
gtagcaggga ggctgagatc tgcctgccat gaactgggag gagaggctcc tctctctctt 67920
cacccccact ctgcccccca acactcctca gaacttatcc tctcctcttc tttccccagg 67980
tgaactttga accaggatgg ctgagccccg ccaggagttc gaagtgatgg aagatcacgc 68040
tgggacgtac gggttggggg acaggaaaga tcagggggc tacaccatgc accaagacca 68100
agagggtgac acggacgctg gcctgaaagg ttagtggaca gccatgcaca gcaggcccag 68160
atcactgcaa gccaaggggt ggcgggaaca gtttgcatcc agaattgcaa agaaatttta 68220
aatacattat tgtcttagac tgtcagtaaa gtaaagcctc attaatttga gtgggccaag 68280
ataactcaag cagtgagata atggccagac acggtggctc acgcctgtaa tcccagcact 68340
ttggaaggcc caggcaggag gatcccttga ggccaggaat ttgagaccgg cctgggcaac 68400
atagcaagac cccgtctcta aaataattta aaaattagcc aggtgttgtg gtgcatgtct 68460
atagtcctag ctactcagga tgctgaggca gaaggatcac ttgagcccag gagttcaagg 68520
ttgcagtaag ctgtgattat aaaactgcac tccagcctga gcaacagagc aagaccctgt 68580
caaaaaaaaa agaaaagaaa aaagaaagaa agaaatttac cttgagttac ccacatgagt 68640
gaatgtaggg acagagattt tagggcctta acaatctctc aaatacaggg tactttttga 68700
ggcattagcc acacctgtta gcttataaat cagtggtatt gattagcatg taaaatatgt 68760
gactttaaac attgcttttt atctcttact tagatcaggc ctgagtggcc tctctttagc 68820
aagagttggt tagccctggg attcttactg tagccacatt aataaacaac atcgacttct 68880
aaacattcta taataccatc ttttggccaa attgacttcg cctcttcctc tctctttcca 68940
aatgaaatgt gtttcatttc actgtcagac cacatggttg gggaccccac agagcacaca 69000
gccctccctc tgccttccca tgctggccct tcacccactg ctggagtgcc aggttggtcc 69060
aagggttgga ccaagttgtc tgaggttgtc tcaaggttgg tcgaggctgt ctccgcgctg 69120
ggttgtgcta caaggagccc ttctttccat gggtgtggct ggcagtgagt gctcacagca 69180
acagcccaca gtgcagcccg agggcaggat ggactcagtc cctgcctcca tacccatttc 69240
taaggaggca aaatggcaaa cactctactt ttctctttta atgctaaaaa taagaaaaca 69300
ccttgcagcc cagggtatgg gtagtgcatg gaagccgtgg agttgtgagg tgggaagtga 69360
cctctgctgg atatgtctat tcaggaagat tgctggagtg ggtggggtct ctgggaggtc 69420
ccctgagtgt gggaagctgg gaccaccagc tttctcgcac agggagtggc catcccagct 69480
tggagaggtt ccaggactgg ttgggaggca cgtttcagat ttctatctgt tgaatcagcg 69540
aagatattgg attatgagga atttgggaat taggaaagtg ggtgcaggtg ggttgggggt 69600
aggtgaagga agacatgggc gtattggggg agcaggggct gctcagaggt gttccagaag 69660
ctctgggtga ggaggtgaga gggaccgggg aatgcagctc ggcccagcct ccctgcctga 69720
ggtcagccat cacgtggtga tggcaagatg gaaatgtgct ttctgactgc tccagccagt 69780
gctgccagat tcagctcccc agggagggca cctgagaggc tccaagccag gagatctgtt 69840
ttctcctttg ttttgttttt ttttgttttg ttttgtttta ttatacttta agttctaggg 69900
tacatgtgca caacgtgcag gtttgttaca tatgtataca tgtgccatgt tggtgtgctg 69960
cacccatcaa cttgtcattt acattaggta tatctcctaa tgctatccct cccccctccc 70020 cccacccccct gttttctcct ttgaatcctt cttagaggcc gggtgcggtg gctcacgcct 70080
gtaatcccag cactttggga ggctgcggca ggaggattgc ttgagcccag gagttccaga 70140
ccagcctggg caacatagtg agacctcgtc tctacagata ataattttaa aaattatccg 70200
ggcatagtgg catgcaccta tagtcccagc tactcaagag gcagaggcag gaggatcact 70260
tgagcccagg aggcggaggt tgccgtgagc caagatccca ccactgcact ccagcctggg 70320
cgacagagac ccccatgtca aataataata ataataaata aatccttctc agtcccttcc 70380
tcactgtgtc cccctccact gaatttttcc acctcctctc ccacttcccc cactcccgct 70440
ttccctctcc ttctctcccc actccatctt tttctttctc tgctgtttct cgtccctccc 70500
tcctctccat cccacaacac tgcctaccct gtccctgccc caccctggtg ctcaggatgt 70560
gtgaagtgag ggtggtagc ccccaagacc tcaaccccga aggttagcct gttgaaacca 70620
ctttctccca gctgcccccc tggcagttgg tgctgctggg ggaaactggg attgggggcc 70680
agattttgcc tcttttcctg acaaagagag atgaagagtt ctctcaccag gtgcctggga 70740
ctggggtgtg ggtgtcccag cctatcccag cgcatctgtt ctgcatcatg attaatagtg 70800
ctgctttcag ccgggcgcgg tggctcacac ctgtaatccc agcactttgg gaggctaagg 70860
tgggcagatc acaaggtcag gagttcgaga ccagcctggc caacatggtg aaacctcgtc 70920
tctactaaaa atacaaaaat taaccaggtg tggtggtggg tgcctgtagt cccagctact 70980
tgggaggctg aggcaggaga atcacttgaa tctgggaagc agaggttgca gtgagccaag 71040
atcgtgccac tgcactccag cctgggtgac agagcgagac tccgtcctaa aaaaaaagga 71100
gttttgctct gtcgcccagg ctggagtgta gtggcgccat ctcggctcac cgcaacctgc 71160
gcctcccggg tgcaagcgat tctcctgcct cagcctccca agtagctagg attacaggcg 71220
cctaccacca cgcccggcca gttcttgtat ttttagaaga gacggggttt caccctgttg 71280
gccaggctcg tctgggactc ctgacctcag gtaatccgcc cacctcagcc tcccaaagtg 71340
ctgggattgc aggcatgagc caccgtgccc agtcaactcc ttctcaaaaa aaaaaaaata 71400
gtgctgcttt ctctttcaag tgtcctgatt tgggtgatag taaatgccac tctacttata 71460
agggatctac ctcagaatgc taattgggac atttttgtag cactctactg ttggcagcag 71520
gtgatgctca caacagcccg tgagggtgga tgacgtccgc ttcacagatg acaaaggagc 71580
ctcatgctca gaccgtgggc tgccagagca ggtccatggc tgcagcccca catggaccat 71640
atttccccct tgtcactctt tccaccaagc tcccttggaa cttcagttat taagctctct 71700
tgggtggaat ccaagttaga atcacaacat gtgcctcata tggattgtgc cagtgaaaaa 71760
tgacattcta tttagaggca gggcagcctg gcttagagtc agtttaaaat atgtattatg 71820
ctgcaacaaa tgtaccatga tcctgtaaga tgttcacaac aagggaactg gatgtggggt 71880
atactgtctg tactaacttc acaagttttc tgtaaatcta aaactgttcc aaaataacaa 71940
gttcgtttaa aattaactcc aggagaccag gtacggtagc taatgcctat aatcccagca 72000
cttcggaagg ctgaggcagg tggattgctt gagcccagga gtttgagaca agcctgggca 72060
acatggtgaa atcctgtctc taaaaaaaat cacaaaaatt agccaggtgt ggtggcgcat 72120
tcctgtagtc ccagctactt gcggggctga ggtgggagaa tcatctgagc ccaggagttt 72180
gaggctgcag tgagctgtga ttgtaccact gcactccaac ctgggcaaca gagcaagacc 72240
ctgtctcaaa aaacaaaaat gaaataaagt ccaggaaaga agtaggtttt accactctta 72300
ttttctgaag agaaaactaa atttaatgtg taaagtgagg acaagttcac caagttagtg 72360
tttgagttgc ctaaaatatg tttgctaaaa ctattcaaag ctttcacata aaacatgatc 72420
agaagttcta tgccaaaaca tatgtgtgtg tatatatata tgcactatat atactgtata 72480
taaaaatgca aaatctaaat tgccaacctt ttagaaattg ctctgaaagg aaagcatttc 72540
aagataattt gcttacccaa agaatatact ttccaagaaa gcaagtaata cttaaggtgt 72600
tcataatcct catcaaatta attcttgcta ctgaaagctt acaaggagct gttttgatgt 72660
cgggtgtgac aggtttgact tggcagaagg tgtcacttta ctaacaacat tttaaataag 72720
tgacagaaga caagaaacta cacgttaaat gccagaacaa agagtgtcta agtggatgct 72780
aagagttgaa atatggctgg atacctgccc aagagagctg aaaagtagat gaaagttggt 72840
tacctataaa ctagtgcacc ctaatgaatt aaaaggtgtt gatgagttaa cttgttatgc 72900
cttccagata agacatgcaa atggggcttc ttcctccttc actacttcca agggatttaa 72960
caaggagacc aatgcaaatg ataaggactg tagggctcaa gctggggaca gattggggaa 73020
agggggacca tcatgcccat atagatgtcc ctgtgccctg gcagtcaagg ctgctgaaaa 73080
ataacaaaac ccagaagtct gcgtgatgct gcctctccat ttgtccaaag ccttcttgcg 73140
gcagtttgca ggcttttgca aaagctccag gaccaaggag ctatgttcat gctggaagct 73200
tgttcaggat tagctgttct ttgtgggatg ggtgcagcca gggccaggtg tccagggaca 73260
gtgttttaac aaagggcatg aggtgtctga tctcacagtg gaactccact tgcctttttt 73320
tcatcttctc attctgcttc atgcacagaa ccagccccat cctgaaactg actctaaatt 73380
actcccgccc caggtggagt gcctttctcg gagttcaaca gagccttcct gtcgcccaag 73440
ggacaactcc actgaatgcc caagccacac ccaaaaccta acaagtaaaa accaaattct 73500
gtgctccccc atcctgggcc attcctggtt tctctactgc tgttggtgat accaccatca 73560
gcttgtccat catgaccctg gccagttcct cccacaaccc tccacagcac ccagggacct 73620
cacctccatt ccatccgaca cagatctcct caccacaaac cttggttttg caacagcagc 73680
catgagacct ttacaccctc cgcccttcat cctgtccccc actgaggccc cagagccatt 73740
ccttaaagca gcgcgccaca aactataacc cacaagccaa ttctggtacc cagcctgttt 73800
tgcacagcca gtgaactgac aatgatcttt tcatacagcc agaaaaacaa aacaaaacaa 73860
aaaacaacaa aaaaaaaccc caccattctg agcatgtgac ttccatgttc aagatgtctc 73920
atgttcagaa aggcccctgg aaaaggagga aggggagctg ggcacaaagg gagaccctct 73980
cagctgagct cctcccatcc agacattttc ctggacttcc tatccaatga cttcccttag 74040
cttcttatca gccacccctg tctgcccagg aggctggaag atgtggcctt ttaactgggc 74100
acagctctgt cctctatcat atcagggctc tgttcccaag gagggtagag agaatggaca 74160
ccaggtggac cctcagcagt ctgtgccaca gagggagtgt ttgcaatttc cagactaaaa 74220
gtccccatgt gcttgacggg gtatgtgact acaacgtgat gcttgacttt tcctcatatg 74280
accagagcca ctttgtccat ctggtacaat gtcagctatc tgctaggggc cctccaggat 74340
tcccagtcaa ttccatatct gcatcaccac cattggcact aaataaaata aaatactcaa 74400
gttcctgctg gtgagcatga gcagtgctac actgggccct tcaaccaagg tgacatgata 74460
atgactgaaa ataatcactg ccacttattg gggacgtctc atctgccagg catggtacaa 74520
agtgctttaa ataagcattc aacaatttca tgctgacaga agccctgtga gccagtggag 74580
ctactactat gcccattata caggggagaa aactgaggca gagagaggtt aggtaattcg 74640
ctcagcctca cacaaccaat aggtggtgga gccaggattt gggccccatc tgcctgactc 74700
tctagaggct ctatcttcca gtcttccaga gttgagtcta agccatgaat aggacaatta 74760
gacagcagag gaaacccatt cagccaccat gtgcatgaag agtaaggaat ttctgtcata 74820
cagaggggag tgaattcact gagctgagag ctgaggaacc attgatctga tggctgagac 74880
accactggga agactggaga ggcttttctg ggcatgcagt gccaggcaca ggaggagctg 74940
agggaagatg actaagaggt actggcaaag aattcagaaa ttctgatgga agctttacat 75000
gttaccatca catccatcca tctatccacc catccatcca cccatatctt cctccctcca 75060
cccaatcatg catacatcca gtcatctata caccacccac ccacccatcc atccatccat 75120
ccatcccttc atccatccca tcatccatcc aattatacat acatccaatc atatatctgt 75180
acataatcca ttcttccctc ggttcatcca tccatccatt catccatcca tccacccatc 75240
ccttccttca tccttcctat catccatcca atcatatatc tgtacataat ccattcttcc 75300
ctcggttcat ccatccatcc attcatccat ccatccaccc atcccttcct tcatccttcc 75360
tatcatccat ccaatcatac atatatccaa tcatacatct gcacatcacc agctcatcca 75420
tctatccatt tatccatcca tccttccttc catccatcat tcatccatca tacatacatc 75480
taaccataca tctctacatc attcattctt ccatcgattc atccaattat ccatcattcc 75540
ttcctccatc catcccatta tccatttgat catacatata tcatctatac atcatccatt 75600
catccatcca tccatccatc cacccatatc ttcatccaat caatcataca tacatcgaat 75660
catctacaca tcacccatcc atccatccat ccattcatct atccacccat ccatccatcc 75720
atccatccat tcatctatcc acccatccat ccatccatcc atccatccat ccatgtaacc 75780
atccagtcat atatccaatt acacatccat ccagttatac attcatacat gcatctaatc 75840
attcaattat acatacacac atccatataa ttctacatcc aattatacct ccatccaatt 75900
acacattcat acacccacct aataaattat taattcatat atccatccat ataattatac 75960
atcaattata catccatcta atcattcagt aattcaccca ccatccagtc atctatccaa 76020
taatacattc atccaatcat ccatccatcc atccacccat tcatccatcc atccgtccgt 76080
ccacccatca tggtatgagc catgatttac cacgatggtc ccctgtggac agcccaggtg 76140
gggcagaact gaagggaagc ccagggctgc ccccataaac atttgcctcc tttacatgga 76200
tgagaactag atccacatgt ataaatcctc atgatttgaa ggtgctttta ccaacattca 76260
ctcatgggat tctcccagga gctctaggag gaggcaggta gagttgaggt catctcacgc 76320
attttacaga tgaggaaacg gaggccctga gaggcaggtc caaggccacc tgaccagaaa 76380
gaagtggaac tgggacttga acccagccat cttgcccctt ggtcccatgc tctctagcct 76440
gtaactcctg cttcctggtg gggcatctcc aggaggaccc tatcggctgg ccatgggcct 76500
gccctggagt cttttgctct gtgtggccat ccttcctccc tcaggagagt gtgtgctccc 76560
agagcacagg ctgtatcttc tgagcatttt gtcccttccc agtacctagc actcagctct 76620
gtatacattg ggctctcaag aattctcaac cttccagagt gtaaggcctt gacctgctca 76680
gccctggata ctgcatgatg cattgataag cccataaaat aaccagggca gattgactcc 76740
cagtggccaa agtgccacag ggaagggaca attcagccct tctaggagga ggaggaggta 76800
gttttctcat ttctattaag gcaacaaaag ctgccttact aaggacattc ttggtggagg 76860
gcgtgactgt caaccactgt gatcatttgg gcctctcttg cccaggcttc ccattctgaa 76920
aggacagttt tattgtaggt acacatggct gccatttcaa atgtaactca cagcttgtcc 76980
atcagtcctt ggaggtcttt ctatgaaagg agcttggtgg cgtccaaaca ccacccaatg 77040
tccacttaga agtaagcacc gtgtctgccc tgagctgact ccttttccaa ggaaggggtt 77100
ggatcgctga gtgtttttcc aggtgtctac ttgttgttaa ttaatagcaa tgacaaagca 77160
gaaggttcat gcgtagctcg gctttctggt atttgctgcc cgttgaccaa tggaagataa 77220

-continued acctttgcct caggtggcac cactagctgg ttaagaggca ctttgtcctt tcacccagga 77280
gcaaacgcac atcacctgtg tcctcatctg atggccctgg tgtggggcac agtcgtgttg 77340
gcagggaggg aggtggggtt ggtccccttt gtgggtttgt tgcgaggccg tgttccagct 77400
gtttccacag ggagcgattt tcagctccac aggacactgc tccccagttc ctcctgagaa 77460
caaaaggggg cgctggggag aggccaccgt tctgagggct cactgtatgt gttccagaat 77520
ctcccctgca gacccccact gaggacggat ctgaggaacc gggctctgaa acctctgatg 77580
ctaagagcac tccaacagcg gaaggtgggc cccccttcag acgccccctc catgcctcca 77640
gcctgtgctt agccgtgctt tgagcctccc tcctggctgc atctgctgct ccccctggct 77700
gagagatgtg ctcactcctt cggtgctttg caggacagcg tggtgggagc tgagccttgc 77760
gtcgatgcct tgcttgctgg tgctgagtgt gggcaccttc atcccgtgtg tgctctggag 77820
gcagccaccc ttggacagtc ccgcgcacag ctccacaaag ccccgctcca tacgattgtc 77880
ctcccacacc cccttcaaaa gccccctcct ctctctttct tcaggggcca gtaggtccca 77940
gagcagccat ttggctgagg gaaggggcag gtcagtggac atctgatctt ggtttagtat 78000
ccttcatttt gggggctctg ggtgtggcct gggcctctgg actttggcca cggtgtttgt 78060
tccagccctt ctcctaacct gtcctttcca gacactcggc atctaggtta ttagcacctc 78120
gcatactttc tgacatgctc ctcagtcctg attttgacca tcttctcttg cttcccatct 78180
gtgtcagtca agactgcatt tggctgtaag aaacagaaac cccaactaac tgtggcattt 78240
acatgaagag gtttactttt ctcacataat cagatgtcta gacttggcca gcacctcaag 78300
ggtcattgat gctctcctgt ctttattttc tgtcatcttt agtggttgga ttgttgcctc 78360
atggttacaa agtggctgct gcacttccag gcatcacatc tgcctttgaa gcaggaacaa 78420
gttgcaaagt aaagtggcca aaagggccct gaaactaaat gtgtcccctt aggaaagcag 78480
gagttttctt gcaagtggca atcttctgct tatgtctcat tggccagagc tgggtcttac 78540
ggccacccct tgctgcgagc aaggctggga cattgagcat tttgccgtcc aacctcttta 78600
gcagaataaa ccaaggggga agaacgttaa tagtggcttt tgagtcacta gttggcagta 78660
tctgcccctc tatctttcca tcctccccat ggagtttcaa ggttcctttc tcagtacttc 78720
ttcaggctct gcacgttcat ttggatcttg tgtcttgggg tgaaaaactg gcccaagtgt 78780
ctccccaagc atccaccttt ggattaattt ggaaaatggc tgtcaagtgc ccgcctcttg 78840
cttggtataa tgctacagct ttagaggacg cagcaggcat gggccttgcc gctgaggttc 78900
ttagcctcat gagaatatcc agatcagatt ctcttggctc cttcttagag ccagtgatgc 78960
aagacacttc ctgctcatct tgtcgggacg gttttacaag ttgcctgcca tcctgagaaa 79020
gtctacaaaa cgatgccaga cctcatgcca gcttcccaag ccttgactct cagtgctccc 79080
tcaacaggat tctggaagaa tctcccaaac aagtcgcaat cccctctgga ccctgtgcag 79140
gcatgagact caagagcatt ggctcccacc cctggtggag ggaacactgc tggggctggg 79200
atcttgcctg gttgctccgc ctgcacccaa gacaaccata attaaaatgt ccttcattga 79260
acttggaaag ccttcaaagc tgacaactcc ttatgtgtac ccggaaaggc ctgggagtgt 79320
gccagggcat tgctcgggag ggacgctgat ttggaagcat ttacctgatg agagactgac 79380
agcagctcct ggtagccgag ctttccctcc tgcctctgct gtgaaggtgg acccatccaa 79440
cagtcaaatg cctgactctg gacaggagcg gacctattta ttgccatgca agggactctg 79500
cacttttgaa ttgtgggtca tgggcttgga tttaggggtt agagctggga gaagtcttgg 79560
aagtcaccta gagatgacac tgccattttg cagatgagga aaccgtccaa tcaaaatgga 79620

```
ccaaggactt gcccaaagcc tcacagcaaa accataggcc cccgcactaa ccccagagtc  79680
cctgtgctgt cttaagaatc aaatagttgt aagcaatcat ctggttttca gtatttcttc  79740
ttttaaaatg cctggggcca tgcccagcag tctgtttcac tgcagcgttt acacagggct  79800
gccgggcttt cctggtggat gagctgggcg gttcatgagc cagaaccact cagcagcatg  79860
tcagtgtgct tcctggggag ctggtagcag gggctccggg ccctacttca gggctgcttt  79920
ctggcatatg gctgatcccc tcctcactcc tcctccctgc attgctcctg cgcaagaagc  79980
aaaggtgagg ggctgggtat ggctcgtcct ggcccctcta aggtggatct cggtggtttc  80040
tagatgtgac agcaccctta gtggatgagg gagctcccgg caagcaggct gccgcgcagc  80100
cccacacgga gatcccagaa ggaaccacag gtgagggtaa gccccagaga cccccaggca  80160
gtcaaggccc tgctgggtgc cccagctgac ctgtgacaga agtgagggag ctttgcgtgt  80220
ttatcctcct gtggggcagg aacatgggtg gattctggct cctgggaatc ttgggttgtg  80280
agtagctcga tgccttggtg ctcagttacc tccctggctg cctgccagcc tctcagagca  80340
tttagggcct tctggacttc tagatgctcc tcatcttgcc tcagtcagcg cgtcagttcc  80400
agagacttct ctgcagggtt ttctggggca ggtggtggca gacccgtgcc ttcttgacac  80460
ctgaggtcag tccaccctcc tgctcagact gcccagcaca gggtcacctc ccaaggggtg  80520
gaccccaaga tcacctgagc gcacagaggg tgcagatgac tggaccacac cttttggtga  80580
tcttaatgag gtggtcccag aggagctcag acatgcaatc tagcatccag ttctgggact  80640
ctgtctcctt ttcaaacgta ttcatgtaga acaggcatga cgagaatgcc ttgtcaacat  80700
gggtgatggg gaatcaatca gacagggcgc cgggctcaag gctgcagtca cccaagagtg  80760
gctcagccca ccaggcccta ggaaacgcct gcacagcctg gagctcctgg agtcatttcc  80820
ttcatgtctt cttcactgca cttacgtaaa gatgccagcc attggtttgg tgatttggag  80880
ggtgcccagt tgcccaacaa gaaatgcaga agaggcctag ccaggatttc accagcagtg  80940
gagagtagag aagatgtggc cagaaaagag tttcctttcc ctcctaaaga tggtactccc  81000
tgcagctact ggggaagcct gcagcattct ctagggctct gtgtgttgag agcagcccca  81060
ccctggcccc ttctgagtgc atttctgctt tgtgacttga tccgtgaagt cccctgagat  81120
gggcagaggg gatgtcctcg aagctggggc agagcctcat ccttgaacgt gaaggacgtt  81180
tgaagactgt ggcatgatca caggatgaga tcacagggaa cttgagtttc tctcctcctc  81240
tcccttcaca gttatttcac tgagggaaat ccctcccctg cccagaatga aaactctagc  81300
caactcttga cttttccatc actccaaagt agttgaaagt acattagtct ccacagtggc  81360
aaaacagtgt gcaaaagcta aataattaga acagccagtc ccatgtgaca gtcaaagctt  81420
ctaactccat tcaaagttgc agccattccc ctcgagggct ggcagggagg ggaggggtaa  81480
gagaaacagg aaggttctta ctgagttggt cctggtgtga gctgcgtcac actccctgca  81540
gaggtttcaa ggagactctc tctctctctg tctccatggg gaccttattt gaattcttct  81600
actcttaccc cagcctgcca tctccagcta tcctcccctg aagagccctt ctgctgcgct  81660
ggattctggt ggccatgtca tctcctcggc cccgtgggag tctgaagatc tggctgcagc  81720
ctcacctctg aggtcctgct agttgccacc tcttaaacat gatctgaggc tcccatgcac  81780
tctgacctgt gcccacatgg ggcccacggg aaacacgctg gcaagcaaac tgtgggtgtg  81840
cagacggttc tcagggctgc agcacctgtc ctttgctctg cccccaaagc aaggccagcc  81900
catcttccat cctctagtgt tccttggtgg ggccctgacc acagtccacc aggtccctaa  81960
```

ccagagggga cacacaccag gtgtcctcaa tgtattgcct tgaaacagtt gtgctgggac 82020
tgtgatgggg ggtggccatg tagccacccc caccaccccc aagccactct ctccaaggaa 82080
atcctcctaa agatcccttt acatcctcca tgtggtgggg aggttctaga gttgggtgca 82140
tgtgtcttca gctactgaca atgcagacct tagttggcac ctcgctctgg cctatcctgt 82200
ttgctgttct tggcgctcca gtgaaactcc ccatgggcca tccagttggg gtgcagtgtg 82260
gccacccccct tgcaggttcc tgccttgctg gagagcacag ggccctcctg gctcttgtaa 82320
aacactcccc atggtacaga gaggccagca gtgatgtgag gcccaacctc cctccatggt 82380
gttcccaagc agctcccttt ctggggtcaa ggggtggcaa agacagtgca gcgtccaatt 82440
tctgactcaa gccgggcctg gctatcgcag ctctgcactg tgtgtgacag caaggcaact 82500
cacccagtgc cgtggcagtg accgtgtccg aggaagcctc ctcacaccct ctgtctcaag 82560
gactctggca tttagctgga cttgctgtag ctctgagcct ttctgccatt gccatcacct 82620
tgtcagaaac tcaggccgaa tctgcactca gagttgtgcc caggcagttg agccaacact 82680
tgctcagcga tattgtcaca tgacaaggca ctgtcaccac tgggcgtcgt gggtagcgca 82740
gtgtcggctg gatggacccg gagggtgtct gtgtcatgct agtgctagtg atgggagccc 82800
cgtgagccca ttgcccgccc tcccatgccc tcagcagctg cctggggaca gccaatggcc 82860
tgggtgtttc tgaggctacc acatggcttc caggaaactc gagaaccttt ctctcccttg 82920
cctacactct tcacacaggc ctgtgctggc cagcggtggg gatccggcat tcctatctta 82980
ggtgcagaaa gtgactgact cattgcaggc ctgggagata agactgatgg cccagccagc 83040
aagatgtatg gatttctcag aggcagtggc ctctgtcatt gtcctcagga aatgctggtg 83100
attctggtgg cctgaggtca atgcatgtca acgtggccaa cttgccttat aaactttttt 83160
tctggacaat tgcgtgcact gtcctgtaac agtgtcctgt tgtttatgat gcagaaatag 83220
gtgtttttaa agcctattga ttttggtact attaatgtgg tcaggaactt tctcagtctt 83280
tcttgtttgg ggtgagctgt ggcttcctaa acaggaaccc aagacacccc caaaagctgc 83340
tcaccagcac tgccagcctc cctcttacca agtagcaccc gttcaggaca ttctgcgaaa 83400
ggcatttgcc cagaagttgg gaggaaggaa atgtaacatt ttggggcacc taccatatgc 83460
caggcaccag gctaaacgtg ttcacacaaa ttctcttact aaccctcacc atccttctac 83520
aagacaaact agtatcttca tcttggggtt caagatgagg aaatggaggc tcagagaggt 83580
tgaatgaatg ccggtgcctg gatatgaacc ccatctgcct gactccgcaa cccaggcaaa 83640
gtctttcctt gaacttccca gcagccactg cttagacaca gcctccacaa ccatggctca 83700
gcagcaaatt gcttctctga cctcactcag cctgtgtgtc cttgttgagt gaggcattca 83760
ggaccctggt cccaaagtgg agaaagtctt tcctactagg tcatagctac acctgcatgt 83820
gggtgctgtg ccttttgttt agtgaacttt tatcaccagc atcctcagca atgacatttg 83880
cagagaagcc agagctgagg caccttggta ttcttgggat gtgactttcc tgaatgttta 83940
agggaaaatg cccgaaggta cagagagctt ggtttctagt aaacaataac tgtcttgctt 84000
ttaccccccct tcatttgctg acacatacac cagctgaaga agcaggcatt ggagacaccc 84060
ccagcctgga agacgaagct gctggtcacg tgacccaagg tcagtgaact ggaattgcct 84120
gccatgactt gggggttggg gggagggaca tggggtgggc tctgccctga aaagatcatt 84180
tggacctgag ctctaattca caagtccagg agattttagg gagttggttc ttatcaaagg 84240
ttggctactc agatatagaa agagccctag tggttttttt ctaataccat ttctgggtaa 84300
ttcctaaggc atttagtgtt ctgaaagatg ctagccttgt ccagcctggg agttgagaat 84360
gaatgtctaa cagaaactct aggccgggcg tggtggctca cgcctctaat cccagcacta 84420
tgggagaccc aggtgggcag atcacctgag gtcaggagtt tgagaccagc ctggccaaca 84480
tgtgaaatcc tgtctcacta caaataaaaa aattagccgg gtgtggtggt aggtgcctat 84540
aatcccagct actcaggagg ctgaggcagg acaatcgctc gaacccagga ggtggacgtt 84600
gcagtgagcc gagatcgcat cattgcactc cagcctgggc aacaaaagca aaactccgtc 84660
tcaaaaaaaa aaaagaaact caaatatgtg tgacaggcga ttctcactgc aggctgccct 84720
gtggctgatc caggagcaag gccttaacca tgtcatcccc aagcgattgc ttgtaaactt 84780
tcttctgtgc agccttcaac ccttattatg attttcttct caggaaccaa actgctgtat 84840
tcaagaaagg cagctttgtg taatcattta tcataaatat cttaagaaaa atcctagaga 84900
ttcctaattt taggaaatgg gagacctatg gtactgatat aatgtgggct gggcttgttt 84960
tctgtcattt gctagataaa tgaacttgag agcctactgt aaaatgtgga agcttctaga 85020
ttgcagaagg gctggaaaga cactgttctt ttctcccgag tgatgggatc tgtccagtat 85080
ttagagctgc ctctgaggcc atctgattct aggagactct gcctcgttga ggatattttg 85140
aggcctaact acacattcct gcccccagag aggtcacagc ctatagcagg ctgatgtttc 85200
tcatgtcaca tggcacagaa aggcacattt tcgttctcag gctaacaaag agcttcaaaa 85260
actattagaa gggacagtgg ctataagaga agaacctcag tcaatgtgtg aaattaacta 85320
ggaacctggc tcctgtttct tttaggtcat gtttttcagc ttaggtaaaa ctagaggctt 85380
tgataaagca tgacctctag aaatcattgc ttttcataaa tggaagtggg tttgagtttt 85440
ttctactgat tgttagtgca ggtgatgtct acatgccccc agaacatatt ccatgcaaca 85500
aaaaaagccc aggtcaccgt ctttgctggg aacttgactt ttgtgctcac tgaattttaa 85560
gctttctgac agcagcctgg aatcatggag ggataaagta cctattagta agatggaaaa 85620
aggtgtttca ggttggagct gcagtctgtt gagagtaagc tatgggaagg cctgtatacg 85680
aggggtggac ttttcttctg taagtgtcca gagaccaggc ctcctgaaga gggcatgggg 85740
gcttaactta cctggactac tgtgtttaca atactcattt atcttgaact cctcctaacc 85800
cctgagaatt gctacattta gtatttgctg agtacttcct agcatcctag ggaatcaata 85860
gaacattctc ccaaccaggc tgggtgcggt ggctcatgtc tgtaatccca gcactttggg 85920
aggccaaggt aggcagatcc cttgaggcca ggagtgcaag actagcctgg ctgacatggt 85980
gaaaccccgt ctttactaaa aatacaaaag ttagccaggc atggtggtac acacctgtaa 86040
tcccagctac atgggaggag taggaggcag gagaattgct tgaacctggg aggtggaggt 86100
tgctgtgagc cgagatcatg ccactgcact ccagcctggg cgacagagtg agtgagactc 86160
tgtttaaaaa aaaaaaaaaa aaagaacatt ctcctaacct ggcttcttcc tccaggggtg 86220
taattaatca tgtcagtttc ctcattgata cacacacaca cacactacaa tcctgtatcc 86280
attactttc aaggtacatt tactatttac gtttggggtc cttgtctctt ttttaatagt 86340
gtttcttaaa gtcttgtatt atatcagagt acagtaacat cccagtcaag agcactctag 86400
taagctctag gaggaaagcg acttccggaa ggcagtggag acctgtcctg ttggggcagc 86460
ataggggcag cccctgcctc tggtcagttc tggcgctcag gctcagggtt gcctctgggc 86520
tgttcttccc agagactgac aaagggctcc cataaggcac ctgcagagcc tgtgagaagc 86580
tgaagtcaat gttttcctga caccagttga tctgtgcagg atccattgat ttaaccacct 86640
gctgtgtggc atgcactgtg gtcgatgcca ggaacaggaa ttggaggggc ccatgagcat 86700

```
ggccagtatc acaggctgga ggtgctgctg cgctctgacc gggcctcttg gggatgagcc  86760
catgtcaacc accttgcctc cgatggggtc gggcccacag gttacctttg tgtgtccatg  86820
accacacctt cctccccgac ctcatccaaa tctctttctt ttccaagccc ctgaatcctt  86880
cagggctgca ggttttgttt aaagcagagc tggtgagttg cataggttgt tgcgttggga  86940
ctagatgggg tgttcaaaga gttgggagtt aaaaaacata aagggtattt attaggagaa  87000
ccaaggagtg taattctcct gttcttaata tgcggccagg ttaatgaatg tcacgtgaat  87060
gaaccagaaa aaaatgaagt gtgcccttga tcagctgggt tggtgtgcag caagctgtgt  87120
gaccagggga cagcagtggt cctgagggcc gtcactgtct gccgtgcaga gcccttcctc  87180
ccacgggggc ctacctcacc tgtgccaagg gcttgtctgt ggtcagtgac ctggatagat  87240
ctgaatgggg cttctttttc gaggagtctt atggcaggtc tctcagtaaa gactccattc  87300
ttgatgatca cacattttgg attttccaaa tctgtcagag aatgggcttg aggcggggtt  87360
tgtgggcact agtttcactg gtttcattta ccaaaaaggg gagcagaagt caagtatggt  87420
ggctcatccc tgtaatccca gaggcaagag aattgcttga gcccaggagt tcgagaccag  87480
cctgagcaac ataaggagac cccgtctcca caaaaatgaa aaataacatt ttagtcagac  87540
gtggtggcat gcatctgtgg tcccagctgc ttgggagggt gagatgggag ggttgtttga  87600
gccctggagt taaagttgca atgagctgtg attgcaccac tgcactctag cctgggtgac  87660
agaacgagac cctgtctcaa aaaaaaaaaa aaagaaagaa aaaaaggaaa aaaaaaactc  87720
atgcctgtaa tcccagcact ttggggaccg gggtgggcag atcacgaggt caggagatca  87780
agactatcct agccaacatg gtgaaacccc gtttctacta aaaatacaaa aattagccag  87840
gtgtggtggc acgtgcctgt aatcccagtt actcgggagg ctgaggcagg agaatcgctt  87900
gaaccaggga gtcagaggtt gcagtgagct gagatcgtgc cactgtactc cagcctgggc  87960
gacagagtga gactctgtct caaaccaaaa aaaaggggtg gggggcgggg gcaggagaac  88020
agtgagaggt agggagagga aaggggattc tcgctacacc caaaccagat accatctaga  88080
ggctagaatc tttgggaggc tcaaattccc tagaaagcag gagaagcttc tgtagccctc  88140
ccgctttccc agtagattaa gcccagggcg gctccagatg tgtgacatgc tctgtgccca  88200
accagagccc atcataggca gaggaataac acccacacca gaagggccct cggaggtcac  88260
cacgtccaag aaccctcttt acagatgagg aaactgaggc ccagagaggg gagagccacc  88320
tagcgagctg gtggcggcta gaccaggaga gctgtcattc caagcaagca aaggcaacga  88380
gacgagccca gagctgtgct cccatctctt tgttaggggg cctgggatgc cctctcagtg  88440
tcattttgtc caggatgatg ctccctctct taagcgatta atgcgccctt gctaaccttt  88500
tgctatcgct gcctcttcaa accagaggag ttgagagttc cgggccggca gaggaaggcg  88560
cctgaaaggc ccctggccaa tgagattagc gcccacgtcc agcctggacc ctgcggagag  88620
gcctctgggg tctctgggcc gtgcctcggg gagaaagagc cagaagctcc cgtcccgctg  88680
accgcgagcc ttcctcagca ccgtcccgtt tgcccagcgc ctcctccaac aggaggccct  88740
caggagccct ccctggagtg gggacaaaaa ggcggggact gggccgagaa gggtccggcc  88800
tttccgaagc ccgccaccac tgcgtatctc cacacagagc ctgaaagtgg taaggtggtc  88860
caggaaggct tcctccgaga gccaggcccc ccaggtctga gccaccagct catgtccggc  88920
atgcctgggg ctcccctcct gcctgagggc cccagagagg ccacacgcca accttcgggg  88980
acaggacctg aggacacaga gggcggccgc cacgcccctg agctgctcaa gcaccagctt  89040
ctaggagacc tgcaccagga ggggccgccg ctgaaggggg cagggggcaa agagaggccg  89100
```

gggagcaagg aggaggtgga tgaagaccgc gacgtcgatg agtcctcccc ccaagactcc 89160
cctccctcca aggcctcccc agcccaagat gggcggcctc cccagacagc cgccagagaa 89220
gccaccagca tcccaggctt cccagcggag ggtgccatcc ccctccctgt ggatttcctc 89280
tccaaagttt ccacagagat cccagcctca gagcccgacg ggcccagtgt agggcgggcc 89340
aaagggcagg atgccccccct ggagttcacg tttcacgtgg aaatcacacc caacgtgcag 89400
aaggagcagg cgcactcgga ggagcatttg ggaagggctg catttccagg ggcccctgga 89460
gaggggccag aggcccgggg cccctctttg ggagaggaca caaaagaggc tgaccttcca 89520
gagccctctg aaaagcagcc tgctgctgct ccgcggggga agcccgtcag ccgggtccct 89580
caactcaaag gtctgtgtct tgagcttctt cgctccttcc ctggggacct cccaggcctc 89640
ccaggctgcg ggcactgcca ctgagcttcc aggcctcccg actcctgctg cttctgacgt 89700
tcctaggacg ccactaaatc gacacctggg tgcagctgct ccactccctc ggcctcctcc 89760
cgtgctcagg ctgtggccgc acgcgcccct cacgcttgcc cgccactctg catgtcacca 89820
gcacccccgc tccgtgctcc ccaccttgtt tgactctctg gccacttgat ttgtccacaa 89880
cggcccatca gcccacagga ggtttggtgg gtgccttcca ccgacaggat gacgggtgcc 89940
ctcatggtgt ctagaactct ccaaccctcc catgtaggca taagcagccc cactttgcag 90000
atgaggaaac ggaggctcag agaagtacag taacttgccg aaggccaatg agtagtaagt 90060
gacagagcca ggtttgggat ccaggtaggt tgtctctgaa agacacgcct gtcctgcatc 90120
ccacaacgcc tcccaggagg tgctggagtg tggacgccta acacagagat gtgcagggca 90180
cacacagcag gtgacacaca cagcatccag aggtggccca gagctcatgc tgtgcctttg 90240
gcccagtgcc ctgcccccac ccactctgcc ttgtggcagg aagacaagga gcagacacaa 90300
gatctccctg gtccacatgc caccacctcc ctctgcagag gacaagggga tcctcatgct 90360
ggcattggag ggggttgagc agggcccacc ttgagccctc aggagcacga ccacagcagc 90420
cctgcaggga gggattggtg ggaggagagt cccaagtatc agggagagga gagttggtgt 90480
cccacaggag acctcagagc cacaaggcga gcttgttcat aaatttggga cccttagcat 90540
ttcacagtta tttgcagagc ccagaaatgg atgttactga agctcacagt tgcaagcatc 90600
tgttaaattt ttattagatt ttacttttag ggaaaacttt gaaatgctat aaagaagcct 90660
gtgtttaaaa gttaagacag aggctggggg cgatggctca cgcctgtaat ctcagcactt 90720
tgggaggcca aggcaggtgg atcatttgag gttaggagtt cgagaccagc ctggccaaca 90780
tggtgagacc ctgtctctac taaaattaca aaaaattagc tgggcgtggt ggcgggcacc 90840
tgtagtccca gctactgggg aggctgaagc aggataagtg cttgaaccca ggaggcggag 90900
gttacagtga gccaagatca caccactgta ccctaagcct gggcgacaga gtgagactct 90960
gtctcaaaaa ataaaataaa ataaagttaa gagagaaaaa aatatatcct atatcctttg 91020
ttaaattcca aaacagtagg ggacaaataa ctgacttgac aggttactac aatatttcct 91080
gaaatgatgt tttcttgaat actggcctac tagaggttca taggtgtgtt tggattaaaa 91140
aagagttcca tggcccagtg actgggggaa aaaaataaaa gactaaagta agttaaacag 91200
gcttttctgc tgcaggactt gtcagagcct ttaatgtact aatggccatt gtgaccctct 91260
gagaaggtca cagagtgggt ttcccaaact tacttgattc tacctgctaa catttcctgg 91320
aggaagtttg ggaaatgccg atttagcaga ttcttttgtt gtgccgtgga tggtgctggt 91380
tgatgtgggc aaaacaaaga acacgtgagt cagatccgcc tggggctctt actaaagtgc 91440
aggttcccag gtgccacttt aggcttacag acccagttgt ggggtaagcc tgggagtctt 91500
ttagcaggtg attctgccac atagtatagt tggaaaacct ctgggcatac tcattgctgg 91560
tccctctaga aatccaggtg acaatagcca atgagaagct ccaagagacc cagttgtcca 91620
tggggtagag ggaatgtgat attgaaacca aagaagaaaa tctatgatca gttttcagca 91680
gtgactgtca agagaaggag aagggtgagt tagcgctgat gctggctgac aggtcagcgg 91740
gttggtttca ccaaggagtg tgatgaaggc tgatgttgtc tgtgggaatg tatgatggta 91800
actggtttgt agctaatttg gggaagcagt gagaattcgt gccctttgaa gaccagtaag 91860
tggcaagaaa cccaccaggc ctggctcagg gctgggctgg gcttggctcg tctcagagca 91920
gctggggctg gtggccaaag ccaccattag tgaggggcag gccctggggg tacaaccagc 91980
aactagggga caaagacaac cctgccagcc tctcctattc tggaggcgtg tgaccagaaa 92040
tggagatggg ttggtcagca taagatggcc aggaaggtgg aaatcaggac tgctggcaat 92100
ctagccacat gggcagggga gccgggtggt tccaggcagt ttccaaggcc aagagggtga 92160
gcaggcacct cacagggaat cagggccaag cctggctgca gtgtggagac aatgcaccca 92220
cccccatcct tggatcttgc aggaggctgg gtcctcactg agctaccaac atccatggcc 92280
ctgaggcttt taaaacaccc atccatggag tggggctggt cccagtgggg tgaggctgac 92340
cctggcagaa acagggcagg agcctgtggg ttagggagac tgcaccttcc ttagatagcc 92400
tccatgccat catgtccccg tgacagtttc tgctgcgtcc cctctgcatg gtcccaccct 92460
cggccagcct gctgcccccct cttgccaggt tgcgctaatc agtgacccca gtgtgctgtg 92520
ttgatactaa caatgcgagg cctagcagat tcaagggaaa agagaaccaa ctgggtttcc 92580
accagaccca actaaacaaa catggaccta tcccagagaa atccagcttc accacagctg 92640
gctttctgtg aacagtgaaa atggagtgtg acaagcattc ttattttata ttttatcagc 92700
tcgcatggtc agtaaaagca aagacgggac tggaagcgat gacaaaaaag ccaaggtaag 92760
ctgacgatgc cacggagctc tgcagctggt caagtttaca gagaagctgt gctttatgtc 92820
tgattcattc tcatatataa tgtggggagt atttgtcact aaagtacagc tgtcatttaa 92880
agtgctttgt attttggggc aggcttttaa aaagtccagc atttattagt tttgatactt 92940
accccaggga agagcagttg gcaggttcat gaagtcatgc tcctaattcc agctttctta 93000
gtgtactttc agtgagaccc tgacagtaaa tgaaggtgtg tttgaaaacc aaacccagga 93060
cagtaaatga aggtgtgttt gaaaaccagc cctaggacag taaatgaagc catcttctca 93120
ctgcataaac tgcacccaga tctttgccca tccttctcag tatttcactt cacccattgt 93180
ttactgtctc aatgactggg gaaatgtctg gggaaatgct cccgtaattg cacagtggcg 93240
tttttcctgg aaaatcccac catggctcta gataagacct atttttctta aaggtatcta 93300
aaatttccag cataaattct gtctgaaaca cctgaatttt aatcagtact ggagcccgga 93360
gggcatctcc agttgccaca tagctctgag cattcagtgg tgtgttgagg gctgctcccg 93420
gaagtgcctg cagagtcagg gctccccagc ctcatctagt gaggcagtgg aagggcctgt 93480
ggggatttgg agagctggcc tgggtctctg aagtgatagt gacagctgct tgtcaatcac 93540
ggtgcacatt tagtgccggg ggcagggggc agggaatacc agcctcatgc atgcatgcat 93600
tcatttgttc cttccttcat tcattcattc agtacacatg ggtacaacat ccctgccctg 93660
gagttgccca gagtctaggg aggggaaaga tctattaccc tgggcctcgg ccagctgggg 93720
agtgctgctg gtggagaggg gccgtgtgca gcgagggaag gaggagtcgt caataccccc 93780
accccagctt tgctttcttg tcatcagccc cagggcccca gcctgtgtcc ctcctctccc 93840

```
attgctactt catctcctgg gtcctcctta ccaagcctga ccacacagag ggccttggcc  93900
gcttccatgg ggaattggaa agcaataaga tagcatcccc tagaagccca gtgaagtctg  93960
ggacaggacc cttctctgag ctctgacttg ctcttggaaa cacttcgagg cttagcctcc  94020
ccactttgtt tcccaagagt gtgacctgtt cccctccaaa cacccccttc tcctccaggg  94080
ccatgcccac ccgtcaaaat cccccacggg caggacgaac tgtgggtgtc agtcaccatc  94140
tatcctgcat cctggttcca gggccccccc cagccccgcc tccataggga caggcgtgca  94200
gacacccgtc cctggctgct tcctcttgtg gaatgggttc aaaagtaagc agtgttgttt  94260
acactgacaa actgaaaaaa aaagaaaaag agataacatt ggaggcttgg cacagtggct  94320
catgcctgta atcccagcac tttgggaggc taaggtggga ggatgtcccc agcccaagag  94380
ttctagacca gcctgggcaa catagcaaga ccccatctca aaaaaaaaat ttaattggcc  94440
aggcagaggt gggaggatca cttgaaccca aagggtggag gctgcagtga gccgtgatgg  94500
caccactgca ctccagccag ggcaacagag ggagaccctg tctctaaaac aaacaaacaa  94560
acaaacaaac aaaagagtta acattggcca gattaggatt caccagatag tgttaatatt  94620
agtttgattt gagactttaa tcagaaagca catgtgtggt gggggtgggt gtaacctaag  94680
tcaggtagaa tctttccaac ttgggggggg cacactcctg attgtagcca tatgagtctg  94740
tcagtgtggt ggaagagacc atgggttaat gggcaggtaa aaaagcacct tgcctggaat  94800
tgagtagaaa gtaaggccct tcagaccccg tgacacactt ggggacattt tcttgagtaa  94860
catcctaaga ttcatgtacc ttgatgatct ccatcaactt actcatgtga agcaccttta  94920
aaccagtcgt ctccaaattc aggggcacag taacatccaa caggctggag aaagaacgta  94980
ctagaacttc cattcctttt tcatgtcctc ttctaaaagc tttgtcaggg ccaggcgcgg  95040
tggctcacgc ctgtaatccc agcactttgg gaggccgaga cgggtggatc acgaggtcag  95100
gagatcgaga ccatcctggc taacacagtg aaaccccatc tctactaaaa atacaaaaaa  95160
acgagccggg cgtggtggtg ggcgcctgta gtcccagcta ctcgggaggc tgaggcagga  95220
gaatggcgtg aacccaggag gcagagcttg cagtgagccg agattgcacc actgcagtcc  95280
agcctgggcg acagagcgag actccgtctc aaaaaagaaa aagaaaaaga aaaagaactg  95340
tgattgggga ggacggtcac tttcctgttc ttactgatca gaagggatat taagggtacc  95400
tgattcaaac agcctggaga tcactgcttt caaccattac ctgccttatt tatttttagt  95460
tactgtcctt ttttcagttt gtttccctcc tccatgtgct gacttttatt ttgattttat  95520
ttatgtttat gtttaagaca tccacacgtt cctctgctaa aaccttgaaa aataggcctt  95580
gccttagccc caaacacccc actcctggta gctcagaccc tctgatccaa ccctccagcc  95640
ctgctgtgtg cccagagcca ccttcctctc ctaaacacgt ctcttctgtc acttcccgaa  95700
ctggcagttc tggagcaaag gagatgaaac tcaaggtaag gaaaccacct ttgaaaagaa  95760
ccaggctgct ctgctgtggt ttgcaaatgt ggggtttgtt tatttgtttt ttagcctcaa  95820
agacctttct tcaaatgagt tctggcatag aagcaccgtg taaaatagtt agaattctgg  95880
gcaaagggga aaagagagct gggggccatc cctctcagca ccccacaggc tctcatagca  95940
gcagctccta agacacctgg tgggaccttg gtttcgaaat cgctactcta aggctgggca  96000
cggtggctca cacctgtaat cccagctctt taggaggccg aggagggtgg atcacctgag  96060
atcaggagtt cgagaccagc ctggctaaca tggcaaaacc ctgtctctac taaaaataca  96120
aaaattagcc gggcgtggtg ttatgcgtgg tggtaatcgc agctactcgg gaggctgagg  96180
```

cacaaggatt gcttgaaccc cagaggcaga ggttgtagtt agctccagct tgggcgacag 96240
agcaagaccc tgtcgcaaaa attgtttaaa aaacaaaccc aaaattgcta ctctcattgg 96300
gttcctttgc ccattcctga ttttggcaag agaaatgctt ccagattgcc ctgatctggg 96360
taggacagca tcacgccata gcaacactgc cccgtgagct cactgccccc tcaactagct 96420
tgtggtcctt ggttaatgtc agtttctttt ttgagtttgt gttatgtcta agggtcatct 96480
gctgggtaac ggaacccagg gactgcccta gtccctagac tgtgccatgc ccgactctgc 96540
cagctttgtc agtgatgctg gtgctcgcct cctcgggtgc tcgcctggtc tgagcacacc 96600
caaggagttc ttgaggcctt agggttgttt gcgagagaat gaaagaacac gacctagctc 96660
tctttagcat ccttggtcag gttcaacact gcccccaggg gcctctggtg gagccaacca 96720
ccatcagcca aataaatcca taattagagt cagaaaatgg atgtctgcat atgtgtagtg 96780
cactaatgtc ctgccgatga ttgacatgga gtggagagtg acctgatcat tgctgtgagc 96840
tctgctggcc ttggcacaac tcatgctgat aactaatgca cacagttcct ctgggaggaa 96900
atgtcctcag ggaacttgga gtttgggtgg ggatgtgggt ttgtgtgccc agcaagccct 96960
tgtggttgta gcagacacta gtggcatcta ggaggcaaag ggtcaccccca gtcttagcca 97020
cgttttgagt caaggtggcg gagtggggct ggtgttgact cttggtggca gtaacttttc 97080
ccaatggtga aaaacccctc tatcatgttt catttacagg gggctgatgg taaaacgaag 97140
atcgccacac cgcggggagc agcccctcca ggccagaagg gccaggccaa cgccaccagg 97200
attccagcaa aaaccccgcc cgctccaaag acaccaccca gctctggtaa gaagaacgtt 97260
ctcttgaatc ttagaggaag ctgaagctct cagaggtaca gccttcattt taggaggcct 97320
taggccactg agaatgaata accctggca gctggtcagc agcttgcagt ttactaagca 97380
ctggagtctt cattgccttc tcagtccttt tgatttctga ggcaaatgtt gaatccctac 97440
cttttttttt ttttttcttt tgagacagag tttcgctttt gttatccagg ccggagtgca 97500
gtggtgtgat ctcagctcac tgcatcctcc acctcccagg ttcaagcgat tctcctacct 97560
cagcctccct agtagctggg attacaggca cctgccacta tgcccggcta attttttgta 97620
tttttagtag agacagggtt tcaccatgtt ggccaggctg gtctcgaacg cctgacctca 97680
ggtgatccac ctgcctcggc ctcccaaagt gctgggatta caggcatgag ccaccactcc 97740
cagcctgaat cctcactttt tatcaatgaa gaaattgagg ctgattctgc agcatgataa 97800
aaaaaaatac agaaaaagga aaaaaaagaa agaaatcgag cctctgagag tttgcttgac 97860
tgagtctaac cagctcattt taaacccgag gaaaatgcag tcacatgact actaagtggc 97920
agctctcgga gcctctctgg ccccaagtcc agggttccat agaggcagcc ccagcatggc 97980
atgttttcag tccccaaatg agactctgga gacaaatgtc tctggagaca gagcagcagc 98040
ctggataagt cacaatgggt gacgtcactc agggctcaac ccctgggcag cttaacttgc 98100
tagggacgtt aggagtctgc tgcaaaacct gagggtctta gctgagcagt cacaggctgg 98160
gcccgttgcc ctgggctcct gtgagtaaaa cccagtcaat tttgagtacc cagtaaggca 98220
tccattgagt tattttgcag ccaggagtgc tattaagaac agtcgcggct gggcgtggtg 98280
gctcatgcct gtaatcccag cactttggga ggccaaggtg ggcggatcac ctgaggtcag 98340
gagttcgaga ccagcttggc caacatggca aaaccccgtc tctaataaaa atacaaaata 98400
attagctggg cgtggtggcg ggcgcctgta atcccagctt ctcaggaggg tgaggaagga 98460
gaatcacttg aacccaggag gcagaggttg cagtgagctg agatcgcacc attgcactcc 98520
agcctggatg acaaaagtga gattccttct caaaaaaaaa aaaaaaaaaa cagtcgtcct 98580

```
ctttggggat tagggacagc ctgcctgcct gcccgagcac ttctctcttc cattgcccca  98640
gtgaagtatt ccaggcccct gggtttagac tctgcaccat gtaggggtgt ctgacctgca  98700
cttgctcctt ggtggcacgg gcagcctatg gcacttgctg cgggctgtga ccaaagcctg  98760
gcctggatct tggatcttgg tgactctgct tctccctggc ctgagggagc tgcccagagc  98820
ctgcccacca cctgctgcgt gtctttgcgg tggcatttct cgcacacatg ccgtgcggtg  98880
gcacccccaa ggatggccat tcactaaggc ccattgtttt tgtcttttcg cttcgtgttt  98940
tctggcctgg tgtttttctc atatacatgt gatccaggga taattcccag aattttgaca  99000
ggattttaag tagcgtttgg atcctgctgt tttttttttca cttaacatcg ggccagttga  99060
ctcacactct gtttttgtt gttgtttttt tgagacggag tctcactgtg tcacccaggc  99120
tgaagtgcag tggcacaatc ttggcatact gcaacctctg cttcccaaat tcaagcagtt  99180
ttcctgcctc agcctcctga gtagctggga ctacaggcac aggccaccac gccctgctaa  99240
tttttgtatt tttagtaaag acagggtttc accattttgg ccagcctagt ctcgaactcc  99300
tgacctcaag tgatccgccc acctcggcct cccaaagtgc tgggattaca ggggactcac  99360
actttgtaac aacctgaaac aacgtgatgc atttcccttt gggtcttacc tgctcttcgg  99420
tggctgcctg caggtggaga gaccctcccc cttgggcccc tcgaccttgt ttcagaatgg  99480
ggcccctgct gggccagctg tgggtgcctg ccacgtgaag gactcattaa ggccctgttt  99540
aagcctgatg ataataaggc tttcgtggat ttttctcttt aagcgactaa gcaagtccag  99600
agaagaccac cccctgcagg gcccagatct gagagaggta ctcgggagcc tacttcgctg  99660
ggagcagcct ccctttgcgt gtgtggccat tcactggctt gtgtttctag agccgggagg  99720
acccttttct gcaatgcagg gttcacacag ggttcgcagc ctgaagatgg agcagtccga  99780
attctcttcc ctgtgcagtt tgcgcagctg tgtttgtctg atgggctttc taatcctgtg  99840
tgctctcctt gacttcaggg acaatggcat tacaggcatg agccaccatg cctggctgtc  99900
tccctatgtt tcagatgaag acataggctt aaggaggtca ggtgacttgc ccacgaccac  99960
tctgtaaata agaggcatga aaagtatttg gagccaccac caccaagccc actggtcacc 100020
ctgggtctct gaagtcaggg aggcaggagg atgggaggtc tgaggaggca gagaggctga 100080
gcctggaggc cctggaggcc gaggccccat ctgttgtttc cttatgtgga aaataagagg 100140
cttcatttgt cctattgcca cagagcgtac tacttcagga acatccaaga catggaaatc 100200
cgcagggcac ggtggctcac gtctataatc ccggcacttt gggaggttga ggtgggagaa 100260
tcgcttgagg ccagaagttc aagaccagcc tgagcaacat agtcagaccc cgtctctata 100320
aaaaacatta tttttaaaaa agacatggaa gtcaaattct aaaaactggt gctggctggg 100380
tgcggtggct catgcctata atcccagcac tttgggaggc cgaggcgggt ggatcacctg 100440
aggtcaggag ttcaagacca gcctggccaa catggtaaaa cctctactaa agaaatcttt 100500
actgaaaata caaaaatcca gtctctacta aaataagtct ctactaaaaa tacaaaaatt 100560
agccaggcgt ggtgctgcac acctgtaata tcagctactc gggaggctga ggcaggagac 100620
tcgcttgatc ccatgcagcg gaggttgcag tgagccgaga tcacgccatt gcactccagc 100680
ctgggcatca gaataagact ccgtctcaaa aaaaaaacca caaaaaaaca aaacaacaac 100740
aaaagaaaac tagtgcttat tcgtcactgg ccaagctgcc cattggctac atgggtgctt 100800
caaagagctg cccttctcca ggtctggcca gcaggtatgt gttacagcaa atgcctgggg 100860
cagcggcagg ggcattgctg cgggaagctt ctggacttgc aggaaagcta agttctcaga 100920
```

ctgcagggga gctaagcaca cctcggcaca gggtgaggcc tgcggttctc agacttcagt 100980
ctttgtggag cttgagaaaa atgaggcttt gcaggtccca cccctagaga ttctgctcta 101040
tccactcttg aaggggatcg agaaatttgc attttgcaac tcccactttc ctccttgaaa 101100
gctccggaga ttctgacgca gggttccgtg ggccacactt tggaaaatac agacccatga 101160
gatagaatac cagactgttg aagtgtaacg gggcctggg aagtgcagta acagaagcaa 101220
gtttgagggt aaaggacacc cagaggaggg agggacagca tctgcatgga gaggagaaga 101280
gaccccccag cagcttccag ggtgttggaa gggtgcgcta gtaactgcta tgcatggcag 101340
gtggggaact gtacgtcagg gcacagcagc atgaagcggt atggctcgtg tggacagcta 101400
gggacaggca ggcgtggagc aggcatcctg ttctgaaggc caaatcccac agaggagcca 101460
gggtgctggc aggagccctg aactagccga acagctgaac agctgaacat tcaccctgtg 101520
gggaaagggt cagaagcgtc caggcttgag ggcacagctg ggtctcgtca ctgcatcacc 101580
cttatttagg ataaaggccc tgaagaattg tattagaggt tggcaaagca tatctaccac 101640
ctcctggagc cacgctggcc gcagggatta taattatttc cattttcaaa ttaaggcctc 101700
tgagctcaga gaggggaagt tacttgtctg aggccacaca gcttgttgga gcccatctct 101760
tgacccaaag actgtggagc cgagttggcc acctctctgg gagcgggtat tggatggtgg 101820
ttgatggttt tccattgctt tcctgggaaa ggggtgtctc tgtccctaag caaaaaggca 101880
gggaggaaga gatgcttccc cagggcagcc gtctgctgta gctgcgcttc caacctggct 101940
tccacctgcc taacccagtg gtgagcctgg gaatggaccc acgggacagg cagcccccag 102000
ggccttttct gaccccaccc actcgagtcc tggcttcact cccttccttc cttcccaggt 102060
gaacctccaa aatcagggga tcgcagcggc tacagcagcc ccggctcccc aggcactccc 102120
ggcagccgct cccgcacccc gtcccttcca accccaccca cccgggagcc caagaaggtg 102180
gcagtggtcc gtactccacc caagtcgccg tcttccgcca agagccgcct gcagacagcc 102240
cccgtgccca tgccagacct gaagaatgtc aagtccaaga tcggctccac tgagaacctg 102300
aagcaccagc cgggaggcgg gaaggtgaga gtggctggct gcgcgtggag gtgtgggggg 102360
ctgcgcctgg aggggtaggg ctgtgcctgg aagggtaggg ctgcgcctgg aggtgcgcgg 102420
ttgagcgtgg agtcgtggga ctgtgcatgg aggtgtgggg ctccccgcac ctgagcaccc 102480
ccgcataaca ccccagtccc ctctggaccc tcttcaagga agttcagttc tttattgggc 102540
tctccactac actgtgagtg ccctcctcag gcgagagaac gttctggctc ttctcttgcc 102600
ccttcagccc ctgttaatcg gacagagatg gcagggctgt gtctccacgg ccggaggctc 102660
tcatagtcag ggcacccaca gcggttcccc acctgccttc tgggcagaat acactgccac 102720
ccataggtca gcatctccac tcgtgggcca tctgcttagg ttgggttcct ctggattctg 102780
gggagattgg gggttctgtt ttgatcagct gattcttctg ggagcaagtg ggtgctcgcg 102840
agctctccag cttcctaaag gtggagaagc acagacttcg gggcctggc ctggatccct 102900 ttccccattc ctgtccctgt gcccctcgtc tgggtgcgtt agggctgaca tacaaagcac 102960
cacagtgaaa gaacagcagt atgcctcctc actagccagg tgtgggcggg tgggtttctt 103020
ccaaggcctc tctgtggccg tgggtagcca cctctgtcct gcaccgctgc agtcttccct 103080
ctgtgtgtgc tcctggtagc tctgcgcatg ctcatcttct tataagaaca ccatggcagc 103140
tgggcgtagt ggctcacgcc tataatccca gcactttggg aggctgaggc aggcagatca 103200
cgaggtcagg agttcgagac caacctgacc aacagggtga aacctcgtct ctactaaaaa 103260
tacaaaaata cctgggcgtg gtggtggtgc gcgcctataa tcccagctac tcaggaggct 103320
gaggcaggag aatcgcttga acccaggagg cagaggttgc agtgagccga gatagtgcca 103380
ctgcactcca gtttgagcaa cagagcgaga ctctgtctca aaacaaaata aaacaaacca 103440
aaaaaaccca ccatggctta gggcccagcc tgatgacctc atttttcact tagtcacctc 103500
tctaaaggcc ctgtctccaa atagagtcac attctaaggt acgggggtgt tggggagggg 103560
ggttagggct tcaacatgtg aatttgcggg gaccacaatt cagcccagga ccccgctccc 103620
gccacccagc actggggagc tggggaaggg tgaagaggag gctgggggtg agaaggacca 103680
cagctcactc tgaggctgca gatgtgctgg gccttctggg cactgggcct cggggagcta 103740
gggggctttc tggaaccctg ggcctgcgtg tcagcttgcc tcccccacgc aggcgctctc 103800
cacaccattg aagttcttat cacttgggtc tgagcctggg gcatttggac ggagggtggc 103860
caccagtgca catgggcacc ttgcctcaaa ccctgccacc tccccccacc caggatcccc 103920
cctgcccccg aacaagcttg tgagtgcagt gtcacatccc atcgggatgg aaatggacgg 103980
tcgggttaaa agggacgcat gtgtagaccc tgcctctgtg catcaggcct cttttgagag 104040
tccctgcgtg ccaggcggtg cacagaggtg gagaagactc ggctgtgccc cagagcacct 104100
cctctcatcg aggaaaggac agacagtggc tcccctgtgg ctgtggggac aagggcagag 104160
ctccctggaa cacaggaggg agggaaggaa gagaacatct cagaatctcc ctcctgatgg 104220
caaacgatcc gggttaaatt aaggtccggc cttttcctgc tcaggcatgt ggagcttgta 104280
gtggaagagg ctctctggac cctcatccac cacagtggcc tggttagaga ccttggggaa 104340
ataactcaca ggtgacccag ggcctctgtc ctgtaccgca gctgagggaa actgtcctgc 104400
gcttccactg gggacaatgc gctccctcgt ctccagactt tccagtcctc attcggttct 104460
cgaaagtcgc ctccagaagc cccatcttgg gaccaccgtg actttcattc tccagggtgc 104520
ctggccttgg tgctgcccaa gaccccagag gggccctcac tggcctttcc tgccttttct 104580
cccattgccc acccatgcac ccccatcctg ctccagcacc cagactgcca tccaggatct 104640
cctcaagtca cataacaagc agcacccaca aggtgctccc ttcccccctag cctgaatctg 104700
ctgctccccg tctggggttc cccgcccatg cacctctggg ggcccctggg ttctgccata 104760
ccctgccctg tgtcccatgg tggggaatgt ccttctctcc ttatctcttc ccttccctta 104820
aatccaagtt cagttgccat ctcctccagg aagtcttcct ggattcccct ctctcttctt 104880
aaagcccctg taaactctga ccacactgag catgtgtctg ctgctcccta gtctgggcca 104940
tgagtgaggg tggaggccaa gtctcatgca tttttgcagc ccccacaaga ctgtgcaggt 105000
ggccggccct cattgaatgc ggggttaatt taactcagcc tctgtgtgag tggatgattc 105060
aggttgccag agacagaacc ctcagcttag catgggaagt agcttccctg ttgaccctga 105120
gttcatctga ggttggcttg gaaggtgtgg gcaccatttg gcccagttct tacagctctg 105180
aagagagcag caggaatggg gctgagcagg gaagacaact ttccattgaa ggcccctttc 105240
agggccagaa ctgtccctcc caccctgcag ctgccctgcc tctgcccatg aggggtgaga 105300
gtcaggcgac ctcatgccaa gtgtagaaag gggcagacgg gagccccagg ttatgacgtc 105360
accatgctgg gtggaggcag cacgtccaaa tctactaaag ggttaaagga gaaagggtga 105420
cttgactttt cttgagatat tttgggggac gaagtgtgga aaagtggcag aggacacagt 105480
cacagcctcc cttaaatgcc aggaaagcct agaaaaattg tctgaaacta aacctcagcc 105540
ataacaaaga ccaacacatg aatctccagg aaaaaagaaa aagaaaaatg tcatacaggg 105600
tccatgcaca agagccttta aaatgacccg ctgaagggtg tcaggcctcc tcctcctgga 105660
ctggcctgaa ggctccacga gcttttgctg agacctttgg gtccctgtgg cctcatgtag 105720
tacccagtat gcagtaagtg ctcaataaat gtttggctac aaaagaggca aagctggcgg 105780
agtctgaaga atccctcaac cgtgccggaa cagatgctaa caccaaaggg aaaagagcag 105840
gagccaagtc acgtttggga acctgcagag gctgaaaact gccgcagatt gctgcaaatc 105900
attgggggaa aaacggaaaa cgtctgtttt cccctttgtg cttttctctg ttttcttctt 105960
tgtgcttttc tctgttttca ggatttgcta cagtgaacat agattgcttt ggggccccaa 106020
atggaattat tttgaaagga aaatgcagat aatcaggtgg ccgcactgga gcaccagctg 106080
ggtaggggta gagattgcag gcaaggagga ggagctgggt ggggtgccag gcaggaagag 106140
cccgtaggcc ccgccgatct tgtgggagtc gtgggtggca gtgttccctc cagactgtaa 106200
aagggagcac ctggcgggaa gagggaattc ttttaaacat cattccagtg cccgagcctc 106260
ctggacctgt tgtcatcttg aggtgggcct cccctgggtg actctagtgt gcagcctggc 106320
tgagactcag tggccctggg ttcttactgc tgacacctac cctcaacctc aaccactgcg 106380
gcctcctgtg caccctgatc cagtggctca ttttccactt tcagtcccag ctctatccct 106440
atttgcagtt tccaagtgcc tggtcctcag tcagctcaga cccagccagg ccagcccctg 106500
gttcccacat ccccttttgcc aagctcatcc ccgccctgtt tggcctgcgg gagtgggagt 106560
gtgtccagac acagagacaa aggaccagct tttaaaacat tttgttgggg ccaggtgtgg 106620
tggctcacac ctaatcccaa cacctgggga ggccaaggca gaaggatcac ttgagtccag 106680
gagttcaaga ccagcctggg caacataggg agaccctgtc tctacaattt ttttttaat 106740
tagctgggcc tgttggcact ctcctgtagt tccagctact ctagaggctg aggtgggagg 106800
actgcttgag cctgggaggt cagggctgca atgagccatg ttcacaccac tgaacgccag 106860
cctgggcgag accctgtatc aaaaaagtaa agtaaaatga atcctgtacg ttatattaag 106920
gtgccccaaa ttgtacttag aaggatttca tagttttaaa tacttttgtt atttaaaaaa 106980
ttaaatgact gcagcatata aattaggttc ttaatggagg ggaaaaagag tacaagaaaa 107040
gaaataagaa tctagaaaca aagataagag cagaaataaa ccagaaaaca caaccttgca 107100
ctcctaactt aaaaaaaaaa atgaagaaaa cacaaccagt aaaacaacat ataacagcat 107160
taagagctgg ctcctggctg ggcgcggtgg cgcatgcctg taatcccaac actttgggag 107220
gccgatgctg gaggatcact tgagaccagg agttcaaggt tgcagtgagc tatgatcata 107280
ccactacacc ctagcctggg caacacagtg agactgagac tctattaaaa aaaaaatgct 107340
ggttccttcc ttatttcatt cctttattca ttcattcaga caacatttat ggggcacttc 107400
tgagcaccag gctctgtgct aagagctttt gcccccaggg tccaggccag gggacagggg 107460
caggtgagca gagaaacagg gccagtcaca gcagcaggag gaatgtagga tggagagctt 107520
ggccaggcaa ggacatgcag ggggagcagc ctgcacaagt cagcaagcca gagaagacag 107580
gcagaccctt gtttgggacc tgttcagtgg cctttgaaag gacagccccc acccggagtg 107640
ctgggtgcag gagctgaagg aggatagtgg aacactgcaa cgtggagctc ttcagagcaa 107700
aagcaaaata aacaactgga ggcagctggg gcagcagagg gtgtgtgttc agcactaagg 107760
ggtgtgaagc ttgagcgcta ggagagttca cactggcaga agagaggttg gggcagctgc 107820
aagcctctgg acatcgcccg acaggacaga gggtggtgga cggtggccct gaagagaggc 107880
tcagttcagc tggcagtggc cgtgggagtg ctgaagcagg caggctgtcg gcatctgctg 107940
gggacggtta agcaggggtg agggcccagc ctcagcagcc cttcttgggg ggtcgctggg 108000
aaacatagag gagaactgaa gaagcaggga gtcccagggt ccatgcaggg cgagagagaa 108060
gttgctcatg tggggcccag gctgcaggat caggagaact ggggaccctg tgactgccag 108120
cggggagaag ggggtgtgca ggatcatgcc cagggaaggg cccaggggcc caagcatggg 108180
ggggcctggt tggctctgag aagatggagc taaagtcact ttctcggagg atgtccaggc 108240
caatagttgg gatgtgaaga cgtgaagcag cacagagcct ggaagcccag gatggacaga 108300
aacctacctg agcagtgggg ctttgaaagc cttggggcgg ggggtgcaat attcaagatg 108360
gccacaagat ggcaatagaa tgctgtaact ttcttggttc tgggccgcag cctgggtggc 108420
tgcttccttc cctgtgtgta ttgatttgtt tctctttttt gagacagagt cttgctgggt 108480
tgcccaggct ggagtgcagt ggtgcgatca tagctcactg cagccttgaa gtcctgagct 108540
caagagatcc ttccacctca gcctcctgag tagttgggac cacaggcttg caccacagtg 108600
cccaactaat ttcttatatt ttttgtagag atggggtttc actgtgtcgc ccaggatggt 108660
cttgaactcc tgggctcaag tgatcctcct gcctcagcct cgcaaattgc tgggattaca 108720
ggtgtgagcc accatgcccg accttctctt tttaagggcg tgtgtgtgtg tgtgtgtgtg 108780
tgggcgcact ctcgtcttca ccttccccca gccttgctct gtctctaccc agtcacctct 108840
gcccatctct ccgatctgtt tctctctcct tttacccctc tttcctccct cctcatacac 108900
cactgaccat tatagagaac tgagtattct aaaaatacat tttatttatt tattttgaga 108960
cagagtctca ctctgtcacc caggctggag tgcagtggtg caatctcggc tcactgcaac 109020
ctccgcctcc caggttgaag caactctcct gcctcagcct ccctagtagc tgggattaca 109080
agcacacacc accatgccta gcaaattttt atatttttag tagaggagga gtgtcaccat 109140
gtttgccaag ctggtctcaa actcctggcc tcaggtgatc tgcctacctt ggtctcccaa 109200
agtgctggga ttacaggtgt gagccaccac gcctgccctt aaaaatacat tatatttaat 109260
agcaaagccc cagttgtcac tttaaaaagc atctatgtag aacatttatg tggaataaat 109320
acagtgaatt tgtacgtgga atcgtttgcc tctcctcaat cagggccagg gatgcaggtg 109380
agcttgggct gagatgtcag accccacagt aagtgggggg cagagccagg ctgggaccct 109440
cctctaggac agctctgtaa ctctgagacc ctccaggcat cttttcctgt acctcagtgc 109500
ttctgaaaaa tctgtgtgaa tcaaatcatt ttaaaggagc ttgggttcat cactgtttaa 109560
aggacagtgt aaataattct gaaggtgact ctaccctgtt atttgatctc ttctttggcc 109620
agctgactta acaggacata gacaggtttt cctgtgtcag ttcctaagct gatcaccttg 109680
gacttgaaga ggaggcttgt gtgggcatcc agtgcccacc ccgggttaaa ctcccagcag 109740
agtattgcac tgggcttgct gagcctggtg aggcaaagca cagcacagcg agcaccaggc 109800
agtgctggag acaggccaag tctgggccag cctgggagcc aactgtgagg cacggacggg 109860
gctgtggggc tgtggggctg caggcttggg gccagggagg gagggctggg ctctttggaa 109920
cagccttgag agaactgaac ccaaacaaaa ccagatcaag gtctagtgag agcttagggc 109980
tgctttgggt gctccaggaa attgattaaa ccaagtggac acacaccccc agccccacct 110040
caccacagcc tctccttcag ggtcaaactc tgaccacaga catttctccc ctgactagga 110100
gttccctgga tcaaaattgg gagcttgcaa cacatcgttc tctcccttga tggtttttgt 110160
cagtgtctat ccagagctga agtgtaatat atatgttact gtagctgaga aattaaattt 110220
caggattctg atttcataat gacaaccatt cctcttttct ctcccttctg taaatctaag 110280
attctataaa cggtgttgac ttaatgtgac aattggcagt agttcaggtc tgctttgtaa 110340 ataccettgt gtctattgta aaatctcaca aaggcttgtt gccttttttg tggggttaga 110400
acaagaaaaa gccacatgga aaaaaaattt cttttttgtt tttttgtttg cttgtttttt 110460
tgagacagag tttcactctg tcgcccaggc tggagtgcag tggtgcgatc tccgcccact 110520
gcaagctcca cctcccgggt tcatgctatt ctcctgtctc agcctcccaa gtagctggga 110580
ctgcaggtgc ccgccaccac acctggctaa tttttttgta tttttagtag agacggggtt 110640
tcaccgtgtt agccaggatg gtctcaatct cctgacctcg tcatctgcct gcctcggcct 110700
cccaaagtgc tgagattaca ggcgtgagcc accgtgcccg gccagaaaaa aacatttcta 110760
agtatgtggc agatactgaa ttattgctta atgtcctttg attcatttgt ttaatttctt 110820
taatggatta gtacagaaaa caaagttctc ttccttgaaa aactggtaag ttttctttgt 110880
cagataagga gagttaaata acccatgaca tttccctttt tgcctcggct tccaggaagc 110940
tcaaagttaa atgtaatgat cactcttgta attatcagtg ttgatgccct tcccttcttc 111000
taatgttact ctttacattt tcctgcttta ttattgtgtg tgttttctaa ttctaagctg 111060
ttcccactcc tttctgaaag caggcaaatc ttctaagcct tatccactga aaagttatga 111120
ataaaaaatg atcgtcaagc ctacaggtgc tgaggctact ccagaggctg aggccagagg 111180
accacttgag cccaggaatt tgagacctgg gctgggcagc atagcaagac tctatctcca 111240
ttaaaactat tttttttat ttaaaaaata atccgcaaag aaggagttta tgtgggattc 111300
cttaaaatcg gagggtggca tgaattgatt caaagacttg tgcagagggc gacagtgact 111360
ccttgagaag cagtgtgaga aagcctgtcc cacctccttc cgcagctcca gcctgggctg 111420
aggcactgtc acagtgtctc cttgctggca ggagagaatt tcaacattca ccaaaaagta 111480
gtattgtttt tattaggttt atgaggctgt agccttgagg acagcccagg acaactttgt 111540
tgtcacatag atagcctgtg gctacaaact ctgagatcta gattcttctg cggctgcttc 111600
tgacctgaga aagttgcgga acctcagcga gcctcacatg gcctccttgt ccttaacgtg 111660
gggacggtgg gcaagaaagg tgatgtggca ctagagattt atccatctct aaaggaggag 111720
tggattgtac attgaaacac cagagaagga attacaaagg aagaatttga gtatctaaaa 111780
atgtaggtca ggcgctcctg tgttgattgc agggctattc acaatagcca agatttggaa 111840
gcaacccaag tgtccatcaa cagacaaatg gataaagaaa atgtggtgca tatacacaat 111900
ggaatactat tcagccatga aaaagaatga gaatctgtca tttgaaacaa catggatgga 111960
actggaggac attatgttaa gtgaaataag ccagacagaa ggacagactt cacatgttct 112020
cacacatttg tgggagctaa aaattaaact catggagata gagagtagaa ggatggttac 112080
cagaggctga ggagggtgga ggggagcagg gagaaagtag ggatggttaa tgggtacaaa 112140
aacgtagtta gcatgcatag atctagtatt ggatagcaca gcagggtgac gacagccaac 112200
agtaatttat agtacattta aaaacaacta aaagagtgta actggactgg ctaacatggt 112260
gaaaccccgt ctctactaaa aatacaaaaa ttagctgggc acggtggctc acgcctgtaa 112320
tcccagcact ttgggaggcc gaggcgggcc gatcacgagg tcaggagatc gagaccatcc 112380
tagctaacat ggtgaaaccc cgtctctact acaaatacaa aaaaaagaaa aaattagccg 112440
ggcatggtgg tgggcgcctg tagtcccagc tactcgggag gctgaggcag gagaatggcg 112500
tgaacccggg aggcggagct tgcagtgagc cgagatcgcg ccactgcact ccagcctggg 112560
cgacaaggca agattctatc tcaaaaaaat aaaaataaaa taaaataaaa taataaaata 112620
aaataaaata aaataaaata aaataaataa aataaaatgt ataattggaa tgtttataac 112680
acaagaaatg ataaatgctt gaggtgatag ataccccatt caccgtgatg tgattattgc 112740
acaatgtatg tctgtatcta aatatctcat gtaccccaca agtatataca cctactatgt 112800
acccatataa atttaaaatt aaaaaattat aaaacaaaaa taaataagta aattaaaatg 112860
taggctggac accgtggttc acgcctgtaa tcccagtgct ttgtgaggct gaggtgagag 112920
aatcacttga gcccaggagt ttgagaccgg cctgggtgac atagcgagac cccatcatca 112980
caaagaattt ttaaaaatta gctgggcgtg gtagcacata ccggtagttc cagctacttg 113040
ggagaccgag gcaggaggat tgcttgagcc caggagttta aggctgcagt gagctacgat 113100
ggcgccactg cattccagcc tgggtgacag agtgagagct tgtctctatt ttaaaaataa 113160
taaaaagaat aaataaaaat aaattaaaat gtaaatatgt gcatgttaga aaaaatacac 113220
ccatcagcaa aaagggggta aaggagcgat ttcagtcata attggagaga tgcagaataa 113280
gccagcaatg cagtttcttt tattttggtc aaaaaaaata agcaaaacaa tgttgtaaac 113340
acccagtgct ggcagcaatg tggtgaggct ggctctctca ccagggctca cagggaaaac 113400
tcatgcaacc cttttagaaa gccatgtgga gagttgtacc gagaggtttt agaatattta 113460
taactttgac ccagaaattc tattctagga ctctgtgtta tgaaaataac ccatcatatg 113520
gaaaaagctc ctttcagaaa gaggttcatg ggaggctgtt tgtatttttt ttttctttgc 113580
atcaaatcca gctcctgcag gactgtttgt attattgaag tacaaagtgg aatcaataca 113640
aatgttggat agcaggggaa caatattcac aaaatggaat gggacatagt attaaacata 113700
gtgcttctga tgaccgtaga ccatagacaa tgcttaggat atgatatcac ttcttttgtt 113760
gtttttgta ttttgagacg aagtctcatt ctgtcaccca ggctggagtt cagtggcgcc 113820
atctcagctc actgcaacct ccatctcccg ggttcaagct attctccttc ctcaacctcc 113880
cgagtagctg ggttgcgcac caccatgcct ggctaacttt tgtattttta gtacagacgg 113940
ggtttcacca cgttggccag gctgctcttg aactcctgac gtcaggtgat ccaccagcct 114000
tgacctccca aagtgctagg attacaggag ccactgtacc cagcctagga tatgatatca 114060
cttcttagag caagatacaa aattgcatgt gcacaataat tctaccaagt ataggtatac 114120
aggggtagtt atatataaat gagacttcaa ggaaatacaa caaaatgcaa tcgtgattgt 114180
gttagggtgg taagaaaacg gtttttgctt tgatgagctc tgttttttaa aatcgttata 114240
ttttctaata aaaatacata gtcttttgaa ggaacataaa agattatgaa gaaatgagtt 114300
agatattgat tcctattgaa gattcagaca agtaaaatta aggggaaaaa aaacgggatg 114360
aaccagaagt caggctggag ttccaacccc agatccgaca gcccaggctg atggggcctc 114420
cagggcagtg gtttccaccc agcattctca aaagagccac tgaggtctca gtgccatttt 114480
caagatttcg gaagcggcct gggcacggct ggtccttcac tgggatcacc acttggcaat 114540
tatttacacc tgagacgaat gaaaaccaga gtgctgagat tacaggcatg gtggcttacg 114600
cttgtaatcg gctttgggaa gccgaggtgg gctgattgct tgagcccagg agtttcaaac 114660
tatcctggac aacatagcat gacctcgtct ctacaaaaaa tacaaaaaat ttgccaggtg 114720
tggtggcatg tgcctgtggt cccagctact tgggaggctg aagtaggaga atcccctgag 114780
ccctgggaag tcgaggctgc actgagccgt gatggtgtca ctgcactcca gcctgggtga 114840
caaagtgaga ccctatctca caaagaaaaa aaacaaaaca aaaaacccaa agcacactgt 114900
ttccactgtt tccagagttc ctgagaggaa aggtcaccgg gtgaggaaga cgttctcact 114960
gatctggcag agaaaatgtc cagtttttcc aactccctaa accatggttt tctatttcat 115020
agttcttagg caaattggta aaaatcattt ctcatcaaaa cgctgatatt ttcacacctc 115080
cctggtgtct gcagaaagaa ccttccagaa atgcagtcgt gggagaccca tccaggccac 115140
ccctgcttat ggaagagctg agaaaaagcc ccacgggagc atttgctcag cttccgttac 115200
gcacctagtg gcattgtggg tgggagaggg ctggtgggtg gatggaagga gaaggcacag 115260
cccccccttg cagggacaga gccctcgtac agaagggaca ccccacattt gtcttcccca 115320
caaagcggcc tgtgtcctgc ctacggggtc agggcttctc aaacctggct gtgtgtcaga 115380
atcaccaggg gaacttttca aaactagaga gactgaagcc agactcctag attctaattc 115440
taggtcaggg ctaggggctg agattgtaaa aatccacagg tgattctgat gcccggcagg 115500
cttgagaaca gccgcaggga gttctctggg aatgtgccgg tgggtctagc caggtgtgag 115560
tggagatgcc ggggaacttc ctattactca ctcgtcagtg tggccgaaca catttttcac 115620
ttgacctcag gctggtgaac gctcccctct ggggttcagg cctcacgatg ccatcctttt 115680
gtgaagtgag gacctgcaat cccagcttcg taaagcccgc tggaaatcac tcacacttct 115740
gggatgcctt cagagcagcc ctctatccct tcagctcccc tgggatgtga ctcgacctcc 115800
cgtcactccc cagactgcct ctgccaagtc cgaaagtgga ggcatccttg cgagcaagta 115860
ggcgggtcca gggtggcgca tgtcactcat cgaaagtgga ggcgtccttg cgagcaagca 115920
ggcgggtcca gggtggcgtg tcactcatcc tttttctgg ctaccaaagg tgcagataat 115980
taataagaag ctggatctta gcaacgtcca gtccaagtgt ggctcaaagg ataatatcaa 116040
acacgtcccg ggaggcggca gtgtgagtac cttcacacgt cccatgcgcc gtgctgtggc 116100
ttgaattatt aggaagtggt gtgagtgcgt acacttgcga gacactgcat agaataaatc 116160
cttcttgggc tctcaggatc tggctgcgac ctctgggtga atgtagcccg gctccccaca 116220
ttcccccaca cggtccactg ttcccagaag ccccttcctc atattctagg agggggtgtc 116280
ccagcatttc tgggtccccc agcctgcgca ggctgtgtgg acagaatagg gcagatgacg 116340
gaccctctct ccggaccctg cctgggaagc tgagaatacc catcaaagtc tccttccact 116400
catgcccagc cctgtcccca ggagccccat agcccattgg aagttgggct gaaggtggtg 116460
gcacctgaga ctgggctgcc gcctcctccc ccgacacctg ggcaggttga cgttgagtgg 116520
ctccactgtg gacaggtgac ccgtttgttc tgatgagcgg acaccaaggt cttactgtcc 116580
tgctcagctg ctgctcctac acgttcaagg caggagccga ttcctaagcc tccagcttat 116640
gcttagcctg cgccaccctc tggcagagac tccagatgca aagagccaaa ccaaagtgcg 116700
acaggtccct ctgcccagcg ttgaggtgtg gcagagaaat gctgcttttg gccctttag 116760
atttggctgc ctcttgccag gagtggtggc tcgtgcctgt aattccagca ctttgggaga 116820
ctaaggcggg aggttcgctt gagcccagga gttcaagacc agcctgggca acaatgagac 116880
ccctgtgtct acaaaaagaa ttaaaattag ccaggtgtgg tggcacgcac ctgtagtccc 116940
agctacttgg gaggctgagg tgggaggatt gcctgagtcc gggaggcgga agttgcaagg 117000
agccatgatc gcgccactgc acttcaacct aggcaacaga gtgagacttt gtctcaaaaa 117060
acaatcatat aataatttta aaataaatag atttggcttc ctctaaatgt ccccggggac 117120
tccgtgcatc ttctgtggag tgtctccgtg agattcggga ctcagatcct caagtgcaac 117180
tgacccaccc gataagctga ggcttcatca tcccctggcc ggtctatgtc gactgggcac 117240
ccgaggctcc tctcccacca gctctcttgg tcagctgaaa gcaaactgtt aacaccctgg 117300
ggagctggac gtatgagacc cttggggtgg gaggcgttga tttttgagag caatcacctg 117360
gccctggctg gcagtaccgg gacactgctg tggctccggg gtgggctgtc tccagaaaat 117420
gcctggcctg aggcagccac ccgcatccag cccagagggt ttattcttgc aatgtgctgc 117480
tgcttcctgc cctgagcacc tggatcccgg cttctgccct gaggcccctt gagtcccaca 117540

```
ggtagcaagc gcttgccctg cggctgctgc atggggctaa ctaacgcttc ctcaccagtg 117600
tctgctaagt gtctcctctg tctcccacgc cctgctctcc tgtcccccca gtttgtctgc 117660
tgtgagggga cagaagaggt gtgtgccgcc cccacccctg cccgggccct tgttcctggg 117720
attgctgttt tcagctgttt gagctttgat cctggttctc tggcttcctc aaagtgagct 117780
cggccagagg aggaaggcca tgtgctttct ggttgaagtc aagtctggtg ccctggtgga 117840
ggctgtgctg ctgaggcgga gctggggaga gagtgcacac gggctgcgtg gccaacccct 117900
ctgggtagct gatgcccaaa gacgctgcag tgcccaggac atctgggacc tccctggggc 117960
ccgcccgtgt gtcccgcgct gtgttcatct gcgggctagc ctgtgacccg cgctgtgctc 118020
gtctgcgggc tagcctgtgt cccgcgctct gcttgtctgc ggtctagcct gtgacctggc 118080
agagagccac cagatgtccc gggctgagca ctgccctctg agcaccttca caggaagccc 118140
ttctcctggt gagaagagat gccagcccct ggcatctggg ggcactggat ccctggcctg 118200
agccctagcc tctccccagc ctgggggccc cttcccagca ggctggccct gctccttctc 118260
tacctgggac ccttctgcct cctggctgga ccctggaagc tctgcagggc ctgctgtccc 118320
cctccctgcc ctccaggtat cctgaccacc ggccctggct cccactgcca tccactcctc 118380
tcctttctgg ccgttccctg gtccctgtcc cagcccccct ccccctctca cgagttacct 118440
cacccaggcc agagggaaga gggaaggagg ccctggtcat accagcacgt cctcccacct 118500
ccctcggccc tggtccaccc cctcagtgct ggcctcagag cacagctctc tccaagccag 118560
gccgcgcgcc atccatcctc cctgtccccc aacgtccttg ccacagatca tgtccgccct 118620
gacacacatg ggtctcagcc atctctgccc cagttaactc cccatccata aagagcacat 118680
gccagccgac accaaaataa ttcgggatgg ttccagttta gacctaagtg gaaggagaaa 118740
ccaccacctg ccctgcacct tgtttttttgg tgaccttgat aaaccatctt cagccatgaa 118800
gccagctgtc tcccaggaag ctccagggcg gtgcttcctc gggagctgac tgataggtgg 118860
gaggtggctg ccccccttgca ccctcaggtg accccacaca aggccactgc tggaggccct 118920
ggggactcca ggaatgtcaa tcagtgacct gccccccagg ccccacacag ccatggctgc 118980
atagaggcct gcctccaagg gacctgtctg tctgccactg tggagtccct acagcgtgcc 119040
ccccacaggg gagctggttc tttgactgag atcagctggc agctcagggt catcattccc 119100
agagggagcg gtgccctgga ggccacaggc ctcctcatgt gtgtctgcgt ccgctcgagc 119160
ttactgagac actaaatctg ttggtttctg ctgtgccacc tacccaccct gttggtgttg 119220
ctttgttcct attgctaaag acaggaatgt ccaggacact gagtgtgcag gtgcctgctg 119280
gttctcacgt ccgagctgct gaactccgct gggtcctgct tactgatggt ctttgctcta 119340
gtgctttcca gggtccgtgg aagcttttcc tggaataaag cccacgcatc gaccctcaca 119400
gcgcctcccc tctttgaggc ccagcagata ccccactcct gcctttccag caagattttt 119460
cagatgctgt gcatactcat catattgatc actttttttct tcatgcctga ttgtgatctg 119520
tcaatttcat gtcaggaaag ggagtgacat ttttacactt aagcgtttgc tgagcaaatg 119580
tctgggtctt gcacaatgac aatgggtccc tgtttttccc agaggctctt ttgttctgca 119640
gggattgaag acactccagt cccacagtcc ccagctcccc tggggcaggg ttggcagaat 119700
ttcgacaaca catttttcca ccctgactag gatgtgctcc tcatggcagc tgggaaccac 119760
tgtccaataa gggcctgggc ttacacagct gcttctcatt gagttacacc cttaataaaa 119820
taatcccatt ttatcctttt tgtctctctg tcttcctctc tctctgcctt tcctcttctc 119880
```

tctcctcctc tctcatctcc aggtgcaaat agtctacaaa ccagttgacc tgagcaaggt 119940
gacctccaag tgtggctcat taggcaacat ccatcataaa ccaggtagcc ctgtggaagg 120000
tgagggttgg gacgggaggg tgcagggggt ggaggagtcc tggtgaggct ggaactgctc 120060
cagacttcag aaggggctgg aaaggatatt ttaggtagac ctacatcaag gaaagtgttg 120120
agtgtgaaac ttgcgggagc ccaggaggcg tggtggctcc agctcgctcc tgcccaggcc 120180
atgctgccca agacaaggtg aggcgggagt gaagtgaaat aaggcaggca cagaaagaaa 120240
gcacatattc tcggccgggc gctgtggctc acgcctgtaa ttccagcact ttgggaggcc 120300
aaggtgggtg gatcatgagg tcaggagatt gagaccatcc tggctaacac agtgaaaccc 120360
cgtctctact aaaaatacaa aaaattagcc gggcgtggtg gtgggcgcct gtagtcccag 120420
ctactccgga ggctgaggca ggaaaatggc gtgaacccgg aaggcggagc ttgcagtgag 120480
cggagtgagc agagatcgcg ccactgcact ccagcctggg cgacagagcg agactccgtc 120540
tcaaaaaaaa aaagcacatg ttctcgcttc tttgtgggat ccaggagata gagaatagaa 120600
ggatggttac cagaggctgg gaagggtagt gaggggatgg tggggggatg gtcaatgggt 120660
acaaaaaaaa tagaataaga cctagtattt gatagtgcaa cagggtgact atagtcaata 120720
ataatttaat tgtacattta aaaataacta aaagatagcc gggtgcagtg gcttacgtct 120780
gtaatcccag tactttggga ggctgaggtg ggcgtttgag accagcctgg ccaacatggt 120840
gaaaccccat ctctactaaa aatacaaaaa ttagccaggc atggtggcgg gcgcctgtaa 120900
tcccagctac tcgggaggct gaggcaggag aatcacttga acctgggagg cagaggttgc 120960
agtgagccga gatcttgcca ctgcactcca gcctgggtga cagtgaaact ccgtctcaaa 121020
aataaaaata aaaatacagc tgggcacggt ggctcacgcc tgtaatccca gcactttggg 121080
aggccgaggc gagcggatca caaggtcagg agatatagac catcctggct aacacggtga 121140
aacccggtct ctactaaaaa tacaaaaaat tagccaggcg tggtggcagg tgcctatagt 121200
cccagctact cacaaggctg aggcaggaga atggcatgaa cctgggaggc ggagcttgca 121260
gtgagccgag attgtgccac tgcactccag cctgggcgag agagtgagac tccgtctcaa 121320
aacaaaaaca aaaacaaaaa caaaaacaaa cacacaacaa aaacctaaaa gaatataaat 121380
ggattgtttg taacacaaag gacaaatgtt tgaggggatg gataccccat tttccatgat 121440
gtgattatta tacattgtgt gtctgtatca aaacatctca tgagccccat aaatatatac 121500
acctaactat gtacccacaa aaattaaaaa aatatatttt ttaaggtgaa gagggaggcg 121560
agatgctggc cttaacccct aacccgttgt tctccctgca agctgtccac agggcctctc 121620
agactcgagg ttcagctata tggatgcatg agcttggtcc ccagccaaca tgggagacac 121680
ttcaccatcg gcagcagcta cagcacagga accctgggtc actgccatgt cccctctgtg 121740
actttgttta aacagaaaat gatgctctgg gccggctgtg gtggcccaca cctataatcc 121800
cagcaccttg ggaggcgggg gtgggcagat tgcctgaggt caggagttgg agatcagcct 121860
ggccgacatg gcgaaacccc atgtctacta aaaatacaaa aactagccag gcatggtggc 121920
acatgcctgt aatcccagct acttgggagg ctgaagcagg agaatcactt gaacccagga 121980
ggcagaggct gagtgagcca agatcgtgcc aatgcactcc agcttgggtg agggagtgag 122040
actccgtctc aaaaaaaaaa aaaaagaaag aaaaagaaaa gaaagtgatc ctactggaac 122100
catgcttact cccctcccca cctcacactg tgtagaaatt agtgctgtcg gccaggcgcg 122160
gtggctcatg cctgtaatcg cagcactttg ggaggccaag gcaggcggat cacgaggtca 122220
ggagatcaag accatcctgg ctaacacagt gaaaccctgt ctctactaaa aatacaaaaa 122280
attagccggg catggtggca ggcacctgta gtcccaacta cttgggaggc tgaggcagga 122340
gaatggcatg aacctgggag gcggagcttg cagtgagcca agatcgcgcc actgcatacc 122400
agcctaggtg acagagtgag actcagcaaa aaaagaaaga aagaaagaaa gaaatcagtg 122460
ctgtctatac ttctttctgc agtgatggaa atattctgta tctgtgctgt ccagtatagt 122520
agccactagc tacatgtggc acttgaaaca tggctggtac agttgaggaa gagtggctgc 122580
catatcggac gacacagcta tagattctgt caccccaccc cgagagtcca gagcggggac 122640
ttctgcctta ggccctattc agggctgatt tttacttgaa cccttactgt gggaagagaa 122700
ggccatgaga agttcagtct agaatgtgac tccttatttt ctggctccct tggacacttt 122760
gtgggattta gtctccctgt ggaaagtatt ccacaagtgg tgccactacc ccagctgtga 122820
gagcagctgg gagctgcttt tgtcatcttt ccctggaaag tcctgtgggc tgtctcttcc 122880
tcatgccttg tcccatgctt gggcatggtg tcaagcgtca ggagggagaa agggtcctta 122940
tttatttatt tagagaggga cccttcttct gttcccaggc tggagtgcag tggtgcgatc 123000
tcggctcact gcaacctccg cctcctgggt tcaagtgatt ctcctgcctc agcctcctga 123060
gtagctgaga ttacaggcac atgccaacat gcccggctaa tttttttttt tttttttttt 123120
tttttttttt tttttttttt gagatggagt tgtactctca ttgcccaggc tggaatgtaa 123180
tggcacaatc tcggctcact gcaacctcca cctcctggat tcaagcaatt ctcctgtctc 123240
agcttcccaa gtagctggga ttacaggtgc ccgccaccat gctcaactaa tttttgtatt 123300
ttttttttag tagagacgag gtttcaccat gttggtcaga ctggtctcaa actcctgacc 123360
tcaggtgatc cacctgcctc ggcctcccaa agtgctagga ttacaggcat gagccaccac 123420
gcccggcctg aaagggttct tatttagtgt gcattttgac attcaattta attccaaggt 123480
cttgtggggt catggtttac aggatgttga tatagaaaag acttcactta atgggccggg 123540
cgcagtggct catgcctgta atcccagcac tttgggaggc cgaggcaggc agatcaggag 123600
gtcaggagat tgagaccatc ctggctaaca cagtgaaacc ccatctctac tgaaaataca 123660
aaaaattagc tgggcgtggt ggcaggcacc tgtagtccca gccactcggt tggctgaggc 123720
aggagaatgg catgaacccg ggaggcggag cttgcagtga gcagagacca tgccactgca 123780
ctccagcctg ggcgacagag caagactctg tctcaagaaa aaaaaaaaaa aacagacttt 123840
acttactgga agccaaccaa tgtatattta gagtaatttt tcctgggctg agctgtcatt 123900
tacttttgca gtatctcaag aagaagagtt tacagtgtaa atatttgatg cacactttga 123960
ttatatagat gaagcaaact attttcaaga gctttgcaag gacttacttg tatccaaaca 124020
ccattctaaa aggagtctta cctacttcta aaggctggtc tctacttgga accacttgct 124080
tggccctggt tcaagtcctg ctgcaaacct ggaagtcctg tcattgtctt cttccctcca 124140
gagcagtggc acccaatcta atttttgctg tgccccagca gcccctggca ctttgccctg 124200
tagactgcag acctcatgta atgtatgtta agtccacaga accacagaag atgatggcaa 124260
gatgctcttg tgtgtgttgt gttctaggag gtggccaggt ggaagtaaaa tctgagaagc 124320
ttgacttcaa ggacagagtc cagtcgaaga ttgggtccct ggacaatatc acccacgtcc 124380
ctggcggagg aaataaaaag gtaaaggggg tagggtgggt tggatgctgc ccttgggtat 124440
atgggcatta atcaagttga gtggacaaag gctggtccag ttcccagagg aggaaaacag 124500
aggcttctgt gttgactggc tggatgtggg ccctcagcag catccagtgg gtctccactg 124560
cctgtctcaa tcacctggag ctttagcacg tttcacacct gggccccaac ctggagaggc 124620

-continued tgaccaatgg gtctcagggg cagctcggtt gctggagttt ttgtttttat ttatttttat 124680
gtatttaagg cagggtctct gtattagtcc attctcacac tgctaataaa gacataccca 124740
agactgggta atttataaag gaaagaggtt taatggactc acagttccac atggctgggg 124800
aggcctcaaa atcatggcgg aaggcaaagg agaagcaaag gcatttctta catggcgaca 124860
ggcaagagag cgtgtgcagg ggaactccca tttataaaac catcagacct catgagattt 124920
attcactatc atgagaacag catgggaaag acccgccccc atgattcagt tacctcccac 124980
tgggtccctc ccatgacaca tggaattatg ggagctacaa ttcaagatga gatttgggtg 125040
gggacacagc caaaccatat cagtctccct ctgtcatcca ggctggagtg cactggcatg 125100
atctcggctc actgcagcct ctacctccct gggtcaggtg atcttcccac ctcagcctcc 125160
caggtagctg gaactacagg tacctgccac tatgcctggc taaatatttt gtatttcctg 125220
tggagacgag gttttgccac gttgcccagg ctggtcttga actcctgagg tcaagcaata 125280
tgcccacctc ggcctcccaa ggtgctggga ttacaggtgt gagccacagt gctcggccta 125340
agtcactgca gtttttaaag ctcccaggtg attcttcagt gcagtcaaaa gtgagaactg 125400
gctgggtgcg gtggctcatg cctgtaatcc cagcaccttg ggaggcgaag gtgggcagat 125460
ggcttgaggt caggagttca agaccagcct ggccaacatg gtaaaacccc atctctacta 125520
aaaatacaaa agttagctgg gtgtggtggt gcgtgcctgt aatcccagct acttgggagg 125580
ctgaggcatg agaattgctt gaacccaggg gacagaggtt gtagtgagcc gagatcgtgc 125640
cactgcactc cagcctgggc aacagagtga gattccatct cacaaaaaaa aaaaaaagcg 125700
agaaccactg tcctaggccc tgatgtttgc aggcaactaa aaaaggaagt ggacatcccc 125760
agtcagctgt ggcgcaccaa gaacaagtca tgggaacata acctaatttt ctaaatgggt 125820
tactaggcac ttagagcaaa acaatgatgc cgaaatcctg atttcagcaa agcctctgcc 125880
tgcctgtctt ggaagtatcc acatgaggct gctggggcct tggtgtcccc agcagtttct 125940
agtctctagg tcttgctgtg ggtgtctgtg cagtgagggt gtgtgtggcg ctgggtgagc 126000
tctgtctagg cctggcacag gatgcggtct ggtagctgct gcttctcttc tgcagaagcg 126060
cagccaagca ccctctgggg tttcaggccc acacccagcc tgaagttctg ggagtggctc 126120
actttccaac cttcagggtc tcccagcagc tgactgggga gtggtggagg gaaaagggat 126180
tgtattagtc cgttttcacg ccgctgatga agacataccc gatactgggc agtctaaaag 126240
atagaggtct gatggactca cagttccacg tgactgggga ggcctgacaa tcatggtgga 126300
aggtgaaagg cttgtctcac acggtggcag acaagagaaa agagcttgtg caggggaact 126360 ccccttata aaaccatcag atctcgggag acttattcac tatcatgaga acagcacggg 126420
aaagaccctc ctctatgatt caattacctc ccaccaggtc cctcccacaa catgtaggaa 126480
ttgtgggaac tacaattcaa gatgacattt gggtggggac acagccaaac catatcaggg 126540
cgtcccagaa agggtatagg gtctgagacc caagtcagca tgagaaagta tgcttctcat 126600
ggtggcccag ttgggtggaa gtggcagccg ggccgtcttt ccaccaggcc actcaagtag 126660
cagctgagag acccctgccc tggccagtcc ccgccctccc ctcttgccac tgcctctggt 126720
tctgaacaga tgggcaccct catcttgtat ttgtgattaa tgtctaacaa tgtagttttg 126780
tgagaagggt ttgctgatac agccttgctg cagatgctgc gaactgtggc ctggggcaga 126840
ccttacctcc agacacgccc tgaggcaggg gagggcactg gcccgtagct ggccgagagc 126900
tctcgggttg cgcgacaggg atacttttca gcggctgggt cgctatccaa agtgagaaaa 126960
cgaggaggga ccaggaggct gtccgcctca agagatgtgg gggccaggtc cagttatctg 127020
gggaagcagt aagcttctct gctgtttcta accccaggcc tcccctggtc taaggcaggg 127080
cctcccagcc tcggggcact ttaaagatat ctgggcctgg ccccatcccc acagtctgac 127140
tgagtgggtc tggatagggc ctgagcattg gtgatttcct gggtgaaagg aggcccctca 127200
cagtctctgg aagcttctct gtgttaggaa aagctctggg cttgactctg ctttgaaagt 127260
caagatccgc aaatcctctc agcctcagtt tctccttcag caagatgaaa tggaaatgct 127320
gtacctacgt cccggggtgg ttgtgagacc caaaaaagac aatgttctgg aaggttcctg 127380
gtgcgttgca gtcctctaag aacctgagtt agagccacgc tgagtctcag cttcttggct 127440
ccttctgttt caaactcgtc catgtgatag ctcaggaagg gtaggcaggg ccctgccccc 127500
tactcagaaa acaccatcct ggtcctgggg atccccgcag cattagtccc ctgttttccc 127560
agtgtattga gaaaaattgc taacaagcag tggggcacac caccagcctc ctgggttcct 127620
ttcagtttgg ggatttttgg acattcccag gaatgtctta aaaaacactt caaaaaacat 127680
taacataaat atttttatca aagcctgtat taaatggtct ttcaagaaaa tacagtaaca 127740
ggtcaggcat ggtggctcat gcctgtaacc ccagcacttt gggaggccaa ggcaggcaga 127800
tcacctgaaa tcaggagttc aagaccaacc tggccaacac agccaaatcc catctctaca 127860
aaaaatacaa aaattagctg ggtgtggtgg cacacacctg tagtcccagc tacttgggag 127920
gccgaggcag gagaattgct tgatcccgga ggcggaggtt gcagtgagcc gagatcgtgc 127980
cactgcactc cagcgtgggt gacaaggtga atctttgtct caaaaaaaaa aaaaaaaaaa 128040
agataaaata cagtatacag taatagagaa caatcctttt ttcaaagtag tgaccccaaa 128100
tgaacaaaat atgcatctag cttaaatgcg aacctggttt tctctacgcc cattcaagcc 128160
cctgcaatag gggcccttca ccccgcatcc atggactcct aaaattatat ggaaaatggc 128220
tgtgtgtgag tgtggatgga catgtgcaca catatttttg gctttaccag atgctcaaag 128280
agcctaggac ccaaaaaggg ctgagaatga ccgtgtcggc cacttcaggg tcatcaggaa 128340
ttgctgtgca ctgctcactt ctccagtgaa cactttctgc ttctgtgttt cctggtatcc 128400
tttgggactc ctggctaggt catgtgtttc tctactttca aaagggcttc agccaggcac 128460
gatggcatga gcctgtagtc ccagttgctc tggaggttaa ggtgggaaga ttgcttgagc 128520
ccaggaattt gaggccagcc tgggcaagta gataggtaga tgattgatag atagatagat 128580
agataaatag atggatagat aagtcgctag acagtcatcc atccacccat ccacacataa 128640
aaaggccttt gtcatgtcat gttttgtggc ccacctgcca gtgttgccca cagttgctgc 128700
ccctccaaac tcatcagtca ctggcaaaca ggaggaatgt gtggctcatg tctgggcatc 128760
agtggctgtg ggagacatcc ttgatcttct ccagcttctc cttccacatt ttcctttgca 128820
atctggcaat atctattaaa ataaaatgtg catgcctttt gacctaagag cttcacttct 128880
aggacccact tacacgtgtg tgacatgatg ttcatacggg tttatttatc tgaggttgtt 128940
catacacacc attgcctgta atcactaaag gcgggagcag cctacacatc catccacaga 129000
ggagtagatg ccttttggta catccgtggc gacggaatac taagcagcct gtgtatctat 129060
acactcacac gtgtttgttt atgtgtggaa tatctctgga gggtacacaa gaaacttaaa 129120
atgatcactg tctctgggga gggtacctgg gtgcctggga ggcaggtcag ggaaggagtg 129180
ggcacaggta ttaccaattg gaagacaata aaaacaacag ctcctggcca ggcgcagtgg 129240
ctcacgcctg taatggcagc actctgagag gctgaggcgg gcagattgct tgcgtccagg 129300
agttcaagac cagcctgggc aacatagcaa aaccccgttt ctattaaaaa tacaaaaaat 129360

```
tagccaggtg tggtggcatg cacctgtaat cccagctact cgggaggctg aggtgggaga 129420
atcacctgag cctgggaggt caaggctgca gtgaggtgag attgtgccac cgcactctag 129480
cctgggcgat agagcaagac cctgtctcaa aaacaaacaa aaaacagtcc ctggcactct 129540
gggccaggcc tggcagggca gttggcaggg ctggtctttc tctggcactt catctcaccc 129600
tccctccctt cctcttcttg cagattgaaa cccacaagct gaccttccgc gagaacgcca 129660
aagccaagac agaccacggg gcggagatcg tgtacaagtc gccagtggtg tctggggaca 129720
cgtctccacg gcatctcagc aatgtctcct ccaccggcag catcgacatg gtagactcgc 129780
cccagctcgc cacgctagct gacgaggtgt ctgcctccct ggccaagcag ggtttgtgat 129840
caggcccctg gggcggtcaa taattgtgga gaggagagaa tgagagagtg tggaaaaaaa 129900
aagaataatg acccggcccc cgccctctgc ccccagctgc tcctcgcagt tcggttaatt 129960
ggttaatcac ttaacctgct tttgtcactc ggctttggct cgggacttca aaatcagtga 130020
tgggagtaag agcaaatttc atctttccaa attgatgggt gggctagtaa taaaatattt 130080
aaaaaaaaac attcaaaaac atggccacat ccaacatttc ctcaggcaat tccttttgat 130140
tctttttttct tccccctcca tgtagaagag ggagaaggag aggctctgaa agctgcttct 130200
gggggatttc aagggactgg gggtgccaac cacctctggc cctgttgtgg gggtgtcaca 130260
gaggcagtgg cagcaacaaa ggatttgaaa cttggtgtgt tcgtggagcc acaggcagac 130320
gatgtcaacc ttgtgtgagt gtgacggggg ttggggtggg gcgggaggcc acgggggagg 130380
ccgaggcagg ggctgggcag aggggagagg aagcacaaga agtgggagtg ggagaggaag 130440
ccacgtgctg gagagtagac atccccctcc ttgccgctgg gagagccaag gcctatgcca 130500
cctgcagcgt ctgagcggcc gcctgtcctt ggtggccggg ggtgggggcc tgctgtgggt 130560
cagtgtgcca ccctctgcag ggcagcctgt gggagaaggg acagcgggta aaaagagaag 130620
gcaagctggc aggagggtgg cacttcgtgg atgacctcct tagaaaagac tgaccttgat 130680
gtcttgagag cgctggcctc ttcctccctc cctgcagggt agggggcctg agttgagggg 130740
cttccctctg ctccacagaa accctgtttt attgagttct gaaggttgga actgctgcca 130800
tgattttggc cactttgcag acctgggact ttagggctaa ccagttctct ttgtaaggac 130860
ttgtgcctct tgggagacgt ccacccgttt ccaagcctgg gccactggca tctctggagt 130920
gtgtgggggt ctgggaggca ggtcccgagc cccctgtcct tcccacggcc actgcagtca 130980
cccctgtctg cgccgctgtg ctgttgtctg ccgtgagagc ccaatcactg cctatacccc 131040
tcatcacacg tcacaatgtc ccgaattccc agcctcacca ccccttctca gtaatgaccc 131100
tggttggttg caggaggtac ctactccata ctgagggtga aattaaggga aggcaaagtc 131160
caggcacaag agtgggaccc cagcctctca ctctcagttc cactcatcca actgggaccc 131220
tcaccacgaa tctcatgatc tgattcggtt ccctgtctcc tcctcccgtc acagatgtga 131280
gccagggcac tgctcagctg tgaccctagg tgtttctgcc ttgttgacat ggagagagcc 131340
ctttcccctg agaaggcctg gccccttcct gtgctgagcc cacagcagca ggctgggtgt 131400
cttggttgtc agtggtggca ccaggatgga agggcaaggc acccagggca ggcccacagt 131460
cccgctgtcc cccacttgca ccctagcttg tagctgccaa cctcccagac agcccagccc 131520
gctgctcagc tccacatgca tagtatcagc cctccacacc cgacaaaggg gaacacaccc 131580
ccttggaaat ggttcttttc ccccagtccc agctggaagc catgctgtct gttctgctgg 131640
agcagctgaa catatacata gatgttgccc tgccctcccc atctgcaccc tgttgagttg 131700
tagttggatt tgtctgttta tgcttggatt caccagagtg actatgatag tgaaaagaaa 131760
```

aaaaaaaaaa aaaaaggacg catgtatctt gaaatgcttg taaagaggtt tctaacccac 131820
cctcacgagg tgtctctcac ccccacactg ggactcgtgt ggcctgtgtg gtgccaccct 131880
gctggggcct cccaagtttt gaaaggcttt cctcagcacc tgggacccaa cagagaccag 131940
cttctagcag ctaaggaggc cgttcagctg tgacgaaggc ctgaagcaca ggattaggac 132000
tgaagcgatg atgtcccctt ccctacttcc ccttggggct ccctgtgtca gggcacagac 132060
taggtcttgt ggctggtctg gcttgcggcg cgaggatggt tctctctggt catagcccga 132120
agtctcatgg cagtcccaaa ggaggcttac aactcctgca tcacaagaaa aaggaagcca 132180
ctgccagctg gggggatctg cagctcccag aagctccgtg agcctcagcc acccctcaga 132240
ctgggttcct ctccaagctc gccctctgga ggggcagcgc agcctcccac caagggccct 132300
gcgaccacag cagggattgg gatgaattgc ctgtcctgga tctgctctag aggcccaagc 132360
tgcctgcctg aggaaggatg acttgacaag tcaggagaca ctgttcccaa agccttgacc 132420
agagcacctc agcccgctga ccttgcacaa actccatctg ctgccatgag aaaagggaag 132480
ccgcctttgc aaaacattgc tgcctaaaga aactcagcag cctcaggccc aattctgcca 132540
cttctggttt gggtacagtt aaaggcaacc ctgagggact tggcagtaga aatccagggc 132600
ctcccctggg gctggcagct tcgtgtgcag ctagagcttt acctgaaagg aagtctctgg 132660
gcccagaact ctccaccaag agcctccctg ccgttcgctg agtcccagca attctcctaa 132720
gttgaaggga tctgagaagg agaaggaaat gtggggtaga tttggtggtg gttagagata 132780
tgccccccctc attactgcca acagtttcgg ctgcatttct tcacgcacct cggttcctct 132840
tcctgaagtt cttgtgccct gctcttcagc accatgggcc ttcttatacg gaaggctctg 132900
ggatctcccc cttgtggggg caggctcttg gggccagcct aagatcatgg tttagggtga 132960
tcagtgctgg cagataaatt gaaaaggcac gctggcttgt gatcttaaat gaggacaatc 133020
cccccagggc tgggcactcc tcccctcccc tcacttctcc cacctgcaga gccagtgtcc 133080
ttgggtgggc tagataggat atactgtatg ccggctcctt caagctgctg actcacttta 133140
tcaatagttc catttaaatt gacttcagtg gtgagactgt atcctgtttg ctattgcttg 133200
ttgtgctatg gggggagggg ggaggaatgt gtaagatagt taacatgggc aaagggagat 133260
cttggggtgc agcacttaaa ctgcctcgta accctttca tgatttcaac cacatttgct 133320
agagggaggg agcagccacg gagttagagg ccccttggggt ttctcttttc cactgacagg 133380
ctttcccagg cagctggcta gttcattccc tccccagcca ggtgcaggcg taggaatatg 133440
gacatctggt tgctttggcc tgctgccctc tttcaggggt cctaagccca caatcatgcc 133500
tccctaagac cttggcatcc ttccctctaa gccgttggca cctctgtgcc acctctcaca 133560
ctggctccag acacacagcc tgtgcttttg gagctgagat cactcgcttc accctcctca 133620
tctttgttct ccaagtaaag ccacgaggtc ggggcgaggg cagaggtgat cacctgcgtg 133680
tcccatctac agacctgcgg cttcataaaa cttctgattt ctcttcagct ttgaaaaggg 133740
ttaccctggg cactggccta gagcctcacc tcctaataga cttagcccca tgagtttgcc 133800
atgttgagca ggactatttc tggcacttgc aagtcccatg atttcttcgg taattctgag 133860
ggtgggggga gggacatgaa atcatcttag cttagctttc tgtctgtgaa tgtctatata 133920
gtgtattgtg tgttttaaca aatgatttac actgactgtt gctgtaaaag tgaatttgga 133980
aataaagtta ttactctgat taaa 134004

<210> SEQ ID NO 2

<211> LENGTH: 132218
<212> TYPE: DNA
<213> ORGANISM: Macaca fascicularis
<220> FEATURE:
<221> NAME/KEY: misc_feature
<222> LOCATION: (108730)..(108735)
<223> OTHER INFORMATION: n is a, c, g, or t

<400> SEQUENCE: 2

```
cgggaaaggg cagcgccgag aggaaccagc cgggaggcgc cggacagccg agcggcaggg      60
cgctcgcgcg cgcccactgg tggccggagg agaaggctcc cgcggaggcc gggctgcccg     120
ccccctcccc tggggaggct cgcgctcccg ctgctcgcgc ctgcgccgcc tgccggcctc     180
gggaacgcgc cctcttcccc ggcgcgcgcc ctcgcagtca ccgccaccca ccagctccgg     240
caccaacagc agcgccgctg ccaccgccca ccttctgccg ccgccaccac agccaccttc     300
tcctcctccg ctgtcctctc ccgtcctcgc ctctgtcgac tatcaggtaa gcgccgcggc     360
tccgaaatct gcctcgccgt ccgcccctgt gcacccctgc gccgccgccc ctcgccctca     420
gcctccacag actggggctt cgtgcgccgg gcatcggtcg gggcgaccgc agggcccctc     480
cttgcctccc ctgctcgggg gctggggcca gggcggcctg gaaagggacg tgagcaaggg     540
atgcacgcac gcctgagtgc gcgcgtgtgt gtgtgctgga gggtcttcac ccgcttcgcg     600
ctgaccccag gtggaggccg tgccggcagg gtggggcgcg gcggcggtga cttgggggag     660
ggggctgccc ttcactctcg accgcagtct tttgccgcaa tgggcgtgcg tggggggga      720
ggggtccgat aacgaccccc gaaaccgaac ctgaaatccg ctgtccctgc cgctgttcgc     780
catcagccct aaggaagatg tggatcgggt tctagaaaag atgactgact ccctgcacgc     840
ccctcccttt acctcccgag cagtgattcc gacagggcct tcactgcccc tgattttagg     900
cgggggccgg ccccctcccc ttttcctcct tcagaaaccc gtaggggaca tttgggggct     960
gggaggaatc gaggagatgg ggaggggtcc aggcgctgtc actttagttg cccttccccc    1020
tgcgcacgcc tggcacagag acgcgagcag cgccgtgcct gagaacagtg cgaggatccc    1080
agtgtgcacg ctcgcaaagg caggggtcac ctggcctggc gatgtggacg gagtcggcgg    1140
ccgccggtcc ccgctcgcgg gcaggcacag cagcagccat gcactgacgg gcgcggggct    1200
gcaggtgcat ctcggggcgg gtttctttct cagcgctccg cgcgcagggt gcccggcgtg    1260
tgcgctccct gccggaggcg cggggctggc gcgcagggct cgcccctcac tgcggcagtg    1320
ggtgtggatc ctggtgggcg aggagggggg aggataggct gtgcctcctc ccactcccga    1380
ggtgccatct tttttcggcg tgtcacgtct ttacggtgcc atgccaaacc gggtggccgg    1440
gcttcgtagg acagggcggg gcctggcatt aaagggaggg ggacaatcag cgctgaaatc    1500
ttggcgtttt gctgctgcgg gcgtgagcgc tgggggcgtt cacccagcac cttcttcggg    1560
ggctctttgc tttgtctgta gaggttacgt gatctgcgct cccagccctg gtttctggct    1620
tttattctga gggtgtttag ccaacctccc cccaccccca agcacctctt tcctttttcg    1680
ttcctcattt ccgagcccat tgttggatct cgaggcttgc tggggtcgac gaacccgagt    1740
caaccccccg acccccggca cgcatggaac gggcgtgacc gcgcgcagcc tcgtctcgga    1800
gtctgcgggc gccaggaagc ttctgaaggg atgggattcg agtctccgtg ctgcgctgcg    1860
ggcggcggca gagggatcac gcccctccca acaccccgag tgtcctgagg gccaagccac    1920
accaggttgc ccaacgaggg acgctggcta cccattcggg gatgggtggg gagccccggt    1980
ggggcctctc cagctttacg ccctgttgct tcgcctggcg ggagaatgtg aggagggggc    2040
ataaggttac tggtgctgcg gccacaccca tttttctgag cccactggag ggggcacaga    2100
```

```
gggggaattg ccatgggaac cacaggcgtc cggagagggg accttggggc tggccccacc   2160
ccttccctgg ggagattggg gaccctgggg taggcggggc cgcgcccagt tggcctcctg   2220
gaggacacgg gaggaagccc ccaacccctg cacctgagac tctaattggc ctctggcggc   2280
cgcagatagg cagcccttgg gtgtattttt attaatatta tgtctgtact gattaatatt   2340
atttatcgta aatgcgggat ttcacccgta tccaagttca ccgtaccccc aaaaccgagt   2400
ctggggctgc aaggagaact cctggccaag gcatccgagc ctcgccctcc tgtgatgaac   2460
ctggtacgcg ccgttttctg gttaattcta tcgatgaaaa ctggtgcggg ggggcgcact   2520
tctgagacga acgagcatct aggagctgaa tcctccacgc gggctgccca ggttgatctg   2580
aatttccggg gaatggcttg actggggaac tagagcccgc ccgggaccag gctgaccttc   2640
ctcgacggtg gcgtcgaggg ctggagcctg agtgctgcga ggcttcccgc atggctgagc   2700
caccgcgagg ggttgcagag cggctcaggg gtcagttcaa gcatcttctc tcctccctcg   2760
cccccagaca gagctgggcg cgggattccg gttccagatg gagtgagggt ctcgggacgg   2820
ccctggaaaa ggggagccca cggtcaaggc tgcctattgc catctcgagc agagatgtca   2880
cctgctgccg ttggaggaaa gggagcccgg tggggatgag cgcatttagc ccaatgctgg   2940
gaacaaagca caatccgcgc ttctgcgatt tcgctccatt ttgaaatgtg ttggcgcttt   3000
ggttgggcca ctgcggtggg caaggccggg gaaggagggg gctgctgtta atggagaaac   3060
ctcaggggga cggtccttcg tgcaacaatt aggaaactcc atcctgactc tgtgcgcgct   3120
ttaaggaggt ggcttcgctc caggtcctcg agggatgcag ctttggcgcg gatgacggtg   3180
gggtgcttgc ctctggaaat gtctgggcac ggatcccggg gccatcgacg actcctcccc   3240
atccccagca ggcgggagct cttacattcc gagcgactgc tctcaccctc tggcgctcac   3300
acacctgtaa ctccaaacct ccgtctcaga atggtccggg ttggaaggga tgatgggggc   3360
tcggacagcg actgcccagc tcacccctct gcgcgctcag gctccaggct cagcaggacc   3420
aatttgagtt atatctgatc cccctgcccc cgtaactgac ccatcctaca ggagacaggg   3480
aaatgtcttt cctaccgcgg ttgattctag ggtgtcattt tgtgttttgc gatggctgct   3540
tatatttact acataagaat tgtttatttt ccatctccaa atcctccctc tacataaata   3600
aataaatgga taaacagata agtgtgtccc ccgcccccac ccccgctagg caggtctgga   3660
gtgacccttg aagctcatcc attccttggc caagtttgcc tccctaacag atatttatac   3720
agcaataacc cggcttggct cttgggttca cctttagacg atttggggaa ggggcttgtt   3780
ggctttgctg gtttttggat gagtgacagt ccatgactgt tcctgctgga agggcgtggc   3840
ttttaagtgg tttctaatat caggcactgc tcctctgaga ggaacaaaag aaatggatac   3900
ctgcccataa attgctagaa aacttagaat tggtttgatt gaggaaaggt tagatttatt   3960
ccggttggaa aaagaggcct ttctattaaa ggggcccttt gaccctcatg cccttggagg   4020
tcagtgccag cctggagatg tgataagatt gtggttttcc ttctgccttt ttaacatccg   4080
ttgatacagt ccatttgttg aaaattttaa gaaacgtgtt ttattccact ttccctcagc   4140
atttatgtgt gtggcttcag tggctctgtg gctacatgta caaacacatg ttatttttcc   4200
aattggacat gttataattt tccaactgga ccttgccttc tattgatgta tttatttagc   4260
atcttcctta ctccctcctt gaaaaagact cactcaaaaa caagtaaaaa caaccgtagg   4320
ggcctaatac agtgctagac atacaagagg tatccggtcc ataccaaatg gattttatcc   4380
atgaaggata aatggggaaa cacaggttaa gagaaacaga aggtggggct ttatttatgg   4440
```

tcacggcaga aggaaggtct ggggacaaac tcagttcagt ctatcccagc cctgtgtccc 4500
agtgacgctc agctgcctgt gctcttgggc cacctcctcc cgccccctcc ccctccccac 4560
tgcagcactc ccatagcctg gtccctatgg cccacctccc tcttattggc cagaggtgaa 4620
gatgagagga aaggagagag accaccctct accctaggga aggaagaccc tgccctggca 4680
ccttttggta cttggtgcag taggtcggtg ggaagcgggt gggaaaccac atttgactct 4740
gctccttcct ccgccaccac tttcctcatc accgtgttca gagaccccca aagccccttc 4800
acactcccag aaacagcccc ctggtcattc ctaacttgcc atgcccagga gttaggcgct 4860
tccactagtg acagggagct ggcgtttggg gggcacctca gcaggtgacg ggagagaag 4920
cctgcagcct caccagctgg gctgcagcag agagaggagc cctcatgttc cagcagggac 4980
tctcagctgt ttgcctgtaa aaccatgctt ctcacctggg ggccactgag atgtctagag 5040
agatgttttt cttttcacaa cttgaggagg gtgctactga catctcgtag atagaggcca 5100
gggatgctgc tgaacatcct acatggcaca ggacagtctc ctacatcaaa atatgaccca 5160
accccagtgt taccactgct ggggctgaca ctggcattgc taccttaatt acattcattg 5220
attgtcttct aggagccctg ttctaagtgc ttgtctcaga ttatctcatt taatcctcac 5280
aacaattccc ctatgtagca ggtgctgtta ttatctccat gctggggaaa ctgaagcaca 5340
gagagggtta gtaacttgct aaaggtcata gagccagtgg gtggtggagc tgggtgcctg 5400
ccactagctc cctcccctct cagccacacg tgggtttact tggccattgt ggactagtct 5460
gggaacccaa atatgatcta taacattgac ccagtagata ttgattctaa aaccactgtt 5520
tcacaaatga acttttacaa gagtctgtaa ttggagcatg acccagaata agtttaggga 5580
gatgtggagt ttaaagctct caatttctta tctggccccg acacagagag caaggcattt 5640
cactctacct tggtgctctg tttataaaac aaagagcaaa tatctcttcc caaggtcctt 5700
aaacttctac tccctaatgc agggtttctg gactgatctg ccagatgaag ggcagctgg 5760
tttgattgac ccagggaagg ctggaaatca agactggggg atcaagatgt agattcagtg 5820
tggccaagtc aagtctctgt ggtttaggga catcagatgc ccagcttagg ttctgtacct 5880
cggcaaggta aaagcgttgg tgcccactga tgaggccagc tctgagattg tgggtgtggg 5940
ttgagttggg tgggcatagg caagtcctca tgtaagaatc ccttggcaaa gataggcccg 6000
ggaggctttt ctcacttcct ggggcccagg ctttgcaata aatattccat tatactatgg 6060
tgccttgggg ctacctgaga atcctctgtc tcgcccctgt tgccttgcca aagaggttgc 6120
tgtccaagaa ttcctttcct gtctccagat gccatgctcc tgccacctct gccaggttcc 6180
ctgcctgccc agatggctcc cacctgagta tgaggaggag tttgaggctg gcccaggaca 6240
ggttttgagc tttctgggtt ctccggttag gaagctttct gtaagcatgc agatacaatg 6300
ggcatcagca aaatacaaac tggaacaatt tccaggtata ttcccttaat tttctttgct 6360
tttttcatat ttcatcaggc tccatgctga gcccaatcag ggacctgata aaaatccaaa 6420
caccatgtca gcgagtcccc aagaaatgca ttttgtgcca aggctattca aggaagtttt 6480
gggagcagct caagggcaga cactgttacc cttcccccag gtccccagtg cagggcagtg 6540
tcctgcatgt ggaggcagtt tggcctaatg gttaaggagg caggctctga ttgggcctcc 6600
tggacataag tcccagctcc ctgctcactg tgggacctaa gccatgttgt ttagctgttt 6660
ggagagtttt ttgtcatcca taacttggag tatgatggtg cctgtctcac gggttgccat 6720
ggggttcaaa caagctaacc tggtactcac cagggcccta cacatagtaa ctgctcagta 6780
aattgcatca ttggcagtgt cctatggata agtgcttgtg attggctgaa tgagcagagg 6840

```
ggtctaaaga ccctggtgat ggaatcagtt gtacagataa attgttacac tgagtaggga   6900
tcaagttagg aaaagtgggt aactgcccag ctcccctgca gccaaacttt gggcagacgt   6960
ggaccctctg aaaattgcac acacccatgt tttttttgt tttttgttt ttttttttt   7020
ttgagacaga gtctcgctct gtcgcccagg ctggagtgca gtggccggat ctcagctcac   7080
tgcaagctcc gcctcccggg tttacgccat tctcctgcct cagcctcctg agtagctggg   7140
actacaggcg cccgccacct cgcccggcta gttttttgta tttttagtag agacggggtt   7200
tcaccgtgtt agccaggatg gtctcgatct cctgacctcg tgatccgccc atctcggcct   7260
cccaaagtgc tgggattaca ggcttgagcc accgcgcccg gcctcacaca cccatgttta   7320
aatgtacaca cagaactctt gccacaggca agcagagatt tgtcatctgc tgtccctgct   7380
tcatattctt cctgaaatcc actccatgcc aggaataaac tgcatgctct ccaccagccc   7440
aaaccgacct gccctccctc cagtcatccc gggaagggtg acctggctta gtacattggg   7500
ttcagagatc tttccagttt acttgttgaa taaaaagtga gggctgatta agaaagtaat   7560
ggcagtcagg gaaggcgaag gaggtgaaga agagatttta caaatgaagt aattcaacgg   7620
agtgctgacg ttggtaaact ggtgaacagg tttcagggtg gtcggttgag agtagagtag   7680
aaaagggtta aataaagcaa acttgtggtg tactgaatct taggaattcc atgtatccaa   7740
taagtatagt catttatgaa ttaataaatt aggcctaaga agccttctta tcccttaaat   7800
caagactgag taacaatata tcagttttaa aaagtcatta catcagaaaa taatgtaaat   7860
gatacacata gattttcaag attttacttt aactgaaact atataaatgt aaattcattc   7920
acccatcttt tcacacaggg cccaggtctt ctcttggtgt ctgatcagcc agttgaaatt   7980
tcgtgtctct cttgcctgtg ccatattaat aatgcactgt ctgggtcttc cgatttcagt   8040
ttggattttg gatttatatt gtggagtcat ctgaatgcag aatccctcag ggattttact   8100
tttttctttt tttgcatggt ctttaccatc ctgtttgata gtaaatatta ctcacctttg   8160
tgaagtcttt ctaaaacatt caacttaatt ttcttaaaat cattgaatga tttgaagagc   8220
ttatccttcc ctctgcactt gtattccctc agcttgcacc ttatttattt atttatttat   8280
ttatttattt attgagacag agtctcgctg tgtcgcccag gctcgagtgc agtggtgcga   8340
tctcggctca ctgcaacctc cacctcctgg gttcaagcaa ttctgcctca gcctccccag   8400
tagccgggac tacaagtaca caccataatg ctcgtttgat ttttgtattt ttgtagagat   8460
ggggttatgc catgttgtcc aggctggtcc tgaacttctg acccaggtga tccacccacc   8520
tcggcctccc aaagtgctgg gattacaggc gggagccacc atgcctggcc agcttgcacc   8580
ttagttaggg tatgtgatta ttatagcaag tctggtgtac gtagaagatt ttgaatgggc   8640
acagatgacc tttaggaagt gctgggctgt ggtaagaggc agtcctaact gcagatcagg   8700
ctgtgaggac cccagccttg catgttgaca gaccttcatg tcttattcgt acagggtatc   8760
agaagaacac ctactgggga aacttttaaa taagtaaaag gtgggcgtcc tccccgcctg   8820
tcttccgtct gtctgccagg actagcacag cactttgaag tcattcacat ggaatcccaa   8880
cttaagaggg cactacaaaa tcctctccat cagactgaaa ataagtttaa attccctttc   8940
ttatattaac tcccctgagg aaagagtctt agatcaatgt ccaatactaa aaacagtttt   9000
aaatcagcga gtgagaatta aatctgaaac cattgataat aacgtttcat tcattcctct   9060
cctttggcct catccaccct actgctaaat ccaggcatca aagagaagag ggacataatt   9120
atctctggtc ccagctgctg gttttccttc cagcctatgg cccagttttc cgttttactg   9180
```

```
agaaggctgg tgatgttggc ttgggatcta catctgcagt tgtaccacaa aaagtccagg   9240
gatgcacttg catccttgta tccgcctccc tgggatagca aggatattag aagacccctg   9300
gatccataat tgcttgtcac gttatctgca gacgccacag aatgccaaga acaaagtgct   9360
gggaaggacc aattcatgga accatgggac ggtgctcgtc cccagcgta aaggacagct    9420
cctcctcctg aattgcagcc agcattctaa atcgtgtgtc aacagagttg tcctggatcg   9480
gatccagttc tcccattgat ttgcaggtca cttcaggggt gcctgttcca gttgttctta   9540
actgaatgct ggcagcaaac tgttgtctta cctcatccct ctaccacggc ctattcctcc   9600
aaaagagact tcttgggtaa tcacggcaac atcaggcagc cgggcgcggt ggctcacgcc   9660
tgtaatccca gcgctttggg aggcggaggc gggcggatca caaggttagg agattgagac   9720
catcctggtt aacacggtga aaccctgtct ctactaaaaa tacaaaaaat tagccaagcg   9780
tggtggcagg tgcctgtagt ctcagctact caggaggctg aggcgggaga atggcttgaa   9840
cccgggaggc ggagcttgca gtgagccgag attgtgccac tgtactctat cctgggtgac   9900
agagcaagat ttcatctcaa aaagattctc tttggtttta tatgtatata agtgaggcca   9960
ggctcggtag ctcacacttg taatcccagc attgtgggag gatcgcttga agccaggagt  10020
ctgagactag cctgggcaac aaagcaagac cctgtcttta caaaagaaaa ctaaaaatta  10080
gctgggcgtg atggcatgct tctgtagccc tgtctacttg ggaggctgaa gcaggaggat  10140
cacttgagcc cgaagttcaa ggctacagtg aactatgatt gtcccactgc actccagcct  10200
gggtaacaca gcaaggtcct gtctctaaac atttttttaa aattctattt atatttacat  10260
gtatttaaat gtgaatattc actacctatt tgttgcatgc ctggattttt tatattgggc  10320
ttgctgaaaa cctgaacagc tttctacttg acaatgcatc agaatttaaa tcagcgtgtt  10380
aataagccaa gcaaaggtta tataggcaaa taaaactgtt gtctgtaacc tcctgtaaca  10440
ttggagcaca gcaaaaatca tggtatagac acatatgaac ctgtcccttt catagctgct  10500
cactgccagg aaacatcagg aatagccgtt tggaagagtc accggccctc ccaccatccg  10560
ttttctgtct tgtcttttcc ctatgagcag gggaaattcc ccactggccc caatccccgg  10620
tgcagcggct cagcctctgc ctctgccgcc gctttccatg aggccagctt agaaacagag  10680
gattttgcag aacatcccta aatccgcttg aataaaggag tgatcattca taaactcacc  10740
tgaaccttct taaaacctat ttaatatttt tcccggataa tcctatcgag ataacttgcc  10800
tcctgggctt ctctccacca ggttcagttc ttcctttagt ggtgaagttc ctcccttctt  10860
agcatctcag ctgtgcctga gaaaaggcca gcggtagctg cactctgttc cctgtggagt  10920
gttaataaag actgaataaa ttgaaataaa tccctttcaa tgtcactaaa gtgctataaa  10980
taatcatgaa ccaatgtttg atggcggatg agaaatgcaa gaaaaaattt ttaatcagta  11040
ggattcatgt tataagttga cagtctgggc caggttaaaa aaataaaaat aaaaagactt  11100
taagaaagat cttatcattt gttaccagca agactgaatt ccagaagcga gccacaccct  11160
cattttgtgg gcccctgtta tcactggctg cttagggttg ccaagccctg aattcatttg  11220
tcaactaaga ggtttttggc caagattaag gtttcccatg cctccatatt tccatctgag  11280
aaatggagat tatgctgtct tccccctcag aatggatgat aatgtggtct ctcttctctt  11340
ctcatagtca tagaactgaa ataaaacaac ttaagagaat tcctttgagc ttctcaaaag  11400
tgctgcagga ctaggggatg cctcccggga gccgcagtcg ggtgctgatc tgaagtcttt  11460
ggtgggctga ctttagcctg acctgaaata gtatagctgc tgccacctgg ctcccttagt  11520
gccaaactgt gcagctggtt cctaggggtg agggctgagc cagcaaggtc tgtgcccagg  11580
```

agggatgcat gggtggccac agaacagcct gcactgatct tgtctgtccc ctgctttaga 11640
aggaaggaga cccaaaccag gatgcaagac agtgggtggc ggtgccttga gcatgacctc 11700
aagtgatttc cagcccctgc cagtgctgac ttctctgggg aagggctggg acttccttct 11760
gagctcaagt catgaccctt acatagaatt tcctgggagc ttttccattt ttctggagtt 11820
ttcagtttct tcctaaccag acagggactt ggtacagaat ctcatattct aattatgccc 11880
aggagcaacc tctccccacc acttacagcg tttagcatgt gacaggaatt gattaaggca 11940
tgagtgatta aattaaagcc aggcattgac ttggatggtg taatattctg atgactgttt 12000
ggtggcaaag gcacggggca gactcattaa ttgaactgct tgcacctgga atttgaattg 12060
agccagagcg gggctgaagt cagtttgcct tcaccctgtg aatggagggt ttctccggag 12120
cgtggatggt gggaggtatt tcaggatgta tgcgtaaccc ccaccctggc aatggcacat 12180
cttttctcca gcgtggccag gtttgagtgc cagtcctggg tgtccatagc cttgcgtttt 12240
agtaaaatgc tgcccccatt accacctggt ctgtccactt cggtcactgg aatttgccgt 12300
cttccagtcc ccagtgtggc aagccatgga gactcaagct cttccccctc cacatcctgg 12360
aacagacccg ccagtttctt ccaggcattg cctcagtttg cccctctctt tccagtcaca 12420
ctctcaccag cgataacatg attttaggcc ttatcacctc accctcggat ccttatggaa 12480
acaatgagtt gttccctgtt tcagttccaa aattcatatc caatccgttt tgcgtgccat 12540
tgccaaattc ttcccagagc aaccccgtca cctgccctgg ccctctccac gtgtggtcct 12600
gccatgagca tcacctgcta agccaagctg gcctcgagct gcctgcctgg gtccccacac 12660
cttggttcac ctccctgccc agtcccacct cccgcttcct gccagcctgc cctgtggctc 12720
cttcatagac gccgtgctct ttctgcccct tgctcaccca tggcagcttt gcccctctct 12780
ccctgcccta ccccatatgt aaatcgccct gaccttcctc agtgtccatc ctccctgaag 12840
ctttccccag ccttgacact caaggtccag aggctgcgcg tttcctctta cctgtggcag 12900
agccgcgctc ctcagtgctc acagttcccc tcttgccccc gcttcctgtg taggactcat 12960
ctgcccacag gttgcacgtc ttatgaaggc aaggactgtg tcttacgtga ctttccttct 13020
ccagtcacag agctgggcac atatatagct caaaaccctc ttgattaaca caggtggatg 13080
ctgagaaatc aaacaggcga tgtcaaatga gctctcctta tttaaatcaa gtcagttctc 13140
cacctcctag ttactcagtt ccagtactgt atatacttgg aaataataaa aaccacattt 13200
cctttaaaac attctataat tgttcctttg ccctacttca gactgactta acacactccc 13260
cattggtcca aatgagtttt gccatacgaa gatgctgata ataatagcag cagtggatta 13320
ttctactaaa accattgcct cgttaatcct cagtcccaac gaggtgggga ttattatcct 13380
cattttgcag agaagcaaac tgaggctcag agatttcaca gctggggagg gagccagatc 13440
atgcttctgt ccaggcccaa gctctccccc gcttgccttc ctgcctctgc aacctcagag 13500
catcccccat ctggttccac tggctatgct agttgtgcgg gaaccaaaag ccccgtctct 13560
agtgctgagg actggagaag ccatggcctc caggctctgt gaatgggtca catgtaacct 13620
gagcctggag aaattgtttg aaactgaagg caagcctcta aaccaggctg ctgcttcatg 13680
gcgccggtga cggcagaacc aaatttagtg ctgtgggcag gtccacactt atcagaaaga 13740
gaagctcatt tttcttctgg ctcacatcaa gcatgaaaaa tgttcacaca cacaccccaa 13800
acacatacac actccggagg ggtccatgtg gctagaggct ggaagatgtg gatgagagga 13860
gcctggcggg taagcccagg gaagatgaca ttcagcttcc cagacagtgt ctacagggag 13920

-continued

```
aaatttaatt aaaagtgggg cgggttccct gagcaaggca gacaaagtca gccctctacg  13980
gttaagaaaa agggtcacag tgagaggaaa ggtgaagaga ctgagtctgt attttccagt  14040
ctgttgggcg acacgcctga tccccccttcc tcaaaaatcc actttacttt ccccatgtct  14100
acaccagtgt ggttcacact ctgggacaag gaaaaggggg agtgatgggg aacagagaag  14160
ggaggagctc acacagctga ggctggggtt atgcatatcg aattacttag aatttgcaac  14220
ctcacagggt acttttatgg cattgaaata cacttcccac agccaccctc cctctaacta  14280
aaagcaagag tcatttctca gttctggtct tgccgcccac cttctcctcc acattttaaa  14340
aaatccaccg gctgcaaagt gaagacacca tatgtgagat cccaccctag tttctgtttt  14400
atcagggttt ggagcaggtg gagcaggcag agggatcatt tcagcctgta cattgtatta  14460
agtattaagc gtgagtgctg agtcattctt caagaaaagt tttatgaagc acccaaaact  14520
gaagggtgga gccacctgga gacagtagcc tcagtcctgg ccctgagcac agcctgcata  14580
ggcccctctg gatcccggcg ggagctgcag agtgtgggca ccttggcaca cagccctgag  14640
tgcaaaatta ggagctgggc agagggcatc tctgtcgcca ttgggaagcc cagggcacac  14700
tggtcatagc cgtagaccac gagcacccta cacccggggg acagatgcaa ccagtgtgcc  14760
ctgggctgcc caatggcaac agagagattg acacctggat cccgtgtcac agggactcca  14820
ctaccaagac tcccgagact gccaccttcc agtgggataa gccctgcctc ctactgggcc  14880
cacaatgtac agagaacact tgggacgacc tggctttctg gatacacaaa tattgatcca  14940
atctgggcta attagaaggt cagtcccagt aaaaaatcaa agtcagctgg gtgtgaggct  15000
cactcctgta atcccagcac tttgaaaggg caaggcaggc agatcatttg aagccagaag  15060
ttcaagacca gcctgggcaa catagcaaaa ccctgtctct actaaaaata caaataatta  15120
ggctgggtgt ggtggctcat gcctataatc ccaacacttt gggaggccga ggcaggtaga  15180
cacctgaggt caggagtttg agaccagcct ggccaacaca gcaaaacccc gtctgtacta  15240
aaaacacaaa aattagccaa gcgtgatggc atgcacctgt aatcctggct accggggagg  15300
ctgagacagg agagaatcat ttgaatccag gaggcagagt tgcagtgagc tgagattgga  15360
ccattacact ccagcctggg tgatacagca agactctgtc tcaaaaaaaa aaaaaaaaaa  15420
aaaaaaaaaa aagctggacc tggtggtgca ctacctgtaa tcccagctat ttggaggctg  15480
aggctcaaga atcacttgaa cccgggaggc agtggttgca gtgagccgag tccagcctgg  15540
gtgacagagt gagtgagact ccatttcaaa aaaataataa atctgagtca ctttaatatt  15600
cttatttgga tgtcaacctc taggtgtttg agacagggga gtgacatggg ggcacggtgt  15660
aacctcacac ttgggaagcc cacatgatgc gatatcaggg tgctgggagg tccccccact  15720
ccctaaatta ctaacaagtg gatagtactt tgcagtttat atgatcttat ttgattcttg  15780
acatgagcct gtgagtgaaa aattccttcc cctcttctac agattaggac attgagattc  15840
agggagcttc agcgggattc aggaagtcaa gtggcacctg gagtcccgcg gctaatttga  15900
ggctggtagg agagtcgaac ccaggacttg tgcttctcac gcctgggttt ctgcttccta  15960
gtgcatggtc ttccccctag ctttcccatt cactgcttta gcctagggct cttacccttt  16020
attaaactgc cagtgcctcc ctgcttttct tgcccaaaga caaaaaagtg tttttgtttc  16080
tgttttgttt ttcatagggc agagacctgg aatttcagct tgagaactta taccatatga  16140
taaataaatc atcaacagat ggctttttcc ttaaaaaaaa aaaaaaaaaa aactctaaga  16200
tgtatatgca gggaggcata atttgtgcca aaaagtgctc accacactgt agtcatgggg  16260
gcaggaggca gccgcaggtg aagggagaaa tctcagagtc caagcagccc ccttctgggc  16320
```

```
tgaactgggg agctgggggc actgccagcc ctgccaggtt ctcctaggag gcggcagttc  16380
atatggccgt gggaggaggc agagggagcc tcatgtgtac ccacatttcc agggatccag  16440
aagacagaag gaggaaaact accatcatgt taaagcagac agttaggtaa cacatcctgt  16500
aatacaagtt attttttcca catctaaagg ctaaaaatag ttgctagaat ttaaagataa  16560
ttggtaaatg agtttctatc cttctagttt cacatcaaat ggaatcacgc tgccttcaca  16620
ttactagtgc ccgttatttg tgtttaattt ccacaatgtt gtctaattcc actctttggg  16680
cttccccagg gatccagact ccctcactcg cccgtcgcgg ggaaatgctt tatttatctt  16740
tgtgtcctct gagctgggca tagcacatgg cactgaataa gcactcagta attgattcgt  16800
gaatgaataa atggatgagt gggtgagttc aatatcgact acaaaacccc taaggccaca  16860
tgctagtgag tggctgcgcc tgtagtccca gctgctcggg aatctgaggc aggaggatct  16920
cttgagccca ggagtttgaa accagcctgg gcgatatagc gagaacctat ctcaaatgac  16980
aaaaacaggg ccaggtgcaa tggcttacgc ctggaatccc agcgctttag gagaccgaga  17040
tgggaggatc acttgaggcc aggagttcaa gaccagcctg ggcaacatag ggagaccctg  17100
tcactacaat tttttttttt ttttttaatt agctgggcat ggcggcgtgc acttgtagtt  17160
ccagatactc gggaagctga ggcaggcaga tcacttgagc ccaggaaatt aaggctgcag  17220
cgagccatga tggcaccact gcactgcagc ctgggcgtca gaatgagacc tgttctcaaa  17280
aaacaaacaa acaacaacaa aaaagtacag cctttcttaa agagacttga gaacagaaag  17340
gggaacagat gcataactta tatatttatt tgttcatctt tccaccttcc tggaaggtag  17400
aggggaaccg gtctgcattt ggagttttga gtgctaaaag tgggaatcat gcactgtttg  17460
ccatgatctg ttcaaaagtt aagccaaatg ccttagattc tcctgaaaac tggaatgcca  17520
ctgtaagcta tgagccccac ttcaaagata aaagatcttg atgaacaggg ttgggtctgt  17580
ggactgggcc tctccctgcc aaacaaggaa gggtggtgac cagttgaagg caaatcactt  17640
aaatccttac cgtctcctaa taggtgtggt cccaggtagg gctgtcagaa ttagcaaatt  17700
aaaacatagg gcatctatgt aaattagaat ttcagataac aacaaataat tggcataggc  17760
tgcataatgt cccccaaaga tatcaggtcc taatctccag aacctgtaaa tgtgatctga  17820
tttggaaaag gggtctttgc agatgtggtt aaattaagga ttttgagatg gggggaattat  17880
cctgtattat ctaggcaggt cctaaatgca gtcacactca tccttgtaag aggaaggaag  17940
agggagatgg aaaacacaga agagaagacg atgtggtgat agaggcagag attggagtga  18000
tgtggccaca agccaaggac tgctggcagc caccagcagc cagaaaaggc caggaaccaa  18060
ttttctcttg gacctccaga gggagtgtgg ccctgctgac accttaactt caacctagtg  18120
atccttattt tggactttgg ccttcagaag tgtgagggaa tgaatatctg ttgttttaag  18180
acaccaagtt tatggtcctt tcctacagca gccacaggaa acaaaaacaa taagtatgcc  18240
ccatgcaatg tttgggacac acaccaaaaa tattgcttgt tgttcacctg aaattcaaat  18300
ttaactgggc atcctgtatt ttatttggcc aacctagtcc ccaggcccaa agaaagaggc  18360
ttttgaaatt tgcaagaaag ctggttggag ctgtcagaaa gtggactttg taaacacagt  18420
accactgaac caatttgaac cttactacct ctaggcaaaa gagagggcag tcagacagtt  18480
tttcgtgatt tattctttca acagtcattt gagtgcttac tacaaaacag aagctatgtg  18540
taagggtgga ggtgttagct gttaatcagg acctccaggc taagttactg tattagtcca  18600
ttttcatgct gctgataaag acatacccga gactgggcaa tttacagaag aaagaggttt  18660
```

-continued aattggactt acagttccat gtgactgggg aagcctcaca tggtagaagg caaggaggag 18720
caagtcacat cttacatgga tggcagcagg caaagagaga gagagcgcac gcttgtgcag 18780
gagaactcct ctttttaaac ccatcagatc tcgttagact tattcactat caagataaca 18840
gcacagaaaa gacctgcccc catgattcag ttacctccca ctgggtccct cccacaacac 18900
gtgggaattc aaggtgagat ttgttaccat gtcagttacc aactgttcca gataaatcac 18960
gtgaaatagc accattaaca gagtgagctc aggtggttct tcagtgcatt tctgatacct 19020
gagccttccc tgggaatttc acagcccatc aggctccccc tacttcgatg gcaggatggc 19080
agggcccagg ttaggcagga ggagatgtta tcacaggcct gaaaggcagg gaggggcaga 19140
tgctacagga aggtgctggc tctggattcc ctggcggagc tttcaaggga agtagatgca 19200
cactgtctcc atcatttcat gtccataaca ctctaaaatg ctttggacaa ggagcaaaag 19260
ttaaagacaa atgtggccca ttttcctgta caaagagggc tgcccccatg ccaggctgtt 19320
ggcatcagtg ggcatgaggc ttttctgctg ccatagtggg ggggttctct cactcaccat 19380
tggctctctg acacctggag agacccccac ccttgggctt ttgtgatgct cacggaatcc 19440
acactgttgg agctttaagg cacctgggtc aactggaaca ggcaggggat actaggacag 19500
cccagcattg ccccaaaata tccgggcctg ataaaagaga aaaacaggta gctcacagga 19560
aacggataaa aaaaggaaga gggatttaac atgaaaaggt gcttgatctc tctcataata 19620
aaaagactgc tgattccatc caggcaagtg acagaaaaaa aaaattttag tttaaaaaga 19680
ttgctgataa aaccacagca agatgctgct gctcagggat ctgagggtgt gggcagccag 19740
gctgccacac atcatgagtg ggagaggaag accacacccc tggaacaaag ggcagctatc 19800
tgtcagatgt cctttgacag caccgcagct tccaagaatt aaccctttcc atgtgagcag 19860
aggcatccat gcgggggaca cactggtgaa tcatctgtta tgcagaagtc tggaaaacat 19920
cagggtggaa ccggcgaaat aagtgtggcc tctgaaggaa tggagcggtc cctctgtgct 19980
gcttcgggtg cccctgagat cctgcgggcc agtgagaaag cagtgaggaa caaggcggat 20040
actgtgcact gtcctctgcg tgcaaggaag gctagtgcat gcgacggagt ccacacagac 20100
acagcctaac tctggaagga agaacaagaa tccagtttca gtggtggcct ctggcgggga 20160
gaaactgggt ggaggaagat gtcatttcca tttttctact attaattttt tattaccatg 20220
cttaaatatt actttttacc tttttttttt tttttttga gacagggtat ctttctgttg 20280
cccaggcagg aatgcagtgg tgcagcctca acttcctagg ctcaagcaat cctcccacct 20340
cagcctcttg agtagctgag actacaggca cgcatgccac cacacccagc tattttttt 20400
tttatcgaga tggaggcttt ctgtgttgcc cagggtggtc tcaaactcct ggactcaagc 20460
agtcctcctg cctcggcctc ccaaaggact gggattacaa cgtgagtcat cctgaccagc 20520
caattacttt tttaaaaaga ttaaatgcat gtatatgctc aggcatcagc acacttggaa 20580
aggacgagaa tatctggaag aagggttctt ttaaaaggct cctcaagtga cgctggcagg 20640
cataacgaat gtccctggtc acaaaagctc tgatctggcc taaccctctc atattagaga 20700
ctggaaagag tgtgtgtgtg tgtggtgtgt gcaaagtgtg gaggatgggg gtgagtgtgt 20760
gtggtgtgta agcatgaatg tgtatgtgtg tggtgggggg gtgtgctgtg tgagcatgta 20820
tgtgagtctg tgtgtgtgta gtgtgtgtga gctatatggt gtgtatgtgt gatgtgtgtg 20880
aggtgtgtgt ggtgtgtgtg tatggtgtgt gtgtgatgtg tgtggtgtgt gagcatgtgt 20940
gaatgtgtga ttgtgtatgt ttgagaatat gtggtgtggt gtgatatgtg tgtgtggtgt 21000
gtgagcgtgt gtgtgtgatg tgtctgtatg tggtgtgtgt gagcgtgtgt gttgtgtgtg 21060
tgtggtgggt gtgtgcagta tgtgagtgtg tgtgtgcaat gtgtctgtga acatgtgtgt 21120
gcagtgtgtc tgtgagcatg tgtgagtgag tgtgtgagtg agtatgtata cagcatatat 21180
aaggcatgaa actgaacaca gcacctttag agtgctctcc tggagtcaga gggggtgggc 21240
aggaggagaa gggaggtggg ctagtgtgct gaagtgtcta ctccttgtca tggtttgtga 21300
caacccagat tagcccatga gccaccctgg tccctgcatt tccaatgaga cctcggtggt 21360
catgttctct gaggtgaggc tgactggtgt catttgatga tcttgatacc aaatcctttt 21420
gtatcaaaaa caaccggaac actctgtttt ctcttagtgc tttcacccag atgaccacat 21480
ttcatcctcc cagccactcc gggccaggtg gcactgctgg tttgaaaggg aagcctcccc 21540
tggagtaact tccgtgggcg gattcacacc ctacccacac tcctgtccca gtcggcccac 21600
catggtggtc tctggttcct ccagaattcc cacttttcag ctcatcccca cattcccgga 21660
gggactgaga gcacagcccc caaggccctg ctctttgggg gcagtctcca cacccagaga 21720
agcagcaagg cattcctagg tttctctttc agatgcagaa cttcagtgct cagaggtgtt 21780
cccaccagtc ctcagagggc tcagttctgc tttaatgatc gtgctgttgc gtgggctcag 21840
cagagggcgg gtggcccagt gtggctgagt gcagttttcc tgacatggag tccgagcctg 21900
ccccgctgtt tattaattca ggatcactct ccttgcagaa ccctgaactc cccagaactg 21960
tgaggtggga gaaccccgag aggccacctg gccctgcttc ccacctactg cccacacccc 22020
ctctctgcct tcctgacagt caccccaact cccagtgatc cccatcaatc atctgacaag 22080
gggactgaga gggaagagaa aggaggggcc caaagagaaa ggtaaaagtg ttgggagcag 22140
cccccaaatg tgtgacatcc ttcagcagag ttgcccactt tccctttct cctccctgca 22200
ggacctccct tctcctcagt cctgcccaac ttctgaggtt acattgagaa aagtccgcag 22260
aggtgccagc atcacaaggt gttaaggacc acgagtttgg cattttaaca gatgccagag 22320
ccacttgaga aatgtggtaa ctaagcccag agaggtacag ttacctcccc agagtcacac 22380
agcaggttca tggcaaagca aaggtgtcct tccccctgca gatccctttc tgtgccccac 22440
atcatcttcc tccagtgtgt gggccacctg gagacaggct ctcacactca cctggccaga 22500
ggtgccatct tgtgggaaag gcttggccag gaagcatcga tatttgagat cccaaaaaat 22560
gaaggcttgg cctgtcagat gacagacttc ggtcatgggg acgcatgatc tgttttacac 22620
acacgtcccc tcagcagcag ccttccagaa cattcccact ttcttctgta atgagaagaa 22680
ctctttccct gcagcctcct gcccatctcc tcctgggaga gccttgcttc agtgtctttg 22740
ataaatcatt ctgttttgca gagtgcgagc tctgcctcgg agggttcgca tccacctgtg 22800
ttgagtaacc aatacgaagg tcgagtggtc acccctcata agagctaggg ttgtctcatg 22860
cctggggact aggacttgcc ctcaaggaaa aaaaaaaatc aaaacaaaag caaaaacaac 22920
aaacatgcct ctctcaaaga aagctctgag tccaggtaaa tttccttcca ctgaagcagc 22980
caggctgaat ttgaattctc tttgcctctg cttaaaaact aatgcaaatt ttcctagaga 23040
atgcccacta attcctggag ggggcacggg cattcctgat gcccatgaga ggaccatttg 23100
ctcttccctc agtgtgctaa ataacagaag cgacatttgt tgctggaaag tatcagtgag 23160
gttaataagg tgtctcctgc ccagggtgag ggagcagttc ccaatgacaa atgctgtgtg 23220
ggaaggggcc ataaaactgc cagccccttt cgtccaccca taatgtggtg aaccctgtgg 23280
atcctggagg atttcagcat ctttttttat ttttattttt attttttaga cggagtctcg 23340
ctctgttgcc caggctggag tgcagtggct ggatctcagc tcattgcaag ctccgcctcc 23400

```
cgggttcacg ccattctcct gcctcagcct cccgagtagc tgggactaca ggcacccgcc  23460
acctcgcccg gctagttttt tgtatttttt agtagagatg gggtttcacc gtgttagcta  23520
ggatggtctt gatctcctga cctcgtgatc cgcccgtctt ggcctcccaa agtgctgggt  23580
ctcggcctcc caaagtgctg ggattacagg cttgagccac cgtgcccggc cttttttttct  23640
ttttcttttt tgagaaggag tctctctgtt gcccagactt gctctgttgc caggctggag  23700
ggcggaagtg cagtggcacg atctcggttc actgcaaccc ccgcctcctg ggttcaagcg  23760
attctcatgt ctcagcctcc cgagtagcta agattacagg tgcgcaccac catgcctgac  23820
taatttttgt attattagta gaggggtgtt tcattatgtt ggccaggctg gtctcaaact  23880
cctgacctca ggtgatccac ccagctcagc ctcccaaagt gatggaatta caggtatgaa  23940
ccaccacacc cagccagcat ctttcatttt tctgtccact ttggcccttt cctctctcac  24000
tgtcttcctt ttccatttcc aaagtcagtc catctcacta ttagcacaaa aactgctaga  24060
gcgctcgtca ttggtcatct ctccctgcac ctggctggtc tgttcttagg cactgaagtg  24120
tttcccccag ctgttgcttt aatcattttg ttatcatgcc ttacttaaga aatgaacatg  24180
agatgcattt atgtgtctct ttctgccact ctgcagagcc agtaagatgt ggtggaaagg  24240
gcccaggctt tggaggaggg ctggctgggg ttggatcttg gctgctccct actagctgtg  24300
tgaccttggg taagtagctg gacctctctg agcctggttc ggaatcatag cacctctctt  24360
tcagggctgc tgtaaggaat agcagcgatt tgtgtaaagc agagagcaca gctagcacct  24420
ggcccctagc cacactacag agcacttact gtgataagct gccattgtgg tgtgtgaagc  24480
aaaagggaaa tgcctgctgt agtaagcttc ctgtagggca gttcgtagaa ccagagatgg  24540
gtttcaaggt tacaaaggga ctcttagtgt attagtccat tctcacatta ctataaagac  24600
ctacctgaga ctggatcatt tataaagaaa agaggtttaa ttggctcaca ctggctgggc  24660
acggtggctt acgcctgtaa tcccaacatt ttgggagacc aaggccggcg gatctcttga  24720
gatcaggaat ttgagaccag cctggccaac atggtgaaac tctgtctctt ctaaaataaa  24780
atacaaaaat tatctgggca tggtggtgtg tgcctggaat cccagctact tgggaggctg  24840
aggtgggaga actgcttgag cccaggaggc ggaagttgca atgagccaag atcgccccac  24900
tgcactccag cctgggcagc cgactgagac tccgtctcga aaaaaagaaa agtaaaagaa  24960
ctgcaagaaa taaattgttg tttgtgagcc atatggtctg tggtacctcg ttgtggtact  25020
gggagtcttt tgtctccctg accctgcctg ttgctgcagc accgctcagc cctgcctgct  25080
ccctaccttc ctccccttgg cctctcctgc ctccactggg cccctggtgc ctcctctaga  25140
gacagtcctc ctgggaccag ttgtgttctc atttacacga ggcatccagg actacagaga  25200
accagaggaa ggggcgcccg cccgccctcc tccctggcat cctcacgctg cagaggtcag  25260
agcctcatcc cggcccctta cctgccccta ccctgcagag aactgtggtc agttcctgag  25320
gccagatcca tgaacggcct tgtggaagat ggtgagctca cacccagagc tggctccgat  25380
gaccctttct cctttacatg tttctacctt cccctcgtta ccttccccca ctgccaggca  25440
cagagtggag gcaggttggg tttaaagctc agaagggctt aaagggggtg gggcgcagtg  25500
gctcatgcct gtaatcccag cactttggga ggccaaggca gaggatcact tgagcccagc  25560
agttcgagac cagcctgggc aacatagtga gaccgcgtct ctacaaaaaa taaaataaat  25620
aaaattagct tggcatggtg gcatgcacct gcagtccctg ctactcagaa ggctgaggtg  25680
ggaggatcac ttgtgcccag gagtttgagg ctgcagtggg ctgtgctggc accacagcac  25740
tccagcctga gtaacagaat gagatcctgt ctcaaaacaa acaaacaaaa aaagaaggct  25800
```

taaaggggac tccaggtggg cctggcagca caaagctatg aaggtctgtc ttagacacaa 25860
gctctgttac taggcctttg cacgctggcc tgggtacctg gctgccatag acagggaacc 25920
ttccagatga gctgtaggcg tggagcacag gagccagggt gctcttcctg ggctgtgtcc 25980
acaggcagta tgtacaccgg ctttgtacac gtccagcggg tccagtgcat atttttgttt 26040
gtgtttttct tttgtttcgg ggggtggatt tggttttccc ctgagtcctc tgtcctcctg 26100
tcacctggct ggtgctcggc aatgttgacc agctgcctgg ctggagttgg cagtggctga 26160
ggctgtgagc taacatgttc ctgagtcctc ccatttcttc accataatgc cctgttgagt 26220
ttgcagatac tgtctctgtt tttatctccc agggaaactg aggttcagag tggctaggcc 26280
accttcccac agtccctcag ctcatgaggg ccacacaggg cattgaggtg gcctcctcct 26340
cagccttgac tctctggccc catctttgct gcctcaaggg gtctcctctc ctgaactgtg 26400
caccttctgc ctggcagctc caactctatg gctgttttca gtggctcagc actgcccctt 26460
gaccttccct ggccctctgc agatgccagg ctggagcact ctggcaaggt ctggggtggt 26520
tacatgggtc ctgtcacttc tatacacctc ccagtgcctg ggaatcctgc agatacgccc 26580
tccttagcca tccctaacac atagaggaca tttctgaggt ccctgagaga gtggggcacc 26640
tctgcaggat ccaactgccg ggcccaggaa ggatagcagc agcgtgaggg gttccattag 26700
ccacaaactc atggcatgga gcctccaccc acctcgcccc tcatctgctg tttagcacct 26760
ggcacgctgt gtatacttac taattattat ataataatag caaattatag tggcaaatgt 26820
atgcatcttt gcacagttgt tatacagcac gatgagcaag tcattaatag taaggaataa 26880
atgtgaaggt gagaaaaatc tgactgccaa agtttttact ccttccttcc ctccccagac 26940
ttttaaatga aagttcaggg ataatccctt agttgtcctg gtagtaggac tcgtaattaa 27000
aataattggg ccaagaaccc ttctgtgctt ctccttttag gtttgggtgt aaattcgggg 27060
tgtttctcac tggcgaaagc ctggtgcagg acagaccctg ggaagctttc tcttccagaa 27120
aggaccatca acatcccttg cagaagaatt ctcttctcca gactcagacc cggtgtcctg 27180
gcacccactg ggcaagtggg tcctagaaga caaacctggt cagagctgga ggctgcttag 27240
cattccccat gcacactagc agctcggaga gctcaggaag ccgcagcccc tccttgcctc 27300
accagcctgg gtcaggacag cgtcccctgg aggatgcaca gggcctggcc tctggtcacc 27360
cagcctggag ggaaagctca atcgagcatc atgtcacccg gtgcccccat gcagggtggc 27420
actggtgaga cccccaagcc aatgatacta cctcacagga gtgcgggccc agtgtggcca 27480
gatcaccttg acttttcaag ataaatcaga aatcgtattt ctgtgagata tccctatttt 27540
ccagtgatgg tgactaaatt agaagttgtt gaattttgta acatgctcct aggctgtttg 27600
tctggtttaa actctatctg gaggaattca agctagactt caggaataac ttcttgaggc 27660
aagggttttg agaccttagg gaaacaggga cgtctcgggg gtattctgac tgttgtcctc 27720
ctggaaggga agaacaggga actagaagat tgcccttagt gaagtccaaa gcacctaaac 27780
ccgggaccct cagcggtgtt cttaagtcac agattctccc tgaggcctct ctctggctcc 27840
atagaatggc tgattctgta actctgtgag tctttttttt ttggagacag agtcttgcac 27900
tgtcacccag gctggagtgc agtggagctg gagtgccata gagcaatctt ggctcactgc 27960
aacctctgtc tcccaggttc aagcaactct cctacctcag cctcccaagt agctgggatt 28020
gcaagcatgc accaccacat ctggctaatt tttgtgtttt tagtactgat ggcccaaagt 28080
gctaggatta caggcatgag ccaccgtgtc cagccataac tcttgttatg taactcttgt 28140

```
tacaaaggcc ttatattttg ctctttgagg ttggttttag tttgatgcct gttggttgcc  28200
atcttttaac tagggatgtt ttatcaaagt acccaaccaa agtatctaaa caaattatac  28260
tttaaagttt gaaaatgtcc agcatgtcta attgaatgcc tgttgtgcca ggcactgggc  28320
tgctgaggaa ctgagtccca tccctggagg ctagctagag aacacacaca cacacacaca  28380
gtggtctcac aagtcagttt tatattctac ctctatgcaa taagggtatt attatgttga  28440
ggtactttga cataaaaagt ttttcttaaa ggagaggatg cctagaacag gcattacctg  28500
aagcctcctc tctccagcat tggttgtctt ctgtcacgac tcagggtttt tcattgagaa  28560
tgggatggaa atgtggtcta aatatagggc ccatgttggg actggatccc ctctgggaag  28620
tcagaccagg ctagggcagg tccctagagt catcaggaaa agcctctgga gccagaaaca  28680
aaacaaaaca aaaaaatgat gttaactaaa ctcagtccca aatcctgaat tggagtcagg  28740
tcaagcaaaa taatcaaagg agtcagcaaa gggcaagtca gagagaccaa gtgacaccag  28800
cgtcttccca ggagccctgt ggcgagtgac agagcctgga ctctggaata ggactcatct  28860
tgtgtctcct gccactcatt agctgggtga ccttgagcca agccccttaa cctgttggac  28920
cccatgttct tacctctaag tgggggctgg taatatcttc cccttcaagg aatgccctct  28980
aaggggtgtt gtgaagatca ggtaaggtgg caggggtggg acttctggcc aggaacagac  29040
gcataatcaa tgctaaatct ctcctcctct ccacctgctg gatgctgcag atcctaaaga  29100
tttcaatgtg aataagacaa aacccctgcc ctccaggagc ctttgagaat cagagaacta  29160
gacccattta cagaacaaag ggatgcagag tctggatgaa gttttgggga ttcatagagc  29220
agagggctac ccagccccag tctggacatc gctaggtcaa ctgtagcccc tcagtggctg  29280
atttagccca gaggatccca tagggttgac tcctaactca agggcatgag acaaccccca  29340
ggaaaggcac cgtggaaagg gtctggctgt ccctgattta cctgtgggca ctgggggaat  29400
gccctcaggg ctctgtgtgg ttctgggttc ctccagtaaa aagtaatcaa attctttcac  29460
gttaatgtct ttctccacct cattgcacat catgcagcta ttcattgact cagcaactat  29520
cagctttgca tgcaaccttg gcctacccgc tttagctttt agtaatagct cccctcttga  29580
gtaacacaaa ccagtgggga aacagaacct aactcttacc tctgggaggg ttatttgctt  29640
tgagaacatc tgtcctgcag tttcgctcat atggcagtga agttttgtgc acacactcta  29700
gagccaggga gcctgggttc aaaccccagc tctgccaggt cctaactgca tgaatttggg  29760
caagtcactc aacctctcca tgcttgagtt tcctcatctg taagattgga gcagtggtaa  29820
tacctgcttc ttagggttca gaagagaatt aaatgaatta agatgggtaa agtgcttaga  29880
atggagcgtt gcaagtagta agtgctatgt aagtgtttga tttaaaatga aagaccctta  29940
aatacattct ttgtgcattt cagaagccct tcattttgca tttctttttt tttttttttt  30000
tttttttttg agatggggtc ttgctctatc acccaggctg gagtgcagtg gcacgatctc  30060
agctcactgc aggtttcacc tcccgggttt acgctattct cctgcctcag cctcccgagt  30120
agctgggact ataggcaccc gccaccacgc ctggctaatt tttttgtatt ttcagtagag  30180
atggggtttc accgtgttag ccaggatagt ctcgatctcc tgacctcgtg atcctcccgt  30240
ctcagcctcc caaagtgctg ggattacaga catgagccac tgcgcccggc ctcattttgc  30300
atttcacaac caagctgtct cccctggaat ccagccataa ctctgctcac aagtgtgaga  30360
caggccccag cagagctgca cgaagaggag agaaggcagc cccccaggtc cccaactccc  30420
tgtccaagat ggcaaaacca gaacacagcc tcctccctac cccagcagga gttcagaatc  30480
tgcaatctcc aaaacccact tcaattttaa gtgtagagcc aggtgcgctt ttaagtcacc  30540
```

```
tgtcactctg gaggctcttt tgctcagttc ctcaccatta gcagggatga cagggagtgc  30600
aggagtacag ttggctccca gatattggag cgtgctgggc cagctgcccg ttctcccagc  30660
ctccactcct ctttgctgtc cagccatcac ttgctccttg aaggctaacg aaacaaaaaa  30720
cagtgccaag agcgtgggaa gaaagccagc ttctcccctg gggtagctgt gatatcatgc  30780
ccaccctccc tgaccacgca gcccctgggg accctcaggg ccccaagcac ccatttccat  30840
tgcacatgta cacccgtgtg cagccatggc cgcccatctc agtcaatagg gctgctcctg  30900
cccacttgga attgcggtga caaccaagag tggcttatgg gaactatccc aatgacctga  30960
cagcatgtcc gctgcaaacc gctgacgggg gacactgccc tcatctctag ctcatcagcg  31020
agaggcacag ttgctttctt aggtaacatt gctgctgtct ctgggcattg ctgggggttg  31080
gcacttaatc tacaccgaat tttccctcc tgtatcttcc gagctgcttg gatcttggtg  31140
ctgaattaga ttggacttta tcttgtgggg aagggaggac tataaacccc caacgtaagc  31200
aatggtcaga ctattctaag gaaacttgcc aaatttaaca tgaggtaaat ttagttctga  31260
cttctgtcca ccccactgct actgtccctt tttatcccat gatcccttgc ttttcttttc  31320
cttctctctc cctatctctt gggttcaaca catgatagga attcagaaat atatgtttgc  31380
gaatttgttt attcacgtag caaaccattt cttgagtgcc taccatgggc caggtagaat  31440
gggcagcccc gggatacagt ggtctctaca gcccctctcc tgggtttgta ctgtgcgaga  31500
tgatttagga tgggttctcc catcaaggac cacagtcttc tttctctgtg ccccttggtc  31560
ctcagtctct gaccccactt caaaggcagc attcactcag ggaagctccc atacggtgct  31620
agtcagagta aaagtttgga caaattgcca ggaagcagct tgtcagtatg cataaacagc  31680
cttaaaaata ttactactct ttgacccaga atttcacttc taggaatctg tcctaaggaa  31740
atagtcacat gcaaaagatt tatataccag gatgttcatc aaagtgttgt ttataacagg  31800
aagtctcaga agctggttaa atatccaacc tctggaaatg gttatgcaga atagtatgta  31860
gctattagaa atttatgtct atggggttta aaatgtcatg ggaaaacact tctgacataa  31920
aagagcatga taattatata tttaacataa tcttaactat gttttagaat gtacaggaag  31980
aaagaaatgt acaaacatat tcattgtgat gtctctggtg gtaggattat gatcagtaag  32040
tgcttctgtc ttcatatttt cctgtgtttg ataatacatg catatgttgt ttataaaata  32100
agaaaaattt taagtttaaa attggagttg aaaagtcttt ttaggctggg cgaggtggct  32160
cacacctgta acaccagcac tttgggaggc tgaggtggtc agatcacttg agcccaggag  32220
tttgagacca gcctggctga catggtgaaa ccccatctct actaaaaatt taaaaattag  32280
ccatgtgtgg tggcgcacac ctgtaatccc agctacttgg gaggcagagg catgagaatt  32340
gcttgaaccc aggaggtgga ggttgcagtg agccaagatc gtgccactgc actccagtct  32400
gggcaacaga gtaagacttt atgtcaaaaa aaaaaaaaaa aaagacaagt ctttttaaac  32460
agtagcagcc ataactaaat ataatccata ctaagccctg gatcaaattt ttatttatgt  32520
atttatttta ttcatttatt atttttagac agggtctcac tctgttgcct gggctggagt  32580
acagtggcat gatcatggct catttcagac ttgacctcct gggctcaagc gatcctcaca  32640
tcttagcctg ccaagtacat gggaccacag gtgcatgcca ccacacctgg ctaatttatt  32700
ttattttatt tttttagaga tggtgtttac tatgttgccc aggctggtct caaactcctg  32760
ggctcaagct atcctcccac ctcggcctcc caaagtgctg gggttaccag catgagccac  32820
tgtacccagc cctcaaattt taaaaaatct ataagggaca ttattggaca attagagaaa  32880
```

-continued

```
ttcgcatatg gacttataat agtatcagag tgtgtggtat gatggttctg gagggaatgg  32940
actttttctt taaagatagg cttttctatg cccacccttt taccttgcta acttatcatc  33000
atccaggttc cagcagaaac attacttcct ccaagaaagt tcttaagggt gcagtatctg  33060
cagcaaattc tcaaatagct caggaaaaaa gtatgtgtgt ggtatacaca cacacacata  33120
tatatacaca tacatacata tattttatgt aattatatat gcagagagtg caaatgttgc  33180
caagttgaag attggtgaat ctaggtgaag agaatatggt atttattgta ttatctgtgc  33240
aacttttctt aggtttgaaa attttcaaaa caaaaaattg gaggaagaag acgtgccagt  33300
ctaccccaag ccctccactg gaatgctgga aatctaaaca atggcaattt catttctttt  33360
ctgttgtggg ccagtagtcc ttagatgttg gggaagcggg tagttgctgg ggtgtggttg  33420
acttaggatg gaagaagcag aagtcaagac tcccagggtc aaggtgcttt gctcttctga  33480
cccaagtgtg ggaggcccag agtcagcgtt tcaagtgtgc taattcagca tggttctgtt  33540
cacggccaaa gtccaccctg ggcacctctc tggcagcaat cttgggtgac tctactaagg  33600
tcaggcctcc ctgaccctat gtctggatcc catacctcca actctcccac tgtctcagga  33660
acagtgctta gcttttcttt tccctctcct gtcttccttg ccagcatcta gaaagtttaa  33720
ataattcccc tctttacaac aaaacaaaac ataccccctt cagtaaccca ccctagctct  33780
cttctccttt tcctagccag attttttaa aagcatcctc agcactttgg caacctccat  33840
ctcctcccag catgccctat tactggaatc cagccaggac tcagccccaa tctttctact  33900
ctaaccactt gtctcagtta acaaggacag gtttatgctg cagtgacaaa caagacccaa  33960
attcctatgg cttcacacat ctggcactac ctcatcttcc agccttagga gtcatctttt  34020
agttccttga aaactctctg cagtttcctc ttggggcctt gtcatatgct attcccctgg  34080
aaatgttctt tcctatcccc tccctttcac cttgctaact tgtgcccatc cttcaggtct  34140
cagcaaaaac atcactttct tggggaagtt ttctccaata cccacactac acaggtgccc  34200
cattgacact cctatgactt tgtggcactt gtctcacttg atttcccact gccttcccca  34260
caagacacct ttacaagggc aaggaccgta ccactgtacc tatttcactc actgctgtgg  34320
tcacctgcac tctggctgcc taccttaact acacattaga atcacctgag gagcttttaa  34380
agccacaatg taagactcca ccctaggcca attggatcca aatccctggg gtagggccag  34440
ccatcagtgg agatatatat atatatatat atttttgaga cagagtttag ctgggactac  34500
aggtgctcac caccacaccc agctaatttt tttgtgtttt tagtagagat ggggtttcac  34560
cgtaagcaag gatggtcttg atctccttac ctcatgatct acctgcctca gcctcccaaa  34620
gtgctggaat tacaggcgtg agccaccatg cctggccatc agtggatata tttttaatgt  34680
actgcaggga attctgttgc atcagcttga gaaccactga tctgccttgt gcttcacatt  34740
taaaactttt tttctaatga ataaataaac ccctgaaaaa attaatctcc ctaagcctcc  34800
ctagaagata ggatggtaag gatattttcc taggtaaaaa tatgttaatt tcatatttca  34860
tgaaatttca tgtttcattt caatcaagct ctgtcataca ccttacatgg ggcaggccca  34920
gtgcctgagc agggtgtaat tattcaggca aggaaaagtc acattaggtg atggagcaca  34980
aataggcagt taatggtttc agggttagtt agaatatgtt tgtctttcaa ttgcaagtaa  35040
tagaagccca aagaaattgg ttattcatat aatataattg attggttccc aaatttgaaa  35100
aattcaggaa tagacccagc ttaggtacag ctggatccag tcactcaaat aatgtcacaa  35160
tgaacccttt gacaggaatg taccgtgtct tgactctact ttgctctgag tagtctttgc  35220
ccaggtgatg ataaaaaatgg ccatcatcat caggcttgtg tcctgtttac taggaatata  35280
```

caagaagagc tcagtaaatg ctggccccac cactaagcaa aaacaaaacc tttggggttg 35340
ttgttgttat tgttgtttta aatcacagct tagaccttcc ttctttcctt gttattctct 35400
ttcatctgta atccagtttt ctaattctga agtatagaat gttcagatca tttattcttc 35460
attacccaca acttgcacat gtttatttaa aatgccagga ttgcctggcc attgtgtgct 35520
gttaaccttt gtttgctgtt agtggatccc tgaagttcag gctcccaggg gagcagataa 35580
tgggtgtcta gttcctgcag tatctaccct ctggcaagcc aagttacttc ctgggtaagg 35640
ttttgcctac cctgcattcc cagggaagtt tctgggcctg accaccaagc cagctctgag 35700
gagaggtgca taagccccac catgctttgg ttctgtccct atagaatatt ttatgttgtt 35760
atcgaaaact aaaggaagat gggtgctgtg gctcaagcct gtaatcccag cactttggga 35820
ggccaagaca ggtggccagg agttcaagac cagcctggcc aacatggtga aaccctgtct 35880
ctacaaaaac aaaacaaaaa ttagccaggt atggtggtgt gcacctgtgg taccagctac 35940
tcaagaggct gaggcacaag aatctcttga acctgggagg tggagtttgc agcgagccga 36000
gatcgcacta ctgcattcca acctgggtaa cagagtgaga ctctgtctcc aaaaaaagaa 36060
aaagaaaagg aaaactaaag gaaagggact aaaatgatat caggttcctg gagaacaaac 36120
agacatgatt ttgcttcatg gcaggacagc tggaagaggt gggattatat cctcacatta 36180
caaataagga aactgagact cagaatggtt aagtcacttg tcccaggcaa cacagccagt 36240
aaattacaga aacagaattt gaacccaaat cttccagctc caaagattgt gttttcacta 36300
cctcctgctt aattttttaa tttctaagat tagaccctac ttcatctatc catgatgcct 36360
acctgtcatc cccccaaaaa gggtgaacgc tgttcagaaa tttttctagc ctgagctcac 36420
tcccaattca cttattttg ctttgtcacg gctgcccagt ccccactggt agaccaggaa 36480
gtaggtcatg gctgcgggga ccacacgctg tcgctgctgc aagggctggc ctctgtttct 36540
ggggctgagt gggggtcaga cctgccagga gcaccacctt ctgtgggtcc tgcctggatg 36600
tcacatccca gccccaagaa gtcactgcaa acctttgtat tgttgagctt cacatcctag 36660
aattcactgt cactgtggct gctgcatgaa gtggtcctgg gagaaatggg cattggcatt 36720
aacagggaaa ttgatggtct ggggaaaaag tcatcctcat tctattgcag atctatgagt 36780
gattgagact ggctgatgtt gaaggggttt ctcagccatg atgtgccaca ttatggaaca 36840
gtggtgtagg cagccatttg acacccagcg ctgacctttg tttaacaacc tcacctatat 36900
atgacaaaat agttgtcaga aataatcatg taatgaaatg actgtaataa tggccagaaa 36960
agaaatgcag ataataaaat gtttctctta ttgaactctg tacatataat tgcaccagga 37020
ttttttcaa ataaaaagta aatatactac aaaaaaggaa aaaagcacaa gtatttatta 37080
aatagctttt ctatatcttt ctgagcttca atcctttgat tgcagactga tgtaatattt 37140
tatgtaaatc attgtttggt tactaagtga actttaagaa aagtaagatg tctgcaaaag 37200
ttgcccataa tttagtaact actgtattgt accattgatg tacagcttta ttttcttgat 37260
taattcttta aacaatataa ttcacaattt taaaataata aatttccact taaaatggta 37320
tttaaactca gcaaaatata taatctatga gtaaactttg tattactaag caaaaatatt 37380
acactttgtg gttcacatgc tgtctcactg ttttaaattt taaatacaaa aactccaagt 37440
aggctgggtg tggtggctca cacctgtaat cccagtattt tgggaggctg aggcaggtgt 37500
atcacttgag ttcaggaatt cgagatttgc ctgggcaaca tgatgagatc ccgtctctac 37560
tgaaaataat tagctgggtg tggtagtgca catctgcggt cccagctact caggaggctg 37620
agatggggac agaggttgca gtgagccaag atcgcaccac cgtactccag cctgggtgac 37680
agactgagac cctgtctcaa aaaaaaaaaa aaaaaaaaaa agaaacaaaa attccaagtg 37740
gttgcacaga atgacaggac tgaagtaact tagctccagt ttctgtcttt ataatcactg 37800
tcctaccatt gtctgtgctt agaatctact tgcttaatgc aggaacatgt gttctcacag 37860
aggtggaaga tgcaaatggc acccgaagca ggctggaaat tctgaaccat taagaattta 37920
ctctctacca ggcacggtgg ctcacgcctg taatcccagg actttgggaa gatgaggcag 37980
gcagatcatc tgaggtcagg agttcaagac cagcctggcc aacatggtga aatcccgtct 38040
ctacaaaaat acaaaaatta gccagacatg atggtgggtg cctataatcc cagctactcg 38100
ggagactgag gtgggagaat cgcttgaacc tgagatgcag aggttgcagt gatctgagat 38160
caatctgcac cattgcactc cagcctggga gacagagtaa gacccatctc aaaacaaaga 38220
aacagaacct actctcaaaa caaatacgtg tggctgactc cacatatggt agggccaact 38280
gtataactag aagttctcca aataacttct gtggagaaaa caaagtttat taaaggatac 38340
ttttttttt taatttattt attattatta tactttaagt tgtagggtac atgtgcataa 38400
cgtgcaggtt tgttacatat gtatacttgt gccatgttgg tgtgctgcac ccatcaactc 38460
gtcatttaca tcaggtataa ctcccaatgc aatccttccc ccctccccc tccccatgat 38520
aggcccctgt gtgtgatgtt ccccttcctg agtccaagtg atctcattgt tcagttccca 38580
cctatgagtg agaacatgca gtgtttggtt ttctgttctt gtgatagttt gctaagaatg 38640
atggtttcca gctgtatcca tgtccctaca aaggacacaa actcatcctt tttgatggct 38700
gcatagtatt ccatggtgta tatgtgccac attttcttaa tccaatctgt cactgatgga 38760
catttgggtt gattccaagt ctttgctatt gtgaatagtg ctgcaataaa catacgtgtg 38820
catgtgtctt tatagcagca taatttataa tcctttgggt atatacccag taatgggatg 38880
gctgggtcgt atggtacatc tagttctaga tccttgagga atcgccatac tgttttccat 38940
aatggttgaa ctagtttaca atcccaccaa cagtgtaaaa gtgttcctat ttctccacat 39000
cctctccagc acctgttgtt tcctgatttt ttaatgattg ccattctaac tggtgtgaga 39060
tggtatctca ttgtggtttt gatttgcatt tctctgatgg ccagtgatga tgagcatttt 39120
ttcatgtgtc tgttggctgt atgaatgtct tcttttgaga aatgtctgtt catatccttt 39180
gcccactttt tgatggggtt gtttgttttt taaaggatac ttttttaaag tgctatctgt 39240
aactttacat atatattact aacactcaga gatcgcacca attgtttata acttagacca 39300
gggccgggca cagtggctca tgcctataat cccaacactt tgggaggctg aggcaggtgg 39360
atcacctgat gtcaggaatt caaaaccagc ctaatctgca tgatgaaacc ccatctctac 39420
taaaaataca aaaattagcc aggcatggtg gtacacacct gtaatcccag ctgctgggga 39480
gggtgaggca ggagaatctc ctgaacccaa gaggcgaaga ttacagtggg ccgagattgc 39540
gccattgcac tccagcccaa gcaacaagag tgaaactctg tctcaaaaaa aaaaaaaaaa 39600
aaaaatctta gaccaggaaa attttttta agggaggagt attttatcac tggcattgtt 39660
taggattgct ggcacatgat gctaataaaa agcagactat tagttggttt tattactgtt 39720
tttgaacttt ttttttttt ttttttttt ttgagaaaga gtctcactct gttgcccagg 39780
ctggagcaca gtgactacga tctcagctcg ctacagcctc cgcctcctca gttcaagtga 39840
ttcttgtgcc tcagtctccc gagttgctgg gattacaggg caccacgcca ggctaagttt 39900
ttgtattttt agtagagaca gggtttcgtc atattaccca ggctggtctc aaactcctgg 39960
cctcaagcga tctgcccacc ttgacctccc aaagtgttgg gattacaggc atgagccacc 40020

-continued

```
atgcccggcc ctgtttttga actctctaga gacagtccag ccctttatta cttctcctga  40080
ggcagctgct cccttcacct gggcccccgc attgtgttcc ggacccttgt cctggtggtg  40140
ctgaagaata tctctgtcaa tccttttggg actggggaaa ctgaggccca gtgccacgcg  40200
atgccatttg ttcagggaac attaggtcac ctgctaggtc cccagtcact tgaccttctt  40260
cccagacagg aagaagctgc tctgggtctg agtcctgact ctctcagtgt cccatgtgtc  40320
tttgcacatt gaaatgtttt ctgatggttt tttgctgtta tatttacttt taaaaaataa  40380
ccagcaataa aatgttaggt ttgagaaggt tgaaatgaga attgatttga gttaaactct  40440
agcagatttt tcttagaaga atgatatcat ctccagccac ctgcaattga tctactctga  40500
attaagaaag aggcttccat atgttgttta tattttgcac tcttgatatg tttctttaaa  40560
ttatggtctt gggccaggta tagtagctca cgcctgtaat cccagcacct tgggagtctg  40620
aggagggagg atcacttgag gccaggagtt cgagacctcg tctctacagt acattttaaa  40680
aattagccag gcatggtagc attcacctgt agttctagct acttgggagg ctgaggtggg  40740
aggatggctt gagccagaac tttgaggcta cagtgagtta ttgtcatgcc actgccctcc  40800
agcctcagtg acagagtgag acctgcctca aaaaaaataa gtaaaaaata aattaaattt  40860
caatcattag cagtcatcag gatatttaaa tacatttgtt gaatcaaagt tatgcatgtg  40920
tgtatttttt tttccagaga gttgtttata atgtggattt taatttaact ttaaaaaaat  40980
tttggctgga ctgttgccca aatggtatca ccagccattt ggttgagaac atatgtcctg  41040
caggctcttc tgtcactgga gttttgctag ctgacagcca ctggctagag actgtggtca  41100
gcacagaagc aggcgtggac ttgcgcacgt aagcaggtca atgcaaagcc atcacttctt  41160
aaaaattctg aaccctgctg tctgagatgg tggtgcagcc aatggagctc tgctctagga  41220
agcagaagct aattccatgt ctttgtttgc ccttgactag ctaggtgact ttgcacaccg  41280
ggcttgcctc tcttgttacc ttgtctgcaa agtggaatca tcttttcctt gctggacaga  41340
aggtggaccc tggacctatg ggctttttga gtttttctcc ctcttagaag gacctctgat  41400
cctactgagt ttaacaccca tgggttaata attgggaaaa gcaaaggaag cgcttctgtt  41460
tagataatta tatgcatgtt tttgtctttt tctggctgga aagatgtcca agctactggg  41520
aaggtctgtg cctacccagg gtagccctct ctggggaggg ctgctgtatc caagatcccc  41580
tcaccggaat ttgaaaatca accatagtag ggcctgctga cttttgacag ctaatggtgt  41640
gctgagaatt gtccctccaa agacaccttt ccattccctc gggagagtct gggcagcccc  41700
tcctgggggc tgggatgctg gctcttccct cagcctccac cccaactgct ctcttccctc  41760
cttccctccc cagctcccta atttctctca caaggctttg ttccacagca acctttccta  41820
atgcagtcct ggccagggcc tcttcgcagc ctcattacat aaccttccac agactcctgg  41880
tccaaggatc accccagaaa gccagtcaga ggtaggcacg cagctggggt ccatttactt  41940
accttcccca ccccctcgga actcagaagt ggtgcaggaa tttggactcc aagaattaac  42000
agctccacca ctgtcaccag agccaaaact tcaggatgca tgctctacgt ctgctgctaa  42060
tttccagctg agagccagtg gcactgtggt tccttaggag ccggttccct gatgccggct  42120
cctggcccca aatccctctg atccgggctc ctccagaatg tcttgtctcc accatcccct  42180
ttgaccaatg gtgtctttgc ctggtaatgt cccctttgcc tgatgatggc cctgtcactc  42240
ctctgtctag cacagaggag gccgtttcat cccttcaagc ctgccctccc ttcaagtctt  42300
agctcaagtt caccttcttc acagagcctt ctccaatctt cttggctacg tctccgctca  42360
```

gctccagcaa cctctgtctc tggcactgat tccttactta gctcagagag tcacagacac 42420
ttgaggctca ggacaatctg ctttctctct tcttacccat agctttggac catgtgtatc 42480
tctttgtctc cactcccaaa cccaaccccc agagggcaga gagcatgttg tctgtccctt 42540
tgctcagcat gaagccctgt gtgtggtagg taggcagagt tgcataactc gtgttgacca 42600
aggggtcact ttgctctgaa attacccctg tgtccttcag tatttgcata gatagcttcc 42660
tggccagccc gaatatatcc aagggcatgg cccacctctg ctcctgtttc taggtccctg 42720
gtggagttag ttcatgcctt cctcataatc tgcccactgg cctggtcctc aaggtcttcc 42780
cagctgctca gctagagctg ggaaaatggg tcgctccatc ctgtttatgt cattctctcc 42840
ctgcctggcc cactctcctg cccacaggta tcctgggact gtctgtagga ttagaggaca 42900
tatgtgcaca tgcttgggca caggacactc acgcagcctc caagcacagc atcaataatg 42960
cattcggtgc attatagcgt ggaaagctgc tctaaacttt attacacagc ggacatgtct 43020
gaagcagctc ccaaatccac ccatgagtgt tttgcaattg gcaagcctat tacttgggag 43080
tccacttttc tctgttcatt aataatagat gcttcctatg gccccagctt ggcaattttg 43140
atttaaagtg atcttaactg aagagactaa tggatgggtc tgaatttgtg ccttttaagc 43200
acaaagtatt gctcttaatt aactggattc tatcctttaa gcaggcagag gctttccccc 43260
aatggcatca ttaatgaacc acatctggac atcttccaaa gccttcttct gtttcaggcc 43320
aatcacaggt gtgttcctga acacccagga ggctgtaaga gccacatatg cctcccaaat 43380
acacacaaca tgtgtgcctg gggacacaga gcagtgtgcg aagtcccatt ccatctctct 43440
ccacttggga gaggatggtt cttccatcta attcatggct caaagtggta aaggagctcc 43500
cccctcccca tgccatgccc actcagagtc tgcaaatatg tatgtgatat aagagctcgt 43560
cagttagctg tcatcagtgt ggcacacatt tgaggagtct gactcccctc cagcacaggc 43620
caatgtgcac tgcactcctt tctttgtgcc tccaccgttg cattgtgcag aagttggggt 43680
catagaagta ccagagctgt gaaaggagag gccccttctc acctctgccc tggtctccat 43740
ccccactttc tctaggaagc tggtaggtgc tgacatggga gagaagggag gggaggggc 43800 caggaacagt ggcttatgcc tgcaatccta gcactttggg aggctgaggc aggaggatca 43860
cttgaggcca ggagtttgag accaggctgg gcaatgtagc aagaccctat ctctacaaaa 43920
agaaaaaatg taattagctg ggtgtggtgg tgggcaccgg tagtcctagc tactcgggag 43980
gatgaggtgg gaggattgat tgagcccagg agtttgaggt tacagtgagc tgtgattgca 44040
ccactgcact ccagcctggg caacagagct gagaccctat ctctaaaaaa aaagaaagaa 44100
agaaagacaa gacaaagaaa gaaagaaaga aagagagaga ggaaagaaag gaaaggaaag 44160
aaagaaaaaa aagagagaga gagagagaag ggaagggaaa gcccagaaga gtagaaggtg 44220
tggggagagg aggtggccgt cattctgggg ccctcagtgt gcactaccag ataacgcatt 44280
ctctgtgggc ttttgcacca ttttgcttga gcataaagaa aggaaggctg cccctaaata 44340
gaaagcactc tggaggcaaa gaaatctggc tccaatcctg gccctgccac tttcccagct 44400
gaggacttag acaagcaccc ttggacattc tcagagccat cagctgcaag tgggtgctgc 44460
catacccacc tcattgggca ggcttggggg accaagggtg gtaaatggct cggggtcttg 44520
catgatgcgg ccacacagca ggtgtgccat ccagatccat ttatttcctt cctttcccca 44580
aaatcaagtt gtcattaaag tgctagtcca cattaatgaa atctgtagac accaactgta 44640
ttagttttct gtttgctgct gtaacaaatc atcagaaatt tagtggctta aaccaacacg 44700
attgtattac tttacagttc tggaggccag aaaccctcca taggtgtccc tgggctgaaa 44760
tcaaggtgtt ggcaaggttg tggtcctttc tggagggtca agggaagagt ccattttctt 44820
ccttttttcca gcttctaaag gtttcatgca ttccttggct catgatcttc tatagctata 44880
gaggaaaaaa aatttacatc aatcatcttc aaagccagcc atggcgggat aagtccttct 44940
cacatcacct tgctctgaca ccagctctcc gcctccctct tccacacgtc aggaccctcg 45000
tgattacttt gggctcactc tgataatctg ggatgatctc tctgtttgga agtcagctga 45060
cccagaacct taattccatc tacaacccca attcctcttt gccatgtata gtaacatatt 45120
cacaggttct ggggattagg acgagcctgt ctctgaaagg ctactttaca tgaaaattca 45180
ttttttaatt aagatttttt tttttcctc ttgagacaag gtctcactct atggtccagg 45240
ctggagtgca gtggagggat cacagctcgc tgtagccttg acgtctctgg gctcaggtga 45300
tcctcccacc tcagcttccc tagtagctgg aactataggt gtgagccacc acgcccagct 45360
aacttttttt ttttttttt ttttttttt tttttgaga cagagtctca ctcagtcacc 45420
caggccggag tgcagtggtg cgatctcagc tcacagcaac ctctgcctcc tgggttcaag 45480
tgattcttgt gcctcagcct cctgagtagc tgtgactaca gttgtgcacc accacgcccg 45540
actaattttt atatttttag tagagatggg gtttcaccat gttggccagg ctggtctcaa 45600
actcctgacc tcaagtgatc cacccacctc tcatattgct gggattacag gcgtgagcca 45660
ccgtgcgcag ccccagctaa tttttaaata tttttttgtg gagatggggt tttgtcatgt 45720
tgtccaggct ggtcttgaac tcctggactc aagcaatcct ctcaccttgg tctcccaaag 45780
tgctgggatt acaggcatga gccactgcac tcggccttaa gagaagattt aataattaat 45840
attttacaat attaattgta aagaggtagg atgagtaact aaattaggat acaagtaacc 45900
agggtcatat ttgctaatac ctttgatcac tttgcactgg atatcttatc agattttcct 45960
catcagctcc tttagcagca gtgtggcagc atcttatctc attttgtatt tttttgcata 46020
gcacacgcct ataaatcact ggattgaggt gtttagatgt ttgttgtccc ttggatgctt 46080
cttacaaatc catattttat ggctcctgga aagtgctatg caaataataa gctgcaagaa 46140
tggaaaggaa attgcagtgc tcctgaattg taaatgggct tttacgagga ggtttctaat 46200
tactctgctc tttctcttga actgaggagt tgaagtgtaa gtggcagatc cataacagat 46260
aatcatgtgt gtgatgttac ttcagcctga gcctcgagga ccaagtcaca gagcaggaac 46320
agccactccc cagtgtccat ggggccacgt ctgaggagaa ctcagggatt tcatatgtga 46380
tctgcagtgg ctggggggct aagagagcat caagaggatg taatgtgtcc ctctgagtgt 46440
gttacagatt ctgacattct tattttcctt ctgtggagag acatgtactc agtgacccaa 46500
ctcactttag catatgtttg ctcatcattt gtgtagcttg aaggaatcag atattacccc 46560
ctccccgcta tttggaagca cagatgcaat gccctagaat tgtactgggg gctcaaagag 46620
aaaagagagt agtaaaatct attaaagggg acaaagacag cctatatact acaagctttc 46680
tatttttgtg gcagagacgt tgtggtattt tctaagtaaa cagagtcgac ctgcaatatc 46740
aaatgcatgg atttgatgct ttggaaagca actgtcttct gtgttaatct gggtgtcttc 46800
tgtgaaatgt ccccctgcct ttggcttaaa cactagcttt gtctacagcc gctccatcct 46860
gaacctgccc attcttgtct gaatcctggc ttgaccactg acaagctgtg tgtccttggg 46920
caagttactt cacctctctg cttcagcgtc ctcatctgtg agttggggaa tctggacaga 46980
atctccccca tagggtatag tgaaggcttg ttgaattatc ccaagtggct acacagagta 47040
agcattcaac tgatgtcatc gttgtcatga ttgctgttac tggagcctag agttcattct 47100

```
gatactcaag gctgtggcgc atgtggcccc ggtaaggaac agttggagga gtcgggcatg  47160
ttcaacttga agaggagacg acagggaatg tgggatggtt gaatctgcga agggccccct  47220
gggatgaaga actggcatgt tctgtgtggc tccagggccc tgagcaggac ccatttacca  47280
aagtctcagg gacacagttt ctagctatag acagaaacat tttctgtcaa tcaaagaggg  47340
cgaaaataga atgagccccc ttaagaggta gtgagctccc tgtcattgga aggattccgg  47400
aagagctagg taaccactgt agtgctctca aggggctttt ttctttaaag tcctttccaa  47460
aaggttctga gagtacgtaa acaataggaa gccaccttgg tgctttaaca caaactctcc  47520
ccagtgatga ggtttgagcc aaagccagac tggcaagcag agaggaggct tgtgtacaag  47580
gagttcctcg ggtcaattgc tttttccttg ttctagccag ccagagggct cctgttggaa  47640
aacaggagac cagggaggcg gaggcctgac caaaccagcc tctgcaggcc agctgggaga  47700
ccacaactcc cacctgcggg aaaactgaag ggcatctcta tttttagatt gagcaaaaga  47760
aaataaattt aagtttgagc ctcctttgca acttctaaaa atcatcttta ttgagatgat  47820
cattcacatt ctataaaatt cccccacttt gagttacaat tcagtggttt tagtcttcct  47880
tgatgatgtt gatggtcttt tcataaggct cttggaagat ccagaagcct ctgagacaca  47940
ggtgggtgtg gagggcatag cacagaggca gacttctcat ttcctgggtc tccccttttaa  48000
tgactctcag agacccctcc ttcccctgcc gctggcttcc accccagggc tgtagagctt  48060
tgccactttc caagcagaac ttaatttcct cttctgtgtc tacactcttt gtgcttcttt  48120
cttgccagct ttttctcctt tgcccaccct ccctcccttc ttcccttctt cccttcctcc  48180
cttcctccct tccttcctgg tatgtgacta atttctgttt caggacatag atgttgtcca  48240
ggctgttctt cggcctttct gttggatgat ggacattggc attgagagag gctgcttttt  48300
ctgaaatcat gttttggggc ccaggaccta ggtgtgtgct tctggctttg ttttcttccc  48360
gatccaaatt ctgatatgtc catttaaatt gatgtagacc cacaggacac tgtgggacag  48420
atcctcagtg gaacatgact ccgtaacgag agcgttttgt tttgtcaaaa tgagaacata  48480
ttattgcttt tcatctgatt gtaaacataa tacatgtcta taagacagta taatgagaca  48540
aaaatgtaga cactaataag agaaaatctc cctaattgta tttgtattct cagagaaagc  48600
ccttgttggg catatatact ctagtttgtt tgtttgttta cacatatatg tactcttttc  48660
ttatttataa aaattctgta catgtacatt tctgcaacta ctatttcact tgatgataca  48720
tagacctctc tagaccagcg tgtacatttc ttcctcctta caaagcagtt ggcttcgccc  48780
agggtgcacc aggacacagt tttggctctg tccccagggt gtcacgggac caggagatga  48840
tctcacaggg tctgccatct gccctgcctg gctggaggct gcatcgagag ggccaagggg  48900
caccacgtgt cgtggacact gtcaaacaag agcctttaga gctttccacg gtctttcttt  48960
tgcttcccag cattgcttcc ccgctggtgg actctgaatc tagaactagc tccaggcgcc  49020
tctccaaact cagacggagg ctgcggcatt attataatgc aaatctaggc aaagccctcc  49080
caataccagg atccagaatg gggtggggcc ctttgcccta aaaagctgtt tggtttgaaa  49140
atacaaacag gagacagaaa ggtttggcta aattaatgga tgaagtttta acaatggtaa  49200
ccatagtagg gttcactgac cgccagcgat ggttctgaat acttgacatg tattaactca  49260
tctaatcgcc acattttaca gacaatacaa aggaggctct gggaggttga atgacttgcc  49320
caaagtcgca cagctcctaa gtgaaggatt tggagtggac tccgggcagc ctggtctgac  49380
gccctgcact gcgctgtgct tatctctggc cccaatgccg ccatacagaa gtgtctgggg  49440
gcactttgtc tctgtcaaag agagaattcg gagatgcgta tgcttgccct ggtgtggcat  49500
```

-continued ttctcttttt ttgagacaga atctcactct atcaccctgg ctcactgcaa cctccgcctc 49560
ccaggttcaa gcaattcttg tgcctcagcc tcctgagtag ctggaattac aggtgtgcac 49620
caccatgccc agctaatttt ttgtattgtt agtagagatg ttgttttgct gtgttggcca 49680
agctgatctc gaatttctgg cctcaagcga tccgcccacc tcagcttcca aagtgctggg 49740
agtacaggca tgagccacca cgcctggccg tgtggcactt tttacgtgtg ttcagcagac 49800
actgtttatc ttctgtcctt ccaagacagt gctgatcagg tcattcatta cagcagacaa 49860
ctgctgattt caaacagaat tgccatcctc ttctcccctg cgactttcag agtgtgacct 49920
cagactcaaa aatcagaagt gaaaacatct taaaaactat caccttttct tcctaatcct 49980
cctctcccct ccctgtcttc cttgttgtcc ccatccaatg aactatcatg gcaaaaagag 50040
cccatttctg gccatttttct gtggcctttc aaactcccac ctaccccact gcttctgggc 50100
tcattccctg aaagctgaga cttcggcgca gaaagtgcca ggccctctgt ccccccagat 50160
cgccttcctt gtcttccctg tgcttgcctg tcacattgtg tgggttccag cgctggaagg 50220
aatgagaaac agactctctg gttctccttt tgaagtttac cttcactcca ccacttctga 50280
gaccttccca gaagttgccc cttgtttctc tcccctccag ggctgaccca gagctgcccc 50340
tcacctcttc ctgctgtcac cccaccgcca tcagggcaga ggttgggaca aagcctctcc 50400
tactggctcc tgctattctc cctcaggtcc agcctcctct tctccatctt caggagtctc 50460
cctctccact cacatgtgat gacttcagca cctcgcatca gtccaggaca tcactacttg 50520
ttcaagtatc ttacccatgc attttttcca gtgacattca cagccaccct gtgagacagg 50580
agtgtcatca tctccatgtt tcaaatgaag aatctgcagt tcagagaggg caagtgactg 50640
gcccagcctc aacagccagc cagtggaccc cactaaaccc agggcttctg actgcagtcc 50700
gggttccctt tccacccaaa tccatggagg gaactgagcc gagaacaggt gtccttcagg 50760
aagacgtgaa gccaaagcct ccacctccaa actcaggggc ccagggagtc caggcaccca 50820
tccactcaca aggctggatg tggtgcattc caggagaggg gttgggggca agtggcctct 50880
ccgtgcaccc atggggatag atgcgcacgt ggcatctcca catcatgagg cctggcttcg 50940
tgggttagct ccaggtccat ggagaagcca agtagggggc cctccaagct cagctttggg 51000
cccaggtcag ggtgcaggat agagcaggcc tccctagcat ctgccatgag gccgaggcag 51060
tgcatcgttc acagggcaca ttcagaaacc acaacctaag agccggtcat cagtccgggt 51120
tacggctgat ggaagagcag gtgcttccaa gaacccacaa tgctctttgg ccagtggccc 51180
aaaggtgcct ccaagaggct tcacagcacc cggaggtgct gctgaggcaa cgccctgact 51240
gtaaggagga ccattcaccc tcagagagcg gccgtgatgc tgttgcgaca gtcctaccat 51300
ccctcccaac tctcactccc aacagacttc ccactctaaa gctgaactct ccagcaaatc 51360
acctctcgcc agactctccc ccgactctct ctgggtccac tggaggttcc tcagcctctc 51420
tgtgccttgg ttttcccagc tgtaaaatgg agcaaagagg gcctgtgtac ccccaaaggt 51480
gtggttggag cagctcctcc tacattaggg ccttgagtgg ggcttcgtga ttggttgatg 51540
gaggtctcca aacccaccca gtgccaccga agcctgggac tgcagatgca atgccacagg 51600
tgtccttcct cagcctgggc agctgcacat catgtgtaaa atgggggtaa taagataata 51660
acagccgctt gcacctatgt ggctatgagg attaaacaag ataaatgtgt aacagtgcct 51720
ggctatagaa atatttactc ctgttattaa gggaagaata tgcatggcta aaaagggagg 51780
gaagatgtaa aagccagtcc gtccccctct agcatattta agggtaatgt tgagttggtt 51840
tgtggaccat ttgctgccta ttagagccgg aaggtaggga ccccctctca acagcgatgc 51900
tacaaattat acccattgga ggtcaaccaa aagacaaagc ttattggctg gacctggtgg 51960
ctcacgcctg taatcctagc actttgggag gccaaggcag gtggatcact tgagatcagg 52020
agttcgagac cagcctggct aacatggtga aaccccatct ctactaaaaa tacaaaaatt 52080
agctgggcgt ggtggtgcac gcctgtaatc ccagctactc aggaagctga ggcaggagaa 52140
tcactagaat ccaggaggtg gaggttgcag tgagccaagg tcatactact gtactccaac 52200
ctaggcaaca gagggagact caatctcaaa aaaagaaaaa aagacaaagc ttgttaatac 52260
cagcatattg ttaagggaat aaagtaggct gcagaacagc tggtgtaata tggtgccatg 52320
tagggaaaat tacaagtgta cacaggagaa gagtctgcaa ggatgtgtcc taagatgtta 52380
gagtggtttg tttgcttttt tcttttatca ttttgtattt gacttttaaa taaggaccat 52440
gaatcacttt tataaaatac attctctcca gcccctacta ctcctttaaa gaataagagt 52500
ggtttgccca agaaaggcag tttttttttgc tctggttttc ttgattctga catcagagga 52560
aactccttct catctacttg gggctctggg ttcaggggat tcatttcagg cagattaaag 52620
tggtgaccag ggacatttgt ggacacaggg agggacggga gcaccatcag tttgtctcac 52680
acaaccactg ccatcctcac tgaaggctgt tgcctgatca aaaaaagtat caggccaggc 52740
acggtgactc acgcctgtaa taccaccact ttgggaggct gaggtgagtg gatcacttga 52800
ggtcatgagt tcgagatcat cctggccaat atggtgaaac cccgtctcta ctaaaaatac 52860
aaaaattagc cgggcgtggt agtgggcgca tagtcccagc tacttgggag gctgaggcag 52920
gagaattgct tgaacccaag aggcagaggt tgcagtgagt ggagatggcc ccacctcact 52980
caagcctggg cgaccgaggg agactctgtc taaaaaattt atatatatat tatatatgtc 53040
aaaaatgggg tagtttttag aactatagta gttctaaaaa caaaggccat ccaagcatga 53100
cagatttaca agcactttgg ttattccagt agttacaatg gaggatagaa gcttttagtt 53160
aaaacaaaca acacaacaaa cccagaaacc ttaggtcaaa accaaaattg tcctctcaga 53220
cacaatctgc gaattttctc atgacagtgg gcattagcca actgacatca gccgcaatca 53280
tccgtgtgca cacagtggca ccacctcctc ccaaaaagcg gccttcatcc atgctctcat 53340
acaatcgttg attattgtct ttggattgac gcccagaatt atttcagttt cttcttgcca 53400
gcatgaatct tttctttctg tatgctcctt atcttctctc tttaatttgg cagttctgct 53460
tgaaatctgg gtctttcatt agtaatagtt cagtttggtt ccagaacatt ctgtggtgtg 53520
atgccatgtg accacaagct cacacttcag agctcttcgg gggccagtct taccgagcac 53580
ctctcagtgg ctgcctgtgt gctgggcgct acttgtggtg ggcaagagag aggaggggac 53640
acaaaaggag acacagctcc ttcttagaag ctcaaagttg gggaccagct gccacagaag 53700
agtatcttta gcatcccaga caccaagatc tggccttaca agggtgttta ttaagccttc 53760
tcagctcttt ttcttttttt ttttttttc agacagagtc tcactctatc acccaggctg 53820
gagtgcagtg ggaagatctc ggctcactgc atgcaaccac cacctcccgg gtttaagcga 53880
ttctctgcct cagcctcccc agtagctgag attacaggcg cccaacacca cacccagcta 53940
atttttgtgt tttcagtaga gacagggttt caccatgttg gtcaggctgg tctcgaactc 54000
ctgacctcag atgatttgcc cacctcggcc tcccagtgtg ttgggattac aggcgtgagc 54060
cactgtgcct ggctttgctg ttgcttcagc aaaaagtatg tttgacttga tgacctccag 54120
ttaccttaga cagaggttct catctaagct ccaactttcc atttccattt tcctcgcctt 54180
tcccccttaac cctccacat ttctctcaaa atcaccccag ttctgtggcc gggtgcggtg 54240
gctcatgcct gtaatcccag cactttggga ggctgaggcg ggcgaatcac gaggtcagga 54300
gattgagacc atcctggcta acacggtgga accccgtctc tactgaaaat acaaaaaatt 54360
agccggacgt ggtggtggac gcctgtagtc ccagctactg ggaggctgag gcaggagaat 54420
ggcgtgaacc caggaggcgg agcttgcagt gagccgagat cgcgccactg caatccagcc 54480
tgggcgacag agtgagagac tccgtctcaa aaaaaaaaaa aaaaaaaaaa aaaatcaccc 54540
cagttctaaa aaatactctt catttttctt ttaaatttca aattatactc attgaaataa 54600
atcaaaatag catagaataa gcaaaaaaaa tggatcccac ccttcctcac tcccattaca 54660
tagggctaac catagttaac catttaatta ctaggttttt ttgttgttat tatttattta 54720
tttatttatt tatttattta tttagagaca gagtctcatt ctgtcaccca ggctggagtg 54780
cagtggtgtg atctccgctc actgcaacct ccgcctccca ggttcaagca attctcctgc 54840
ctctgcctcc tgagtagctg agattacagg tgcccgccac cacacctggc taatttttgt 54900
acttttggta gagacaaggt ttctccacgt tagccaagct ggtctccaac tcctggcctc 54960
aagttatccg cccaccttcg cctcccaaag tgctgggatt aaggcatgag ccaccacacc 55020
cagccctcct gggctctctt ttcctttagt tgcacacact cccctgttcc tggagtagag 55080
ggatttccta gagactgtgg gctccagcct tcacctaaac ccaggactag gatgcctgtc 55140
ctatcactta tctttataga ttaaagcaaa atagctggac cataagcatt cgagaacaaa 55200
tggtgaataa ggagaaagtt ctcccaggaa acaagagctt tacttcagtt gggccagtgt 55260
ccttatattc cttagctgtt gccagtcact gcttgattta atctcggcta tcacttggcc 55320
tgacaggtct gctgctggtg ccaggatgtc tgggttttta agcctggctc cattacatac 55380
ttcctgtgtg accttgggca acttactcag cctgtctgtt cctcagtttc ctcagctgta 55440
tgatgtcggc ataatagttt gttgtgtgaa ttaaatgagg caataactgg aaatgcttca 55500
aacatggttc ctattaggag aaatcctgct ttctgcctaa atgtgctgca aaattcctgg 55560
tggtgcagag caggagacca gagcaaagga aagacagggt gcagaagcca aaaattacct 55620
tggaggacaa agcgcatgtt aaggttaatt ttggattcta ggtttatctc tgcttggtct 55680
tcagttacct gcgagagatc catttagggg atttttgttt gtttttaacg atagctttat 55740
tgagatataa ttcatatgcc ataaaagtca ctcttttaaa atgtttccgg tatattcaca 55800
aggctgtgca ggcttccctg tgcttgattc cagtctgggt ttttaaccta gcgggtaagg 55860
gggaccagac cagaaccgcg ggccaggcgg cgattccgct gagtcaccgc gggcgcgggt 55920
gcgcggcggc ggagcccggg accttccttg gctgcccccct agcgagggcc gcagggcggc 55980
ctgagacacc ggccggggcc gccccacggc cgtcggattt agactggaag cttggtccag 56040
gtcaccagct tgatgcgccc gcggtatggg agaccagccc cactcgggct tcccctgagc 56100
gcccggactc ttgactccag cagggcctgg gttatgacca tcaactcccc tttgccaaag 56160
cgatgctctg ttgggaaggc acccatttga tacagtagcg tagagatggg ttttagcatc 56220
aaaatatcag aattcaaggc ttgctctctg cttactagct gtgtgaccct gaaaagattt 56280
ctgaacgtct ctgagcttca gtttcctcat cattccttct cacggggtgg ttgtgagcat 56340
tacagagatc ctctctggga agcccctgtg agtggctcat cctcagggct gaagtaaaca 56400
tgttattaat aatccaatac tggcaagggg tgttgactga tccccctccc ttccccaagg 56460
agctttctag aacctgagtt atcattacca aactgtgctg ccttgagtaa gaacgataga 56520
aggaacagga aggatggtgg caggtgcagg aaggcagatt ggtcctcgcc tccttgcagc 56580

```
aagaaacagc cccagatcgt gggaaaccta cagacctgcc agacagacta ggagcaaaag  56640
ctggggcgtt aagaatcccc agggaggttc tcctgaggga gcagccagtt ggattttgta  56700
agcagagatt tggctgggga ggagtgagga cgtggggagc agagggacaa aactgtcggg  56760
aatcctgcct tgagggcagg ggtgtgtgtt ggggggagtt aggtccctgg ggctcggtgg  56820
ccttgggcaa gtttctaccc ctcaggtctt ttacccatct agggactcca tctgtccacc  56880
tcacaggtta cagtgagcct ggatgcactg tcatgggcag gtgcccagga aaatggcaga  56940
catgttccaa atagcaagca gtgttcccca gtgacgtcca gggtcacctc ggaggtgggc  57000
aagatgcctg gggtttcttg tccaccccac aacacctcag gggacagcca aaactgtccc  57060
ttcaggtaag ctgcacagaa gacgtgaact ctgctgggaa gaccctcttc tttgggagca  57120
aaagggaccc agggtctcac ctgcacatcc ctgtccctga gggcctgggg gttcttggag  57180
gcccagcctt ggcaaaatga ggaagaatgt gagggttgtc caggcccctg ccaggctcct  57240
tccttagcca agcactcccc ttcctgcaca catacccttc tccctccact gcgtctccac  57300
tgttgtcaga aaagtcacaa taaaaaggtc cgtattatct agttcccaca cttttaattt  57360
ttttaatttt atttatttat ttatttattt atttatttat tgagacagag tctcactctg  57420
tcacccaggc tggagtgcag tggcacaatc taggctcact gcaacctctg cctcctgggt  57480
tcaagtgatt ctcatgcctc agcctctcaa gtagctgagg ttacaggtac gtgccaccat  57540
gcccagctaa tttttgtatt tttggtagag atggagtttc accttgttgg ccaggctggt  57600
ctcaaactcc tggcctcaag tgatctgcct gcctcagcct ctcgaagtgc tgggatttca  57660
ggcgtcagcc actgcacccg gctccacact tttcacttat taaaagactg tggtgtccat  57720
caatggatga atggataaac caatgtggac tatccctccc attacccaag gaatgaagac  57780
ggaactttgc caagatgtgg attcacagtg aaagaagcca gtcaccaaaa gccacgtgct  57840
atgtgacttc ccttatacga aatatccaga agagatacat ccatggtgac agaaagtaga  57900
tgagcagctg ggggctggca gaggggagaa gggggagcag ctgtctatga gatccagcct  57960
ttcttctggg tttggtgaga atgttttgga actagagaga ggtgatagtt gtacaacatt  58020
gtgaatgtac taaatgccac tgaatcattc attttaaatc gttcgttgta tgttgcatga  58080
attttaagtc aatcaaaaac aattgtttga aaagggaaaa gccaatgggt agtggcagca  58140
gtgattggat tcatgattcg attccatggc tatccctccc cttaccctcc agcgtcttct  58200
tcttttactc tgcactgtca tctttgttcc catctctctc tctctcaacc ctgcagacac  58260
ttttcccttt ctttgtctgc cttcaccctc cagatttctc tgtctcccta tgaggcatga  58320
gttgaggctg ggagggtatg attctgaaga aggcactagg agtgactcag ctagcccctt  58380
cccctcccag ggcctcaatt tagctacaaa accacaggga gggactcagg aggcagtgcc  58440
tttccaaggg tccctaaaaa atgtcccatt ttagtgtcca gtttcactca actttagcgc  58500
ttcccctaaa atgtgttcgt tacctcccac cccactgcct ctaagtcact gcctgagaaa  58560
acaggattga ggaaaggaga aaggaagaga gagagagagg aggagagaga gaaagggagg  58620
aaggctgatg gacttagaaa agcaagaaaa caagtggtct gaggaaaaca gccttggtgt  58680
gtttattttc ctgtctgtgt atcgcttctc ggccttttgg ctaagatcag gtgtattttt  58740
ctgtctgtgt gtctcactta gattacaggg atctgtgggt gataacatgt ctggtccagg  58800
ctgcgtagcc acctcaaggg catgcttatt tatgtgtttt tcaattcact atctttgctt  58860
gggagtccca ggccaagagg cacagctgcg ccatttgtct attggtttag atatccttta  58920
tccagttctt ccagagaaat catcctgccc ttggctctgg aggaggtggg cagtagcggt  58980
```

cagagagggg agggaaagga aggagccagg tccctggcta ggatgccagg gtcccctgcc 59040
tctcacctgg cctgggctgg agacctcctg ctgtcctgtc actgatcacc accccgcccc 59100
aggctcctga gttagaagac acaggctaaa gtagactatc tctccattga aaaacccata 59160
caaaataaag gttcataaaa aatagaaatt tagaccaagt gctgtggctc acacctgtga 59220
tcccagcact ttgggaagcc aaggcaggtg gattgcttga gccctggagt tcatgaccag 59280
cctgggcaac atagcgaaac tccatctcta caaaaaatac aaaaaattag ccaggcatgg 59340
tggtgcacgt ctgtggtccc agctactcag cctgtggacc tacatagaat acaatgtcag 59400
cataagaagg gagccctggg gtcaccaaat ggtttggggg gcaaagaact tgaaggttga 59460
gagaagtggc ttggtcaccc agctgtcggt tgtgagacct ggccactgct tcttccatac 59520
cctagacctg caccctgaca tctcaggtaa aaagttgggg aatgttttat ggtccaggat 59580
gaaggaacag gcagtgaggg gcagcggagt gtcactttgc atttctgtct gcctggtact 59640
ggctgtgtga cttggacagg taacttccca gactcctggg aatcataata tctatgatga 59700
tgatgatgat gatgacacct acctcaagga ctgccctgaa gggtcacaga gatgcctgca 59760
aggcacctgc atggagcaag cgccccttct ctggcaggtg ccaggtaagc acctcctgtt 59820
gccaggccct gaggctatgg cactgagtga ccctgcaaat cctacctggc gaggctggca 59880
ttcttgtgct cagtcagtgt tggttgtaag accaagagga gtcacttcat tttgctctcc 59940
aggaacatct ttctgggtcc tattttttgc ctatgtcaag cagagcctca aggatgctcc 60000
tgaaaatggg cttgtcttta ttaacatggc aggtaggtcc caaagcatta gcatggggca 60060
gctgacctcc cccagccaat gcagtgcagt gactcttgca accgagtcta atcaggtcca 60120
tgaacctacg agcatttcct gtccaggact ggggtgaagg ctgagcctct ctgcttagag 60180
attcttccca tgcattccac tatttctccc caaagaaaag tattgaccct cgagaggcac 60240
acagtttatt tcttttgcat agtaaatagt agcctgtatt ttaaggaaga attgatttct 60300
gcatcagccc ctgtaagtca tcagccttct attggtgcat ctgactctct ctagctctgc 60360
aggggtgttg gagggggagg ggaaggaggg atctttatta gaaaccagaa tagtgagatc 60420
cattgccctg tcatctgttc catggcgctg aatgaggcgg cccagcagtg aaacaccgtg 60480
agcgagcatc cccagcctgc agaacagtgg ggcactgccc cgagtcctag gaatgaccct 60540
tgattctcct gctcctgact tggaacccat ggaaacctgt agaagcagct gaggaaaacc 60600
caacatgaaa agcagaactc cacactgaga atataggagg tgatcggaac atacagtgat 60660
tcttgctaag actgattcac tgtttttatt ttttttcgat tgaagaaata ctggagaagc 60720
ctaaagaagg agtctaaaaa ctctggccca tgggccaaaa ttgtccttgt gctaagaata 60780
attttcacat tattaaatga ttgaaaaata aaataagaat gttttgtgac acatgaaagc 60840
tatgtgaaat tcaaattcca atatctataa atagtgtttt atcagaacac agtcatgctt 60900
attcattcat ctttgatggc tgctttccca ctgcaaccac gttgagcagt tacaacagag 60960
atcacgtggc ccacaaagtc ttacaatatt tactatctgg ccctttccag aaaaaatgtg 61020
ctgactcttg accttgacct cagcactttg ggaggctgag gcaggtggat cgcttgagcc 61080
ctggagttca tgaccagcct ggacaatatt agtgagactc catctctaca aaaaatacaa 61140
aacattagcc aggcatggtg gtgcacacct gtggtcccag ccacttggga ggctgaggcg 61200
ggaggatagc ctgaacccag gaagttgaag ctgcagtgag ctgtgatagt gccattgcac 61260
ctcagcctgg atgacagagc aagaccttgt ctccaaataa ataaataata caaagtaaag 61320
taaataaaat aatataaaaa cgaatcaatt taaaattata atgaaagcca aggggcatag 61380
tagaacaaat tttctagagc tcattaagtc aaatgagtca ccagttagta aaacgcagtc 61440
agggggaaga gagggcagga ttctttgaag cagcggctct cctaaaaaca gaacccaccc 61500
ttgtccagct gccttccctc ctgagggtgt tccctttgac catgtgaccc ccacccccta 61560
tttcccagcc atccaagccc acctctagca taatacgagc ttctaatccc tctccctgac 61620
cccatcccaa ttttgaagcc cagtctagta ttttctcaac tatacttctt ggctctgttc 61680
cttcctttct atcacctctg ccttttcact gcaagcttgg accactgcag tcacctccct 61740
accaacagtc gttccctacc catccagtcg gccccgcctg ctgctgcaaa attcacctag 61800
ggcacctctg tggtgctgcc cctgcctgtg gacaaagtcc aagccagcca cctcacccac 61860
ctacaggtga gtggggagca gccagcgtgt ccagtggttt accccatcgc cacagacttg 61920
gtgatgtatt gatgtgcaga gaaggggtgt tcgcagccac aacacaagca atcctgcccc 61980
acgtgggacc taagatggac atgctgcaag ccacctctaa gaatccaaca taaggcagag 62040
gggagaatgg ctcacacggc acaaacactc ctttttgttt tgtttttttt ctttttgaga 62100
ggagtctcac tctattgccc aagcaggagt gcagtggcac aatctcagct caccgcaacc 62160
tccgcctccc aggttcaagc gattctccag cctcagcctt ccaagtagct gggatttcag 62220
gggtgcccca ccacacctgg ctaatttttg tgtttttggt agagacgggg tttcaccatg 62280
ttggccaggc tggtcttagc tcctgacctc aggtgatctg cctgccttga cctcccaaag 62340
tgctgggatt acaggtgtga gccatggggc ctagcctcct tccattttaa tgtatgccta 62400
atctgcccat tgagaatggt tgagacacat tttaggtggc cagggtctac ttagagttag 62460
tgctcatgat caggcccagg tccagcctgg ctggccaaat ggtgcctttg acctgctatg 62520
gctctgtgca aaggaatgag ctgatggatg gggcgcagt gtgtgggcag tgggctgggg 62580
ctggcaggac tcagtgacca agggaagaga actttcctca ccaccaacct gtcttttcag 62640
ggcactgcag gggggctttg ggacttggtg atgaacacag catagtgagc tgtccagcat 62700
gtgggctcct ggattctcac agttcccggg ctccttcaga ggctctctct aaagagagct 62760
gctctctcta gaacccacac atttagaata taggcaacca ctgcaatggg gacaactgac 62820
ctcaaacata gagaccagag tagatggggc tcatcgtgtg aaactcatct tgaactctag 62880
cagcttcttt tcacaagttc atggagagag gttttccact gagggaatca catctgtctg 62940
atcaaacgag gcttgggaaa tggctctcct gttcattccc tggaaacctc tgatggaacc 63000
actgccactg tggcggcccc ggcactggca ccccagccat gattggtgcc ccagccacat 63060
ctctgctgtg agccctggtt aattaatcat ccgtgtgttg acggggagag gcccgttcac 63120
gaaagcggtg taaagcccag ggcgatgtgg ccatggcagg aagggtgcgg gactacgttc 63180
cacccccaac tgagagattc agaaaccaga agaaaatgga aaagcatact gtgctcttgg 63240
gtgggaaaac taaatatgaa gagagcaatt tttatagtgt tggcctataa tacaattcca 63300
gccgaaatcc caatggagct ttgagaattt gcaggaaaaa aaaaattcta aaatatatct 63360
ggaagacaaa acttacaaga aggtttcaaa aataattttg aaaaagaaaa tgatatctga 63420
gcccacctag agaataagac ttgagatcca aagcttaaat caggaggctc tagcaccaaa 63480
actgacagat aaacgggaca gagtacatgg tgcattgacc tgggaaagag ggcagattgg 63540
tctgcaaata ggcctgggtc cattggcttt agctgttgtg tttggggaga aagttttcaa 63600
cctcactcca tcttaaacct aaaaatattc cagatgaatc agtaaatatg aaaaattaga 63660
ccactaaaaa cctagaagaa aatggatgat ctttctgtac catagagcaa tggaataaat 63720

```
cacaaaggaa aacagatttg actatataaa aattaaaccc tgcctatcaa aaaccatcag  63780
aaaccaaaat aaaaggcaac caactggaga agacagttgc cacaaatatg atcaagggtt  63840
aatgttattc ataaattaat agtccacaca agtcgttaga atgagcactg agacctgaac  63900
agagaagcaa aaagaatgtg agggggtcag cgcggaggct cacgcctata atcccagcac  63960
tttgggaggc caaggcaggc ggatcacgag gtcaggaaat tgcaactata ttttttaatg  64020
catagactaa gaggctagag ggaaatatca cagatcctta acatacattc ccaaaccttt  64080
gtaaatccac agattcatga aaacagacac gtttgcgcaa gtgcctgatc tttcctgtta  64140
tacattcatt agaagtcaag ccctcgtacc acacagtatc tgccttttca aatgtgatca  64200
aaatgttctc ttttgcttca aggccatttt tcataaggca atggcatttt tgcctcttca  64260
tcagagtcac tgtgtgccct ggaggactga aaacagcaga gccgtgttgg gatgggacag  64320
ggcagctggg aagattgggc tcattcccta ctaaatgcct cactcctgta ctgcccccat  64380
agaggaagag gggttcaaat ttattcctca gccagatggc atgtgccccc tctcctggaa  64440
tctcacgtca cttatgatgg accaaaattc caaaagctga atccatgact gtcaaagtct  64500
ggtatggcag gatgtcaaca gtaatcattt ctgggcagag ggatgatttt ctcttcccat  64560
cttgctttgt ataaatacat tttctataat aagattgtat tacttttctc atgaggaaat  64620
agcaaagtac tgttttactc aaaatatgaa tagagccagg catgctagca gcttatgtca  64680
gtaatcccaa cacttttgga ggcggaaatg ggagggtcac tttagcccag gagtttgaga  64740
ccagcctggg taacatagtg agaccccgtc cctcctcccc ccaaaaaaat ctacaaagca  64800
tttatcctgg attattcaca ggggccaaaa aaaaaaagaa aaaaaaaaga aaattcaggc  64860
ctcttatagc catgagctat gaatatgaaa atatgcaaat gtgaaagaaa agccagcaca  64920
tctgagtttt acttttactt tcacacctct gtctaccata ttccaagagg agaaacttgg  64980
tcattgaaag gaatcgatca aatccaaaga acaaaactac tgtgttcatt aaacttctta  65040
gtgttcacaa agctttagct gcaggttgaa tgggacaccc cgaattgggc tcacctgggc  65100
tgcagggagc agagatagca ccactgcact ccagcctggg caacaaagcg agactctctc  65160
ttaaaaaaaa aacaaagttc agaaattcaa agttgtgagt tatttttaaa ataataataa  65220
ttataataat aattcacaat aaagatgagg acaaagtgtg agcaaatggt ggtttctgtc  65280
cggctttgtt gagctgaagc agcctctccc tgctgggact tttggggaaa aagggtatgt  65340
gttgctcttc agatcccaag cctcatgccc ctactgggcc ctgtgtggtg cttctcagca  65400
cactgggaga gccaccgttg gaacgcacac ctgggggacc tggtgggtga cggtgcggtg  65460
agtgggggcc acagcctgac tccagggaag ccagcgagct cagagctgga ggagtcagga  65520
cacccctgat gggtcaagag ttggttttgc tgccagttgg catctgattg aaccatccct  65580
tcacttctcc gtgcctcact ttccttacca gacgtgctct gctgatgcca ttctctcctg  65640
ttcagtccta ccttcaccat tgaagagaaa gagcaaactg ctaggcagca gcattgattt  65700
ttttaaggaa gtggaaagag agctgggaat aacaagtcag gctcacctcc cctacctcac  65760
ctggtgggtt tgtttgtttc gttttgtttt tgttttgaga ctgagtttcg ccctgtcacc  65820
caggctggag tgcagtggtg taatctcggc tcactgcaat ctccacctgc caggttcaat  65880
tgattctcct gcctcagtct cccgagtagc tgggattata ggcacctgcc acacgcctag  65940
ctaattcttg tatttttagt agagatgggg tttcacccta ttggccaggt tggcctcgat  66000
cttctgacct caggtgatcc acccacctcg gcctcccaaa gtgctgggat tacaggcatg  66060
```

-continued agccaccatg cctcgctctc acctggtggt tttgaatgtg aactgaatgt gttggtaaat 66120
taagcatgcg gatagacgta aataacactt gggcaggaat atggagcaag ggatgaggat 66180
gggtgcccag ctgttggaga gggtgatggg gaggctgcga tctgcctgcc atgaactggg 66240
aggaggggct cctctctctc ttcacccccca ctctgccccc caacactccc tagaacttat 66300
cctcccctct tctttcccca ggcgagcctt gaaccaggat ggctgagccc cgccaggagt 66360
tcgatgtgat ggaagatcac gctgggacgt acgggttggg ggacaggaaa gatcaagagg 66420
gctacaccat gctccaagac caagagggtg acacggacgc tggcctgaaa ggttagtgga 66480
cagccatgca cagcaggccc agatcactgc aagccaaggg gtggcaggaa caatttgcat 66540
ccagaattgt aaagacgttt taaatacatt attgtcttag attgtcagta gagtgaaacc 66600
tcattaattt gagtgggcca agataactca agcagtgaga taatggccag gcacagtggc 66660
tcacgcctat aatcccagca ctttggaagg cccaggcagg agaatccctt gaggccacga 66720
atttgagacc agcctgggca acatagcaag accccgtctc taagaaaaat ttaaaaatta 66780
gctgggtgtt gtggtgcatg tctatagtcc tagctactca ggatgctgag gcggaagaat 66840
cacttgagcc caggagttca aggttgcagt aagctgtgat tatgaaactg cactccaacc 66900
tgagcaacag agcaagaccc tgttggaaaa aaaaaaaagg aagaaattta ccttgagtta 66960
ccctcatgag tgaatgtacg gacaaagatt gcaggggctt gacaatcttt caaatacagg 67020
gtactttttg aggcgttagc cacacctgtt ggcttataaa tcagtagtat tgattagcat 67080
gtaaaatatg tgactttaaa cgttgctttt tatctcttcc ttagatcagg cctgactggc 67140
ctctctttag caagagttgg ttagccctgg gattcttact gtagccacat taataaacga 67200
catcaacttc taaatattct ataataccat cttttgggca aattgacttc gcctcttcct 67260
ttctctttcc aaatgaaatg tttcatttca ctgtcagacc acatggtccg ggacccccacg 67320
gagcacacag ccttccctcc gtctccccat gctggccctt cacccactgc tggagtgccg 67380
agttggtcca agggttggac caagttctca ggttgtctca aggttggtcc aggctgtctc 67440
agtgctggct tgtgctacaa ggagcccttc tttccacggg tgtggcagtg agtgctcaca 67500
gcaacagccc acggtgcagc ccgagggcag ggtggactca gtccctgcct ccatacccat 67560
ttctaagcaa gcaaaatggc aaacactcta cttttctctt ttaatgctaa aaataagaaa 67620
acatgctgca gcccagggta tgggtagtgg atggaagcca tggagttcca aggtgggaag 67680
tgacctctac tggatgcgtc tattcaggaa gatcactgga gtgggtgggg tctctgggag 67740
gtcccctgat tgtgggaagc tgggaccacc agctttctca cacagggagt ggccatccca 67800
gcttggagag gttccaggac tggtttcgac gctcgtttca gatttccatc tgttgaatca 67860
gggaaggtgt tggattatga ggaatttggg aattaggaaa gtgggtgcag gtaggttggg 67920
gggaggtgaa ggaagacatg ggcacattac aggaacaggg gctgctcaga ggtgtccgag 67980
aagctctggg tgaggaggtg agagggagag gggaatgcag cttggcgcag cctccctgcc 68040
tgaggtcagc catcacgtgg tgatggaaag agggaaatgt gctttctgac ggctccagcc 68100
agtgctgcca gattcagctc cccagggagg gcagctgagc ggctccaagc taggagatct 68160
gttttctcct ttgaatcctt cttagaggct gggcatggtg gctcacgcct gtaatcccag 68220
cactttggga ggctgtggcg ggaggatcgc ttgagcccag gagttccaga ccagcctggg 68280
caacataatg ggacctcgtc tctacagata ataattttta aaattacctg ggcatagtgg 68340
catgcaccta tagtcccagc tactcaagag gctgaggcag gaggatcgct tgagcccagg 68400
aggcagaggt tgcagtgagc caagatccca tcactgcact ccagcctagg caaaagagtg 68460

```
agactcccat gtccaattat aataataata aataaatctt tctcagtccc ttcctcactg  68520
tgtccccctc cactaaactt ttccaccacc tctcccactt ccctcgctcc cgctttccct  68580
ctccttctct ccccactcca tctttttctt tctctgctgt ttcccacccc ttcctcctct  68640
ccatcctgca acactgccta ccctgtcccc gccccaccct ggtgctcagg atgtgttaag  68700
tgagggtggt agcctccaag acctcaaccc cgaaggttag cctgttgaaa ccactctccc  68760
agctgcccct cggcagttgg tgctgttggg ggaaactggg attgggagcc tcttttcctg  68820
acaaagagat gaagagttcc ctcaccaggt gcctgggact ggggtgtggg tgtcacagcc  68880
tatcccagcg catctgtttg catcatgatt aatagtgcta ctttcaactg ggggcggtgg  68940
ctcacgcctg taatcccagc actttgggag gctgaggtgg gtggatcacg aggtcaggag  69000
ttcaagacca gcctggccaa catggtgaaa tcccgtctct actaaaaata caaaaactaa  69060
ccgggtatgg tggtgggcgc ctgtagtccc agttactcag gacgctgagg caggaggatc  69120
aattgaacct gagaggtgga ggttgcagtg agcctagatc atgccactgc actccagcct  69180
gggcaataag cgcaaaactc catctcaaga gaaaaaaaaa atagtgctgc tttcagcctg  69240
ggcacggtgg ctcatgcctg caatcccagc actttgggag gccgatgtgg gtggatcacg  69300
aggtcaggag tccaagacga gcctggttaa catggtgaaa ccatgtcaag gagagactcc  69360
ttctctctct ctcttttttt tttttttttt taagacagag tttcgctctg tcgccaaggc  69420
tggagtgcag tggcaccatc tcggctcact gcaacctccg cctcctgggt tcaagcgatt  69480
ctgctgcctc agtctcccaa gtagctagga ttacaggtgc ccgccaccac gcccagctaa  69540
tttttgtatt tttagtagag acagggtttt accatgttgg ccaggctgat ctcggactcc  69600
tgacctcatg atctgcccac ctcggcctcc cgaagtgctg gctttacacg cacgagccac  69660
tacgcccaat caactccttc tcaaaagaaa aaaaaatagt gctgctttct ctttcaagtg  69720
tcctgatttg agtgatagta aatgccaccc tacttataag ggaactacct cagaatgcta  69780
attgggacat ttttgtagca ctctactatt ggcaataggt gatgctcaca acagcccgtg  69840
agggtggatg acatccactt cacagatgac aaaggagcct cgtggtcaga ccgtgggctg  69900
ccggagcagg tccatggctg cagccccaca tgggccatat ttccccccttg tcactgtttc  69960
caccaagccc ccttggaact tcagttatta aactctcttg ggtggaattc aagttagaat  70020
cacaacagat gcctcatatg aattgtgcca gtgaaaaatg acattctatt tagaggcagg  70080
gcagcctggc ttagagtaag tttaaaatat gtgttatgct gcagcaaatg taccatgatc  70140
ctgtaagatg ttcacaacag gggaactgga tgtggggtat attctctgta ctaacttcgc  70200
aagttttcta taaatctaaa actgttccaa aataacaagt tcctttaaaa ttaactccag  70260
gagaccagat gcagtggcta atgcctgtaa tcccagcact ttggaaggct gaggcaggtg  70320
gattgcttga gcccaggagt ttgaggccag cctgggcaac gtggtgaaat cccatctcta  70380
caaaaaatac aaaaattagc caggtgtggt ggcgcactcc tgtagtccca gctacttggg  70440
ggactgaggt gggagaatca tctgagccca ggagtttgag gctgcagtga gctatgatta  70500
taccactgca ctccaacctg ggcaacagag cgagaccctg tctcaaaaaa caaaaatgaa  70560
ataaagtctg ggaaagaagt gggttttacc actcttattt tctgaagaga aactaaattt  70620
aatgtgtaaa gtgaggacaa gttcaccaag ttagtgtttg agttgcctaa aatatgtttg  70680
ctaaaactat tcaatgcttt cacataaaac atgatcagaa gttctatgcc aaaacatatg  70740
tgtgtgtgta tatatatatg cactatatat actgtatgca aaaatgcaaa atctaaattg  70800
```

ccaacctttt tgaaactgct ctgaagggaa agcatttgaa gataaattgc ttacccaaag 70860
aacatacttt ccaagaaagc aagtaatact taaggtgttc atagtcctca tcaaattaat 70920
tcttgctact gaaagcttac aaggagctgt ttttatgtcg ggtgtgacag gtttgacttg 70980
gcagaaggtg tcactttact aacaacattt taaataagtg acagaagaca agaaactaca 71040
tgttaaatac cagaacaaag agtgtctaag tggatgctaa gagttgaaat atggctggat 71100
acctgcccaa gacagctgaa aagtagatga aagttggtta cctataaact agtgcaccct 71160
aatgaattaa aaggtgttga tgagttaact tgttatgcct tccagataag acatgcaaat 71220
ggggcttctt cctccttccc tccttccaag gaatttaaca aggagaccaa tgcaaatgat 71280
aagaactgta gggctcaagc tgggaacaga ttggggaaag ggggaccatc atgcccatat 71340
agatgcccct gtgccctggc agtcaaggct tctgaaaaat aacgaaaccc agaagtctgc 71400
atgatgctgc cttatcattt gtccaaagcc ttcttgcggc agtttgcagg ctcttgcgag 71460
ctccaggacc aaggagctat gttcgtgctg gaagcttgtt taggacgagc tgttctttgt 71520
gggatgggtg cagccaaggc caggtgtcca gggatggtgt tttaacaaag cgtgtgaggt 71580
gtctgatctc acagtgcact tgaattccac ttgcattttt ttcatcttct cattctgttt 71640
catgcacaga accagcccca tcctgaaagt gactctaaat tactcctgcc ccaggtggag 71700
tgcctttctc agagttcaac agagccttcc tgtcgcccaa gggacaactc cactgaatgc 71760
ccaggcctaa caaataaaaa ccaaactctg tgctccccca tcctgggcca ttactggttt 71820
ctctactgct gttggtggta ccaccatcaa cttgtccatc atgaccctgg ccagttcctc 71880
ccacaaccct ccacagcacc cagggacctc acctccattc catccgacac agacctcctc 71940
accacaaacc ttggttttgc aacagcagcc ctgagacctt tacaccctcc tcccttcatc 72000
ctgtccccca ccaaggcccc agagccattc cttaaagcag ggctccacaa actatgagcc 72060
acaggccaat tctggtaccc agcctgtttt gcacagccag tgaactgaca atgatctttt 72120
catacaacca gaaaaaaaaa aaaaaaaagc ccaccattct gagtatgtga cttccatgtt 72180
caagatgtct catgttcaga aaggcccctg gaaaaggagg aagggtatga gctgggcaca 72240
aagggagacc ctctcagctg agctcctccc atccagacat tttcctggac ttcctatcca 72300
atgacttccc ttagcttctc atcagccacc cctgcctgcc caggaagctg gcagatgtgg 72360
ccttttaact gggcacagct ctgttctata tcatatcagg gctctgttcc caaggaaggt 72420
agagagaatg gacaccaggt ggaccctcag cagtctgtgc cacagaggga gtgtttgcag 72480
tttccacact aaaagtcccc atgtgcttga cgggatctgt gactacaacg tgatgcttga 72540
cttttcctca tatgaccaga gccactttgt ccatctggtg caatggtcag ctacctgcta 72600
ggggccctcc aggattccca gttgattcca tatctgcatc accaccatca gcactaaata 72660
aaatactcaa gttcctgctg gtgagcatga gcagtgctac attgggccct tcaaccaagg 72720
tgacaaggac tgaaaataat cactgccact tattgggggc ttctcatctg ccaggcatgg 72780
tacaaagtgc tttaaataag cattcaacag tttcatgctg acagaagccc tgtgagccag 72840
tggagctact tccatgccca ttatacaagg gagaaaactg aggcagaggg aggttaggta 72900
attcggtcag catcacacaa ccaataggtg gtggagccag gatttgggcc ccatctgcct 72960
gactctctag aggctctgat ctatccagag ttgagtctaa gccatgaata gggcaattag 73020
aaagcagagg aaacccattc agccaccatg tgcatgagag tgaggaattt ctgtcataca 73080
gaggggagtg aattcactga gctgagagct gaggaaccac tgatctgatg gctgagacac 73140
cactgggaag actggagagg cttttctggg catgcattgc caggcacagg agaagctgag 73200
ggaagatgac taagaggtac tggcaaagaa ctcagaaatt ctgatggaag ctttacatgc 73260
taccatcaca tccatccatc tatccaccca tccatccacc catatcttcc tccatccacc 73320
caatcataca tacatccagt catctgtaca ccacccaccc atccatccat ccatccatcc 73380
atccatccat ccatccatcc atccatccat ccatccattc cttcatccat cccatcatcc 73440
atccaattat acatacatcc aatcatatat atctgtacat catccattct tccctccatt 73500
catccatcca tccacccatc ccttccttca tccttctcat catccatcca atcatacata 73560
tatccagtca tatatctgta catcaccagc tccatctatc catttatcca tccatccttt 73620
ctttcatcca tcaatcatcc atccatcata catacatcca accatacatc tctacatcat 73680
tcattcttcc atcgattcat ccaattatcc atctattcct tcctgtatct atcccattat 73740
ccatttgatc atacatacat catctataca tcatccattc atccaaccat ccattcatcc 73800
atccatccat ccacccatat cttcatccaa tcaatcatac atacatccaa tcatctacac 73860
atcacccatc catccatcca tccacccatc catccaccca tccatccatc catccatcca 73920
tccaatcatc cagtcgtata ttcaattaca catccatcca attatacatt catacatgca 73980
tctaatcatt caattataca tatacacatc catataatta tacatccaat catacctcta 74040
tccaattata cattcataca tccaactaat aaattattaa ttcatatatc catccttata 74100
attatacatc catctaatca ttcagtaatt cacccatcca tccagtcatc tatccaataa 74160
tacattcatc caatcatcca tccatccatc cacccatcca tccatccacc cattcatcca 74220
tccatccatc cacccaccca tcatggtttg agccatgatt tactaccatg gtccactgtg 74280
gacagcccag gtgggattga attgaagaga agcccagggc tgcccccata aacatttggc 74340
tcctttacat cgatgagaac tagatccaca tgtataaatc ctcatgattt gaaggtgctt 74400
ttaccaacat tcactcatgg gattctccca gcagctctag gaggtagagt tgaggtcatc 74460
tcacccattt tacaaatgag gaaacagagg ccctgagagg caggtccaag tccacctgac 74520
cagaaagaag tggaactggg acttgaaccc agccatcttg ccccttggtc ccgtgctctc 74580
tagcctataa ctcccgcttc ctggtagggc acctccagga ggaccctatc ggctggcctt 74640
gggcctgcct ttgagtcttt tgctgtgtgt ggccatcctt cctccctcag gagagtgtgt 74700
actcccagag cacagactgt atcttctgag cattttgtcc cttcccagta cctagcactc 74760
agctctgtat acatcaggct ctcaagaagt ctcaagcttc cagagggtaa ggtcttgacc 74820
tgctctgccc cggatactgc aggatgcatt gataagccca taaaataacc agggcagatt 74880
gactcccagt ggccaaagta ccacagggaa gggacaattc agtccttcta ggaggaggaa 74940
gtagttttct aatttctatt aagccaacaa aagctgcctt actaagggca ttattggtgg 75000
agggtgtgac tgtcaaccac tgtgatcatt tgggcctctc ttgcccaagc ttcccattct 75060
gaaaggacag ttttcttgta ggtacccatg gctgccattt caaatgtaac tcacagcttg 75120
tccatcagtc cttggagatc tttctgtgga cgcttgatgg catccaaaca ccacctaatg 75180
tccacttaga agtaagcacc gtgtctgccc tgagctgact ccttttccaa ggaaggggtt 75240
ggatctctga gtgttttcct aggtgtctgc ttgttaatta atagcaataa acaaagcaga 75300
aggttcatgc gtagctgggc tttctggtat ttgctgcccg ttgaccaatg gaagataaac 75360
ctttgcctca ggtggcacca ctagctggtt aagaggcact ttctcctgtc acccaggagc 75420
aaacgcacat cacctgtgtc ctcgtctgat ggccctggtg tggggcacag tcgtgttggc 75480
agggaaggag gtggggttgg tccctttttgt gggtttgtca caaggccgtg ttccaactgt 75540

-continued

```
ttccatgggg agcaattttc agctccacaa gacactgctc cccagttcct cctgagatta  75600
aaagggggcg ctggggagag gccgccgttc tgaggcctca ccatgtgtgt tccagaatct  75660
cccctgcaga cccccgctga ggatggatct gaggaactgg gctctgaaac ctctgatgct  75720
aagagcactc caacggcgga aggtgggccc cgcttcagac gccccctcca tgcctccagc  75780
ctgtgcttag ctgtgctttg agcctccctc ctggctgcat ctgctgctcc ccctggctga  75840
gaaatgtgct cactcattcg gtgctttgca ggacagtgtg gcgggagctg agccctgctt  75900
cgatgccttg cttgctggtg ctgagcgtgg gcaccttcat cccatgtgtg ctctggaggc  75960
agccaccctt ggagagtccc gcgcacagct ccacaaaacc ccgctccata cgattgtcct  76020
cccataccc cttcaaaagc cacctcttct ctctttcttc aggggccagc aggtcccaga  76080
gcagccattt ggctgaggga aggggcaggt cagtgcacat ctgatcttgg cttagtatct  76140
ttcattttgg gggttctggg tgtggcctgg gcctctggac tttggccacg atgtttgttc  76200
cggcccttct aacctgtcct ttccagacac tcagcatcta ggttattagg actcacatac  76260
ttcctgacgt gctcctcagt cctgattttg accatcttct cttgcttccc atctgtatca  76320
gtcaagactg catttggctg taagaaacag aaaccccaac taactgtggc atttacatga  76380
agaggtttac ttttctcaca taatcagatg cctgaacttg gccagcacct caagggtcac  76440
tgatgctctc ccgtctttat tttctgtcat ctttagtggt tggattgttg cctcatggtt  76500
acaaagtggc tgctgcactt ccaggcatca catctgcctt tgaagcagga atgagttgca  76560
aagtaaagtg gccaaaaggg ccctgaaact aaatgcgtcc ccttaggaaa acaggagttt  76620
tcttgcaagt ggcagtcttc cacttatgtc tcatcagcca gagctgggtc ttatggccac  76680
cccttgctgc aggcaaggct aggacattga gcattttgcc ttccagcctc tttagcagaa  76740
taaatcaagg gagaagaatg ttaataatgg ctttcaagtg actagttggc agtatctgcc  76800
cgtctgtctc tccatcctcc ccttggaggt tcaaggttcc tttcttagca cttcttcagg  76860
ctctgcacat tcatttggat cttgtgtctt ggggtgaaaa acttgcccaa gtgtctctgc  76920
aagcatctac ctttggatga atttggaaag tggctgtcaa gtgcccgccc cttgcttggt  76980
acaatgctgc atctttagag gatgcagcag gcgtgggcct tgctgctgag gttcttagcc  77040
tcataagaat atccaggtta gattctcttg gctccttctt agagctagtg atgcaagaca  77100
cttcctgttc atcttgtcgg gatggttttg caagttgcct gccatcctga gaaagtctac  77160
aaaacgatgc cagacctcat gccagcttcc caagccttgg ctctcagtgc tccctcaaca  77220
gtctggaaga atctcccaaa caagtctcaa tgccctctgg accctgtgca ggcgtgagac  77280
tcaagagcac tggctcccac ccctggtgga gggagccctg ctggggctgg gatcttgcct  77340
ggttgctctg cctgcaccca agacaaccat aattaaaatg tccttcattg aacttggaaa  77400
gccttcaaag ctgacaactc cttacgtgta cctggagtgg cctgggagtg tgccagggca  77460
ttgcttgaga ggaacactga tttggaagcg tttaccttga tgagagactg acagcagctc  77520
ctggtagccg agctttccct cctgcctctg ctgtgaaggt ggacccatgc gacagtcaaa  77580
tgcctgactt tggataggac cggacctatt tattgccatg caagggactc tgcatttttg  77640
aattatgggt catgggcttg gagacagggg ttagagctgg gagaagtctt ggaagtcacc  77700
tagagaagac actgccattt tgcagatgag gaaactgtcc aatcaaaatg gaccaaggat  77760
ttgcccaaag tctcacagca aaaccatagc ccccgcccta acccccccag tccccgtgct  77820
gtctcagttg taattctcgc cttaaggatc aaatagttat gagcaatcat ctggttttca  77880
gtattctttt aaaatgcctg gggccatgcc cagcagtccc tttcactggg gtttagacag  77940
```

ggctgccggg ctttcctggt ggatgagctg ggcagttcat gagccagtag cactcagcag 78000
catgtcagtg tgcttcctgg ggagctggca gcaggggctt caggccctgc ttcagggctg 78060
ctttcttgca tatggctgat cccctcctca ctcctcctcc ctgcattgct cctgcacaag 78120
aagcaaaggt gatgggcatg gctcatcctg gctcctctaa ggtggttctc ggtggtttcc 78180
agatgtgaca gcgcccttag tggatgagag agctcccggc gagcaggctg ccgcccagcc 78240
ccacatggag atcccagaag gaaccacagg tgagggtgag ccccagagac cccccaggcag 78300
tcaaggccct gcccggtgcc ccagctgacc tgcgacagaa gtgagggcac tttgcgtgtt 78360
tatcctcctg tggggcagga acatgggtgg attctggctc ctgggaatct tgggttgtga 78420
gtagcttgat gtcttggtgc ccagctacct ccctggctgc ctgccagcct ctcagagcat 78480
ttagggcctt ctggacttct tctagacgct cctcatcttg cctcagtcag cgcatcagtt 78540
ccagggagtt ctctgcagga ttttctgggg caggtggtgg cagacccgtg ccttcttggc 78600
acctgaggtc agccaccctc ctgctcagac tgtccggcac agggccacct cccaaggggt 78660
ggacccaaag atcacctgag cgcacagagg gtgcagatga ctggaccgca tcttttggtg 78720
atcttaatga ggtggtccca gaggagctga gacatgtgat ctagcatcca gttctgggac 78780
tctgtctcct tttcaaacat attcgtgtag gacaggcatg acgagaatgc cttgtcaaca 78840
cgggtgatgg ggaattgatc ggacagggcg ctgggctcaa ggctgcagtc acccaagagt 78900
ggctcagctc cccaggccct aggaaacgcc cgcacagcct ggagctcctg gagtcatttc 78960
cttcatgtct cttcactgca cttacgtaaa gatgccagcc attggtctgg tgatttggag 79020
ggtgcccagt tgcccaacaa gaaatgcaga agaggcctag acaggatttc atcagcaatg 79080
gagagcaggg aagatgtgcc cagaaaagag tttcttttcc ttcctaaaga tggtgctccc 79140
tgcagctact ggggaagcct gcagcgttct ctagggctct gtgtgttgag accagcccca 79200
ccctggcccc ttctgagtgc atttctgctt tgtgacttga tccgtgaggt cccctgagat 79260
gggcagaggg gatgtcctcg aagctggggc agagcctcat ccttgaacgt gaaggatgtt 79320
tgaagaccgt ggcacgatca cgggatgcga tcacggggaa cttcagtttc tctcctcctc 79380
tcccttcagt tatttcactg ggggaaatcc ctcccctgcc cagaatgaaa actctagcca 79440
actcttgact tttccatcac tccaaagtaa ttgaaagtac gttagtctcc acagtggcaa 79500
aacacagtgt gcaaatgcta aataattaga acagccagtc ccatgtgaca gtcaaagctt 79560
ctaactccat tcaaagttgc cgccattccc cttgggggct ggcggggaag ggaggggtag 79620
gagaaacagg aaggttctta ctgagtcggt cctggtgtga gccatgtcac actccctgca 79680
taggtttcaa ggagatactc tttctctctc tctccatggg gaccttattt gaattcttct 79740
agactcttcc cccagcctgc catctccagc tatcctcccc tgaagagccc ttcctctgca 79800
ctggattctg gtggccgtgt catctcggcc ctgtgggagt ctgaagatct ggctgcagcc 79860
tcacctctga ggtcctgctg gttgccacct cttagacatg atctgaggct cccatgcact 79920
ctctctgacc tgtgcccaca tggggcccac gggaaacatg ctggcaagca aactgtgggt 79980
gtgcggacag ttctcaggac tgtagcatct gtcctttgct ctgcccccaa agcaaggcca 80040
gcccatcttc catctgagaa tgggcagatt ctcagtgttc cttggtgggg ccctgatcat 80100
agaccaccag gtccctaacc agaggggaca tgcaccacat gtcctcaacg tattgacttg 80160
aaacattgta ctgggactgt gatgggggtg gccatgtagc cactcccacc acccccaagc 80220
cactctctcc aaggaaatcc tcctaaagat ccctttacac cctccgtgtg gtggggtggt 80280

```
tctagagttg ggtgcatgtg tcttcagcta ctgacaatgc agaccttagt tggcacctcg  80340
ctctggccca tcctatttgc tgttcttggc actccagtga aactccccat gggccatcca  80400
gttagggtgc agagtggcca ccccccttgca ggatcctgcc ttgctggaga gcacagggcc  80460
ctcctggctc ttgtaaaaca ttccgcaggg tacagagagg ccattggtga tgtgaggtcc  80520
aacctccact gtgccctccc tccctccttg ttgtttccaa gcagctccct tgctggggtc  80580
aagcggtggc aaagacagca cagcctccaa tttctgactc acgccaggcc cggctatcac  80640
agctctgcgc tggtgtgtga cagcaaggtg actcacccag tgccgtggca gtgacagtgt  80700
ccagggaagc ctccacatgc tctctgtctc aaggactctg gcatttagtg ggatttgctg  80760
tcactctgag cctttctacc attgccatca ccttgtcaga aactcaggcc gaatctgcac  80820
tcagagctgt gcccaggcag ttgagccaac actcgctcag tgatgttgtt gcatgacaag  80880
gcactgtcac cactgggcct cgtgggcagc gcagtgtcgg ctggatggac ccggagggtg  80940
tctgtgtcat gctagtgcta gtgatgggag ccccctgagc ccattgccta ccctcccatc  81000
cccttagcag ctgcctgggg acagccaatg gcctgggtgt ttctgaggct accacatggc  81060
taccaggaac ctcgagaacc tttctctccc ttgcctacag tcttcacaca ggcctgtgct  81120
ggccagtggt ggggatccag cattcctgtc ttaggtgcag agagtgactg actcattgca  81180
ggcctgggag ataagactga tggcccaacc agcaacatgt atgcatttct cagaggcagt  81240
gacctctatc actgccctca ggaaatgctg gtgattctgg tggcctgagg tcaatgcatg  81300
tcaacgtggc caacttgcct tataaactct tcttctgaac aattgcatgc attgtcctgt  81360
aacagtgtcc tgttgtttat gatgcagaaa ttggtgtttt taaagcacgt tgattttggt  81420
actattgatg tggtcaggaa ctttctcagt ctttcttgtt tggggtgagc tgtggcttcc  81480
taaacaggaa cccaagatac ccccaaaaac tgctcagtag cactgccagc ctccctctta  81540
ccaagtagca cccattcagg gcattctgtg aaaggcattt acccagaagt tgggaggaag  81600
gaaacgtaac attttggggc acctaccata tgccaggcac caggctaaac gtgttcacac  81660
aaattctctt actaaccctc accatccttc tacaagacaa actagtatct tcatctgggg  81720
ttctagatga ggaaatggag gctcagagag gttgaatgaa tgctggtgcc tggatacgaa  81780
ctccgtctgc ctgactccac aacccaggca aagtctttcc ttgaacttcc cagcagccac  81840
tgcttagaca cagtctccac gaccacggct cagcagcaaa ctgcttctct gacctcactc  81900
agcctgtgtg tccttgtgga gtggggcatt cagggcccca gtggagaaag tctttcctac  81960
taggtcatag ccacacctgc atgtgggtgc tgtgcatttt acttagtgaa cttttaccac  82020
cagcatcctc agcaatgaca tttgcagaga agccagagct gaggcacctt agtattcttg  82080
ggacgtgact ttcctgaatg ttttagggaa aataccagaa gacacagaga gcttggtttc  82140
tagcaaacaa taactgtttt gcttttaccc cccttcattt gctgacacat acaccagctg  82200
aggaagcagg catcggagac acccccagcc tggaagacga agctgctggt cacgtgaccc  82260
aaggtcagtg aactggaatt gcctgccgtg actttggggt tgggaggagg gacatggggt  82320
gggctctgcc ctgaaaagat catttaaatg gacccgagcc ctaattcaca aatccaggag  82380
attctaggga gttggttctt atcaaaggtt ggctactcag atatagaaag agccctggtg  82440
gtttttttct aataccattt ctgggcaatt cctaaggcat ttagagttct gaaagaccta  82500
gtccgacctg ggagctgaga atgaatgtct aacaggaact ctaggctggg tatggtgact  82560
cacaccacta atcccaacac aggcgggccg atcacctgag gtcaggcgtt tgagaccagc  82620
ctggccaaca tggtgaattc ctgtctcact acaaataaaa aaattagcca ggtgtccatg  82680
```

ctggctaaca cggtgaaacc ccatctctac taaaaataca aaaaattagc caggtgtggt 82740
ggcgggtgcc tgttgtccca gctactcggg aagctgaggc aggagaatgg cctgaacccg 82800
ggaggcggag cttacagtga gccgaggtcg cgccactgca ctccagcctg ggcgacagag 82860
cgagactcca tctcaaaaaa aaaaaaaaaa ttagctgggc gtggtggtgg gtgcctgtaa 82920
tcccagctac tcaggaggct gaggcaggac aatcgctcga acccaagagg cggacattgc 82980
agggagccga gatcatgcac tccagcctgg gcaacaagag cgaaactctg tctcaaaaag 83040
aaaaaagaaa ctcaaataca gcgattctca gtgcaggctg ccctctggcc gatccaggag 83100
caaggcctta accatgtcac ccccaagcga ttgcttttaa actttcttct ctgcagcctt 83160
caacccttat gattttcttc tcaggtatca gactgctgtg ttcaagaaag acagctttgt 83220
gtaatcattt atcataaata tcttaagaac tttaaaaatc ctagagattc ctaactttag 83280
gaaatgggag acctgtgata ctgatataat gtgggctggg cttgttttct gtcatttgct 83340
agataaatga acttgaaagc ctactgtaaa atgtggaagc ttctagattg caaaagggct 83400
gggaagatgc tgttcttttc tcctgagtga tgggctctgt ccagtgttca gagctgcctc 83460
tgaggccgtc tgatcctagg agactctgcc tcgttgaggg aattttgagg cctaactaca 83520
cattcctgcc cccagagagg tcacagccta tagcaggctg acgtttctca tctcacatgg 83580
cacagaaagg cacattttca ttcttaggct aacaaagagc ttcaaaaact agaagcttgg 83640
ctcctgtttc ttttaggtca tgtttttcaa cttaggtaaa actagaggtt ttgataacgt 83700
atgacctcta gaaatcattg ctttccataa acagaagtgg atctgagttt tttctactga 83760
tttttagtgc aggctatgtc tacatgccca cagaacatat tccatgcaag agaaaaagcc 83820
caggccacca tctttgctgg gaacttgact tttgcgctca ctgaatttta agctttctga 83880
cagcagcctg gaatcatgga gggataaagt acctattagt aagatggaaa aaggtgtttc 83940
aggatggagc tgcagtcttt tgagagtaag ccatgggaag gcctgtatac gatgggtggg 84000
cttttcttct gtaagtgtct agagaccagg cctcctgaag agggcatggg ggcttaactt 84060
acctggacta ctgtgtttac aatactcatt tatctcgaac tcctcctaac ccctgagaat 84120
tgctacattt aatatttgct gagtacttcc tagcattctc ccaaccaggc tgggtgccgt 84180
ggctcatgtc tgtaatccca gcactttggg aggccaaggc aggcagattt cttgaggcca 84240
gaagtgtgag actagcctgg ctgacatcgt aaaatcccat ctctactaaa aatacaaaag 84300
ttagccgggc atggtggtac acacctgtaa tcccagctac atgggaggag taggaggcag 84360
gagagttgct actgaggcag gagaattgct tgaacctggg aggtggaggt tgctgtgagc 84420
cgagatcata ccactgcact ccagcctggg cgacagagtg agcgagagtc tgtctcaaaa 84480
aaaaaaaaaa aaaagaacgt tctcctaacc tggcttcttc ctccaggggt gtaattaatc 84540
atgtcagttt cctcattgat acacacacac ccccacacct acacacgctg tacaatcctg 84600
tatccattac ttttcaaggt acgtttacta tttatgtttg ggatccttgt ctcttttta 84660
atagtgtttc ttaaagtctt gtattatatc agagtactgt aacatcacag tcaagagcac 84720
tctagtaagc tctaggagga aagcgcctta tggaaggcag tggagacctg tcctgttggg 84780
gcggcatagg ggcagcccct gtctctggtc agttctggcg ctcaggctca gggtttcctg 84840
taggctgctc ttcccagaga ctgaccaagg gctctcataa ggcacctgca gaccctgtaa 84900
gaagcagaag tcagtgtttc ctgacaccag ttgatacgtt caggatccac tgattaaact 84960
acctgctgtg tggcatgcat tgtggtcgat gccagaaata ggaattggag gggcccatga 85020

-continued

```
gcatggccag tatcagactg aaggtgctgc tggaggtgct gctgcgctgt gaccaggcct  85080
cttggggatg agcccgtggc aaccaccctg cctccgatgg ggtgggccca catgttacct  85140
gtgtgtgtcc atgaccacac cttcctcccc cacctcatcc aaatttcttt cttttccaag  85200
cccccgaatc cttcagggct gcaggttttg tttaaagcag agctggtgag ttgcatgggt  85260
ggttgtgttg cgactagatg gggtgttcaa agagttggga gttaaaaaac ataaagggtg  85320
cttattagga gaaccaagga gtataattgt cctgttctta atatgcagcc agattaatga  85380
atgtcacatg aatgaaccag aaaaacatga aatgtgccct tgatcagctg ggttggtgtg  85440
cagcaagctg tgtgaccaag ggacagcagt gctcctgagg gccgtcactg tctgctgtgc  85500
agagcccttc ctcccacggg agcctacctc acctgtgcaa ggggcttgtc tgtggtcagt  85560
gacctggata gatctgaatg gggcttattt tttgaggagt cttatggcag gtctatcagt  85620
aaagactcta ttcttgatga tcacacattt tggattttcc aaatctatca gaggatgggc  85680
ttgaggcaga gtttgtagac actagtttca ctggtttcat ttaccaaaaa ggggagcaga  85740
agtcaagtat ggtggctcat gcctgtaatc ccagaggcag gagaactgct tgagcccagg  85800
aattcgagac cagcctaagc aacataagga gacctgtctc tacaaaaata aaaaataata  85860
tcttagtcag acgtggtggc gtgcctctgt ggtcccagct actcgggaga gtgagatggg  85920
aggatcgttt gagccctgga gttaaagttg caatgagctg tgattgcacc actgcactct  85980
agcctgggtg acagagcgag accctgtctc aaaaaaaaaa aaaaaaaaga aaagaaaaga  86040
aaaaagaaag aaaaaaactc atgcctgtaa tcccagcagt ttgggggggct ggggtgggcg  86100
gatcacaagg tcaggagatc gagaccatcc tggccaacat ggtgaaactc catctctact  86160
aaaaacacaa aaattagccg ggtgcggtgg cgtgtgccta taatcccagc tactcaggag  86220
gctgaggcag gagaatcact tgaaccaggg agccggaggt tgcagtgagc cgagatcgcg  86280
ccactgcact ccagcctcgg caacagagtg aaactctgtc tcaaaaaaaa gggaggcggg  86340
ggaacagtga gaggtaggga gaggaaaggg gattctcgct acacccaagc caggtaccat  86400
ctagaggcta gactctttgg gaagctcaaa ttccctagaa agcaggagaa gcttccttag  86460
ccctcccgct ttcccagtag attaagccca tgagcccaag gcggctctag atgtgtgaca  86520
tgctctgtgc acaaccagag cccatcacag gcagaggaat aacacccaca ccagaagggc  86580
cctcagaggt caccacgtcc aggaaccctc cttacagatg aggaaactga ggcccagaga  86640
ggggaggacc cagggagctg gtggcagcta gaccaggaga gttgtcattc caagcaagca  86700
aaggcaacga gatgagccca gagctgtgct cccatctctt tgttaggggg ctaggatgcc  86760
ctctcaatgt cattttgtcc aggatgatgc tccctctctt aagcaattaa tgcgcccttg  86820
ttaacctttt gctatcgctg cctcttcaaa ccagaggagt tgagagttcc gggccagcag  86880
aggaaggcac ctgaaaggcc cctggccaat gagattagtg ctcacgtcca gcctggaccc  86940
tgcaaagagg cctctggggt ctctgggctg tgcatggggg agaaagagcc agaagctccc  87000
atcccactga ccgcgagcct tcctcagcac cgtcccattt gctcagcgcc tcctccaaca  87060
ggaggccctc gagagccctc ccaggagtgg ggacgaaaag gtggggactg ggccgagaag  87120
ggtccgacct ttccgaagtc cgccacccct gcgtatctcc acacagagcc tgaaagtggt  87180
aaggtggtcc aggaagtctt cctcggagag ccaggccccc caggtctgag ccaccagctc  87240
gtgtccagca tgcctggggc tcccctcctg cctgagggcc ccagagaggc cacacgccag  87300
ccttcaggga caggacctga ggacacagag ggtggccaac acgcccctga gctgctcaag  87360
caccagcttc tgggagacct gcaccaggag gggccgccac tgaagggagc cgggggcaaa  87420
```

-continued gagaggctgg ggagcaagga ggaggtggat gaagaccgcg acgtcgatga gtcctccccg 87480
caagactccc ctccatccag ggtctcccca gtccaagatg ggcagcctcc ccagacagcc 87540
gccagagaag ccaccagcgt cccaggcttc ccagcggagg gtgccattgc cctccctgtg 87600
gatttcctct ccagagtttc cacagagatc ccagcctctg agcccgaggg gcccagtgca 87660
gggtgggctg aagggcagga catgcccccct gagttcacgt tccacgtgga aatcacaccc 87720
aacgtgcaga aggagcaggc gcacccggag gaggattcgg gaagggctgc atttccaggg 87780
gctcctggag aggagccaga ggcccggggc ccctctttgg gagaggacac aaaagaggct 87840
gagcttccag agcccactga aaagcagcct gctgctgctc cgcggggaaa acccgtcagc 87900
cgggtccctc aactcaaagg tctgtgtctt gagcttcctc gctccttccc tggggacctc 87960
ccgggcctcc caggctgcgg ttactgccac tgagcttcag gccttcccaa ctcctgctgc 88020
ttccgacatt cctaggacgc cactaaaccg actcctgggt gcagctgctc cactccctcg 88080
gtctcctccc gtgctcaggc tgtggccaca cgcgcccctc acgcttgcct gccactctgc 88140
atgtcaccag cacccccacc gcgtgctccc caccttgttt gactctctgg ccacttgatg 88200
tgtccacaat ggcccatcag cccacaggag gttggtgggt gccctccacc ggcagggtgg 88260
cagcttccct cacggtgtct agaactcgcc aaccctccca tgtaggcaca agcagcccca 88320
ctttgcagat gaggaaacgg aggcccagag aagtgcagta acttgccgaa ggtcactgag 88380
tagtaagtga cagagccagg tttgggatcc aggtaggttg gctctgaaag acatacctgt 88440
cctgcatccc acagcaggac aaccctccca ggaggtgctg gagtgtggac tcctaacacg 88500
gagatgggca gggtacacac agcaggcgac acacacagca ttcagaggtg gcccagagcc 88560
cacactgtgc ctttggccca gcaccctgcc cccacccgct ctgccttgtg gcaggaagat 88620
gaggagcaga cacaagatct ccctggtcca catgccgcca cctccctcag cagaggacga 88680
ggagatccac atgctggcat tgcagggggc tgagcagggc ccatcttgag ccctcaggag 88740
catgaccaca gcagccccac agggtgggat tggtgtgggg agagtcccaa gtatcaggga 88800
gaggagagtt ggtgtcccgc gggagacctc atagccacaa ggcaagcttg tccataaatt 88860
tggggccctt ggaatttcac agttatttgc caagcccaga aatggatgtt actgaagctc 88920
acagttgcaa gcatctgtta aatttttatt agattttact tttagagaaa actttgaaat 88980
gctatagata aagaagcctg tgttgaaaag ttaagacaga ggccaggcac ggtggctcat 89040
gcctgtaatc tcagcacttt gggaggccga ggcaggtgga tcacttgtgg ttagaagttc 89100
gagaccagtc tggccaacat ggtgagaccc tgtctctact aaaaatacaa aaaaattagc 89160
tgggcgtggt gacgggcacc tgtagtccca actacggggg aggctaaagc agaagtgctt 89220
gaacccagga ggcagcagtt acagtgagcc aagatcacac caccgtaccc caagcctggg 89280
cgacagagca agactctgtc tcaaaaaatg aaatgaagta aaataaaata aagttaagag 89340
agaaaaagta tatcctatat cctataacag taggggacaa ataactgacc tgacaggtta 89400
ctacaatatt tcctgaaatg atgttttctt gactaccagc ctactggagg tgtgtctggg 89460
ttaaaaaaga gttccatggc ccagtgactg cgggaaaaaa aaaaaaaaca gactaaacta 89520
agttaaacag gcttttctgc tgctggactt gtcagaacct ttaacgtact aacagtcatt 89580
gtgaccctct gagaaggtca caagtgggtt tcccaaactt actcgattct acctgctaac 89640
atttcctgga ggaggacttg ttcagtgctt ctgcagtttg ggaaatgttg atttagcagg 89700
ggatgttgtt gtgccatgga tggtgctggc tgatatgggc aaaggaaaga acacgtgagt 89760
cagattcgcc tggggctctt attaaagtgc aggttaccgg ggccactttc ggcttacaaa 89820
cccagttgtg gggtaagcct gggagtcttt gagcaggtga ttctgccata tagtatagtt 89880
ggaaaacctc tgggcatact cattgctggt ccctctagaa atccaggtga caatagccaa 89940
cgagaagctc caagagaccc gattgtctgt ggggtagagg gaatatgata ttaaaaccaa 90000
agaaaaaaat ctatcatcag ttttcagcag tgactgtcaa gagaaggaga agggtgagtt 90060
agcactgatg ctggcagaca ggccagtggg ttggtttcac cagggagtgt gatgaaggct 90120
gatgttatct gggatgatgt atgatggtaa ctggtttgta gctaactggg ggaagcggtg 90180
aggatttgtg cccttcgaag accagcaagt ggcaagaaac ccaccaggcc tggctcagcg 90240
ctaggccggg cttggctcgt ctgagagcag ctggggctgg tggccaaagc ccctattagt 90300
gaggggtaag ctttgggggt acaaccagca actaggggac aaagacaagc ctgccaggct 90360
ctcctattct ggaggcaggt gaccaggaat ggagatgggg tggtcagcat aagatggcca 90420
ggaaggtggg aatcagggct gctggcaatc tagccgcatg ggcaagggag ctgggtgact 90480
ccaggcagtt tccaaggccc agagggtgag caggcacctc gcagggaacc agggccaagc 90540
ctggctgcag tgtggagaca actcacccac ccccgtcctt ggatcttgca ggaggctggg 90600
tcctcactga gctaccaata tccatggccc tgaggctttt aaaacacctg tccgtggagt 90660
ggggctggtc ccagtggggt gaggctgacc ctggcagaaa cagggcagga gcctgtgggt 90720
tagggagact gcaccttcct tagatagcct ccgtgtcatc atgtccctgt gacagtttct 90780
gctgcgtccc ttctgcatgg tcccaccctc agccagcctg ctgccccctc ttgccaggtt 90840
gctctaatca gtgaccccag tgtgctatgc tgatactaac aatgtgagac ctagcacatt 90900
caagggagaa gagaaccaac tggtttccac cagacccaac taaacaaaac acggacctat 90960
cccagagaaa tgcaacttca ccacagctgg ctgtttctgt gaacagtgaa aatggagtgt 91020
gacaagcatt cttattttat attttatcag ctcgcatggt cagtaaaagc aaagacggga 91080
ctggaagcga tgacaaaaaa gccaaggtaa gctgacgatg ccacggaact ctgcagctgg 91140
tccagtttac agagaagctg tgctttatgt ctgattcatt ctcatatata atgtggggag 91200
catttgtcac taaagcacag ctgtcattta aagtgctttg tattttgggg caggcttttt 91260
aaaagtccag catttattag ttttgatact taccccaggg aagagaagtt ggcaggttca 91320
tgaagtcatg ctgctaattc cagctttctt agtgtagttt cagtgagacc ctgacagtaa 91380
atgaaggtgt gtttgaaaac caaccccagg acagtaaatg aagttgtgtt tgaaaaccaa 91440
ccccaggaca gtaaatgaag ccatctgctc actgcataaa ctgcaccctg atctttgccc 91500
atccttctca gtatttcact tcacccatcg tttactccct caatgacttg gtgtctggga 91560
aaatgctccc gtaattgcac agtggcgttt ttcctggaaa atcccaccat ggctctagat 91620
aagacctatt tttcttaaag gtatctaaaa tttccagcat aaattctgtc tgaaacagct 91680
gaattttaat cagtcctgga gcccagaggg catctccagt tgccacatag ctctgagcat 91740
tcggtggtgt gttggtgtgt tgggggctgc tcccggaagt gcctgcagag tcagggctcc 91800
ccagcctcac ctagtgaggc agcggaaggg cctgcgggaa tttggagagc tgccctttgg 91860
gtccctgaag tgatagtgac agctgcttgt caatcatggt gcacatttag tgccgggggc 91920
aggggtcagg gaataccagc ctcatgcatg catgcattcg ttcattcatt catgcagcac 91980
acatgggtac gacatccctg ccctggagtt gcctagattc tagggagggg aaagatctat 92040
taccgtggac ctcggccagg tggggagtgc tgctggtgga gaggggccat gtgcagcgag 92100
gaaggagggg tcatcaatac ccccacccca gctttgcttt cttgtcatca gccccagggc 92160
cccagcctgt gtccctcctc tcccactact gcttcatctc ctgggttctc cttaccaagc 92220
ctggccacac agagggtctc ggccgcttcc atggggaatt ggaaagcaat aagataacat 92280
ccccaagaag cccaatgaag tctgggtcag gacccttctc tgagctgact cgctctcgga 92340
aacactttga ggcttagcct ccccactttg ttttctgaga gcgctacctc ttcccctcca 92400
aacatcccct tctcctctgg ggccatgccc acccatcaaa atcccccatg ggtaggatga 92460
attgtgggtg tcagtcacca tctatcccac atcccggttc caggtccccc caccccccgc 92520
cgcctccaca gggacaggta tgcagacacg tgtctctggc tgcttcctca tgtggaatgg 92580
gttcaaaagt tagcagtgtt gtttacactg gcaaactgaa aaagagaaaa cattggaggc 92640
ttggcacagt ggctcatgcc tgtaatccca gcactttggg aggctaaggt gggaggacct 92700
cccgagccca agagttctag accagcctgg gcaacatagc aagaccccat ctctaaaacg 92760
aaaatttaat tggccaggca gaggtgggag gatcacttga gcccaaaagg tagaggctgc 92820
agtgagccgt gatggcacca ctgcactcca gccagggcaa cagagggaga ccctgtctct 92880
aaaaccaaca atgacaaaaa aagagttaac attggccaga ttaggattca ccaaatagtg 92940
ttaatattag tttgatttga gactttaatc agaaagcaca tgtgtggtgg gggtgggcat 93000
aacctaagat agaatctttc caacgtgggg tgggcacact cctgattgag tctatcagtg 93060
tggtggaaga ggccatgggt taatgggcag gcaaaaaagc cccttgcctg gaattgagta 93120
gaaagtaagg cccttcagac ccatgacaca cttggcgaca ttttcttgag taacatccta 93180
agattcatgt accttgatga tctccatcaa cttactcatg tgaagcaccc ttacaccagt 93240
ggtctccaaa ttcaggggca caatcacatc taacaggctg gagaaagaac atactagaac 93300
ttccattcct ttgtcatgtc ctcttctaaa gctttgtcag atgtgagttg agtaagttgg 93360
tcatataaga agtatgactg gggaggatgg tcactttcct gttcttactg atcagatggg 93420
atgttaaggg tacctgattc aaacagcctg gagatcactg ctttcaacca ttacctgcct 93480
tatttatttt tagttactgt ccttttttca gtttgttttc ctcctccatg tgctgacttt 93540
tattttgatt ttatttatgt ttatgtttaa gacatccaca cgttcctctg ctaaaacctt 93600
gaaaaatagg ccttgcctta gccccaaaca ccccactcct ggtagctcag accctctgat 93660
ccaaccctcc agccctgccg tgtgcccaga gccaccttcc tctcctaaat acgtctcttc 93720
tgtcactccc cgaactggca gttctggagc aaaggagatg aaactcaagg taaggaaacc 93780
acctttgaaa agaaccaggc tgctctgctg tggtttgcaa atgtggggtg ttttttgttt 93840
tttgtttttt tagcctcaaa gacctttctt caaatgagct ctgacacaga agcaccgtgt 93900
aaatagttag aattctgggc aaagaggaaa agagagctgg gggccatacc tttcagcacc 93960
ccacaggctc tcatagcagc agcccctcag acacctggtg ggaccttggt ttcgaaattg 94020
ctactctaag gctgggcgcg gtggctcaca ctgtaatccc agctctttgg gaggccgagg 94080
agggtggatc acctgaggtc aggagttcga gaccagcctg gccaacatag tgaaaccctg 94140
tctctactat aaatacaaaa attagccgag catggtggtg tgcacctgta attgcagcta 94200
ctcgggaggc tgaggcacaa gaattgctcg aactccagta gcagaggttg cagtgagcca 94260
agattgtgcc actgggctcc agcttgggtg acagagcaag actctgtcgc aaaatttttt 94320
ttaaaaacaa acccaaaatg gctactctca ttgggttcct ttgcccattc ctgattttgg 94380
taacagaaat gcttccagat tgccctgatc tgggtaggac agcatcaggc cacagcaaca 94440
ctgccctgtg agcccactcc cccctggact agcttgtggt ccttagttaa tgtcagtttc 94500
ttctttgagt ttgtgttatg tctaagggtc atctgctggg tagccgaacc cagggactgc 94560
cctagtccct agactatgcc atgcccgact ctgccagctt tgtcagtgat gctggtgctc 94620
ccctcctcgg gtgctcacct gctctgagca cacccaagga gttcctgacg ccttagggtt 94680
gtatgggaga gaatgaaaga acacaacgta gctctcttta gcatccttgg ccaggttcaa 94740
cactgtctcc aagggcctct ggtggaacca accaccatca gccaaataaa tccataatta 94800
gagtcagaaa atggatgtcc gcctatgcat agtgcactaa tgtcctgccg attgattgac 94860
atggagtgga gagtgacttg atcattgctg taagctctgc tggccttggc acaactcatg 94920
ctgataacca gtgcacatag ttcctctgag aggaaatgtc ctcagggaac ttggagtttg 94980
ggtggggatg tggatttgtg tgcccagcaa gccctcatga ttgtagcaga cacttgtggc 95040
atctagaagg caaagggtca ccccagtctt aaccgcgttt tgagtcaagg tgcggagtgg 95100
ggctggtgtt gactcggtgg cagcaacttt tcccaatggt gaaaaaaccc tcgaccctgt 95160
ttcatttaca gggggctgat gggaaaacga agatcgccac accccgggga gcggcccctc 95220
caggccagaa gggccaagcc aacgccacca ggattccagc aaaaaccccg cccgccccaa 95280
agacaccacc cagctctggt aagaagaatg ttctcttgaa tcttagagga agctgaagct 95340
ctcagaggta tagccttcat tttaggaggc cttaggccac tgagagtgaa cggcccctgg 95400
cagctggtca gcaccttgca gttcactaag caccagagtc ttcatttcct tcgcagttct 95460
tctgatttct gaggcagatg ttgaatcccc acgtttttgt ttgtttgttt tgttttgttt 95520
ttgagatgga gtttcgctct tgttgcccag gctggagtgt ggtggcgcaa tctcagctca 95580
ctgcaacctc cacctcctgg gtttaagcaa ttctcctacc tcagcctccc tagtagctgg 95640
cattacaggc acctgccacc acgcctggct aatttttttgt atttttaata gagacggggt 95700
ttcgccatgt tggccaggct ggtctcgaac tcctgacctc aggtgatcca cttgccttga 95760
cctcccatag tgctgggatt acaggcgtga gccaccactg ccagcctgaa tcctcacttt 95820
ttatcagtga agaaattgag gctgattctg cagcacgata aaaaaatata tagaaaaagg 95880
aaaaaaaaaa gaaagaaatc gagcctctga gagtttgctt gactgagtct aaccagctca 95940
ttttaagcct gaggaaaatg tggtcatatg gctactaaat ggcagctctt ggagcctctc 96000
tggccccaag tccagggttc cacagaggca gccccagcat ggtgtgtttg cagtccccaa 96060
atgcgaccgg agacaaatgt ctctggagac agagcagcag cctggatagg tcacaatggg 96120
tgatgtcact tagggctcaa cccccaggca gcttaacttg ctggggacgt taggagtctg 96180
ctgcaaaacc tgagggtctt agctgagcag tcgcaggctg ggcccattgc cctgggctcc 96240
tgtgagtaaa acccagtcag ttttgagtac ccagtaaggc atccatctag ttattttgca 96300
gccggggtgc tattaagaat agtcacggct gggcatggtg gctcacgcct gtaatcccag 96360
cactttggag gctgaggagg gtggatcacc tgaggtcagg agttcgagac cagcctggcc 96420
aacatggcga aaccgtctct actaaaaata caaaaaagtt agctgggcgt ggtagcagat 96480
gcctgtaatc ccaactactc aggaagctga ggcaggagaa tcgcttgaac ccgggaggcg 96540
gaggttgcag cgagccgaga tcatgccatt gcactccagc ctgagcaaca aaagtgtgag 96600
actctttctc gaaaacaaac aaaacaaaca ggccgggcac agtggctcat gcctgtaatc 96660
ccagcacttt gggaggccga ggcgggcgga tcacaaggtc aggaggtcaa gaccatcctg 96720
gctaactcag tgaaatcctg tctactaaaa atacaaaaaa ttagccaggc ttggtggtgg 96780
gcacccgtag tcccagctac tcaggaggct gaggcaggag aatggcgtga acccgggagg 96840
cggagcttgc agtgagccaa gatcgcacca ctgcactcca gcctgggcaa cagagtgaga 96900

```
cagagtgaga ctcaaaacaa acaaacaaaa aaacgaagaa aacagtcatc ctctttgggg  96960
attagggaca gcctgcctga gcacttctct ctcccattgc cccagtgaag tgttccacca  97020
ttgggtttag accctgcacc acgtaggggt gtctgacctg cacttgctcc ttggcagtgt  97080
gcaggcagcc tgtggctctt gctgcaggct gtggccaaag cctggcctgg atcttggtga  97140
ctctacttct ccctggcctg agggagctgc ccagagcctg cctgtcacct gctgcctgtc  97200
tttgcagtgg catttcacac acacgtggtg cggtggcagc cccaaggatg gccgttcact  97260
aaggcccgtt gtttttgtct ttttgcttcg tgttttctgg cctggtgttt ttctcatata  97320
cgtggtgatc cagggataat tcccagaatt ttgacaggat tttaggtagg gtttggatcc  97380
tgctgttttt tcacttaaca tggggctagt tgactcacac gctgtttttt gttgttgttg  97440
ttttgtgtcg cccactgtgt cgcccaggct ggagtgcagt ggcatgatct tggctcactg  97500
caacctcttc ttcccaggtt caagcaattc tcctgcctca gcctcctgag tagctaggac  97560
tataagcaca ggccaccaag ccctgctaat ttttgtattt ttagtaaaga cagggtttca  97620
ccatgttgac caggctggtc tcgaactcct gacctcaagt gatctgtcca cctcggcctc  97680
ccaaagtgct ggaattacag gggactcaca ctttgtaaca acctgaaaca aggtcatgca  97740
tttccctttg ggtcttacct gctcttcggt ggctgcctgc atgtggagag accctccccc  97800
ttgggcctcc tccaccttgt ttcagaacgg ggcctctgct gggccggccg tgggtgcctg  97860
ccatgtgaag gactcattaa ggccccgttt aaacctgatg ataatgaggt ttttgtggat  97920
ttttctcttt aagcgaccaa gcaagtgcag agaaaaccac cccctgcaga gcccacatct  97980
gagagaggta ctcaggagcc tgcttcactg ggagcagcct ccctttgcat gtgtggctgt  98040
tcactggctt gtgttcctag agccgacagg accctttttct gcaatgcagg gttcacacag  98100
ggttcgcagc ttgaagatgg agcagtccga attctcttcc ccagattttg tgcagctgtg  98160
tttgtccgat gggctttcta atcctgtgtg ctctccttga cttcagggac aatggcatta  98220
caggcatgaa ccaccatgca tggctgtctc cctattttt tcagctgaag acataggctt  98280
agggaggtca ggtgacttgc ccaagacctc tctgcaagta agaggcatga aaaggatttg  98340
gagccaccac caccaagccc attggtcacc ctgggtctct gaagtcaggg aagcaggagg  98400
atgggagatc tcaggaggca gagaggctga gcctggaggc cctggaggcc gaggccccat  98460
ctgttgtttc cttatgtgga aaagaagagg cttcgtgtgt tctattgcca caaagcttga  98520
ctacttcagg aacatccaag acatggaaat cagcagggca cggtggctaa tgtctataat  98580
cctggcactt tgggaggctg aggtgggaga attgcttgag gccagaagtt caagaccagc  98640
ctgcgtaaca tagtcagacc ccgtctctat aaaaaacatt atttaggccg ggcgcggtgg  98700
ctcaagcctg taatcccagc actgtgggag gcagagacgg gtggatcacg aggtcaggag  98760
atcgagacca tcctggctaa cagggtgaaa ccccgtctct actaaaaaat acaaaaaact  98820
agccgggcga ggtggcgggc gcctgtagtc ccagatactc aggaggctga ggcaggagaa  98880
tggcgtaaac ccgggaggcg gagcttgcag tgagctgaga tccggccact gcactccagc  98940
ctgggcgaca gagcgagact ccgtctcaaa aacaaaacaa aacaaacaaa caaaaaaaaa  99000
cattatttaa aaaagagaca tggaattctt taaatcctaa aaactggtgc tggctgggcg  99060
tggtagctca cgcctgtatt cccagcactt tgggaggctg aggcaggtgg atcacctgag  99120
gtcaggagtt caagaccagc ctggccaaca tgataaaacc tctactaaag aagtctctac  99180
tggcccggcg tggtggctca cgcctgtaat cccagcagtt tgggaggcgg aggcgggcag  99240
```

```
atcaggagat caagaccatc ctggctaaca cggtgaaacc ccgtctctac taaaaataca  99300
aaaaattatc caggcgtagt ggcgggcgcc tgtagtccca gctactcggg aggctgaggc  99360
aggagaatgg tgtaaaccca ggaggcggag cttgcagtga gccaagattg cgccactgca  99420
ctccagcctg ggcaacaaag cgagactcca tctcaaaaaa aaagaagtct ctactaaaaa  99480
tacaaaaata cagtctctac taaagtctct actaaaaata caaaaattag ccgggcatgg  99540
cactgcattc ctgtaatccc aggattccca ggattctcct cccagccacg ggaggctgag  99600
gcaggagaat cgcttgaacc cgggaggcgg agcttgcagt gagccgagat cacgccactg  99660
cactccagcc tgggtgacag agcgagactc catctcaaaa caaaacaaaa caaaacaata  99720
acaacaacaa aactagtgct tattcgtcgc tgaccaagct gcccattggc tacatgggtg  99780
cttcaaacaa agagctgccc ttctccagct ctggccagca ggtatgtgtt acagcgaatg  99840
ccaggggcag cggcaggggc attcttgtgg gaagcttcca gaccagcagg aaagctaagt  99900
tctcagactg caggggagca aagcacacct gggcacagag tgaggcctgc agttctcaga  99960
cttcagtctt tggggagctt gagaaaaatg agcttttcag gccccacccc tagagattct 100020
gctctatcca ctctcagtgg ggcccagaaa tgtgcacttt acaagtccta ctttcctcct 100080
tgaaagctcc agagattctg atgcagggtt ccgtgggcca gacttcggaa aacatggacc 100140
catgagacag aatagcagag tgttgaagtg taacagggac ctgggaagtg cagtaacaga 100200
agcaaatctg gggtaaaggg acacccagag gaggaaggga cagcatctgc gtggagagga 100260
gacccccca gcagcttctgg ggtgttggaa aggtgcactt actgctatgc atggcaggtg 100320
gggaactgta tggcagggca cagcagcatg aagtggcatg gctcatgtgg acagttaggg 100380
acaagcaggt atggagcagg catcctgttc tggagcccag atcccacaga ggagccaggg 100440
agctggcagg agccctgaac tagccgaaca gctgaacatt caccctgtgg agaaagggtc 100500
agaagcgtcc aggcttgagg gcacagctgg gtcccgtcac tgtgtcaccc ttatttagga 100560
taaaggccct aaagaattgc actagagatt ggcaaagcat atctaccacc tcctggagcc 100620
accctggctg cagggattat aattatatcc attttcaaat taaggcctct gagctcagag 100680
aggagaagtg acttgtctga gaccacacag cttgttggag cccatctctt gacccaaaga 100740
ccgaggggcc gagttggcca cctctctggg aactggtgtt gtatagtggt tgatggtttt 100800
ccattgcttt cctgggaaag gggtgtctct gtccctaagc aaaaaggcag ggaggaggag 100860
atgcttctcc agggcggccg cctcctgctg ctgtagctgc gcttccaacc tggcttccac 100920
ctgcctaacc cagtggtgag cctgggaatg gacctgcggg acgggcagcc cccagggcct 100980
tttctgaccc ccacctgagt cctggcttca ctcccttcct tcctccccag gtgaacctcc 101040
aaaatcaggg gatcgcagtg gctacagcag ccccggctcc ccgggcactc ccggcagccg 101100
ctcccgcacc ccgtcccttc caacccctcc agcccgggag cccaagaagg tggcggtggt 101160
ccgtactcca cctaagtcgc cgtcttccgc caagagccgc ctgcagacag cccccgtgcc 101220
catgccagac ctgaagaacg tcaagtccaa gatcggctcc accgagaacc tgaagcacca 101280
gccgggaggc gggaaggtaa gagaggctgg ctgcgcgtgg agatgtgggg ggctgcgcct 101340
ggaggggtag ggctgcgcct ggaagggtag ggctgcgcct ggaggggtag ggctgcgcct 101400
ggaggggtag ggctgcgcct ggaggggtag ggctgcacgt ggaggtacgc ggctgaacgt 101460
ggagccatgg ggctgcgcac ggagacatgg ggctgcgcgt ggaggtgcgc ggctgcgtct 101520
ggaggtatgg ggctccccgc acctgggctc ggctaccacc cccgcataac accccggtcc 101580
catccagacc ctcttcaagg aaatttagtt ctttattggg ctctccacta cactgagagt 101640
```

gctctcctca ggcgagagta cgttctggct cttctcttgc cccttcagcc cctgttaatc 101700
ggacagagat ggcagggctg tgtctccacg gccggaagct ctcatagggc acccacaggg 101760
gctccccacc ttccttctgg gtagaacacg ctgctacccg taggtgggca tctccactta 101820
tgggccatct gcttaggttg ggttcctctg gattctggga agattggggg ttctgttttc 101880
atcagctgat tcttctgggg gcaagtgggt gctcgccagc tctccagctt cctaaaggtg 101940
gagaagcacg gacttccagg ggcctggcct ggaccccttt ctctgctcct gtccctgtgc 102000
ccctcatctg ggtgcgttag gctgacatac aaagcaccgc agtgaaagag cagcagtgtg 102060
cctcctcacc agccagatgt gggcggtggg tatcttccaa ggcctctctg tggcggtgcg 102120
tagccacctc cgccctgcgc cgccagggtc ttctctctgt gtgtgctcct ggtggctctg 102180
cacacgctca tcttataaga acaccatggc ggctgggcgt gatggctcat gcctgtaatc 102240
ccagcatttt gggaggccga ggggggcgga tcatgaggtc aggagttcga gaccagcctg 102300
agcaacagag tggaacctcg tctctactaa aaatacaaaa attagctggg cgtggtggta 102360
gcgcatgcct gtaatcccag ctactcagga ggttgaggca ggagaaccgc ttgaacccag 102420
gaggcagagg ttgccgtgag ctgagatagt gccattgcac tccagtctgc gcgacagagt 102480
gagactccat ctcaaaacaa gaaaagaaaa aagaaagaaa gaaaagaacg ccgttgctta 102540
gggcccagcc tgatgacctc atatttcact taatcacctc tctaaaggcc ctgtctccaa 102600
atagagtcac attctaaggt acgggggggtt agggcttcaa catatgaatt tgtggggacc 102660
acagttcagc ccaggacccc cttcccacca cccagcagag ctggggaagg gtgaagagga 102720
ggctggggggt gcagaggacc acggctcact ctgaggctgc agatgtgctg ggccttctgg 102780
gcactgggcc tcggggagct aaggggcttt ctgaaaccct gggcctgtgt gtcagcttgc 102840
cgcccccacg caggcgctct ccacaccgtt gaatttcttt tttttttttt tttttttgag 102900
acggagtctt gctctgtcgc ccaggctgga gtgcagtggc cggatctcag ctcactgcaa 102960
gctccgcctc ccgggttcac gccattctcc tgcctcagcc tcccgagtag ctgggactac 103020
aggcacccgc cacatcgccc ggctagtttt ttgtattttt tagtagagac ggggtttcac 103080
cgtgttagcc aggatggtct cgatctcctg acctcgtgat ccacccgtct cggcctccca 103140
aagtgctggg attacaggct tgagccaccg cgcccggccg aatttcttat cacttgggcc 103200
tgagcctggg ccatgtggag ggagggtggc caccagtgca tgtgagcacc ttgcctcaaa 103260
ccctgccacc taccctggcc caggcttcga tgcaggagcc cccctgcccc tgaacaagcc 103320
tgtgggtgca gcatcgcatc ccgtcaggat ggaaatggac ggttgggtta aaagagatgc 103380
atgtgtagac cctgcctctc tgcatcaagc ctcctttgag tgcccctgcg tgccagaccg 103440
tgcatagagg tggagaagac tcagctgtgc cccggagcac ctcctctcat cgaggaaagg 103500
acagacagtg gctcccctgt ggccgtgggg acaagggcag agctccctgg aacacaggag 103560
ggagggaagg aagagaacat ctcaggatct ccctcttgat ggcaaatgat ctgggttaaa 103620
ttaaaagtcc ggcctctccc tgcttaggca tgtggagctt gtagtggaag agggtctctg 103680
gaccctcacc taccacaatg gcctggttag aggccttggg gaaataactc acaggcgacc 103740
cagggcctct gtcctgtacc acagctgagg gaaactgtcc tgcgcttcca ctggggataa 103800
tgcgctccct cgtctccaga ctttccagtc ctcattcggt tctcgaaagt cgcctccaga 103860
agccccatct cgggaccatt gtgaccttca ttctccaggg tgcctggccc tggtgctgcc 103920
caagaaccca gaggggccct cactggcctt tcctgccttt tctcccattg cccacccatg 103980
tacccccatc ctgctccagc atccagactg ccatccacgc atacccagga tctcctcaag 104040
tcacatgaca ggcagtaccc tcaaagtgct cccttccccc cagtctgaat ctgctgctcg 104100
ctgtctgggg ttccccgccc atgcaccccc gggggcccct gggttctgcc atgccctgcc 104160
cagtgtccca cagcagggaa tgtccttctc tccttatctc ttcccttccc ttaaacccaa 104220
gttcagttgc catctcctcc aggaagtctt cctggatttc cctctctctt ctcaaagccc 104280
ctgaaaaccc tgacgacact gaacatgcgt gtgctgctcc ctagtctggg ccgtgactga 104340
gggtgaaggc cgagtctcac gcgtttttgt agcccccaca agactgcgca ggtggccggc 104400
cctcactgaa tgcggggtta atttaactcg ggctctgtgt gagtggatga ttcaggttgc 104460
cagagacaga accctcagct tagcatggga ggtagctccg ctcttgaccc tgagttcatc 104520
tgaggttgac ttggaaggtg tgggcaccat ttggcccagt tcttacagct ctgaagagat 104580
cagcaggaat ggggctgagc agccaagaca gctttccatc cagaactgtc cctcccactc 104640
tgtgactgcc ctgcctgtgc ccatgagggg tgagagtcag gcgacctcat gccaagtata 104700
gaaaggggca cggccgggcg cggtggctca agcctgtaat cccagcactt tgggaggccg 104760
agacgggtgg atcacgaggt caggagatcg agaccatcct ggcgaacatg gtgaaacccc 104820
gtctctacta aaaaatacaa aaaactagcc gggcgaggta gcgggcgcct gtggtcccag 104880
ctactcggga ggctgaggca ggagaatggc gtgaacccgg gaggcggagc ttgcagtgag 104940
ctgcgatctg gtcactgcac tgcagcctgg gcgacagagc aagactccgt ctcaaaaaaa 105000
aaaaaaaaaa gaaaggggca gacagggtcc caggttacga cgtcatcacg ctgggcggag 105060
acggcacatc caaatgtact aaagggttaa aggagaaagg gtgactttat ttttcttgag 105120
atattttggg ggacgaagta tggaaaagtg gcagaggaca cagtcacagc ctcccttaaa 105180
tgccaggaaa gcctagaaaa attgtctgaa accaaacctc agccatcaca aagaccaaca 105240
catgaatctc caggaaagaa gaaaaaaaag tcatacgggg tccacgcaca agggccttta 105300
aaacgacccg ctggagggtc tcaggcctcc tcctcctcct agactggcct gaagtctcca 105360
cgaggttttg ctgagacctt tgggtccctg tggcctcatg tagtgcccag catacagtaa 105420
gtgctcaata aatgtttggc tacaaaagag acaaagctgg aggagtctga agaatcactc 105480
agtcctgccg gaacagatgc tcacactgaa gacagaagag caggagccaa gtcaggtttg 105540
ggaacctgta gaggctgaaa accaccgcag atcgctgtaa atcgtttggg aacaaaacag 105600
aaaacgtctg ttttctcctt tgtgcttgtc tctgttttcg ggatgtgcta cagtgaacat 105660
gtattgcttt gggggcccca aatggaatta tttttaaagg aaaatgcaga tgatcgggtg 105720
gccacactgg agcactgact gggtaggggt ggagattgca gggaaggaag aagagctggg 105780
tgggatgcca ggcaggaaaa gcccatagac ccccaccgat cttgtggtga gccgtgggca 105840
gcggtgttcc atcctaactg caaaagggag cacctggggg gaagagggga ttcttttaaa 105900
caccattcca gtgcccgagc cccccggacc tgttgtcatc ttgggttggc ttcccctggg 105960
tgactccagt gtgcagctgg ctgagactca gtgaccctgg gttcttactg ctgacaccta 106020
ccctcaacct caaccactgt ggcctcctgt gcaccctgat ctccagtgac tcattttcca 106080
ctttcagtcc caactctatt cctatttgca gattccaagc gcctggctcc tcagtcaact 106140
cagacccagc caggccagcc catgggtccc acatgcccct tgccaaggtt gtccccgccc 106200
tgtctggcct gcgagggtgg gggtatgtcc agacacagag acaaaggacc agcttttaaa 106260
acattttgtt ggagccaggt gtggtgactc acacttaatc ccaacacttg gggaggccaa 106320
ggcagaagga tcacttgagt ccaggagttc gagaccagcc tgggcaacat acggagaccc 106380
tgtctttaca cttttttttt tttttttaat tagctgggca tgttggcact cgcctgtagt 106440
tccagctact ccagaggctg aggtgggagg actgcttgag cctgggaggt caaggctgca 106500
atgagccatg ttcacgccac tgaacgccag cctgggcgag accctgtgtc aaaaaagtaa 106560
agtaaaatga atcctgtaca ttacattaag gcgccccaaa ttgtacttag aaggatttca 106620
tagttttaaa tacttttgtt atttaaaaaa ttaaataact gcagcatata aattaggttc 106680
ttaatggagg gggaaaagaa tacaaggaaa aaaaagaatc tagaaacaaa gataagagca 106740
gaaataaata aaaaaacaca accttgcact cctaacttta aaaaaaaaaa aagtgaagaa 106800
aacacaacca gtaaaacaga acatataaca gcatcaaaag ctgactcctg gctgggcgca 106860
gtggtgcatg cctgtaatcc cagcactttg ccaggctgat gctggaggat cgcttgagac 106920
caggagttca aggttgcagt gagctatgat cacaccacta caccccagcc tgggcaatag 106980
agcgagactg agacctattt aaaaaaaaag aaagaaagaa cagaaaagct ggttccttcc 107040
ttatttcatt cctttattca ttcattcaga caacatttat ggggtacctc tgaacaccag 107100
gctctgtgct aagagctttt gcccccaggg cccaggccag gggacagggg cagatgagca 107160
gagaaacagg gccagttgca gcagcaggag gaattaggat ggagagcttg gccaggaaag 107220
gacatgcaag gggagcaacc cgcacaagtc agcaagccag agaagacaga cagacccttg 107280
tttgggacct gttcagtggc ctttgaaagg acagccccca cccagactgc tgggtgcagg 107340
agctgaagga ggatagtgga acacggtaac gtggagctct tcagagcaaa agcaaaataa 107400
agctagaact ggaggcggct ggagcagccg agggcgtgtg tccagcgtta aggggtgtga 107460
agcttgggcg ctaggagagt tcacactggc agaagagagg ttgcggctgc tgcgagccgc 107520
tggacatcgc ccaataggac agagggtggt ggaggggggg cctgaagaga ggctcagttc 107580
agctgcagtg gccgtgggag tgctgaagtg ggcgggctgt gggcagctgc tggggagggt 107640
tacgcggggg tgagggccca gcaacagcaa cccttcttgg ggggtcactg ggaaacaaag 107700
aggagagctg aagaagcagg gagtcccagg ggccatgcag ggcaagagag aatttgctca 107760
tatggggccc aggctgcagg atcaggagaa ctggggaccc tgtggctgcc agcagggaga 107820
agggagtgta caggatcatg gccaggaaag ggcccggggg ctatgggggg gcctggttgg 107880
ctccgagaag ttggagctga agtcactttc tcggaggatg tccaggccag tagttgggat 107940
gtgaagacct gaagcagcac agagcctgga agcccaggat ggacagaaac ctacctgagc 108000
agtggggctt tgaaagcctt gagtgtgcaa tattgaagat ggccacaaga tggcgataga 108060
atgctgtaac tgtttcttgg ttctgggccg cagcctgggt ggcttgcttc cttccctgtg 108120
tgtgttgatt tgtttctctt ttttgagaca gggtcttgct gagttgccca ggctggagtg 108180
cagtggtgcg atcgtagctc actgcaacct tgaagtcctg agctcaagcg atccttccac 108240
ctcagcctcc tgagtagttg ggaccacagg cttgcaccac agtgcccggc taatttcttg 108300 tatttttgc agagatgtgg tttcactgtg ttgcccagga tggtcttgaa cgcctgggct 108360
caagtgatcc tcctgcctca gcctcccaaa ctgctggtgt gagccaccat gcccgacctt 108420
cacttttttt tttttgaga cagagtctcg ctctgtcgcc caggctggag tgcagtggcc 108480
ggatctcagc tcactgcaag ctccgcctcc cgggtttacg ccattctcct gcctcagcct 108540
cccgagtagc tgggactaca ggcgcccgcc acctcgcccg gctagttttt tgtatttttt 108600
tttagtagag acggggtttc accgtgttcg ccaggatggt ctcgatctcc tgacctcgtg 108660
atccgcccgt ctcggcctcc caaagtgctg ggattagagg cttgagccac cacgcccggc 108720
cctcttctcn nnnnngggcg tctgtgtgtg cgcctgtgtg cgcgtgtgtg cgtgtgcgtg 108780
cgcctgtgtg tgtgcacgtg cgtgtgtgcg tacgtgcatg tgcgcgcata cgtgtgcgcg 108840
cacacactcg tcttcacctt ctcccagcct tgctctctct ctacccagtc acctctgccc 108900
atctctctga tctatttctc tctcctttta cccctctttc ctcccttctc atacaccact 108960
gacaattata gagaactgag tattctaaaa atactttctt tatttatttt gagacagagt 109020
ctcactctgt catccaggct ggagtgcgat ggtgcaatct cggctcactg caacctccgc 109080
ctcccaggtt caagcaactc tcctgcctca gcctccctag tagctgggat tacagacgcc 109140
caccaccacg cctggctaat tttatattt gtagtagaga cagggtttca ccatgttggc 109200
caagctggtc tcaaactcct ggcctcaggt gatctgcctg ccctggcctc ccaaagtact 109260
gggattgcag gcctgagtca ccgtgcctgg ccttaaaaat acattatatt taatatcaaa 109320
gccccagttg tcactttaaa aagcatctat gtagaactta tgtggaataa atacagtgaa 109380
tttgtacgtg ggatcgtttg cctctccttc tcaatcaggg ccagggatgc aggtgagctt 109440
gggctgagat gtcagactcc acagtaagtg gggggcagtg ccaggctggg accctcctct 109500
aggacagatc tgtaactctg agaccctcca ggcatctttc cctgtacatc agtgcttctg 109560
aaaaatcttg tgtaaatcaa atcattttaa aggagcttgt ttaaaggaca gtgtaaataa 109620
ttctgaaggt gactctaccc tgttatttga tctcttcctt ggccggttga cttgacagga 109680
catagacagg ttttcctgtg tcagttccca agctgatcac cttggacttg aagagaaggc 109740
ttgtgtgggc atccagtgtc caccccgggt taaattccca gcagagcatt gcactggccc 109800
tgctgagcct ggtgaggcaa agcgcagctc agcaagcagg cagcgctgga gacaggccaa 109860
gcctgggcca gcctgggagc caactgtgag gcacggggct gtggggctgc aggcttgagg 109920
ccagggagag agggctgggc tctttggagt agccttgaga gacctgaacc caaacaaaac 109980
cagatcaagg tctagtgaga gcttagggct gctttgggtg ctccaggaaa ttgattaaac 110040
caagtggaca cacaccccca gccccacctc accacagcct ctccttcagg gtcaaactct 110100
gactcagaca tttctcccct gactgggagt tccctggatc caaattggga gcttgcaacg 110160
ctttgttctc tcccttgatg gtttttgtca gtgcctcccc agagccgaag tgtaatatat 110220
atgtttctgt agctgagaaa ttcaatttca ggattctgat ttcataatga cagccattcc 110280
ccttttctct cccttctgta aatctaagat tctgtaaagg atgttgactt aatgtgacaa 110340
ttggcagtag ttcatgtctg ctttgtaaat acccttgtgt ctattgcaaa atctcataaa 110400
ggcttgttga cttttttgtg ggttagaac aagaaaaagc cacatggaaa aaaatttctt 110460
ttttgttttt tgtttgtttg tttgcgacag agtctcactc tgtcgcccag actggagtgc 110520
agtggcacga tctcggctca ctgcaagttc tgcctcctgg ggtcatgcta ttctcctgcc 110580
tcagcctcct gagtagctag gactacaggc gcctgccatc acacctggct aatttttttg 110640
tattttttag tagagacagg gtttcaccgt gttaaccagg atggtctcga tctcatgacc 110700
tcatgatctg cctgccttgg cttcccaaaa tgctgggatt acaggcgtga gccaccgcgc 110760
ccagctggaa aaaacatttc tatgtatgtg acagacactg agttattgct taatgtcctt 110820
tgattcattt gcttaatttc ttttatggat tagtacagaa aacaaagttc tcttccttga 110880
aaaactggta agtttccttt gtcagataag gagagttatg taacccatga catttccctt 110940
tttgccttgg cttctaggaa gctcaaagct aaatggaatg atcactcttg taattgtcag 111000
tattgatgcc ctccccttct tctaatgtta ctctttacgt tttcctgttt tattattgtg 111060
agtgtgtgtt ttctaattct aagctgttcc cactcctttt tgaaagcagg caaatcggcc 111120
gggcgcggtg gctcaagcct gtaatcccag cactttggga ggctgagacg ggcggatcac 111180
gaggtcagga gatcgagacc atcctggcga acacggtgaa accccgtctc tactaaaaag 111240
tacaaaaaaa ctagccgggc aaggtggcgg gcgcctgtag tcccagctac tcgggaggct 111300
gaggcaggag aatggtgtaa acccgggagg cggagcttgc agtgagctga gatccggcca 111360
ctgcactcca gcctacgcga cagagcgaga ctctgtctca aaaaaaaaaa aaaaaaaaga 111420
aagcaggcaa atcttcttct aagacttatc cagtgaaaag ttatgaataa aaaatgatca 111480
tcaagtctac aggtgctgag gctactacag aggctgaggc cagaggacta cttgagccca 111540
ggaatttgag acctgggctg ggcaacatag caagacccca tctccattaa aactattttt 111600
tattaaaaaa ataatccgca aaggagttta tgtggggttc cttaaaatcg gagggtgaca 111660
tgaattgatt caaagacttg tgcaaagggc gacagcaact ccttgagaag cagtatgaga 111720
aatcctgtcc tacctcctcc cccagctcca gcctgggctg aggcactgtc acagtgtctc 111780
cttgctggca ggagagaatt tcagtgttca ccaaaaagta gtattgtttt tattaggttt 111840
atgaggctgt agccttgagg acaacccagg acaactttgt tgtcacaaag gtagcctgcg 111900
gctacgggaa ctctgagatc tagattcttc tgtggctgct tctgacctga gaaagttgca 111960
gaacctctgt gggcctcaca tggcctcctt gtcctttatg aggggatggt gggcaagaaa 112020
ggtgatgtga cattagagat ttatccatct ctaagggagg agtggattgt acgttgaaac 112080
accagagaag gaattacaaa ggaagaattt gagtatctaa aactgtaggt cggacactcc 112140
tgtattgatt gcagcactat tcacaatagc caagatttgg aagcaacacg agtgtccatc 112200
agcagacgaa tggagaaaga aaatgtggtt catatatgca atggagtatt cagccatgaa 112260
aaagaataag attctgtcat ttgaaacaac atggatggaa ctggaggaca tcatgttaag 112320
tgaaataagc cagacagagg gacagacttc acatgttctc acacatttgt gggagctaaa 112380
aattaaactc atggagacag aaagtagaag gatggttacc agaggctgag aagggtggag 112440
gggagtgggg agaaagtggg gatggttaat gggcacaaaa acatagttag catgaataga 112500
tctagtattg gatagcacaa catcgtgact acagtcaaca ggaatttata gtacatttta 112560
aaacaactaa aagagtgtaa ttggaatgtt cataacacaa gaaatgatca gtgcttgagg 112620
tgatggatac cccatcaccc tgatgtgatt attacacaat gtatgtctgt ttctaaatat 112680
ctcatgtacc ccacaagtat atacacctac tatgtaccca tataaattta aaattaaaaa 112740
tttataaaac acacataaat aagtacattc aaatgtaggc tggacactgt ggttcacacc 112800
tgtaatccca gtgctttgag aggctgaggt gagagaatca cttgagccca ggagtttgag 112860
acctcatcac cacaaagaat ttttaaaaat tagctgggtg ttgtggcaca taccggtagt 112920
cccagctact tgggagacgg aggcaggagg atcgcttgag cccaggagtt taaggctgca 112980
gtgagctacg atggcgccac tgcattccag cctggatgac agagtgagac cctgtctcta 113040
ttttaaaaat aataaaaaga ataaataata aaaataaatt aaaatgtaag tatttgtatg 113100
ttagaaaaaa tacacccatc agccaaaggg gtaaaggagt gatttcagtc ataatcagat 113160
gcaggataag ccagcaatgc agtttctttt attttggtca aagaaataag caaaacaata 113220
ttgtaaacac ccagtcagtg ctggcagcaa tatgaggctg gctctctcac cagggctcac 113280
aggggaaact catgcaaccc ttttagaaag ccatgtggag agttgtactg agaggttttc 113340
gaatatttat aactttgacc cagaaattct attctaggac tctgtgttat gaaaataacc 113400
catcatatgg aaaaagctcc tttcagaaag aggttcatgg gaggctgttt gtatttttct 113460
ttctttgcat caaatccagc tcctgcagga ctgtttgtat tattggagta caaaatggaa 113520
tcaatacaaa tgttggctag cagggggaaa atattcacaa aatggaatgg aacatattat 113580
taaacatagt gcttctgatg accgtagacc atacagaatg cttaggatat gatatcactt 113640
cttttgttct tttttgtttt ttgagacaaa atctccttct gtcacctggg ctggagttca 113700
gtggcacgat ctcagctgac tgcaacttcc atctcccagg ttctcctgcc tcaacctccc 113760
aagtagctgg gactacagtt gcttgccacc atgcccggct aacttttgta tttttttacta 113820 tagacagggt ttcaccttgt tggccaggct gttctcgaac tcctgacctc cggtgatcca 113880
cctgccttgg cctcccaaag tgctgggatt accggtgtga gccaccgcgc ccagcctagg 113940
atatgatatc acttcttaga gcaagataca aaattgcatg tgcacagtaa ttctcccaag 114000
tttaggtaca cagggatggt tacatctaaa cgagacttaa aggaaataca aaaaatgcaa 114060
tcctgattgt gttagggtgg taagaaaacg gttttgtttt tgctttgatg agctgttttt 114120
taaaattgtt atattttcta ataaaaatac atagtgtgtt tgaaggaata taaaagatta 114180
tgaagagatg agttagatgt tgattcatat tgaagattca gatgagtaaa attaaggggg 114240
aaaaacggga tgaaccagaa gccaggctgg agtcccagtc ccagacccga cagcccaggc 114300
tgatggggcc tccagggcag tggtctccac ccagcattct caaaagagcc actgagctct 114360
tgccattttc aagatttcag aaaccacctt ggcatggctg gtctttcact gggatctcca 114420
cttggcaatt atttacatct gagacgaata aaaaccaaag tgctgagatt acatgcgcag 114480
tggctcaggc ttgtaatccc agcactttgg gaagctgagg tgggctgatt gcttgagccc 114540
aggagtttca gaccatcctg gacaacatag cgtgacctca tctctacaaa aaatacaaaa 114600
aaattgccag gtgtggtggc atgtgcctgt ggtcccagct acttgggagg ctgaagtagg 114660
agaatccctt gagtccaggg aggtcgaggc tgcagtgtgc cgggaagatg tcactgcact 114720
ccagcctggg ggacaaagtg agaccctgtc tcactaagaa aaaaaaaaaa aaaaagcact 114780
gtttccagag ttcctgaggg gaaggtcacc gggtgaggaa gacgttctca ctgatctggc 114840
agacaaaatg tcaagttttt ccaactccct aaaccctggt tttctatttc atagttttta 114900
ggcaaattgg taaaaatcat ttctcatcaa aacgctgatt tttcgtacct cccgggtgtc 114960
tacagaaaga accttccaga aatgcagtcg cgggagaccc atccaggcca cccctgctta 115020
tggaagagct gagaaaaagc cccacgggcg catttgctca gcttccgtta cgcacctggt 115080
ggcactgtgg gtgggagggg gctggtgggt ggatggaagg agaaggcact gccccccttgc 115140 agggacagag ccctcttaca gaggggacac cccgcatttg tcttccccac aaagcggcct 115200
gtgtcctgcc tgcgggctca gggcttctta aacctggctg tgtgtcagaa tcaccagggg 115260
aacttttcaa aaccagaggg actggaaaga ctcctccaga tttgaattct aggttagggc 115320
tggggtctga gattttaaaa atccacaggt gattcccatg cccaacaggc ttgagaacag 115380
ccacaggaag ttctctggga atgttccggt gggtctagct aggggtgagt ggagatgcca 115440
gggaacttcc tgttactcac tcatcagtgt ggcctaacac gtttttcact gaccccaggc 115500
tggtgaacgc tcccctctgg ggttcgggcc tgacgatgcc atccttttgt gaagtgagtc 115560
cctgcccctg aggacctgca atcccagctt cgtaaagccc gcggggaatc actcacagtt 115620
ccgggatgcc ttcggggcag ccctctctct gtcccttcag ctcccctggg gtgtgactca 115680
atctcccgcc actccccaga ctgcctctgc caagtccaaa agtggaggca tcctttcgag 115740
caagcaggcg ggtccagggt gacgcgtgtc actcatcgaa aatggaggcg tccttgtgag 115800
aaagcaggcg ggtccagggt gacgcgtgtc actcatcgaa aatggaggcg tccttgtgag 115860
aaagcaggcg ggtccagggt ggtgtgtgtc actcatcaaa agtggaggca tccttgcgag 115920
caagcaggcg ggtccagggt gacgtgtcac tcatcctttt ttctggctat caaaggtgca 115980
gataattaat aagaagctgg atcttagcaa cgtccagtcc aagtgtggct caaaggataa 116040
tatcaaacac gtcccgggag gcggcagtgt gagtaccttc acacgtcccg tgcgccgtgc 116100
tgtggcttga atttttagga agtggcgtga gtgcgtacac ttgcgagaca ctgcatagaa 116160
taaatcctcc ttgggctctg aggatctggc tgcgccccct gggtgaatgt agcccggctc 116220
cccacattcc ctcacacagt caactgttcc cagaagcccc ctcctcatgt tctaggaggg 116280
agtgtcccag catttctggg tccccaggcc gtgcaggctg cgtgtacaga atagggtgtc 116340
tgacggaccc tctctccagc ccctgcctgg gaagctgaga atacccgtca aggtctccct 116400
ccactcacac ccagccctgt ccccaggagc cccatagcgc attgaaagtt gggctgaagg 116460
tggtggcacc tgagactggg ctgccgcctc cacccccgac acctgggcag gttgacgttg 116520
actggctcca ctgtggacag gtgacccgtt tgttctgatg agtggacacc aaggtcttac 116580
cttcctgctc agctgtgcct cctatgtgtt caaggcagga gcggattcct aagcctccaa 116640
cttatgctta gcctgcacca ccctctggca gagactccag atgcaaagag ccaaaccaaa 116700
gtgtgacagg tccctctgcc cagcgttgag gtatggcaga gaaatgctgc ttttggccct 116760
tttagatttg gctgcctctg gtcagaagcg gtggctcatg cctgtaatcc cagcactttg 116820
ggagatgaag acggtaggtt tgcttgagcc caggagttca agtccagcct gggcaacagt 116880
gagacccctg tctctacaaa aaaaatttaa attacccagg tgtggtggtg tgcacctgta 116940
gtcccagcta cttgggaggc tgaggtggga ggatcacctg agtccgggag gcagaggttg 117000
taaggagcca tgatcgcgcc actgcacttc aactgaggca acagagcgag actttgtctc 117060
aaaaaacaat ggtataataa ttttaaaata aatagatttg gcttcctgta aatgtccctg 117120
gtgagattcg ggactcagat cctcaagtcc cactgactca cccgatgagc tgaggcttca 117180
tcatcccctg gccggtctat gtccacgggg caccggaggc tcctctccca ccagcagtct 117240
tggtgagctg aaagcaaact gttaacaccc tggggagctg gaggtatgag accctcgagg 117300
tccaccccaa gggaggcgtt gatttttgag agcaatcacc tgaccctggc tggcagtacc 117360
aggacactgc tgtggctctg gggcgggctg tctccggaaa atgcctggcc tggggcagcc 117420
acccgcatcc agcccagagg gtttattctt gcaatgtgct gctgcttcct gcactgagca 117480
cctggatcct ggcttctgcc ctgaggcccc tggagtccca caagtagcaa gcgcttggcc 117540
tgcggctgct gcatggggct actaacgctt cctcaccagt gtctgctaag tgtctcctct 117600
gtctcccacg ccctgctctc ctgtcgcccc agtttgtctg ctgtgagggg acaaaagaga 117660
tgtgtgcccc cacccctgcc caggtccttg ttcctgggat tgctgttcag ctgtttgagc 117720
tttgatcctg gttctctggc ttcctcaaag tgggctcggc cagaggagga aggccatgtg 117780
ctttctggtt aaagtcgagt ctggtggcct ggtggagact gcgctcctga ggcggagctg 117840
gggatagagc actcatgggc tgcgtggcca acccctctgg tagctgatgc ccaaagacgc 117900
tgcagtgccc aggacatccg ggacctccct ggggcccgcc cgtgtgtcct acgctgtgct 117960
cgtctgtggg ctagcctgtg acccgcgctg tgctcatctg tgggctagcc tgtgacctgg 118020
cagagagcca ccagatgtcc cgggctgagc accgccctct gagcaccttc acaggaagcc 118080
tttctcctgg tgagaagaga tgccagcctc tggcatctgg gggcactgga tccctggcgg 118140
cggctagggc taggtggccc tagtctctcc ccagcctggg ggccccttcc cagcaggttg 118200

-continued gccctgctcc ttctccacct gggacccttc ttcctcctgg ctgggccctg gaagttctgc 118260
aggacctgcc gtccccctcc ctggcctcca ggtatcttga ccaccgccct ggctcccact 118320
gccacccact cctctcctat ctggccgttc cctggtccct gtcccagccc ccctccccct 118380
ctcatgagtt tcctcaccaa ggccagaggg aagagggaag gaggccctgg tcataccagc 118440
acgtccttcc acctccctca gccctggtcc accccccttgg cgccagcctc agagcacagc 118500
tctctccaac ccaggccgca caccgtccgt cctccctgcc cccacgtcct tgccgcagat 118560
cctgtccgcc ctgacacaca ttggcctcag ccatctctgc cccagttaac tccccatcca 118620
taaagagcac acgccagctg acgttaaaat aatttgggat ggttccagtg tagacctaag 118680
tagaagcggg aaccgctgcc cccactgcac cttggtttct ggtggccttg ataaaccatc 118740
ttcagccatg aagccagctg tctcccaggc agctccaggg cagggcttcc tggggagctg 118800
actgataggt gggaggtggc tgcccccttg caccctcagg tgacccacac aaggccactg 118860
ccggaggccc tggggactcc agaatgtcag tcatgacccg cccccaggcc gcacacagcc 118920
acggtttcac agatgccggc ctccagggga cctgtctgtc tgccactcgg agtccccaca 118980
gggtgccccc ccaggggagc tggctctcgg actgagatca gctggcagtc cggactgtca 119040
ttccccgagg gagcggtgcc ctggatccca caggcctccg catgtgtgtc tgtgtccgtt 119100
cgagcttgct gagacattca atctgttggt ttctgttgtg ccgcctaccc accctgtcga 119160
tgatgctttg ctcctgttgc taaagacagg aatgcccagg accctgagtg tgcaggtgcc 119220
cgctggctct cacgtccgag ctgctgaact ccgctgggtc ctgcttactg accgtctttg 119280
ctctagtgct gtccgtggaa gcttttcctg gaataaagcc cacccatcaa ccctcacagc 119340
gcctcccctc tttgaggccc agcagatagc gcactccagc ctttccagca agatttttca 119400
gatgctgtgc atactcatca tattgatcac ttttttcttc atgtctgatt gtgatctgtc 119460
gatttcatgt taggaaaagg agtgactttt ttacccttaa gcctttgctg agcaaatgtc 119520
tgggccttgc acaatgacaa cgggtccctg tttttcccag aggctctttt gttctgcagg 119580
gattgaagac actccaatcc cacagtcccc agctcccctg gagcagggtt ggcagaattt 119640
cgacaacaca tttttccacc ctgaataggg tgcgctcctc atggcagctg ggaaccactg 119700
tccaatcagg gcctgggctt acacagctgc ttctcattgc attacaccct taataaaata 119760
atcccatttt atcctctttg tctctctgtc ttcttctctc tctgcctctc ctcttctcgc 119820
tcctctctca tctccaggtg caaatagtct acaaaccagt tgacctgagc aaggtgacct 119880
ccaagtgtgg ctcattaggc aacatccatc ataaaccagg tagccctgtg gaaggcgagg 119940
gttgggatgg gaaggtgcac ggggtggagg agtcctggcg aggctggaac tgccccagac 120000
ttcgaaaggg gctggaaagg atttgctggg tagaccatca aggagagttg agtgtggaac 120060
ttgcgggagc ccaggaggcg tggtggctcc agctcgctcc tgcccaggcc atgctggcca 120120
agacaaggta aggcgggagt gaagtcaaat aaggcaagca cagaaagaaa gcacatgttc 120180
ttggctgggc gcggtggctc acacctgtaa tcccagcact ttgggaggcc aaggcaggcg 120240
gatcacgagg tcaggagatt gagaccatcc tggctaacac ggtgaaaccc catctctact 120300
aaaattacaa aaaattagcc gggcatggtg gcgggcacct gtagtcccag ctactcagaa 120360
agctgaggca ggaaaatggc atgaacccag gaggcggagc ttgcagtgag ccgagatggc 120420
gccactgcac tccagcctgg gtgacagagc gagactctgt ctcaaaaaaa aaaaaaacac 120480
acacacatgt tctcgcttat ttgtgggatc caggagatag ataatagaag gatgattatc 120540
agaggctggg aagggtagtg aggggatggt ggggagatgg ttaatgggta caaaaaaaaa 120600
tagaataaga cctagtattt gatagtgcaa cagggtgact atagtcaata ataatttaat 120660
tgtacattta aaaataacta aaagatagcc agatgcactg gcttacgtct gtactcccag 120720
cactttggga ggccgaggtg ggcatttgag accagcctgg ccaacatggt aaaaccccat 120780
ctctactaaa aatacaaaaa ttagctgggc gtggtggcgg gcacctgtaa tcccagctac 120840
tcgagaggct gaggcaggag aatcacttga acctggaggc agaggttgca gtgagccaag 120900
atcttgccac tacactccag cctgggtgac agagcgaaac tctgtctcaa aaataaaaat 120960
aactaaaaga atataaatgg attgtttgta acacaaagga caaatgtttg cggggatgga 121020
taccccattt tccatgatgt gattattaca cattgtgttt ctgcatcaaa acatctcatg 121080
aaccccataa atatatatac ctactatgta cccataaaca ttttttaaa aaaatttttc 121140
aaggtgaaga gggaggcaag atgctggcct taagccctaa cccgggattc tcccagcaag 121200
ctgtccacag gtcttctcag gcttgaggtg cagctatatg gatgtgtgag cttggtcccc 121260
agccaacatg gagacacttc actatcggca gcagctacag cacaggaacc ctgggtcact 121320
gccgtgtccc ctctgtgact ttgtttaaac agaaaatgat gctctgggct ggccgcggtg 121380
gctcacgcct ataattccag cactttggga ggctgaggtg ggcagatcat gaggtcagga 121440
gatcgagact atcctggcta acacggtgaa accccatctc tgctaaaaat acaaaaaact 121500
agccgggcgt ggtggcgggc gcctgtagtc ccagctactt gggaggctga ggcaggagaa 121560
tggcgtgaac ccaggaggca gagctgcagt gagctgagat cgcgccactg cactccagcc 121620
tgggtgacag agtgagactc catctcaaag aaaaaataaa ataaaaaaat acttgactta 121680
ctggaagcca accaatgtat aatttagaat aatttctcct gggttgagct gtcacttacc 121740
tttgcagtat ctcaagagga agagttcact gtgtaaatat tgatgcatac tttgattaga 121800
tagatgaagc aaactatttt caagcacttt tcaaggactt acttgtatcc aaacagcatt 121860
ctaaaggaaa gtcttaccta cttctaaagg ctggtctcta cttgaaacct cttgcttggc 121920
cctggttcaa gtcctgctgc aaacctggaa gtcccgtcac tgtcttcttc cctgcagagc 121980
agtggctccc gatctaattt ttgctgtgcc ccagcagccc ctggcacttt gccctgtaga 122040
ccacagacct catgtaatgt gtgctaagtc cacggaactg cggaagatga tggcaagatg 122100
ctcttgtgtg tgttgtgttc taggaggtgg ccaggtggaa gtaaaatctg agaagctgga 122160
cttcaaggac agagtgcagt cgaagatcgg gtccctggac aatatcaccc atgtccctgg 122220
cggaggaaat aaaaaggtaa agggggcggg ttggatgctg cacttgggta tgggcattaa 122280
tcaagtcgag tggacaaaga ctggtccagt tcccagagga ggaaaacaga ggcttctgtg 122340
ttgactggct ggatgtgggc cctcagcagc atccagtggg tctcgactgc ctgtctcaat 122400
caccttcacc aggagcttta gcacatttca cagctgggct ccaacctgga gaggctgact 122460
gatcggtctt aggtgcagct cagttgctgg agtttttgtt tttatttatt tttaagtatt 122520
tgaggcaggg tctctgtatt agtctgttct cacactgcta ataaagacat acccaagact 122580
gcgtaattta taaaggaaag aggtttaatg gactcacagt tccacatggc tggggaggcc 122640
tcaaaatcat ggtggaaagc aaaggagaag caaaggcatg tcttacatag cagcaggcaa 122700
gagagcgtgt gcagggcaac tcccatttat aaaaccatca gacctcatga gacttattca 122760
ctatcatgag aacggcatgg gaaagacccg cccccatgat tcagttacct cccactgggt 122820
ccctcccatg atacatggaa ttatgggaac tacaattcaa gatgagattt gggtggggac 122880
acagccagcc cgtatcattc tccctctgtc atccaggctg gagtgcatta gcatgatctc 122940
agctcactgc agcctctacc tccctgggtc aggtgatcct cccacctcag cctcccaagt 123000
agctggaact acaggtatct gccactatgc ccggctaaat attttgtatt tcctgtggag 123060
acgaggtttt gccatgttgc ccaggctggt cttgaactcc tgaggtcaag caatatgccc 123120
acctcagcct cccaaggtgc tgggattaca ggtgtgagcc acagtgcttg gcctaagtgg 123180
ctgcagtttt taaagctccc aggtgattct ttagtgcagt caaaagtgag aactagctgg 123240
gtgcggtggc tcatgcctgt aatcccagca ccttgggagg ccaaggtggg cagatggttt 123300
agtagagatg atctctacta aaaatacaaa agttagctgg gtgtggtggt gcatgcctgt 123360
aatcccagct acttgggagg ctgaggcatg agaatcgctt taacccaggt ggcagaggtt 123420
gtagtgagcc aagatcatgc cactgcactc cagtctgggg aacagagtga gactccatct 123480
caaaaaaaaa aaaaaaaaaa atgagaacca ctgtcctagg ccctgatgtt tgcagacaac 123540
taaaaaagga agtggacatc cccagtcacc tgtggcgcac caagaacaca tgggaacata 123600
atctaatttt ctaaatgggt tactaggcac ttagagcaaa acaatgatgc tgaaatcctg 123660
atttcaggaa agcctctgcc tgcctgttgt ggaagtgtcc acacgaggct cctggggcct 123720
tggtgtcccc agcagtttct agtctccagg tcttgctgtg ggtgtctgtg cagtgagggt 123780
gtgtgtggcg ctaagcgaga tctgtctagg gctggcacag gatgcggtct ggtagctgct 123840
gcttctcttc tgcagaagcg cagccaagca ccctctgggg tttcctgccc acacccagcc 123900
tgaagttctg ggagtggctc actttccaac cttcagggtc tcccaggagc tgactggggc 123960
gtggtagagg gaaaaggatt gtattagtct gttttcatgc tgccgatgaa gacctatccg 124020
atactgggca atttacaaaa gaaagaggtc tgatggagtt acagttccac gtggctgggg 124080
aggcctcaca atcatggcgg aaggtgagag gcttgtttca catggtggca gacaagaaaa 124140
gagagcttgt gcaggggaac tcccctttat aaagccatca gatctcggga gacttactat 124200
catgagaaca gcactatcat gagaacatag gggcagggaa aacccgcccc tacgattcaa 124260
tcctctccca tcgggtccct cccacaacgt gtaggaattg tgggaactat aattcaagat 124320
gagatttggg tggggtcaca gccaaaccgt atcggggtgt cccagaaagg gtgtgggatc 124380
tgagacccag ctcggcgtga ggaagtttgc ttctcgaggt ggcccagtcg ggtggaagtg 124440
gcaaccaggc tgtctctcca ccaggccact caggtggcag ctgagagacc cctgccctgg 124500
tcagtctccg ccctcccctc ttgccactgc atctggttct gaacagatgg gcaccctcat 124560
cttgtgtttg tgataaatgt ctaaccatgt agttttgtga gaagtgtttg ccgcagatgc 124620
tgtaaactgt ggcctggggc agacctcacc tccagacagg ccctgaggct ggcgagggca 124680
ctggcccata gtagctggcc gagagctctc aggttgtgcc acgcaggaca cagggatact 124740
tttcagtgcc tgggtcacta tccaaagtga gaaaacagcg ggggaccagg aggctgcccg 124800
cctcaaggga tgtgggggcc gggcccagtt atctgaggaa gcagtcagct tctctgctgt 124860
ttccaccagc caggcctccc ctggtctaag gcagggcctc ccagccttgg ggcgctttaa 124920
agatacctgg gcctggcccc atccccacag tctgactgag tgggtcggga taggggcatg 124980
ggcattggcg atttcctggg tgaagggagg cccgctgcag tctctggaag cttctctgtg 125040
ttaggaagag ctctgggctt gactctgctc ggagagtcaa gatccgcaaa tcctctcagc 125100
ctcagtttct ccttcagcaa gatgaaatgg aaatgctgta cctacgtccc agggtggttg 125160
tgagaccccc ccccccaaaa aaaacaatgt tctggaaggt tcctggtgcg ttgcagtcct 125220
ctaagaacct gagttagagc catgctgagt ctcagcttct tggctccttc tgtttccaac 125280
ttgtccatgt gatggctcag gaaggtgggc agggccctgc ccctactcag aaaacatcat 125340
cctggtccca gggatccccg cagcgttagt cccgttttcc gtgtgttgag aaaaattgct 125400
aacaagcagt ggggcacacc accagcctcc tgggttcttt tcagtttggg gatttttgga 125460
cattcccagg aatgtcaact ttctcttaaa aaacacttca aaaaacatta acataaatat 125520
ttttatcaaa gcttgtatta aatggtcttt caagaaaata cagtaacagg ccaggcatgg 125580
tggctcacgc ctgtaacccc agcactttgg gaggccaagg caggcagatc acctgaaatc 125640
aggagttcga caccagcccg gccaatgcag cagaaccccg tctctacaaa aaatacaaaa 125700
attagctggg tgtggtggca cacacctgta gtcccagcta ctcgggaggc cgaggcagaa 125760
ttgcttgatc ccaggaggtg gaggttgcag tgagctgaga ttgcgccact gcactccagc 125820
ctgggtgaca agagtgaaac tttgtctaaa aaaaaaaaaa aaaagaaaaa gaaaatacac 125880
taatagagaa caatctgttt ttcaaagtag tgactgcaaa tgaacaaaat atgcatctag 125940
cttaaacggg agcatggttt tctctatgcc cattcaagcc tgctgcaata ggggcccttc 126000
agcctggatc catggactcc taaaattata tggaaaatgg ctgtgtgggt gtgagcgtgg 126060
gtggacatgt gcacacatat ttttggcttt accagatgct caaagagcct aggacccaac 126120
aagggctgag gataaccctg tcggccgctt cagggtcatc aggaattcct gtgcgctgct 126180
cacttctcca gtgagcgcct tctgcttccg cgtttcctgg tatccttcgg ggctcctggc 126240
taggtcatgt gtttctctac tttcttttt tttcttttt ttttttgag acggagtctc 126300 gctctgccgc ccagactgga gtgcagtggc tggatctcag ctcactgcaa gctccgcctc 126360
ccgggttcac gccattctcc tgcctcagcc tcccgagtag ctgggactac aggcgcccgc 126420
cacctcgccc ggctagtttt ttgtattttt tttttagtag agacggggtt tcaccgtgtt 126480
agccaggatg gtcttgatct cctgacctcg tgatccgccc atctcggcct cccaaagtgc 126540
tgggattaca ggcttgagcc accgcgcctg gcctgtttct ctactttcaa aagggcttca 126600
gccaggcacg gtggcatgag cctgtagtcc cagctgcccg ggaggttcag gtgggaagat 126660
tgcttgagcc caggaatttg aggccagcct gggcaagtag atagataggt agatgataga 126720
tagatagata gatagataga tagatagata gatagataga tagatagata gatagataga 126780
tagatagata gatgtataat agatggatag ataagtcgct agacagactc catcctaaat 126840
cacccatcca cctacccaca cataaaaagg cctttgtcat gtcatgtttt gtggcccacc 126900
tgccagtgct gcccacagtt gctgcccctc caaactcatc agtcactggc aaacaggagg 126960
aatgtgtgtg gctcatgtct gggcatcagt ggctgtggga gacatccttg atcttctcca 127020
gcttctcctt ccacatttc ctttgcaatc tggcaatatc tatcaaaata aaatgcgcat 127080
gccttttgac ctaagagctc cacttctagg acacacttac aggtgtgtga catgatgttc 127140
attcagggtt atttatctga ggttgttcat acacaccatt gcctgtaatc actaaaggcg 127200
ggagcagcct aggcatccat tcacagagga gtagacgcct ttggatacat ccgtggtgac 127260
ggaatactaa gcagcctgtg tacatataca ctcacacatg tgtttgttta tgtgtggaat 127320
atctctgcag gatacacaag aaacttaaaa tgatcactgt ctctggggag ggtacctggg 127380
tgcctgggag gcaggtcagg ggaggagtgg gcacagggat tacgaattgg aagacaataa 127440
aaacaacagc ttctggccag gcacagtggc tcacgcctgt aatggcagca ctctgagagg 127500
ccgaggcggg cggattgctt ccgcccaaga gttcgagacc agcctgggca acatagtgaa 127560
accccgtttc tattaaaaat acaaaaaact agccaggtgt ggtggcatgc acctgtaatc 127620
ccagctaccc gggaggctga ggtgggagaa tcacctgagc ctgggaggtt gaggctgcag 127680
tgaggtgaga ttgcaccacc tcactctagc ctgggtgata gagcaagacc ctgtctcaaa 127740
aacaaacaaa caacagtccc tggcactgtg ggccaggcct ggcagggcag ttggcagggc 127800
tggtctttct ctggcacttc atctcaccct ccctcccttc ctcttctcct tgcagattga 127860
aacccacaag ctgaccttcc gcgagaacgc caaagccaag acagaccacg gggcggaaat 127920
cgtgtacaag tcgccggtgg tgtctgggga cacgtctcca cggcacctca gcaatgtctc 127980
ctccaccggc agcatcgaca tggtagactc gccccagctc gccacgctag ccgacgaggt 128040
gtctgcctcc ctggccaagc agggtttgtg atcaggcccc cggggcggtc aataatcgtg 128100
gagagaagag agagtgagag tgtggaaaaa aaaagaataa tgacccggcc ccgccctctg 128160
cccccagctg ctcctcgcag ttcggttaat cggttcatca cttaaccggc ttttatcgct 128220
cggctttggc tcgggacttc aaaatcagtg atgggaataa gagcaaattg catctttcca 128280
aattgatcgg tgggctaata ataaaatatt ttttaaaaaa cattcaaaaa catggccaca 128340
cccaacattt cctcgggcaa ttccttttga ttcttttttt ttccccctcc atgtagaaga 128400
gggagaagga gaggctgtga aagctgcttc ggggggattt caagagactg gggtgcccca 128460
ccgcctctgg ccctgtcgtg gggtgtcac agaggcagcg gcagcaacaa aggatttgaa 128520
acttggtgtg ttcgtggagc cacaggcaga cgatgtcaac cttgtgtgag tgtgacgggt 128580
gggggtgggg cgggaggcca tgggggaggc caaggcaggg gctgggcaga ggggagagga 128640
aggacgagaa gggggagtgg gagaggaagc cacatgctgg agaggagatg ccctcctccg 128700
cgccactggg agggccaagg cctccgccac ctgcagtgtc tcagactgag cggctgcctg 128760
tccttggtgg ccagggtctg ctgcgagttg atgtgccacc ctctgcaggg cagcctgtgg 128820
gagaaggggc ggcgggtaag aagagaaggc aagctggcgg gagggtggca ccccgtggat 128880
gacctccttg gaaaagactg accttgatgt cggagggcgc tggcctcttc ctccctccct 128940
gcagggtagg gggcctgagc cgaggggctt ccctctgctc cacagaaacc ctgttttatt 129000
gagttctgaa ggttggaact gcagccatga ttttggccac tttgcagacc tgggacttta 129060
gggctaacca gttctctttg taaggacttg tgcctcttgg gagacgtcca cccgtttcca 129120
agcctgggcc accggcatct ctggagtgtg caggggtctg ggaggcgggt cccgagcccc 129180
ctgtccttcc cacggccact gcagtcaccc ctgtctgccc cactgtgctg tcgtctgcca 129240
tgagaaccca gtcactgcct ataccccctca tcacgtcaca atgtccaaat tcccagcctc 129300 accaccccc ttctcagtaa ggaccctggt tggctgtggg aggcacctac tccatactga 129360
gggtgaaatt aagggaaggt aaagtccagg cacaagagtg ggaccccagc ctctcactct 129420
cagttccact catccaactg ggtccctcac cacgaatctc acgacctgat tcggttccct 129480
gcctcctcct cccatcacag atgtgagcca gggcactgct cagctgtgac cctcggtgtt 129540
tctgccttgt tgacatagag agagcccttt ccccccgaga aggcctggcc ccttcctgtg 129600
ctgagcccgc agcaggaggc tgggtgtcct ggttgtcggt gacggcacca ggatgggcgg 129660
gcaaggcacc cagggcaggc ccacagtccc gctgtccccc acttgcaccc cagcttgtgg 129720
ctgccagcct cccagacagc ccagcccgct gctcagctcc acatgcatag aatcagccct 129780
ccacatccca aaaaggggaa cacaccccct tcgaaatggt tttctccccg gtcccagctg 129840
gaagccatgc tgtctgttct gctggagcag ctgaacatat acatagatgt tgccctgccc 129900
tccccatctg caccctgttg cgttgtagtt ggatttgtct gtttatgctt ggattcacca 129960
gagtgactat gatagtgaaa agaaaaaaaa aaaaaaaaaa aggacgcatg tatcttgaaa 130020
tgcttgtaaa gaggtttcta acccaccctc acaaggtgtc tctcaccccc acgctgggac 130080
gcgtgtggcc tgtgtggcgc cgccctgctg gggcctccca aggtttgaaa ggctttcctc 130140
agcatccggg acccaacaga gaccagattc tagcatctaa ggaggccgtt cagctgtgaa 130200
gaaggcctga agcacaggat taggactgaa gcgatgacat ctccttccct acttcccctt 130260
ggggctctct gtgtcagggc agagagtagg tcttgtggct ggtctggctt gcggcacgag 130320
gatggttctc tctggtcaca gcccgaagtc ccacagcagt cctaaaggag gcttacaact 130380
cctgcatcac aagaagaagg aagccagtgc cagctggggg gatctgcagc tcccagaagc 130440
tccatgagcc tcagccaccc cgcagactgg gttcctcgcc aagctcgccc tctggagggg 130500
cagccagcct cccaccaagg gccctgcgac cacagcaggg attgggatga atggcctatc 130560
ctggatctgc tccagaggcc cgagccacct gcctgaggaa ggataagtca ggagacaccg 130620
ttcccaaagc cttgaccaga gcacctcagc ccactgacct tgcacaaact ccatctgctg 130680
ccatgagaaa agggaagccg cctttgcaaa aaattgctgc ctaaagaaac tcagcagcct 130740
caggctcaat tctgccgctt ctggtttggg tacagttaaa ggcaaccctg agggacttgg 130800
cagtagaaat ccagggcatc ccctagggct ggcaacttcg tgtgcagcta gagctttccc 130860
tgcaagaagt ttctgggccc agaactctcc accaggaagc tccctgctgt tcgctaagtc 130920
ccagcaattc tctaagtgaa gggatctgag aatgaggagg aaatgtgggg tagagatttg 130980
gtggtggtta gagacatgcc cccctcatta ctgccaacag tttcggctgc atttttcacg 131040
tacctcggtt cctcttcctg aagttcttgt gccctgctct tcagcaccgt gggccttatc 131100
cggtaggctc tgggatctcc cccttgtggg gcaggctctt ggggccagcc taagatcatg 131160
gtttagggtg atcagtgctg gcagataaat tgcaaaggca cgctggcttg tgacctcaaa 131220
tgacaatccc cccagggctg ggcactcctc ccctcccctc acttctccca cctgcagagc 131280
cagtgtccgt gggtgggcta gataggatat actgtatgcc ggctccttca agctgttgac 131340
tcactttatc aatagttcca tttaaattga cttcaatggt gagactgtat cctgtttgct 131400
attgcttatt gtgctatggg gggagggggg aggaatgtgt aacatagtta acatgggtaa 131460
agggagatct tggggtgcag cacttcaatt gcctcgtaac ccttttcatc atttcaacca 131520
catttgctaa agggagggag cagccacgcg gttagaggcc cttggggttt ctcttttcca 131580
ctgacagcct ttcccaggca gctggccagt tccccattcc ctccccagcc aggtgcaggc 131640
gtagcaatat ggacatctgg ttgctttggc ctgctgccct ctttcagggg tcctaagccc 131700
acaatcatgc ctccctaaga ccctggcatc cttcctttta agccgttggc acctctgtgc 131760
cacctctcac actggctcca gacacagcct gtgcttctgg cagctgagat cactcacttc 131820
cccctcctca tctttgttgg agctccaagt caagccacga ggtcagggcg agggcagagg 131880
tggtcaccag cgtgtcccat ctacagacct gtggcttcgt aagacttctg atttctcttc 131940
agctttgaaa agggttaccc tgggcactgg cctagagtct cacctcctaa tagacttacc 132000
cccatgagtt tgccatgttg agcaggacaa tttctggcac ttgcaagtcc catgatttct 132060
tcggtaattg tgagggtggg gggagggaca tgaaatcatc ttagcttagc ttcctgtctg 132120
tgaatgtcta tatagtgtat tgtgtgtttt aacaaatgat ttacactgac tgttgccgta 132180
aaagtgaatt tggaaataaa gttattactc tgattaaa 132218

<210> SEQ ID NO 3
<211> LENGTH: 61
<212> TYPE: DNA
<213> ORGANISM: Artificial
<220> FEATURE:

<223> OTHER INFORMATION: Target region

<400> SEQUENCE: 3
gattaaggca tgagtgatta aattaaagcc aggcattgac ttggatggtg taatattctg 60
a 61

<210> SEQ ID NO 4
<211> LENGTH: 32
<212> TYPE: DNA
<213> ORGANISM: Artificial
<220> FEATURE:
<223> OTHER INFORMATION: Target region

<400> SEQUENCE: 4
gaaggttgaa atgagaattg atttgagtta aa 32

<210> SEQ ID NO 5
<211> LENGTH: 104
<212> TYPE: DNA
<213> ORGANISM: Artificial
<220> FEATURE:
<223> OTHER INFORMATION: Target region

<400> SEQUENCE: 5
tggttaccta taaactagtg caccctaatg aattaaaagg tgttgatgag ttaacttgtt 60
atgccttcca gataagacat gcaaatgggg cttcttcctc cttc 104

<210> SEQ ID NO 6
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 6
tcactcatgc cttaatc 17

<210> SEQ ID NO 7
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 7
taatcactca tgcctta 17

<210> SEQ ID NO 8
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 8
taatcactca tgcctt 16

<210> SEQ ID NO 9
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 9
ctttaattta atcactcat 19

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
gctttaattt aatcactcat 20

<210> SEQ ID NO 11
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 11
ctttaattta atcactca 18

<210> SEQ ID NO 12
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 12
ctttaattta atcactc 17

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
tccaagtcaa tgcctggctt 20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
atccaagtca atgcctggct 20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
accatccaag tcaatgcctg 20

<210> SEQ ID NO 16
<211> LENGTH: 20
<212> TYPE: DNA

<213> ORGANISM: Artificial sequence
<220> FEATURE:
<223> OTHER INFORMATION: Synthetic oligonucleotide

<400> SEQUENCE: 16
caccatccaa gtcaatgcct 20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
tacaccatcc aagtcaatgc 20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
ttacaccatc caagtcaatg 20

<210> SEQ ID NO 19
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 19
acaccatcca agtcaat 17

<210> SEQ ID NO 20
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 20
tacaccatcc aagtcaa 17

<210> SEQ ID NO 21
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 21
ttacaccatc caagtca 17

<210> SEQ ID NO 22
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 22
ttacaccatc caagtc 16

<210> SEQ ID NO 23
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 23
aatattacac catccaa 17

<210> SEQ ID NO 24
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 24
agaatattac accatccaa 19

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
cagaatatta caccatccaa 20

<210> SEQ ID NO 26
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 26
gaatattaca ccatccaa 18

<210> SEQ ID NO 27
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 27
aatattacac catcca 16

<210> SEQ ID NO 28
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 28
agaatattac accatcca 18

<210> SEQ ID NO 29
<211> LENGTH: 19
<212> TYPE: DNA
<213> ORGANISM: Artificial sequence
<220> FEATURE:

<223> OTHER INFORMATION: Synthetic oligonucleotide

<400> SEQUENCE: 29
cagaatatta caccatcca 19

<210> SEQ ID NO 30
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 30
gaatattaca ccatcca 17

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
tcagaatatt acaccatcca 20

<210> SEQ ID NO 32
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 32
agaatattac accatcc 17

<210> SEQ ID NO 33
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 33
cagaatatta caccatcc 18

<210> SEQ ID NO 34
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 34
gaatattaca ccatcc 16

<210> SEQ ID NO 35
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 35
tcagaatatt acaccatcc 19

<210> SEQ ID NO 36
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 36
agaatattac accatc 16

<210> SEQ ID NO 37
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 37
cagaatatta caccat 16

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
caattctcat ttcaaccttc 20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
tcaattctca tttcaacctt 20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
atcaattctc atttcaacct 20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
aatcaattct catttcaacc 20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
aaatcaattc tcatttcaac 20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
caaatcaatt ctcatttcaa 20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
tcaaatcaat tctcatttca 20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
ctcaaatcaa ttctcatttc 20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
actcaaatca attctcattt 20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
aactcaaatc aattctcatt 20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
taactcaaat caattctcat 20

<210> SEQ ID NO 49
<211> LENGTH: 20

<212> TYPE: DNA
<213> ORGANISM: Artificial sequence
<220> FEATURE:
<223> OTHER INFORMATION: Synthetic oligonucleotide

<400> SEQUENCE: 49
ttaactcaaa tcaattctca 20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
tttaactcaa atcaattctc 20

<210> SEQ ID NO 51
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 51
tttaactcaa atcaattct 19

<210> SEQ ID NO 52
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 52
ccttttaatt cattag 16

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
caacaccttt taattcatta 20

<210> SEQ ID NO 54
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 54
aacacctttt aattcatt 18

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
catcaacacc ttttaattca 20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
ctcatcaaca ccttttaatt 20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
actcatcaac accttttaat 20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
aactcatcaa caccttttaa 20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
taactcatca acacctttta 20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
ttaactcatc aacacctttt 20

<210> SEQ ID NO 61
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 61
ttaactcatc aacaccttt 19

<210> SEQ ID NO 62
<211> LENGTH: 18
<212> TYPE: DNA
<213> ORGANISM: Artificial sequence -continued

```
<220> FEATURE:
<223> OTHER INFORMATION: Synthetic oligonucleotide

<400> SEQUENCE: 62

ttaactcatc aacacctt                                                    18


<210> SEQ ID NO 63
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 63

ttaactcatc aacacct                                                     17


<210> SEQ ID NO 64
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 64

gttaactcat caacacc                                                     17


<210> SEQ ID NO 65
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 65

gttaactcat caacac                                                      16


<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66

atttccaaat tcacttttac                                                  20


<210> SEQ ID NO 67
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 67

ccgttttctt accaccct                                                    18
```